US011913052B2

(12) United States Patent
Jewett et al.

(10) Patent No.: US 11,913,052 B2
(45) Date of Patent: Feb. 27, 2024

(54) CELL-FREE PROTEIN SYNTHESIS DRIVEN METABOLIC ENGINEERING

(71) Applicant: Northwestern University, Evanston, IL (US)

(72) Inventors: Michael Christopher Jewett, Evanston, IL (US); Ashty Stephen Karim, Chicago, IL (US); Jian Li, Evanston, IL (US); Quentin Dudley, Evanston, IL (US)

(73) Assignee: Northwestern University, Evanston, IL (US)

( * ) Notice: Subject to any disclaimer, the term of this patent is extended or adjusted under 35 U.S.C. 154(b) by 366 days.

(21) Appl. No.: 16/807,147

(22) Filed: Mar. 2, 2020

(65) Prior Publication Data

US 2020/0291445 A1 Sep. 17, 2020

Related U.S. Application Data

(63) Continuation-in-part of application No. 15/175,497, filed on Jun. 7, 2016, now Pat. No. 10,577,632.

(60) Provisional application No. 62/173,818, filed on Jun. 10, 2015.

(51) Int. Cl.
*C12N 15/67* (2006.01)
*C12P 21/02* (2006.01)

(52) U.S. Cl.
CPC .............. *C12P 21/02* (2013.01); *C12N 15/67* (2013.01)

(58) Field of Classification Search
CPC ................................ C12N 15/67; C12P 21/02
See application file for complete search history.

(56) References Cited

U.S. PATENT DOCUMENTS

| | | | |
|---|---|---|---|
| 8,357,529 | B2 | 1/2013 | Swartz |
| 2004/0209321 | A1 | 10/2004 | Swartz |
| 2007/0154983 | A1 | 7/2007 | Calhoun |
| 2016/0060301 | A1 | 3/2016 | Jewett |
| 2018/0016614 | A1 | 1/2018 | Jewett |

OTHER PUBLICATIONS

Swati B. Jadhav A green process for the production of butanol from butyraldehyde using alcohol dehydrogenase: process details. Royal Society of Chemistry Advances, 2014, 4, 14597-14602 (Year: 2014).*

Jung Ku et al Expression of a functional non-ribosomal peptide synthetase module *in Escherichia co/i* by coexpression with a phosphopantetheinyl transferase. Chemistry & Biology Mar. 1997, 4:203-207 (Year: 1997).*

Shen, C. R. et al. Driving forces enable high-titer anaerobic 1-butanol synthesis in *Escherichia coli*. Applied and environmental microbiology 77, 2905-2915, doi: 10.1128/AEM.03034-10 (2011).

Siegal-Gaskins, D., Tuza, Z. A., Kim, J., Noireaux, V. & Murray, R. M. Gene circuit performance characterization and resource usage in a cell-free "breadboard". ACS synthetic biology 3, 416-425, doi:10.1021/sb400203p (2014).

Smanski, M. J. et al. Functional optimization of gene clusters by combinatorial design and assembly. Nat Biotechnol 32, 1241-1249, doi:10.1038/nbt.3063 (2014).

Steen, E. J. et al. Metabolic engineering of *Saccharomyces cerevisiae* for the production of n-butanol. Microbial cell factories 7, 36, doi:10.1186/1475-2859-7-36 (2008).

Sun, Z. Z., Yeung, E., Hayes, C. A., Noireaux, V. & Murray, R. M. Linear DNA for rapid prototyping of synthetic biological circuits in an *Escherichia coli* based TX-TL cell-free system. ACS synthetic biology 3, 387-397, doi:10.1021/sb400131a (2014).

Swartz, J. R. Transforming biochemical engineering with cell-free biology. AlChE Journal 58, 5-13, doi:10.1002/ic.13701 (2012).

Voloshin, A. M. & Swartz, J. R. Efficient and scalable method for scaling up cell free protein synthesis in batch mode. Biotechnol Bioeng 91, 516-521, doi:10.1002/bil.20528 (2005).

Welch, P. & Scopes, R. K. Studies on cell-free metabolism: Ethanol production by a yeast glycolytic system reconstituted from purified enzymes. Journal of biotechnology 2, 257-273, doi:10.1016/0168-1656(85)90029-x (1985).

Yadav, V. G., De Mey, M., Giaw Lim, C., Kumaran Ajikumar, P. & Stephanopoulos, G. The future of metabolic engineering and synthetic biology: Towards a systematic practice. Metabolic engineering 14, 233-241, doi:10.1016/j.ymben.2012.02.001 (2012).

Yin, G. et al. A glycosylated antibodies and antibody fragments produced in a scalable in vitro transcription-translation system. MAbs 4, 217-225, doi:10.4161/mabs.4.2.19202 (2012).

You, C. & Zhang, Y. H. Cell-free biosystems for biomanufacturing. Advances in biochemical engineering/biotechnology 131, 89-119, doi:10.1007/10_2012_159 (2013).

Zawada, J. F. et al. Microscale to manufacturing scale-up of cell-free cytokine production—a new approach for shortening protein production development timelines. Biotechnol Bioeng 108, 1570-1578, doi: 10.1002/bil.23103 2011).

(Continued)

*Primary Examiner* — Tekchand Saidha
(74) *Attorney, Agent, or Firm* — Quarles & Brady LLP

(57) ABSTRACT

Disclosed are cell-free systems for metabolic engineering, methods for cell-free metabolic engineering, kits for preparing the disclosed systems, and kits for performing the disclosed methods. The disclosed systems, methods, and kits may be utilized to prepare a chemical product or natural product and to optimize conditions for preparing a chemical product or natural product. The disclosed systems, methods, and kits also may be utilized for combinatorial cell-free metabolism engineering.

15 Claims, 210 Drawing Sheets

Specification includes a Sequence Listing.

(56) References Cited

OTHER PUBLICATIONS

Zemella, A., Thoring, L., Hoffmeister, C. & Kubick, S. Cell-Free Protein Synthesis: Pros and Cons of Prokaryotic and Eukaryotic Systems. Chembiochem 16, 2420-2431, doi:10.1002/cbic.201500340 (2015).
Zhang, Y. H. Production of biofuels and biochemicals by in vitro synthetic biosystems: Opportunities and challenges. Biotechnology advances 33, 1467-1483, doi:10.1016/j.biotechadv.2014.10.009 (2015).
Zhu, F. et al. In vitro reconstitution of mevalonate pathway and targeted engineering of farnesene overproduction in *Escherichia coli*. Biotechnol Bioeng 111, 1396-1405, doi:10.1002/bil.25198 (2014).
Atsumi, S. et al. Metabolic engineering of *Escherichia coli* for 1-butanol production. Metabolic engineering 10, 305-311, doi:10.1016/j.ymben.2007.08.003 (2008).
Bogorad, I. W., Lin, T. S. & Liao, J. C. Synthetic non-oxidative glycolysis enables complete carbon conservation. Nature 502, 693-697, doi:10.1038/nature12575 (2013).
Bond-Watts, B. B., Bellerose, R. J. & Chang, M. C. Enzyme mechanism as a kinetic control element for designing synthetic biofuel pathways. Nature chemical biology 7, 222-227, doi:10.1038/nchembio.537 (2011).
Bornscheuer, U. T. et al. Engineering the third wave of biocatalysis. Nature 485, 185-194, doi:10.1038/nature11117 (2012).
Boyle, P. M. & Silver, P. A. Parts plus pipes: synthetic biology approaches to metabolic engineering. Metabolic engineering 14, 223-232, doi:10.1016/j.ymben.2011.10.003 (2012).
Bujara, M., Schumperli, M., Pellaux, R., Heinemann, M. & Panke, S. Optimization of a blueprint for in vitro glycolysis by metabolic real-time analysis. Nat Chem Biol 7, 271-277, doi:10.1038/nchembio.541 (2011).
Carlson, E. D., Gan, R., Hodgman, C. E. & Jewett, M. C. Cell-free protein synthesis: applications come of age. Biotechnology advances 30, 1185-1194, doi:10.1016/j.biotechadv.2011.09.016 (2012).
Curran, K. A. & Alper, H. S. Expanding the chemical palate of cells by combining systems biology and metabolic engineering. Metabolic engineering 14, 289-297, doi:10.1016/j.ymben.2012.04.006 (2012).
Dai, Z. & Nielsen, J. Advancing metabolic engineering through systems biology of industrial microorganisms. Current opinion in biotechnology 36, 8-15, doi:10.1016/j.copbio.2015.08.006 (2015).
Daugherty, A. B., Govindarajan, S. & Lutz, S. Improved biocatalysts from a synthetic circular permutation library of the flavin-dependent oxidoreductase old yellow enzyme. J Am Chem Soc 135, 14425-14432, doi:10.1021/ja4074886 (2013).
Demain, A. L. Importance of microbial natural products and the need to revitalize their discovery. Journal of industrial microbiology & biotechnology 41, 185-201, doi:10.1007/s10295-013-1325-z (2014).
Dodevski, I., Markou, G. C. & Sarkar, C. A. Conceptual and methodological advances in cell-free directed evolution. Curr Opin Struct Biol 33, 1-7, doi:10.1016/j.sbi.2015.04.008 (2015).
Dong, H. et al. Engineering *Escherichia coli* Cell Factories for n-Butanol Production. Advances in biochemical engineering/biotechnology, doi:10.1007/10_2015_306 (2015).
Dudley, Q. M., Karim, A. S. & Jewett, M. C. Cell-free metabolic engineering: biomanufacturing beyond the cell. Biotechnology journal 10, 69-82, doi:10.1002/biot.201400330 (2015).
Dudley, Q., et al., ACS Synth. Biol. 2016, 5, 1578-1588.
Dudley, Q., et al., Synthetic Biology, 2019, 4(1): ysz003.
Erickson, B., Nelson & Winters, P. Perspective on opportunities in industrial biotechnology in renewable chemicals. Biotechnology journal 7, 176-185, doi:10.1002/biot.201100069 (2012).
Fritz, B. R., Timmerman, L. E., Daringer, N. M., Leonard, J. N. & Jewett, M. C. Biology by design: from top to bottom and back. Journal of biomedicine & biotechnology 2010, 232016, doi: 10.1155/2010/232016 (2010).
Goering, A., et al., ACS Synth. Biol. 2017, 6, 39-44.
Goshima, N. et al. Human protein factory for converting the transcriptome into an in vitro-expressed proteome. Nature Methods 5, 1011-1017, doi:10.1038/nmeth.1273 (2008).
Green, E. M. Fermentative production of butanol—the industrial perspective. Current opinion in biotechnology 22, 337-343, doi:10.1016/j.copbio.2011.02.004 (2011).
Gulevich, A. Y., Skorokhodova, A. Y., Sukhozhenko, A. V., Shakulov, R. S. & Debabov, V. G. Metabolic engineering of *Escherichia coli* for 1-butanol biosynthesis through the inverted aerobic fatty acid beta-oxidation pathway. Biotechnol Lett 34, 463-469, doi:10.1007/s10529-011-0797-z (2012).
Guterl, J. K. et al. Cell-free metabolic engineering: production of chemicals by minimized reaction cascades. ChemSusChem 5, 2165-2172, doi:10.1002/cssc.201200365 (2012).
Harvey, A. L., Edrada-Ebel, R. & Quinn, R. J. The re-emergence of natural products for drug discovery in the genomics era. Nature reviews. Drug discovery 14, 111-129, doi:10.1038/nrd4510 (2015).
Henrich, E., Hein, C., Dotsch, V. & Bernhard, F. Membrane protein production in *Escherichia coli* cell-free lysates. FEBS Lett 589, 1713-1722, doi:10.1016/j.febslet.2015.04.045 (2015).
Hodgman, C. E. & Jewett, M. C. Cell-free synthetic biology: thinking outside the cell. Metabolic engineering 14, 261-269, doi:10.1016/j.ymben.2011.09.002 (2012).
Hong, S. H. et al. Improving cell-free protein synthesis through genome engineering of *Escherichia coli* lacking release factor 1. Chembiochem 16, 844-853, doi:10.1002/cbic.201402708 (2015).
Inui, M. et al. Expression of Clostridium acetobutylicum butanol synthetic genes in *Escherichia coli*. Appl Microbiol Biotechnol 77, 1305-1316, doi:10.1007/s00253-007-1257-5 (2008).
Jensen, M. K. & Keasling, J. D. Recent applications of synthetic biology tools for yeast metabolic engineering. FEMS Yeast Res, doi:10.1111/1567-1364.12185 (2014).
Jewett, M. C. & Swartz, J. R. Mimicking the *Escherichia coli* cytoplasmic environment activates long-lived and efficient cell-free protein synthesis. Biotechnol Bioeng 86, 19-26, doi:10.1002/bit.20026 (2004).
Jewett, M. C., Calhoun, K. A., Voloshin, A., Wuu, J. J. & Swartz, J. R. An integrated cell-free metabolic platform for protein production and synthetic biology. Mol Syst Biol 4, 220, doi:10.1038/msb.2008.57 (2008).
Jewett, M. C., Fritz, B. R., Timmerman, L. E. & Church, G. M. In vitro integration of ribosomal RNA synthesis, ribosome assembly, and translation. Mol Syst Biol 9, 678, doi:10.1038/msb.2013.31 (2013).
Karim, A., et al., Metabolic Engineering36(2016)116-126.
Kay, J. E. & Jewett, M. C. Lysate of engineered *Escherichia coli* supports high-level conversion of glucose to 2,3-butanediol. Metabolic engineering 32, 133-142, doi:10.1016/j.ymben.2015.09.015 (2015).
Keasling, J. D. Manufacturing molecules through metabolic engineering. Science 330, 1355-1358, doi:10.1126/science.1193990 (2010).
Keasling, J. D. Synthetic biology and the development of tools for metabolic engineering. Metabolic engineering 14, 189-195, doi:10.1016/j.ymben.2012.01.004 (2012).
Kern, A., Tilley, E., Hunter, I. S., Legisa, M. & Glieder, A. Engineering primary metabolic pathways of industrial microorganisms. Journal of biotechnology 129, 6-29, doi:10.1016/j.jbiotec.2006.11.021 (2007).
Korman, T. P. et al. A synthetic biochemistry system for the in vitro production of isoprene from glycolysis intermediates. Protein Sci 23, 576-585, doi:10.1002/pro.2436 (2014).
Krutsakorn, B. et al. In vitro production of n-butanol from glucose. Metabolic engineering 20, 84-91, doi:10.1016/j.ymben.2013.09.006 (2013).
Kwok, R. Five hard truths for synthetic biology. Nature 463, 288-290, doi:10.1038/463288a (2010).
Lee, J. W. et al. Systems metabolic engineering of microorganisms for natural and non-natural chemicals. Nature chemical biology 8, 536-546, doi:10.1038/nchembio.970 (2012).
Lee, S. Y. & Kim, H. U. Systems strategies for developing industrial microbial strains. Nat Biotechnol 33, 1061-1072, doi:10.1038/nbt.3365 (2015).

(56) References Cited

OTHER PUBLICATIONS

Lutke-Eversloh, T. & Bahl, H. Metabolic engineering of Clostridium acetobutylicum: recent advances to improve butanol production. Current opinion in biotechnology 22, 634-647, doi:10.1016/j.copbio.2011.01.011 (2011).
Nielsen, D. R. et al. Engineering alternative butanol production platforms in heterologous bacteria. Metabolic engineering 11, 262-273, doi:10.1016/j.ymben.2009.05.003 (2009).
Nielsen, J. et al. Engineering synergy in biotechnology. Nature chemical biology 10, 319-322, doi:10.1038/nchembio.1519 (2014).
Nielsen, J. Metabolic engineering. Applied Microbiology and Biotechnology 55, 263-283, doi:10.1007/s002530000511 (2001).
Ninh, P. H., Honda, K., Sakai, T., Okano, K. & Ohtake, H. Assembly and multiple gene expression of thermophilic enzymes in *Escherichia coli* for in vitro metabolic engineering. Biotechnol Bioeng 112, 189-196, doi:10.1002/bit.25338 (2015).
Noireaux, V., Bar-Ziv, R. & Libchaber, A. Principles of cell-free genetic circuit assembly. Proc Natl Acad Sci U S A 100, 12672-12677, doi:10.1073/pnas.2135496100 (2003).
Record, M. T., Courtenay, E. S., Cayley, S. & Guttman, H. J. Biophysical compensation mechanisms buffering *E. coli* protein-nucleic acid interactions against changing environments. Trends in Biochemical Sciences 23, 190-194, doi:10.1016/s0968-0004(98)01207-9 (1998).
Rollié, S., Mangold, M. & Sundmacher, K. Designing biological systems: Systems Engineering meets Synthetic Biology. Chemical Engineering Science 69, 1-29, doi:10.1016/j.ces.2011.10.068 (2012).

* cited by examiner

A.

FIGURE 28, CON'T.
B.
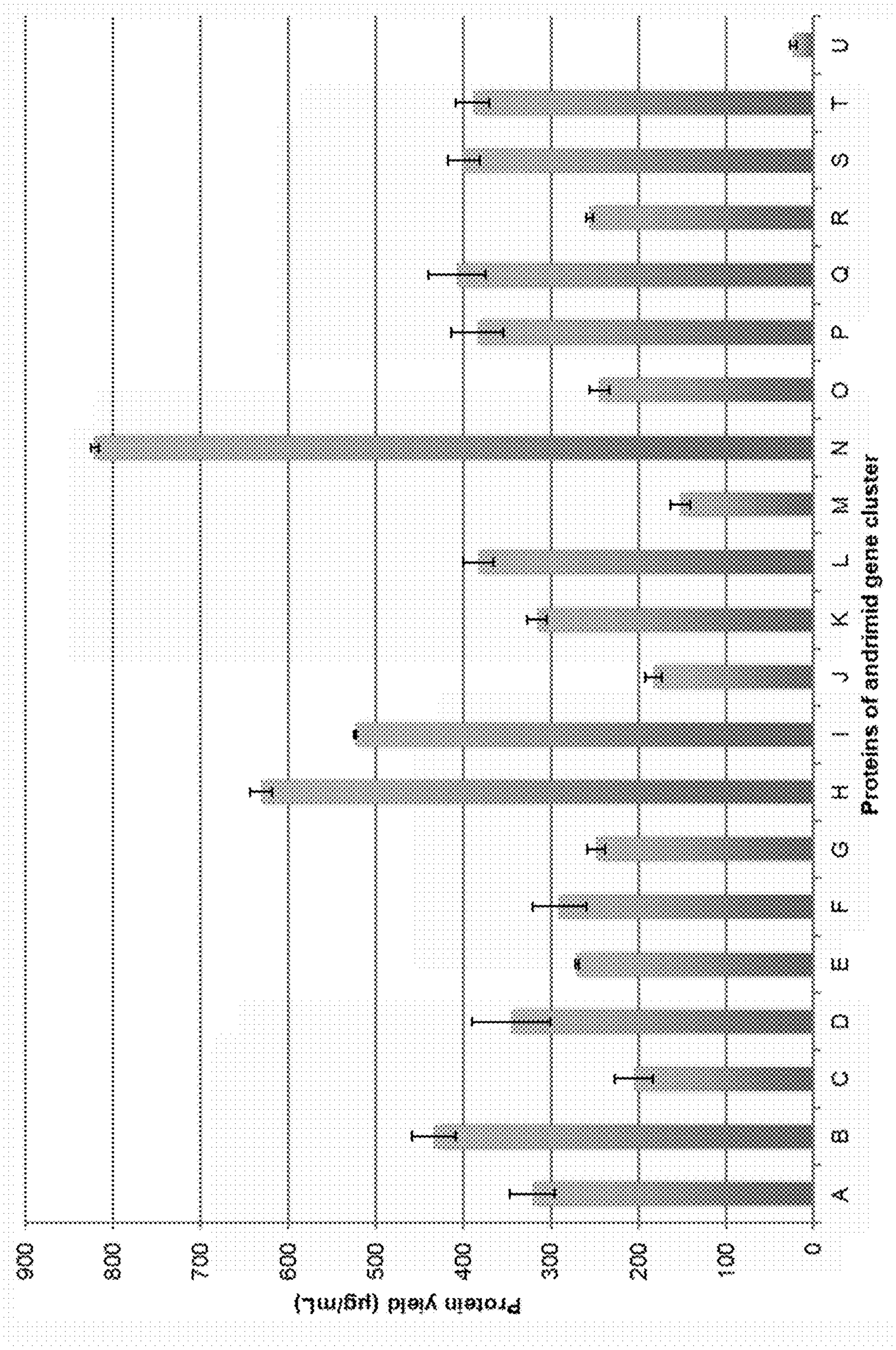

FIGURE 28, CON'T.
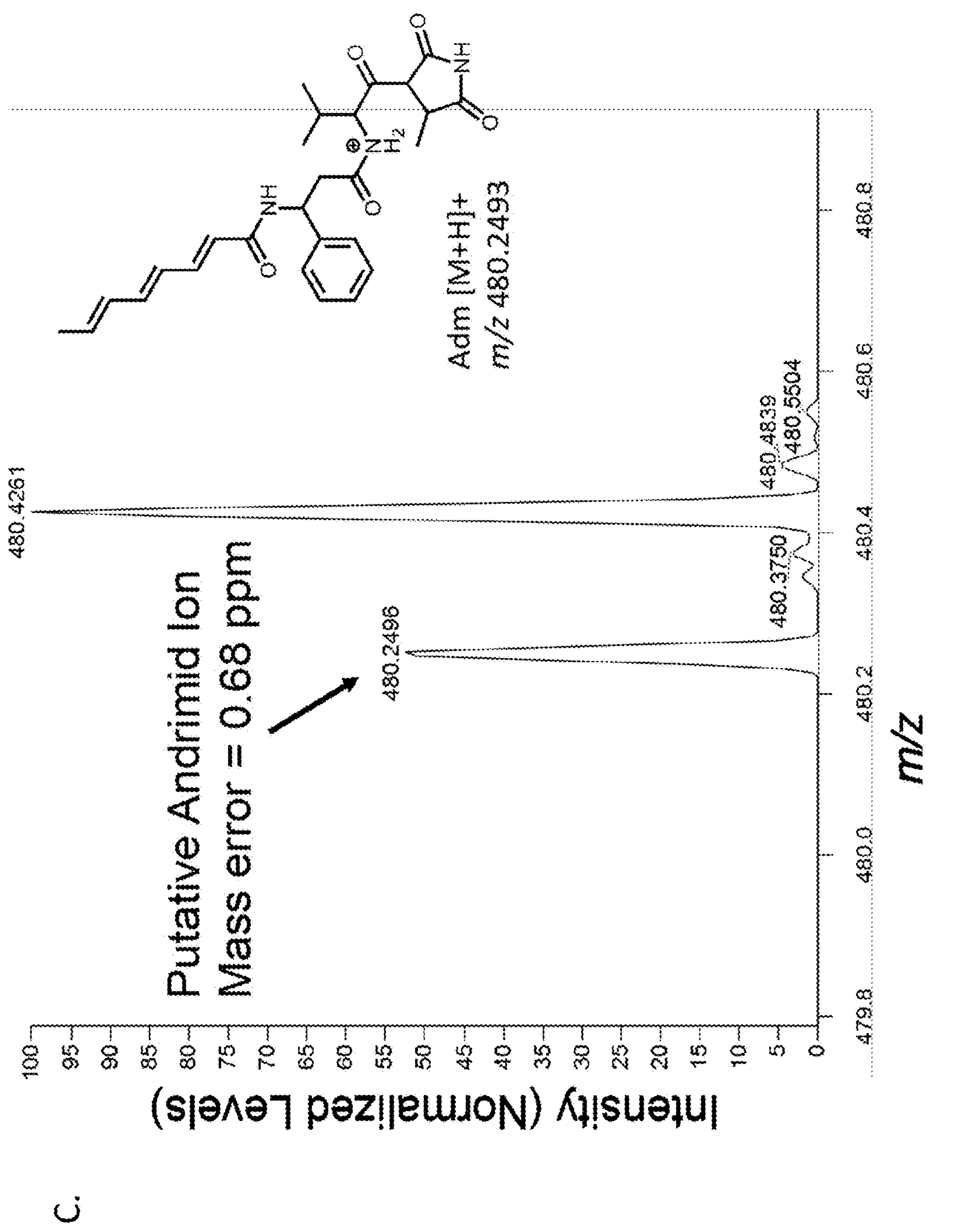
LC-MS analysis of cell-free synthesized andrimid

FIGURE 29, CON'T.
D
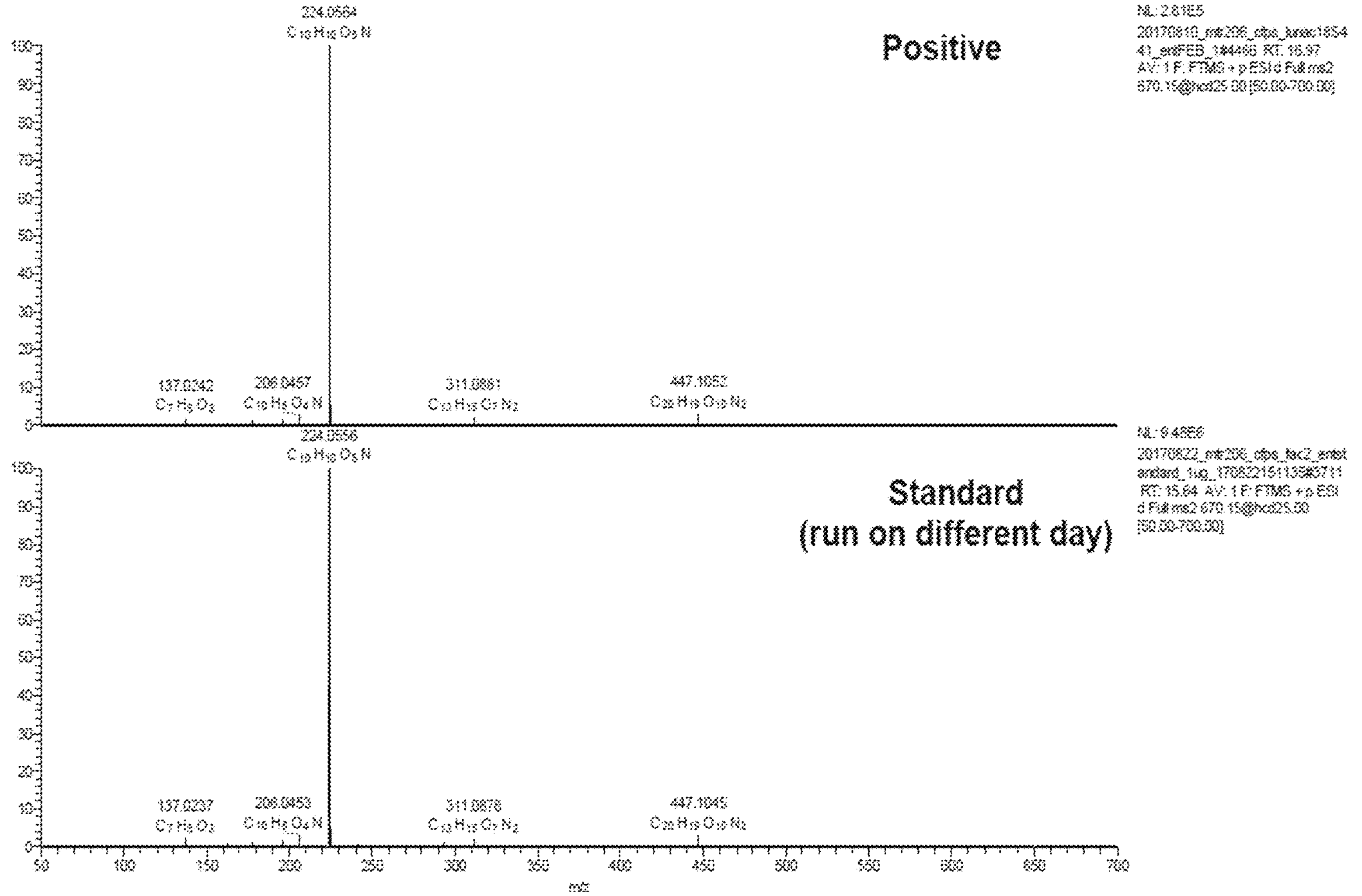

FIGURE 39

| Gene | Source Organism | Sequence (SEQ ID NO:1) |
|---|---|---|
| PAL2 | *Arabidopsis thaliana* | atggatcaaatcgaagcaatgttgtgcggcggaggagagaagacaaaagtgg<br>cggttactacgaagactttggcagatccattgaattggggtttagcagcggatcaa<br>atgaaaggaagtcatttagatgaagtgaagaagatggtcgaagagtatcgtaga<br>ccagtcgtgaatcttggcggagaaacactgacgatcggacaagttgctgccatct<br>ccaccgtaggaggcagcgttaaggttgagttagcggagacttcaagagccggtg<br>tgaaagctagcagtgattgggttatggagagcatgaacaaaggtactgacagtta<br>cggagtcaccaccggctttggtgctacttctcaccggagaaccaaaaacggcac<br>cgcattacaaacagaactcattagatttgaacgccggaatattcggaaacacg<br>aaggagacatgtcacacactgccgcaatccgccacaagagccgccatgctcgt<br>cagagtcaacactcttctccaaggatactccgggatccgattcgagatcctcgaa<br>gcgattacaagtctcctcaaccacaacatctctccgtcactacctctccgtggaacc<br>attaccgcctccggcgatctcgttcctctctcttacatcgccggacttctcaccggcc<br>gtcctaattccaaagccaccggtcccgacggtgaatcgctaaccgcgaaagaa<br>gctttgagaaagccggaatcagtactggattcttcgatttacaacctaaggaaggt<br>ttagctctcgttaatggcacggcggttggatctggaatggcgtcgatggttctattcg<br>aagcgaatgtccaagcggtgttagcggaggttttatcagcgatcttcgcggaggtt<br>atgagcgggaaacctgagtttaccgatcatctgactcatcgtttaaaacatcatccc<br>ggacaaatcgaagcggcggcgataatggagcacatactcgacggaagctcat<br>acatgaaattagctcaaaaggttcacgagatggatccattgcagaaaccaaaac<br>aagatcgttacgctcttcgtacatctcctcaatggctaggtcctcaaattgaagtaat<br>ccgtcaagctacgaaatcgatagagcgtgaaatcaactccgttaacgataatccg<br>ttgatcgatgtttcgaggaacaaggcgattcacggtggtaacttccaaggaacac<br>caatcggagtttctatggataacacgagattggcgattgctgcgattgggaagcta<br>atgtttgctcaattctctgagcttgttaatgatttctacaacaatggacttccttcgaatct<br>aactgcttcgagtaatccaagtttggattatggattcaaaggagcagagattgctat<br>ggcttcttattgttctgagcttcaatacttggctaatccagtcacaagccatgttcaatc<br>agctgagcaacataatcaagatgtgaactctcttggtttgatctcgtctcgtaaaac<br>atctgaagctgtggatattcttaagctaatgtcaacaacgttccttgtggggatatgtc<br>aagctgttgatttgagacatttggaggagaatctgagacaaactgtgaagaacac<br>agtttctcaagttgctaagaaagtgttaaccactggaatcaacggtgagttacatcc<br>gtcaaggttttgcgagaaggacttgcttaaggtgttgatcgtgagcaagtgttcacg<br>tatgtggatgatccttgtagcgctacgtacccgttgatgcagagactaagacaagtt<br>attgttgatcacgctttgtccaacggtgagactgagaagaatgcagtgacttcgatc<br>tttcaaaagattggagcttttgaagaggagcttaaggctgtgcttccaaaggaagtt<br>gaagcggctagagcggcttatgggaatggaactgcgccgattcctaaccggatt<br>aaggaatgtaggtcgtatccgttgtataggttcgtgagggaagagcttggaacga<br>agttgttgactggagaaaaggttgtgtctccgggagaggagtttgataaggtcttca<br>ctgctatgtgtgaaggtaaacttattgatccgttgatggattgtctcaaggaatggaa<br>cggagctccgattccgatttgctaa |

FIGURE 39, CON'T.

| Gene | Source Organism | Sequence (SEQ ID NO:2) |
|---|---|---|
| FDC1 | *Saccharomyces cerevisiae* | atggaattcgggaggaattatatgaggaagctaaatccagctttagaatttagaga<br>ctttatccaggtcttaaaagatgaagatgacttaatcgaaattaccgaagagattga<br>tccaaatctcgaagtaggtgcaattatgaggaaggcctatgaatcccacttaccag<br>ccccgttatttaaaaatctcaaaggtgcttcgaaggatcttttcagcattttaggttgcc<br>cagccggtttaagaagtaaggagaaaggagatcatggtagaattgcccatcatct<br>ggggctcgacccaaaaacaactatcaaggaaatcatagattatttgctggagtgt<br>aaggagaaggaacctctccccccaatcactgttcctgtgtcatctgcaccttgtaaa<br>acacatatactttctgaagaaaaaatacatctacaaagcctgccaacaccatatct<br>acatgtttcagacggtggcaagtacttacaaacgtacggaatgtggattcttcaaa |
| | | ctccagataaaaaatggactaattggtcaattgctagaggtatggttgtagatgac<br>aagcatatcactggtctggtaattaaaccacaacatattagacaaattgctgactct<br>tgggcagcaattggaaaagcaaatgaaattcctttcgcgttatgttttggcgttcccc<br>cagcagctattttagttagttccatgccaattcctgaaggtgtttctgaatcggattatg<br>ttggcgcaatcttgggtgagtcggttccagtagtaaaatgtgagaccaacgatttaa<br>tggttcctgcaacgagtgagatggtatttgagggtactttgtccttaacagatacaca<br>tctggaaggcccatttggtgagatgcatggatatgttttcaaaagccaaggtcatcc<br>ttgtccattgtacactgtcaaggctatgagttacagagacaatgctattctacctgtttc<br>gaaccccggtctttgtacggatgagacacataccttgattggttcactagtggctact<br>gaggccaaggagctggctattgaatctggcttgccaattctggatgcctttatgcctt<br>atgaggctcaggctcttggcttatcttaaaggtggatttgaaagggctgcaagcatt<br>gaagacaacgcctgaagaattttgtaagaaggtaggtgatatttactttaggacaa<br>aagttggttttatagtccatgaaataatttggtggcagatgatatcgacatatttaact<br>tcaaagaagtcatctgggcctacgttacaagacatacacctgttgcagatcagatg<br>gcttttgatgatgtcacttcttttcctttggctccctttgtttcgcagtcatccagaagtaa<br>gactatgaaaggtggaaagtgcgttactaactgcatatttagacagcaatatgagc<br>gcagttttgactacataacttgtaattttgaaaagggatatccaaaaggattagttga<br>caaagtaaatgaaaattggaaaaggtacggatataaataa |

FIGURE 42, CON'T.
B.
GrsA: DNFYALGGDSIK+PPant (SEQ ID NO:3)
[M+2H]+ = m/z 820.357
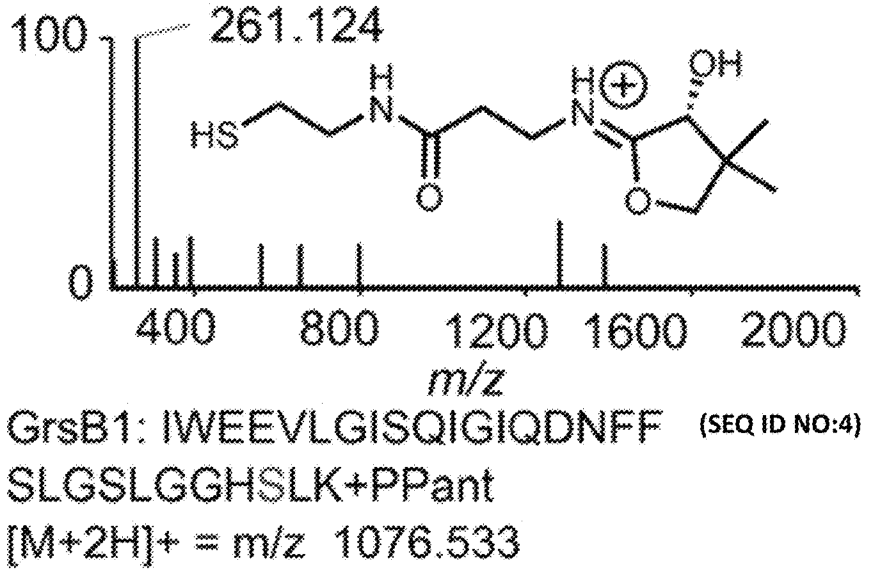
GrsB1: IWEEVLGISQIGIQDNFF (SEQ ID NO:4)
SLGSLGGHSLK+PPant
[M+2H]+ = m/z 1076.533
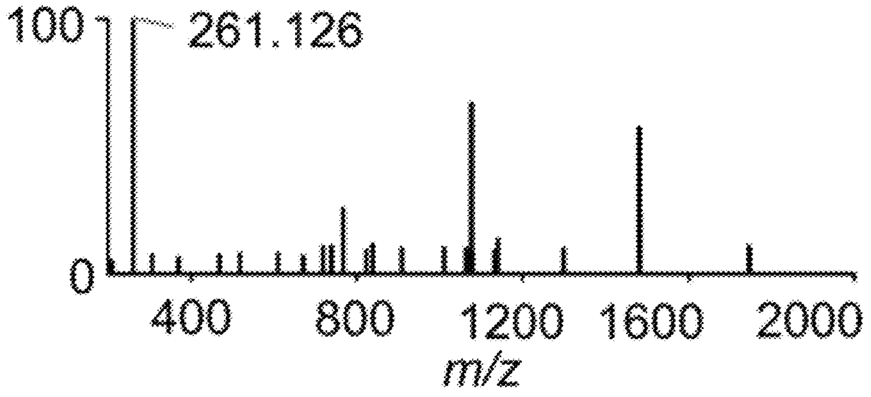

Synthetic preparation of racemic DKP

FIGURE 51, CON'T.
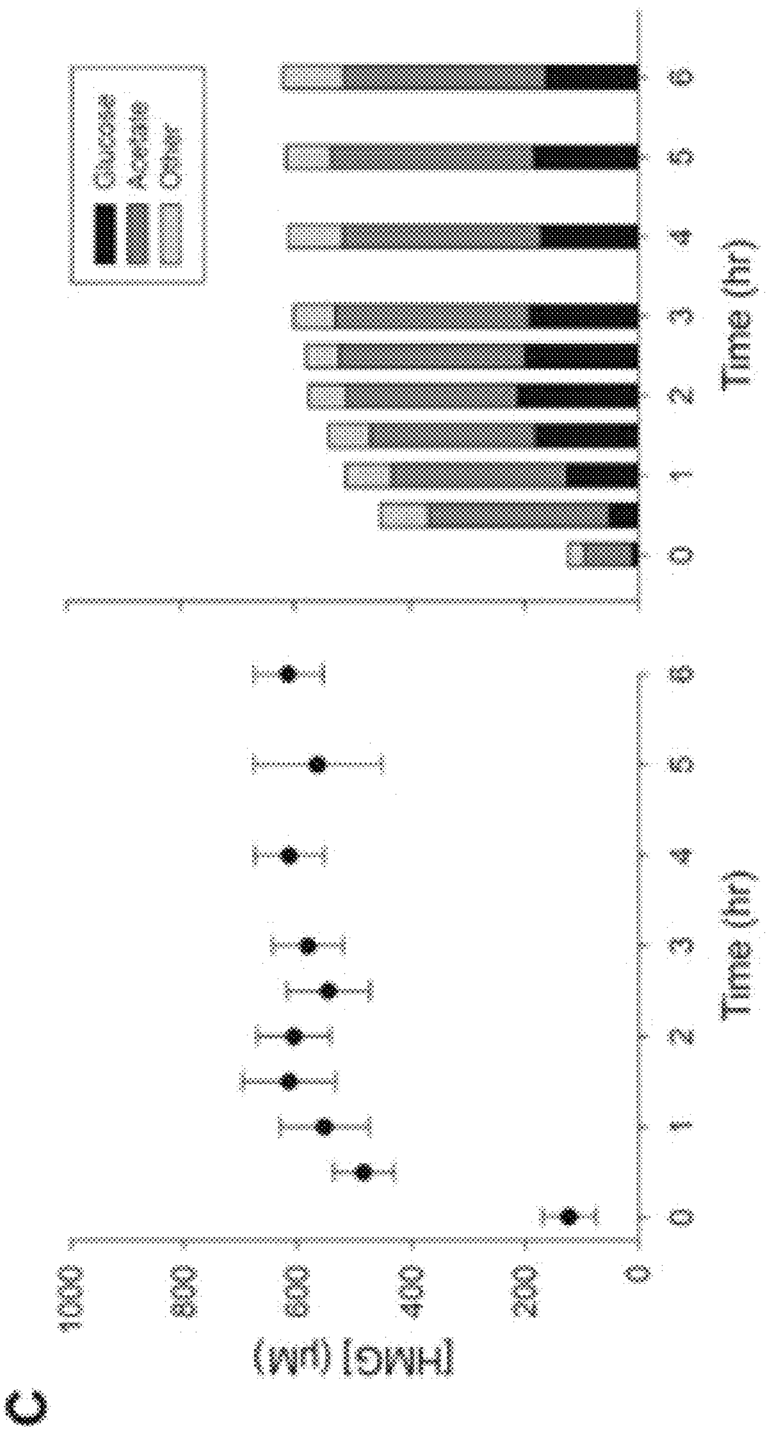

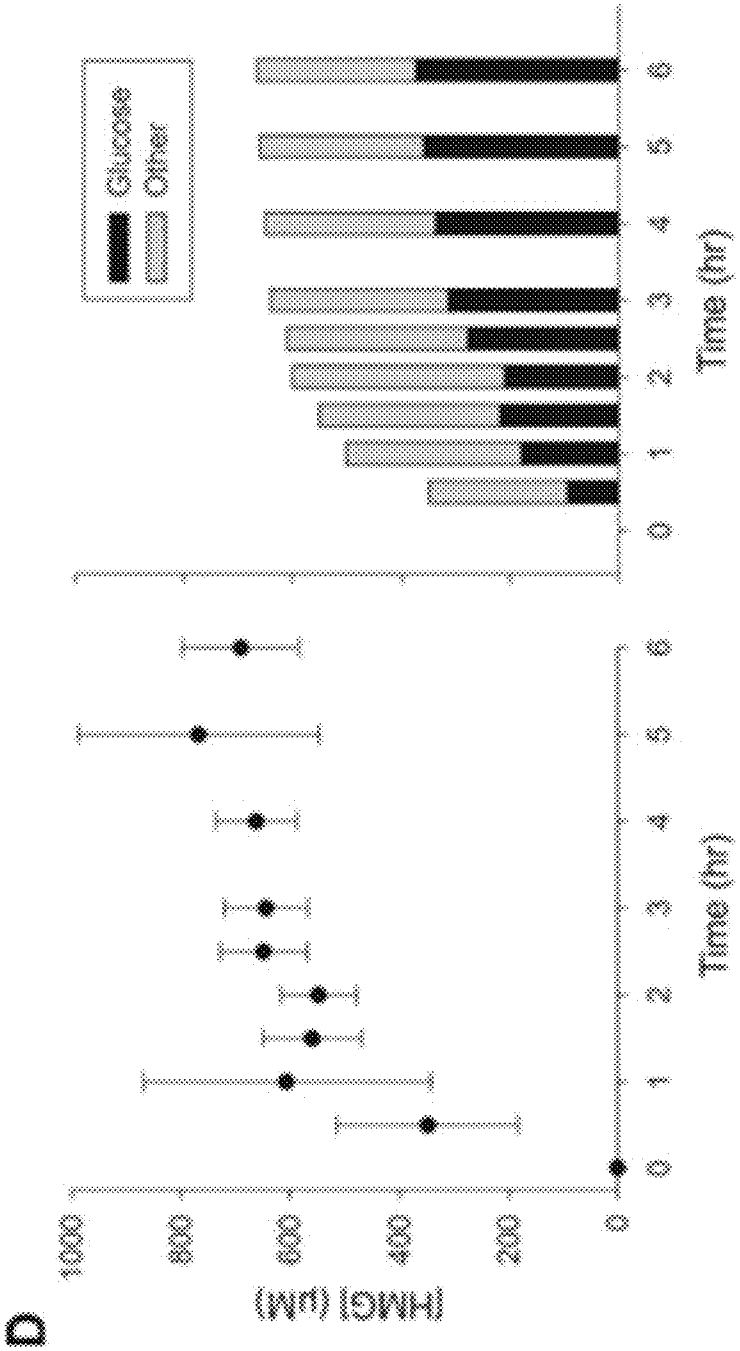
FIGURE 51, CON'T.

FIGURE 55, CON'T.
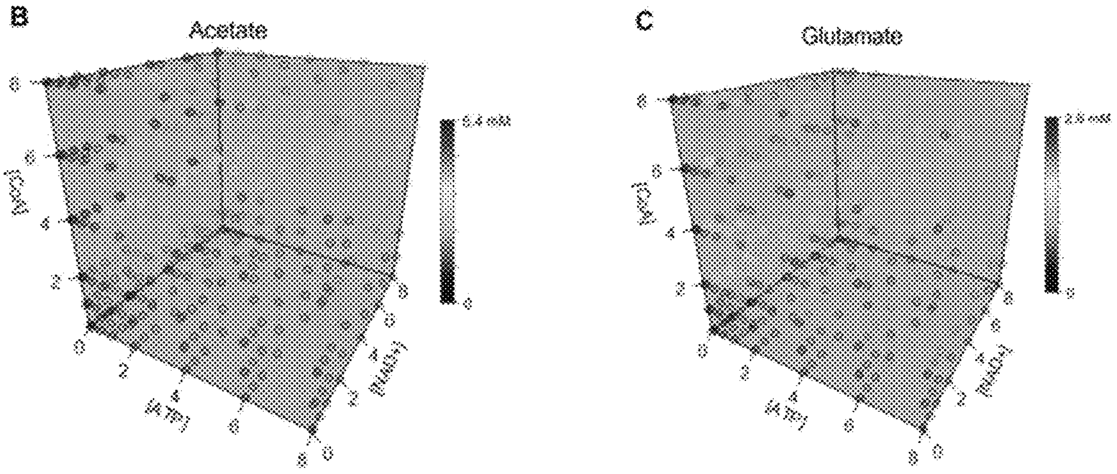

FIGURE 56, CON'T.
C
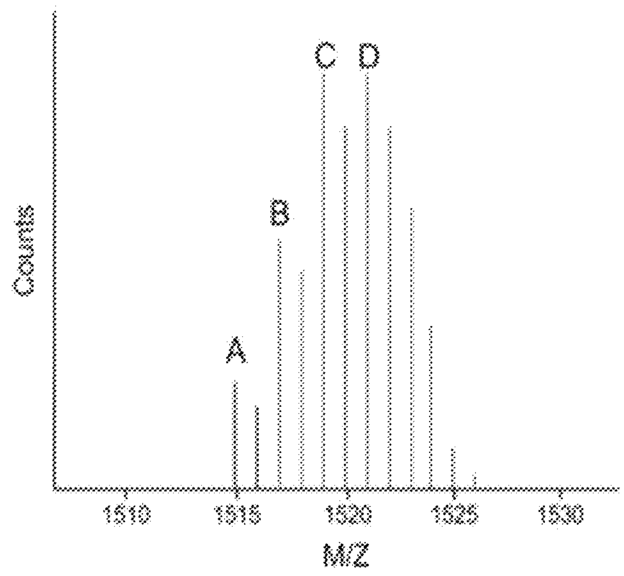
$AUP\ ^{13}C_0 = A$
$AUP\ ^{13}C_2 = B - (AUP\ ^{13}C_0)(0.503)$
$AUP\ ^{13}C_4 = C - (AUP\ ^{13}C_2)(0.503) - (AUP\ ^{13}C_0)(0.101)$
$AUP\ ^{13}C_6 = D - (AUP\ ^{13}C_4)(0.503) - (AUP\ ^{13}C_2)(0.101) - (AUP\ ^{13}C_0)(0.02)$
$$f^{C13} = \frac{AUP\ ^{13}C_6 + \frac{2}{3}(AUP\ ^{13}C_4) + \frac{1}{3}(AUP\ ^{13}C_2)}{AUP\ ^{13}C_0 + AUP\ ^{13}C_2 + AUP\ ^{13}C_4 + AUP\ ^{13}C_6}$$
$$f^{C12} = \frac{AUP\ ^{13}C_0 + \frac{2}{3}(AUP\ ^{13}C_2) + \frac{1}{3}(AUP\ ^{13}C_4)}{AUP\ ^{13}C_0 + AUP\ ^{13}C_2 + AUP\ ^{13}C_4 + AUP\ ^{13}C_6}$$

FIGURE 59, CON'T.
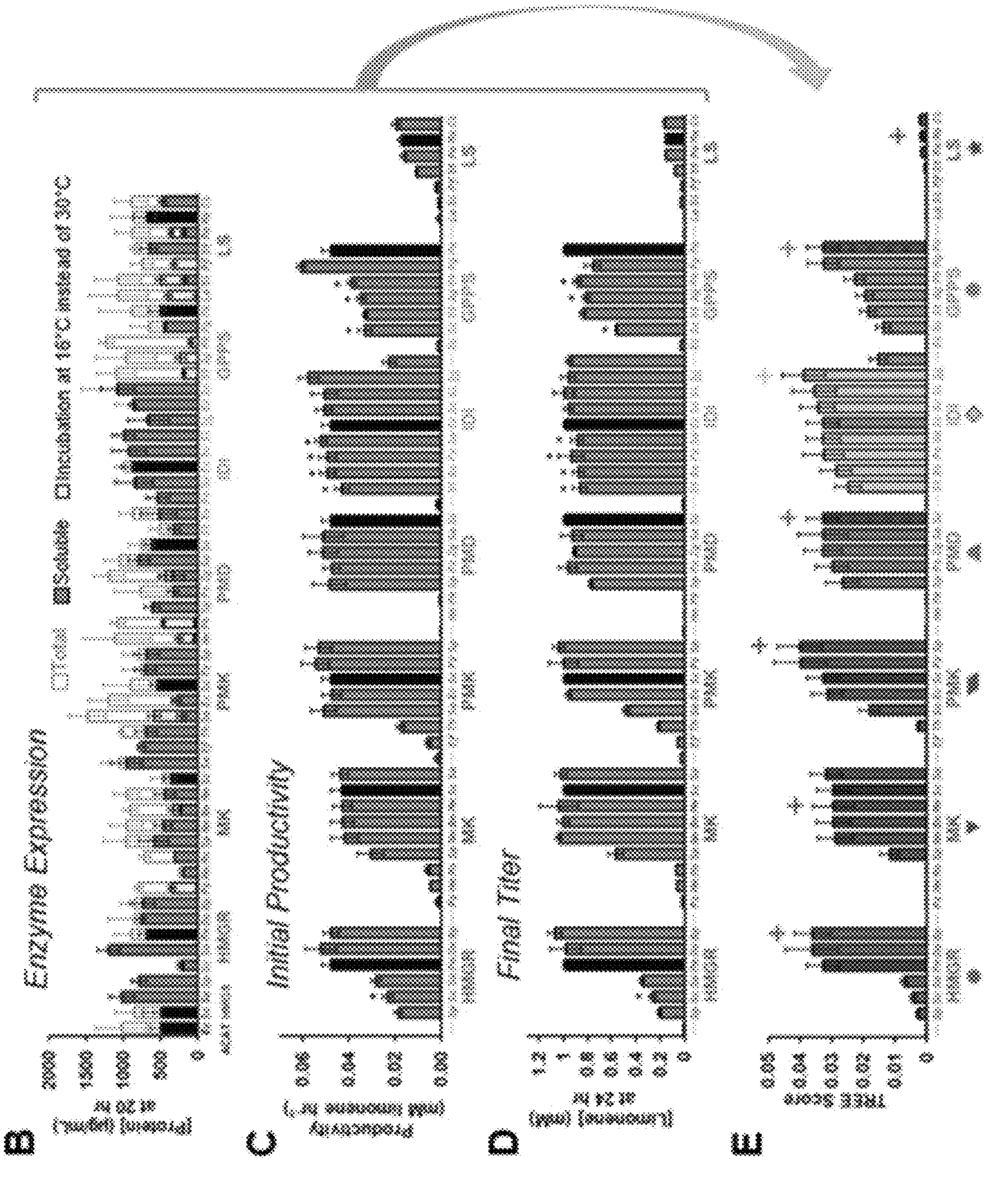

FIGURE 63

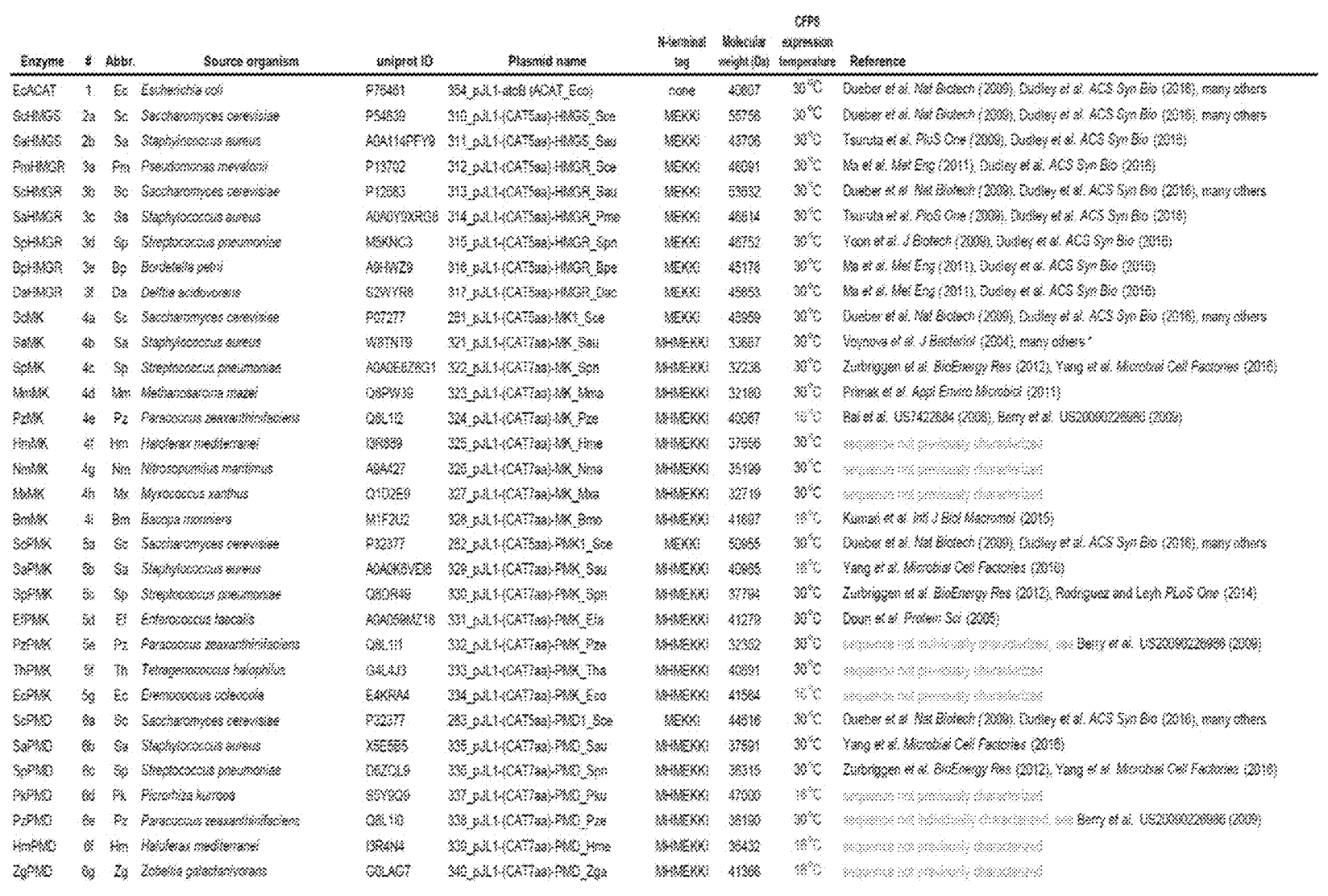

| Enzyme | # | Abbr. | Source organism | uniprot ID | Plasmid name | N-terminal tag | Molecular weight (Da) | CFPS expression temperature | Reference |
|---|---|---|---|---|---|---|---|---|---|
| EcACAT | 1 | Ec | *Escherichia coli* | P76461 | 354_pJL1-atoB (ACAT_Eco) | none | 40807 | 30 °C | Dueber *et al. Nat Biotech* (2009), Dudley *et al. ACS Syn Bio* (2016), many others |
| ScHMGS | 2a | Sc | *Saccharomyces cerevisiae* | P54839 | 310_pJL1-(CAT5aa)-HMGS_Sce | MEKKI | 55756 | 30 °C | Dueber *et al. Nat Biotech* (2009), Dudley *et al. ACS Syn Bio* (2016), many others |
| SaHMGS | 2b | Sa | *Staphylococcus aureus* | A0A114PFY9 | 311_pJL1-(CAT5aa)-HMGS_Sau | MEKKI | 43706 | 30 °C | Tsuruta *et al. PloS One* (2009), Dudley *et al. ACS Syn Bio* (2016) |
| PmHMGR | 3a | Pm | *Pseudomonas mevalonii* | P13702 | 312_pJL1-(CAT5aa)-HMGR_Sce | MEKKI | 46091 | 30 °C | Ma *et al. Met Eng* (2011), Dudley *et al. ACS Syn Bio* (2016) |
| ScHMGR | 3b | Sc | *Saccharomyces cerevisiae* | P12683 | 313_pJL1-(CAT5aa)-HMGR_Sau | MEKKI | 53632 | 30 °C | Dueber *et al. Nat Biotech* (2009), Dudley *et al. ACS Syn Bio* (2016), many others |
| SaHMGR | 3c | Sa | *Staphylococcus aureus* | A0A0Y9XRG8 | 314_pJL1-(CAT5aa)-HMGR_Pme | MEKKI | 46814 | 30 °C | Tsuruta *et al. PloS One* (2009), Dudley *et al. ACS Syn Bio* (2016) |
| SpHMGR | 3d | Sp | *Streptococcus pneumoniae* | M5KNC3 | 315_pJL1-(CAT5aa)-HMGR_Spn | MEKKI | 46752 | 30 °C | Yoon *et al. J Biotech* (2009), Dudley *et al. ACS Syn Bio* (2016) |
| BpHMGR | 3e | Bp | *Bordetella petrii* | A9HWZ9 | 316_pJL1-(CAT5aa)-HMGR_Bpe | MEKKI | 45176 | 30 °C | Ma *et al. Met Eng* (2011), Dudley *et al. ACS Syn Bio* (2016) |
| DaHMGR | 3f | Da | *Delftia acidovorans* | S2WYR6 | 317_pJL1-(CAT5aa)-HMGR_Dac | MEKKI | 45853 | 30 °C | Ma *et al. Met Eng* (2011), Dudley *et al. ACS Syn Bio* (2016) |
| ScMK | 4a | Sc | *Saccharomyces cerevisiae* | P07277 | 281_pJL1-(CAT5aa)-MK1_Sce | MEKKI | 48959 | 30 °C | Dueber *et al. Nat Biotech* (2009), Dudley *et al. ACS Syn Bio* (2016), many others |
| SaMK | 4b | Sa | *Staphylococcus aureus* | W8TNT9 | 321_pJL1-(CAT7aa)-MK_Sau | MHMEKKI | 33687 | 30 °C | Voynova *et al. J Bacteriol* (2004), many others * |
| SpMK | 4c | Sp | *Streptococcus pneumoniae* | A0A0E8Z8G1 | 322_pJL1-(CAT7aa)-MK_Spn | MHMEKKI | 32238 | 30 °C | Zurbriggen *et al. BioEnergy Res* (2012), Yang *et al. Microbial Cell Factories* (2016) |
| MmMK | 4d | Mm | *Methanosarcina mazei* | Q8PW39 | 323_pJL1-(CAT7aa)-MK_Mma | MHMEKKI | 32180 | 30 °C | Primak *et al. Appl Enviro Microbiol* (2011) |
| PzMK | 4e | Pz | *Paracoccus zeaxanthinifaciens* | Q8L112 | 324_pJL1-(CAT7aa)-MK_Pze | MHMEKKI | 40067 | 18 °C | Bai *et al.* US7422884 (2008), Berry *et al.* US20090226986 (2009) |
| HmMK | 4f | Hm | *Haloferax mediterranei* | I3R889 | 325_pJL1-(CAT7aa)-MK_Hme | MHMEKKI | 37656 | 30 °C | sequence not previously characterized |
| NmMK | 4g | Nm | *Nitrosopumilus maritimus* | A9A427 | 326_pJL1-(CAT7aa)-MK_Nma | MHMEKKI | 35129 | 30 °C | sequence not previously characterized |
| MxMK | 4h | Mx | *Myxococcus xanthus* | Q1D2E9 | 327_pJL1-(CAT7aa)-MK_Mxa | MHMEKKI | 32719 | 30 °C | sequence not previously characterized |
| BmMK | 4i | Bm | *Bacopa monniera* | M1F2U2 | 328_pJL1-(CAT7aa)-MK_Bmo | MHMEKKI | 41687 | 18 °C | Kumari *et al. Intl J Biol Macromol* (2015) |
| ScPMK | 5a | Sc | *Saccharomyces cerevisiae* | P32377 | 282_pJL1-(CAT5aa)-PMK1_Sce | MEKKI | 50655 | 30 °C | Dueber *et al. Nat Biotech* (2009), Dudley *et al. ACS Syn Bio* (2016), many others |
| SaPMK | 5b | Sa | *Staphylococcus aureus* | A0A0K8VEI8 | 329_pJL1-(CAT7aa)-PMK_Sau | MHMEKKI | 40865 | 18 °C | Yang *et al. Microbial Cell Factories* (2016) |
| SpPMK | 5c | Sp | *Streptococcus pneumoniae* | Q8DR49 | 330_pJL1-(CAT7aa)-PMK_Spn | MHMEKKI | 37794 | 30 °C | Zurbriggen *et al. BioEnergy Res* (2012), Rodriguez and Leyh *PLoS One* (2014) |
| EfPMK | 5d | Ef | *Enterococcus faecalis* | A0A069MZ18 | 331_pJL1-(CAT7aa)-PMK_Efa | MHMEKKI | 41279 | 30 °C | Doun *et al. Protein Sci* (2005) |
| PzPMK | 5e | Pz | *Paracoccus zeaxanthinifaciens* | Q8L111 | 332_pJL1-(CAT7aa)-PMK_Pze | MHMEKKI | 32392 | 30 °C | sequence not individually characterized, see Berry *et al.* US20090226986 (2009) |
| ThPMK | 5f | Th | *Tetragenococcus halophilus* | G4L4J3 | 333_pJL1-(CAT7aa)-PMK_Tha | MHMEKKI | 40891 | 30 °C | sequence not previously characterized |
| EcPMK | 5g | Ec | *Eremococcus coleocola* | E4KRA4 | 334_pJL1-(CAT7aa)-PMK_Eco | MHMEKKI | 41584 | 18 °C | sequence not previously characterized |
| ScPMD | 6a | Sc | *Saccharomyces cerevisiae* | P32377 | 283_pJL1-(CAT5aa)-PMD1_Sce | MEKKI | 44616 | 30 °C | Dueber *et al. Nat Biotech* (2009), Dudley *et al. ACS Syn Bio* (2016), many others |
| SaPMD | 6b | Sa | *Staphylococcus aureus* | X5E6B5 | 335_pJL1-(CAT7aa)-PMD_Sau | MHMEKKI | 37591 | 30 °C | Yang *et al. Microbial Cell Factories* (2016) |
| SpPMD | 6c | Sp | *Streptococcus pneumoniae* | D6ZQL9 | 336_pJL1-(CAT7aa)-PMD_Spn | MHMEKKI | 36316 | 30 °C | Zurbriggen *et al. BioEnergy Res* (2012), Yang *et al. Microbial Cell Factories* (2016) |
| PkPMD | 6d | Pk | *Picrorhiza kurrooa* | S5Y9Q9 | 337_pJL1-(CAT7aa)-PMD_Pku | MHMEKKI | 47030 | 18 °C | sequence not previously characterized |
| PzPMD | 6e | Pz | *Paracoccus zeaxanthinifaciens* | Q8L110 | 338_pJL1-(CAT7aa)-PMD_Pze | MHMEKKI | 36190 | 30 °C | sequence not individually characterized, see Berry *et al.* US20090226986 (2009) |
| HmPMD | 6f | Hm | *Haloferax mediterranei* | I3R4N4 | 339_pJL1-(CAT7aa)-PMD_Hme | MHMEKKI | 36432 | 18 °C | sequence not previously characterized |
| ZgPMD | 6g | Zg | *Zobellia galactanivorans* | G0LAG7 | 340_pJL1-(CAT7aa)-PMD_Zga | MHMEKKI | 41366 | 18 °C | sequence not previously characterized |

FIGURE 63, CON'T.

| Enzyme | # | Abbr. | Source organism | uniprot ID | Plasmid name | N-terminal tag | Molecular weight (Da) | CFPS expression temperature | Reference |
|---|---|---|---|---|---|---|---|---|---|
| EcIDI | 7a | Ec | *Escherichia coli* (Type I) | Q46822 | 284_pJL1-(CAT5aa)-IDI_Eco | MEKKI | 21506 | 30°C | Dueber et al. *Nat Biotech* (2009), Dudley et al. *ACS Syn Bio* (2016), many others |
| BsIDI | 7b | Bs | *Bacillus subtilis* (Type II) | P50740 | 285_pJL1-(CAT5aa)-IDI_Bsu | MEKKI | 37720 | 30°C | Wang et al. *Process Biochem* (2015) |
| SceIDI | 7c | Sc | *Saccharomyces cerevisiae* (Type I) | P15496 | 341_pJL1-(CAT7aa)-IDI_Sce | MHMEKKI | 34119 | 30°C | Anderson et al. *J Biol Chem* (1989) |
| SlIDI | 7d | Sl | *Solanum lycopersicym* (tomato) (Type I) | A8LRT7 | 342_pJL1-(CAT7aa)-IDI_Sly | MHMEKKI | 27954 | 30°C | Berthelot et al. *Biochimie* (2016) |
| StIDI | 7e | St | *Streptomyces sp strain CL190* (Type II) | Q9KWG2 | 343_pJL1-(CAT7aa)-IDI_Str | MHMEKKI | 39610 | 30°C | Kaneda et al. *Proceedings of the National Academy of Sciences* (2001) |
| PzIDI | 7f | Pz | *Paracoccus zeaxanthinifaciens* (Type II) | Q8L1I4 | 344_pJL1-(CAT7aa)-IDI_Pze | MHMEKKI | 38072 | 30°C | sequence not individually characterized, see Berry et al. US20080226606 (2008) |
| SaIDI | 7g | Sa | *Staphylococcus aureus* (Type II) | P58052 | 345_pJL1-(CAT7aa)-IDI_Sau | MHMEKKI | 39586 | 30°C | Kao et al. *Organic Letters* (2005) |
| SclIDI | 7h | Sc | *Streptomyces clavuligerus* (Type I) | E2PYC0 | 346_pJL1-(CAT7aa)-IDI_Scl | MHMEKKI | 23009 | 30°C | sequence not previously characterized |
| PaGPPS | 8a | Pa | *Picea abies* (Norway spruce) | B1A0K0 | 286_pJL1-(CAT5aa)-GPPS_Agr_F3F | MEKKI | 33025 | 30°C | Schmidt and Gershenzon *Phytochem* (2008), Sarria et al. *ACS Syn Bio* (2014) |
| AgGPPS | 8b | Ag | *Abies grandis* (grand fir) | Q8LKJ2 | 287_pJL1-(CAT5aa)-GPPS2_Pab | MEKKI | 32919 | 16°C | Sarria et al. *ACS Syn Bio* (2014) and many others** |
| StGPPS | 8c | St | *Streptomyces sp. strain KO-3988* | Q2L6D1 | 288_pJL1-(CAT5aa)-GPPS_Str | MEKKI | 28580 | 16°C | Willrodt et al. *Biotech J* (2014) |
| PgGPPS | 8d | Pg | *Picea glauca* (white spruce) | V9Y208 | 347_pJL1-(CAT7aa)-GPPS_Pgl | MHMEKKI | 33002 | 30°C | sequence not previously characterized |
| PkGPPS | 8e | Pk | *Picrorhiza kurrooa* | Q5G1J1 | 348_pJL1-(CAT7aa)-GPPS_Pku | MHMEKKI | 41180 | 16°C | Singh et al. *Gene* (2013) |
| Sc*GPPS | 8f | Sc* | *Saccharomyces cerevisiae* (K197E) | P08524 | 349_pJL1-(CAT7aa)-GPPS*_Sce | MHMEKKI | 41252 | 30°C | Fischer et al. *Biotech Bioeng* (2011) |
| EcFPPS | 8g | Ec | *Escherichia coli* | P22939 | 318_pJL1-(CAT5aa)-ispA_Ec | MEKKI | 32659 | 30°C | Dudley et al. *Syn Bio* (2019) |
| MsLS | 9a | Ms | *Mentha spicata* (spearmint) | Q40322 | 246_pJL1-(CAT5aa)-LS_Msp | MEKKI | 64317 | 30°C | Dudley et al. *Syn Bio* (2019) and many others*** |
| ClLS | 9b | Cl | *Citrus limon* (lemon) | Q8L5K3 | 247_pJL1-(CAT5aa)-LS_Cli | MEKKI | 65350 | 30°C | Lücker et al. *Eur J Biochem* (2002), Jongedijk et al. *Yeast* (2015) |
| PfLS | 9c | Pf | *Perilla frutescens* (wild sesame) | Q9AXM7 | 248_pJL1-(CAT5aa)-LS_Pfr | MEKKI | 64449 | 16°C | Yuba et al. *Arch Biochem Biophys* (1996), Jongedijk et al. *Yeast* (2015) |
| StLS | 9d | St | *Schizonepeta tenuifolia* (Jap. catnip) | Q9FUW5 | 350_pJL1-(CAT7aa)-LS_Ste | MHMEKKI | 65095 | 30°C | Kiyota et al. *J Biotechnol* (2014) |
| LaLS | 9e | La | *Lavandula angustifolia* (lavender) | Q2XSC5 | 351_pJL1-(CAT7aa)-LS_Lan | MHMEKKI | 64819 | 16°C | Landmann et al. *Arch Biochem Biophys* (2007) |
| SlLS | 9f | Sl | *Solanum lycopersicum* (tomato) | G1JUH1 | 352_pJL1-(CAT7aa)-LS_Sly | MHMEKKI | 65586 | 16°C | Falara et al. *Plant Physiol* (2011) |
| PaLS | 9g | Pa | *Picea abies* (Norway spruce) | Q675L1 | 353_pJL1-(CAT7aa)-LS-Pab | MHMEKKI | 66801 | 16°C | sequence not previously characterized |
| AgBS | | Ag | *Abies grandis* (grand fir) | O81086 | 320_pJL1-(CAT5aa)-BS_Agr | MEKKI | 94038 | 16°C | Peralta-Yahya et al. *Nat Comm* (2011) |
| AgPS | | Ag | *Abies grandis* (grand fir) | O24475 | 249_11a_pJL1_CATribs(5aa)_PS_Agr | MEKKI | 68104 | 30°C | Sarria et al. *ACS Syn Bio* (2014) |
| PaPS | | Pa | *Picea abies* (Norway spruce) | Q675L3 | 250_11b_pJL1_CATribs(5aa)_PS_Pab | MEKKI | 65454 | 30°C | Sarria et al. *ACS Syn Bio* (2014) |

FIGURE 64

| Protein enriched in the lysate | Band % | overexpressed protein molecular weight (Da) | Amount of crude lysate typically loaded into cell-free reaction (mg/mL total protein) | µM overexpressed protein in cell-free reaction * | Reference for original SDS-PAGE gel | |
|---|---|---|---|---|---|---|
| ACAT_Eco (i.e. EcACAT) | 14.2% | 40607 | 1.33 | 4.6 | Dudley *et al. ACS Syn Bio* (2016) Fig. S | Lane 2 |
| HMGS_Sce (i.e. ScHMGS) | 22.9% | 55756 | 1.33 | 5.5 | Dudley *et al. ACS Syn Bio* (2016) Fig. S | Lane 3 |
| HMGS_Sau (i.e. SaHMGS) | 12.6% | 43706 | 1.33 | 3.8 | Dudley *et al. ACS Syn Bio* (2016) Fig. S | Lane 5 |
| HMGR_Pme (i.e. PmHMGR) | 15.4% | 46091 | 1.33 | 4.5 | Dudley *et al. ACS Syn Bio* (2016) Fig. S | Lane 8 |
| ACAT_Eco (i.e. EcACAT) | 8.1% | 40607 | 4 | 8.0 | Dudley *et al. Syn Bio* (2019) Fig. S4 | Lane 3 |
| HMGS_Sce (i.e. ScHMGS) | 8.4% | 55756 | 4 | 6.0 | Dudley *et al. Syn Bio* (2019) Fig. S4 | Lane 3 |
| HMGR_Pme (i.e. PmHMGR) | 6.8% | 46091 | 4 | 5.9 | Dudley *et al. Syn Bio* (2019) Fig. S4 | Lane 3 |
| MK_Sce (i.e. ScMK) | 10.1% | 48959 | 1 | 2.1 | Dudley *et al. Syn Bio* (2019) Fig. S4 | Lane 4 |
| PMK_Sce (i.e. ScPMK) | 16.1% | 50955 | 1 | 3.2 | Dudley *et al. Syn Bio* (2019) Fig. S4 | Lane 5 |
| PMD_Sce (i.e. ScPMK) | 3.7% | 44616 | 1 | 0.8 | Dudley *et al. Syn Bio* (2019) Fig. S4 | Lane 6 |
| IDI_Eco (i.e. EcIDI) | 18.2% | 21008 | 1 | 8.7 | Dudley *et al. Syn Bio* (2019) Fig. S4 | Lane 7 |
| LS_Msp (i.e. MsLS) | 16.3% | 64317 | 1 | 2.5 | Dudley *et al. Syn Bio* (2019) Fig. S4 | Lane 9 |
| LS_Msp (i.e. MsLS) | 16.3% | 64317 | 1.33 | 3.4 | Dudley *et al. Syn Bio* (2019) Fig. S4 | Lane 9 |

** = % overexpressed band of total protein * crude lysate loaded / overexpressed protein molecular weight*

FIGURE 65

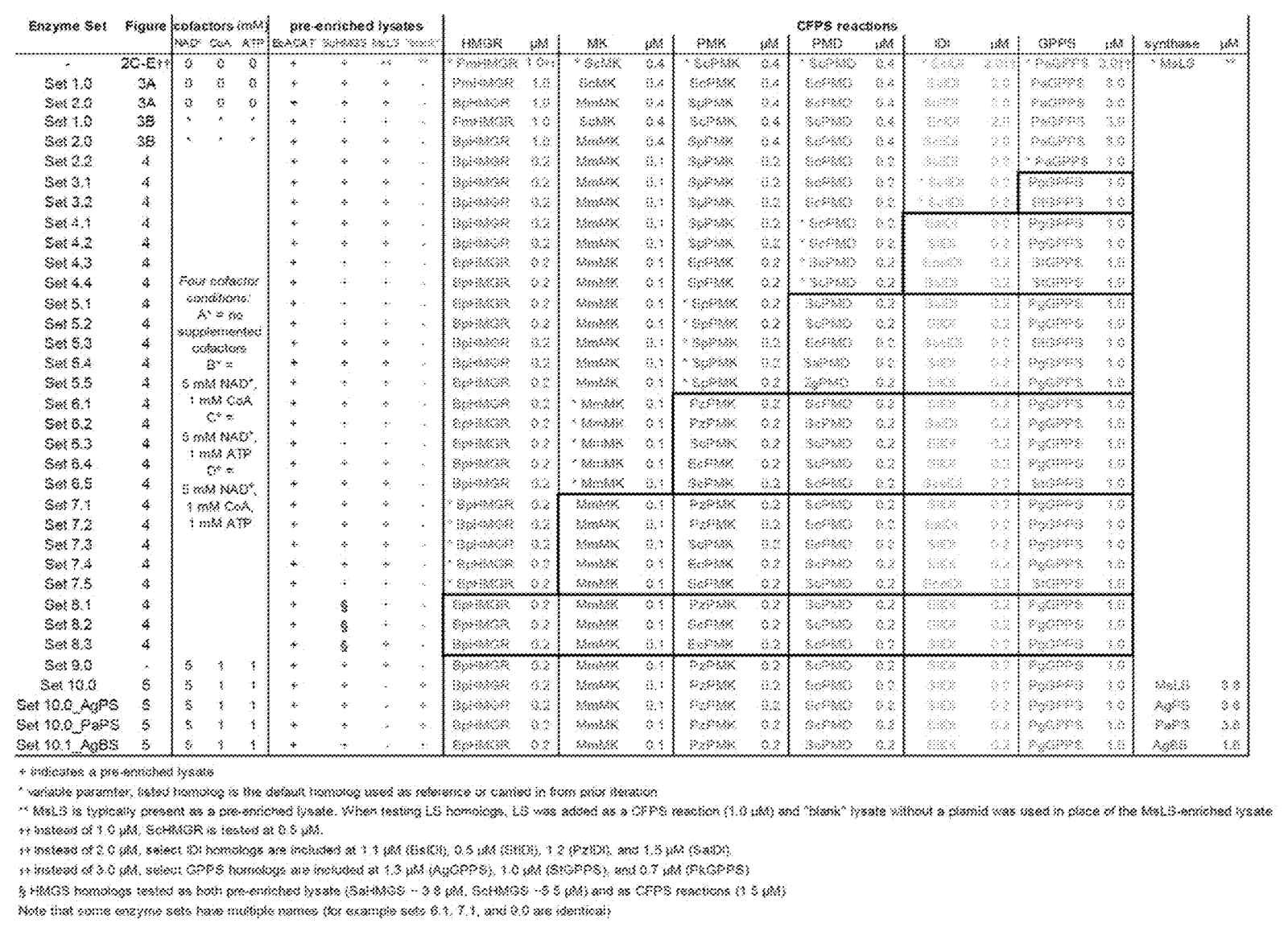

| Enzyme Set | Figure | cofactors (mM) NAD+ | CoA | ATP | pre-enriched lysates EcACAT | SaHMGS | MsLS | "blank" | CFPS reactions HMGR | µM | MK | µM | PMK | µM | PMD | µM | IDI | µM | GPPS | µM | synthase | µM |
|---|---|---|---|---|---|---|---|---|---|---|---|---|---|---|---|---|---|---|---|---|---|---|
| - | 2C-E†† | 0 | 0 | 0 | + | + | ** | ** | * PmHMGR | 1.0++ | * ScMK | 0.4 | * ScPMK | 0.4 | * ScPMD | 0.4 | * [illegible] | 2.0++ | * PaGPPS | 3.0++ | * MsLS | ** |
| Set 1.0 | 3A | 0 | 0 | 0 | + | + | + | - | PmHMGR | 1.0 | ScMK | 0.4 | ScPMK | 0.4 | ScPMD | 0.4 | [illegible] | 2.0 | PaGPPS | 3.0 | | |
| Set 2.0 | 3A | 0 | 0 | 0 | + | + | + | - | BpHMGR | 1.0 | MmMK | 0.4 | SpPMK | 0.4 | ScPMD | 0.4 | [illegible] | 2.0 | PaGPPS | 3.0 | | |
| Set 1.0 | 3B | * | * | * | + | + | + | - | PmHMGR | 1.0 | ScMK | 0.4 | ScPMK | 0.4 | ScPMD | 0.4 | [illegible] | 2.0 | PaGPPS | 3.0 | | |
| Set 2.0 | 3B | * | * | * | + | + | + | - | BpHMGR | 1.0 | MmMK | 0.4 | SpPMK | 0.4 | ScPMD | 0.4 | [illegible] | 2.0 | PaGPPS | 3.0 | | |
| Set 2.2 | 4 | | | | + | + | + | - | BpHMGR | 0.2 | MmMK | 0.1 | SpPMK | 0.2 | ScPMD | 0.2 | [illegible] | [illegible] | * AgGPPS | 1.0 | | |
| Set 3.1 | 4 | | | | + | + | + | - | BpHMGR | 0.2 | MmMK | 0.1 | SpPMK | 0.2 | ScPMD | 0.2 | * [illegible] | [illegible] | PgGPPS | 1.0 | | |
| Set 3.2 | 4 | | | | + | + | + | - | BpHMGR | 0.2 | MmMK | 0.1 | SpPMK | 0.2 | ScPMD | 0.2 | * [illegible] | [illegible] | StGPPS | 1.0 | | |
| Set 4.1 | 4 | | | | + | + | + | - | BpHMGR | 0.2 | MmMK | 0.1 | SpPMK | 0.2 | * ScPMD | 0.2 | [illegible] | [illegible] | PgGPPS | 1.0 | | |
| Set 4.2 | 4 | | | | + | + | + | - | BpHMGR | 0.2 | MmMK | 0.1 | SpPMK | 0.2 | * ScPMD | 0.2 | [illegible] | [illegible] | PgGPPS | 1.0 | | |
| Set 4.3 | 4 | | | | + | + | + | - | BpHMGR | 0.2 | MmMK | 0.1 | SpPMK | 0.2 | * BsPMD | 0.2 | [illegible] | [illegible] | StGPPS | 1.0 | | |
| Set 4.4 | 4 | *Four cofactor conditions:* A* = no supplemented cofactors B* = 5 mM NAD+, 1 mM CoA C* = 5 mM NAD+, 1 mM ATP D* = 5 mM NAD+, 1 mM CoA, 1 mM ATP | | | + | + | + | - | BpHMGR | 0.2 | MmMK | 0.1 | SpPMK | 0.2 | * ScPMD | 0.2 | [illegible] | [illegible] | StGPPS | 1.0 | | |
| Set 5.1 | 4 | | | | + | + | + | - | BpHMGR | 0.2 | MmMK | 0.1 | * SpPMK | 0.2 | ScPMD | 0.2 | [illegible] | [illegible] | PgGPPS | 1.0 | | |
| Set 5.2 | 4 | | | | + | + | + | - | BpHMGR | 0.2 | MmMK | 0.1 | * SpPMK | 0.2 | ScPMD | 0.2 | [illegible] | [illegible] | PgGPPS | 1.0 | | |
| Set 5.3 | 4 | | | | + | + | + | - | BpHMGR | 0.2 | MmMK | 0.1 | * SpPMK | 0.2 | ScPMD | 0.2 | [illegible] | [illegible] | StGPPS | 1.0 | | |
| Set 5.4 | 4 | | | | + | + | + | - | BpHMGR | 0.2 | MmMK | 0.1 | * SpPMK | 0.2 | SaPMD | 0.2 | [illegible] | [illegible] | PgGPPS | 1.0 | | |
| Set 5.5 | 4 | | | | + | + | + | - | BpHMGR | 0.2 | MmMK | 0.1 | * SpPMK | 0.2 | SgPMD | 0.2 | [illegible] | [illegible] | PgGPPS | 1.0 | | |
| Set 6.1 | 4 | | | | + | + | + | - | BpHMGR | 0.2 | * MmMK | 0.1 | PzPMK | 0.2 | ScPMD | 0.2 | [illegible] | [illegible] | PgGPPS | 1.0 | | |
| Set 6.2 | 4 | | | | + | + | + | - | BpHMGR | 0.2 | * MmMK | 0.1 | PzPMK | 0.2 | ScPMD | 0.2 | [illegible] | [illegible] | PgGPPS | 1.0 | | |
| Set 6.3 | 4 | | | | + | + | + | - | BpHMGR | 0.2 | * MmMK | 0.1 | ScPMK | 0.2 | ScPMD | 0.2 | [illegible] | [illegible] | PgGPPS | 1.0 | | |
| Set 6.4 | 4 | | | | + | + | + | - | BpHMGR | 0.2 | * MmMK | 0.1 | EcPMK | 0.2 | ScPMD | 0.2 | [illegible] | [illegible] | PgGPPS | 1.0 | | |
| Set 6.5 | 4 | | | | + | + | + | - | BpHMGR | 0.2 | * MmMK | 0.1 | SaPMK | 0.2 | ScPMD | 0.2 | [illegible] | [illegible] | StGPPS | 1.0 | | |
| Set 7.1 | 4 | | | | + | + | + | - | * BpHMGR | 0.2 | MmMK | 0.1 | PzPMK | 0.2 | ScPMD | 0.2 | [illegible] | [illegible] | PgGPPS | 1.0 | | |
| Set 7.2 | 4 | | | | + | + | + | - | * BpHMGR | 0.2 | MmMK | 0.1 | PzPMK | 0.2 | ScPMD | 0.2 | [illegible] | [illegible] | PgGPPS | 1.0 | | |
| Set 7.3 | 4 | | | | + | + | + | - | * BpHMGR | 0.2 | MmMK | 0.1 | ScPMK | 0.2 | ScPMD | 0.2 | [illegible] | [illegible] | PgGPPS | 1.0 | | |
| Set 7.4 | 4 | | | | + | + | + | - | * BpHMGR | 0.2 | MmMK | 0.1 | EcPMK | 0.2 | ScPMD | 0.2 | [illegible] | [illegible] | PgGPPS | 1.0 | | |
| Set 7.5 | 4 | | | | + | + | + | - | * BpHMGR | 0.2 | MmMK | 0.1 | SaPMK | 0.2 | ScPMD | 0.2 | [illegible] | [illegible] | StGPPS | 1.0 | | |
| Set 8.1 | 4 | | | | + | § | + | - | BpHMGR | 0.2 | MmMK | 0.1 | PzPMK | 0.2 | ScPMD | 0.2 | [illegible] | [illegible] | PgGPPS | 1.0 | | |
| Set 8.2 | 4 | | | | + | § | + | - | BpHMGR | 0.2 | MmMK | 0.1 | SaPMK | 0.2 | ScPMD | 0.2 | [illegible] | [illegible] | PgGPPS | 1.0 | | |
| Set 8.3 | 4 | | | | + | § | + | - | BpHMGR | 0.2 | MmMK | 0.1 | EcPMK | 0.2 | ScPMD | 0.2 | [illegible] | [illegible] | PgGPPS | 1.0 | | |
| Set 9.0 | - | 5 | 1 | 1 | + | + | + | - | BpHMGR | 0.2 | MmMK | 0.1 | PzPMK | 0.2 | ScPMD | 0.2 | [illegible] | [illegible] | PgGPPS | 1.0 | | |
| Set 10.0 | 5 | 5 | 1 | 1 | + | + | - | + | BpHMGR | 0.2 | MmMK | 0.1 | PzPMK | 0.2 | ScPMD | 0.2 | [illegible] | [illegible] | PgGPPS | 1.0 | MsLS | 3.8 |
| Set 10.0_AgPS | 5 | 5 | 1 | 1 | + | + | - | + | BpHMGR | 0.2 | MmMK | 0.1 | PzPMK | 0.2 | ScPMD | 0.2 | [illegible] | [illegible] | PgGPPS | 1.0 | AgPS | 3.8 |
| Set 10.0_PaPS | 5 | 5 | 1 | 1 | + | + | - | + | BpHMGR | 0.2 | MmMK | 0.1 | PzPMK | 0.2 | ScPMD | 0.2 | [illegible] | [illegible] | PgGPPS | 1.0 | PaPS | 3.8 |
| Set 10.1_AgBS | 5 | 5 | 1 | 1 | + | + | - | + | BpHMGR | 0.2 | MmMK | 0.1 | PzPMK | 0.2 | ScPMD | 0.2 | [illegible] | [illegible] | PgGPPS | 1.0 | AgBS | 1.8 |

+ indicates a pre-enriched lysate

* variable paramter, listed homolog is the default homolog used as reference or carried in from prior iteration

** MsLS is typically present as a pre-enriched lysate. When testing LS homologs, LS was added as a CFPS reaction (1.0 µM) and "blank" lysate without a plasmid was used in place of the MsLS-enriched lysate ++ instead of 1.0 µM, ScHMGR is tested at 0.5 µM.

++ instead of 2.0 µM, select IDI homologs are included at 1.1 µM (BsIDI), 0.5 µM (StIDI), 1.2 (PzIDI), and 1.5 µM (SaIDI).

++ instead of 3.0 µM, select GPPS homologs are included at 1.3 µM (AgGPPS), 1.0 µM (StGPPS), and 0.7 µM (PkGPPS)

§ HMGS homologs tested as both pre-enriched lysate (SaHMGS ~ 3.8 µM, ScHMGS ~5.5 µM) and as CFPS reactions (1.5 µM)

Note that some enzyme sets have multiple names (for example sets 6.1, 7.1, and 9.0 are identical)

FIGURE 66

| Monoterpenoid product | Host | Pathway | Synthase enzyme source organism | Maximum titer (mg/L) | Volumetric productivity (mg/L/day) | Reference |
|---|---|---|---|---|---|---|
| 3-Carene | *E. coli* | MEP/DXP | *Picea abies* | 0.003 | 0.01 | Reiling *et al. Biotechnol Bioeng* (2004) |
| Linalool | *S. cerevisiae* | MVA | *Lavandula angustifolia* | 0.1 | n/a | Amiri et al. *Biotechnol Letters* (2016) |
| α/β-Pinene | *C. glutamicum* | MEP/DXP | *Abies grandis* | 0.2 | 0.1 | Kang et al. *Biotechnol Letters* (2014) |
| Limonene | *Synechocystis* | MEP/DXP | *Schizonepeta tenuifolia* | 0.4 | 0.1 | Kiyota et al. *J Biotechnol* (2014) |
| Limonene | *E. coli* | MVA, glucose | *Mentha spicata* | 0.3 | 0.2 | Willrodt et al. *Biotechnol J* (2014) |
| Limonene | *S. cerevisiae* | MVA | *Citrus limon, Perilla frutescens* | 0.5 | 0.2 | Jongedijk et al. *Yeast* (2015) |
| Sabinene | *S. cerevisiae* | MVA | *Slavia pomifera* | 17.5 | n/a | Ignea et al. *ACS Syn Biol* (2014) |
| Limonene | *S. cerevisiae* | MVA | *Mentha spicata, Citrus limon* | 1.5 | 0.3 | Behrendorff et al. *Microb Cell Fact* (2011) |
| Limonene | *S. cerevisiae* | MVA | *Citrus limon* (H570Y) | 130 | 0.9 | Ignea et al. *Nat Comm* (2019) |
| Limonene | *Synechococcus* | MEP/DXP | *Mentha spicata* | 4.0 | 1.3 | Davies et al. *Front Bioeng Biotechnol* (2014) |
| Limonene | *E. coli* | MVA | *Mentha spicata* | 57.0 | 2.4 | Dunlop et al. *Mol Syst Biol* ( 2011) |
| Limonene | *E. coli* | MEP/DXP | *Mentha spicata* | 5.0 | 4.0 | Carter et al. *Phytochem* (2003) |
| α/β-Pinene | *E. coli* | MVA | *Abies grandis* | 32.4 | 10.8 | Sarria et al. *ACS Syn Bio* (2014) |
| Limonene | *E. coli* | MEP/DXP | *Mentha spicata* | 35.8 | 11.9 | Du et al. *Biores Bioproc* (2014) |
| Geraniol | *E. coli* | MVA | *Camptotheca acuminata* | 48 | - | Chen et al. *J Ind Microbiol Biotechnol* (2016) |
| Myrcene | *E. coli* | MVA | *Quercus ilex* | 58.2 | 19.4 | Kim et al. *J Agric Food Chem* (2015) |
| Cineole | *S. cerevisiae* | MVA | *Salvia fruticosa* | 1100 | 57.9 | Ignea et al. *Microb Cell Fact* (2011) |
| Limonene | *E. coli* | MVA | *Mentha spicata* | 230 † | 77 | Jervis et al. *ACS Syn Biol* (2019) |
| Sabinene | *E. coli* | MVA | *Slavia pomifera* | 82.2 | 82.2 | Zhang et al. *Microb Cell Fact* (2014) |
| Limonene | Cell-free* | MVA | *Mentha spicata* | 90.2 | 90.2 | Dudley et al. *Syn Bio* (2019) |
| Geraniol | *E. coli* | MVA | *Ocimum basilicum* | 183 | 91.3 | Zhou et al. *J Biotechnol* (2014) |
| Geraniol | *S. cerevisiae* | MVA | *Valeriana officinalis* | 293 | 97.7 | Zhao et al. *Appl Microbiol Biotechnol* (2016) |
| Limonene | *S. cerevisiae* | MVA | *Citrus limon* | 917 | 183 | Cheng et al. *ACS Syn Biol* (2019) |
| Limonene | *E. coli* | MVA | *Mentha spicata* | 604 | 202 | Alonso-Gutierrez et al. *Met Eng* (2015) |
| Limonene | *E. coli* | MVA | *Citrus limon* | 1290 | 369 | Wu et al. *J Agric Food Chem* (2019) |
| **Limonene** | **Cell-free**** | **MVA** | ***Mentha spicata*** | **610** | **610** | **This work** |
| Geraniol | *E. coli* | MVA | *Ocimum basilicum* | 2000 | 706 | Liu et al. *Biotechnol Biofuels* (2016) |
| Limonene | *E. coli* | MVA, glycerol | *Mentha spicata* | 1350 | 736 | Willrodt et al. *Biotech J* (2014) |
| Limonene | Cell-free*** | MVA | *Mentha spicata* | 12500 | 1786 | Korman et al. *Nat Comm* (2017) |

† 1150 mg/L organic phase * 20% overlay

* CFME approach using pre-enriched *E. coli* lysates

** CFPS-ME approaching combining pre-enriched *E. coli* lysates with CFPS-enriched lysates

*** purified enzymes

| Monoterpenoid product | Host | Pathway | Synthase enzyme source organism | Titer (μg/g fresh weight) | Reference |
|---|---|---|---|---|---|
| Linalool | *A. thaliana* | MVA + MEP/DXP | *Fragaria × ananassa* | 83 | Aharoni et al. *Plant Cell* (2003) |
| Geraniol | *N. benthamiana* | MVA + MEP/DXP | *Ocimum basilicum* | 110 | Fischer et al. *J Biotechnol* (2013) |
| Geraniol | *N. benthamiana* | MVA + MEP/DXP | *Valeriana officinalis* | 129 | Dong et al. *New Phytol* (2016) |

FIGURE 67

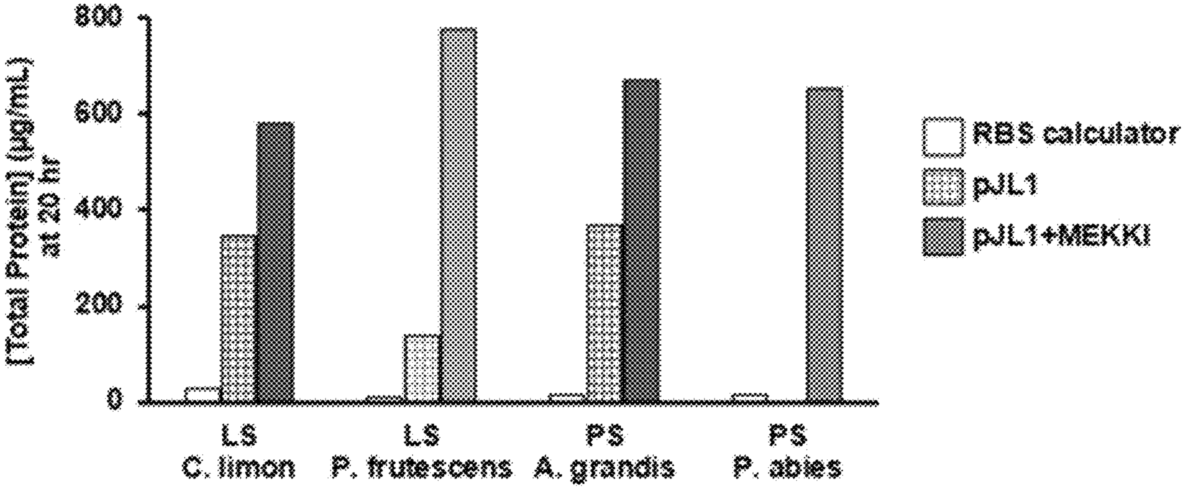

RBS Calculator: tctagaaatagatctNNNNNNNNNNNNNNNNNNNNNNNNNNNATGCGT(SEQ ID NO:5)
pJL1: tctagaaataattttGTTTAACTTTAAGAAGGAGATATACATATGCGT(SEQ ID NO:6)
pJL1-MEKKI: tctagaaataattttGTTTAACTTTAAGAAGGAGATATACATATGGAGAAAAAAATCNNNNNNN(SEQ ID NO:7)

NNNNNNNNNNNNNNNNNNNNNNNNNNN(SEQ ID NO:8) = ribosome binding site that was optimized using the Salis RBS Calculator v1.1
GAAGGAGATATACAT(SEQ ID NO:9) = ribosome binding site upstream of ATG in the pJL1 backbone
ATGGAGAAAAAAATC(SEQ ID NO:10) = nucleotide sequence encoding the first five amino acids of chloramphenicol acetyl transferase
ATGCGT (SEQ ID NO:11) = sample nucleotide sequence for gene of interest FIGURE 72,CON'T.
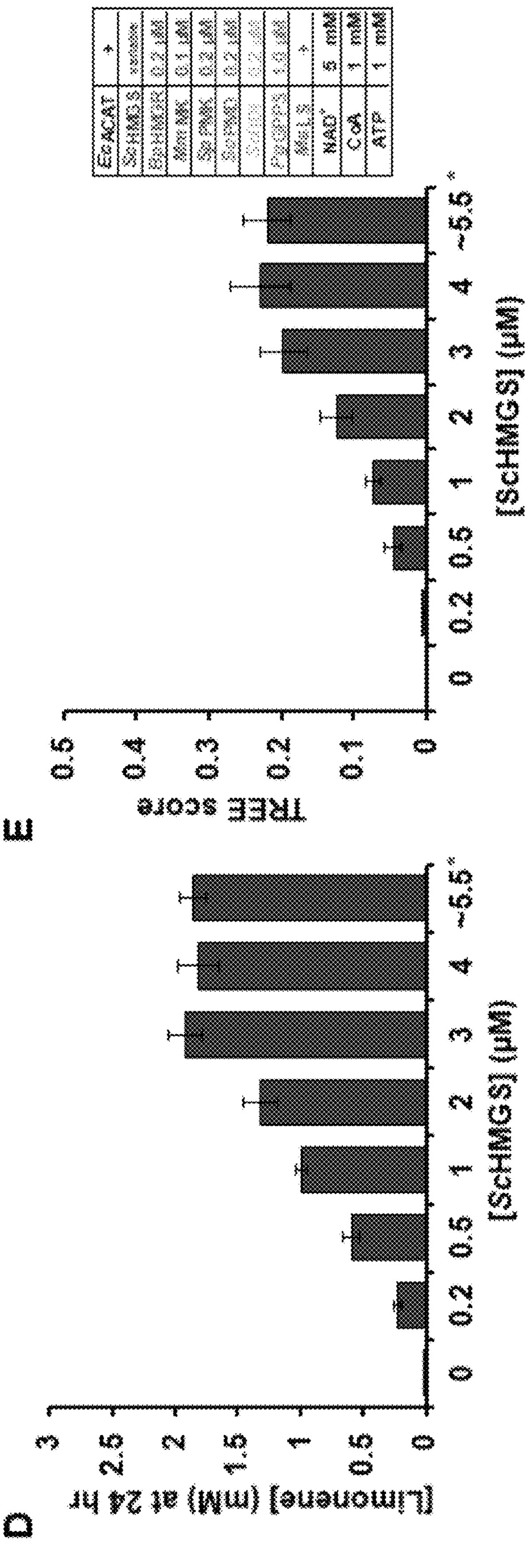

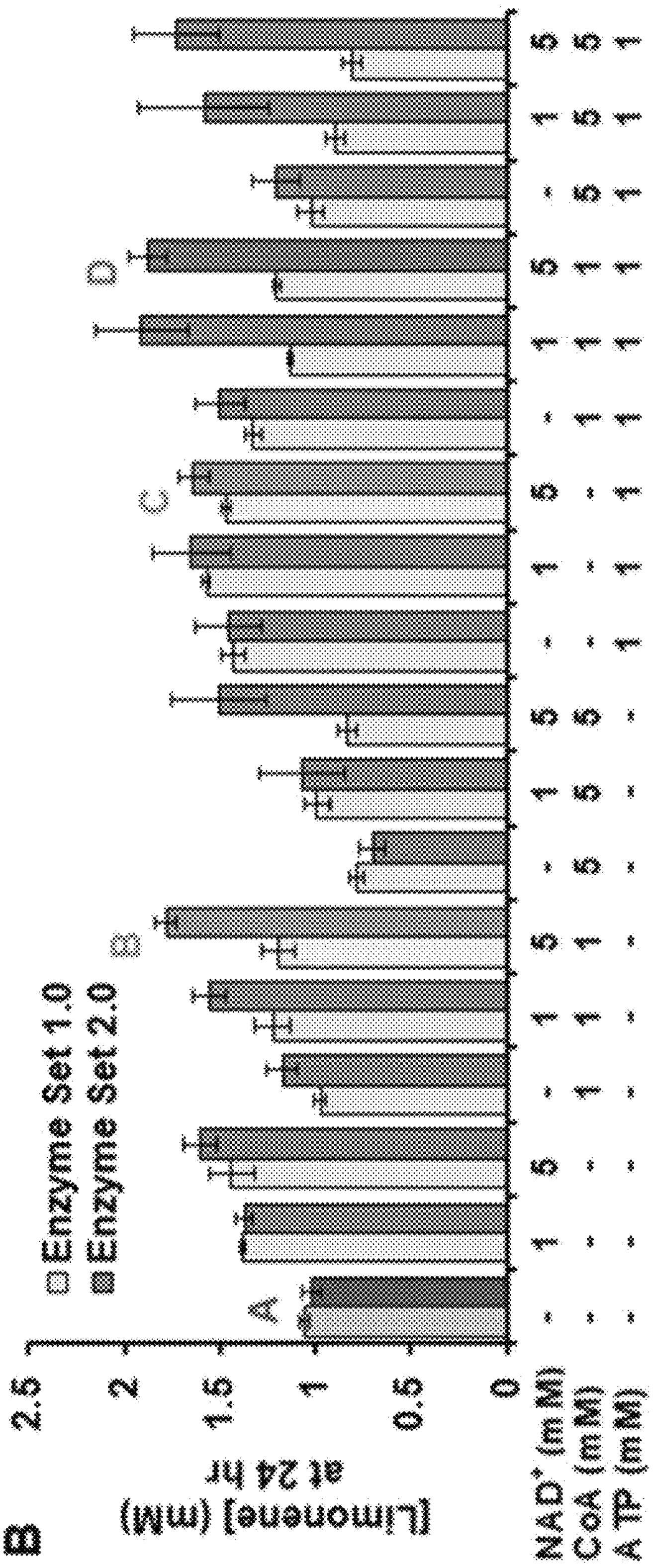
FIGURE 73, CON'T.

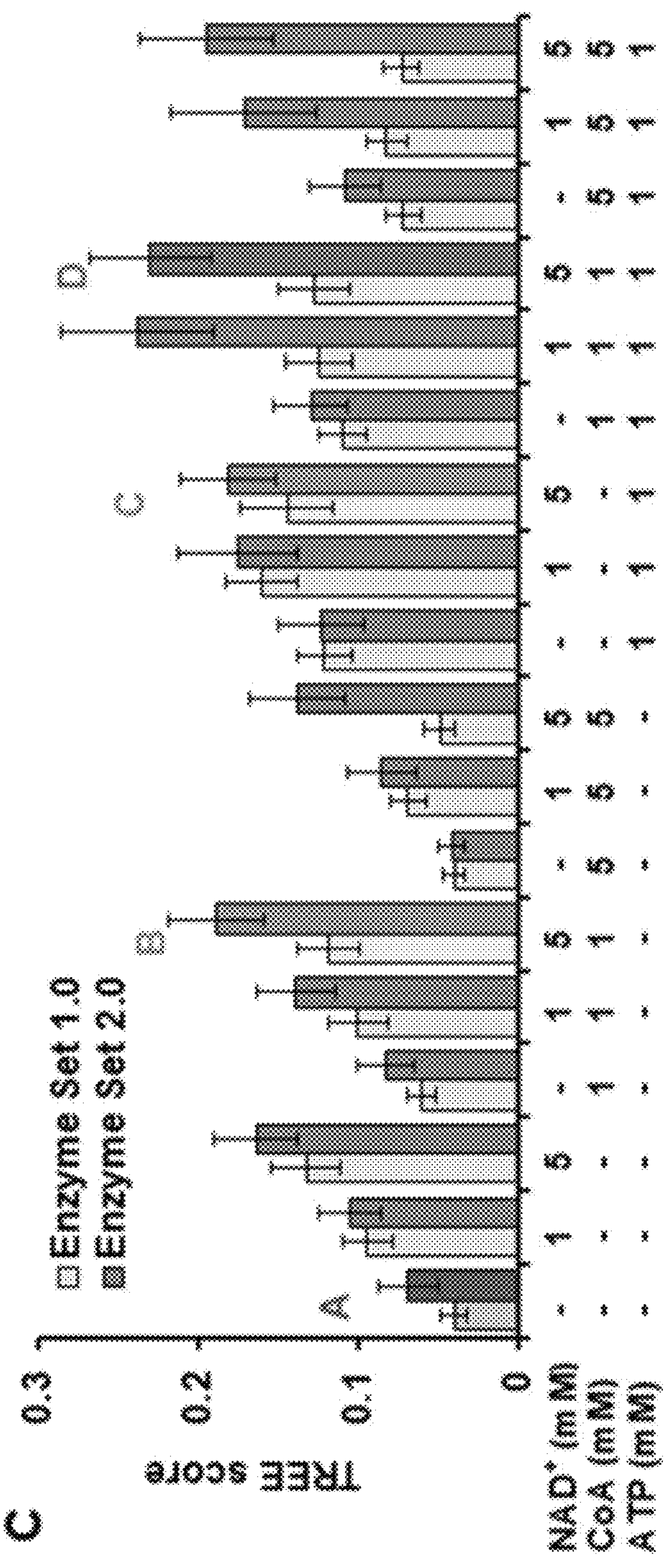
FIGURE 73, CON'T.

| | |
|---|---|
| *Ec*ACAT | + |
| ScHMGS | + |
| *Bp*HMGR | 0.2 µM |
| *Mm* MK | 0.1 µM |
| SpPMK | 0.2 µM |
| ScPMD | 0.2 µM |
| ScIDI | 0.2 µM |
| XxGPPS | 1.0 µM |
| XxLS | variable |
| $NAD^+$ | 5 mM |
| CoA | 1 mM |
| ATP | 1 mM |

FIGURE 79, CON'T.
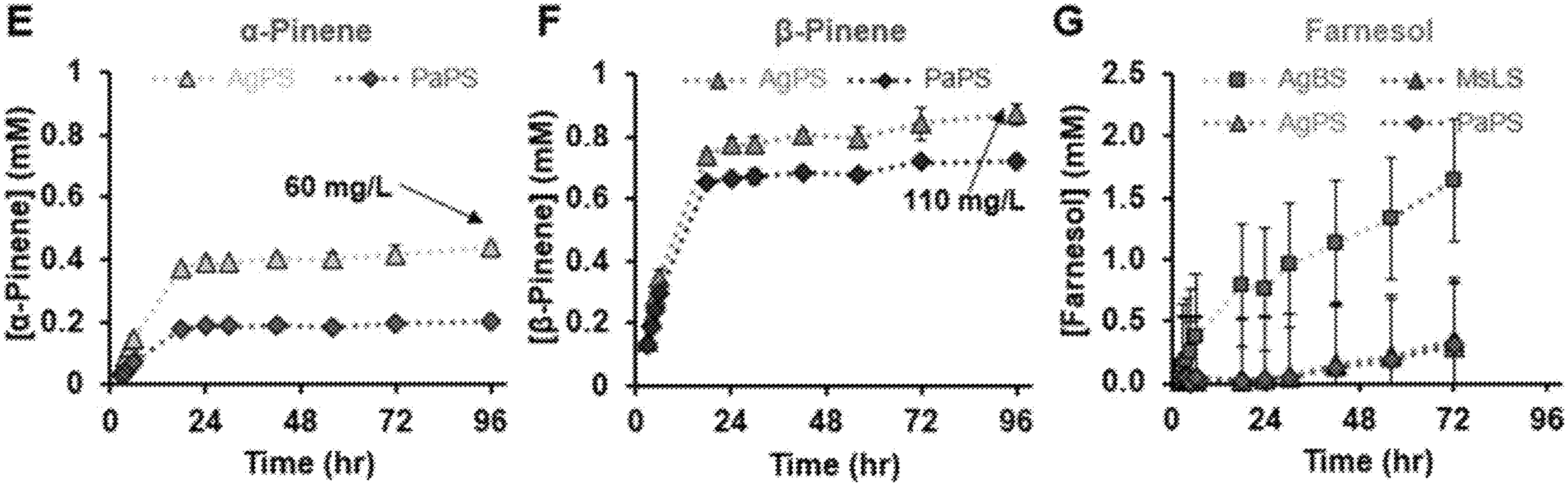
H
| Pinene Synthase | Purified enzymes *in vitro* | This study - lysates *in vitro* | (Sarria et al., 2014) *in vivo* |
|---|---|---|---|
| *Abies grandis* grand fir | 52% α-Pinene<br>48% β-Pinene | 33% α-Pinene<br>67% β-Pinene | 50% α-Pinene<br>50% β-Pinene |
| *Picea abies* Norway spruce | 57% α-Pinene<br>27% β-Pinene | 22% α-Pinene<br>78% β-Pinene | 47% α-Pinene<br>53% β-Pinene |

FIGURE 80, CON'T.
E-F: One pot synthesis of one to six enzymes (x-axis), remaining provided by pre-enriched lysates
E
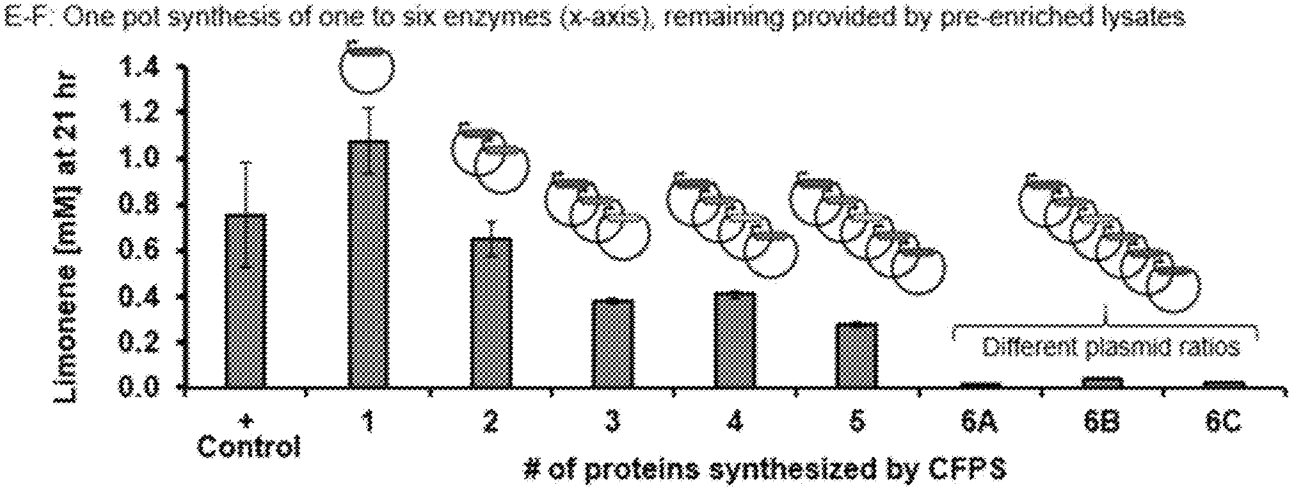
F
| Plasmid ratio | 6A ng/µL | 6B ng/µL | 6C ng/µL |
|---|---|---|---|
| ScMK | 4 | 14 | 14 |
| ScPMK | 4 | 1 | 6.7 |
| ScPMD | 4 | 1 | 3 |
| EcIDI | 4 | 1 | 2.9 |
| PaGPPS | 4 | 1 | 2.3 |
| MsLS | 4 | 11 | 11 |
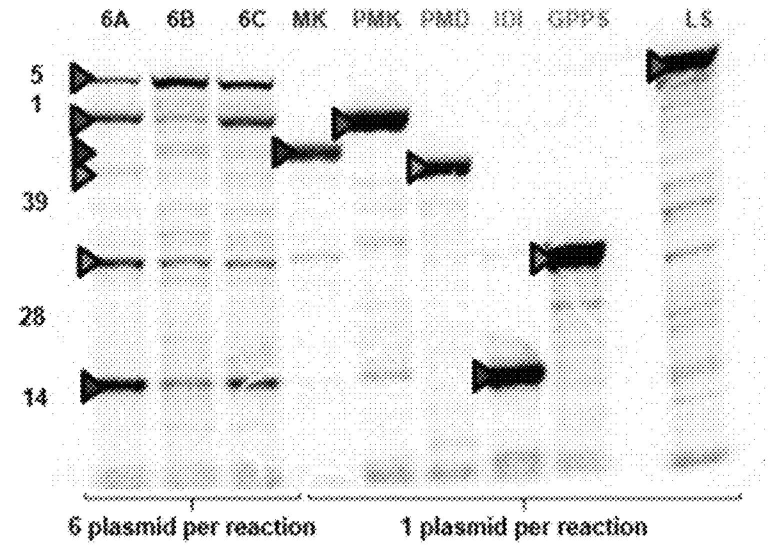

FIGURE 83, CON'T.
C
| | |
|---|---|
| EcACAT | + |
| ScHMGS | + |
| [illegible] | 0.2 µM |
| Mm MK | 0.1 µM |
| PzPMK | 0.2 µM |
| ScPMD | 0.2 µM |
| [illegible] | [illegible] |
| [illegible] | 1.0 µM |
| MsLS | + |
| $NAD^+$ | 5 mM |
| CoA | 1 mM |
| ATP | 1 mM |
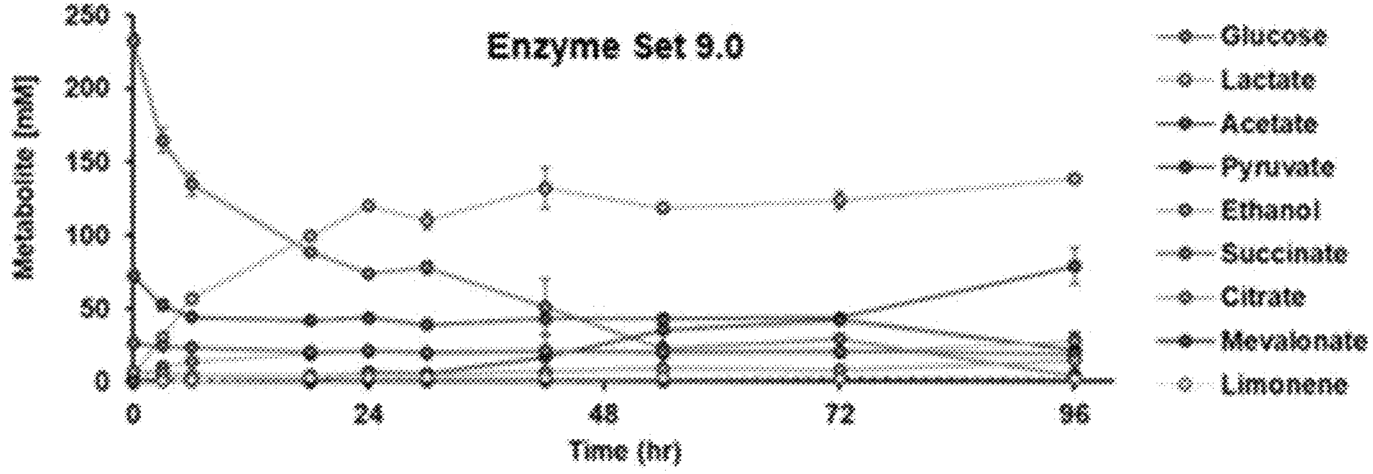
D
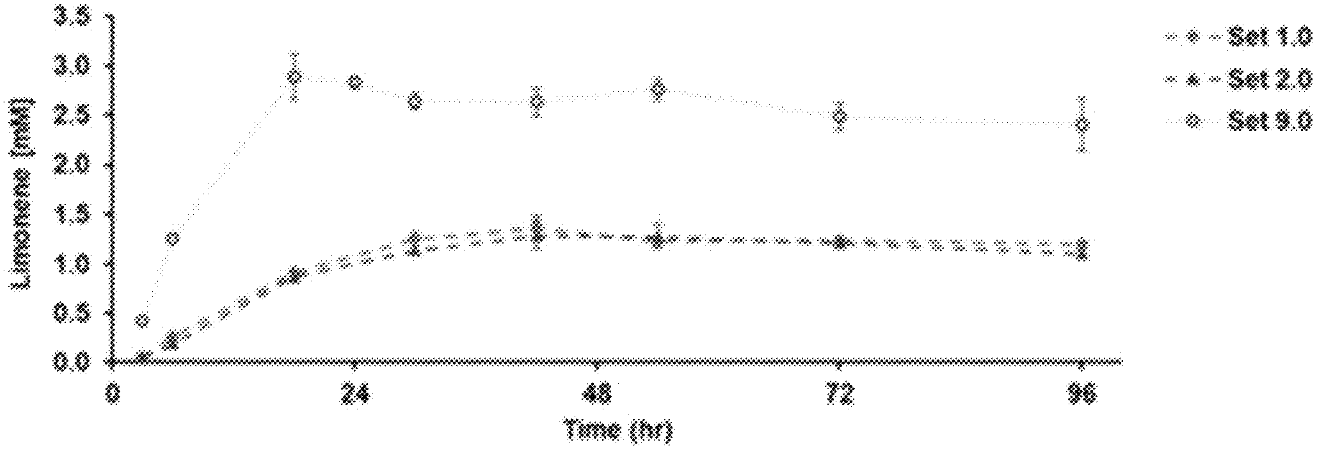

FIGURE 85 (SEQ ID NO:16)

354_pJL1-atoB (ACAT_Eco)

TCTAGAAATAATTTTGTTTAACTTTAAGAAGGAGATATACATATGAAAAATTGTGTCA
TCGTCAGTGCGGTACGTACTGCTATCGGTAGTTTTAACGGTTCACTCGCTTCCACC
AGCGCCATCGACCTGGGGGCGACAGTAATTAAAGCCGCCATTGAACGTGCAAAAA
TCGATTCACAACACGTTGATGAAGTGATTATGGGTAACGTGTTACAAGCCGGGCTG
GGGCAAAATCCGGCGCGTCAGGCACTGTTAAAAAGCGGGCTGGCAGAAACGGTG
TGCGGATTCACGGTCAATAAAGTATGTGGTTCGGGTCTTAAAAGTGTGGCGCTTGC
CGCCCAGGCCATTCAGGCAGGTCAGGCGCAGAGCATTGTGGCGGGGGGTATGGA
AAATATGAGTTTAGCCCCCTACTTACTCGATGCAAAAGCACGCTCTGGTTATCGTCT
TGGAGACGGACAGGTTTATGACGTAATCCTGCGCGATGGCCTGATGTGCGCCACC
CATGGTTATCATATGGGGATTACCGCCGAAAACGTGGCTAAAGAGTACGGAATTAC
CCGTGAAATGCAGGATGAACTGGCGCTACATTCACAGCGTAAAGCGGCAGCCGCA
ATTGAGTCCGGTGCTTTTACAGCCGAAATCGTCCCGGTAAATGTTGTCACTCGAAA
GAAAACCTTCGTCTTCAGTCAAGACGAATTCCCGAAAGCGAATTCAACGGCTGAAG
CGTTAGGTGCATTGCGCCCGGCCTTCGATAAAGCAGGAACAGTCACCGCTGGGAA
CGCGTCTGGTATTAACGACGGTGCTGCCGCTCTGGTGATTATGGAAGAATCTGCG
GCGCTGGCAGCAGGCCTTACCCCCCTGGCTCGCATTAAAAGTTATGCCAGCGGTG
GCGTGCCCCCCGCATTGATGGGTATGGGGCCAGTACCTGCCACGCAAAAAGCGTT
ACAACTGGCGGGGCTGCAACTGGCGGATATTGATCTCATTGAGGCTAATGAAGCA
TTTGCTGCACAGTTCCTTGCCGTTGGGAAAAACCTGGGCTTTGATTCTGAGAAAGT
GAATGTCAACGGCGGGGCCATCGCGCTCGGGCATCCTATCGGTGCCAGTGGTGC
TCGTATTCTGGTCACACTATTACATGCCATGCAGGCACGCGATAAAACGCTGGGG
CTGGCAACACTGTGCATTGGCGGCGGTCAGGGAATTGCGATGGTGATTGAACGGT
TGAATTAAGTCGAC

FIGURE 85, CON'T. (SEQ ID NO:17)

310_pJL1-(CAT5aa)-HMGS_Sce

TCTAGAAATAATTTTGTTTAACTTTAAGAAGGAGATATACATATGGAGAAAAAAATCA
AACTGAGCACCAAGCTGTGCTGGTGTGGCATCAAGGGTCGCCTGCGCCCACAAAA
GCAGCAACAGCTGCACAACACGAACCTGCAAATGACCGAGCTGAAAAAGCAGAAG
ACGGCCGAGCAAAAGACCCGCCCGCAGAACGTTGGCATCAAGGGCATCCAGATTT
ATATCCCGACGCAGTGTGTCAACCAATCTGAGCTGGAGAAATTCGATGGCGTCAG
CCAGGGTAAGTACACCATCGGCCTGGGCCAGACCAACATGAGCTTCGTGAACGAC
CGTGAGGACATCTATTCTATGAGCCTGACGGTGCTGTCTAAGCTGATCAAGAGCTA
CAACATCGACACGAATAAGATCGGTCGTCTGGAGGTGGGTACGGAGACGCTGATT
GACAAGAGCAAAAGCGTGAAGTCTGTCTTAATGCAGCTGTTCGGCGAGAACACGG
ATGTCGAGGGTATCGACACCCTGAACGCGTGTTACGGCGGCACCAACGCACTGTT
CAATAGCCTGAACTGGATTGAGAGCAACGCCTGGGATGGCCGCGATGCGATCGTC
GTGTGCGGCGATATCGCCATCTATGACAAGGGTGCGGCACGTCCGACCGGCGGT
GCAGGCACCGTTGCGATGTGGATTGGCCCGGACGCACCAATTGTCTTCGATTCTG
TCCGCGCGTCTTACATGGAGCACGCCTACGACTTTTACAAGCCGGACTTCACGAG
CGAATACCCGTACGTGGACGGCCACTTCTCTCTGACCTGCTATGTGAAGGCGCTG
GACCAGGTTTATAAGTCTTATAGCAAAAAGGCGATTTCTAAGGGCCTGGTCAGCGA
CCCGGCAGGCAGCGACGCCCTGAACGTGCTGAAGTATTTCGACTACAACGTGTTC
CATGTCCCGACCTGCAAATTAGTGACCAAATCTTATGGCCGCCTGTTATATAATGAT
TTCCGTGCCAACCCGCAGCTGTTCCCGGAGGTTGACGCCGAGCTGGCGACGCGT
GATTACGACGAGAGCCTGACCGACAAGAACATCGAGAAGACCTTCGTCAACGTCG
CGAAGCCGTTCCACAAAGAGCGTGTGGCCCAAAGCCTGATCGTCCCGACCAACAC
GGGCAACATGTATACCGCGTCTGTCTACGCGGCATTCGCGAGCCTGCTGAATTAC
GTCGGTTCTGACGACCTGCAGGGCAAGCGCGTTGGCCTGTTCAGCTACGGTAGC
GGCTTAGCGGCCAGCCTGTATAGCTGCAAAATTGTCGGCGACGTCCAGCACATCA
TCAAGGAGCTGGACATCACCAACAAGCTGGCGAAGCGCATCACCGAGACGCCGA
AAGATTACGAGGCAGCGATCGAGTTACGCGAGAATGCGCATCTGAAGAAGAACTT
CAAGCCGCAAGGTAGCATCGAGCACCTGCAGAGCGGCGTCTACTACCTGACGAAC
ATTGACGACAAGTTCCGCCGTTCTTATGACGTCAAAAAGCTGGAGTGAGTCGAC

FIGURE 85, CON'T. (SEQ ID NO:18)

311_pJL1-(CAT5aa)-HMGS_Sau

TCTAGAAATAATTTTGTTTAACTTTAAGAAGGAGATATACATATGGAGAAAAAAATCA
CCCTGGGCATTGATAAAATCAACTTCTATGTGCCGAAATATTACGTGGATATGGCA
AAACTGGCAGAAGCACGTCAGGTTGATCCGAACAAATTTCTGATTGGTATTGGTCA
GACCGAAATGGCAGTTAGTCCGGTTAATCAGGATATTGTTAGCATGGGTGCAAATG
CAGCCAAAGATATTATCACCGATGAAGATAAAAAAAAAATCGGCATGGTTATCGTT
GCAACCGAAAGCGCAGTTGATGCAGCAAAAGCAGCAGCAGTTCAGATTCATAATCT
GCTGGGTATTCAGCCGTTTGCACGTTGTTTTGAAATGAAAGAAGCATGTTACGCAG
CAACACCGGCAATTCAGCTGGCAAAAGATTATCTGGCAACCCGTCCGAATGAAAAA
GTTCTGGTTATTGCCACCGATACCGCACGTTATGGTCTGAATAGCGGTGGTGAACC
GACCCAGGGTGCCGGTGCAGTTGCAATGGTTATTAGCCATAATCCGAGCATTCTG
GCACTGAATGAAGATGCAGTTGCCTATACCGAAGATGTGTATGATTTTTGGCGTCC
GACCGGTCATAAATATCCGCTGGTTGATGGTGCACTGAGCAAAGATGCATATATTC
GTAGCTTTCAGCAGAGCTGGAATGAATATGCAAAACGTCAGGGTAAAAGCCTGGC
AGATTTTGCAAGCCTGTGTTTTCATGTTCCGTTTACCAAAATGGGTAAAAAAGCCCT
GGAAAGCATTATTGATAATGCCGATGAAACCACCCAAGAACGTCTGCGTAGCGGTT
ATGAGGATGCCGTTGATTATAACCGTTATGTGGGTAACATTTATACCGGTAGCCTG
TATCTGAGCCTGATTAGCCTGCTGGAAAATCGTGATCTGCAGGCAGGCGAAACCA
TTGGTCTGTTTAGCTATGGTAGCGGTAGCGTTGGTGAGTTTTATAGCGCAACCCTG
GTTGAAGGTTATAAAGATCATCTGGATCAGGCAGCACATAAAGCACTGCTGAATAA
TCGTACCGAAGTTAGCGTTGATGCGTATGAAACCTTTTTCAAACGCTTCGATGATGT
GGATTTTGATGAACAGCAGGATGCAGTTCATGAAGATCGCCATATCTTTTATCTGA
GCAACATTGAAAACAATGTGCGCGAATATCATCGTCCGGAATAAGTCGAC

Figure 85, con't. (SEQ ID NO:19)

312_pJL1-(CAT5aa)-HMGR_Sce

TCTAGAAATAATTTTGTTTAACTTTAAGAAGGAGATATACATATGGAGAAAAAAATC
GTGCTGACGAACAAAACCGTCATTAGCGGCAGCAAGGTGAAGTCTCTGAGCAGCG
CCCAAAGCTCTAGCAGCGGCCCGTCTAGCAGCAGCGAGGAGGACGACAGCCGTG
ACATTGAGTCTCTGGACAAGAAGATCCGCCCGCTGGAGGAGTTAGAGGCCCTGCT
GAGCAGCGGCAACACCAAGCAGCTGAAGAACAAGGAAGTTGCAGCGCTGGTGAT
CCACGGTAAGCTGCCACTGTATGCGCTGGAAAAGAAACTGGGCGATACGACGCGT
GCGGTCGCGGTGCGTCGCAAAGCCTTAAGCATCTTAGCGGAGGCCCCGGTGTTA
GCCAGCGACCGCCTGCCGTACAAGAACTACGACTACGACCGCGTGTTTGGCGCG
TGCTGCGAGAATGTCATTGGCTACATGCCGTTACCGGTTGGTGTGATCGGCCCGC
TGGTCATTGATGGCACGAGCTATCACATTCCAATGGCGACCACGGAAGGTTGCTTA
GTCGCCAGCGCCATGCGTGGCTGTAAGGCGATTAACGCCGGCGGTGGCGCGACG
ACCGTGTTAACCAAGGATGGTATGACGCGCGGTCCGGTCGTCCGCTTCCCAACGC
TGAAGCGCAGCGGCGCGTGTAAGATTTGGCTGGATTCTGAGGAGGGCCAAAACG
CGATCAAGAAAGCCTTCAACTCTACGAGCCGTTTCGCGCGTTTACAGCATATCCAG
ACCTGCCTGGCCGGCGACCTGCTGTTCATGCGCTTCCGCACCACCACGGGCGAT
GCGATGGGCATGAACATGATCAGCAAGGGCGTCGAATATAGCCTGAAACAAATGG
TGGAAGAATATGGCTGGGAGGACATGGAGGTTGTCTCTGTGAGCGGCAACTATTG
CACCGACAAGAAGCCGGCAGCCATTAACTGGATTGAGGGTCGCGGCAAAAGCGT
CGTGGCAGAAGCGACCATCCCAGGCGACGTGGTCCGTAAGGTTCTGAAGAGCGA
CGTCAGCGCCCTGGTTGAGTTAAATATCGCGAAAAACCTGGTCGGCAGCGCGATG
GCGGGCAGCGTGGGTGGCTTTAACGCACATGCAGCGAATCTGGTTACGGCGGTTT
TCTTAGCCTTAGGTCAGGACCCAGCCCAAAATGTCGAGAGCAGCAACTGCATTAC
CTTAATGAAAGAGGTTGACGGTGACCTGCGCATCAGCGTTTCTATGCCGTCTATCG
AGGTCGGCACGATCGGCGGCGGCACCGTTTTAGAACCGCAAGGTGCGATGCTGG
ATCTGCTGGGCGTGCGCGGCCCACATGCAACGGCCCCAGGCACCAATGCCCGCC
AACTGGCCCGTATCGTGGCCTGCGCGGTTCTGGCGGGTGAGCTGAGCCTGTGCG
CCGCATTAGCCGCGGGCCATTTAGTTCAATCTCACATGACCCACAACCGCAAGCC
GGCAGAACCAACCAAGCCAAATAACCTGGACGCAACCGACATTAACCGTCTGAAG
GATGGCAGCGTCACGTGCATTAAAAGCTAAGTCGAC

FIGURE 85, CON'T. (SEQ ID NO:20)

313_pJL1-(CAT5aa)-HMGR_Sau

TCTAGAAATAATTTTGTTTAACTTTAAGAAGGAGATATACATATGGAGAAAAAAATC
CAGAGCCTGGATAAAAACTTTCGTCATCTGAGCCGTCAGCAGAAACTGCAGCAGC
TGGTTGATAAACAGTGGCTGAGCGAAGAACAGTTTAACATTCTGCTGAATCATCCG
CTGATTGATGAAGAAGTTGCAAACAGCCTGATTGAAAATGTTATTGCACAGGGTGC
ACTGCCGGTTGGTCTGCTGCCGAACATTATTGTTGATGATAAAGCATATGTGGTGC
CGATGATGGTTGAAGAACCGAGCGTTGTTGCAGCAGCAAGCTATGGTGCAAAACT
GGTTAATCAGACCGGTGGCTTTAAAACCGTTAGCAGCGAACGTATTATGATTGGCC
AGATTGTTTTTGATGGTGTGGATGATACCGAAAAACTGAGCGCAGATATTAAAGCC
CTGGAAAAACAAATTCATCAGATTGCCGATGAAGCCTATCCGAGCATTAAAGCACG
TGGTGGTGGTTATCAGCGTATTGCAATTGATACCTTTCCGGAACAGCAACTGCTGA
GCCTGAAAGTGTTTGTTGATACCAAAGATGCAATGGGTGCCAATATGCTGAATACC
ATTCTGGAAGCAATTACCGCCTTTCTGAAAAATGAATTTCCGCAGAGCGATATCCT
GATGAGCATTCTGAGCAATCATGCAACCGCAAGCGTTGTTAAAGTTCAGGGTGAAA
TTGATGTTAAAGACCTGGCACGCGGTGAACGTACCGGTGAAGAGGTTGCCAAACG
TATGGAACGTGCAAGCGTTCTGGCACAGGTTGATATTCATCGTGCAGCAACCCATA
ATAAAGGTGTGATGAACGGTATTCATGCAGTTGTTCTGGCAACCGGTAATGATACC
CGTGGTGCGGAAGCAAGCGCACATGCATATGCCAGCAAAGATGGTCAGTATCGTG
GTATTGCAACCTGGCGTTATGATCAAGAACGTCAGCGTCTGATTGGTACAATTGAA
GTTCCGATGACCCTGGCAATTGTTGGTGGTGGCACCAAAGTTCTGCCGATTGCAAA
AGCAAGCCTGGAACTGCTGAATGTTGAAAGCGCACAAGAACTGGGTCATGTTGTT
GCCGCAGTGGGTCTGGCCCAGAATTTTGCAGCATGTCGTGCACTGGTTAGCGAAG
GTATCCAGCAGGGTCATATGAGTCTGCAGTATAAAAGCCTGGCCATTGTGGTTGGT
GCCAAAGGTGATGAAATTGCGCAGGTTGCAGAAGCACTGAAACAAGAACCGCGTG
CAAATACCCAGGTTGCGGAACGTATTCTGCAGGATCTGCGTAGCCAGCAGTAAGT
CGAC

FIGURE 85, CON'T.
(SEQ ID NO:21)

314_pJL1-(CAT5aa)-HMGR_Pme

TCTAGAAATAATTTTGTTTAACTTTAAGAAGGAGATATACATAT
GGAGAAAAAAATCAGCTTGGACAGCCGCCTGCCAGCTTTTC
GGAACCTGAGCCCCGCGGCGCGCCTGGATCATATTGGCCA
GCTCTTGGGCCTGAGCCATGATGACGTGAGCCTGCTGGCG
AACGCGGGAGCGCTGCCGATGGATATTGCGAACGGCATGAT
TGAGAACGTGATTGGCACCTTTGAACTGCCATACGCGGTGG
CGAGCAACTTTCAGATTAATGGCCGGGACGTGCTGGTGCCG
CTGGTGGTGGAGGAACCAAGCATTGTGGCGGCTGCTAGCT
ATATGGCGAAACTGGCGCGGGCGAACGGCGGCTTTACCAC
CAGCAGCAGCGCGCCGCTGATGCACGCGCAGGTACAGATT
GTGGGCATACAaGATCCGTTGAATGCTCGCCTGAGCCTGCT
GCGCCGCAAGGATGAGATTATAGAGCTGGCGAACCGCAAAG
ATCAGCTCTTAAACAGCTTAGGCGGCGGCTGCCGCGATATT
GAGGTGCATACCTTTGCGGACACCCCGCGGGGCCCGATGC
TGGTGGCGCATCTGATTGTGGACGTACGCGACGCGATGGG
CGCGAACACCGTGAATACCATGGCGGAAGCGGTAGCGCCG
CTGATGGAGGCGATTACCGGAGGCCAGGTACGCCTGCGCA
TACTGAGCAACCTGGCGGATCTGCGCCTGGCGAGGGCGCA
GGTtCGGATAACACCGCAGCAACTGGAGACAGCGGAGTTTT
CAGGCGAAGCTGTGATTGAGGGCATTTTGGATGCGTATGCG
TTTGCTGCGGTtGATCCCTATCGCGCGGCGACCCATAACAAA
GGCATTATGAATGGCATTGATCCCCTGATTGTGGCGACAGG
CAACGATTGGCGGGCTGTGGAGGCGGGCGCGCACGCGTA
CGCGTGCCGCTCAGGACATTATGGCAGCCTGACCACCTGG
GAGAAAGATAACAACGGCCACCTTGTGGGCACCCTGGAGAT
GCCGATGCCAGTAGGCCTGGTGGGCGGCGCGACCAAGAC
CCACCCGCTGGCGCAACTGAGCCTGCGCATTTTAGGCGTG
AAGACAGCGCAGGCGTTGGCTGAAATAGCGGTGGCGGTAG
GCCTGGCGCAAAACTTAGGAGCGATGCGCGCGCTGGCGAC
CGAGGGCATTCAGCGCGGCCATATGGCGCTGCACGCGCGC
AATATAGCGGTGGTGGCGGGCGCGAGGGGCGACGAAGTG
GATTGGGTAGCGCGGCAGCTTGTGGAGTATCATGATGTGCG
CGCGGATCGCGCGGTAGCTCTGCTGAAGCAAAAACGCGGC
CAATAAGTCGAC

FIGURE 85, con't. (SEQ ID NO:22)

315_pJL1-(CAT5aa)-HMGR_Spn

TCTAGAAATAATTTTGTTTAACTTTAAGAAGGAGATATACATATGGAGAAAAAAATCA
AGATCAGCTGGAACGGTTTTAGCAAAAAAAGCTACCAGGAGCGGCTTGAGCTCTT
GAAAGCGCAAGCTCTCTTAAGCCCAGAGCGGCAGGCGAGCCTTGAGAAGGATGA
ACAAATGAGCGTAACGGTAGCCGACCAACTTAGCGAGAACGTCGTAGGTACGTTT
AGCCTCCCATATTCACTTGTGCCaGAGGTCTTAGTCAATGGCCAAGAATACACTGT
GCCTTATGTAACGGAAGAACCtAGCGTAGTGGCTGCTGCATCATATGCATCAAAAA
TCATCAAGCGCGCCGGCGGCTTTACGGCCCAGGTCCATCAACGGCAAATGATTG
GGCAAGTCGCATTGTATCAGGTGGCGAACCCAAAATTGGCTCAGGAGAAGATTGC
ATCAAAGAAAGCTGAGCTCTTGGAGTTTGCAAACCAGGCATATCCAAGCATCGTG
AAACGCGGTGGCGGGGCTCGCGATCTTCATGTCGAGCAAATcAAAGGGGAACCG
GACTTTCTTGTGGTGTATATTCATGTCGATACTCAAGAAGCAATGGGCGCAAACAT
GCTTAATACTATGCTTGAAGCATTAAAACCGGTCTTAGAAGAACTCAGCCAAGGTC
AAAGCCTTATcGGTATCCTCTCAAATTACGCTACTGATAGCCTTGTAACGGCCTCAT
GCCGGATGGCATTTCGGTACTTGTCACGGCAGAAGGATCAGGGTCGGGAGATTG
CTGAGAAAATTGCTTTGGCGAGCCAATTTGCTCAAGCcGATCCATACCGGGCGGC
GACGCATAACAAAGGTATTTTTAACGGCATTGATGCTATTTTGATTGCAACGGGCA
ACGACTGGCGCGCAATCGAAGCGGGGGCACATGCATTTGCAAGCCGGGATGGT
CGGTATCAGGGCTTAAGCTGTTGGACACTCGACTTGGAACGGGAAGAATTGGTC
GGCGAGATGACTCTTCCtATGCCAGTCGCTACGAAGGGCGGGAGCATCGGGCTC
AATCCGCGCGTCGCGTTCAGCCATGATTTGTTAGGTAACCCAAGCGCACGGGAAT
TGGCACAAATTATCGTATCAATCGGCTTGGCACAGAACTTTGCCGCACTTAAAGCG
TTAGTCAGCACAGGAATCCAACAGGGGCACATGAAATTACAAGCAAAATCATTAGC
GCTTTTAGCGGGGGCGAGCGAAAGCGAAGTGGCGCCtTTAGTCGAGCGGCTCAT
CAGCGATAAAACTTTTAATTTGGAGACGGCACAACGGTATCTCGAAAACTTACGGA
GCTAAGTCGAC

FIGURE 85, CON'T.

(SEQ ID NO:23)

316_pJL1-(CAT5aa)-HMGR_Bpe

TCTAGAAATAATTTTGTTTAACTTTAAGAAGGAGATATACATAT
GGAGAAAAAAATC
AGCACCGATGCAAAAAATAGCCGTATTAGCGGCTTTCACAAA
GATGATATTCCGACCCGTCTGGCACGTGTTGCAGCATTTGC
AGGTCTGGATGATGAAACCGTTCAGCATCTGGCAAATATGG
GTAATCTGGACCCGCAGCTGGCAGATCGTCTGATTGAAAAT
GTTGTTGCAACCCTGAATGTGCCGATTGGTATTGCAACCAAT
ATGAAAGTTGATGGCGAAGATGTTCTGGTTCCGATGGCAAC
CGAAGAAAGCAGCGTTGTTGCAGCCGTTTGTAATGCAGCAC
GTCAGTGTTATGATCAGGGTGGTTTTACCACCAGTATGAGCG
GTAGCCTGATGATTGCACAGGTTCAGCTGGTTGATGTTCCG
GATGCAGCACATGCACGTATGCGTATTCTGGAACATAAAGCC
GAAGTTAAAGCACTGTGTGATGATTGTGATCCGCTGCTGGTT
AAACTGGGTGGTGGTCTGCAGGATGTTGAAGTTCGTATTGT
TGATGCAGCCGGTGGTCCGATGGTTGTTACCCATCTGATTG
TTGATACCCGTGATGCAATGGGTGCAAATGCAGTTAATAGCA
TGGCAGAAAAACTGGCACCGCATATTGAAAGCTGGACCGGT
GGTCGTGTTTATCTGCGCATTCTGAGCAATCTGGCCGATCG
TCGCCTGGCACGCGCACGTGCAGTTTGGACCTGTGATGCC
ATTGGTGGTGCAAGCGTTCGTGATGGTATTATTAGCGCATAT
CGTTTTGCAGCAGCAGATCCGTATCGTGCAGCAACCCATAA
CAAAGGTATTATGAATGGTGTTAGCGCAGTTGTTCTGGCAAC
CGGTAATGATACACGTGCCGTTGAAGCCGGTGCACATGCAT
ATGCCGCACGTAAAGGTTGGTATAGCAGCCTGACCGATTGG
GAAGTTACCGCAGAAGGTCATCTGGCAGGCACCCTGGAAAT
GCCGATGGCAGTTGGTCTGGTGGGTGGTGCCACAAAACTG
CATCCGACCGCACGTGCCTGTCTGAAAATTCTGGGTGTTAG
CACCGCAGAACGGCTGGCACGCCTGATTGCAGCAGTGGGT
CTGGCACAGAATTTTAGCGCACTGAAAGCACTGGCAACCAC
CGGTATTCAGAAAGGTCATATGAGCCTGCATGCACAGAATAT
TGCAATGATGGCAGGCGCAGTTGGTGATGAAATTGAACCGG
TTGCAAAAGCCCTGGTTGCACAGGGTGCAGTTCGTGTTGAT
GTTGCAGAAGCAGAACTGGCACGTCTGCGTGGTCAGGGTT
AAGTCGAC

FIGURE 85, CON'T.
(SEQ ID NO:24)

317_pJL1-(CAT5aa)-HMGR_Dac

TCTAGAAATAATTTTGTTTAACTTTAAGAAGGAGATATACATAT
GGAGAAAAAAATC
GTCGCCGATTCCCGCCTGCCGAACTTCCGCGCCCTGACTC
CGGCCCAGCGTCGTGATTTTCTGGCAGATGCATGTGGTCTG
AGTGATGCAGAACGTGCACTGCTGGCAGCACCGGGTGCAC
TGCCTCTGGCACTGGCCGATGGTATGATTGAAAATGTTTTTG
GCTCATTTGAACTGCCGCTGGGTGTTGCAGGTAATTTTCGC
GTTAATGGTCGTGATGTGCTGGTTCCGATGGCAGTTGAAGA
ACCGAGCGTTGTTGCAGCAGCAAGCTATATGGCAAAACTGG
CACGTGAAGATGGTGGTTTTCAGACCAGCAGCACCCTGCC
GCTGATGCGTGCACAGGTTCAGGTTCTGGGTGTTACCGATC
CGCATGGTGCACGTCTGGCAGTTCTGCAGGCACGTGCACA
GATTATTGAACGTGCAAATAGCCGTGATAAAGTGCTGATTGG
TCTGGGTGGTGGTTGTAAAGATATTGAAGTTCATGTGTTTCC
GGATACACCGCGTGGTCCGATGCTGGTTGTTCATCTGATTG
TTGATGTTCGTGATGCAATGGGTGCCAATACCGTTAATACCA
TGGCAGAAAGCGTTGCACCGCTGGTTGAGCAGATTACCGGT
GGTAGCGTTCGTCTGCGTATTCTGAGCAATCTGGCCGATCT
GCGTCTGGCACGCGCACGTGTTCGTCTGACACCGCAGACC
CTGGCAACCCAAGAACGTAGCGGTGAAGAAATTATTGAAGG
TGTTCTGGATGCATATACCTTTGCAGCAATTGATCCGTATCGT
GCAGCAACCCATAATAAAGGTATTATGAATGGTATCGATCCG
GTTATTGTTGCGACCGGTAATGATTGGCGTGCCGTTGAAGC
CGGTGCACATGCCTATGCAAGCCGTAGCGGTAGCTATACCA
GCCTGACCCGTTGGGAAAAAGATGCCGGTGGTGCACTGGT
TGGTAGCATCGAACTGCCGATGCCGGTTGGTCTGGTTGGC
GGTGCCACCAAAACCCATCCGCTGGCACGCCTGGCACTGA
AAATTATGGATCTGCAGAGCGCACAGCAGCTGGGTGAAATT
GCAGCCGCAGTGGGTCTGGCACAGAATCTGGGTGCCCTGC
GTGCACTGGCAACCGAAGGTATTCAGCGTGGTCATATGGCA
CTGCATGCACGTAATATTGCCCTGGTTGCGGGTGCAACCGG
TGATGAAGTTGATGCAGTTGCACGTCAGCTGGCAGCCGAAC
ATGATGTGCGTACCGATCGTGCCCTGGAAGTTCTGGCAGCA
CTGCGTGCCCGTGCATAAGTCGAC

FIGURE 85, CON'T.

(SEQ ID NO:25)

281_pJL1-(CAT5aa)-MK1_Sce

TCTAGAAATAATTTTGTTTAACTTTAAGAAGGAGATATACATAT
GGAGAAAAAAATCAGTTTACCCTTCTTAACGAGCGCCCCCG
GGAAGGTGATCATCTTTGGCGAACACAGCGCGGTCTACAAT
AAGCCAGCAGTCGCGGCGTCGGTCAGCGCTTTGCGCACTT
ACCTCTTAATCTCAGAGTCCAGCGCCCCGGATACGATCGAAT
TAGACTTCCCCGACATCTCATTTAACCATAAGTGGTCCATCAA
CGATTTCAACGCAATCACTGAGGATCAGGTCAATTCCCAGAA
ATTGGCAAAGGCGCAGCAGGCAACTGATGGGTTAAGCCAA
GAACTAGTGAGTTTATTAGATCCCTTATTGGCGCAGTTATCCG
AATCCTTCCACTACCATGCCGCTTTTTGCTTCCTCTATATGTT
TGTGTGTTTATGTCCTCATGCAAAGAACATCAAGTTTAGCTT
GAAGAGCACGTTGCCTATCGGCGCGGGATTAGGGTCTTCAG
CAAGCATCAGCGTCAGTCTTGCATTGGCGATGGCATACTTAG
GAGGATTAATCGGGAGCAACGACTTGGAAAAGCTCAGTGAA
AATGATAAGCATATCGTCAACCAGTGGGCATTCATCGGCGAA
AAGTGCATCCACGGCACTCCATCTGGGATCGATAATGCGGT
CGCAACGTATGGCAACGCACTCTTGTTTGAAAAAGACTCCC
ATAACGGGACGATCAATACGAATAACTTTAAGTTCTTAGATGA
TTTCCCGGCAATCCCGATGATCTTAACTTATACGCGCATCCC
GCGGAGCACGAAAGATTTAGTGGCGCGAGTGCGGGTCTTA
GTCACTGAGAAATTTCCAGAAGTGATGAAGCCGATCTTAGAT
GCAATGGGCGAATGCGCATTACAGGGGTTAGAGATCATGAC
GAAGTTGAGTAAATGCAAAGGGACTGATGACGAGGCGGTC
GAAACGAACAACGAACTTTATGAACAGTTGTTGGAATTGATC
CGCATCAACCATGGGCTCTTGGTTTCGATCGGCGTGAGCCA
TCCAGGGTTAGAATTAATCAAAAACCTCTCAGATGATTTACG
CATCGGGTCTACGAAATTAACTGGCGCGGGCGGTGGGGGC
TGTAGCTTGACGTTGTTACGACGCGACATCACGCAGGAGCA
GATCGACTCATTCAAAAAGAAATTGCAGGATGATTTTAGTTAC
GAGACGTTTGAAACGGACTTGGGCGGAACGGGGTGTTGCT
TATTATCAGCCAAAAACTTAAACAAAGATTTAAAAATCAAATC
GTTGGTCTTCCAGTTATTTGAAAACAAAACGACTACGAAGCA
GCAGATCGACGATTTGTTATTACCGGGGAATACAAACTTACC
GTGGACGTCTTGAGGATCCGCACTCGAGCACCACCACCAC
CACCACTGAGATCGTCGAC

FIGURE 85, CON'T.
(SEQ ID NO:26)

321_pJL1-(CAT7aa)-MK_Sau

TCTAGAAATAATTTTGTTTAACTTTAAGAAGGAGATATACATATGCA
TATGGAGAAAAAAATCACCCGTAAAGGTTATGGTGAAAGCACCG
GTAAAATCATTCTGATTGGTGAACATGCAGTGACCTTTGGTGAAC
CGGCAATTGCAGTTCCGTTTAATGCAGGCAAAATCAAAGTTCTGA
TTGAAGCACTGGAAAGCGGTAACTATAGCAGCATTAAATCCGATG
TGTATGATGGCATGCTGTATGATGCACCGGATCATCTGAAAAGCC
TGGTTAATCGTTTTGTGGAACTGAACAACATTACCGAACCGCTGG
CAGTTACCATTCAGACCAATCTGCCTCCGAGCCGTGGTCTGGGT
AGCAGCGCAGCAGTTGCAGTTGCATTTGTTCGTGCAAGCTATGA
TTTTCTGGGTAAAAGCCTGACCAAAGAAGAACTGATTGAAAAAG
CAAATTGGGCAGAGCAGATTGCACATGGTAAACCGAGCGGTATT
GATACCCAGACAATTGTTAGCGGTAAACCGGTGTGGTTTCAGAA
AGGTCATGCAGAAACCCTGAAAACCCTGTCACTGGATGGTTATAT
GGTTGTGATTGATACCGGTGTTAAAGGTAGCACCCGTCAGGCAG
TTGAAGATGTTCATAAACTGTGTGAAGATCCGCAGTATATGAGCC
ATGTTAAACATATTGGTAAACTGGTTCTGCGTGCCAGTGATGTTAT
TGAACATCATAATTTTGAAGCCCTGGCCGATATCTTTAATGAATGT
CATGCCGATCTGAAAGCACTGACCGTTAGCCATGATAAAATTGAG
CAGCTGATGAAGATCGGCAAAGAAAATGGTGCCATTGCAGGTAA
ACTGACCGGTGCAGGTCGTGGTGGTAGCATGCTGCTGCTGGCA
AAAGACCTGCCGACCGCAAAAAACATTGTTAAAGCAGTGGAAAA
AGCCGGTGCAGCACATACCTGGATTGAAAATTTAGGTGGTTAAGT
CGACGTCGAC

FIGURE 85, CON'T.

(SEQ ID NO:27)

322_pJL1-(CAT7aa)-MK_Spn

TCTAGAAATAATTTTGTTTAACTTTAAGAAGGAGATATACATATGCAT
ATGGAGAAAAAAATCACCAAAAAAGTTGGTGTTGGTCAGGCACAT
AGCAAAATTATCCTGATTGGTGAACATGCCGTGGTTTATGGTTATC
CGGCAATTAGCCTGCCGCTGCTGGAAGTTGAAGTTACCTGTAAAG
TTGTTAGCGCAGAAAGCCCGTGGCGTCTGTATGAAGAGGATACCC
TGAGCATGGCAGTTTATGCAAGCCTGGAATATCTGGATATCACCGA
AGCATGTGTTCGTTGTGAAATTGATAGCGCAATTCCGGAAAAACG
TGGTATGGGTAGCAGCGCAGCAATTAGCATTGCAGCAATTCGTGC
AGTGTTCGATTATTATCAGGCCGATCTGCCGCATGATGTTCTGGAA
ATTCTGGTTAATCGTGCAGAAATGATTGCACACATGAATCCGAGCG
GTCTGGATGCAAAAACCTGTCTGAGCGATCAGCCGATTCGTTTTA
TCAAAAATGTGGGTTTTACCGAACTGGAAATGGATCTGAGCGCAT
ATCTGGTTATTGCAGATACCGGTGTTTATGGTCATACCCGTGAAGC
AATTCAGGTTGTTCAGAATAAAGGTAAAGATGCACTGCCGTTTCTG
CATGCACTGGGTGAACTGACCCAGCAGGCAGAAGTTGCCATTAG
CCAGAAAGATGCAGAAGGTCTGGGTCAGATTCTGAGCCAGGCAC
ATCTGCATCTGAAAGAAATTGGTGTTAGCAGTCCGGAAGCAGATT
TTCTGGTTGAAACCACACTGAGCCATGGTGCCCTGGGTGCAAAA
ATGAGCGGTGGTGGTTTAGGTGGTTGTATTATTGCACTGGTTACC
AATCTGACACATGCACAAGAACTGGCAGAACGTCTGGAAGAAAAA
GGTGCCGTTCAGACCTGGATTGAAAGCCTGTAAGTCGACGTCGA
C

FIGURE 85, CON'T.
(SEQ ID NO:28)

323_pJL1-(CAT7aa)-MK_Mma

TCTAGAAATAATTTTGTTTAACTTTAAGAAGGAGATATACATAT
GCATATGGAGAAAAAAATCGTTAGCTGTAGCGCACCGGGTA
AAATCTACCTGTTTGGTGAACATGCAGTTGTGTATGGTGAAA
CCGCAATTGCATGTGCAGTTGAACTGCGTACCCGTGTTCGT
GCAGAACTGAATGATAGCATTACCATTCAGAGCCAGATTGGT
CGTACCGGTCTGGATTTTGAAAAACATCCGTATGTTAGCGCA
GTGATCGAAAAAATGCGTAAAAGCATTCCGATTAACGGTGTT
TTTCTGACCGTTGATAGCGATATTCCGGTTGGTAGCGGTCTG
GGTAGCAGCGCAGCAGTTACCATTGCAAGCATTGGTGCACT
GAATGAACTGTTTGGTTTTGGTCTGAGCCTGCAAGAAATTG
CAAAACTGGGTCATGAAATCGAGATTAAAGTTCAGGGTGCA
GCAAGCCCGACCGATACCTATGTTAGCACCTTTGGTGGTGT
TGTTACCATTCCGGAACGTCGTAAACTGAAAACACCGGATTG
TGGTATTGTTATTGGTGATACCGGTGTGTTTAGCAGCACCAA
AGAACTGGTTGCAAATGTTCGTCAGCTGCGTGAAAGCTATC
CGGATCTGATTGAACCGCTGATGACCAGCATTGGTAAAATTA
GTCGTATTGGCGAACAGCTGGTTCTGAGCGGTGATTATGCG
AGCATTGGTCGTCTGATGAATGTTAATCAGGGTCTGCTGGAT
GCACTGGGTGTTAATATTCTGGAACTGAGCCAGCTGATTTAT
AGCGCACGTGCAGCCGGTGCATTTGGTGCAAAAATTACCGG
TGCCGGTGGTGGTGGTTGTATGGTTGCACTGACCGCACCG
GAAAAATGTAATCAGGTTGCCGAAGCAGTTGCCGGTGCAGG
CGGTAAAGTGACCATTACCAAACCGACCGAACAGGGTCTGA
AAGTTGATTAAGTCGACGTCGAC

FIGURE 85, CON'T.

(SEQ ID NO:29)

324_pJL1-(CAT7aa)-MK_Pze

TCTAGAAATAATTTTGTTTAACTTTAAGAAGGAGATATACATAT
GCATATGGAGAAAAAAATCAGCACCGGTCGTCCGGAAGCGG
GTGCACATGCACCGGGTAAACTGATTCTGAGCGGTGAACAT
AGCGTTCTGTATGGTGCACCGGCACTGGCAATGGCAATTGC
ACGTTATACCGAAGTTTGGTTTACCCCGTTAGGTATTGGTGA
AGGTATTCGTACCACCTTTGCAAATCTGAGTGGTGGTGCAA
CCTATAGCCTGAAACTGCTGAGCGGTTTTAAAAGCCGTCTG
GATCGTCGTTTTGAACAGTTTCTGAATGGTGATCTGAAAGTG
CATAAAGTTCTGACCCATCCTGATGATCTGGCAGTTTATGCC
CTGGCAAGCCTGCTGCATGATAAACCGCCTGGCACCGCAG
CAATGCCTGGTATTGGCGCAATGCATCATCTGCCTCGTCCG
GGTGAACTGGGTAGCCGTACCGAACTGCCGATTGGTGCCG
GTATGGGTAGCAGCGCAGCAATTGTTGCAGCAACCACCGTT
CTGTTTGAAACCCTGCTGGATCGCCCTAAAACACCGGAACA
GCGTTTTGATCGTGTTCGTTTTTGTGAACGTCTGAAACATGG
TAAAGCAGGTCCGATTGATGCAGCAAGCGTTGTTCGTGGTG
GTCTGGTTCGTGTTGGTGGTAATGGTCCGGGTAGCATTAGC
TCATTTGATCTGCCTGAAGATCACGATCTGGTTGCAGGTCGT
GGTTGGTATTGGGTTCTGCATGGCCGTCCGGTTAGCGGCAC
CGGTGAATGTGTTAGCGCAGTTGCAGCAGCACATGGTCGTG
ATGCAGCCCTGTGGGATGCATTTGCAGTTTGTACCCGTGCA
CTGGAAGCAGCACTGCTGTCAGGTGGTAGTCCGGATGCAG
CCATTACCGAAAATCAGCGTCTGCTGGAACGTATTGGTGTTG
TTCCGGCAGCAACCCAGGCACTGGTTGCACAGATTGAAGAA
GCAGGCGGAGCAGCAAAAATTTGTGGTGCAGGTAGCGTGC
GTGGTGATCATGGTGGTGCCGTTCTGGTGCGTATTGATGAT
GCACAGGCCATGGCAAGCGTTATGGCACGTCATCCGGATCT
GGATTGGGCACCGCTGCGTATGAGTCGTACCGGTGCAGCA
CCTGGTCCGGCACCGCGTGCACAGCCGTTACCTGGTCAGG
GTTAAGTCGACGTCGAC

FIGURE 85, CON'T.

(SEQ ID NO:30)

325_pJL1-(CAT7aa)-MK_Hme

TCTAGAAATAATTTTGTTTAACTTTAAGAAGGAGATATACATAT
GCATATGGAGAAAAAAATCACCGTTAGCAGCGCACCGGGTA
AAGTTTACCTGTTTGGTGAACATGCAGTTGTTTATGGTGAAC
CGGCAGTTCCGTGTGCAGTTGAACGTCGTGCAACCGTTAG
CGTTAGCGCACGTGATGATGATCATGTTCGTGTTCGTGCAG
AGGATCTGAGCCTGAATGGTTTTACCGTTGAATATAGCGGTA
GCACCGGTAATCATCCTGATGTTGATGTTCCGACACCGCTG
GTTGAAGCAGCAATGGGTTATATTGATGCAGCAGTTGCACAG
GCTCGTGATGCAGCCGATGCACCGGATGCAGGTTTTGATAT
TACCGTTAAAAGCGATATTCCGCTTGGTGCAGGTCTGGGTA
GCAGTGCAGCCGTTGTTGTTGCAGGTATTGATGCGGCAACC
CGTGAACTGGGTGTTGAACTGAGTCCGCGTGAAATTGCAGA
TCGTGCATATCGTGCAGAACATGAAGTTCAGGATGGTCAGG
CAAGCCGTGCAGATACCTTTTGTAGCGCAATGGGTGGTGCA
GTTCGTGTTGAAGGTGATGATTGTCGTACCATTGATGCACCG
CCTCTGCCGTTTGTTATTGGTTTTGATGGTGGTGCCGGTGAT
ACCGGTGCACTGGTTAGCGGTGTGCGTGCACTGCGTGAAG
AATATGATTTTGCAGCAGATACCGTGAGCACCATTGGTGATAT
TGTTCGTCGTGGTGAGGATCTGCTGGCAGATGCAGATCCGG
AAGAACCGAGCGAAGCACTGCTGAGCGAACTGGGTCGTTT
TATGAATTTTAACCATGGTCTGCTGGAAGCCCTGGGTGTTAG
CAGCCGTAGCCTGGATAGCATGGTTTGGGCAGCACGTGAA
GCCGGTGCCTATGGTGCAAAACTGACCGGTGCAGGCGGTG
GTGGTTGTATTGTTGCACTGGACCCGACACCGGAAACACAG
ACCGCACTGCGTTTTACACCGGGTTGTGAAGATGCATTTCG
TGCCGAACTGGCAACCGAAGGTGTTCGTGTGGAAGAACCT
CCGGCAAGCGCAGCCAGCGCAGAAAGCAATGTTGGTGATG
ATCAGAGTCCGGAAGGTAGCGCATAAGTCGACGTCGAC

FIGURE 85, CON'T.

(SEQ ID NO:31)

326_pJL1-(CAT7aa)-MK_Nma

TCTAGAAATAATTTTGTTTAACTTTAAGAAGGAGATATACATAT
GCATATGGAGAAAAAAATCAAAAGCAAAGCAAGCGCACCGG
GTAAAGTTATTCTGTTTGGTGAACATTTTGTGGTGTATGGCG
TTAAAGCAATTCTGTGCGCAATTAACAAACGTATTGCAGTGA
CCGCAGAAAAAATCGATGAACGCAAAATCAGCATCAAAAGC
AATATTGGTCATCTGGAACTGGAACCGAATAAACCGATTAGC
GAAATTAATAGTCCGCTGAAACCGTTCTATTATCTGGCCAATA
AAATCATCCAGGACAAGAACTTTGGCATCAAAATTGATGTGG
AAAGCGAAATTCCGTTAGGTGTTGGTCTGGGTAGCAGCAGC
GCATGTTGTGTTGCCGGTGCAGCAGCAATTAGCAACCTGTT
TGAAAATAACAGCAAAGAAGAGATCCTGAAACTGGCAATTGA
AGCCGAAAAAACCATTTTTCAGAATACCAGCGGTGCAGATTG
TACCGTTTGTACCTTTGGTGGTCTGATGGAATATGATAAAGA
AAACGGCTTCAGCAAAATCGAAAGCGAACCGAATTTTCATCT
GGTGATTGCCAATAGCAATGTGGAACATAGCACCGAAAGCG
TTGTTGCGGGTGTTCGTAAATTCAAAAAAAACAACGAAGCC
GAGTTCAGCAAACTGTGTAAAGATGAAAGCCATCTGATTGAG
AATGTGCTGGAACTGCTGAAAGAAAACAATATTCGTGAACTG
GGTGAACGCGTGATCAAAAATCAAGAATATCTGGAACGCATT
GGCATCAGCAATGCAAAACTGCGTGAAATGATTCAGACAGG
TCAGAATAGCAGCTTTGGTGCAAAAATTACCGGTGCCGGTG
GTGGTGGTTGTATTTTTGCCCTGACCGATGAAAGTAATCTGG
AAAACACCATCAAAGAATTTAAAGAAAAAAACCACGAGTGCT
TTAGCGTGAAAATCGACTTTAAAGGTCTGGACACCTTTTAAG
TCGACGTCGAC

FIGURE 85, CON'T.

(SEQ ID NO:32)

327_pJL1-(CAT7aa)-MK_Mxa

TCTAGAAATAATTTTGTTTAACTTTAAGAAGGAGATATACATAT
GCATATGGAGAAAAAAATCGCACCGCGTCCGGAAAGCCTGA
GCGCATTTGGTGCAGGTAAAGTTATTCTGCTGGGTGAACATA
GCGTTGTTTATGGTCATCCGGCACTGGCAGGTCCGCTGAGC
CAGGGTGTTACCGCACGTGCAGTTCCGGCAAAAGCATGTCA
GCTGGCACTGCCGAGCACACTGAGCCGTCCGCAGCGTGCA
CAGCTGACCGCAGCATTTGCCCGTGCAGCCGAAGTTACCG
GTGCACCTCCGGTTAAAGTTAGCCTGGAAGCCGATCTGCCG
CTGGCAGTTGGTCTGGGTAGCAGCGCAGCACTGAGCGTTG
CATGTGCACGTCTGCTGCTGCAGGCAGCCGGTAAAGTTCC
GACACCGAAAGATGCAGCACGTGTTGCCTGGGCAATGGAA
CAAGAATTTCATGGCACCCCGAGCGGTGTTGATCATACCAC
CAGTGCAGCAGAACAGCTGGTGCTGTATTGGCGTAAACCGG
GTGCAGCAAAAGGCACCGGTCAGGTTGTTGAAAGTCCGCG
TCCGCTGCATGTTGTTGTTACCCTGGCAGGCGAACGTAGCC
CGACCAAAAAAACCGTTGGTGCACTGCGTGAACGTCAGGC
ACGTTGGCCGAGCCGTTATGAACGTCTGTTTGCAGAAATTG
GTCGTGTTAGCAGCGAAGGTGCAAAAGCAGTTGCAGCCGG
TGATCTGGAAGCACTGGGTGATGCAATGAATGTTAATCAGG
GTCTGCTGGCAGCCCTGGGTCTGAGCAGCCCTCCGCTGGA
AGAAATGGTTTATCGTCTGCGCGAACTGGGTGCCCTGGGTG
CAAAACTGACAGGTGCCGGTGGTGATGGTGGTGCAGTTATT
GGTCTGTTTCTGGAACCGAAACCGGTTGTTACCAAACTGAC
CCGTATGGGTGTTCGTTGTTTTAGCTCACAGCTGGCTGGTC
CGCGTGCAAGCTAAGTCGACGTCGAC

FIGURE 85, CON'T.

(SEQ ID NO:33)

328_pJL1-(CAT7aa)-MK_Bmo

TCTAGAAATAATTTTGTTTAACTTTAAGAAGGAGATATACATAT
GCATATGGAGAAAAAAATCGAAGTTCGTGCCCGTGCACCGG
GTAAAATCATTCTGGCAGGCGAACATGCAGTTGTTCATGGTA
GCACCGCAGTTGCAGCAGCAATTGATCTGTATACCTATATCA
GCCTGCATTTTCCGACACCGGCAGAAAATGATGATGCACTG
AAACTGCATCTGAAAGATATGGGCTTAGAATTTAGCTGGCCT
GTGGGTCGTATTAAAGATGTTCTGCCGGAAGTTAGCAGCCAT
GATGTGAGCAGCCCGAGCAGCTGTAGCCTGGAAACCCTGA
AAGCAATTGCAGCACTGGTTGAAGAACAGAATATTCCGGAA
GCAAATGTTGGTCTGGCAAGCGGTGTTAGCACCTTTCTGTG
GATGTATAGCAGCATTCATGGTTACAAACCGGCAAAAGTTGT
TGTTACCAGCGAACTGCCGTTAGGTAGCGGTCTGGGTAGCA
GCGCAGCATTTTGTGTTAGCCTGAGCGCAGCACTGCTGGCA
CTGAGCGATAGCGTTAAACTGGATTTTAGCAATCAAGGCTGG
CAGATGTTTGCAGAAACCGAACTGGAACTGGTGAATAAATG
GGCATTTGAAGGCGAAAAAATCATCCATGGTAAACCGAGCG
GTATTGATAATACAGTGAGCACCTATGGCAACATGATCAAATT
CAAAAGCGGTGAAATGGTGCGCATCAAAACCAATATGCCGC
TGAAAATGCTGATCACCAATACCAAAGTTGGCCGTAATACAA
AAGCCCTGGTTGCGGGTGTTAGCGAACGTACCGTTCGTCAT
AGCAATGCAATGAGCAGCGTTTTTAATGCCGTTGATTGCATT
AGCAATGAACTGGCAGCAATTATTCAGAGTCCGGTTAGTGAT
GATCTGGCCATTACCGAAAAAGAAGAAAAACTGGGCGAACT
GATGGAAATGAATCAGGGTCTGCTGCAGTGTATGGGTGTGA
GCCATGCAAGCATTGAAACCGTTATTCGTACCACGCTGAAAT
ACAAACTGGCAACCAAACTGACCGGTGCCGGTGGTGGTGG
TTGTGTTCTGAGCCTGCTGCCGACACTGCTGAGCGGCACC
GTTGTTGATATTGTTATTAGTGAACTGGAAGCCTGTGGTTTT
CAGTGTCTGATTGCAGGTATTGGCGGTAATGGTGTTGAAATT
AGCTTTAGCCCGAGCTAAGTCGACGTCGAC

FIGURE 85, CON'T.
(SEQ ID NO:34)

282_pJL1-(CAT5aa)-PMK1_Sce

TCTAGAAATAATTTTGTTTAACTTTAAGAAGGAGATATACATAT
GGAGAAAAAAATCAGTGAGTTGCGCGCATTCTCGGCACCGG
GAAAAGCTTTATTAGCGGGCGGGTATTTAGTGTTGGATACGA
AATATGAAGCCTTTGTCGTCGGGTTATCAGCCCGCATGCATG
CGGTCGCACATCCATACGGCTCTTTACAGGGAAGCGATAAG
TTTGAAGTCCGGGTCAAATCTAAACAGTTTAAAGATGGAGAG
TGGCTTTACCATATCAGTCCAAAAAGTGGGTTCATCCCAGTG
TCAATCGGTGGGAGCAAGAATCCATTCATCGAAAAAGTGATC
GCGAATGTCTTTTCATACTTTAAACCAAATATGGACGACTACT
GTAACCGCAATTTATTCGTGATCGATATCTTCAGCGATGATGC
ATACCATAGCCAAGAGGATTCAGTGACTGAACATCGGGGGA
ATCGCCGCTTGTCTTTTCATTCACACCGCATCGAAGAAGTGC
CTAAAACGGGACTTGGGTCGTCAGCCGGCTTGGTCACGGT
GTTGACGACGGCGTTAGCATCCTTTTTTGTCTCAGACCTCG
AAAACAACGTCGACAAATATCGCGAAGTGATCCATAACTTGG
CCCAGGTGGCGCATTGCCAGGCGCAAGGCAAAATCGGGTC
AGGATTTGATGTCGCTGCTGCCGCCTATGGGAGCATCCGCT
ATCGCCGCTTCCCGCCTGCCTTGATCAGCAACTTGCCGGAT
ATCGGGTCGGCGACGTACGGGTCTAAACTTGCTCATTTAGT
GGATGAAGAAGACTGGAACATCACAATCAAATCGAATCATTT
ACCATCAGGGTTGACGTTATGGATGGGGGATATCAAGAACG
GCAGTGAAACGGTCAAACTTGTCCAAAAGGTCAAAAACTGG
TATGATTCACATATGCCGGAATCATTAAAAATCTATACGGAAC
TAGATCATGCCAACAGCCGCTTTATGGATGGGTTGAGCAAAT
TAGATCGATTGCACGAGACGCATGACGATTACTCAGATCAAA
TCTTTGAGAGCTTGGAGCGGAACGACTGCACTTGCCAGAA
GTATCCAGAAATCACGGAAGTGCGCGATGCCGTGGCAACGA
TCCGCCGGTCGTTTCGCAAAATCACGAAAGAAAGCGGCGC
AGATATCGAACCACCTGTCCAGACGTCATTATTGGATGATTG
TCAAACTTTGAAAGGGGTGTTGACGTGTTTGATCCCAGGCG
CGGGCGGCTATGACGCAATCGCCGTCATCACGAAGCAGGAT
GTGGATTTGCGGGCGCAGACTGCGAACGACAAACGCTTTA
GCAAGGTGCAGTGGCTCGATGTCACGCAAGCGGACTGGGG
CGTGCGGAAAGAAAAAGATCCCGAAACGTATTTGGATAAATG
AGGATCCTGACTCGAGCACCACCACCACCACCACTGAGATC
GTCGAC

FIGURE 85, CON'T.

(SEQ ID NO:35)

329_pJL1-(CAT7aa)-PMK_Sau

TCTAGAAATAATTTTGTTTAACTTTAAGAAGGAGATATACATAT
GCATATGGAGAAAAAAATCATCCAGGTTAAAGCACCGGGTAA
ACTGTATATTGCCGGTGAATATGCAGTTACCGAACCGGGTTA
TAAAAGCGTTCTGATTGCACTGGATCGTTTTGTTACCGCAAC
CATTGAAGAAGCCGATCAGTATAAAGGCACCATTCATAGCAA
AGCCCTGCATCACAATCCGGTTACCTTTAGCCGTGATGAAGA
TAGCATTGTTATTAGCGATCCGCATGCAGCAAAACAGCTGAA
TTATGTTGTGACCGCCATCGAAATCTTTGAGCAGTATGCAAA
AAGCTGCGACATTGCCATGAAACATTTTCATCTGACCATCGA
TAGCAACCTGGATGATAGCAATGGTCATAAATATGGTCTGGG
TAGCAGCGCAGCAGTTCTGGTTAGCGTTATTAAAGTGCTGAA
CGAGTTCTACGATATGAAACTGAGCAACCTGTACATCTATAAA
CTGGCCGTTATTGCCAACATGAAACTGCAGAGCCTGAGCAG
CTGTGGTGATATTGCAGTTAGCGTTTATAGCGGTTGGCTGGC
ATATAGCACCTTTGATCATGAATGGGTGAAACACCAGATTGA
AGATACCACCGTTGAAGAAGTGCTGATTAAAAACTGGCCTG
GTCTGCATATTGAACCGCTGCAGGCACCGGAAAATATGGAA
GTTCTGATCGGTTGGACCGGTAGTCCGGCAAGCAGTCCGC
ATTTTGTTAGCGAAGTTAAACGTCTGAAAAGCGATCCGAGCT
TTTATGGTGATTTTCTGGAAGATAGCCATCGGTGTGTTGAAA
AACTGATCCATGCCTTTAAAACCAACAACATTAAAGGCGTGC
AGAAAATGGTTCGTCAGAATCGTACCATTATTCAGCGCATGG
ATAAAGAAGCAACCGTTGATATTGAAACCGAGAAACTGAAAT
ACCTGTGCGATATTGCCGAAAAATATCATGGTGCAAGCAAAA
CCAGCGGTGCCGGTGGTGGTGATTGTGGTATTACCATTATC
AACAAAGATGTGGACAAAGAGAAAATCTACGACGAATGGAC
CAAACATGGTATCAAACCGCTGAAATTCAACATCTATCATGG
CCAGTAAGTCGACGTCGAC

FIGURE 85, CON'T.

(SEQ ID NO:36)

330_pJL1-(CAT7aa)-PMK_Spn

TCTAGAAATAATTTTGTTTAACTTTAAGAAGGAGATATACATAT
GCATATGGAGAAAAAAATCATTGCCGTTAAAACCTGCGGTAA
ACTGTATTGGGCAGGCGAATATGCAATTCTGGAACCGGGTC
AGCTGGCACTGATTAAAGATATTCCGATTTATATGCGTGCCG
AAATCGCATTTAGCGATAGCTACCGTATTTATAGCGATATGTTT
GATTTTGCCGTTGACCTGCGTCCGAATCCTGATTATAGCCTG
ATTCAAGAAACCATTGCACTGATGGGTGATTTTCTGGCAGTT
CGTGGTCAGAATCTGCGTCCGTTTAGCCTGGCCATTTATGG
TAAAATGGAACGCGAAGGCAAAAAATTCGGTCTGGGTAGCA
GCGGTAGCGTTGTTGTTCTGGTTGTTAAAGCACTGCTGGCC
CTGTATAATCTGAGCGTTGATCAGAACCTGCTGTTTAAACTG
ACCAGCGCAGTTCTGCTGAAACGTGGTGATAATGGTAGCAT
GGGTGATCTGGCATGTATTGCAGCAGAGGATCTGGTTCTGT
ATCAGAGCTTTGATCGTCAGAAAGTTGCAGCATGGCTGGAA
GAAGAAAATCTGGCAACCGTTCTGGAACGTGATTGGGGTTT
TAGCATTAGCCAGGTTAAACCGACACTGGAATGTGACTTTCT
GGTTGGTTGGACCAAAGAAGTTGCAGTTAGCAGCCACATGG
TTCAGCAGATTAAACAGAATATTAACCAGAACTTCCTGACCA
GCAGCAAAGAAACCGTTGTTAGCCTGGTTGAAGCACTGGAA
CAGGGTAAAAGCGAAAAAATCATTGAACAGGTTGAAGTGGC
AAGCAAACTGCTGGAAGGTCTGAGCACCGATATCTATACACC
GCTGCTGCGTCAGCTGAAAGAAGCAAGCCAGGATCTGCAG
GCAGTTGCAAAAAGCAGTGGTGCCGGTGGTGGTGATTGTG
GTATTGCACTGTCATTTGATGCACAGAGCACCAAAACACTGA
AAAATCGTTGGGCTGATCTGGGTATTGAACTGCTGTATCAAG
AACGTATTGGCCACGATGATAAAAGCTAAGTCGACGTCGAC

FIGURE 85, CON'T.
(SEQ ID NO:37)

331_pJL1-(CAT7aa)-PMK_Efa

TCTAGAAATAATTTTGTTTAACTTTAAGAAGGAGATATACATAT
GCATATGGAGAAAAAAATCATCGAAGTTACCACACCGGGTAA
ACTGTTTATTGCCGGTGAATATGCAGTTGTTGAACCGGGTCA
TCCGGCAATTATTGTTGCAGTTGATCAGTTTGTTACCGTGAC
CGTTGAAGAAACCACCGATGAAGGTAGCATTCAGAGCGCAC
AGTATAGCAGCCTGCCGATTCGTTGGACCCGTCGTAATGGT
GAACTGGTTCTGGATATTCGTGAAAACCCGTTTCATTATGTT
CTGGCAGCAATTCATCTGACCGAAAAATATGCACAAGAGCA
GAATAAAGAGCTGAGCTTCTATCATCTGAAAGTTACCAGCGA
ACTGGATAGCAGCAATGGTCGTAAATATGGTCTGGGTAGCA
GCGGTGCAGTTACCGTTGGCACCGTTAAAGCACTGAATATC
TTTTATGATCTGGGCCTTGAAAACGAGGAAATCTTTAAACTG
AGCGCACTGGCACATCTGGCAGTTCAAGGTAATGGTAGCTG
TGGTGATATTGCAGCAAGCTGTTATGGTGGTTGGATTGCATT
TAGCACCTTTGATCATGATTGGGTGAATCAGAAAGTTGCAAC
CGAAACACTGACCGATCTGCTGGCAATGGATTGGCCTGAAC
TGATGATTTTTCCGCTGAAAGTTCCGAAACAGCTGCGTCTG
CTGATTGGCTGGACCGGTAGTCCGGCAAGCACCAGCGATC
TGGTTGATCGTGTTCATCAGAGCAAAGAAGAAAAACAGGCA
GCCTATGAACAGTTCCTGATGAAAAGCCGTCTGTGTGTTGA
AACCATGATCAATGGCTTTAACACCGGTAAAATTAGCGTGATT
CAGAAGCAGATTACCAAAAATCGTCAGCTGCTGGCAGAACT
GAGCAGCCTGACCGGTGTTGTTATTGAAACCGAAGCGCTGA
AAAATCTGTGTGATCTGGCAGAAAGCTATACCGGTGCAGCA
AAAAGCAGTGGTGCCGGTGGTGGTGATTGTGGTATTGTGAT
TTTTCGCCAGAAAAGCGGTATTCTGCCGCTGATGACCGCAT
GGGAAAAAGATGGTATTACACCGCTGCCGCTGCATGTTTATA
CCTATGGTCAGAAAGAATGCAAAGAGAAACACGAAAGCAAA
CGTTAAGTCGACGTCGAC

FIGURE 85, CON'T.

(SEQ ID NO:38)

332_pJL1-(CAT7aa)-PMK_Pze

TCTAGAAATAATTTTGTTTAACTTTAAGAAGGAGATATACATAT
GCATATGGAGAAAAAAATCGATCAGGTTATTCGTGCAAGCGC
ACCGGGTAGCGTTATGATTACCGGTGAACATGCAGTTGTTTA
TGGTCATCGTGCAATTGTTGCAGGTATTGAACAGCGTGCAC
ATGTTACCATTGTTCCGCGTGCAGATCGTATGTTTCGTATTAC
CAGCCAGATTGGTGCACCGCAGCAGGGTAGCCTGGATGAT
CTGCCTGCCGGTGGCACCTATCGTTTTGTTCTGGCAGCAAT
TGCCCGTCATGCACCGGATCTGCCGTGTGGTTTTGATATGG
ATATTACCAGTGGTATTGATCCGCGTTTAGGTCTGGGTAGCA
GCGCAGCAGTTACCGTTGCATGTCTGGGTGCACTGAGCCG
TCTGGCAGGTCGTGGCACCGAAGGTCTGCATGATGATGCAC
TGCGTATTGTTCGTGCCATTCAAGGTCGTGGTAGCGGTGCC
GATCTGGCAGCCAGCCTGCATGGTGGTTTTGTTGCATATCG
CGCACCGGATGGTGGTGCAGCACAGATTGAAGCACTGCCG
GTTCCGCCTGGTCCGTTTGGTCTGCGTTATGCAGGTTATAAA
ACCCCGACCGCAGAAGTGCTGCGTCTGGTTGCCGATCGTAT
GGCAGGTAATGAAGCAGCATTTGATGCCCTGTATAGCCGTAT
GGGTGCCAGCGCAGATGCAGCAATTCGTGCAGCCCAAGGT
CTGGATTGGGCAGCATTTCATGATGCGCTGAATGAATATCAG
CGTCTGATGGAACAGCTGGGTGTTAGTGATGATACCCTGGA
TGCAATTATTCGCGAAGCACGTGATGCCGGTGCAGCAGTTG
CAAAAATTTCAGGTAGCGGTCTGGGTGATTGTGTTCTGGCC
CTGGGTGATCAGCCGAAAGGCTTTGTTCCGGCAAGCATTGC
AGAAAAAGGTCTGGTTTTTGATGATTAAGTCGACGTCGAC

FIGURE 85, CON'T.

(SEQ ID NO:39)

333_pJL1-(CAT7aa)-PMK_Tha

TCTAGAAATAATTTTGTTTAACTTTAAGAAGGAGATATACATAT
GCATATGGAGAAAAAAATCATCGAAGTTAGCACACCGGGTAA
ACTGTATATTGCCGGTGAATATGCAGTTGTTGAACCGGGTCA
TCTGGCAATTATTGCAGCAGTTGATCAGTTTATCAACGTGAC
CATTGAAAGCGCAACCGAAAATGGTAGCATTCAGAGCCAGC
AGTATAGCGATCTGCCGATTCGTTGGACCCGTCGTGAAGGT
GAACTGGTTCTGGATCATCGTGAAAATCCGTTTCATTATATTC
TGGCAGCAATTCGTCTGACCGAACGTTATGCAAAAGAACAG
GGCACCCTGCTGAGCTTTTATCATCTGAAAGTTACCAGCGAA
CTGGATAATAGCAGCGGTCGTAAATATGGTCTGGGTAGCAGT
GGTGCAGTTACCGTTGGCACCGTTAAAGCACTGAACCTGTT
TTATGATCTGCAAATGGACCCGCTGATGCAGTTTAAAATCGC
AGCACTGGCACATCTGGCAGTTCAAGGTAATGGTAGCTGTG
GTGATATTGCAGCCAGCTGTTTTGGTGGTTGGCTGGCATTTA
GCACCTTTGATCATCAGTGGGTTAAAAAACGTCAAGAAACCT
GGAAAATCAGCGACCTGCTGAAAAGCGATTGGCCGAAACTG
AGCATTCAGCCGCTGCAGAGCCCGAAAAATATGCGTCTGCT
GATTGGCTGGACCGGTAGTCCGGCAAGCACCAGCGATCTG
GTTGATCAGGTTAATCAGAGCAAAGAGGATAAAGACGACATC
CAGAAAAACTATGAACAGTTTCTGACCGATAGCCATCATTGT
GTTGAGGATCTGATGGATGGTTTCGTTAAAGATGATGTGACC
AAAATCAAGAAAATGATCCGCAAAAATCGTACCCTGCTGCAG
AATCTGGCAAAAGCAACCAATGTTGTTATTGAAACACCGGCA
CTGAAACAGCTGTGTGATCTGGCAGAAAATTGTGGTGGTGC
AGCAAAAAGCAGCGGTGCCGGTGGTGGTGATTGTGGTATT
GTTATTGCCGATCAGAAAACCGGTATCCTGCCGCTGATGAG
CAAATGGGAAAAAGCAGATATTATTCCGCTGCCGCTGCATGT
TTATCATTATCGTGGTGGTCCGAAATAAGTCGACGTCGAC

FIGURE 85, CON'T.
(SEQ ID NO:40)

334_pJL1-(CAT7aa)-PMK_Eco

TCTAGAAATAATTTTGTTTAACTTTAAGAAGGAGATATACATAT
GCATATGGAGAAAAAAATCCTGAAGAAAATCAAACATGATCC
GACGCTGAATAGCCAAGGTCAGGGTTTTGCACCGGGTAAAC
TGTATCTGGCAGGCGAATATGCAGTTCTGGCACCGCGTCAG
CCTGCAATTCTGCTGGCACTGAATCGTTATGTTAAAGTGACC
ATTAAACCGAGCAGCACCCTGAATCAGGGCATTCTGAGCCA
GGCAAAAGGTCAGGCAGATTATCATTATCAGCGTCAGAATGG
TAGCATTCCGCAGAAAGAAGCATATTGGACCTATTGTCTGGC
AGCCATTCAGATTGTTGAAGTTCTGTTTCGTCAGAAAGGCCA
GGTTATTGCCGATTATCATCTGGAAACCATGAGCGATCTGGT
TGAAGAAGTTAGCGGCAAAAAATTCGGTCTGGGTAGCAGCG
GTGCAATTACCGTTGCAACCATTCGTGCACTGCTGGATTTTT
ATGGTTATCAGGCCGATAGTCCGCTGGATGTGTATAAACTGG
CCGTTCTGGCCCTGGTTAATCTGGGTAATAATGGTAGCTTTG
GTGATCTGGCAGCAGCAGCATTTGGTGGTTGGGTTTATTATC
AGGCACCGGATCGTCAGTGGCTGGCAGATCAGGTTAGCCA
GAATCAGACCATTGATTTCTTTCTGGAAAATAGCTGGCCGAA
CCTGCAGATTGAAAGCCTGCCGGTTCCGAGCAAAATTGATT
TCCTGGTTGCATGGACCCAGAGTCCGGCAAGCAGCGATCAT
TTTGTTGCAAACTTTAAAGAAGCCAGCCAGCAAGAACCGCA
GCGTTATCAAGAATTTCTGGCCGAAAATAAAGATGCAGTGCT
GGCCCTGAAAACCGCACTGATCCAGGATGATGTTGGTCAGA
GCCAGAGCCTGATTAACAAAATTGGTCAGCAGCTGGATAATC
TGAGCCATCATCTGAAACTGGGTATTCTGACACCGCAGCTG
GAAACAATGATTAGCCTGGCACAGGTGTATGGTTATGCAGCA
AAAAGCAGTGGTGCCGGTGGTGGTGATTGTGGTATTGCATT
AGGTGGTCTGGAAGCACGTAAAACCGATCTGATTCGTGCAT
GGGAAAAACAAGAAATCACCTATCTGGATCTGCAAATCAGCC
AGACCTTTTAAGTCGACGTCGAC

FIGURE 85, CON'T.

(SEQ ID NO:41)

283_pJL1-(CAT5aa)-PMD1_Sce

TCTAGAAATAATTTTGTTTAACTTTAAGAAGGAGATATACATAT
GGAGAAAAAAATCACTGTGTACACGGCCTCTGTGACTGCCC
CTGTCAATATCGCCACTTTGAAGTATTGGGGAAAACGGGACA
CAAAGTTGAACCTTCCTACTAACTCATCTATCTCGGTCACGT
TATCACAGGATGACCTACGCACATTAACTAGCGCTGCGACG
GCCCCAGAGTTTGAACGAGACACGTTATGGTTAAACGGGGA
ACCGCACTCAATCGACAACGAACGCACGCAGAACTGCCTTC
GAGACTTGCGACAGTTACGCAAGGAAATGGAATCAAAGGAC
GCAAGTTTGCCTACGTTAAGCCAGTGGAAACTACACATCGTC
TCCGAAAACAATTTTCCAACGGCCGCGGGCTTGGCGTCTTC
TGCGGCGGGGTTTGCGGCCTTGGTCAGCGCCATCGCGAAG
TTGTACCAGTTGCCGCAATCCACGTCCGAAATCAGCCGCAT
CGCCCGCAAGGGAAGCGGCTCTGCGTGCCGCTCATTGTTT
GGTGGGTACGTCGCATGGGAAATGGGGAAAGCGGAAGATG
GCCATGATTCCATGGCCGTCCAGATCGCCGACTCAAGCGAC
TGGCCACAAATGAAAGCGTGCGTCTTAGTGGTTTCAGATATC
AAAAAGGATGTCTCCTCTACGCAAGGCATGCAGTTGACTGT
CGCCACTTCTGAATTATTTAAAGAACGCATCGAACATGTCGT
CCCGAAGCGCTTTGAAGTCATGCGGAAAGCAATCGTGGAAA
AAGATTTCGCAACTTTTGCCAAGGAAACGATGATGGATTCTA
ATAGCTTCCATGCAACGTGCTTAGACAGCTTCCCACCGATCT
TCTACATGAACGACACGAGTAAGCGGATCATCTCTTGGTGTC
ACACTATCAACCAATTTTACGGGGAAACGATCGTGGCCTACA
CATTTGATGCCGGCCCGAACGCGGTCTTATACTACTTAGCG
GAAAACGAGTCAAAACTATTTGCCTTTATCTATAAATTATTTGG
GAGCGTGCCAGGGTGGGACAAGAAATTTACGACGGAGCAA
TTGGAGGCGTTCAATCATCAGTTTGAATCGAGCAATTTTACG
GCCCGGGAATTGGATTTAGAGTTACAGAAGGATGTGGCACG
CGTCATCTTGACGCAGGTCGGCTCCGGGCCGCAGGAAACG
AATGAAAGCTTAATCGACGCCAAGACGGGCTTGCCGAAGGA
ATAAGGATCCTGACTCGAGCACCACCACCACCACCACTGAG
ATCGTCGAC

FIGURE 85, CON'T.

(SEQ ID NO:42)

335_pJL1-(CAT7aa)-PMD_Sau

TCTAGAAATAATTTTGTTTAACTTTAAGAAGGAGATATACATAT
GCATATGGAGAAAAAAATCATCAAAAGCGGTAAAGCACGTGC
CCATACCAATATTGCACTGATCAAATATTGGGGCAAAAAAGAT
GAAGCCCTGATTATTCCGATGAACAATAGCATTAGCGTTACC
CTGGAAAAGTTCTACACCGAAACCAAAGTGACCTTTAATGAT
CAGCTGACCCAGGATCAGTTTTGGCTGAATGGTGAAAAAGT
TAGCGGCAAAGAACTGGAAAAAATCAGCAAATATATGGATAT
CGTGCGTAATCGTGCAGGCATTGATTGGTATGCAGAAATTGA
AAGCGATAACTTTGTTCCGACCGCAGCAGGTCTGGCAAGCA
GCGCAAGCGCCTATGCAGCACTGGCAGCAGCATGTAATCAG
GCACTGGATATGCAGCTGAGCGATAAAGACCTGAGCCGTCT
GGCACGTATTGGTAGCGGTAGCGCAAGCCGTAGCATTTATG
GTGGTTTTGCAGAATGGGAGAAAGGTTATAGTGATGAAACC
AGCTATGCAGTTCCGCTGGAAAGCAATCATTTTGAAGATGAT
CTGGCCATGATCTTCGTTGTGATTAACCAGCATAGCAAAAAA
GTTCCGAGCCGTTATGGTATGAGTCTGACCCGTAATACCAGC
CGTTTTTATCAGTACTGGCTGGATCATATTGATGAGGACCTG
GCAGAAGCAAAAGCAGCAATTCAGGATAAAGATTTCAAACGT
CTGGGCGAAGTGATTGAAGAAAATGGTCTGCGTATGCATGC
AACCAATCTGGGTAGCACCCCTCCGTTTACCTATCTGGTTCA
AGAAAGCTATGACGTTATGGCACTGGTTCATGAATGTCGTGA
AGCAGGTTATCCGTGTTATTTTACCATGGATGCAGGTCCGAA
TGTGAAAATTCTGGTGGAAAAAAAGAACAAACAGCAGATCAT
CGATAAACTGCTGACGCAGTTTGATAACAACCAGATTATTGA
CAGCGATATCATTGCCACCGGCATTGAAATTATCGAATAAGTC
GACGTCGAC

FIGURE 85, CON'T.

(SEQ ID NO:43)

336_pJL1-(CAT7aa)-PMD_Spn

TCTAGAAATAATTTTGTTTAACTTTAAGAAGGAGATATACATAT
GCATATGGAGAAAAAAATCGATCGTGAACCGGTTACCGTTCG
TAGCTATGCAAATATTGCCATCATCAAATACTGGGGCAAAAAG
AAAGAAAAAGAGATGGTTCCGGCAACCAGCAGCATTAGTCT
GACCCTGGAAAATATGTATACCGAAACCACACTGAGTCCGCT
GCCTGCAAATGTTACCGCAGATGAATTTTACATTAATGGCCA
GCTGCAGAACGAAGTTGAACATGCAAAAATGAGCAAAATCAT
CGATCGTTATCGTCCGGCAGGCGAAGGTTTTGTTCGTATTG
ATACCCAGAATAATATGCCGACCGCAGCAGGTCTGAGCAGC
AGCAGTAGCGGTCTGAGCGCACTGATTAAAGCATGTAATGC
CTATTTCAAACTGGGCTTAGATCGTAGTCAGCTGGCACAAGA
AGCAAAATTTGCAAGCGGTAGCAGCAGCCGTTCATTTTATGG
TCCGTTAGGTGCATGGGATAAAGATAGCGGTGAAATTTATCC
GGTTGAAACCGATCTGAAACTGGCAATGATTATGCTGGTTCT
GGAAGATAAGAAAAAACCGATTAGCAGCCGTGATGGTATGAA
ACTGTGTGTTGAAACCAGCACCACCTTTGATGATTGGGTTC
GTCAGAGCGAAAAAGATTATCAGGATATGCTGATCTATCTGA
AAGAGAACGATTTCGCCAAAATTGGTGAACTGACCGAAAAA
AATGCCCTGGCAATGCATGCAACCACCAAAACCGCAAGTCC
GGCATTTAGCTATCTGACCGATGCAAGCTATGAAGCAATGGC
ATTTGTTCGTCAGCTGCGTGAAAAAGGTGAAGCATGTTATTT
TACCATGGATGCAGGTCCGAATGTGAAAGTTTTTTGCCAAGA
AAAGGATCTGGAACACCTGAGCGAAATTTTTGGTCAGCGTT
ATCGCCTGATTGTTAGCAAAACCAAAGACCTGAGCCAGGAT
GATTGTTGTTAAGTCGACGTCGAC

FIGURE 85, CON'T.

(SEQ ID NO:44)

337_pJL1-(CAT7aa)-PMD_Pku

TCTAGAAATAATTTTGTTTAACTTTAAGAAGGAGATATACATAT
GCATATGGAGAAAAAAATCGCCAATGCAGAAAAATGGGTTCT
GACCGTTACCGCACAGACCCCGACCAATATTGCAGTTATCAA
ATATTGGGGTAAAGGCGACGAGGATCTGATTCTGCCGATTAA
TGATAGCATTAGCGTTACCTTAGATCCGGACCATCTGTGTAC
CACCACCAGTGTTGCAGTTAGTCCGGCATTTACCCATGATCG
TATGTGGCTGAATGGTAAAGAAGTTAGCCTGTCAGGCGGTC
GTTTTCAGAATTGTCTGCGTGAAGTTCGTAGCTGTGCAAATG
ATGTTGAAGATGAAAAAGAAGGCGTTCTGAAAAGCCTGAAA
GGTCTGGGTGATCTGCATGTTCACATGTGTCCGACCATTGAT
TTTCCGACCGCAGCAGGTCTGGCAAGCAGCGCAGCTGGCC
TGGCATGTCTGGTTTTTAGCCTGGCAAAACTGATGAACGTG
AAAGAAGATCATAGCCGTCTGAGCGCAATTGCACGTCAAGG
TAGCGGTAGCGCATGTCGTAGCCTGTATGGTGGTTTTGTTAA
TGGTAGCTTTCTGAAAGAGGAAAACGGTAGCGATAGCATTG
CAGTTCAGCTGGCCGATGAAAAACATTGGGATGATCTGGTT
ATTATCATTGCCGTTGTTAGCAGCCGTCAGAAAGAAACCAGC
AGCACCAGCGGTATGCGTGAAACCGTTGAAACCAGTATGCT
GCTGCAACATCGTGCAAAAGAAGTTGTGCCGGAACGTATTAT
TCAGATGGAAGAGGCCATTAAAAACCGCGATTTTCCAGCATT
TGCACGTCTGACCTGTGCAGATAGCAATCAGTTTCATGCAGT
TTGTCTGGATACCCTGCCTCCGATCTTTTATATGAATGATACC
AGCCATCGTATCATCAGCTGTGTGGAAAAATGGAATTGTAGC
GAAGGTACACCGCAGGTTGCATATACCTTTGATGCAGGTCC
GAAATGCCGTATTAACTTTACCCAGACCGAAAAACTGCTGCC
GAATTTTTTCAAAGGTTGCAGCTTTCATTTTCCGCCTAATAGC
GATACCGATCTGAATAGCTATGTTATTGGTGATCAGACCATTC
TGCAGGATGCAGGTATTAAAGACCTGAAAGATATTGAAGCAC
TGAGCACCCCTCCGGAAACCAAAGAAAATCTGAGTGCACAG
AAATATCGTGGTGATGTGAGCTATTTTATCTGCACCAAACCT
GGTCGTGGTCCGGCAGTTGTTAATGATGAAAGCCGTAGCCT
GATTAATCCGGAATTTGGTCTGCCGAAATAAGTCGACGTCGA
C

FIGURE 85, CON'T.

(SEQ ID NO:45)

338_pJL1-(CAT7aa)-PMD_Pze

TCTAGAAATAATTTTGTTTAACTTTAAGAAGGAGATATACATAT
GCATATGGAGAAAAAAATCACCGATGCAGTTCGTGACATGAT
TGCCCGTGCAATGGCAGGCGCAACCGATATTCGTGCAGCC
GAAGCCTATGCACCGAGTAATATTGCACTGAGCAAATATTGG
GGTAAACGTGATGCAGCACGTAATCTGCCGCTGAATAGCAG
CGTTAGCATTAGCCTGGCAAATTGGGGTAGTCATACCCGTGT
TGAAGGTAGCGGCACCGGTCATGATGAAGTGCATCATAATG
GCACCCTGTTAGATCCGGGTGATGCATTTGCACGTCGTGCA
CTGGCATTTGCAGACCTGTTTCGTGGTGGTCGTCATCTGCC
TCTGCGTATTACCACACAGAATAGCATTCCGACCGCAGCAG
GTCTGGCAAGCAGCGCAAGCGGTTTTGCAGCACTGACCCG
TGCATTAGCCGGTGCATTTGGTCTGGATCTGGATGATACCGA
TCTGAGCCGTATTGCACGTATTGGTAGCGGTAGCGCAGCCC
GTAGCATTTGGCATGGTTTTGTTCGTTGGAATCGTGGTGAA
GCCGAAGATGGTCATGATAGCCATGGTGTTCCGCTGGATCT
GCGTTGGCCTGGTTTTCGTATTGCAATTGTTGCAGTTGATAA
AGGTCCGAAACCGTTTAGCAGCCGTGATGGCATGAATCATA
CCGTTGAAACCAGTCCGCTGTTTCCGCCTTGGCCTGCACAG
GCCGAAGCAGATTGTCGTGTTATTGAAGATGCAATTGCCGC
ACGTGATATGGCAGCACTGGGTCCGCGTGTGGAAGCAAATG
CCCTGGCAATGCATGCAACCATGATGGCAGCCCGTCCGCCT
CTGTGTTATCTGACCGGTGGTAGCTGGCAGGTTCTGGAACG
TCTGTGGCAGGCACGTGCAGATGGTCTGGCAGCATTTGCCA
CCATGGATGCAGGTCCGAATGTTAAACTGATTTTTGAAGAAA
GCAGTGCCGCAGATGTTCTGTACCTGTTTCCGGATGCAAGC
CTGATTGCACCGTTTGAAGGTCGTTAAGTCGACGTCGAC

FIGURE 85, CON'T.

(SEQ ID NO:46)

339_pJL1-(CAT7aa)-PMD_Hme

TCTAGAAATAATTTTGTTTAACTTTAAGAAGGAGATATACATAT
GCATATGGAGAAAAAAATCAAAGCAACCGCAAAAGCACATCC
GATTCAAGGTCTGGTTAAATATCATGGTATGCGCGATCCGGA
AATTCGTCTGCCGTATCATGATTCAATTAGCGTTTGTACCGCA
CCGAGCCATACCAAAACCACCGTTGAATTTCTGCCGGATGC
AGATGAAGATGTTTATGTTATTGGTGGTGAAGAGGTTGAAGG
TCGTGGTGCAGAACGTATTCGTGATGTTGTTGAACATGTGC
GTGATCTGGCAGATTTTGATCATCGTGTTCGTCTGGAAAGC
GAAAATAGCTTTCCGAGCAATATTGGTTTTGGCAGCAGCAGC
TCAGGTTTTGCCGCAGCCGCAATGGCACTGGCAGAAGCAG
CCGATCTGGATCTGACCCGTCCGGAAATCAGCACCATTGCA
CGTCGTGGTAGCAGCAGCGCAGCACGTGCAGTTACCGGTG
CATTTAGCCATCTGTATAGCGGTATGAATGATACCGATTGTCG
TAGCGAACGTATTGAAACGGATCTGGAAGATGATCTGCGTAT
TGTTGCAGCCCATGTTCCGGCATATAAAGAAACCGAACAGG
CACATGCAGAAGCCGCAGATAGCCACATGTTTCAGGCACGT
ATGGCACACATGCATAAGCAGATTGATGATATGCGTGATGCA
CTGTATGAAGCCGATTTTGATGCAGCATTTGAACTGGCCGAA
CATGATAGCCTGAGCCTGGCAGCAACCACCATGACCGGTCC
GGCAGGTTGGGTTTATTGGCAGCCTCGTACCATTGCAGTTT
TTAATGCAATTCGTGAACTGCGTGCCGAAGAAGATATTCCTG
CATATTTTAGCACCGATACCGGTGCCAGCGTTTATATCAATAC
CACCACCGAATATGTTGACCGTGTTGAAAAAGTTGTTGCCG
ATTGTAATGTTGAAACCGATGTTTGGGAAGTTGGTGGTCCTG
CCGAAATTCTGGATGAAAGTGATGCCCTGTTTTAAGTCGACG
TCGAC

FIGURE 85, CON'T.

(SEQ ID NO:47)

340_pJL1-(CAT7aa)-PMD_Zga

TCTAGAAATAATTTTGTTTAACTTTAAGAAGGAGATATACATAT
GCATATGGAGAAAAAAATCACCGTGAAAGAATTTATCCCGAG
TCCGTATACCAAACCGGTTGCAAGCGGTAATACCCGTTATAA
AAGCCCGAGTAATATTGCCCTGGTGAAATATTGGGGCAAAAA
AGAAAATCAGATTCCGGCAAATCCGAGCATTAGCTTTACCCT
GAATGAATGTGCAACCGTTACCACACTGAGCTATCGTAAAGC
AGATCGTCCGAATGATGCATTTAGCTTTGAAATTAGCCTGGA
CGGCAAGAAAGAAGAAGGTTTTAAACCGAAAATCAAAACCTT
TTTCGAACGCGTGTATCCGTATCTGCCGTTTCTGAAAGAATA
TCACTTTGAGATTGAAACCAGCAACAGCTTTCCGCATAGCAG
CGGTATTGCAAGCAGCGCCAGCGGTATGAGCGCACTGGCA
CTGTGTCTGATGGAAATTGAACGTAATTTAGATCCGGGTATG
AGTGCCGATTTTTTCAACCGTAAAGCAAGCTTTCTGGCACGT
TTAGGTAGCGGTAGCGCAGCACGTAGCATTAAAGGTAGCCT
GGTTCAGTGGGGTGAACATGCAGGCACCGAAGGTAGCAGC
GATCTGTATGGTATTGAATATCCGTATAAAGTGCACAGCGTGT
TCAACGATTATTGCGATACCATTCTGCTGGTTGATAAAGGTC
AGAAACAGGTTAGCAGCACCGTTGGTCATGATCTGATGCATA
ATCATCCGTTTAGCAAACAGCGTTTTGATCAGGCACATGAAA
ATCTGAGCAAACTGCGTAGCATTTTTGAAAGCGGCAATCTG
GATGAATTTATTGGTCTGGTTGAAAGCGAAGCACTGACCCT
GCATGCAATGATGATGACCAGCCGTCCGTATTTTATCCTGAT
GAAACCGAATACGCTGGAAATTATCAATCGCATTTGGGCATA
TCGTGAAGCCACCAAAACACATGTTTGTTTTACCCTGGATGC
CGGTGCAAATGTTCATGTTCTGTATCCGAAAAATGAAAAGGC
ACTGGTGGAACGTTTTATTGCAGATGAACTGGCAGGTTATTG
TCAGAATGGTCAGTTTATTCATGATCATGTTGGTCGTGGTGC
CCGTAAAATCAATTAAGTCGACGTCGAC

FIGURE 85, CON'T.

(SEQ ID NO:48)

284_pJL1-(CAT5aa)-IDI_Eco

TCTAGAAATAATTTTGTTTAACTTTAAGAAGGAGATATACATAT
GGAGAAAAAAATC
CAAACGGAACACGTCATTTTATTGAATGCACAGGGAGTTCCC
ACGGGTACGCTGGAAAAGTATGCCGCACACACGGCAGACA
CCCGCTTACATCTCGCGTTCTCCAGTTGGCTGTTTAATGCCA
AAGGACAATTATTAGTTACCCGCCGCGCACTGAGCAAAAAA
GCATGGCCTGGCGTGTGGACTAACTCGGTTTGTGGGCACC
CACAACTGGGAGAAAGCAACGAAGACGCAGTGATCCGCCG
TTGCCGTTATGAGCTTGGCGTGGAAATTACGCCTCCTGAATC
TATCTATCCTGACTTTCGCTACCGCGCCACCGATCCGAGTG
GCATTGTGGAAAATGAAGTGTGTCCGGTATTTGCCGCACGC
ACCACTAGTGCGTTACAGATCAATGATGATGAAGTGATGGAT
TATCAATGGTGTGATTTAGCAGATGTATTACACGGTATTGATG
CCACGCCGTGGGCGTTCAGTCCGTGGATGGTGATGCAGGC
GACAAATCGCGAAGCCAGAAAACGATTATCTGCATTTACCCA
GCTTAAATAAGGATCCTAACTCGAGCACCACCACCACCACCA
CTGAGATCGTCGAC

FIGURE 85, CON'T.

(SEQ ID NO:49)

285_pJL1-(CAT5aa)-IDI_Bsu

TCTAGAAATAATTTTGTTTAACTTTAAGAAGGAGATATACATAT
GGAGAAAAAAATCACCCGTGCAGAACGTAAACGTCAGCATA
TCAATCATGCACTGAGCATTGGTCAGAAACGTGAAACCGGT
CTGGATGATATTACCTTTGTTCATGTTAGCCTGCCGGATCTG
GCACTGGAACAGGTTGATATTAGCACCAAAATTGGTGAACTG
AGCAGCAGCAGCCCGATTTTTATCAATGCAATGACCGGTGG
TGGTGGTAAACTGACCTATGAAATTAACAAAAGCCTGGCACG
TGCAGCAAGCCAGGCAGGTATTCCGCTGGCAGTTGGTAGC
CAGATGAGCGCACTGAAAGATCCGTCAGAGCGTCTGTCTTA
TGAGATCGTGCGGAAAGAAAATCCGAATGGACTCATTTTTGC
GAATTTAGGTAGCGAGGCTACCGCCGCGCAGGCTAAAGAG
GCGGTCGAAATGATTGGCGCGAACGCGCTGCAGATCCATCT
GAACGTAATTCAGGAGATCGTGATGCCGGAAGGCGATCGTT
CGTTTAGTGGTGCCCTCAAGCGTATTGAGCAGATTTGTTCTC
GCGTCTCAGTGCCGGTTATCGTGAAAGAGGTAGGATTTGGA
ATGTCGAAAGCTTCCGCGGGTAAGCTGTACGAGGCAGGGG
CCGCTGCAGTTGATATTGGCGGCTATGGGGGTACGAACTTC
AGCAAAATTGAAAACCTCCGTCGCCAGCGCCAAATCTCCTT
CTTCAACAGCTGGGGCATCTCTACGGCTGCATCATTAGCAG
AGATCCGTTCTGAATTTCCGGCAAGCACCATGATTGCAAGC
GGTGGTCTGCAGGATGCACTGGATGTTGCAAAAGCAATTGC
ACTGGGTGCAAGCTGTACCGGTATGGCAGGTCATTTTCTGA
AAGCACTGACCGATAGCGGTGAAGAAGGTCTGCTGGAAGA
AATTCAGCTGATTCTGGAAGAACTGAAACTGATTATGACCGT
TCTGGGTGCACGTACCATTGCCGATCTGCAGAAAGCACCGC
TGGTTATTAAAGGTGAAACCCATCATTGGCTGACAGAACGTG
GTGTTAATACCAGCAGCTATAGCGTTCGTTAAGGATCCTGAC
TCGAGCACCACCACCACCACCACTGAGATCGTCGAC

FIGURE 85, CON'T.
(SEQ ID NO:50)

341_pJL1-(CAT7aa)-IDI_Sce

TCTAGAAATAATTTTGTTTAACTTTAAGAAGGAGATATACATAT
GCATATGGAGAAAAAAATCACCGCAGATAATAACAGCATGCC
GCATGGTGCAGTTTCAAGCTATGCAAAACTGGTTCAGAATCA
GACACCGGAAGATATCCTGGAAGAATTTCCTGAAATTATTCC
GCTGCAGCAGCGTCCGAATACACGTAGCAGCGAAACCAGC
AATGATGAAAGCGGTGAAACCTGTTTTAGCGGTCATGATGAA
GAACAAATCAAGCTGATGAACGAAAACTGCATTGTTCTGGAT
TGGGATGATAATGCAATTGGTGCAGGCACCAAAAAAGTTTGT
CATCTGATGGAAAACATCGAGAAAGGTCTGCTGCATCGTGC
ATTTAGCGTGTTTATCTTTAATGAACAGGGTGAACTGCTGCT
GCAACAGCGTGCAACCGAAAAAATCACCTTTCCGGATCTGT
GGACCAATACCTGTTGTAGCCATCCGCTGTGTATTGATGATG
AACTGGGTCTGAAAGGTAAACTGGACGATAAAATCAAAGGT
GCAATTACCGCAGCCGTTCGCAAACTGGATCACGAACTGGG
TATTCCGGAAGATGAAACCAAAACACGTGGCAAATTTCATTT
TCTGAACCGCATCCATTATATGGCACCGAGCAATGAACCGTG
GGGTGAACATGAAATTGATTACATCCTGTTCTACAAAATCAAC
GCCAAAGAAAACCTGACCGTTAATCCGAATGTTAATGAAGTG
CGTGATTTCAAATGGGTGAGCCCGAATGATCTGAAAACCATG
TTTGCCGATCCGAGCTATAAATTCACCCCGTGGTTTAAAATC
ATCTGCGAAAACTACCTGTTTAACTGGTGGGAACAGCTGGA
TGATCTGAGCGAAGTTGAAAATGATCGTCAGATTCATCGTAT
GCTGTAAGTCGACGTCGAC

FIGURE 85, CON'T.

(SEQ ID NO:51)

342_pJL1-(CAT7aa)-IDI_Sly

TCTAGAAATAATTTTGTTTAACTTTAAGAAGGAGATATACATAT
GCATATGGAGAAAAAAATCGTTGATGTTATTGCCGATGCAAAT
ATGGATGCAGTTCAGCGTCGTCTGATGTTTGATGATGAATGT
ATTCTGGTGGACGTGAACGATAAAGTTGTTGGTCATGAGAG
CAAATATAACTGCCACCTGATGGAAAAAATCGAAAGCGAAAA
TCTGCTGCATCGTGCCTTTAGCGTTTTTCTGTTTAACAGCAA
ATATGAGCTGCTGCTGCAACAGCGTAGCGCAACCAAAGTTA
CCTTTCCGCTGGTTTGGACCAATACCTGTTGTAGCCATCCGC
TGTATCGTGAAAGCGAACTGATTGAAGAAAATGCACTGGGT
GTTCGTAATGCAGCACAGCGTAAACTGCTGGATGAACTGGG
TATTCCGGCAGAAGATGTTCCGGTTGATCAGTTTACACCGCT
GGGTCGTATGCTGTATAAAGCACCGAGTGATGGTAAATGGG
GTGAACATGAACTGGATTATCTGCTGTTTATTGTGCGTGATG
TTAACGTTCATCCGAATCCTGATGAAGTTGCCGATATCAAATA
CGTGAATCAAGAACAGCTGAAAGAACTGCTGCGTAAAGCAG
ATGCCGGTGAAGAAGGTCTGAAACTGAGCCCGTGGTTTCGT
CTGGTTGTTGATAATTTTCTGTTCAAATGGTGGGACCATGTT
GAAAAAGGCACCATTCAAGAGGCAGCAGATATGAAAACCATT
CACAAACTGACCTAAGTCGACGTCGAC

FIGURE 85, CON'T.

(SEQ ID NO:52)

343_pJL1-(CAT7aa)-IDI_Str

TCTAGAAATAATTTTGTTTAACTTTAAGAAGGAGATATACATAT
GCATATGGAGAAAAAAATCACCAGCGCACAGCGTAAAGATG
ATCATGTTCGTCTGGCAATTGAACAGCATAATGCACATAGCG
GTCGTAACCAGTTTGATGATGTTAGCTTTGTTCATCATGCACT
GGCAGGTATTGATCGTCCGGATGTTAGCCTGGCAACCAGCT
TTGCAGGTATTAGCTGGCAGGTTCCGATTTATATCAATGCAAT
GACCGGTGGTAGCGAAAAAACCGGTCTGATTAATCGTGATC
TGGCAACCGCAGCACGTGAAACCGGTGTTCCGATTGCAAG
CGGTAGCATGAATGCATATATCAAAGATCCGAGCTGTGCAGA
TACCTTTCGTGTTCTGCGTGATGAAAATCCGAATGGTTTTGT
GATTGCCAATATTAACGCAACCACCACCGTTGATAATGCCCA
GCGTGCAATTGATCTGATTGAAGCAAATGCACTGCAGATCCA
TATTAACACCGCACAAGAAACCCCGATGCCGGAAGGTGATC
GTAGCTTTGCAAGCTGGGTTCCGCAGATTGAAAAAATTGCA
GCAGCAGTTGATATTCCGGTGATCGTTAAAGAAGTTGGTAAC
GGTCTGAGCCGTCAGACCATTCTGCTGCTGGCCGATCTGG
GTGTTCAGGCAGCAGATGTGAGCGGTCGTGGTGGCACCGA
TTTTGCACGTATTGAAAATGGTCGTCGTGAACTGGGTGATTA
TGCATTTCTGCATGGTTGGGGTCAGAGCACCGCAGCATGTC
TGCTGGATGCACAGGATATTAGCCTGCCGGTTCTGGCAAGC
GGTGGTGTTCGTCATCCGCTGGATGTTGTTCGTGCACTGGC
CCTGGGTGCACGTGCCGTTGGTAGCAGCGCAGGTTTTCTG
CGTACCCTGATGGATGATGGTGTTGATGCACTGATTACCAAA
CTGACCACCTGGCTGGATCAGCTGGCAGCCCTGCAGACCA
TGCTGGGAGCACGTACCCCTGCCGATCTGACCCGTTGTGAT
GTTCTGCTGCATGGTGAACTGCGCGATTTTTGTGCAGATCG
TGGTATTGATACCCGTCGTCTGGCCCAGCGTAGCAGCAGTA
TTGAAGCGCTGCAGACAACCGGTAGCACCCGTTAAGTCGAC
GTCGAC

FIGURE 85, CON'T.

(SEQ ID NO:53)

344_pJL1-(CAT7aa)-IDI_Pze

TCTAGAAATAATTTTGTTTAACTTTAAGAAGGAGATATACATAT
GCATATGGAGAAAAAAATCACCGATAGCAAAGATCATCATGT
TGCAGGTCGTAAACTGGATCATCTGCGTGCACTGGATGATG
ATGCAGATATTGATCGTGGTGATAGCGGTTTTGATCGTATTG
CACTGACCCATCGTGCACTGCCGGAAGTTGATTTTGATGCA
ATTGATACCGCAACCAGCTTTCTGGGTCGTGAACTGAGCTTT
CCGCTGCTGATTAGCAGCATGACCGGTGGTACAGGTGAAGA
AATTGAACGTATTAATCGTAATCTGGCAGCCGGTGCCGAAGA
GGCACGTGTTGCAATGGCAGTTGGTAGCCAGCGTGTTATGT
TTACCGATCCGAGCGCACGTGCATCATTTGACCTGCGTGCC
CATGCACCGACCGTGCCGCTGCTGGCAAATATTGGTGCAGT
GCAGCTGAATATGGGTCTGGGTCTGAAAGAATGTCTGGCAG
CAATTGAAGTTCTGCAGGCAGATGGTCTGTATCTGCACCTG
AATCCGCTGCAAGAAGCAGTTCAGCCGGAAGGTGATCGTGA
TTTTGCCGATCTGGGTAGCAAAATTGCAGCCATTGCACGTG
ATGTTCCGGTTCCGGTGCTGCTGAAAGAAGTTGGCTGCGGT
CTGAGCGCAGCCGATATTGCAATTGGTCTGCGTGCCGGTAT
TCGTCATTTTGATGTTGCCGGTCGCGGTGGCACCAGTTGGA
GCCGTATTGAATATCGTCGTCGTCAGCGTGCAGATGATGATT
TAGGTCTGGTTTTTCAGGATTGGGGACTGCAGACCGTTGAT
GCACTGCGTGAAGCACGTCCGGCACTGGCAGCACATGATG
GCACCAGCGTTCTGATTGCAAGCGGTGGTATTCGTAATGGT
GTTGATATGGCCAAATGTGTTATTCTGGGTGCCGATATGTGT
GGTGTTGCAGCACCGCTGTTAAAAGCAGCACAGAATAGCCG
TGAAGCAGTTGTTAGCGCAATTCGCAAACTGCATCTGGAATT
TCGTACCGCAATGTTTCTGTTAGGTTGTGGCACCCTGGCCG
ATCTGAAAGATAATAGCAGCCTGATTCGTCAGTAAGTCGACG
TCGAC

FIGURE 85, CON'T.
(SEQ ID NO:54)

345_pJL1-(CAT7aa)-IDI_Sau

TCTAGAAATAATTTTGTTTAACTTTAAGAAGGAGATATACATAT
GCATATGGAGAAAAAAATCAGCGATTTTCAGCGTGAACAGC
GCAAAAATGAACATGTTGAAATTGCAATGGCACAGAGTGATG
CAATGCATAGCGATTTTGATAAAATGCGCTTTGTGCATCATTC
CATTCCGAGCATTAATGTGAACGATATTGATCTGACCAGCCA
GACACCGGATCTGACAATGACCTATCCGGTTTATATCAATGC
AATGACCGGTGGTAGCGAATGGACCAAAAACATTAATGAAAA
ACTGGCAGTTGTTGCCCGTGAAACCGGTCTGGCAATGGCA
GTTGGTAGCACCCATGCAGCACTGCGTAATCCGCGTATGGC
AGAAACCTTTACCATTGCACGTAAAATGAATCCGGAAGGCAT
GATTTTTAGCAATGTTGGTGCAGATGTTCCGGTTGAAAAAGC
ACTGGAAGCCGTTGAACTGCTGGAAGCACAGGCACTGCAG
ATTCATGTTAATAGTCCGCAAGAACTGGTTATGCCGGAAGGT
AATCGTGAATTTGTTACCTGGCTGGATAATATTGCAAGCATTG
TTAGCCGTGTTTCAGTTCCGGTTATCATTAAAGAAGTTGGTT
TCGGCATGAGCAAAGAACTGATGCATGATCTGCAGCAGATT
GGTGTTAAATATGTTGATGTTAGCGGTAAAGGTGGCACCAAC
TTTGTGGATATTGAAAATGAACGTCGTGCCAACAAAGATATG
GATTATCTGAGCAGCTGGGGTCAGAGCACCGTTGAAAGCCT
GCTGGAAACCACCGCATATCAGAGCGAAATTAGCGTTTTTGC
AAGCGGTGGTCTGCGTACACCGCTGGATGCAATTAAAAGCC
TGGCACTGGGTGCAAAAGCAACCGGTATGAGCCGTCCGTTT
CTGAATCAGGTTGAAAATAATGGTATTGCCCATACCGTTGCC
TATGTGGAAAGCTTTATTGAACACATGAAAAGCATCATGACC
ATGCTGGATGCGAAAAATATCGATGATCTGACACAGAAGCAG
ATCGTTTTTAGTCCGGAAATTCTGAGCTGGATTGAACAGCGT
AATCTGAACATTCATCGTGGCTAAGTCGACGTCGAC

FIGURE 85, CON'T.

(SEQ ID NO:55)

346_pJL1-(CAT7aa)-IDI_Scl

TCTAGAAATAATTTTGTTTAACTTTAAGAAGGAGATATACATAT
GCATATGGAGAAAAAAATCGTTATGCCGACCAGTCCGACCTC
ACCGACCGCAGCAAATAGCGTTAGCAATGGCACCAGCAATG
ATGTTCCGGATGGTGCAGCACGTGAAATTCTGCTGGAACTG
GTTGATGAACATGGCACCACCATTGGCACCGCAGAAAAACT
GGCAGCACATCAGCCTCCGGGTCTGCTGCATCGTGCATTTA
GCGTTTTTCTGTTTGATGATCGTGGTCGTCTGCTGCTGCAA
CAGCGTGCACTGGGTAAATATCATAGCCCTGGTGTTTGGAG
CAATACCTGTTGTGGTCATCCGTATCCGGGTGAAGCACCGT
TTGCAGCCGCAGCACGTCGTACCCATGAAGAACTGGGTATT
AGTCCGGCACTGCTGGCAGAAGCAGGCACCGTTCGTTATAA
TCATCCTGATCCGGATAGCGGTCTGGTTGAACAAGAATATAA
TCACCTGTTTGTTGGTCTGGTTCAGGCAAGTCCGGAACCAG
ATCCGGAAGAAGTTGGCGGTACAGTTTTTGTTACACCGGGT
GAACTGGCAGAACGTCATGCAGCGGCACCGTTTAGCTCATG
GTTTATGACCGTTCTGGATGCAGCCCGTCCGGCAATTCGTG
AACTGACCGGTCCGAGCGGTGGTTGGTAAGTCGACGTCGA
C

FIGURE 85, CON'T.

(SEQ ID NO:56)

286_pJL1-(CAT5aa)-GPPS_Agr_F3F

TCTAGAAATAATTTTGTTTAACTTTAAGAAGGAGATATACATAT
GGAGAAAAAAATCGAATTCGACTTCAACAAATACATGGATAG
CAAAGCCATGACCGTTAATGAAGCACTGAATAAAGCAATTCC
GCTGCGTTATCCGCAGAAAATCTATGAAAGCATGCGTTATAG
CCTGCTGGCAGGCGGTAAACGTGTTCGTCCGGTTCTGTGTA
TTGCAGCATGTGAACTGGTTGGTGGCACCGAAGAACTGGC
AATTCCGACCGCATGTGCAATTGAAATGATTCATACCATGAG
CCTGATGCATGATGATCTGCCGTGTATTGATAATGATGACCT
GCGTCGTGGTAAACCGACCAATCATAAAATCTTTGGTGAAGA
TACCGCAGTGACCGCAGGTAATGCACTGCATAGTTATGCATT
TGAACATATTGCAGTGAGCACCAGCAAAACCGTTGGTGCAG
ATCGTATTCTGCGTATGGTTAGCGAACTGGGTCGTGCAACC
GGTAGCGAAGGTGTTATGGGTGGTCAGATGGTTGATATTGC
AAGTGAAGGTGATCCGAGCATTGATCTGCAGACCCTGGAAT
GGATTCATATTCATAAAACCGCAATGCTGCTGGAATGTAGCG
TTGTTTGTGGTGCAATTATTGGTGGTGCAAGCGAAATTGTTA
TTGAACGTGCCCGTCGTTATGCACGTTGTGTTGGTCTGCTG
TTTCAGGTTGTTGATGATATTCTGGATGTGACCAAAAGCAGT
GATGAACTGGGCAAAACCGCAGGCAAAGACCTGATTAGCGA
TAAAGCAACCTATCCGAAACTGATGGGTCTGGAAAAAGCCA
AAGAATTTTCAGATGAACTGCTGAATCGTGCCAAAGGTGAAC
TGAGCTGTTTTGATCCGGTTAAAGCAGCACCGCTGCTGGGT
CTGGCAGATTATGTTGCATTTCGTCAGAACTAAGGATCCTGA
CTCGAGCACCACCACCACCACCACTGAGATCGTCGAC

FIGURE 85, CON'T.

(SEQ ID NO:57)

287_pJL1-(CAT5aa)-GPPS2_Pab

TCTAGAAATAATTTTGTTTAACTTTAAGAAGGAGATATACATAT
GGAGAAAAAAATC
GAGTTCGACTTTGACAAGTATATGCACAGTAAAGCAATCGCC
GTAAACGAGGCTTTGGATAAAGTGATCCCGCCCCGCTACCC
CCAAAAGATTTATGAATCAATGCGCTATAGTTTACTGGCAGGT
GGAAAACGTGTGCGCCCGATCCTGTGTATTGCGGCTTGCGA
GCTGATGGGAGGCACTGAGGAGTTAGCTATGCCGACCGCAT
GCGCAATTGAGATGATTCATACCATGTCTCTTATCCACGACG
ACTTGCCGTATATCGATAATGATGACTTACGTCGGGGAAAAC
CGACCAACCATAAAGTTTTCGGCGAAGACACCGCTATTATCG
CAGGAGATGCTCTGCTGAGCTTAGCATTCGAGCATGTTGCA
GTGAGTACTAGCCGGACTCTGGGTACTGATATCATCCTGCG
CCTGCTGAGCGAAATCGGTCGTGCAACGGGCTCGGAGGGC
GTCATGGGCGGGCAAGTAGTTGATATTGAATCGGAGGGAGA
TCCCTCTATCGACCTGGAAACCCTGGAGTGGGTACATATCCA
TAAAACGGCAGTTTTGCTCGAATGCTCGGTCGTTTGCGGTG
CAATTATGGGGGGTGCCTCAGAGGATGATATTGAACGTGCC
CGTCGTTACGCGCGCTGCGTCGGCTTGCTGTTTCAGGTCG
TCGATGATATCCTTGATGTCAGCCAGTCTAGTGAAGAACTGG
GAAAAACCGCTGGCAAGGATCTGATTAGCGACAAAGCCACT
TACCCAAAATTAATGGGTCTGGAAAAAGCTAAAGAATTTGCC
GACGAATTATTGAACCGTGGTAAGCAGGAACTGTCATGTTTT
GACCCCACGAAAGCAGCACCTCTGTTTGCGCTTGCAGACTA
TATTGCCAGCCGGCAGAACTAAGGATCCTGACTCGAGGTCG
AC

FIGURE 85, CON'T.

(SEQ ID NO:58)

288_pJL1-(CAT5aa)-GPPS_Str

TCTAGAAATAATTTTGTTTAACTTTAAGAAGGAGATATACATAT
GGAGAAAAAAATCACCACCGATACCGGTCAGGATGCAGTTG
GTCTGGCACGTCGTACCGGTGCAGACCTGCTGCATCGTGTT
GAAGATCGTCTGCGTAGCCTGCTGGCAGTCGAACGTGATGC
ATGGGCGGCCGTGCACGAGCAGGCAGTTGTGCCGGTTGAC
GCCTTATCAGAGCTGATCGCAAGTGGCGGCAAACGCATCCG
CCCGGCATTCTGTATCACGGGTTATTTAGCTGCCGGTGGCG
ATCCAGCCGAACCAGGTATTGTGGCTGCGGGCGCGGCTCT
GGAAATGTTGCATCTTTCAGCCCTGGTGCACGACGACGTTT
TAGATGACTCCAGCTCACGCCGTGGGGTACCGACCGTACAT
ACCCAAGCTATGGCCCTGCATGAATCTAGCGGTTGGCAGGG
CGAACCGCGCCGCTACGGGGAAGGCGTGGCTATCCTGGTA
GGCGACCTGGCCTTAGTATACTCAGAAGAGTTAATGGCGGA
AGCGCCTCGCCGCGTCCTGCCAGAATGGAATAAACTGCGTT
CGGAAGTTATGATCGGTCAATACATGGACGTACATGCAGCCG
CTGAATTTAGCGTGGATCCGCGTAGCTCCCGCCTTATTGCG
CGCATTAAATCTGGGCGTTATACTATCCATCGTCCATTAGTAG
TAGGCGCCAAACGGGGCCGCGGTCGCGGTGATCTGGCGC
CAGCATTAGAAGAGTACGGTGAAGCCGTGGGCGAGGCCTT
CCAACTGCGCGATGACTTACTGGATGCGTCTGCAACGCCGG
CCGAAACCGGGAAGCCAACTGGCCTGGATTTCACACAGCAT
AAAATGACCTTACTGCTGGGCTGGGCGATGCAGCGCGATGA
GCATATCCATACGCTGGTAACGGAACCAGGGCACACGCCCG
ATGAGGTGCGCCGGCGTCTGTTAGATACGGGCGTTCCGGC
CGATGTAGAACGGCATATCGCGGGCTTAGTGGAACGTGGCT
GCAAAGCCATCGCTGATGCACCTGTCGATCAGGTTTGGCGG
GGCGAGCTGGCAGCCATGGCCGGCCGTGTCGCGTATCGTA
CGGCATAAGGATCCTGACTCGAGGTCGAC

Figure 85, con't.

(SEQ ID NO:59)

347_pJL1-(CAT7aa)-GPPS_PgI

TCTAGAAATAATTTTGTTTAACTTTAAGAAGGAGATATACATAT
GCATATGGAGAAAAAAATCGAATTTGACTTCAAAGAATACATG
CGCAGCAAAGCCATGAGCGTTAATGAAGCACTGGATCGTGC
AGTTCCGCTGCGTTATCCGGAAAAAATTCATGAAGCAATGCG
TTATAGCCTGCTGGCAGGCGGTAAACGTGTTCGTCCGATTC
TGTGTATTGCAGCATGTGAACTGGTTGGTGGTAGCGAAGAA
CTGGCAATGCCGACCGCATGTGCAATGGAAATTATTCATACC
ATGAGCCTGATCCATGATGATCTGCCTCCGATGGATAATGAT
GACCTGCGTCGTGGTAAACCGACCAATCATAAAGTTTTTGGT
GAAGGCACCGCAGTTTTAGCCGGTGATGCACTGCTGAGCTT
TGCATTTGAACATATTGCAGTTAGCACCAGCAAAACCGTTGA
AAGCGATCGTGTTCTGCGTGTTGTTAGCGAACTGGGTCGTG
CAATTGGTAGTGAAGGTGTTGCCGGTGGTCAGGTTGCAGAT
ATTACCAGCCAGGGTAATCCGAGCGTTGGTCTGGAAACCCT
GGAATGGATTCATATTCATAAAACCGCAGTTCTGCTGGAATG
TAGCGTTGCAAGCGGTGCAATTATTGGTGGTGCAAGCGAAG
ATGAAATTGAACGTGTGCGTAAATATGCACGTTGTGTTGGTC
TGCTGTTTCAGGTTGTTGATGATATTCTGGATGTTACCAAAA
GCAGCGAGGAACTGGGTAAAACAGCAGCAAAAGACCTGCT
GAGCGATAAAGCAACCTATCCGAAACTGATGGGTCTTGAAAA
AGCAAAAGAATTTGCAGATGAACTGCTGGGCAAAGCCAAAG
AAGAACTGAGCTTTTTTAACCCGACCAAAGCAGCACCGCTG
CTGGGTTTAGCAGATTATATTGCACAGCGTCAGAACTAAGTC
GACGTCGAC

FIGURE 85, CON'T.

(SEQ ID NO:60)

348_pJL1-(CAT7aa)-GPPS_Pku

TCTAGAAATAATTTTGTTTAACTTTAAGAAGGAGATATACATAT
GCATATGGAGAAAAAAATCAGCCTGGTTAATAGCATTACCTG
GTCACAGACCAGCAGCATTCTGAACATTCAGAGCAACATTAG
CAAAAAACTGACCCCGTTTAGCATTCTGCCGCATCCGCTGA
CCAATAATCTGCCGATTAGCCTGTTTCCGAATCCGAAAAGCA
ATATCAGCAATAGCAATACACCGCTGAGCGCAATTCTGACCA
AAGATCAGAAACCGCAGAATCCGCCTACCACACCGACCTTT
GATTTCAAAAGCTATATGCTGCAGAAAGCCGATAGCGTTAATA
AAGCACTGGATGATAGCATTCCGCTGACAGAACCGCTGAAA
ATTCAAGAAAGCATGCGTTATAGCCTGCTGGCAGGCGGTAA
ACGTATTCGTCCGATGCTGTGTATTGCAGCATGTGAACTGGT
TGGTGGTGATGAAAGCACCGCAATGCCTGCAGCCTGTGCA
GTTGAAATGGTTCATACCATGAGCCTGATGCATGATGATCTG
CCGTGTATGGATAATGATGACCTGCGTCGTGGTAAACCGAC
CAATCATAAAGTTTTTACCGAAGATGTTGCCGTGTTAGCCGG
TGATGCAATGCTGGCATTTAGCTTTGAACATGTTGCAAGCCT
GACAAAAGGTGTTTGTAGCGAACGTATTGTGCGCGTTATTTA
TGAACTGGCAAAATGTGTTGGTTGCGAAGGTCTGGTTGCAG
GTCAGGTTGTTGATATTTGCAGCGAAGGTATGGATGAAGTTG
GTCTGGAACATCTGGAATTTATCCATCTGAATAAAACCGCAG
CACTGCTGGAAGGTAGCGTTGTTCTGGGTGCAATTTTAGGT
GGTGGTAGTGATGAAGAAGTTGAAAAACTGCGTAATTTTGCC
CGTTGTATTGGTCTGCTGTTTCAGGTTGTGGATGATATTCTG
GATGTTACCAAAAGCAGCAAAGAACTGGGTAAAACAGCAGG
TAAAGACCTGGTTGCCGATAAAACCACCTATCCGAAACTGAT
TGGTATCGAGAAAAGCAAAGAATTTGCCGAACGTCTGAATC
GTGAAGCAAAAGAACACCTGGCAGGTTTTGATCAGAATAAA
GCAGCACCGCTGATTGCACTGGCCGATTATATTGCATATCGT
GACAATTAAGTCGACGTCGAC

FIGURE 85, CON'T.

(SEQ ID NO:61)

**349_pJL1-(CAT7aa)-GPPS*_Sce**

TCTAGAAATAATTTTGTTTAACTTTAAGAAGGAGATATACATAT
GCATATGGAGAAAAAAATCGCCAGCGAAAAAGAAATTCGTC
GTGAACGTTTTCTGAACGTGTTTCCGAAACTGGTTGAAGAA
CTGAATGCAAGCCTGCTGGCCTATGGTATGCCGAAAGAAGC
ATGCGATTGGTACGCACATAGCCTGAATTATAACACCCCTGG
TGGTAAACTGAATCGTGGTCTGAGCGTTGTTGATACCTATGC
AATTCTGAGCAATAAAACCGTGGAACAGCTGGGTCAAGAGG
AATATGAAAAAGTTGCAATTCTTGGCTGGTGCATTGAACTGC
TGCAGGCATATTTTCTGGTTGCAGATGATATGATGGACAAAA
GCATTACCCGTCGTGGTCAGCCGTGTTGGTATAAAGTTCCG
GAAGTTGGTGAAATTGCCATCAATGATGCATTTATGCTGGAA
GCAGCAATCTACAAACTGCTGAAAAGCCATTTTCGCAACGA
GAAATATTACATCGATATCACCGAACTGTTTCACGAAGTTACC
TTTCAGACCGAACTGGGTCAGCTGATGGATCTGATTACCGC
ACCGGAAGATAAAGTTGATCTGAGCAAATTCAGCCTGAAAAA
GCATAGCTTTATCGTGACCTTTGAAACCGCCTATTATAGCTTT
TATCTGCCGGTTGCACTGGCAATGTATGTTGCAGGTATTACC
GATGAAAAAGACCTGAAACAGGCACGTGATGTTCTGATTCC
GCTGGGTGAATATTTTCAGATCCAGGATGATTATCTGGATTG
CTTTGGTACACCGGAACAAATTGGTAAAATTGGCACCGATAT
CCAGGATAACAAATGTAGCTGGGTTATTAACAAAGCACTGGA
ACTGGCAAGCGCAGAACAGCGTAAAACCCTGGATGAAAATT
ATGGCAAAAAAGATAGCGTTGCCGAGGCCAAATGCAAGAAA
ATCTTTAACGACCTGAAAATCGAGCAGCTGTATCACGAATAT
GAAGAATCAATTGCCAAGGACCTGAAAGCCAAAATTAGCCA
GGTTGATGAAAGCCGTGGTTTTAAAGCAGATGTGCTGACCG
CATTTCTGAACAAAGTGTATAAACGCAGCAAATAAGTCGACG
TCGAC

FIGURE 85, CON'T.

(SEQ ID NO:62)

318_pJL1-(CAT5aa)-ispA_Ec

TCTAGAAATAATTTTGTTTAACTTTAAGAAGGAGATATACATAT
GGAGAAAAAAATCGACTTTCCGCAGCAACTCGAAGCCTGCG
TTAAGCAGGCCAACCAGGCGCTGAGCCGTTTTATCGCCCCA
CTGCCCTTTCAGAACACTCCCGTGGTCGAAACCATGCAGTA
TGGCGCATTATTAGGTGGTAAGCGCCTGCGACCTTTCCTGG
TTTATGCCACCGGTCATATGTTTGGCGTTAGCACAAACACGC
TGGACGCACCCGCTGCTGCCGTAGAGTGTATCCACGCTTAC
TCATTAATTCATGATGATTTACCGGCGATGGATGATGACGATC
TGCGCCGCGGTTTGCCGACCTGCCATGTGAAGTTTGGCGA
AGCAAACGCGATTCTCGCTGGCGACGCTTTACAAACGCTGG
CGTTCTCGATTCTAAGCGATGCCGATATGCCGGAAGTGTCG
GATCGCGACAGAATTTCGATGATTTCTGAACTGGCGAGCGC
CAGCGGTATTGCCGGAATGTGCGGTGGTCAGGCACTAGATT
TAGACGCGGAAGGCAAACACGTACCTCTGGACGCGCTTGA
GCGTATTCATCGTCATAAAACCGGCGCATTGATTCGCGCCGC
CGTTCGCCTTGGTGCATTAAGCGCCGGAGATAAAGGGCGTC
GTGCTCTGCCAGTACTCGACAAGTACGCAGAGAGCATCGGC
CTTGCCTTCCAGGTTCAAGATGACATCCTGGATGTGGTAGG
AGATACTGCAACGTTGGGAAAACGCCAGGGTGCCGACCAG
CAACTTGGTAAAAGTACCTACCCTGCACTTCTGGGTCTTGAG
CAAGCCCGGAAGAAAGCCCGGGATCTGATCGACGATGCCC
GTCAGTCGCTGAAACAACTGGCTGAACAGTCACTCGATACC
TCGGCACTGGAAGCGCTAGCGGACTACATCATCCAGCGTAA
TAAATAAGTCGAC

FIGURE 85, CON'T.

(SEQ ID NO:63)

246_pJL1-(CAT5aa)-LS_Msp

TCTAGAAATAATTTTGTTTAACTTTAAGAAGGAGATATACATATGGAGAAAAAAATCCGTCGTT
CGGGGAACTATAACCCGTCACGTTGGGATGTGAACTTCATCCAGTCTTTACTGAGCGATTAT
AAGGAAGACAAACATGTCATTCGTGCATCCGAACTGGTTACGTTAGTCAAAATGGAATTAGA
GAAAGAAACAGACCAGATTCGGCAACTGGAATTGATCGACGATTTGCAACGCATGGGCTTA
TCTGATCACTTCCAAAACGAATTTAAGGAGATTCTGAGCTCCATCTATCTGGATCATCATTAC
TATAAAAATCCTTTTCCCAAAGAAGAACGCGACCTGTACAGTACCTCTCTGGCATTCCGGCT
GCTGCGTGAACATGGCTTCCAGGTAGCACAAGAGGTTTTCGATAGTTTCAAAAATGAAGAA
GGTGAATTTAAAGAAAGTCTGTCCGATGATACTCGGGGGCTCCTGCAACTTTATGAAGCCT
CCTTTCTGCTGACCGAGGGCGAAACCACCCTGGAGTCCGCCCGCGAGTTCGCAACCAAG
TTTCTGGAAGAAAAAGTGAATGAAGGGGGCGTAGATGGCGACCTGCTCACCCGCATTGCG
TATAGCCTGGACATCCCGCTCCACTGGCGCATTAAACGCCCGAACGCTCCGGTTTGGATTG
AGTGGTACCGTAAGCGCCCTGATATGAACCCGGTTGTTTTAGAGCTGGCCATCTTAGACCT
GAACATCGTCCAGGCCCAGTTTCAAGAGGAACTGAAAGAAAGCTTTCGCTGGTGGCGTAA
CACCGGTTTTGTGGAAAAGTTACCATTTGCACGCGACCGTCTTGTCGAGTGCTACTTTTGG
AATACAGGCATTATCGAACCGCGTCAGCACGCCAGTGCCCGTATCATGATGGGAAAAGTTA
ATGCGCTGATCACCGTGATCGACGACATCTATGATGTGTACGGCACCTTAGAAGAGCTCGA
ACAATTCACCGACCTTATCCGGCGCTGGGATATTAATTCGATCGATCAGCTTCCGGATTATAT
GCAGCTGTGTTTTCTGGCGCTTAATAATTTTGTTGATGACACGAGTTACGACGTTATGAAAG
AAAAAGGTGTGAACGTGATCCCGTACTTACGCCAATCATGGGTGGACCTGGCGGACAAGT
ATATGGTTGAAGCCCGGTGGTTTTATGGTGGACATAAACCTTCGTTGGAAGAATATTTAGAA
AATTCTTGGCAGTCTATCTCCGGCCCCTGTATGTTGACCCATATTTTCTTCCGTGTCACCGA
CAGCTTTACGAAAGAAACGGTAGACTCTCTCTATAAGTACCATGACCTGGTTCGTTGGTCCT
CCTTTGTACTGCGCCTTGCAGATGATCTGGGCACAAGTGTAGAAGAAGTTTCTCGTGGTGA
TGTCCCTAAAAGCCTCCAGTGTTATATGTCTGACTACAATGCATCGGAAGCGGAGGCGCGC
AAGCATGTAAAATGGCTTATCGCTGAGGTGTGGAAGAAAATGAACGCAGAGCGCGTAAGCA
AGGATTCGCCATTCGGTAAGGATTTCATTGGATGTGCGGTGGACTTAGGGCGGATGGCTCA
GTTAATGTACCACAACGGCGACGGTCATGGCACGCAGCACCCAATTATTCATCAGCAGATG
ACGCGGACGCTGTTCGAGCCGTTCGCGTAAGGATCCTGACTCGAGGTCGAC

FIGURE 85, CON'T.

(SEQ ID NO:64) 247_pJL1-(CAT5aa)-LS_Cli

TCTAGAAATAATTTTGTTTAACTTTAAGAAGGAGATATACATATGGAGAAAAAAATCCGTC
GGAGCGCTAACTATCAACCGTCAATTTGGGACCATGATTTTCTGCAATCGCTGAACTCA
AACTATACAGACGAGGCGTACAAACGGCGCGCCGAGGAACTTCGCGGTAAGGTCAAAA
TTGCCATTAAAGACGTGATTGAACCGCTGGACCAGCTCGAACTGATTGACAACCTGCAA
CGTCTCGGTCTGGCGCATCGCTTCGAAACGGAAATTCGTAATATCTTAAATAACATCTATA
ATAACAACAAAGATTATAACTGGCGCAAAGAAAATCTGTATGCAACTAGCCTCGAATTTC
GGCTGCTGCGTCAGCATGGCTACCCGGTGTCGCAGGAGGTCTTCAATGGTTTCAAAGA
TGATCAGGGTGGTTTCATTTGTGATGACTTTAAAGGAATCCTTTCGCTCCACGAGGCCA
GCTATTATTCACTGGAAGGTGAATCAATTATGGAGGAAGCATGGCAGTTTACGTCAAAAC
ACCTGAAGGAAGTGATGATCTCTAAAAACATGGAAGAAGATGTGTTCGTCGCGGAACAA
GCTAAACGTGCTCTGGAACTGCCGCTGCATTGGAAAGTCCCGATGCTGGAAGCACGCT
GGTTTATCCATATTTACGAACGCCGCGAAGATAAAAATCACCTGCTGCTGGAATTAGCGA
AAATGGAATTTAACACCCTGCAGGCCATTTACCAGGAAGAATTAAAGGAAATCTCGGGTT
GGTGGAAGGATACGGGGCTTGGAGAGAAACTGTCCTTTGCTCGCAACCGGTTAGTGG
CGTCGTTCTTGTGGTCTATGGGGATCGCGTTCGAACCACAATTCGCCTATTGTCGCCGT
GTGTTAACTATCTCTATTGCACTGATTACGGTGATCGATGACATTTACGACGTATACGGTA
CCCTGGACGAGTTAGAAATCTTTACGGACGCCGTCGAACGGTGGGATATCAATTATGCG
CTCAAACACTTACCTGGTTATATGAAAATGTGCTTTCTGGCGCTGTATAATTTTGTAAACG
AATTTGCATATTATGTGCTGAAGCAACAGGACTTTGATCTGCTGTTGTCTATCAAAAACG
CCTGGCTGGGATTGATTCAAGCTTACCTTGTTGAAGCGAAGTGGTACCACAGCAAATAC
ACCCCGAAACTGGAAGAGTATCTGGAGAACGGCCTGGTTAGCATCACCGGGCCCCTGA
TTATTACCATCTCTTATCTGTCAGGGACCAACCCAATTATCAAAAAAGAACTGGAATTTCT
TGAAAGTAACCCGGATATTGTTCACTGGTCTTCCAAAATCTTCCGCCTGCAGGATGATCT
GGGCACCAGCTCAGACGAAATTCAACGGGGCGACGTACCAAAATCAATTCAGTGCTATA
TGCATGAAACCGGTGCGAGTGAGGAGGTAGCCCGTCAGCACATCAAGGATATGATGCG
CCAAATGTGGAAAAAAGTCAATGCTTATACCGCAGACAAGGACAGTCCGCTGACCGGC
ACTACAACGGAATTTCTGCTGAACTTAGTCCGTATGAGCCATTTTATGTATTTGCATGGC
GACGGACACGGCGTTCAGAACCAGGAAACCATTGATGTCGGCTTCACCTTGCTGTTTC
AGCCAATCCCTTTGGAAGATAAGCACATGGCGTTTACCGCAAGCCCGGGCACCAAAGG
CTAAGGATCCTGACTCGAGGTCGAC

FIGURE 85, CON'T.

(SEQ ID NO:65)

248_pJL1-(CAT5aa)-LS_Pfr

TCTAGAAATAATTTTGTTTAACTTTAAGAAGGAGATATACATATGGAGAAAAAAATCCGTCGTAG
CGGTAATTATAGCCCGAGCTTTTGGAATGCAGATTATATTCTGAGCCTGAACAACCATTATAAA
GAAGAAAGCCGTCATATGAAACGTGCCGGTGAACTGATTGTTCAGGTTAAAATGGTTATGGGC
AAAGAAACCGATCCGGTTGTGCAGCTGGAACTGATCGATGATCTGCATAAACTGGCACTGAG
CCATCATTTTGAGAAAGAAATTAAAGAGATCCTGTTCAACATCAGCATCTACGACCATAAAATC
ATGGTTGAACGTGATCTGTATAGCACCGCACTGGCATTCCGGTTGCTCCGTCAGTATGGCTTC
AAGGTGCCGCAGGAGGTTTTCGATTGTTTTAAAAACGACAATGGAGAATTTAAACGGTCTTTA
AGCTCCGATACGAAAGGTCTGCTGCAGTTGTATGAAGCCTCCTTTCTGCTGACGGAAGGTGA
AATGACACTGGAACTGGCGCGTGAGTTCGCGACCATCTTTCTTCAGGAGAAACTGAACGATA
AAACAATCGACGACGACGATGATGCGGATACAAACCTCATTTCTTGCGTGCGTCATTCACTCG
ATATCCCGATCCATTGGCGCATCCAACGTCCGAACGCCAGTTGGTGGATCGATGCCTACAAA
CGCCGCAGTCACATGAATCCTCTGCTTGAGTTAGCAAAGTTAGACCTGAATATTTTTCAGGCA
CAGTTTCAACAGGAACTGAAACAGGACCTGGGTTGGTGGAAAAATACATGTCTCGCAGAGAA
GCTGCCGTTTACCCGTGACCGCCTGGTGGAATGCTACTTCTGGTGCACCGGTATCATTCAGC
CGCTGCAGCATGAGAACGCTCGCGTTACTCTGGCAAAAGTTAACGCCTTGATCACCACGCTG
GACGACATTTACGATGTATACGGCACCCTGGAGGAACTGGAACTGTTCACGGAAGCGATTCG
GCGTTGGGACGTTAGTAGCATTGACCACTTACCGAACTATATGCAGCTGTGCTTCCTCGCCCT
GAACAATTTTGTCGATGACACCGCGTACGATGTTATGAAAGAAAAGGACATTAACATTATCCCG
TATCTGCGGAAATCGTGGTTGGACCTCGCCGAGACATACCTGGTGGAAGCTAAATGGTTCTAT
TCAGGCCATAAACCGAATATGGAAGAATATTTAAATAATGCGTGGATCTCGATTAGCGGTCCGG
TTATGTTGTGCCATGTATTCTTCCGCGTGACTGATTCCATTACCCGCGAAACCGTAGAATCTCT
GTTCAAATATCACGACCTTATTCGTTACTCCTCTACCATCCTTCGCCTGGCGGATGACTTAGGC
ACAAGCCTGGAAGAGGTTAGCCGTGGTGATGTTCCGAAAAGCATTCAGTGTTATATGAATGAT
AACAACGCCAGCGAAGAAGAAGCACGTCGTCACGTTCGTTGGCTGATTGCAGAAACCTGGA
AAAAAATCAACGAAGAAGTTTGGAGCGCAGATAGCCCGTTTTGCAAAGATTTTATTGCATGTG
CAGCAGATATGGGTCGTATGGCGCAGTTTATGTATCATAATGGTGATGGTCATGGCATTCAGAA
TCCGCAGATTCATCAGCAGATGACCGATATTCTGTTTGAACAGTGGCTGTAAGGATGTCGAC

FIGURE 85, CON'T.

(SEQ ID NO:66)

350_pJL1-(CAT7aa)-LS_Ste

TCTAGAAATAATTTTGTTTAACTTTAAGAAGGAGATATACATATGCATATGGAGAAAAAAATCCGTCGTAG
CGGTAACTATAAACCGAGCCGTTGGGATGTTGATTTTATGCAGAGCCTGAATAGCGATTATCAAGAAGA
ACGTCATCGTACCAAAGCAAGCGAACTGATTACCCAGGTTAAAAACCTGCTGGAAAAAGAAACCAGTG
ATGATCCGATTCGTCAGCTGGAACTGATTGATGATCTGCAGCGTCTGGGTCTGAGCGATCATTTTGAAC
ATGAATTTAAAGAGGTGCTGAACAGCATCTACCTGGACAACAAATATTACAACATCAACATCATGAAAGA
AACGACCAGCAGCCGTGATCTGTATAGCACCGCACTGGCATTTCGTCTGCTGCGTGAACATGGTTTTC
AGGTTGCACAAGAAGTTTTCGACTGCTTCAAAAATGAAGAGGGTGAGTTTAAAGCAAGCCTGTCAGAT
GATCCGCGTGGTCTGCTGCAGCTGTATGAAGCAAGCTTTCTGTTTAAAGAAGGCGAAAACACCCTGGA
AATTGCCCGTGAATTTGCAACCAAACTGCTGCAAGAAAAAGTGAACAGCTCCGATGAAATTGATGATAA
TCTGCTGAGCAGCATTCGTTATAGTCTGGAAATTCCGACCTATTGGAGCGTTATTCGTCCGAATGTTAG
CGTTTGGATTGATGCATATCGTAAACGTCCGGATATGAATCCGGTTGTTCTGGAACTGGCAATTCTGGA
TGCCAATATTATGCAGGCACAGCTGCAACAAGAACTGAAAGAAGCATTAGGTTGGTGGCGTAATACCTG
GTTTGTTGAAAAACTGCCGTTTGCACGTGATCGTCTGGTTGAAAGCTATTTTTGGAGCACCGGTATGGT
TCCGCGTCGTCAGCATAAAACCGCACGTCAGCTGATGGCAAAAGTTATTGCCCTGATTACCGTGATGG
ATGATATCTATGACGTTTATGGTACACTGGAAGAACTGGAACTGTTTACCGATGCCTTTCGTCGCTGGG
ATGTTAGCAGCATTGATCATCTGCCGACCTATATGCAACTGTGTTTTCTGAGCATTAACAACTTTGTTGT
TGACACCGCCTACAACATTCTTAAAGAAACCGGTGTTAATGTGACCACCTATCTGGAAAAAAGCTGGGT
TGATCAGGCAGAAAATTATCTGATGGAAAGCAAATGGTTCTACAGCGGTCATAAACCGTCACTGGATGA
ATACCTGGAAAATAGTTGGATTAGCGTTAGCGGTCCGTGTGTTCTGACCCATGAATTTTTTGGTGTTAC
CGATAGCCTGGCAAAAGATACCCTGGATAGCCTGTATGAATATCACGATATTGTTCGTTGGAGCAGCTAT
CTGCTGCGCCTGGCCGATGATCTGGGCACCAGCGTTGAAGAGGTTAGCCGTGGTGATGTTCCGAAAA
GCATTCAGTGTTATATGAACGATAATAACGCCAGCGAAGAAGAAGCACGCGAACACGTTAAAGGTCTGA
TTCGTGTTATGTGGAAAAAAATGAATGCCGAACGTGTTAGCGAAGATAGCCCGTTTTGTAAAGATTTTAT
TCGTTGTTGTGAGGACCTGGGTCGTATGGCACAGTTTATGTATCATTATGGTGATGGTCATGGCACCCA
GCATGCCAAAATTCATCAGCAGATCACCGATTGTCTGTTTCAGCCGTTTGCCTAAGTCGACGTCGAC

FIGURE 85, CON'T.

(SEQ ID NO:67)

351_pJL1-(CAT7aa)-LS_Lan

TCTAGAAATAATTTTGTTTAACTTTAAGAAGGAGATATACATATGCATATGGAGAAAAAAATCCGTCGTAGCGGTAAC
TATAATCCGACCGCATGGGATTTTAACTATATTCAGAGCCTGGACAACCAGTACAAAAAAGAACGTTATAGCACCC
GTCATGCAGAACTGACCGTTCAGGTTAAAAAACTGCTGGAAGAAGAAATGGAAGCCGTTCAGAAACTGGAACTG
ATTGAGGATCTGAAAAATCTGGGTATCAGCTATCCGTTCAAAGATAACATTCAGCAGATCCTGAACCAGATTTACAA
CGAACATAAATGCTGCCATAACAGCGAAGTGGAAGAAAAAGACCTGTATTTTACCGCACTGCGTTTTCGTCTGCT
GCGTCAGCAGGGTTTTGAAGTTAGCCAAGAAGTTTTCGACCACTTCAAAAATGAAAAAGGCACCGATTTTAAACC
GAACCTGGCAGATGATACCAAAGGTCTGCTGCAGCTGTATGAAGCAAGCTTTCTGCTGCGCGAAGCCGAAGATA
CCCTGGAACTGGCACGTCAGTTTAGCACCAAACTGCTGCAGAAAAAAGTGGATGAAAATGGCGACGATAAAATC
GAAGATAATCTGCTGCTGTGGATTCGTCGTAGTCTGGAACTGCCGCTGCATTGGCGTGTTCAGCGTCTGGAAGC
ACGTGGTTTTCTGGATGCCTATGTTCGTCGTCCGGATATGAATCCGATTGTTTTTGAACTGGCAAAGCTGGATTTC
AATATTACCCAGGCAACCCAGCAAGAAGAACTGAAAGACCTGAGCCGTTGGTGGAATAGCACCGGTCTGGCAGA
AAAACTGCCGTTTGCACGTGATCGTGTTGTTGAAAGCTATTTTTGGGCAATGGGCACCTTTGAACCGCATCAGTA
TGGTTATCAGCGTGAACTGGTTGCAAAAATCATTGCACTGGCAACCGTTGTTGATGATGTCTATGATGTTTATGGC
ACCCTGGAAGAATTAGAACTGTTTACCGATGCAATTCGTCGTTGGGATCGTGAAAGCATTGATCAGCTGCCGTATT
ATATGCAGCTGTGTTTTCTGACCGTGAACAACTTTGTGTTTGAGCTGGCACATGATGTGCTGAAAGATAAAAGCTT
TAATTGTCTGCCGCATCTGCAGCGTAGCTGGCTGGATCTGGCCGAAGCATATCTGGTTGAAGCAAAATGGTATCA
TAGCCGTTATACCCCGAGCCTGGAAGAGTATCTGAATATTGCACGTGTTAGCGTTACCTGTCCGACCATTGTTAGC
CAGATGTATTTTGCACTGCCGATTCCGATTGAAAAACCGGTGATTGAAATCATGTACAAATACCACGATATCCTGTA
TCTGAGCGGTATGCTGCTGCGCCTGCCGGATGATCTGGGCACCGCATCATTTGAACTGAAACGTGGTGATGTTC
AGAAAGCGGTTCAGTGCTATATGAAAGAACGTAATGTTCCGGAAAATGAAGCCCGTGAACATGTGAAATTTCTGAT
TCGTGAAGCCAGCAAGCAGATCAATACCGCAATGGCCACCGATTGTCCGTTTACCGAAGATTTTGCAGTTGCAGC
AGCCAATCTGGGTCGTGTTGCAAATTTTGTTTATGTGGATGGTGATGGTTTTGGTGTTCAGCACAGCAAAATCTAT
GAGCAGATTGGTACACTGATGTTTGAACCGTATCCGTAAGTCGACGTCGAC

FIGURE 85, CON'T.

(SEQ ID NO:68)

352_pJL1-(CAT7aa)-LS_Sly

TCTAGAAATAATTTTGTTTAACTTTAAGAAGGAGATATACATATGCATATGGAGAAAAAAATCCGTC
GTAGCGGTAATTATGAACCGACCATGTGGAACTATGAATATATCCAGAGCACCCATAATCATCATG
TGGGCGAGAAATATATGAAACGCTTTAATGAACTGAAAGCCGAAATGAAAAAGCATCTGATGATG
ATGCTGCACGAAGAAAGCCAAGAACTGGAAAAACTGGAACTGATTGATAATCTGCAGCGTCTGG
GTGTTAGCTATCACTTTAAAGATGAAATCATTCAGATCCTGCGCAGCATTCATGATCAGTCAAGC
AGCGAAGCAACCAGCGCAAATAGCCTGTATTATACCGCACTGAAATTTCGTATTCTGCGTCAGCA
TGGCTTTTATATCAGCCAGGATATTCTGAACGACTTCAAAGATGAGCAGGGCCATTTTAAACAGA
GCCTGTGTAAAGATACCAAAGGTCTGCTGCAGCTGTATGAAGCAAGCTTTCTGAGCACCAAAAG
CGAAACCAGCACACTGCTGGAAAGCGCCAATACCTTTGCAATGAGCCATCTGAAAAACTATCTG
AATGGTGGTGATGAAGAGAACAACTGGATGGTTAAACTGGTTCGTCATGCACTGGAAGTTCCGC
TGCATTGTATGATGCTTCGTGTTGAAACCCGTTGGTATATCGACATCTATGAAAATATTCCGAATG
CCAATCCGCTGCTGATTGAACTGGCCAAACTGGATTTTAACTTTGTTCAGGCAATGCACCAGCA
AGAACTGCGTAATCTGAGCCGTTGGTGGAAAAAAAGCATGCTGGCAGAAAAACTGCCGTTTGC
ACGTGATCGTATTGTTGAAGCATTTCAGTGGATTACCGGCATGATTTTTGAGAGCCAAGAAAATG
AATTTTGCCGCATCATGCTGACCAAAGTTACCGCAATGGCAACCGTTATTGATGATATCTATGATG
TTTATGGCACCCTGGATGAGCTGGAAATCTTTACCCATGCAATTCAGCGCATGGAAATTAAAGCA
ATGGATGAACTGCCGCACTACATGAAACTGTGTTATCTGGCACTGTTTAATACCAGCAGCGAAAT
TGCATATCAGGTGCTGAAAGAACAGGGCATTAACATTATGCCGTATCTGACCAAAAGCTGGGCT
GATCTGAGCAAAAGTTATCTGCAAGAAGCACGTTGGTATTATAGCGGTTATACCCCGAGCCTGG
ATGAATACATGGAAAATGCATGGATTAGCGTTGGTAGCCTGGTTATGGTTGTTAATGCATTTTTTC
TGGTGACCAATCCGATCACCAAAGAAGTTCTGGAATACCTGTTCAGCAACAAATATCCGGACATT
ATTCGTTGGCCTGCAACCATTATTCGCCTGACCGATGATCTGGCGACCAGCAGCAATGAAATGA
AACGTGGTGATGTTCCGAAAAGCATTCAGTGCTATATGAAAGAAAATGGTGCCAGCGAAGAAGA
AGCCCGTAAACATATTAACCTGATGATCAAAGAAACCTGGAAAATGATCAATACCGCACAGCATG
ATAACAGCCTGTTTTGCGAAAAATTCATGGGTTGTGCAGTTAATATTGCACGTACCGGTCAGACC
ATTTATCAGCATGGTGATGGTCATGGTATCCAGAATTACAAAATTCAGAACCGCATCAGCAAACT
GTTTTTTGAACCGATTACCATCAGCATGCCGTAAGTCGACGTCGAC

FIGURE 85, CON'T.

(SEQ ID NO:69)

353_pJL1-(CAT7aa)-LS-Pab

TCTAGAAATAATTTTGTTTAACTTTAAGAAGGAGATATACATATGCATATGGAGAAAAAAATC
CGTCGTCGTGGTAATTATCATAGCAATCTGTGGGATGATGATTTCATTCAGAGCCTGAGCA
CCCCGTATGGTGAACCGAGCTATCGTGAACGTGCAGAACGTCTGAAAGGTGAGATCAAA
AAAATGTTTCGCAGCATGAGCAAAGATGATGGCGAACTGATTACACCGCTGAATGATCTG
ATTCAGCGTCTGTGGATGGTTGATAGCGTGCAGCGTCTGGGTATTGATCGTCATTTCAAA
AACGAAATCAAAAGCGCACTGGACTATGTGTATAGCTATTGGAATGAAAAAGGTATTGGTT
GCGGTCGTGATAGCGTTGTTGCCGATCTGAATAGCACCGCACTGGGTTTTCGTACCCTG
CGTCTGCATGGTTATAATGTTAGCAGCGAAGTTCTGAAAGTGTTCGAAGATCAGAATGGT
CAGTTTGCATGTAGCCCGAGCAAAACCGAAGGTGAAATTCGTAGCGCACTGAATCTGTAT
CGTGCAAGCCTGATTGCATTTCCGGGTGAAAAAGTTATGGATGATGCAGAAATCTTTAGC
AGCCGCTATCTGAAAGAAGCCGTTCAAGAAATTCCGGATTGTAGCCTGAGCCAAGAAATT
GCCTATGCACTGGAATATGGTTGGCATACCAATATGCCTCGTCTGGAAGCACGCAATTATA
TGGATGTTTTTGGTCATCCGAGCAGCCCGTGGCTGAAAAAAAACAAAACACAGTATATGG
ACGGCGAGAAACTGCTGGAACTGGCAAAACTGGAATTTAACATTTTTCACAGCCTGCAG
CAAGAGGAACTGCAGTATATTAGCCGTTGGTGGAAAGATAGTGGTCTGCCGAAACTGGC
ATTTAGCCGTCATCGTCATGTTGAGTATTATACCCTGGGTAGCTGTATTGCAACCGATCCG
AAACATCGTGCATTTCGTCTGGGTTTTGTTAAAACCTGTCATCTGAATACCGTGCTGGATG
ATATCTATGATACCTTTGGCACCATGGATGAAATCGAACTGTTTACCGAAGCAGTTCGTCG
TTGGGACCCGAGTGAAACCGAAAGCCTGCCGGATTATATGAAAGGTGTTTATATGGTTCT
GTATGAAGCCCTGACCGAAATGGCACAAGAAGCACAGAAAACACAGGGTCGCGATACCC
TGAATTATGCACGTAAAGCATGGGAAATTTATCTGGACAGCTATATCCAAGAGGCAAAATG
GATTGCAAGCGGTTATCTGCCGACCTTTCAAGAATATTTTGAGAACGGTAAAATCAGCAG
CGCATATCGTGCAGCAGCACTGACCCCGATTCTGACCCTGGATGTTCCGCTGCCGGAAT
ACATTCTGAAAGGCATTGATTTTCCGAGCCGCTTTAATGATCTGGCAAGCAGCTTTCTGC
GCCTGCGTGGTGATACCCGTTGTTATAAAGCAGATCGTGCACGTGGTGAAGAAGCAAGC
TGTATTAGCTGTTACATGAAAGATAATCCGGGTAGCACCGAAGAAGATGCCCTGAATCATA
TTAACAGCATGATCAACGAGATCATCAAAGAACTGAATTGGGAACTGCTGCGTCCGGATA
GCAATATTCCGATGCCAGCGCGTAAACATGCATTTGATATTACCCGTGCACTGCATCACCT
GTATAAATACCGTGATGGTTTTAGCGTTGCAACCAAAGAAACCAAAAGTCTGGTTAGCCG
CATGGTTCTGGAACCGGTGCCGCTGTAAGTCGACGTCGAC

FIGURE 85, CON'T. (SEQ ID NO:70)

320_pJL1-(CAT5aa)-BS_Agr

TCTAGAAATAATTTTGTTTAACTTTAAGAAGGAGATATACATATGGAGAAAAAAATCAGCGCGGGTGTTTCTGCGGTTTCTA
AAGTTTCTTCTCTGGTTTGCGACCTGTCTTCTACCTCTGGTCTGATCCGTCGTACCGCGAACCCGCACCCGAACGTTTG
GGGTTACGACCTGGTTCACTCTCTGAAATCTCCGTACATCGACTCTTCTTACCGTGAACGTGCGGAAGTTCTGGTTTCT
GAAATCAAAGCGATGCTGAACCCGGCGATCACCGGTGACGGTGAATCTATGATCACCCCGTCTGCGTACGACACCGCG
TGGGTTGCGCGTGTTCCGGCGATCGACGGTTCTGCGCGTCCGCAGTTCCCGCAGACCGTTGACTGGATTCTGAAAAA
CCAGCTGAAAGACGGTTCTTGGGGTATCCAGTCTCACTTCCTGCTGTCTGACCGTCTGCTGGCGACCCTGTCTTGCGT
TCTGGTTCTGCTGAAATGGAACGTTGGTGACCTGCAGGTTGAACAGGGTATCGAGTTCATCAAATCTAACCTGGAACTG
GTTAAAGACGAAACCGACCAGGACTCTCTGGTTACCGACTTCGAAATCATCTTCCCGTCTCTGCTGCGTGAAGCGCAGT
CTCTGCGTCTGGGTCTGCCGTACGACCTGCCGTACATCCACCTGCTGCAGACCAAACGTCAGGAACGTCTGGCGAAAC
TGTCTCGTGAAGAAATCTACGCGGTTCCGTCTCCGCTGCTGTACTCTCTGGAAGGTATCCAGGACATCGTTGAATGGGA
ACGTATCATGGAAGTTCAGTCTCAGGACGGTTCTTTCCTGTCTTCTCCGGCGTCTACCGCGTGCGTTTTCATGCACACC
GGTGACGCGAAATGCCTGGAGTTCCTGAACTCTGTTATGATCAAATTCGGTAACTTCGTTCCGTGCCTGTACCCGGTTG
ACCTGCTGGAACGTCTGCTGATCGTTGACAACATCGTTCGTCTGGGTATCTACCGTCACTTCGAAAAAGAAATCAAAGAA
GCGCTGGACTACGTTTACCGTCACTGGAACGAACGTGGTATCGGTTGGGGTCGTCTGAACCCGATCGCGGACCTGGAA
ACCACCGCGCTGGGTTTCCGTCTGCTGCGTCTGCACCGTTACAACGTTTCTCCGGCGATCTTCGACAACTTCAAAGAC
GCGAACGGTAAATTCATCTGCTCTACCGGTCAGTTCAACAAAGACGTTGCGTCTATGCTGAACCTGTACCGTGCGTCTC
AGCTGGCGTTTCCGGGTGAAAACATCCTGGACGAAGCGAAATCTTTCGCGACCAAATACCTGCGTGAAGCGCTGGAAA
AATCTGAAACCTCTTCTGCGTGGAACAACAAACAGAACCTGTCTCAGGAAATCAAATACGCGCTGAAAACCTCTTGGCA
CGCGTCTGTTCCGCGTGTTGAAGCGAAACGTTACTGCCAGGTTTACCGTCCGGACTACGCGCGTATCGCGAAATGCGT
TTACAAACTGCCGTACGTGAACAACGAAAAATTCCTGGAACTGGGTAAACTGGACTTCAACATCATCCAGTCTATCCACC
AGGAAGAAATGAAAAACGTTACCTCTTGGTTCCGTGACTCTGGTCTGCCGCTGTTCACCTTCGCGCGTGAACGTCCGC
TGGAGTTCTACTTCCTGGTTGCGGCGGGTACCTACGAACCGCAGTACGCGAAATGCCGTTTCCTGTTCACCAAAGTTGC
GTGCCTGCAGACCGTTCTGGACGACATGTACGACACCTACGGTACCCTGGACGAACTGAAACTGTTCACCGAAGCGGT
TCGTCGTTGGGACCTGTCTTTCACCGAAAACCTGCCGGACTACATGAAACTGTGCTACCAGATTTACTACGACATCGTTC
ACGAAGTTGCGTGGGAAGCGGAAAAAGAACAGGGTCGTGAACTGGTTTCTTTCTTCCGTAAAGGTTGGGAAGACTACC
TGCTGGGTTACTACGAAGAAGCGGAATGGCTGGCGGCGGAATACGTTCCGACCCTGGACGAATACATCAAAAACGGTAT
CACCTCTATCGGTCAGCGTATCCTGCTGCTGTCTGGTGTTCTGATCATGGACGGTCAGCTGCTGTCTCAGGAAGCGCT
GGAAAAAGTTGACTATCCGGGTCGTCGTGTTCTGACCGAACTGAACTCTCTGATCTCTCGTCTGGCGGACGACACCAA
AACCTACAAAGCGGAAAAAGCGCGTGGTGAACTGGCGTCTTCTATCGAATGCTACATGAAAGACCACCCGGAATGCACC
GAAGAAGAAGCGCTGGACCACATCTACTCTATCCTGGAACCGGCGGTTAAAGAACTGACCCGTGAGTTCCTGAAACCG
GACGACGTTCCGTTCGCGTGCAAAAAAATGCTGTTCGAAGAAACCCGTGTTACTATGGTTATCTTCAAAGACGGTGACG
GTTTCGGTGTTTCTAAACTGGAAGTTAAAGACCACATCAAAGAATGCCTGATCGAACCGCTGCCGCTGTAAGTCGAC

FIGURE 85, CON'T. (SEQ ID NO:71)

249_11a_pJL1_CATrbs(5aa)_PS_Agr

TCTAGAAATAATTTTGTTTAACTTTAAGAAGGAGATATACATATGGAGAAAAAAATCCGTCGTGGCAAATC
CATTACCCCGAGTATCTCGATGAGCTCTACGACGGTTGTGACAGACGACGGCGTCCGCCGTCGTATG
GGTGATTTTCATTCCAATTTATGGGACGACGATGTGATTCAGAGCTTACCAACAGCGTACGAAGAAAAA
TCCTATCTTGAACGTGCGGAAAAACTGATTGGAGAAGTAAAAAACATGTTTAATTCCATGAGCCTTGAG
GATGGTGAACTTATGAGTCCACTGAATGATCTGATCCAGCGCCTGTGGATCGTAGACAGCCTGGAGCG
GTTAGGCATCCACCGTCACTTCAAAGATGAGATTAAATCGGCTTTGGATTATGTGTATTCATACTGGGGA
GAGAATGGTATTGGGTGTGGGCGGGAAAGTGTGGTAACAGACTTGAACAGCACTGCACTGGGCCTGC
GGACCCTGCGCCTCCACGGCTATCCAGTCAGCTCTGATGTGTTTAAGGCTTTTAAAGGACAAAACGGA
CAGTTTTCTTGTTCCGAGAATATTCAAACCGATGAAGAAATCCGTGGCGTGCTGAATTTGTTCCGTGCA
AGCCTGATTGCCTTTCCGGGTGAGAAAATCATGGACGAGGCCGAAATCTTTTCAACCAAATACCTGAA
GGAAGCTCTGCAAAAGATCCCTGTATCCTCCTTATCCCGGGAAATCGGCGATGTGTTGGAATACGGCT
GGCATACTTATTTGCCGCGTTTAGAGGCACGCAATTATATTCAGGTGTTTGGTCAGGACACCGAAAATA
CCAAAAGCTACGTTAAAAGCAAAAAACTTTTGGAACTGGCTAAGCTGGAATTTAACATTTTCCAGAGCTT
GCAGAAACGTGAACTGGAATCGTTGGTTCGCTGGTGGAAAGAAAGCGGCTTTCCGGAGATGACCTTT
TGTCGTCATCGTCATGTGGAATATTATACCCTGGCCTCCTGCATTGCGTTCGAACCGCAGCATAGTGGT
TTCCGCCTCGGATTTGCGAAAACTTGTCATCTGATTACCGTACTGGATGATATGTATGATACCTTCGGCA
CGGTTGATGAATTAGAACTGTTCACCGCCACTATGAAACGCTGGGACCCGTCTTCGATCGATTGCTTAC
CGGAATACATGAAAGGCGTATATATCGCCGTATACGACACCGTGAATGAGATGGCGCGCGAAGCGGAG
GAGGCCCAAGGGCGCGATACCTTGACCTATGCACGTGAGGCGTGGGAAGCCTATATCGATAGTTACAT
GCAAGAAGCCCGTTGGATCGCCACCGGCTATTTACCTTCATTTGATGAGTATTATGAAAATGGCAAAGT
CAGTTGCGGACATCGTATCTCGGCCCTGCAGCCTATCTTAACCATGGACATTCCGTTTCCCGACCACAT
CCTGAAAGAAGTTGATTTCCCGAGCAAACTCAATGATCTCGCGTGTGCCATTCTCCGCCTGCGCGGTG
ATACGCGCTGCTATAAGGCGGATCGTGCACGTGGCGAAGAAGCGAGCAGCATCTCCTGTTATATGAAA
GATAACCCTGGCGTGAGCGAGGAAGATGCTTTAGATCACATTAATGCCATGATCTCAGATGTAATTAAAG
GGCTTAACTGGGAGTTATTAAAACCTGATATTAATGTGCCCATCAGTGCGAAAAAACACGCGTTCGACA
TTGCGCGCGCTTTCCACTATGGTTATAAATATCGCGATGGTTATAGCGTGGCGAATGTAGAGACGAAAT
CGCTGGTGACCCGGACCCTGCTGGAATCTGTGCCCTTATGAGGATCCTGACTCGAGGTCGAC

FIGURE 85, CON'T. (SEQ ID NO:72)

250_11b_pJL1_CATrbs(5aa)_PS_Pab

TCTAGAAATAATTTTGTTTAACTTTAAGAAGGAGATATACATATGGAGAAAAAAATCCGCCGTATG
GGTGATTTTCACTCTAATCTGTGGAACGACGATTTTATTCAAAGCCTGAGCACGTCGTACGGCG
AACCTAGTTACCGCGAACGCGCTGAGCGTCTCATTGGCGAAGTCAAGAAAATGTTTAATAGCAT
GTCATCTGAAGACGGCGAGCTGATTAGCCCCCATAATGACTTAATTCAACGCGTGTGGATGGTG
GACAGCGTCGAACGTCTGGGCATTGAACGCCACTTCAAGAATGAGATTAAAAGCGCTCTCGATT
ATGTCTATTCCTACTGGTCAGAAAAAGGCATCGGCTGCGGGCGCGAATCGGTGGTAGCCGACC
TGAACAGTACGGCCTTAGGCTTACGTACACTGCGCCTGCATGGATATGCAGTGTCCGCGGACG
TTCTCAATTTGTTTAAAGATCAGAATGGTCAATTTGCATGCTCACCATCTCAGACCGAAGAAGAA
ATCCGTAGTGTATTAAACCTTTATCGCGCAAGTTTAATTGCCTTCCCGGGGGAAAAAGTGATGGA
AGAGGCGGAAATTTTCTCGGCCAAGTATCTGGAAGAGGCCCTGCAGAAAATCTCCGTCAGCTC
ACTTAGCCAAGAAATCCGTGATGTGCTGGAATATGGTTGGCATACCTACCTGCCCCGGATGGAG
GCGCGCAATCATATTGACGTGTTTGGCCAGGACACACAGAACTCTAAAAGCTGCATTAATACCG
ATAAATTATTAGAGCTTGCGAAATTGGAGTTTAATATCTTTCACTCGTTGCAGAAACGCGAGCTG
GAATATCTGGTGCGGTGGTGGAAAGACAGCGGCTCCCCGCAGATGACCTTTGGCCGCCATCG
GCATATTGAATACTATACCCTGGCTAGCTGTATTGCATTTGAACCACAGCACTCTGGCTTTCGTCT
CGGCTTTGCGAAAACTTGCCATATCATCACCATCCTGGACGACATGTATGATACCTTTGGCACCG
TTGATGAGTTAGAACTTTTTACGGCAGCCATGAAGCGCTGGGACCCGAGCGCAGCAGACTGCC
TTCCTGAGTACATGAAAGTAATGTATATGATCGTGTACGACACCGTGAACGAAATGTGTCAGGAG
GCGGAAAAAGCGCAGGGTCGTGACACCCTGGATTATGCCCGTCAGGCGTGGGAAGACTACCT
GGATTCTTATATGCAGGAAGCTAAGTGGATCGCCACCGGTTACTTACCGACCTTCGAAGAATACT
ATGAGAATGGGAAAGTTTCATCGGGGCATCGTGTGGCTGCACTGCAGCCGATCTTGACCATGG
ACATTCCGTTTCCTCCGCACATTTTGAAAGAAGTGGATTTTCCCTCAAAGCTGAGTGATCTGGC
CTGTGCTATCCTGCGCCTGCGTGGAGACACTCGTTGTTACAAAGCCGACCGTGCCCGTGGCGA
AGAAGCTTCATCGATTTCGTGTTACATGAAAGATAATCCTGGCGCGACGGAAGAAGATGCCTTG
GATCATATTAATGCCATGATCAGCGATGTAATTCGTGGGTTGAACTGGGAGCTGTTAAAGCCTAA
TTCGAGCGTGCCGATCAGCAGCAAAAAGCACGTTTTCGATATTTCACGCGCTTTTCATTACGGC
TACAAATACCGCGATGGCTACTCAGTGGCAAATATCGAAACCAAAAGCTTGGTCAAACGTACAGT
TATTGATCCGGTGACTTTATAAGGATCCTGACTCGAGGTCGAC

FIGURE 88, CON'T.
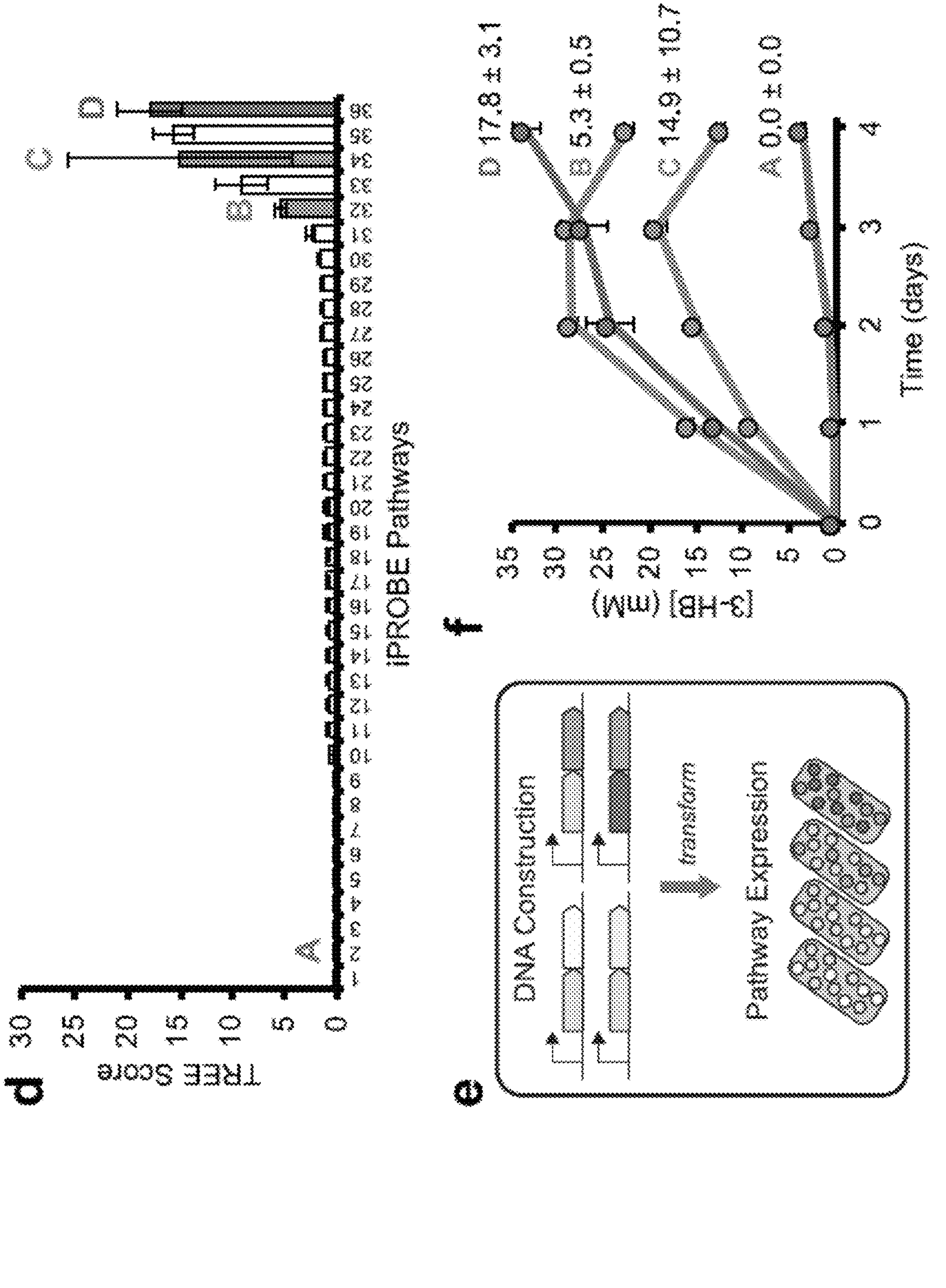

FIGURE 89, CON'T.
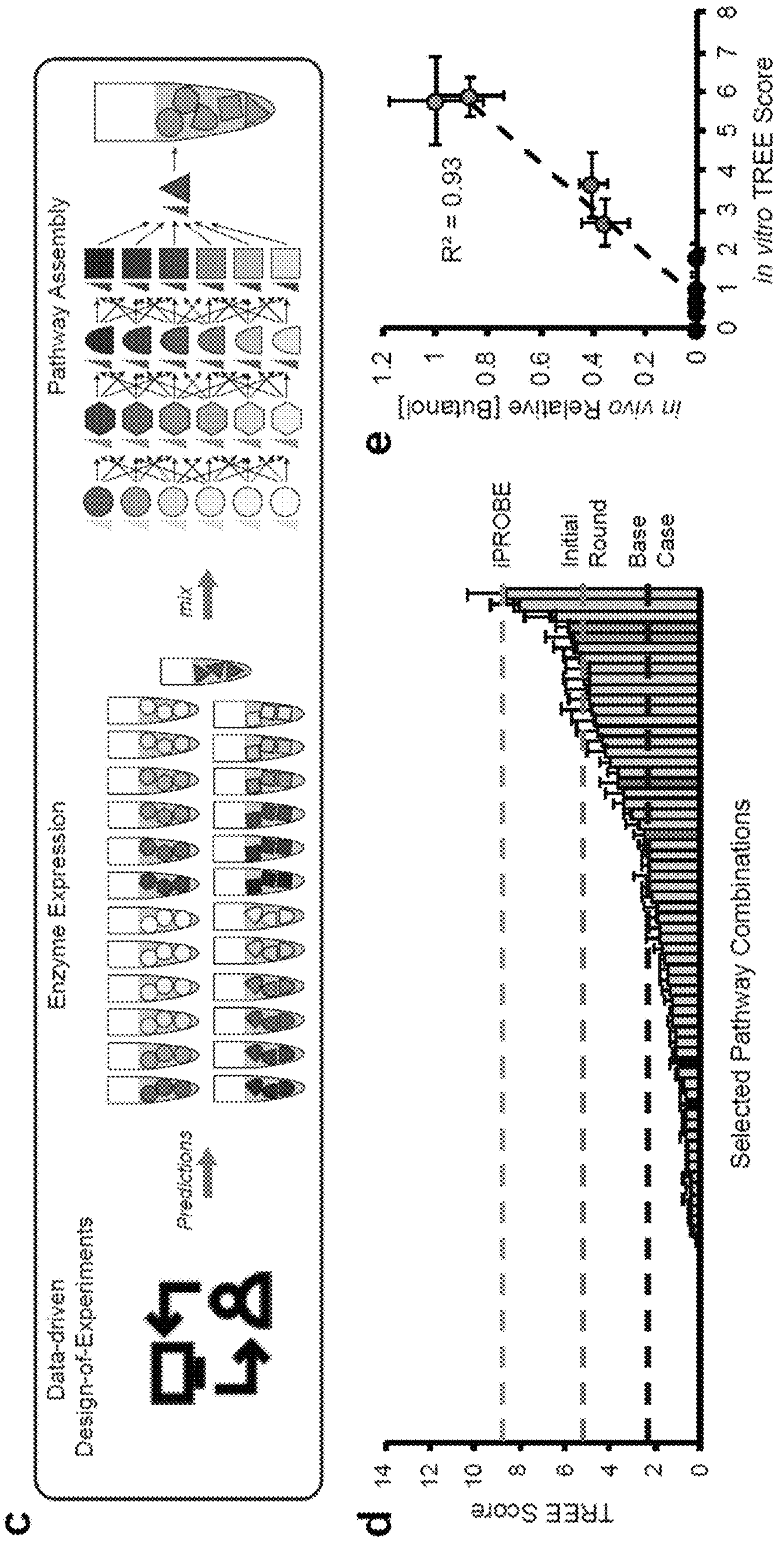

FIGURE 101

| Enzyme ID | Enzyme Activity | Organism | Source |
|---|---|---|---|
| EcoTHL | thiolase | *Escherichia coli* | P76461 |
| CacTHL | thiolase | *Clostridium acetobutylicum* | P45359 |
| CklTHL1 | thiolase | *Clostridium kluyveri* | A5N3I5 |
| ReuTHLa | thiolase | *Ralstonia eutropha* | P14611 |
| ReuTHLb | thiolase | *Ralstonia eutropha* | Q0KBP1 |
| CklTHL2 | thiolase | *Clostridium kluyveri* | A5N3I6 |
| CacTHLm | thiolase | *Clostridium acetobutylicum (engineered)* | Ref. 1 |
| CbeHBD | hydroxybutyryl-CoA dehydrogenase | *Clostridium beijerinckii* | A6LQ83 |
| CacHBD | hydroxybutyryl-CoA dehydrogenase | *Clostridium acetobutylicum* ATCC824 | P52041 |
| CpaHBD | hydroxybutyryl-CoA dehydrogenase | *Clostridium pasteurianum NRRL B-598* | A0A0K2MK58 |
| CsaHBD | hydroxybutyryl-CoA dehydrogenase | *Clostridium saccharoperbutylacetonicum* | M1LN99 |
| CklHBD1 | hydroxybutyryl-CoA dehydrogenase | *Clostridium kluyveri* DSM555 | A5N5D1 |
| CklHBD2 | hydroxybutyryl-CoA dehydrogenase | *Clostridium kluyveri* DSM555 | A5N111 |
| CacCRT | crotonyl-CoA dehydrogenase | *Clostridium acetobutylicum* | P52046 |
| PpuCRT | enoyl-CoA hydratase | *Pseudomonas putida* | I7AXZ7 |
| CbeCRT | crotonyl-CoA dehydrogenase | *Clostridium beijerinckii* | Q8RMI7 |
| CklCRT | crotonyl-CoA dehydrogenase | *Clostridium kluyveri* | A5N5C7 |

FIGURE 101, CON'T.

| Enzyme ID | Enzyme Activity | Organism | Source |
|---|---|---|---|
| CpaCRT | crotonyl-CoA dehydrogenase | *Clostridium pasteurianum* | P81357 |
| CsaCRT | crotonyl-CoA dehydrogenase | *Clostridium saccharobutylicum* | B2RGG3 |
| TdeTER | trans-2-enoyl-CoA reductase | *Treponema denticola* | Q73Q47 |
| FsuTER | trans-2-enoyl-CoA reductase | *Fibrobacter succinogenes* | C9RMX0 |
| FjoTER | trans-2-enoyl-CoA reductase | *Flavobacterium johnsoniae* | A5FE91 |
| SbaTER | trans-2-enoyl-CoA reductase | *Spirochaeta bajacaliforniensis* | WP_020613762 |
| ChuTER | trans-2-enoyl-CoA reductase | *Cytophaga hutchinsonii* | A0A0H3J994 |
| CpaTER | trans-2-enoyl-CoA reductase | *Clostridium pasteurianum* | Q11W68 |
| CacADH | acetaldehyde-CoA/alcohol dehydrogenase | *Clostridium acetobutylicum* | P33744 |

1 Mann, M. S. and Lütke-Eversloh, T. (2013), Thiolase engineering for enhanced butanol production in *Clostridium acetobutylicum*. Biotechnol. Bioeng., 110: 887-897. doi:10.1002/bit.24758

FIGURE 102, A (SEQ ID NO:73)

*EcoTHL*

ATGAAAAATTGTGTCATCGTCAGTGCGGTACGTACTGCTATCGGTAGTTTTAA
CGGTTCACTCGCTTCCACCAGCGCCATCGACCTGGGGGCGACAGTAATTAA
AGCCGCCATTGAACGTGCAAAAATCGATTCACAACACGTTGATGAAGTGATT
ATGGGTAACGTGTTACAAGCCGGGCTGGGGCAAAATCCGGCGCGTCAGGCA
CTGTTAAAAAGCGGGCTGGCAGAAACGGTGTGCGGATTCACGGTCAATAAA
GTATGTGGTTCGGGTCTTAAAAGTGTGGCGCTTGCCGCCCAGGCCATTCAG
GCAGGTCAGGCGCAGAGCATTGTGGCGGGGGGTATGGAAAATATGAGTTTA
GCCCCCTACTTACTCGATGCAAAAGCACGCTCTGGTTATCGTCTTGGAGACG
GACAGGTTTATGACGTAATCCTGCGCGATGGCCTGATGTGCGCCACCCATG
GTTATCATATGGGGATTACCGCCGAAAACGTGGCTAAAGAGTACGGAATTAC
CCGTGAAATGCAGGATGAACTGGCGCTACATTCACAGCGTAAAGCGGCAGC
CGCAATTGAGTCCGGTGCTTTTACAGCCGAAATCGTCCCGGTAAATGTTGTC
ACTCGAAAGAAAACCTTCGTCTTCAGTCAAGACGAATTCCCGAAAGCGAATT
CAACGGCTGAAGCGTTAGGTGCATTGCGCCCGGCCTTCGATAAAGCAGGAA
CAGTCACCGCTGGGAACGCGTCTGGTATTAACGACGGTGCTGCCGCTCTGG
TGATTATGGAAGAATCTGCGGCGCTGGCAGCAGGCCTTACCCCCCTGGCTC
GCATTAAAAGTTATGCCAGCGGTGGCGTGCCCCCCGCATTGATGGGTATGG
GGCCAGTACCTGCCACGCAAAAAGCGTTACAACTGGCGGGGCTGCAACTGG
CGGATATTGATCTCATTGAGGCTAATGAAGCATTTGCTGCACAGTTCCTTGCC
GTTGGGAAAAACCTGGGCTTTGATTCTGAGAAAGTGAATGTCAACGGCGGG
GCCATCGCGCTCGGGCATCCTATCGGTGCCAGTGGTGCTCGTATTCTGGTC
ACACTATTACATGCCATGCAGGCACGCGATAAAACGCTGGGGCTGGCAACA
CTGTGCATTGGCGGCGGTCAGGGAATTGCGATGGTGATTGAACGGTTGAAT
TAA

FIGURE 102, B (SEQ ID NO:74)

*CacTHL*

ATGAAGGAAGTGGTGATAGCTAGTGCAGTGCGGACCGCTATTGGGAGTTAC
GGCAAGTCATTGAAGGATGTCCCTGCTGTTGATTTGGGAGCCACCGCGATTA
AAGAGGCCGTAAAGAAAGCTGGCATAAAGCCCGAGGATGTCAATGAAGTTAT
CCTGGGGAACGTTTTGCAAGCTGGCTTGGGGCAAAATCCGGCCCGGCAAGC
ATCTTTTAAAGCCGGCCTTCCAGTAGAAATACCCGCTATGACGATCAACAAG
GTATGCGGTAGCGGACTTAGAACAGTGTCGCTTGCGGCTCAGATAATTAAGG
CAGGGGACGCTGACGTTATCATTGCGGGTGGTATGGAGAACATGAGTCGTG
CGCCCTACCTGGCGAACAATGCTAGATGGGGTTATCGCATGGGGAACGCGA
AGTTCGTCGATGAAATGATAACTGACGGCCTTTGGGACGCATTTAATGACTA
CCACATGGGAATCACCGCTGAGAACATTGCCGAACGCTGGAATATATCGAGA
GAAGAGCAGGACGAATTTGCCCTTGCCTCACAGAAAAAGGCGGAAGAGGCC
ATTAAATCTGGACAATTCAAAGATGAAATCGTCCCAGTCGTGATAAAGGGCA
GAAAAGGGGAAACTGTTGTGGACACGGATGAGCACCCCCGGTTCGGGTCAA
CAATAGAGGGCTTGGCAAAACTGAAACCCGCGTTCAAGAAAGATGGTACAGT
CACCGCGGGTAACGCATCGGGGTTGAATGATTGCGCGGCGGTATTGGTGAT
TATGTCTGCTGAAAAGGCTAAAGAATTAGGAGTAAAACCTTTGGCCAAAATTG
TCAGCTATGGGAGTGCTGGAGTAGACCCCGCGATCATGGGATATGGCCCGT
TCTACGCCACAAAAGCTGCTATTGAGAAAGCTGGGTGGACCGTTGATGAGCT
GGACTTGATTGAGTCAAATGAAGCATTCGCCGCTCAGTCGTTGGCGGTGGCT
AAGGATCTTAAATTTGATATGAACAAGGTCAATGTAAACGGAGGCGCGATCG
CATTAGGACATCCTATAGGTGCAAGCGGAGCACGCATTCTGGTTACTTTAGT
CCACGCTATGCAAAAGCGGGACGCTAAGAAAGGCCTGGCTACACTTTGTATC
GGCGGAGGCCAGGGCACTGCCATTTTGTTAGAAAAATGCTAA

FIGURE 102, C (SEQ ID NO:75)

*CkITHL1*

ATGCGTGAAGTAGTGATAGTATCTGCCGTTCGCACGGCTATAGGATCATTCG
GGGGTACTTTGAAGGATGTATCTGCAGTAGATTTGGGTGCTATTGTAATAAA
GGAAGCTGTAAAGCGGGCGGGTATTAAGCCCGAGCAAGTGGATGAGGTAAT
TTTTGGTAACGTGATACAGGCGGGTGTAGGACAGTCATTAGCAAGACAGTCA
GCCGTGTACGCCGGCTTGCCCGTCGAGGTACCTGCGTTTACAGTGAATAAG
CTGTGCGGTAGCGGACTTCGCACAGTATCTCTTGCTGCCTCCTTGATCTCGA
ACGGTGATGCGGACACAATAGTCGTTGGCGGCAGTGAAAATATGTCTGCGA
GCCCTTATTTAATACCCAAGGCTCGGTTCGGTTACCGTATGGGCGAAGCCAA
AATCTATGATGCAATGCTGCACGATGGTTTGATAGATTCGTTCAACAACTACC
ACATGGGAATTACCGCCGAGAATATAGCGGAGAAATGGGGTATTACGAGAG
AGGATCAGGACAAATTCGCTTTAGCTAGTCAGCAGAAGGCCGAAGCAGCGA
TCAAAGCTGGCAAATTCAAAGACGAAATCGTACCTGTAACGGTCAAAATGAA
AAAAAAAGAGGTCGTGTTCGACACCGACGAGGATCCGCGCTTTGGGACTAC
AATTGAAACTTTAGCGAAATTGAAGCCTGCTTTTAAACGGGATGGGACTGGT
ACCGTCACGGCAGGAAACAGTTCTGGGATCAACGATTCTAGTGCCGCACTTA
TCCTGATGTCGGCTGATAAGGCTAAGGAACTTGGGGTTAAACCGATGGCAAA
ATATGTAGATTTTGCCTCGGCAGGGCTTGATCCTGCAATTATGGGTTATGGT
CCATATTATGCCACAAAGAAAGTATTGGCTAAAACTAATCTTACGATTAAAGA
TTTTGATTTGATAGAGGCTAACGAGGCTTTCGCTGCTCAATCGATTGCAGTC
GCGCGTGACTTGGAGTTTGACATGTCGAAGGTTAATGTGAACGGTGGGGCC
ATAGCTCTGGGGCATCCTGTGGGATGTAGTGGGGCACGTATCCTTGTTACCC
TGCTGCACGAAATGCAGAAACGCGACGCAAAGAAGGGCTTGGCTACCTTAT
GTATTGGGGGAGGTCAAGGAACAGCGGTCGTAGTGGAGCGCTAA

FIGURE 102, D (SEQ ID NO:76)

*ReuTHLa*

ATGACAGACGTCGTAATCGTTTCGGCAGCAAGAACAGCAGTTGGGAAATTTG
GAGGGAGTTTAGCTAAAATTCCCGCTCCCGAGCTGGGGGCCGTAGTGATCA
AAGCGGCGTTAGAGCGCGCTGGTGTGAAACCCGAGCAGGTTAGTGAAGTAA
TCATGGGACAGGTACTGACGGCTGGTAGTGGACAAAATCCAGCTAGACAAG
CTGCAATCAAGGCAGGACTTCCTGCGATGGTGCCTGCGATGACCATTAACAA
GGTGTGCGGTTCAGGATTGAAGGCGGTCATGTTAGCAGCCAACGCGATAAT
GGCCGGAGACGCCGAGATAGTAGTGGCTGGAGGCCAAGAGAATATGTCTGC
GGCCCCCCACGTCCTTCCAGGTAGTAGAGATGGTTTTCGGATGGGAGACGC
CAAGTTAGTAGACACTATGATTGTAGACGGTTTATGGGACGTATACAACCAAT
ATCACATGGGAATAACGGCTGAGAACGTCGCTAAGGAATATGGGATAACTCG
GGAAGCCCAGGACGAATTTGCGGTAGGATCGCAAAATAAAGCCGAGGCTGC
TCAAAAGGCGGGGAAGTTTGATGAGGAAATTGTTCCTGTTTTAATTCCGCAG
CGGAAAGGAGACCCAGTAGCATTCAAAACGGACGAGTTTGTCCGCCAGGGC
GCTACCTTGGACTCAATGTCGGGTCTTAAACCTGCGTTCGATAAAGCAGGCA
CTGTTACAGCCGCCAACGCCAGCGGCTTAAATGATGGCGCGGCTGCAGTCG
TCGTAATGTCAGCAGCCAAGGCGAAAGAGCTTGGCTTGACACCATTAGCTAC
GATTAAATCGTACGCGAATGCTGGTGTAGACCCCAAAGTCATGGGAATGGG
GCCTGTACCCGCGTCGAAGAGAGCATTGTCCCGGGCGGAATGGACGCCACA
AGACCTGGACCTGATGGAGATCAATGAAGCTTTCGCTGCACAGGCTTTGGC
GGTTCATCAACAGATGGGATGGGATACTTCCAAAGTCAACGTGAACGGAGG
GGCTATCGCAATAGGTCATCCTATCGGCGCGAGCGGCTGCCGGATACTTGT
CACTTTATTGCATGAAATGAAGCGGAGAGATGCCAAGAAGGGATTGGCATCT
CTGTGTATAGGAGGTGGCATGGGTGTAGCTTTGGCTGTAGAACGTAAGTAA

FIGURE 102, E (SEQ ID NO:77)

*ReuTHLb*

ATGACACGTGAAGTTGTCGTAGTAAGTGGGGTTCGTACGGCCATAGGTACTT
TCGGAGGTTCTCTGAAGGATGTTGCCCCCGCCGAGTTAGGTGCATTAGTAGT
ACGTGAGGCATTAGCGCGGGCCCAAGTGTCGGGTGATGACGTAGGGCATGT
GGTTTTCGGCAACGTCATACAGACTGAGCCACGTGATATGTACTTGGGTCGG
GTAGCCGCCGTGAACGGCGGGGTGACAATTAACGCTCCGGCCTTGACGGTC
AATCGGCTTTGCGGCAGCGGGCTTCAAGCTATTGTCAGTGCAGCCCAGACC
ATTCTTTTGGGTGATACCGATGTCGCAATCGGCGGAGGAGCAGAATCAATGT
CGCGCGCGCCATATTTAGCGCCAGCAGCGAGATGGGGGGCCCGGATGGGT
GATGCAGGGTTAGTAGATATGATGTTAGGAGCGTTGCATGACCCATTTCATC
GTATACACATGGGAGTGACAGCCGAAAACGTCGCTAAAGAATACGACATCTC
GCGCGCGCAACAAGATGAGGCAGCATTGGAGAGTCACAGACGTGCCTCAGC
AGCTATAAAAGCTGGGTATTTCAAGGACCAGATCGTACCTGTTGTATCCAAG
GGCCGGAAAGGTGACGTTACTTTTGACACTGACGAACACGTCCGCCACGAT
GCTACCATTGATGATATGACGAAATTACGTCCTGTGTTTGTAAAGGAAAACGG
AACTGTTACCGCTGGGAACGCCTCAGGGCTGAACGACGCGGCCGCTGCCGT
TGTAATGATGGAACGGGCCGAGGCGGAACGTCGTGGTTTGAAACCGCTGGC
ACGGTTGGTAAGCTATGGCCACGCTGGCGTAGATCCAAAGGCAATGGGTAT
CGGACCTGTTCCAGCAACTAAAATTGCTCTTGAACGCGCTGGTCTTCAAGTC
AGTGATTTAGATGTAATCGAAGCAAATGAGGCGTTCGCCGCACAAGCTTGTG
CCGTAACCAAGGCGCTGGGGTTGGATCCAGCAAAGGTGAACCCCAATGGGA
GTGGCATATCATTGGGGCACCCTATAGGTGCGACAGGCGCGTTGATTACTGT
CAAGGCGCTGCATGAGTTAAATCGCGTACAGGGCCGTTACGCGCTTGTCAC
AATGTGTATAGGAGGGGGCCAGGGGATTGCCGCCATTTTCGAACGCATCTA
A

FIGURE 102, F (SEQ ID NO:78)

*CkITHL2*

ATGAAAGATGCAGTTATTGTAAGTGCAGTAAGAACAGCTATAGGGAGTTTTG
GTGGAACTTTAAAAGATATTTCTGCTGTAGATTTGGGGGCAATAGTTATAAAA
GAGGCTGTAAAAAGAGCAGGTATAAAACCAGAACAAGTAGATGAAGTTATAT
TTGGAAATGTAATACAGGCAGGTCTTGGACAAAGTCCAGCGAGGCAAGCTG
CTGTAAAAGCAGGCATTCCTGTAGAAGTACCAGCGTTTACACTAAATAAGGTT
TGCGGTTCAGGACTTAGATCAGTAAGTTTGGCAGCTCAGCTCATAAAAATTG
GAGATGATGATATTGTTGTAGTTGGTGGAACAGAAAACATGTCCGCTGCACC
ATATCTACTTCCAAAGGCCAGATGGGGACATAGAATGGGAGAGGGAAAATTA
GTTGATGCCATGATAAAAGATGGACTTTGGGAAGCATTTAACAATTACCACAT
GGGAATTACAGCTGAAAACATAGCAGAAAAATGGGGAATAACAAGAGATATG
CAGGATGAATTTGCATTAGCATCCCAACAGAAGGCAGAAGCAGCCATAAAGG
CAGGAAAATTTAAAGATGAAATAGTTCCAGTAACCGTTAAGCAGAAAAAGAAA
GAAATAATTTTTGATACTGATGAATTCCCTAGATTTGGGACAACTATAGAAGC
ATTAGCAAAATTGAAACCATCATTCAAAAAAGATGGAACAGTTACAGCAGGTA
ATGCTTCGGGAATAAATGATGCAGCAGCAGCTTTAGTTGTAATGAGTGCAGA
TAAGGCAAAAGAACTTGGAATTAAGCCTCTTGCAAAGATTGTTTCCTATGGAA
GTAAAGGATTAGACCCAACCATAATGGGATACGGACCTTTCTATGCAACAAA
GTTGGCACTTGAAAAAGCTAACTTGTCAATTGCAGATTTAGACTTAATAGAAG
CAAATGAAGCATTCGCTTCACAAAGTTTAGCAGTAGCAAAAGATTTAGAATTT
GATATGAGCAAAGTAAATGTAAATGGAGGAGCAATAGCTCTTGGACATCCAG
TTGGCTGCTCTGGTGCAAGAATACTCGTTACATTACTTTATGAAATGCAGAGA
AGAGATGCGAAAAAGGGACTTGCAACATTATGTATAGGGGGAGGAATGGGA
ACTGCACTAATAGTTGAAAGATAA

FIGURE 102, G (SEQ ID NO:79)

*CacTHLm*

ATGAAAGAAGTTGTAATAGCTAGTGCAGTAAGAACAGCGATTGGATCTTATG
GAAAGTCTCTTAAGGATGTACCAGCAGTAGATTTAGGAGCTACAGCTATAAA
GGAAGCAGTTAAAAAAGCAGGAATAAAACCAGAGGATGTTAATGAAGTCATT
TTAGGAAATGTTCTTCAAGCAGGTTTAGGACAGAATCCAGCAAGACAGGCAT
CTTTTAAAGCAGGATTACCAGTTGAAATTCCAGCTATGACTATTAATAAGGTTT
GTGGTTCAGGACTTAGAACAGTTAGCTTAGCAGCACAAATTATAAAAGCAGG
AGATGCTGACGTAATAATAGCAGGTGGTATGGAAAATATGTCTAGAGCTCCT
TACTTAGCGAATAACGCTAGATGGGGATATGGAATGGGAAACGCTAAATTTG
TTGATGAAATGATCACTGACGGATTGTGGGATGCATTTAATGATTACAATATG
GGAATAACAGCAGAAAACATAGCTGAGAGATGGAACATTTCAAGAGAAGAAC
AAGATGAGTTTGCTCTTGCATCACAAAAAAAAGCTGAAGAAGCTATAAAATCA
GGTCAATTTAAAGATGAAATAGTTCCTGTAGTAATTAAAGGCAGAAAGGGAGA
AACTGTAGTTGATACAGATGAGCACCCTAGATTTGTATCAACTATAGAAGGAC
TTGCAAAATTAAAACCTGCCTTCAAAAAAGATGGAACAGTTACAGCTGGTAAT
GCATCAGGATTAAATGACTGTGCAGCAGTACTTGTAATCATGAGTGCAGAAA
AAGCTAAAGAGCTTGGAGTAAAACCACTTGCTAAGATAGTTTCTTATGGTTCA
GCAGGAGTTGACCCAGCAATAATGGGATATGGACCTTTCTATGCAACAAAAG
CAGCTATTGAAAAAGCAGGTTGGACAGTTGATGAATTAGATTTAATAGAATCA
AATGAAGCTTTTGCAGCTCAAAGTTTAGCAGTAGCAAAAGATTTAAAATTTGA
TATGAATAAAGTAAATGTAAATGGAGGAGCTATTGCCCTTGGTCATCCAATTG
GAGCATCAGGTGCAAGAATACTCGTTACTCTTGTACACGCAATGCAAAAAG
AGATGCAAAAAAAGGCTTAGCAACTTTATGTATAGGTGGCGGACAAGGAACA
GCAATATTGCTAGAAAAGTGCTAG

FIGURE 102, H (SEQ ID NO:80)

*CbeHBD*

ATGAAAAAGATTTTTGTGTTGGGCGCGGGCACCATGGGTGCGGGTATCGTG
CAGGCGTTCGCGCAGAAAGGTTGCGAAGTGATCGTGCGCGACATTAAGGAA
GAATTTGTGGACCGCGGCATTGCGGGCATCACCAAAGGCCTGGAAAAGCAG
GTGGCGAAAGGCAAAATGAGCGAAGAAGATAAAGAAGCGATTTTAAGCCGC
ATCAGCGGCACCACCGATATGAAACTGGCGGCGGACTGCGATCTGGTGGTG
GAAGCGGCGATCGAAAATATGAAAATCAAGAAGGAAATCTTCGCGGAACTGG
ATGGCATCTGCAAGCCGGAAGCTATCCTGGCGAGCAATACCAGCAGCCTGA
GCATCACCGAAGTGGCGAGCGCGACCAAGCGCCCGGATAAAGTGATCGGC
ATGCATTTCTTTAACCCGGCGCCGGTGATGAAGTTGGTGGAAATCATCAAAG
GCATTGCGACCAGCCAGGAAACCTTTGATGCGGTGAAGGAACTGAGCGTGG
CGATCGGCAAAGAACCGGTGGAAGTGGCGGAAGCGCCGGGCTTCGTGGTG
AATCGCATTCTGATCCCGATGATCAATGAAGCGAGCTTTATCTTACAGGAAG
GCATTGCGAGCGTGGAAGATATCGATACCGCGATGAAATATGGTGCGAATCA
TCCGATGGGCCCGCTGGCGCTGGGCGATTTGATCGGCCTGGACGTGTGTCT
GGCGATCATGGATGTGCTGTTCACCGAAACCGGTGATAATAAGTACCGCGC
GTCATCAATTCTGCGCAAATATGTGCGCGCGGGCTGGTTGGGCCGCAAAAG
CGGCAAAGGCTTCTATGATTACAGCAAATAA

FIGURE 102, I (SEQ ID NO:81)

*CacHBD*

ATGAAAAAAGTATGTGTCATCGGTGCCGGCACGATGGGCTCGGGGATTGCT
CAAGCCTTCGCTGCAAAGGGATTCGAAGTTGTGCTGCGTGATATCAAGGACG
AATTTGTGGATCGCGGCCTGGATTTCATCAACAAAAATCTCAGCAAACTGGT
GAAGAAAGGCAAAATTGAGGAAGCCACTAAAGTGGAAATTCTGACCCGTATT
TCCGGCACGGTTGACCTGAATATGGCGGCCGATTGTGACCTGGTTATTGAAG
CGGCGGTCGAACGCATGGATATCAAGAAACAAATCTTTGCCGATCTTGATAA
CATTTGCAAACCGGAGACTATCCTCGCCTCAAATACAAGCAGTTTAAGTATTA
CCGAAGTGGCAAGCGCTACAAAACGGCCCGATAAAGTGATTGGAATGCATTT
TTTCAACCCAGCCCCGGTTATGAAACTGGTTGAAGTGATTCGCGGCATCGCT
ACCTCCCAAGAAACCTTTGATGCAGTTAAAGAAACCTCGATCGCCATTGGTA
AAGATCCAGTGGAGGTAGCCGAAGCGCCGGGCTTCGTGGTTAATCGGATCT
TAATTCCGATGATTAACGAAGCTGTTGGCATTCTGGCCGAAGGCATTGCGTC
CGTGGAAGACATCGACAAAGCAATGAAATTGGGTGCAAATCACCCTATGGGT
CCACTCGAACTTGGCGATTTTATCGGTCTTGATATTTGCCTGGCGATCATGG
ACGTGCTGTATTCAGAGACAGGCGATAGTAAATACCGCCCGCACACGCTGCT
GAAAAAATATGTTCGGGCTGGCTGGCTGGGGCGTAAATCTGGTAAGGGTTTT
TACGATTATTCCAAATAA

FIGURE 102, J (SEQ ID NO:82)

*CpaHBD*

ATGAAAAAGATCTTTGTGTTGGGCGCCGGCACCATGGGTGCCGGTATTGTG
CAGGCCTTTGCACAGAAAGGGTGCGAAGTGATTGTGCGCGATATCAAAGAA
GAATTTGTAGATCGCGGAATCGCTGGTATTACGAAAGGGTTAGAAAAACAAG
TGGCTAAAGGGAAAATGAGCGAGGAGGATAAAGAGGCCATTCTTTCGCGCA
TTAGCGGCACCACCGATATGAAATTAGCTGCGGATTGTGATCTGGTGGTTGA
AGCAGCAATTGAAAACATGAAAATCAAAAAAGAAATTTTTGCCGAGCTGGATG
GCATTTGTAAACCGGAAGCCATTTTAGCCTCAAATACCTCTAGCCTGAGTATC
ACCGAAGTAGCCAGCGCGACCAAACGCCCCGATAAAGTTATTGGAATGCATT
TCTTCAACCCTGCACCAGTGATGAAACTGGTGGAAATTATTAAGGGAATTGC
AACCAGTCAAGAAACGTTTGATGCGGTTAAAGAACTGTCGGTCGCTATTGGC
AAAGAGCCAGTGGAAGTCGCCGAAGCCCCGGGCTTTGTGGTCAATCGGATT
CTGATCCCGATGATTAACGAAGCCAGCTTTATCTTGCAGGAAGGAATTGCGA
GCGTGGAAGATATCGATACGGCGATGAAATACGGGGCAAATCACCCGATGG
GCCCGCTGGCTTTGGGGGACCTGATTGGCCTGGACGTTTGCCTGGCGATTA
TGGACGTGTTGTTTACTGAAACCGGCGACAACAAGTATCGTGCGAGTTCAAT
CCTCCGTAAATATGTGCGGGCCGGGTGGCTCGGTCGCAAATCGGGCAAAGG
CTTTTATGACTACAGCAAATAA

FIGURE 102, K (SEQ ID NO:83)

*CsaHBD*

ATGAAGATTTTCGTGTTGGGAGCGGGGACAATGGGGGCTGGGATCGTCCAG
ATTTTTGCAGAGGCCGGTTATCAGGTGATCATGCGTGATATCGAAGAGAGTT
TCGTCCAGAAGGGTATCACAAATATTACTAAAAACTTAGACAAAGCCGTTAAA
AAAGAAAAAATCACGGAGGAAAGCAAAAACGAAGTGCTGGGACGCATCATC
GCCACCACGGACATTAACCTTGCAAAAGACGCAGATTTAGTTATCGAAGCAG
CCATTGAAAACATGAATATTAAAAAAAAGATCTTTGCGGAGCTTGACGACGTT
TGTAAACCCGAAACTATTCTGGCGACAAACACGTCATCCTTAAGTATCACCGA
CGTGGCATCCGCGACTAAGCGTCCTGACAAGGTTATTGGGATGCACTTTTTT
AATCCTGTTCCAGTCATGAAACTGGTAGAAGTAATCACCGGTATGGCGACGT
CGGCGGAAACGAAAGATACCGTTATTGAAATTACCAAGAAGGTAGGTAAGGA
TCCGGTAGAAGTGAAAGAAGCACCGGGCTTTGTAGTGAATCGCATTTTAATC
CCGATGATCAATGAAGCGGTAGGTATCCTGGCGGATAATGTCGCTACCGCC
GAAGATATTGATATCGCAATGAAACTGGGCGCGAACCACCCGATGGGTCCG
CTGGCCCTGGCCGATCTGATTGGGAACGATGTGTGTCTGGCCATCATGGAA
ATTCTGTACATTGAATTTGGGGATCCTAAATATCGGCCGAATCCAATGCTGCG
GAAAATGGTGCGCGCAGGTTATCTGGGCCGTAAAACGGGCAAGGGCTTTTA
TGATTATTCCAAGTAA

FIGURE 102, L (SEQ ID NO:84)

*CkIHBD1*

ATGAGCATCAAATCTGTGGCCGTACTGGGCTCGGGGACGATGAGCCGTGGT
ATTGTTCAGGCTTTCGCAGAAGCGGGTATCGATGTGATCATCCGCGGTCGCA
CGGAAGGCAGTATCGGGAAAGGGCTTGCTGCTGTTAAAAAGGCGTATGATA
AGAAAGTCTCAAAAGGTAAAATTAGCCAAGAAGACGCAGACAAAATCGTGGG
CCGTGTGAGTACAACCACTGAGCTCGAAAAACTGGCTGATTGTGATCTCATC
ATCGAAGCGGCCTCTGAGGACATGAACATTAAAAAGACTACTTCGGCAAGC
TGGAAGAGATCTGCAAACCTGAAACAATTTTTGCGACGAACACATCTTCGTTG
TCCATCACGGAAGTCGCGACAGCGACTAAACGCCCGGATAAATTCATCGGTA
TGCATTTTTTCAATCCGGCAAACGTTATGAAATTAGTTGAGATTATCCGCGGG
ATGAATACGTCCCAGGAGACGTTTGACATCATCAAAGAAGCCAGCATCAAAA
TTGGCAAAACCCCTGTGGAAGTGGCGGAAGCGCCGGGTTTTGTGGTTAACA
AAATCCTGGTGCCAATGATCAACGAAGCCGTTGGCATCCTGGCCGAAGGGA
TTGCATCAGCGGAAGACATTGACACTGCAATGAAACTGGGCGCCAACCATCC
TATGGGGCCGCTTGCCCTCGGAGACTTAATTGGGTTAGACGTGGTCTTAGCT
GTGATGGATGTGCTGTATTCGGAAACCGGCGACTCTAAATACCGTGCGCATA
CTCTGCTGCGCAAGTATGTCCGTGCAGGTTGGCTGGGCCGCAAAAGCGGTA
AAGGTTTTTTCGCCTACTAA

FIGURE 102, M (SEQ ID NO:85)

*CkIHBD2*

ATGGATATCAAAAATGTGGCCGTACTCGGCACGGGCACTATGGGTAACGGC
ATCGTCCAGCTGTGCGCTGAGAGCGGTCTTAATGTAAATATGTTTGGTCGGA
CCGATGCTAGCCTCGAACGCGGATTTACAAGTATCAAAACGTCCCTGAAAAA
CCTGGAGGAAAAAGGGAAAATTAAAACGAATATTTCTAAAGAAATTCTGAAGC
GTATCAAAGGCGTAAAAACAATTGAAGAAGCAGTCGAAGGCGTGGACTTCGT
GATTGAATGTATTGCGGAAGACCTGGAACTGAAACAAGAAGTCTTTAGCAAG
CTGGACGAGATCTGTGCTCCCGAAGTGATCTTAGCGAGCAATACCAGTGGC
CTGTCGCCGACCGACATCGCTATCAACACGAAACACCCGGAGCGGGTTGTA
ATTGCGCACTTTTGGAACCCGCCACAGTTTATTCCGCTGGTAGAGGTTGTGC
CGGGAAAACATACTGATAGTAAAACCGTGGACATCACCATGGATTGGATCGA
ACATATCGGTAAAAAAGGCGTGAAAATGCGCAAAGAGTGCCTGGGGTTTATC
GGCAACCGTCTGCAACTGGCCCTTCTGCGTGAGGCACTTTATATCGTTGAAC
AAGGTTTCGCCACGGCGGAGGAAGTTGATAAGGCAATTGAGTATGGGCATG
GCCGGCGTCTCCCTGTGACGGGCCCGATCTGTTCCGCGGATCTGGGCGGT
CTGGATATTTTCAATAACATCAGTTCGTATTTGTTTAAAGATTTATGTAACGAT
ACTGAACCAAGCAAGCTTTTGAAATCGAAAGTCGACGGCGGTAATCTGGGCT
CTAAAACCGGTAAAGGTTTCTATAACTGGACACCCGAGTTCTTACAAAAAAAG
CAGAATGAACGTATTCAGCTGCTGATGGACTTCCTGGAAAAAGACAAAAACG
ATAAAAGCATTGAACGCAACATTTAA

FIGURE 102, N (SEQ ID NO:86)

*CacCRT*

ATGGAACTTAATAACGTAATCTTAGAAAAGGAAGGTAAAGTGGCGGTGGTGA
CAATCAATCGCCCGAAAGCGCTGAACGCTCTGAACAGCGATACCCTCAAAGA
AATGGATTATGTGATTGGTGAAATCGAAAACGATTCAGAAGTGTTAGCGGTG
ATCCTGACCGGCGCGGGCGAAAAAGCTTTGTGGCGGCGCGGATATCAGC
GAGATGAAGGAAATGAACACAATCGAAGGTCGCAAATTCGGAATTTTGGGCA
ACAAAGTATTTCGCCGCCTGGAATTATTAGAAAAGCCGGTGATTGCGGCGGT
GAACGGTTTTGCGCTGGGCGGAGGCTGTGAAATTGCGATGAGCTGCGATAT
TCGCATTGCGAGCTCAAATGCGCGCTTTGGTCAGCCGGAAGTGGGTCTAGG
CATTACCCCGGGTTTTGGTGGTACCCAGCGCTTAAGCCGCCTGGTGGGCAT
GGGAATGGCGAAGCAATTGATTTTTACCGCGCAGAACATTAAGGCGGATGAA
GCGCTGCGCATCGGCTTGGTGAACAAGGTGGTGGAACCGAGCGAACTGATG
AACACCGCGAAAGAAATCGCGAATAAAATCGTATCAAACGCGCCGGTGGCG
GTGAAGCTGTCAAAACAAGCGATCAACCGCGGCATGCAATGCGATATCGATA
CCGCGCTGGCGTTTGAAAGCGAAGCGTTTGGCGAATGTTTTAGCACCGAGG
ATCAGAAGGATGCGATGACCGCGTTCATTGAGAAACGCAAAATCGAAGGATT
CAAAAACCGCTGA

FIGURE 102, O (SEQ ID NO:87)

*PpuCRT*

ATGACAACCCCGAGCAGCCCTCTGTTAAGCAAAGTTGAGGCTGGCGTAGCG
TGGATTACCTTGAACCGCCCAGAACAGCGCAACGCCCTGGATATCCCAACCT
TAAAACAACTGCATGCGTTATTAGATAGCCACGCGGATGATCCAGCGGTACG
CGTGGTGGTGCTGACCGGCAGCGGCCGCAGCTTTTGCGCTGGCGCGGATC
TGGCGGAGTGGGCTGCGGCGGAGGCTGCGGGCACCCTGGAGAGCTACGG
CTGGACCGAGACAGCGCACGCGCTGATGTTGCGCCTGCATAGCTTGGATAA
GCCAACCATTGCGGCGATTAACGGCACCGCGGTGGGCGGGGGCATGGATC
TCAGCCTGTGCTGCGATCTGCGCATTGCGGCGGCGAGCGCCCGCTTTAAAG
CGGGCTATACCAGCATGGGCTATAGCCCAGACGCGGGCGCGAGCTGGCAT
CTGCCTCGGCTGATTGGCAGCGAACAGGCGAAACGCTTGTTATTTTTGGACG
AGCTGTGGGGCGCGGAACACGCGCTGGCCGCTGGGCTGGTTAGCGAGGTT
TGCGCGGATGAACAACTGCCAGCGGTGGCCGCGGAATTAGCGGGGCGCCT
GGCGAATGGCCCGACTTTTGCGTACGCCCAGACCAAACAGCTGATTCGCGA
TGGCGCGCGGCGCACCTTAGCGGAACAGCTGGAAGCTGAACGCCATGCGG
GCCTGCTGTGCGGCCGCAGCCAGGACGGCGCGGAAGCGCTGCAAGCGAGC
GTAGAGCGCCGCGCGCCACGGTTCACCGGCCAGTGA

FIGURE 102, P (SEQ ID NO:88)

*CbeCRT*

ATGGAGTTAAAGAATGTAATCCTTGAAAAGGAGGGCCACCTTGCTATAGTTA
CGATCAATCGCCCGAAGGCATTAAATGCACTGAACTCAGAAACCCTTAAAGA
CTTGAATGTTGTTCTGGACGATCTTGAAGCCGACAACAATGTTTACGCCGTAA
TCGTCACAGGAGCAGGCGAAAAGTCGTTTGTAGCTGGCGCGGACATCGCAG
AGATGAAAGACTTAAATGAAGAGCAAGGAAAAGAGTTCGGGATACTGGGCAA
CAATGTCTTCAGAAGACTTGAAAAATTAGATAAGCCCGTAATTGCAGCTGTGA
GCGGTTTTGCATTAGGTGGGGGCTGCGAGCTGGCTATGAGCTGCGACATAC
GCATAGCATCGGTTAAGGCCAAATTCGGTCAACCCGAGGTTGGATTGGGCAT
AACGCCGGGATTCGGCGGTACTCAGCGGTTAGCAAGAATTGTTGGGCCGGG
GAAAGCTAAAGAACTTATATACACTTGTGACATCATAAACGCCGAAGAAGCCT
ACCGGATTGGGTTAGTTAATAAGGTAGTTGAGTTGGAGAAGCTGATGGAAGA
GGCAAAAGCGATGGCAAACAAGATTGCAGCCAATGCTCCCAAAGCTGTCGC
ATATTGCAAGGACGCTATTGATCGGGGGATGCAAGTTGACATTGACGCCGCT
ATATTGATAGAAGCGGAAGACTTTGGGAAATGTTTCGCAACGGAAGATCAAA
CGGAAGGAATGACAGCATTCTTGGAAAGACGCACCGAAAAGAACTTCCAGAA
TAAGTAA

FIGURE 102, Q (SEQ ID NO:89)

*CkICRT*

ATGGAGTTTAAGAATATAATTCTGGAGAAAGACGGGAACGTCGCTTCCATAA
CATTAAATCGCCCGAAAGCCCTGAATGCCTTAAATGCTGCTACGCTGAAGGA
AATCGACGCAGCAATCAATGACATCGCTGAAGACGACAATGTTTATGCCGTG
ATAATCACAGGTTCGGGGAAAGCATTCGTCGCGGGAGCCGATATCGCAGAA
ATGAAGGACTTAACGGCCGTAGAGGGTCGTAAATTTTCGGTGTTGGGCAATA
AGATATTTCGCAAGCTGGAGACCTTGGAAAAGCCAGTGATTGCAGCTATTAA
CGGATTCGCACTGGGTGGAGGATGCGAGTTGTCCCTTTCATGCGATATACG
CATAGCGTCGAGTAAGGCGAAATTCGGGCAACCCGAGGTTGGCTTAGGGAT
CACCCCAGGCTTCGGAGGGACTCAGCGCCTGGCCCGTGCTATTGGCGTGG
GAATGGCAAAAGAACTGATTTACACCGGTAAGGTCATAAACGCCGAAGAGGC
ACTTCGGGTCGGACTGGTAAATAAAGTGGTCGAGCCAGATAAGTTATTAGAA
GAAGCAAAGTCTCTGGTGGACGCGATCATTGTTAATGCTCCAATAGCCGTAC
GGATGTGCAAAGCTGCCATAAACCAAGGATTGCAGTGTGATATTGATACCGC
AGTTGCATACGAAGCAGAGGTTTTCGGGGAATGTTTTGCTACGGAAGATCGT
GTCGAGGGCATGACGGCTTTCGTGGAGAAGCGTGATAAGGCTTTTAAGAATA
AGTAA

FIGURE 102, R (SEQ ID NO:90)

*CpaCRT*

ATGGAGCTGAAAAACGTCATACTGGACAAGGAAGGAAAGATCGCTGTGGTTA
CCATTAACCGTCCGAATGCTCTTAATGCACTTAATTCCGAGACACTTAAAGAA
TTGGATTACGTCATCGATGAAATAGAAAACGATTCGAACGTCTTTGCCGTTAT
TCTTACAGGAGCTGGTGAGAAATCATTTGTCGCTGGAGCGGACATCGCCGA
GATGAAGGACATGAACACCATCGAGGGTCGGAAATTTGGTATTTTAGGAAAT
CGTGTATTTCGTCGTATTGAACTGCTGGAAAAGCCAGTGATTGCGGCGGTCA
ATGGGTTTGCCCTGGGTGGCGGGTGTGAGCTGAGCATGTCATGCGATATTA
GAATCGCTTCCTCGAACGCCCGGTTTGGACAGCCTGAGGTCGGATTGGGCA
TTACTCCGGGGTTTGGAGGTACACAGCGTCTGGCTCGTTTGGTTGGCATGG
GTATGGCGAAGCAGATTATTTTCACTGCCAAGAATATCAAAGCGGATGAAGC
ACTGAGAATTGGGTTGGTCAACAAGGTGGTGGAGCCGGGAGAATTGATGGA
TACTGCAAAGGATATTGCAAACACAATTGCATCCAAGGCTCCAATCGCTGTAA
AACTTTCGAAACAGGCAATCAATAGAGGATTTCAGTGCGACATCGACACGGC
TCTGTCGTTTGAGTCCGAAGCCTTCGGCGAGTGTTTCTCGACGGAAGACCAG
AAAGATGCAATGACCGCATTTGTGGAGAAGAAAAAAATCGATGGGTTCAAGA
ATAGATAA

FIGURE 102, S (SEQ ID NO:91)

*CsaCRT*

ATGGAGTTAAAGAACGTAATCTTGGAAAAGGAGGGCCATCTGGCCATTGTGA
CGATTAATAGACCGAAAGCTTTAAACGCCTTGAACTCGGAGACACTGAAAGA
CTTGGATACCGTTATTGAAGACCTTGAAAAGGACTCGAACGTATATAGCGTTA
TCTTGACTGGCGCAGGCGAAAAGTCATTCGTGGCAGGAGCAGATATAAGTG
AGATGAAAGACTTGAACGAACAGCAGGGTAAGGAATTTGGGATCTTGGGGAA
CAATGTCTTTCGGCGTTTGGAAAAGCTTGATAAGCCAGTCATCGCTGCCATT
AGTGGGTTTGCGTTGGGCGGGGGTTGTGAATTGGCAATGAGCTGTGACATT
CGTATCGCCTCGGAGAAAGCCAAATTTGGTCAACCTGAGGCCGGTCTGGGA
ATAACGCCTGGCTTTGGTGGTACTCAACGCTTAGCGCGTATTGTTGGGTTAG
GCAAGGCAAAAGAGATGATTTATACTTGTGATATAATAAAAGCTGAAGAGGCA
TATCGCATAGGGCTGGTGAATAAGATAGTACCCCTGGAGAACTTAATGGACG
AGGCTAAAGCTATGGCCAATAAAATCATGGCAAATGCACCAAAGGCCGTAAA
GTACTGCAAGGATGCTATTAATCGGGGTATGCAAGTCGATATTGACGCCGCA
ATTTTAATTGAAGCTGAGGATTTCGGTAAATGCTTCGCCACCGAGGATCAAAC
GGAGGGCATGACCGCATTCCTTGAAAGAAGAACCGAGAAGAACTTCCAGAA
CAAGTAA

FIGURE 102, T (SEQ ID NO:92)

*TdeTER*

ATGAAGGTAACCAACCAGAAAGAGCTGAAACAAAAATTAAACGAACTCCGCG
AAGCGCAAAAAAAATTCGCGACGTATACTCAGGAACAAGTCGATAAGATCTTT
AAACAATGTGCCATTGCAGCGGCCAAAGAACGCATCAACCTGGCGAAGTTG
GCCGTTGAAGAAACCGGAATTGGTTTAGTGGAAGACAAAATTATTAAGAACC
ATTTCGCTGCGGAATATATTTATAATAAATACAAAAATGAGAAGACCTGCGGA
ATTATTGATCATGATGATAGCCTTGGTATCACTAAAGTAGCAGAACCAATCGG
TATCGTCGCCGCCATCGTTCCTACAACCAATCCGACCTCTACGGCGATCTTT
AAATCATTGATTAGCCTGAAAACGCGTAACGCGATTTTTTTCAGCCCTCACCC
ACGCGCCAAAAAAAGCACTATCGCTGCGGCGAAACTGATTCTGGATGCGGC
AGTTAAAGCCGGCGCACCTAAAAACATTATCGGCTGGATCGACGAGCCTAGC
ATCGAGTTGAGCCAGGACCTCATGAGTGAAGCAGATATTATCCTCGCCACGG
GTGGGCCATCTATGGTTAAAGCGGCCTACTCATCTGGTAAACCAGCCATCGG
TGTGGGTGCGGGCAATACCCCGGCGATCATTGACGAGAGCGCCGATATTGA
TATGGCCGTTAGTAGCATCATTCTGAGCAAAACCTACGATAACGGCGTAATTT
GCGCGAGTGAACAGAGCATTTTAGTGATGAACTCGATCTATGAAAAAGTGAA
AGAAGAATTTGTGAAGCGCGGTTCTTACATCCTCAACCAAAATGAAATCGCG
AAAATCAAAGAAACGATGTTCAAAAATGGCGCGATCAACGCGGATATTGTTG
GCAAATCAGCCTACATTATTGCGAAAATGGCGGGTATTGAAGTCCCCCAGAC
CACAAAGATCCTGATCGGTGAAGTACAGAGCGTCGAAAAGAGCGAGCTGTT
CAGCCACGAGAAACTGAGCCCTGTTCTGGCCATGTACAAGGTAAAAGATTTT
GACGAAGCACTTAAAAAAGCCCAACGCCTTATCGAATTAGGAGGGTCTGGCC
ACACGAGCAGCTTGTACATCGACAGCCAGAATAACAAAGACAAAGTCAAAGA
ATTCGGCCTTGCAATGAAAACTTCTCGCACCTTTATTAATATGCCGTCCAGCC
AGGGCGCCTCTGGTGATCTGTACAATTTTGCCATTGCCCCGTCGTTTACCCT
GGGGTGTGGGACCTGGGGCGGGAATTCGGTATCACAGAACGTCGAACCAAA
ACACCTGTTGAATATTAAATCCGTGGCAGAGCGCCGCGAGAACATGCTGTGG
TTCAAAGTCCCTCAGAAAATTTACTTCAAGTACGGCTGCCTGCGTTTTGCGCT
GAAAGAACTCAAAGACATGAACAAAAAACGTGCGTTCATCGTTACCGATAAG
GACCTGTTTAAACTGGGCTACGTAAACAAAATTACTAAAGTGTTGGACGAAAT
CGATATTAAATACTCCATTTTTACCGACATTAAGTCAGACCCGACCATCGACA
GCGTCAAAAAAGGGGCAAAAGAAATGCTGAACTTTGAGCCAGATACGATTAT
CTCAATCGGTGGGGGCTCGCCTATGGACGCTGCGAAAGTGATGCACCTGCT
GTATGAGTACCCGGAAGCGGAGATTGAGAACCTGGCCATCAATTTTATGGAT
ATTCGTAAGCGTATTTGCAATTTTCCGAAACTTGGGACGAAAGCCATCTCCGT
CGCGATTCCGACCACTGCAGGTACGGGCAGCGAAGCCACGCCTTTTGCAGT
TATCACGAACGATGAGACCGGTATGAAATATCCGCTCACCTCGTACGAACTG
ACCCCAAATATGGCCATCATTGATACCGAACTGATGCTCAATATGCCCCGTA
AACTCACCGCAGCCACTGGCATTGACGCACTCGTGCACGCCATTGAGGCTT

FIGURE 102, T, CON'T. (SEQ ID NO:92 CON'T)

TdeTER, con't.

ATGTCAGCGTGATGGCGACCGATTACACCGATGAATTAGCTCTCCGTGCAAT
CAAAATGATTTTTAAGTACCTCCCGCGTGCGTACAAAAATGGCACGAATGATA
TCGAGGCGCGTGAAAAGATGGCTCATGCCAGCAACATCGCCGGTATGGCGT
TCGCTAATGCCTTCCTGGGTGTATGCCACAGTATGGCACACAAGCTCGGCG
CCATGCATCATGTACCACACGGGATTGCCTGTGCCGTGTTAATCGAGGAAGT
CATTAAGTACAATGCCACCGATTGCCCGACTAAACAGACCGCCTTTCCGCAG
TATAAGAGCCCGAATGCAAAACGTAAATACGCCGAGATCGCTGAGTATTTGA
ATCTCAAAGGAACGAGTGATACTGAGAAAGTCACCGCCTTGATCGAAGCCAT
CAGCAAACTTAAAATCGATCTGTCGATTCCGCAGAACATTAGCGCGGCCGGT
ATTAACAAGAAAGATTTTTACAACACGCTGGACAAAATGTCTGAACTGGCGTT
TGACGATCAGTGCACCACGGCGAACCCGCGCTATCCTCTGATTTCCGAGCT
CAAGGATATCTACATCAAAAGCTTCTAA

FIGURE 102, U (SEQ ID NO:93)

*FsuTER*

ATGATTATTAAACCACTGATCCGCTCTAATATGTGTATCAACGCGCATCCGAA
AGGTTGTGCCGCCGACGTGAAACATCAAATCGAGTTCATCAAAAAGAAATTC
ACGACCCGCTCAATCCCGGCGGACGCGCCAAAAACAGTGTTAGTCCTGGGC
TGCTCCACTGGATACGGCTTAGCATCACGCATCGTCGCGGCTTTTGGTTACA
AGGCTGCAACGATTGGGGTATCGTTCGAAAAAGAAGGCTCCGACGGAGGAA
TCGGTGAGAGTCGTGAGAAAACAGGCACCCCGGGCTGGTATAACAACATGG
CGTTTGATAAGTTCGCGAAGGAAGCCGGTCTGGATGCGGTCACCTTCAACG
GTGACGCCTTTAGCCATGAAATGCGTCAGAATGTTATCGATACCCTGAAAAA
AATGGGTCGCAAAGTAGATCTCTTGGTCTATTCTGTCGCAAGCTCAGTCCGC
GTTGATCCAGATAACGGGACCATCTACCGCTCAGTTCTGAAGCCCATCGACA
AAGTGTTCACCGGGGCGACGATCGATTGCCTGTCTGGTAAGATTTCGACAAT
TTCGGCCGAACCTGCGACGGCAGAAGAAGCGGCGAACACGGTCAAAGTGAT
GGGTGGCGAGGATTGGGCGTTGTGGGTGCGCAAACTGAAAGAGGCAGGCG
TCCTTGCGGAAGGTGTTAAAACTGTGGCCTATTCCTATATCGGCCCGAAACT
CAGCCACGCTATCTATCGCGACGGCACTATCGGGGGTGCCAAAAAACACTT
GGAAGCTACGGCTCTTGAACTTAACAAAGAGCTCCAGAATGATCTCCATGGG
GAGGCGTATGTGTCGGTGAATAAAGGTTTAGTGACGCGCAGCTCAGCAGTG
ATCCCGATCATTCCGATGTACATTTCGGTTCTGTTTAAAGTCATGAAAGAAAT
GGGCAACCACGAAGGCTGTATTGAACAGATGGAACGCCTGATGACGGAACG
CTTGTATACCGGCTCTAAAGTGCCCACCGACGAAAACCATTTGATCCGTATT
GACGATTATGAATTGGATCCGAAGGTCCAGGCGGAAGTTGATAAGCGCATG
GCTACAGTGACTCAGGAAAATTTGGCGGAAGTGGGTGATCTGGAAGGATAC
CGTCACGACTTTTTGGCAACCAATGGCTTCGATATTGACGGTGTGGACTACG
AGGCCGATGTGCAAACGTTAACCTCAATTTGA

FIGURE 102, V (SEQ ID NO:94)

*FjoTER*

ATGATCATCGAGCCGCGCATGCGCGGTTTTATCTGCCTGACTGCGCATCCG
GCGGGATGTGAACAGAATGTTAAAAATCAGATCGAGTATATTAAATCGAAAG
GGGCAATCGCCGGCGCCAAAAAGGTTCTGGTGATCGGCGCATCCACGGGTT
TCGGTTTAGCATCCCGTATCACCAGTGCGTTCGGCTCAGATGCTGCTACGAT
TGGCGTGTTCTTCGAAAAACCGCCCGTCGAAGGTAAGACAGCGTCGCCAGG
GTGGTATAATTCGGCCGCATTTGAGAAAGAGGCACATAAAGCGGGTCTTTAC
GCTAAATCTATCAATGGAGACGCTTTCAGCAACGAAATTAAACGTGAAACCTT
AGATCTGATCAAAGCGGATTTAGGTCAGGTTGATCTGGTAATTTATTCGCTGG
CGTCCCCGGTTCGTACGAACCCGAACACAGGTGTGACTCACCGCAGTGTGT
TGAAACCGATCGGTCAGACTTTTACAAACAAAACTGTGGATTTTCATACGGG
GAACGTGTCCGAAGTTTCTATCGCGCCGGCTAATGAAGAAGATATTGAAAAT
ACGGTAGCAGTGATGGGCGGAGAAGATTGGGCGATGTGGATTGATGCCCTC
AAAAATGAAAATCTGCTGGCAGAGGGGGCGACGACAATTGCATATTCCTATA
TTGGCCCGGAATTGACCGAAGCGGTCTACCGTAAAGGCACCATTGGTCGTG
CAAAAGACCACCTGGAGGCGACCGCTTTCACCATTACTGATACCCTTAAATC
GTTAGGCGGAAAAGCGTACGTGTCGGTGAATAAAGCCTTGGTTACGCAAGC
CTCGTCGGCGATTCCTGTGATCCCGCTGTATATCTCGCTGCTTTATAAAATTA
TGAAGGAGGAAGGAATTCACGAGGGATGCATCGAACAAATTCAGCGCTTGTT
CCAAGATCGTTTGTATAACGGTAGCGAAGTGCCGGTTGATGAGAAAGGCCG
CATCCGCATTGACGATTGGGAGATGCGCGAGGATGTGCAGGCTAAAGTTGC
GGCTCTGTGGAAGGAAGCCACCACCGAAACCCTGCCATCCATCGGCGACCT
GGCAGGTTACCGTAATGACTTCTTAAACCTGTTTGGGTTTGAATTTGCGGGA
GTGGATTACAAGGCGGATACGAACGAGGTCGTAAACATTGAAAGCATCAAAT
AA

FIGURE 102, W (SEQ ID NO:95)

*CacADH*

ATGAAGGTAACCAACCAGAAAGAGCTGAAACAAAAATTAAACGAACTCCGCG
AAGCGCAAAAAAAATTCGCGACGTATACTCAGGAACAAGTCGATAAGATCTTT
AAACAATGTGCCATTGCAGCGGCCAAAGAACGCATCAACCTGGCGAAGTTG
GCCGTTGAAGAAACCGGAATTGGTTTAGTGGAAGACAAAATTATTAAGAACC
ATTTCGCTGCGGAATATATTTATAATAAATACAAAAATGAGAAGACCTGCGGA
ATTATTGATCATGATGATAGCCTTGGTATCACTAAAGTAGCAGAACCAATCGG
TATCGTCGCCGCCATCGTTCCTACAACCAATCCGACCTCTACGGCGATCTTT
AAATCATTGATTAGCCTGAAAACGCGTAACGCGATTTTTTTCAGCCCTCACCC
ACGCGCCAAAAAAAGCACTATCGCTGCGGCGAAACTGATTCTGGATGCGGC
AGTTAAAGCCGGCGCACCTAAAAACATTATCGGCTGGATCGACGAGCCTAGC
ATCGAGTTGAGCCAGGACCTCATGAGTGAAGCAGATATTATCCTCGCCACGG
GTGGGCCATCTATGGTTAAAGCGGCCTACTCATCTGGTAAACCAGCCATCGG
TGTGGGTGCGGGCAATACCCCGGCGATCATTGACGAGAGCGCCGATATTGA
TATGGCCGTTAGTAGCATCATTCTGAGCAAAACCTACGATAACGGCGTAATTT
GCGCGAGTGAACAGAGCATTTTAGTGATGAACTCGATCTATGAAAAAGTGAA
AGAAGAATTTGTGAAGCGCGGTTCTTACATCCTCAACCAAAATGAAATCGCG
AAAATCAAAGAAACGATGTTCAAAAATGGCGCGATCAACGCGGATATTGTTG
GCAAATCAGCCTACATTATTGCGAAAATGGCGGGTATTGAAGTCCCCCAGAC
CACAAAGATCCTGATCGGTGAAGTACAGAGCGTCGAAAAGAGCGAGCTGTT
CAGCCACGAGAAACTGAGCCCTGTTCTGGCCATGTACAAGGTAAAAGATTTT
GACGAAGCACTTAAAAAAGCCCAACGCCTTATCGAATTAGGAGGGTCTGGCC
ACACGAGCAGCTTGTACATCGACAGCCAGAATAACAAAGACAAAGTCAAAGA
ATTCGGCCTTGCAATGAAAACTTCTCGCACCTTTATTAATATGCCGTCCAGCC
AGGGCGCCTCTGGTGATCTGTACAATTTTGCCATTGCCCCGTCGTTTACCCT
GGGGTGTGGGACCTGGGGCGGGAATTCGGTATCACAGAACGTCGAACCAAA
ACACCTGTTGAATATTAAATCCGTGGCAGAGCGCCGCGAGAACATGCTGTGG
TTCAAAGTCCCTCAGAAAATTTACTTCAAGTACGGCTGCCTGCGTTTTGCGCT
GAAAGAACTCAAAGACATGAACAAAAAACGTGCGTTCATCGTTACCGATAAG
GACCTGTTTAAACTGGGCTACGTAAACAAAATTACTAAAGTGTTGGACGAAAT
CGATATTAAATACTCCATTTTTACCGACATTAAGTCAGACCCGACCATCGACA
GCGTCAAAAAAGGGGCAAAAGAAATGCTGAACTTTGAGCCAGATACGATTAT
CTCAATCGGTGGGGGCTCGCCTATGGACGCTGCGAAAGTGATGCACCTGCT
GTATGAGTACCCGGAAGCGGAGATTGAGAACCTGGCCATCAATTTTATGGAT
ATTCGTAAGCGTATTTGCAATTTTCCGAAACTTGGGACGAAAGCCATCTCCGT
CGCGATTCCGACCACTGCAGGTACGGGCAGCGAAGCCACGCCTTTTGCAGT
TATCACGAACGATGAGACCGGTATGAAATATCCGCTCACCTCGTACGAACTG
ACCCCAAATATGGCCATCATTGATACCGAACTGATGCTCAATATGCCCCGTA
AACTCACCGCAGCCACTGGCATTGACGCACTCGTGCACGCCATTGAGGCTT
ATGTCAGCGTGATGGCGACCGATTACACCGATGAATTAGCTCTCCGTGCAAT
CAAAATGATTTTTAAGTACCTCCCGCGTGCGTACAAAAATGGCACGAATGATA
TCGAGGCGCGTGAAAAGATGGCTCATGCCAGCAACATCGCCGGTATGGCGT
TCGCTAATGCCTTCCTGGGTGTATGCCACAGTATGGCACACAAGCTCGGCG

FIGURE 102, W, CON'T. (SEQ ID NO:95 CON'T)

CacADH, con't.

CCATGCATCATGTACCACACGGGATTGCCTGTGCCGTGTTAATCGAGGAAGT
CATTAAGTACAATGCCACCGATTGCCCGACTAAACAGACCGCCTTTCCGCAG
TATAAGAGCCCGAATGCAAAACGTAAATACGCCGAGATCGCTGAGTATTTGA
ATCTCAAAGGAACGAGTGATACTGAGAAAGTCACCGCCTTGATCGAAGCCAT
CAGCAAACTTAAAATCGATCTGTCGATTCCGCAGAACATTAGCGCGGCCGGT
ATTAACAAGAAAGATTTTTACAACACGCTGGACAAAATGTCTGAACTGGCGTT
TGACGATCAGTGCACCACGGCGAACCCGCGCTATCCTCTGATTTCCGAGCT
CAAGGATATCTACATCAAAAGCTTCTAA

FIGURE 103, A (SEQ ID NO:96)

*Tde*TER

ATGATAGTTAAACCAATGGTAAGAAATAATATATGTTTAAATGCTCACCCACAA
GGATGTAAGAAAGGAGTAGAAGATCAAATAGAATATACGAAAAAAAGAATAAC
AGCTGAAGTAAAGGCTGGCGCCAAAGCACCTAAAAATGTTTTGGTACTAGGA
TGTTCAAATGGTTATGGATTGGCATCGAGAATAACCGCTGCTTTTGGTTACG
GTGCAGCTACAATAGGAGTAAGTTTTGAAAAAGCTGGCAGTGAAACTAAGTA
CGGAACTCCTGGTTGGTACAATAATTTAGCTTTTGATGAAGCAGCTAAGAGA
GAAGGATTATATTCTGTAACTATAGATGGAGATGCATTTTCAGATGAAATAAA
AGCACAGGTTATAGAAGAAGCCAAAAAAAAGGGAATAAAGTTTGATTTAATAG
TATATTCATTAGCATCTCCTGTAAGGACAGATCCAGATACAGGAATAATGCAT
AAATCAGTACTTAAACCTTTTGGAAAGACCTTTACCGGAAAAACTGTAGACCC
TTTTACAGGTGAATTAAAAGAAATAAGTGCTGAACCAGCTAATGATGAAGAGG
CTGCTGCTACTGTTAAAGTAATGGGCGGCGAGGATTGGGAAAGATGGATAAA
GCAGCTTTCAAAGGAAGGATTATTAGAAGAAGGCTGCATTACACTTGCTTATT
CTTATATAGGACCAGAAGCAACGCAGGCATTATATAGAAAAGGTACAATAGG
AAAAGCAAAAGAACATCTAGAGGCAACTGCACATAGACTAAATAAGGAAAAT
CCAAGCATTAGAGCATTTGTATCTGTTAATAAGGGATTAGTAACCAGAGCCAG
CGCTGTTATACCTGTTATACCTTTGTATTTAGCTTCCCTTTTTAAAGTTATGAA
GGAAAAAGGAAATCATGAAGGATGTATAGAGCAAATTACTAGACTCTATGCT
GAACGATTGTATAGAAAAGATGGAACTATTCCTGTTGATGAAGAAAATAGAAT
AAGAATAGATGATTGGGAGCTTGAAGAGGATGTTCAAAAAGCAGTTTCCGCT
CTTATGGAAAAAGTTACCGGTGAAAATGCAGAAAGCTTAACAGACCTTGCTG
GATATAGACATGATTTTCTTGCTTCAAATGGATTTGATGTTGAAGGAATAAACT
ATGAAGCGGAAGTTGAAAGATTTGATAGAATTTAA

FIGURE 103, B (SEQ ID NO:97)

*Fsu*TER

ATGATAATAAAACCACTAATAAGAAGCAATATGTGTATAAATGCCCACCCAAA
GGGATGTGCTGCTGATGTAAAACATCAAATAGAGTTTATTAAAAAGAAATTCA
CTACTAGATCCATACCTGCAGATGCACCTAAAACAGTATTAGTTTTAGGATGT
AGTACAGGATATGGACTAGCTTCTAGGATAGTGGCAGCTTTTGGATATAAAG
CAGCTACAATTGGTGTTTCCTTTGAAAAGGAAGGTTCAGATGGCGGCATAGG
AGAAAGTAGAGAAAAGACAGGAACTCCGGGATGGTATAACAATATGGCTTTT
GACAAGTTTGCTAAAGAAGCAGGTCTGGATGCAGTTACGTTTAATGGAGATG
CTTTTTCTCATGAAATGAGACAGAATGTAATAGATACATTAAAAAAAATGGGA
AGAAAAGTAGATTTACTTGTATATTCAGTAGCTAGTTCAGTTAGGGTAGATCC
AGACAATGGAACAATTTATAGATCAGTTTTAAAACCAATAGACAAAGTGTTTA
CAGGTGCTACTATAGACTGTTTGTCTGGAAAAATAAGTACTATATCAGCTGAA
CCTGCAACTGCTGAGGAAGCTGCAAATACAGTAAAAGTTATGGGCGGCGAA
GATTGGGCCTTGTGGGTTAGAAAACTTAAGGAAGCAGGAGTTTTAGCAGAAG
GAGTAAAGACAGTTGCCTACAGTTATATAGGACCAAAGTTAAGTCATGCTATT
TACAGAGATGGAACTATTGGCGGCGCTAAGAAACATTTGGAAGCTACGGCAC
TTGAACTTAACAAAGAACTTCAAAATGATTTGCATGGAGAAGCTTATGTATCT
GTAAATAAGGGATTAGTAACTAGGTCATCTGCTGTAATACCTATTATACCTAT
GTATATTAGTGTTTTGTTTAAAGTGATGAAAGAAATGGGCAATCATGAAGGAT
GTATAGAACAAATGGAAAGATTAATGACTGAGAGACTTTATACAGGATCAAAA
GTACCTACAGATGAAAATCATCTTATACGTATTGATGATTATGAACTTGATCCA
AAAGTACAGGCAGAAGTAGATAAAAGGATGGCAACTGTTACTCAAGAAAACT
TAGCTGAAGTTGGCGATTTAGAGGGTTATCGTCACGATTTTCTGGCAACTAAT
GGATTCGATATAGATGGAGTAGATTATGAGGCTGATGTGCAAACGCTTACAT
CTATTTAA

FIGURE 103, C (SEQ ID NO:98)

*Fjo*TER

ATGATAATTGAACCAAGAATGAGAGGATTTATTTGCTTAACTGCTCATCCTGC
AGGATGTGAACAAAATGTTAAAAATCAAATAGAATATATAAAATCAAAAGGGG
CAATTGCAGGAGCAAAGAAAGTATTAGTCATAGGAGCTTCAACAGGATTTGG
TCTTGCTTCAAGAATAACATCGGCTTTCGGTTCAGATGCAGCTACAATAGGA
GTATTTTTTGAAAAACCACCAGTAGAAGGTAAAACAGCAAGTCCTGGATGGTA
CAATAGTGCAGCATTTGAAAAAGAAGCCCATAAAGCAGGATTATATGCAAAAT
CTATAAATGGAGATGCTTTTAGTAATGAAATAAAGAGGGAAACTTTGGACCTT
ATAAAAGCAGACCTTGGTCAGGTAGATTTAGTTATTTATTCATTGGCCTCTCC
TGTCAGAACCAATCCTAATACTGGTGTAACTCATAGATCAGTACTTAAACCTA
TAGGGCAAACCTTTACAAACAAAACTGTTGATTTTCATACTGGTAATGTATCT
GAAGTAAGCATAGCTCCTGCCAATGAAGAAGATATTGAAAATACGGTAGCTG
TGATGGGCGGCGAGGATTGGGCAATGTGGATAGATGCACTGAAAAATGAAA
ATCTTCTAGCTGAGGGAGCAACTACTATTGCTTACAGCTATATAGGACCTGA
GTTGACTGAAGCTGTGTACAGGAAGGGTACTATAGGAAGAGCAAAAGATCAT
CTTGAAGCAACTGCTTTTACTATTACTGATACATTAAAAAGTTTAGGCGGCAA
AGCTTATGTTAGTGTAAATAAAGCATTAGTAACTCAGGCAAGCAGTGCTATAC
CTGTTATTCCTCTATACATAAGCTTATTATATAAGATTATGAAAGAGGAAGGTA
TTCATGAGGGATGCATTGAACAGATTCAGAGACTATTTCAAGATAGATTATAT
AACGGTTCCGAAGTACCAGTAGATGAAAAAGGAAGAATAAGAATAGATGATT
GGGAAATGAGAGAAGATGTTCAGGCAAAAGTAGCAGCTTTATGGAAAGAGG
CTACAACAGAGACGCTTCCTTCAATAGGAGACTTAGCAGGATATAGAAATGA
TTTTTTGAATTTATTTGGTTTTGAGTTCGCAGGTGTTGATTATAAAGCGGACAC
AAATGAAGTAGTAAACATAGAATCTATAAAATAA

FIGURE 103, D (SEQ ID NO:99)

*Cac*ADH

ATGAAGGTAACCAACCAGAAAGAGCTGAAACAAAAATTAAACGAACTCCGCG
AAGCGCAAAAAAAATTCGCGACGTATACTCAGGAACAAGTCGATAAGATCTTT
AAACAATGTGCCATTGCAGCGGCCAAAGAACGCATCAACCTGGCGAAGTTG
GCCGTTGAAGAAACCGGAATTGGTTTAGTGGAAGACAAAATTATTAAGAACC
ATTTCGCTGCGGAATATATTTATAATAAATACAAAAATGAGAAGACCTGCGGA
ATTATTGATCATGATGATAGCCTTGGTATCACTAAAGTAGCAGAACCAATCGG
TATCGTCGCCGCCATCGTTCCTACAACCAATCCGACCTCTACGGCGATCTTT
AAATCATTGATTAGCCTGAAAACGCGTAACGCGATTTTTTTCAGCCCTCACCC
ACGCGCCAAAAAAAGCACTATCGCTGCGGCGAAACTGATTCTGGATGCGGC
AGTTAAAGCCGGCGCACCTAAAAACATTATCGGCTGGATCGACGAGCCTAGC
ATCGAGTTGAGCCAGGACCTCATGAGTGAAGCAGATATTATCCTCGCCACGG
GTGGGCCATCTATGGTTAAAGCGGCCTACTCATCTGGTAAACCAGCCATCGG
TGTGGGTGCGGGCAATACCCCGGCGATCATTGACGAGAGCGCCGATATTGA
TATGGCCGTTAGTAGCATCATTCTGAGCAAAACCTACGATAACGGCGTAATTT
GCGCGAGTGAACAGAGCATTTTAGTGATGAACTCGATCTATGAAAAAGTGAA
AGAAGAATTTGTGAAGCGCGGTTCTTACATCCTCAACCAAAATGAAATCGCG
AAAATCAAAGAAACGATGTTCAAAAATGGCGCGATCAACGCGGATATTGTTG
GCAAATCAGCCTACATTATTGCGAAAATGGCGGGTATTGAAGTCCCCCAGAC
CACAAAGATCCTGATCGGTGAAGTACAGAGCGTCGAAAAGAGCGAGCTGTT
CAGCCACGAGAAACTGAGCCCTGTTCTGGCCATGTACAAGGTAAAAGATTTT
GACGAAGCACTTAAAAAAGCCCAACGCCTTATCGAATTAGGAGGGTCTGGCC
ACACGAGCAGCTTGTACATCGACAGCCAGAATAACAAAGACAAAGTCAAAGA
ATTCGGCCTTGCAATGAAAACTTCTCGCACCTTTATTAATATGCCGTCCAGCC
AGGGCGCCTCTGGTGATCTGTACAATTTTGCCATTGCCCCGTCGTTTACCCT
GGGGTGTGGGACCTGGGGCGGGAATTCGGTATCACAGAACGTCGAACCAAA
ACACCTGTTGAATATTAAATCCGTGGCAGAGCGCCGCGAGAACATGCTGTGG

FIGURE 103, D, CON'T. CacADH, con't.

(SEQ ID NO:99 CON'T)

TTCAAAGTCCCTCAGAAAATTTACTTCAAGTACGGCTGCCTGCGTTTTGCGCT
GAAAGAACTCAAAGACATGAACAAAAAACGTGCGTTCATCGTTACCGATAAG
GACCTGTTTAAACTGGGCTACGTAAACAAAATTACTAAAGTGTTGGACGAAAT
CGATATTAAATACTCCATTTTTACCGACATTAAGTCAGACCCGACCATCGACA
GCGTCAAAAAAGGGGCAAAAGAAATGCTGAACTTTGAGCCAGATACGATTAT
CTCAATCGGTGGGGGCTCGCCTATGGACGCTGCGAAAGTGATGCACCTGCT
GTATGAGTACCCGGAAGCGGAGATTGAGAACCTGGCCATCAATTTTATGGAT
ATTCGTAAGCGTATTTGCAATTTTCCGAAACTTGGGACGAAAGCCATCTCCGT
CGCGATTCCGACCACTGCAGGTACGGGCAGCGAAGCCACGCCTTTTGCAGT
TATCACGAACGATGAGACCGGTATGAAATATCCGCTCACCTCGTACGAACTG
ACCCCAAATATGGCCATCATTGATACCGAACTGATGCTCAATATGCCCCGTA
AACTCACCGCAGCCACTGGCATTGACGCACTCGTGCACGCCATTGAGGCTT
ATGTCAGCGTGATGGCGACCGATTACACCGATGAATTAGCTCTCCGTGCAAT
CAAAATGATTTTTAAGTACCTCCCGCGTGCGTACAAAAATGGCACGAATGATA
TCGAGGCGCGTGAAAAGATGGCTCATGCCAGCAACATCGCCGGTATGGCGT
TCGCTAATGCCTTCCTGGGTGTATGCCACAGTATGGCACACAAGCTCGGCG
CCATGCATCATGTACCACACGGGATTGCCTGTGCCGTGTTAATCGAGGAAGT
CATTAAGTACAATGCCACCGATTGCCCGACTAAACAGACCGCCTTTCCGCAG
TATAAGAGCCCGAATGCAAAACGTAAATACGCCGAGATCGCTGAGTATTTGA
ATCTCAAAGGAACGAGTGATACTGAGAAAGTCACCGCCTTGATCGAAGCCAT
CAGCAAACTTAAAATCGATCTGTCGATTCCGCAGAACATTAGCGCGGCCGGT
ATTAACAAGAAAGATTTTTACAACACGCTGGACAAAATGTCTGAACTGGCGTT
TGACGATCAGTGCACCACGGCGAACCCGCGCTATCCTCTGATTTCCGAGCT
CAAGGATATCTACATCAAAAGCTTCTAA

FIGURE 103, E (SEQ ID NO:100)

*Cna*PhaB ATGACACAGAGAATAGCTTATGTAACTGGAGGAATGGGGGAATTGGCACG
GCAATATGTCAGAGATTAGCAAAGGATGGTTTTAGAGTAGTTGCGGGTTGTG
GCCCAAACTCACCGAGGAGAGAAAAATGGTTGGAACAGCAGAAAGCTCTCG
GATTTGACTTTATAGCTAGTGAGGGTAATGTTGCTGATTGGGATTCAACAAAG
ACAGCTTTTGATAAGGTTAAGTCAGAAGTGGGTGAAGTAGATGTGCTCATAA
ATAATGCTGGGATCACAAGAGATGTAGTTTTTAGAAAAATGACAAGAGCTGAC
TGGGATGCTGTAATAGATACAAATCTTACTAGCTTATTCAATGTAACGAAACA
GGTTATAGATGGAATGGCAGATAGGGGATGGGGTAGGATAGTAAATATTTCA
TCAGTAAATGGTCAAAAAGGACAATTTGGACAAACAAATTATTCAACTGCCAA
GGCAGGACTTCATGGATTTACGATGGCACTTGCACAGGAAGTAGCTACTAAA
GGAGTTACTGTAAATACAGTTTCTCCAGGATACATAGCTACTGATATGGTAAA
AGCTATTAGGCAGGATGTATTAGATAAGATTGTAGCAACAATACCTGTGAAGA
GACTTGGCTTACCTGAAGAAATAGCATCAATATGTGCTTGGTTATCCAGTGAA
GAATCAGGATTTTCTACAGGAGCTGATTTCTCCTTGAATGGTGGACTTCACAT
GGGATAA

FIGURE 103, F (SEQ ID NO:101)

*Ppu*CRT

ATGACTACCCCATCTTCTCCATTATTAAGCAAAGTAGAAGCAGGAGTTGCATG
GATTACATTAAATAGACCAGAGCAGAGAAATGCTTTAGATATTCCAACTCTAA
AACAATTACATGCACTTCTAGATTCTCATGCAGATGATCCTGCTGTAAGAGTT
GTAGTATTGACAGGTTCCGGTAGGAGTTTCTGTGCTGGAGCAGATTTAGCAG
AGTGGGCTGCTGCAGAAGCAGCAGGAACTCTTGAAAGTTATGGCTGGACTG
AAACAGCACATGCTTTGATGCTGCGTTTGCACTCTTTGGATAAGCCTACGATT
GCAGCTATAAATGGCACTGCAGTAGGCGGCGGCATGGATTTGTCTCTTTGCT
GTGATTTGAGAATAGCAGCAGCATCAGCAAGATTTAAAGCTGGATATACCAG
CATGGGATATTCACCAGATGCAGGAGCATCTTGGCATCTTCCAAGACTTATA
GGATCAGAACAAGCCAAAAGACTTTTATTTTTAGATGAATTATGGGGAGCTGA
ACATGCATTAGCAGCAGGCTTAGTTTCAGAAGTATGTGCTGATGAACAGCTT
CCAGCTGTAGCAGCTGAACTTGCAGGAAGATTGGCAAACGGCCCTACTTTTG
CATATGCACAAACAAAACAGCTTATAAGGGATGGTGCTAGAAGAACTCTAGC
AGAGCAACTTGAAGCTGAAAGACATGCAGGACTTTTGTGCGGTCGTTCTCAG
GACGGAGCAGAAGCCTTGCAGGCATCAGTTGAAAGAAGAGCACCTAGATTTA
CTGGACAATAA

SEQUENCE LISTING

```
<160> NUMBER OF SEQ ID NOS: 111

<210> SEQ ID NO 1
<211> LENGTH: 2154
<212> TYPE: DNA
<213> ORGANISM: Arabidopsis thaliana
<220> FEATURE:
<221> NAME/KEY: misc_feature
<222> LOCATION: (1)..(2154)
<223> OTHER INFORMATION: PAL2
```

<400> SEQUENCE: 1
atggatcaaa tcgaagcaat gttgtgcggc ggaggagaga agacaaaagt ggcggttact 60
acgaagactt tggcagatcc attgaattgg ggtttagcag cggatcaaat gaaaggaagt 120
catttagatg aagtgaagaa gatggtcgaa gagtatcgta gaccagtcgt gaatcttggc 180
ggagaaacac tgacgatcgg acaagttgct gccatctcca ccgtaggagg cagcgttaag 240
gttgagttag cggagacttc aagagccggt gtgaaagcta gcagtgattg ggttatggag 300
agcatgaaca aaggtactga cagttacgga gtcaccaccg gctttggtgc tacttctcac 360
cggagaacca aaaacggcac cgcattacaa acagaactca ttagattttt gaacgccgga 420
atattcggaa acacgaagga gacatgtcac acactgccgc aatccgccac aagagccgcc 480
atgctcgtca gagtcaacac tcttctccaa ggatactccg ggatccgatt cgagatcctc 540
gaagcgatta caagtctcct caaccacaac atctctccgt cactacctct ccgtggaacc 600
attaccgcct ccggcgatct cgttcctctc tcttacatcg ccggacttct caccggccgt 660
cctaattcca aagccaccgg tcccgacggt gaatcgctaa ccgcgaaaga agcttttgag 720
aaagccggaa tcagtactgg attcttcgat ttacaaccta aggaaggttt agctctcgtt 780
aatggcacgg cggttggatc tggaatggcg tcgatggttc tattcgaagc gaatgtccaa 840
gcggtgttag cggaggtttt atcagcgatc ttcgcggagg ttatgagcgg gaaacctgag 900
tttaccgatc atctgactca tcgtttaaaa catcatcccg gacaaatcga agcggcggcg 960
ataatggagc acatactcga cggaagctca tacatgaaat tagctcaaaa ggttcacgag 1020
atggatccat tgcagaaacc aaaacaagat cgttacgctc ttcgtacatc tcctcaatgg 1080
ctaggtcctc aaattgaagt aatccgtcaa gctacgaaat cgatagagcg tgaaatcaac 1140
tccgttaacg ataatccgtt gatcgatgtt tcgaggaaca aggcgattca cggtggtaac 1200
ttccaaggaa caccaatcgg agtttctatg gataacacga gattggcgat tgctgcgatt 1260
gggaagctaa tgtttgctca attctctgag cttgttaatg atttctacaa caatggactt 1320
ccttcgaatc taactgcttc gagtaatcca agtttggatt atggattcaa aggagcagag 1380
attgctatgg cttcttattg ttctgagctt caatacttgg ctaatccagt cacaagccat 1440
gttcaatcag ctgagcaaca taatcaagat gtgaactctc ttggtttgat ctcgtctcgt 1500
aaaacatctg aagctgtgga tattcttaag ctaatgtcaa caacgttcct tgtggggata 1560
tgtcaagctg ttgatttgag acatttggag gagaatctga gacaaactgt gaagaacaca 1620
gtttctcaag ttgctaagaa agtgttaacc actggaatca acggtgagtt acatccgtca 1680
aggttttgcg agaaggactt gcttaaggtt gttgatcgtg agcaagtgtt cacgtatgtg 1740
gatgatcctt gtagcgctac gtacccgttg atgcagagac taagacaagt tattgttgat 1800
cacgctttgt ccaacggtga gactgagaag aatgcagtga cttcgatctt tcaaaagatt 1860
ggagcttttg aagaggagct taaggctgtg cttccaaagg aagttgaagc ggctagagcg 1920
gcttatggga atggaactgc gccgattcct aaccggatta aggaatgtag gtcgtatccg 1980
ttgtataggt tcgtgaggga agagcttgga acgaagttgt tgactggaga aaaggttgtg 2040
tctccgggag aggagtttga taaggtcttc actgctatgt gtgaaggtaa acttattgat 2100
ccgttgatgg attgtctcaa ggaatggaac ggagctccga ttccgatttg ctaa 2154

<210> SEQ ID NO 2
<211> LENGTH: 1533
<212> TYPE: DNA
<213> ORGANISM: Saccharomyces cerevisiae
<220> FEATURE:
<221> NAME/KEY: misc_feature
<222> LOCATION: (1)..(1533)
<223> OTHER INFORMATION: FDC1

<400> SEQUENCE: 2

```
atggaattcg ggaggaatta tatgaggaag ctaaatccag ctttagaatt tagagacttt     60

atccaggtct taaaagatga agatgactta atcgaaatta ccgaagagat tgatccaaat    120

ctcgaagtag gtgcaattat gaggaaggcc tatgaatccc acttaccagc cccgttattt    180

aaaaatctca aaggtgcttc gaaggatctt ttcagcattt taggttgccc agccggttta    240

agaagtaagg agaaaggaga tcatggtaga attgcccatc atctggggct cgacccaaaa    300

acaactatca aggaaatcat agattatttg ctggagtgta aggagaagga acctctcccc    360

ccaatcactg ttcctgtgtc atctgcacct tgtaaaacac atatactttc tgaagaaaaa    420

atacatctac aaagcctgcc aacaccatat ctacatgttt cagacggtgg caagtactta    480

caaacgtacg gaatgtggat tcttcaaact ccagataaaa aatggactaa ttggtcaatt    540

gctagaggta tggttgtaga tgacaagcat atcactggtc tggtaattaa accacaacat    600

attagacaaa ttgctgactc ttgggcagca attggaaaag caaatgaaat tcctttcgcg    660

ttatgttttg gcgttccccc agcagctatt ttagttagtt ccatgccaat tcctgaaggt    720

gtttctgaat cggattatgt tggcgcaatc ttgggtgagt cggttccagt agtaaaatgt    780

gagaccaacg atttaatggt tcctgcaacg agtgagatgg tatttgaggg tactttgtcc    840

ttaacagata cacatctgga aggcccattt ggtgagatgc atggatatgt tttcaaaagc    900

caaggtcatc cttgtccatt gtacactgtc aaggctatga gttacagaga caatgctatt    960

ctacctgttt cgaaccccgg tctttgtacg gatgagacac ataccttgat tggttcacta   1020

gtggctactg aggccaagga gctggctatt gaatctggct tgccaattct ggatgccttt   1080

atgccttatg aggctcaggc tctttggctt atcttaaagg tggatttgaa agggctgcaa   1140

gcattgaaga caacgcctga agaattttgt aagaaggtag gtgatattta ctttaggaca   1200

aaagttggtt ttatagtcca tgaaataatt ttggtggcag atgatatcga catatttaac   1260

ttcaaagaag tcatctgggc ctacgttaca agacatacac ctgttgcaga tcagatggct   1320

tttgatgatg tcacttcttt tcctttggct ccctttgttt cgcagtcatc cagaagtaag   1380

actatgaaag gtggaaagtg cgttactaac tgcatattta gacagcaata tgagcgcagt   1440

tttgactaca taacttgtaa ttttgaaaag ggatatccaa aaggattagt tgacaaagta   1500

aatgaaaatt ggaaaaggta cggatataaa taa                                 1533
```

<210> SEQ ID NO 3
<211> LENGTH: 12
<212> TYPE: PRT
<213> ORGANISM: Artificial Sequence
<220> FEATURE:
<223> OTHER INFORMATION: GrsA peptide containing the phosphopantetheine
      modification

<400> SEQUENCE: 3

```
Asp Asn Phe Tyr Ala Leu Gly Gly Asp Ser Ile Lys
1               5                   10
```

<210> SEQ ID NO 4
<211> LENGTH: 29
<212> TYPE: PRT
<213> ORGANISM: Artificial Sequence
<220> FEATURE:

<223> OTHER INFORMATION: GrsB1 T-domain active-site peptide

<400> SEQUENCE: 4

Ile Trp Glu Glu Val Leu Gly Ile Ser Gln Ile Gly Ile Gln Asp Asn
1 5 10 15

Phe Phe Ser Leu Gly Ser Leu Gly Gly His Ser Leu Lys
20 25

<210> SEQ ID NO 5
<211> LENGTH: 48
<212> TYPE: DNA
<213> ORGANISM: Artificial Sequence
<220> FEATURE:
<223> OTHER INFORMATION: RBS calculator plasmid insertion site
<220> FEATURE:
<221> NAME/KEY: misc_feature
<222> LOCATION: (15)..(42)
<223> OTHER INFORMATION: n is a, c, g, or t
<220> FEATURE:
<221> NAME/KEY: misc_feature
<222> LOCATION: (15)..(42)
<223> OTHER INFORMATION: optimized ribosome binding site

<400> SEQUENCE: 5
tctagaaata gatctnnnnn nnnnnnnnnn nnnnnnnnnn nnatgcgt 48

<210> SEQ ID NO 6
<211> LENGTH: 48
<212> TYPE: DNA
<213> ORGANISM: Artificial Sequence
<220> FEATURE:
<223> OTHER INFORMATION: pJL1 plasmid insertion site
<220> FEATURE:
<221> NAME/KEY: misc_feature
<222> LOCATION: (15)..(42)
<223> OTHER INFORMATION: ribosome binding site from the pJL1 backbone

<400> SEQUENCE: 6
tctagaaata attttgttta actttaagaa ggagatatac atatgcgt 48

<210> SEQ ID NO 7
<211> LENGTH: 64
<212> TYPE: DNA
<213> ORGANISM: Artificial Sequence
<220> FEATURE:
<223> OTHER INFORMATION: pJL1-MEKKI plasmid insertion site
<220> FEATURE:
<221> NAME/KEY: misc_feature
<222> LOCATION: (15)..(42)
<223> OTHER INFORMATION: ribosome binding site from the pJL1 backbone
<220> FEATURE:
<221> NAME/KEY: misc_feature
<222> LOCATION: (45)..(57)
<223> OTHER INFORMATION: N-terminal tag encoding MEKKI (SEQ ID NO:13)
<220> FEATURE:
<221> NAME/KEY: misc_feature
<222> LOCATION: (58)..(64)
<223> OTHER INFORMATION: n is a, c, g, or t

<400> SEQUENCE: 7
tctagaaata attttgttta actttaagaa ggagatatac atatggagaa aaaaatcnnn 60 nnnn 64

<210> SEQ ID NO 8
<211> LENGTH: 27
<212> TYPE: DNA
<213> ORGANISM: Artificial Sequence
<220> FEATURE:
<223> OTHER INFORMATION: Optimized ribosome binding site for RBS calculator plasmid
<220> FEATURE:
<221> NAME/KEY: misc_feature
<222> LOCATION: (1)..(27)
<223> OTHER INFORMATION: n is a, c, g, or t

<400> SEQUENCE: 8
nnnnnnnnnn nnnnnnnnnn nnnnnnn 27

<210> SEQ ID NO 9
<211> LENGTH: 27
<212> TYPE: DNA
<213> ORGANISM: Artificial Sequence
<220> FEATURE:
<223> OTHER INFORMATION: ribosome binding site from the pJL1 backbone

<400> SEQUENCE: 9
gtttaacttt aagaaggaga tatacat 27

<210> SEQ ID NO 10
<211> LENGTH: 12
<212> TYPE: DNA
<213> ORGANISM: Artificial Sequence
<220> FEATURE:
<223> OTHER INFORMATION: N-terminal tag encoding MEKKI (SEQ ID NO:13)

<400> SEQUENCE: 10
gagaaaaaaa tc 12

<210> SEQ ID NO 11
<211> LENGTH: 6
<212> TYPE: DNA
<213> ORGANISM: Artificial Sequence
<220> FEATURE:
<223> OTHER INFORMATION: Sample nucleotide sequence for the N-terminus of a gene of interest

<400> SEQUENCE: 11 atgcgt 6

<210> SEQ ID NO 12
<211> LENGTH: 18
<212> TYPE: DNA
<213> ORGANISM: Artificial Sequence
<220> FEATURE:
<223> OTHER INFORMATION: N-terminal expression tag variant 1 encoding MEKKI (SEQ ID NO:13)

<400> SEQUENCE: 12
catatggaga aaaaaatc 18

<210> SEQ ID NO 13
<211> LENGTH: 5
<212> TYPE: PRT
<213> ORGANISM: Artificial Sequence
<220> FEATURE:
<223> OTHER INFORMATION: N-terminal expression tag variant 1 (MEKKI)

<400> SEQUENCE: 13

Met Glu Lys Lys Ile
1               5

<210> SEQ ID NO 14
<211> LENGTH: 24
<212> TYPE: DNA
<213> ORGANISM: Artificial Sequence
<220> FEATURE:

<223> OTHER INFORMATION: N-terminal expression tag variant 2 encoding
MHMEKKI (SEQ ID NO:15)

<400> SEQUENCE: 14
catatgcata tggagaaaaa aatc 24

<210> SEQ ID NO 15
<211> LENGTH: 7
<212> TYPE: PRT
<213> ORGANISM: Artificial Sequence
<220> FEATURE:
<223> OTHER INFORMATION: N-terminal expression tag variant 2 (MHMEKKI)

<400> SEQUENCE: 15

Met His Met Glu Lys Lys Ile
1 5

<210> SEQ ID NO 16
<211> LENGTH: 1233
<212> TYPE: DNA
<213> ORGANISM: Artificial Sequence
<220> FEATURE:
<223> OTHER INFORMATION: 354_pJL1-atoB (ACAT_Eco)

<400> SEQUENCE: 16
tctagaaata attttgttta actttaagaa ggagatatac atatgaaaaa ttgtgtcatc 60
gtcagtgcgg tacgtactgc tatcggtagt tttaacggtt cactcgcttc caccagcgcc 120
atcgacctgg gggcgacagt aattaaagcc gccattgaac gtgcaaaaat cgattcacaa 180
cacgttgatg aagtgattat gggtaacgtg ttacaagccg ggctggggca aaatccggcg 240
cgtcaggcac tgttaaaaag cgggctggca gaaacggtgt gcggattcac ggtcaataaa 300
gtatgtggtt cgggtcttaa aagtgtggcg cttgccgccc aggccattca ggcaggtcag 360
gcgcagagca ttgtggcggg gggtatggaa aatatgagtt tagcccccta cttactcgat 420
gcaaaagcac gctctggtta tcgtcttgga gacggacagg tttatgacgt aatcctgcgc 480
gatggcctga tgtgcgccac ccatggttat catatgggga ttaccgccga aaacgtggct 540
aaagagtacg gaattacccg tgaaatgcag gatgaactgg cgctacattc acagcgtaaa 600
gcggcagccg caattgagtc cggtgctttt acagccgaaa tcgtcccggt aaatgttgtc 660
actcgaaaga aaaccttcgt cttcagtcaa gacgaattcc cgaaagcgaa ttcaacggct 720
gaagcgttag gtgcattgcg cccggccttc gataaagcag gaacagtcac cgctgggaac 780
gcgtctggta ttaacgacgg tgctgccgct ctggtgatta tggaagaatc tgcggcgctg 840
gcagcaggcc ttacccccct ggctcgcatt aaaagttatg ccagcggtgg cgtgcccccc 900
gcattgatgg gtatggggcc agtacctgcc acgcaaaaag cgttacaact ggcggggctg 960
caactggcgg atattgatct cattgaggct aatgaagcat ttgctgcaca gttccttgcc 1020
gttgggaaaa acctgggctt tgattctgag aaagtgaatg tcaacggcgg ggccatcgcg 1080
ctcgggcatc ctatcggtgc cagtggtgct cgtattctgg tcacactatt acatgccatg 1140
caggcacgcg ataaaacgct ggggctggca acactgtgca ttggcggcgg tcagggaatt 1200
gcgatggtga ttgaacggtt gaattaagtc gac 1233

<210> SEQ ID NO 17
<211> LENGTH: 1542
<212> TYPE: DNA
<213> ORGANISM: Artificial Sequence
<220> FEATURE:
<223> OTHER INFORMATION: 310_pJL1-(CAT5aa)-HMGS_Sce

<400> SEQUENCE: 17

```
tctagaaata attttgttta actttaagaa ggagatatac atatggagaa aaaaatcaaa     60
ctgagcacca agctgtgctg gtgtggcatc aagggtcgcc tgcgcccaca aaagcagcaa    120
cagctgcaca acacgaacct gcaaatgacc gagctgaaaa agcagaagac ggccgagcaa    180
aagacccgcc cgcagaacgt tggcatcaag ggcatccaga tttatatccc gacgcagtgt    240
gtcaaccaat ctgagctgga gaaattcgat ggcgtcagcc agggtaagta caccatcggc    300
ctgggccaga ccaacatgag cttcgtgaac gaccgtgagg acatctattc tatgagcctg    360
acggtgctgt ctaagctgat caagagctac aacatcgaca cgaataagat cggtcgtctg    420
gaggtgggta cggagacgct gattgacaag agcaaaagcg tgaagtctgt cttaatgcag    480
ctgttcggcg agaacacgga tgtcgagggt atcgacaccc tgaacgcgtg ttacggcggc    540
accaacgcac tgttcaatag cctgaactgg attgagagca acgcctggga tggccgcgat    600
gcgatcgtcg tgtgcggcga tatcgccatc tatgacaagg gtgcggcacg tccgaccggc    660
ggtgcaggca ccgttgcgat gtggattggc ccggacgcac caattgtctt cgattctgtc    720
cgcgcgtctt acatggagca cgcctacgac ttttacaagc cggacttcac gagcgaatac    780
ccgtacgtgg acggccactt ctctctgacc tgctatgtga aggcgctgga ccaggtttat    840
aagtcttata gcaaaaaggc gatttctaag ggcctggtca gcgacccggc aggcagcgac    900
gccctgaacg tgctgaagta tttcgactac aacgtgttcc atgtcccgac ctgcaaatta    960
gtgaccaaat cttatggccg cctgttatat aatgatttcc gtgccaaccc gcagctgttc   1020
ccggaggttg acgccgagct ggcgacgcgt gattacgacg agagcctgac cgacaagaac   1080
atcgagaaga ccttcgtcaa cgtcgcgaag ccgttccaca aagagcgtgt ggcccaaagc   1140
ctgatcgtcc cgaccaacac gggcaacatg tataccgcgt ctgtctacgc ggcattcgcg   1200
agcctgctga attacgtcgg ttctgacgac ctgcagggca agcgcgttgg cctgttcagc   1260
tacggtagcg gcttagcggc cagcctgtat agctgcaaaa ttgtcggcga cgtccagcac   1320
atcatcaagg agctggacat caccaacaag ctggcgaagc gcatcaccga gacgccgaaa   1380
gattacgagg cagcgatcga gttacgcgag aatgcgcatc tgaagaagaa cttcaagccg   1440
caaggtagca tcgagcacct gcagagcggc gtctactacc tgacgaacat tgacgacaag   1500
ttccgccgtt cttatgacgt caaaaagctg gagtgagtcg ac                      1542
```

<210> SEQ ID NO 18
<211> LENGTH: 1227
<212> TYPE: DNA
<213> ORGANISM: Artificial Sequence
<220> FEATURE:
<223> OTHER INFORMATION: 311_pJL1-(CAT5aa)-HMGS_Sau

<400> SEQUENCE: 18

```
tctagaaata attttgttta actttaagaa ggagatatac atatggagaa aaaaatcacc     60
ctgggcattg ataaaatcaa cttctatgtg ccgaaatatt acgtggatat ggcaaaactg    120
gcagaagcac gtcaggttga tccgaacaaa tttctgattg gtattggtca gaccgaaatg    180
gcagttagtc cggttaatca ggatattgtt agcatgggtg caaatgcagc caaagatatt    240
atcaccgatg aagataaaaa aaaaatcggc atggttatcg ttgcaaccga aagcgcagtt    300
gatgcagcaa aagcagcagc agttcagatt cataatctgc tgggtattca gccgtttgca    360
cgttgttttg aaatgaaaga agcatgttac gcagcaacac cggcaattca gctggcaaaa    420
```

```
gattatctgg caacccgtcc gaatgaaaaa gttctggtta ttgccaccga taccgcacgt    480

tatggtctga atagcggtgg tgaaccgacc cagggtgccg gtgcagttgc aatggttatt    540

agccataatc cgagcattct ggcactgaat gaagatgcag ttgcctatac cgaagatgtg    600

tatgattttt ggcgtccgac cggtcataaa tatccgctgg ttgatggtgc actgagcaaa    660

gatgcatata ttcgtagctt tcagcagagc tggaatgaat atgcaaaacg tcagggtaaa    720

agcctggcag attttgcaag cctgtgtttt catgttccgt ttaccaaaat gggtaaaaaa    780

gccctggaaa gcattattga taatgccgat gaaaccaccc aagaacgtct gcgtagcggt    840

tatgaggatg ccgttgatta taaccgttat gtgggtaaca tttataccgg tagcctgtat    900

ctgagcctga ttagcctgct ggaaaatcgt gatctgcagg caggcgaaac cattggtctg    960

tttagctatg gtagcggtag cgttggtgag ttttatagcg caaccctggt tgaaggttat   1020

aaagatcatc tggatcaggc agcacataaa gcactgctga ataatcgtac cgaagttagc   1080

gttgatgcgt atgaaacctt tttcaaacgc ttcgatgatg tggattttga tgaacagcag   1140

gatgcagttc atgaagatcg ccatatcttt tatctgagca acattgaaaa caatgtgcgc   1200

gaatatcatc gtccggaata agtcgac                                       1227
```

<210> SEQ ID NO 19
<211> LENGTH: 1569
<212> TYPE: DNA
<213> ORGANISM: Artificial Sequence
<220> FEATURE:
<223> OTHER INFORMATION: 312_pJL1-(CAT5aa)-HMGR_Sce

<400> SEQUENCE: 19

```
tctagaaata attttgttta actttaagaa ggagatatac atatggagaa aaaaatcgtg     60

ctgacgaaca aaaccgtcat tagcggcagc aaggtgaagt ctctgagcag cgcccaaagc    120

tctagcagcg gcccgtctag cagcagcgag gaggacgaca gccgtgacat tgagtctctg    180

gacaagaaga tccgcccgct ggaggagtta gaggccctgc tgagcagcgg caacaccaag    240

cagctgaaga acaaggaagt tgcagcgctg gtgatccacg gtaagctgcc actgtatgcg    300

ctggaaaaga aactgggcga tacgacgcgt gcggtcgcgg tgcgtcgcaa agccttaagc    360

atcttagcgg aggccccggt gttagccagc gaccgcctgc cgtacaagaa ctacgactac    420

gaccgcgtgt ttggcgcgtg ctgcgagaat gtcattggct acatgccgtt accggttggt    480

gtgatcggcc cgctggtcat tgatggcacg agctatcaca ttccaatggc gaccacggaa    540

ggttgcttag tcgccagcgc catgcgtggc tgtaaggcga ttaacgccgg cggtggcgcg    600

acgaccgtgt taaccaagga tggtatgacg cgcggtccgg tcgtccgctt cccaacgctg    660

aagcgcagcg gcgcgtgtaa gatttggctg gattctgagg agggccaaaa cgcgatcaag    720

aaagccttca actctacgag ccgtttcgcg cgtttacagc atatccagac ctgcctggcc    780

ggcgacctgc tgttcatgcg cttccgcacc accacgggcg atgcgatggg catgaacatg    840

atcagcaagg gcgtcgaata tagcctgaaa caaatggtgg aagaatatgg ctgggaggac    900

atggaggttg tctctgtgag cggcaactat tgcaccgaca agaagccggc agccattaac    960

tggattgagg gtcgcggcaa aagcgtcgtg gcagaagcga ccatcccagg cgacgtggtc   1020

cgtaaggttc tgaagagcga cgtcagcgcc ctggttgagt taaatatcgc gaaaaacctg   1080

gtcggcagcg cgatggcggg cagcgtgggt ggctttaacg cacatgcagc gaatctggtt   1140

acggcggttt tcttagcctt aggtcaggac ccagcccaaa atgtcgagag cagcaactgc   1200

attaccttaa tgaaagaggt tgacggtgac ctgcgcatca gcgtttctat gccgtctatc   1260
```

-continued

```
gaggtcggca cgatcggcgg cggcaccgtt ttagaaccgc aaggtgcgat gctggatctg   1320

ctgggcgtgc gcggcccaca tgcaacggcc ccaggcacca atgcccgcca actggcccgt   1380

atcgtggcct gcgcggttct ggcgggtgag ctgagcctgt gcgccgcatt agccgcgggc   1440

catttagttc aatctcacat gacccacaac cgcaagccgg cagaaccaac caagccaaat   1500

aacctggacg caaccgacat taaccgtctg aaggatggca gcgtcacgtg cattaaaagc   1560

taagtcgac                                                          1569
```

<210> SEQ ID NO 20
<211> LENGTH: 1341
<212> TYPE: DNA
<213> ORGANISM: Artificial Sequence
<220> FEATURE:
<223> OTHER INFORMATION: 313_pJL1-(CAT5aa)-HMGR_Sau

<400> SEQUENCE: 20

```
tctagaaata attttgttta actttaagaa ggagatatac atatggagaa aaaaatccag     60

agcctggata aaaactttcg tcatctgagc cgtcagcaga aactgcagca gctggttgat    120

aaacagtggc tgagcgaaga acagtttaac attctgctga atcatccgct gattgatgaa    180

gaagttgcaa acagcctgat tgaaaatgtt attgcacagg gtgcactgcc ggttggtctg    240

ctgccgaaca ttattgttga tgataaagca tatgtggtgc cgatgatggt tgaagaaccg    300

agcgttgttg cagcagcaag ctatggtgca aaactggtta atcagaccgg tggctttaaa    360

accgttagca gcgaacgtat tatgattggc cagattgttt ttgatggtgt ggatgatacc    420

gaaaaactga gcgcagatat taaagccctg gaaaaacaaa ttcatcagat tgccgatgaa    480

gcctatccga gcattaaagc acgtggtggt ggttatcagc gtattgcaat tgataccttt    540

ccggaacagc aactgctgag cctgaaagtg tttgttgata ccaaagatgc aatgggtgcc    600

aatatgctga ataccattct ggaagcaatt accgcctttc tgaaaaatga atttccgcag    660

agcgatatcc tgatgagcat tctgagcaat catgcaaccg caagcgttgt taaagttcag    720

ggtgaaattg atgttaaaga cctggcacgc ggtgaacgta ccggtgaaga ggttgccaaa    780

cgtatggaac gtgcaagcgt tctggcacag gttgatattc atcgtgcagc aacccataat    840

aaaggtgtga tgaacggtat tcatgcagtt gttctggcaa ccggtaatga tacccgtggt    900

gcggaagcaa gcgcacatgc atatgccagc aaagatggtc agtatcgtgg tattgcaacc    960

tggcgttatg atcaagaacg tcagcgtctg attggtacaa ttgaagttcc gatgaccctg   1020

gcaattgttg gtggtggcac caaagttctg ccgattgcaa aagcaagcct ggaactgctg   1080

aatgttgaaa gcgcacaaga actgggtcat gttgttgccg cagtgggtct ggcccagaat   1140

tttgcagcat gtcgtgcact ggttagcgaa ggtatccagc agggtcatat gagtctgcag   1200

tataaaagcc tggccattgt ggttggtgcc aaaggtgatg aaattgcgca ggttgcagaa   1260

gcactgaaac aagaaccgcg tgcaaatacc caggttgcgg aacgtattct gcaggatctg   1320

cgtagccagc agtaagtcga c                                            1341
```

<210> SEQ ID NO 21
<211> LENGTH: 1347
<212> TYPE: DNA
<213> ORGANISM: Artificial Sequence
<220> FEATURE:
<223> OTHER INFORMATION: 314_pJL1-(CAT5aa)-HMGR_Pme

<400> SEQUENCE: 21

```
tctagaaata attttgttta actttaagaa ggagatatac atatggagaa aaaaatcagc     60
ttggacagcc gcctgccagc ttttcggaac ctgagccccg cggcgcgcct ggatcatatt    120
ggccagctct tgggcctgag ccatgatgac gtgagcctgc tggcgaacgc gggagcgctg    180
ccgatggata ttgcgaacgg catgattgag aacgtgattg gcacctttga actgccatac    240
gcggtggcga gcaactttca gattaatggc cgggacgtgc tggtgccgct ggtggtggag    300
gaaccaagca ttgtggcggc tgctagctat atggcgaaac tggcgcgggc gaacggcggc    360
tttaccacca gcagcagcgc gccgctgatg cacgcgcagg tacagattgt gggcatacaa    420
gatccgttga atgctcgcct gagcctgctg cgccgcaagg atgagattat agagctggcg    480
aaccgcaaag atcagctctt aaacagctta ggcggcggct gccgcgatat tgaggtgcat    540
acctttgcgg acaccccgcg gggcccgatg ctggtggcgc atctgattgt ggacgtacgc    600
gacgcgatgg gcgcgaacac cgtgaatacc atggcggaag cggtagcgcc gctgatggag    660
gcgattaccg gaggccaggt acgcctgcgc atactgagca acctggcgga tctgcgcctg    720
gcgagggcgc aggttcggat aacaccgcag caactggaga cagcggagtt ttcaggcgaa    780
gctgtgattg agggcatttt ggatgcgtat gcgtttgctg cggttgatcc ctatcgcgcg    840
gcgacccata acaaaggcat tatgaatggc attgatcccc tgattgtggc gacaggcaac    900
gattggcggg ctgtggaggc gggcgcgcac gcgtacgcgt gccgctcagg acattatggc    960
agcctgacca cctgggagaa agataacaac ggccaccttg tgggcaccct ggagatgccg   1020
atgccagtag gcctggtggg cggcgcgacc aagacccacc cgctggcgca actgagcctg   1080
cgcattttag gcgtgaagac agcgcaggcg ttggctgaaa tagcggtggc ggtaggcctg   1140
gcgcaaaact taggagcgat gcgcgcgctg gcgaccgagg gcattcagcg cggccatatg   1200
gcgctgcacg cgcgcaatat agcggtggtg gcgggcgcga ggggcgacga agtggattgg   1260
gtagcgcggc agcttgtgga gtatcatgat gtgcgcgcgg atcgcgcggt agctctgctg   1320
aagcaaaaac gcggccaata agtcgac                                       1347
```

<210> SEQ ID NO 22
<211> LENGTH: 1335
<212> TYPE: DNA
<213> ORGANISM: Artificial Sequence
<220> FEATURE:
<223> OTHER INFORMATION: 315_pJL1-(CAT5aa)-HMGR_Spn

<400> SEQUENCE: 22

```
tctagaaata attttgttta actttaagaa ggagatatac atatggagaa aaaaatcaag     60
atcagctgga acggttttag caaaaaaagc taccaggagc ggcttgagct cttgaaagcg    120
caagctctct taagcccaga gcggcaggcg agccttgaga aggatgaaca aatgagcgta    180
acggtagccg accaacttag cgagaacgtc gtaggtacgt ttagcctccc atattcactt    240
gtgccagagg tcttagtcaa tggccaagaa tacactgtgc cttatgtaac ggaagaacct    300
agcgtagtgg ctgctgcatc atatgcatca aaaatcatca agcgcgccgg cggctttacg    360
gcccaggtcc atcaacggca aatgattggg caagtcgcat tgtatcaggt ggcgaaccca    420
aaattggctc aggagaagat tgcatcaaag aaagctgagc tcttggagtt tgcaaaccag    480
gcatatccaa gcatcgtgaa acgcggtggc ggggctcgcg atcttcatgt cgagcaaatc    540
aaaggggaac cggactttct tgtggtgtat attcatgtcg atactcaaga agcaatgggc    600
gcaaacatgc ttaatactat gcttgaagca ttaaaaccgg tcttagaaga actcagccaa    660
ggtcaaagcc ttatcggtat cctctcaaat tacgctactg atagccttgt aacggcctca    720
```

```
tgccggatgg catttcggta cttgtcacgg cagaaggatc agggtcggga gattgctgag    780
aaaattgctt tggcgagcca atttgctcaa gccgatccat accgggcggc gacgcataac    840
aaaggtattt ttaacggcat tgatgctatt ttgattgcaa cgggcaacga ctggcgcgca    900
atcgaagcgg gggcacatgc atttgcaagc cgggatggtc ggtatcaggg cttaagctgt    960
tggacactcg acttggaacg ggaagaattg gtcggcgaga tgactcttcc tatgccagtc   1020
gctacgaagg gcgggagcat cgggctcaat ccgcgcgtcg cgttcagcca tgatttgtta   1080
ggtaacccaa gcgcacggga attggcacaa attatcgtat caatcggctt ggcacagaac   1140
tttgccgcac ttaaagcgtt agtcagcaca ggaatccaac aggggcacat gaaattacaa   1200
gcaaaatcat tagcgctttt agcgggggcg agcgaaagcg aagtggcgcc tttagtcgag   1260
cggctcatca gcgataaaac ttttaatttg gagacggcac aacggtatct cgaaaactta   1320
cggagctaag tcgac                                                    1335
```

<210> SEQ ID NO 23
<211> LENGTH: 1341
<212> TYPE: DNA
<213> ORGANISM: Artificial Sequence
<220> FEATURE:
<223> OTHER INFORMATION: 316_pJL1-(CAT5aa)-HMGR_Bpe

<400> SEQUENCE: 23

```
tctagaaata attttgttta actttaagaa ggagatatac atatggagaa aaaaatcagc     60
accgatgcaa aaaatagccg tattagcggc tttcacaaag atgatattcc gacccgtctg    120
gcacgtgttg cagcatttgc aggtctggat gatgaaaccg ttcagcatct ggcaaatatg    180
ggtaatctgg acccgcagct ggcagatcgt ctgattgaaa atgttgttgc aaccctgaat    240
gtgccgattg gtattgcaac caatatgaaa gttgatggcg aagatgttct ggttccgatg    300
gcaaccgaag aaagcagcgt tgttgcagcc gtttgtaatg cagcacgtca gtgttatgat    360
cagggtggtt ttaccaccag tatgagcggt agcctgatga ttgcacaggt tcagctggtt    420
gatgttccgg atgcagcaca tgcacgtatg cgtattctgg aacataaagc cgaagttaaa    480
gcactgtgtg atgattgtga tccgctgctg gttaaactgg gtggtggtct gcaggatgtt    540
gaagttcgta ttgttgatgc agccggtggt ccgatggttg ttacccatct gattgttgat    600
acccgtgatg caatgggtgc aaatgcagtt aatagcatgg cagaaaaact ggcaccgcat    660
attgaaagct ggaccggtgg tcgtgtttat ctgcgcattc tgagcaatct ggccgatcgt    720
cgcctggcac gcgcacgtgc agtttggacc tgtgatgcca ttggtggtgc aagcgttcgt    780
gatggtatta ttagcgcata tcgttttgca gcagcagatc cgtatcgtgc agcaacccat    840
aacaaaggta ttatgaatgg tgttagcgca gttgttctgg caaccggtaa tgatacacgt    900
gccgttgaag ccggtgcaca tgcatatgcc gcacgtaaag gttggtatag cagcctgacc    960
gattgggaag ttaccgcaga aggtcatctg gcaggcaccc tggaaatgcc gatggcagtt   1020
ggtctggtgg gtggtgccac aaaactgcat ccgaccgcac gtgcctgtct gaaaattctg   1080
ggtgttagca ccgcagaacg gctggcacgc ctgattgcag cagtgggtct ggcacagaat   1140
tttagcgcac tgaaagcact ggcaaccacc ggtattcaga aaggtcatat gagcctgcat   1200
gcacagaata ttgcaatgat ggcaggcgca gttggtgatg aaattgaacc ggttgcaaaa   1260
gccctggttg cacagggtgc agttcgtgtt gatgttgcag aagcagaact ggcacgtctg   1320
cgtggtcagg gttaagtcga c                                              1341
```

<210> SEQ ID NO 24
<211> LENGTH: 1350
<212> TYPE: DNA
<213> ORGANISM: Artificial Sequence
<220> FEATURE:
<223> OTHER INFORMATION: 317_pJL1-(CAT5aa)-HMGR_Dac

<400> SEQUENCE: 24
tctagaaata attttgttta actttaagaa ggagatatac atatggagaa aaaaatcgtc 60
gccgattccc gcctgccgaa cttccgcgcc ctgactccgg cccagcgtcg tgattttctg 120
gcagatgcat gtggtctgag tgatgcagaa cgtgcactgc tggcagcacc gggtgcactg 180
cctctggcac tggccgatgg tatgattgaa aatgtttttg gctcatttga actgccgctg 240
ggtgttgcag gtaattttcg cgttaatggt cgtgatgtgc tggttccgat ggcagttgaa 300
gaaccgagcg ttgttgcagc agcaagctat atggcaaaac tggcacgtga agatggtggt 360
tttcagacca gcagcaccct gccgctgatg cgtgcacagg ttcaggttct gggtgttacc 420
gatccgcatg gtgcacgtct ggcagttctg caggcacgtg cacagattat tgaacgtgca 480
aatagccgtg ataaagtgct gattggtctg ggtggtggtt gtaaagatat tgaagttcat 540
gtgtttccgg atacaccgcg tggtccgatg ctggttgttc atctgattgt tgatgttcgt 600
gatgcaatgg gtgccaatac cgttaatacc atggcagaaa gcgttgcacc gctggttgag 660
cagattaccg gtggtagcgt tcgtctgcgt attctgagca atctggccga tctgcgtctg 720
gcacgcgcac gtgttcgtct gacaccgcag accctggcaa cccaagaacg tagcggtgaa 780
gaaattattg aaggtgttct ggatgcatat acctttgcag caattgatcc gtatcgtgca 840
gcaacccata ataaaggtat tatgaatggt atcgatccgg ttattgttgc gaccggtaat 900
gattggcgtg ccgttgaagc cggtgcacat gcctatgcaa gccgtagcgg tagctatacc 960
agcctgaccc gttgggaaaa agatgccggt ggtgcactgg ttggtagcat cgaactgccg 1020
atgccggttg gtctggttgg cggtgccacc aaaacccatc cgctggcacg cctggcactg 1080
aaaattatgg atctgcagag cgcacagcag ctgggtgaaa ttgcagccgc agtgggtctg 1140
gcacagaatc tgggtgccct gcgtgcactg gcaaccgaag gtattcagcg tggtcatatg 1200
gcactgcatg cacgtaatat tgccctggtt gcgggtgcaa ccggtgatga agttgatgca 1260
gttgcacgtc agctggcagc cgaacatgat gtgcgtaccg atcgtgccct ggaagttctg 1320
gcagcactgc gtgcccgtgc ataagtcgac 1350

<210> SEQ ID NO 25
<211> LENGTH: 1432
<212> TYPE: DNA
<213> ORGANISM: Artificial Sequence
<220> FEATURE:
<223> OTHER INFORMATION: 281_pJL1-(CAT5aa)-MK1_Sce

<400> SEQUENCE: 25
tctagaaata attttgttta actttaagaa ggagatatac atatggagaa aaaaatcagt 60
ttacccttct taacgagcgc ccccgggaag gtgatcatct ttggcgaaca cagcgcggtc 120
tacaataagc cagcagtcgc ggcgtcggtc agcgctttgc gcacttacct cttaatctca 180
gagtccagcg ccccggatac gatcgaatta gacttccccg acatctcatt taaccataag 240
tggtccatca acgatttcaa cgcaatcact gaggatcagg tcaattccca gaaattggca 300
aaggcgcagc aggcaactga tgggttaagc caagaactag tgagtttatt agatccctta 360
ttggcgcagt tatccgaatc cttccactac catgccgctt tttgcttcct ctatatgttt 420

```
gtgtgtttat gtcctcatgc aaagaacatc aagtttagct tgaagagcac gttgcctatc    480

ggcgcgggat tagggtcttc agcaagcatc agcgtcagtc ttgcattggc gatggcatac    540

ttaggaggat taatcgggag caacgacttg gaaaagctca gtgaaaatga taagcatatc    600

gtcaaccagt gggcattcat cggcgaaaag tgcatccacg gcactccatc tgggatcgat    660

aatgcggtcg caacgtatgg caacgcactc ttgtttgaaa aagactccca taacgggacg    720

atcaatacga ataactttaa gttcttagat gatttcccgg caatcccgat gatcttaact    780

tatacgcgca tcccgcggag cacgaaagat ttagtggcgc gagtgcgggt cttagtcact    840

gagaaatttc cagaagtgat gaagccgatc ttagatgcaa tgggcgaatg cgcattacag    900

gggttagaga tcatgacgaa gttgagtaaa tgcaaaggga ctgatgacga ggcggtcgaa    960

acgaacaacg aactttatga acagttgttg gaattgatcc gcatcaacca tgggctcttg   1020

gtttcgatcg gcgtgagcca tccagggtta gaattaatca aaaacctctc agatgattta   1080

cgcatcgggt ctacgaaatt aactggcgcg ggcggtgggg gctgtagctt gacgttgtta   1140

cgacgcgaca tcacgcagga gcagatcgac tcattcaaaa agaaattgca ggatgatttt   1200

agttacgaga cgtttgaaac ggacttgggc ggaacggggt gttgcttatt atcagccaaa   1260

aacttaaaca aagatttaaa aatcaaatcg ttggtcttcc agttatttga aaacaaaacg   1320

actacgaagc agcagatcga cgatttgtta ttaccgggga atacaaactt accgtggacg   1380

tcttgaggat ccgcactcga gcaccaccac caccaccact gagatcgtcg ac           1432
```

```
<210> SEQ ID NO 26
<211> LENGTH: 993
<212> TYPE: DNA
<213> ORGANISM: Artificial Sequence
<220> FEATURE:
<223> OTHER INFORMATION: 321_pJL1-(CAT7aa)-MK_Sau

<400> SEQUENCE: 26

tctagaaata attttgttta actttaagaa ggagatatac atatgcatat ggagaaaaaa     60

atcacccgta aaggttatgg tgaaagcacc ggtaaaatca ttctgattgg tgaacatgca    120

gtgacctttg gtgaaccggc aattgcagtt ccgtttaatg caggcaaaat caaagttctg    180

attgaagcac tggaaagcgg taactatagc agcattaaat ccgatgtgta tgatggcatg    240

ctgtatgatg caccggatca tctgaaaagc ctggttaatc gttttgtgga actgaacaac    300

attaccgaac cgctggcagt taccattcag accaatctgc ctccgagccg tggtctgggt    360

agcagcgcag cagttgcagt tgcatttgtt cgtgcaagct atgattttct gggtaaaagc    420

ctgaccaaag aagaactgat tgaaaaagca aattgggcag agcagattgc acatggtaaa    480

ccgagcggta ttgataccca gacaattgtt agcggtaaac cggtgtggtt tcagaaaggt    540

catgcagaaa ccctgaaaac cctgtcactg gatggttata tggttgtgat tgataccggt    600

gttaaaggta gcacccgtca ggcagttgaa gatgttcata aactgtgtga agatccgcag    660

tatatgagcc atgttaaaca tattggtaaa ctggttctgc gtgccagtga tgttattgaa    720

catcataatt ttgaagccct ggccgatatc tttaatgaat gtcatgccga tctgaaagca    780

ctgaccgtta gccatgataa aattgagcag ctgatgaaga tcggcaaaga aaatggtgcc    840

attgcaggta aactgaccgg tgcaggtcgt ggtggtagca tgctgctgct ggcaaaagac    900

ctgccgaccg caaaaaacat tgttaaagca gtggaaaaag ccggtgcagc acatacctgg    960

attgaaaatt taggtggtta agtcgacgtc gac                                 993
```

<210> SEQ ID NO 27
<211> LENGTH: 951
<212> TYPE: DNA
<213> ORGANISM: Artificial Sequence
<220> FEATURE:
<223> OTHER INFORMATION: 322_pJL1-(CAT7aa)-MK_Spn

<400> SEQUENCE: 27
tctagaaata attttgttta actttaagaa ggagatatac atatgcatat ggagaaaaaa 60
atcaccaaaa aagttggtgt tggtcaggca catagcaaaa ttatcctgat tggtgaacat 120
gccgtggttt atggttatcc ggcaattagc ctgccgctgc tggaagttga agttacctgt 180
aaagttgtta gcgcagaaag cccgtggcgt ctgtatgaag aggataccct gagcatggca 240
gtttatgcaa gcctggaata tctggatatc accgaagcat gtgttcgttg tgaaattgat 300
agcgcaattc cggaaaaacg tggtatgggt agcagcgcag caattagcat tgcagcaatt 360
cgtgcagtgt tcgattatta tcaggccgat ctgccgcatg atgttctgga aattctggtt 420
aatcgtgcag aaatgattgc acacatgaat ccgagcggtc tggatgcaaa aacctgtctg 480
agcgatcagc cgattcgttt tatcaaaaat gtgggtttta ccgaactgga aatggatctg 540
agcgcatatc tggttattgc agataccggt gtttatggtc atacccgtga agcaattcag 600
gttgttcaga ataaaggtaa agatgcactg ccgtttctgc atgcactggg tgaactgacc 660
cagcaggcag aagttgccat tagccagaaa gatgcagaag gtctgggtca gattctgagc 720
caggcacatc tgcatctgaa agaaattggt gttagcagtc cggaagcaga ttttctggtt 780
gaaaccacac tgagccatgg tgccctgggt gcaaaaatga gcggtggtgg tttaggtggt 840
tgtattattg cactggttac caatctgaca catgcacaag aactggcaga acgtctggaa 900
gaaaaaggtg ccgttcagac ctggattgaa agcctgtaag tcgacgtcga c 951

<210> SEQ ID NO 28
<211> LENGTH: 978
<212> TYPE: DNA
<213> ORGANISM: Artificial Sequence
<220> FEATURE:
<223> OTHER INFORMATION: 323_pJL1-(CAT7aa)-MK_Mma

<400> SEQUENCE: 28
tctagaaata attttgttta actttaagaa ggagatatac atatgcatat ggagaaaaaa 60
atcgttagct gtagcgcacc gggtaaaatc tacctgtttg gtgaacatgc agttgtgtat 120
ggtgaaaccg caattgcatg tgcagttgaa ctgcgtaccc gtgttcgtgc agaactgaat 180
gatagcatta ccattcagag ccagattggt cgtaccggtc tggattttga aaaacatccg 240
tatgttagcg cagtgatcga aaaaatgcgt aaaagcattc cgattaacgg tgtttttctg 300
accgttgata gcgatattcc ggttggtagc ggtctgggta gcagcgcagc agttaccatt 360
gcaagcattg gtgcactgaa tgaactgttt ggttttggtc tgagcctgca agaaattgca 420
aaactgggtc atgaaatcga gattaaagtt cagggtgcag caagcccgac cgatacctat 480
gttagcacct ttggtggtgt tgttaccatt ccggaacgtc gtaaactgaa aacaccggat 540
tgtggtattg ttattggtga taccggtgtg tttagcagca ccaaagaact ggttgcaaat 600
gttcgtcagc tgcgtgaaag ctatccggat ctgattgaac cgctgatgac cagcattggt 660
aaaattagtc gtattggcga acagctggtt ctgagcggtg attatgcgag cattggtcgt 720
ctgatgaatg ttaatcaggg tctgctggat gcactgggtg ttaatattct ggaactgagc 780
cagctgattt atagcgcacg tgcagccggt gcatttggtg caaaaattac cggtgccggt 840
ggtggtggtt gtatggttgc actgaccgca ccggaaaaat gtaatcaggt tgccgaagca 900
gttgccggtg caggcggtaa agtgaccatt accaaaccga ccgaacaggg tctgaaagtt 960
gattaagtcg acgtcgac 978

<210> SEQ ID NO 29
<211> LENGTH: 1209
<212> TYPE: DNA
<213> ORGANISM: Artificial Sequence
<220> FEATURE:
<223> OTHER INFORMATION: 324_pJL1-(CAT7aa)-MK_Pze

<400> SEQUENCE: 29
tctagaaata attttgttta actttaagaa ggagatatac atatgcatat ggagaaaaaa 60
atcagcaccg gtcgtccgga agcgggtgca catgcaccgg gtaaactgat tctgagcggt 120
gaacatagcg ttctgtatgg tgcaccggca ctggcaatgg caattgcacg ttataccgaa 180
gtttggttta ccccgttagg tattggtgaa ggtattcgta ccacctttgc aaatctgagt 240
ggtggtgcaa cctatagcct gaaactgctg agcggtttta aaagccgtct ggatcgtcgt 300
tttgaacagt ttctgaatgg tgatctgaaa gtgcataaag ttctgaccca tcctgatgat 360
ctggcagttt atgccctggc aagcctgctg catgataaac cgcctggcac cgcagcaatg 420
cctggtattg gcgcaatgca tcatctgcct cgtccgggtg aactgggtag ccgtaccgaa 480
ctgccgattg gtgccggtat gggtagcagc gcagcaattg ttgcagcaac caccgttctg 540
tttgaaaccc tgctggatcg ccctaaaaca ccggaacagc gttttgatcg tgttcgtttt 600
tgtgaacgtc tgaaacatgg taaagcaggt ccgattgatg cagcaagcgt tgttcgtggt 660
ggtctggttc gtgttggtgg taatggtccg ggtagcatta gctcatttga tctgcctgaa 720
gatcacgatc tggttgcagg tcgtggttgg tattgggttc tgcatggccg tccggttagc 780
ggcaccggtg aatgtgttag cgcagttgca gcagcacatg gtcgtgatgc agccctgtgg 840
gatgcatttg cagtttgtac ccgtgcactg gaagcagcac tgctgtcagg tggtagtccg 900
gatgcagcca ttaccgaaaa tcagcgtctg ctggaacgta ttggtgttgt tccggcagca 960
acccaggcac tggttgcaca gattgaagaa gcaggcggag cagcaaaaat ttgtggtgca 1020
ggtagcgtgc gtggtgatca tggtggtgcc gttctggtgc gtattgatga tgcacaggcc 1080
atggcaagcg ttatggcacg tcatccggat ctggattggg caccgctgcg tatgagtcgt 1140
accggtgcag cacctggtcc ggcaccgcgt gcacagccgt tacctggtca gggttaagtc 1200
gacgtcgac 1209

<210> SEQ ID NO 30
<211> LENGTH: 1149
<212> TYPE: DNA
<213> ORGANISM: Artificial Sequence
<220> FEATURE:
<223> OTHER INFORMATION: 325_pJL1-(CAT7aa)-MK_Hme

<400> SEQUENCE: 30
tctagaaata attttgttta actttaagaa ggagatatac atatgcatat ggagaaaaaa 60
atcaccgtta gcagcgcacc gggtaaagtt tacctgtttg gtgaacatgc agttgtttat 120
ggtgaaccgg cagttccgtg tgcagttgaa cgtcgtgcaa ccgttagcgt tagcgcacgt 180
gatgatgatc atgttcgtgt tcgtgcagag gatctgagcc tgaatggttt taccgttgaa 240
tatagcggta gcaccggtaa tcatcctgat gttgatgttc cgacaccgct ggttgaagca 300

-continued

```
gcaatgggtt atattgatgc agcagttgca caggctcgtg atgcagccga tgcaccggat    360

gcaggttttg atattaccgt taaaagcgat attccgcttg gtgcaggtct gggtagcagt    420

gcagccgttg ttgttgcagg tattgatgcg gcaacccgtg aactgggtgt tgaactgagt    480

ccgcgtgaaa ttgcagatcg tgcatatcgt gcagaacatg aagttcagga tggtcaggca    540

agccgtgcag ataccttttg tagcgcaatg ggtggtgcag ttcgtgttga aggtgatgat    600

tgtcgtacca ttgatgcacc gcctctgccg tttgttattg gttttgatgg tggtgccggt    660

gataccggtg cactggttag cggtgtgcgt gcactgcgtg aagaatatga ttttgcagca    720

gataccgtga gcaccattgg tgatattgtt cgtcgtggtg aggatctgct ggcagatgca    780

gatccggaag aaccgagcga agcactgctg agcgaactgg gtcgttttat gaattttaac    840

catggtctgc tggaagccct gggtgttagc agccgtagcc tggatagcat ggtttgggca    900

gcacgtgaag ccggtgccta tggtgcaaaa ctgaccggtg caggcggtgg tggttgtatt    960

gttgcactgg acccgacacc ggaaacacag accgcactgc gttttacacc gggttgtgaa   1020

gatgcatttc gtgccgaact ggcaaccgaa ggtgttcgtg tggaagaacc tccggcaagc   1080

gcagccagcg cagaaagcaa tgttggtgat gatcagagtc cggaaggtag cgcataagtc   1140

gacgtcgac                                                           1149
```

<210> SEQ ID NO 31
<211> LENGTH: 1014
<212> TYPE: DNA
<213> ORGANISM: Artificial Sequence
<220> FEATURE:
<223> OTHER INFORMATION: 326_pJL1-(CAT7aa)-MK_Nma

<400> SEQUENCE: 31

```
tctagaaata attttgttta actttaagaa ggagatatac atatgcatat ggagaaaaaa     60

atcaaaagca aagcaagcgc accgggtaaa gttattctgt ttggtgaaca ttttgtggtg    120

tatggcgtta aagcaattct gtgcgcaatt aacaaacgta ttgcagtgac cgcagaaaaa    180

atcgatgaac gcaaaatcag catcaaaagc aatattggtc atctggaact ggaaccgaat    240

aaaccgatta gcgaaattaa tagtccgctg aaaccgttct attatctggc caataaaatc    300

atccaggaca agaactttgg catcaaaatt gatgtggaaa gcgaaattcc gttaggtgtt    360

ggtctgggta gcagcagcgc atgttgtgtt gccggtgcag cagcaattag caacctgttt    420

gaaaataaca gcaaagaaga gatcctgaaa ctggcaattg aagccgaaaa aaccattttt    480

cagaatacca gcggtgcaga ttgtaccgtt tgtacctttg gtggtctgat ggaatatgat    540

aaagaaaacg gcttcagcaa aatcgaaagc gaaccgaatt ttcatctggt gattgccaat    600

agcaatgtgg aacatagcac cgaaagcgtt gttgcgggtg ttcgtaaatt caaaaaaaac    660

aacgaagccg agttcagcaa actgtgtaaa gatgaaagcc atctgattga gaatgtgctg    720

gaactgctga aagaaaacaa tattcgtgaa ctgggtgaac gcgtgatcaa aaatcaagaa    780

tatctggaac gcattggcat cagcaatgca aaactgcgtg aaatgattca gacaggtcag    840

aatagcagct ttggtgcaaa aattaccggt gccggtggtg gtggttgtat ttttgccctg    900

accgatgaaa gtaatctgga aaacaccatc aaagaattta aagaaaaaaa ccacgagtgc    960

tttagcgtga aaatcgactt taaaggtctg gacacctttt aagtcgacgt cgac         1014
```

<210> SEQ ID NO 32
<211> LENGTH: 1005
<212> TYPE: DNA
<213> ORGANISM: Artificial Sequence
<220> FEATURE:
<223> OTHER INFORMATION: 327_pJL1-(CAT7aa)-MK_Mxa

<400> SEQUENCE: 32

```
tctagaaata attttgttta actttaagaa ggagatatac atatgcatat ggagaaaaaa      60
atcgcaccgc gtccggaaag cctgagcgca tttggtgcag gtaaagttat tctgctgggt     120
gaacatagcg ttgtttatgg tcatccggca ctggcaggtc cgctgagcca gggtgttacc     180
gcacgtgcag ttccggcaaa agcatgtcag ctggcactgc cgagcacact gagccgtccg     240
cagcgtgcac agctgaccgc agcatttgcc cgtgcagccg aagttaccgg tgcacctccg     300
gttaaagtta gcctggaagc cgatctgccg ctggcagttg gtctgggtag cagcgcagca     360
ctgagcgttg catgtgcacg tctgctgctg caggcagccg gtaaagttcc gacaccgaaa     420
gatgcagcac gtgttgcctg ggcaatggaa caagaatttc atggcacccc gagcggtgtt     480
gatcatacca ccagtgcagc agaacagctg gtgctgtatt ggcgtaaacc gggtgcagca     540
aaaggcaccg gtcaggttgt tgaaagtccg cgtccgctgc atgttgttgt taccctggca     600
ggcgaacgta gcccgaccaa aaaaaccgtt ggtgcactgc gtgaacgtca ggcacgttgg     660
ccgagccgtt atgaacgtct gtttgcagaa attggtcgtg ttagcagcga aggtgcaaaa     720
gcagttgcag ccggtgatct ggaagcactg ggtgatgcaa tgaatgttaa tcagggtctg     780
ctggcagccc tgggtctgag cagccctccg ctggaagaaa tggtttatcg tctgcgcgaa     840
ctgggtgccc tgggtgcaaa actgacaggt gccggtggtg atggtggtgc agttattggt     900
ctgtttctgg aaccgaaacc ggttgttacc aaactgaccc gtatgggtgt tcgttgtttt     960
agctcacagc tggctggtcc gcgtgcaagc taagtcgacg tcgac                    1005
```

<210> SEQ ID NO 33
<211> LENGTH: 1233
<212> TYPE: DNA
<213> ORGANISM: Artificial Sequence
<220> FEATURE:
<223> OTHER INFORMATION: 328_pJL1-(CAT7aa)-MK_Bmo

<400> SEQUENCE: 33

```
tctagaaata attttgttta actttaagaa ggagatatac atatgcatat ggagaaaaaa      60
atcgaagttc gtgcccgtgc accgggtaaa atcattctgg caggcgaaca tgcagttgtt     120
catggtagca ccgcagttgc agcagcaatt gatctgtata cctatatcag cctgcatttt     180
ccgacaccgg cagaaaatga tgatgcactg aaactgcatc tgaaagatat gggcttagaa     240
tttagctggc ctgtgggtcg tattaaagat gttctgccgg aagttagcag ccatgatgtg     300
agcagcccga gcagctgtag cctggaaacc ctgaaagcaa ttgcagcact ggttgaagaa     360
cagaatattc cggaagcaaa tgttggtctg gcaagcggtg ttagcacctt tctgtggatg     420
tatagcagca ttcatggtta caaaccggca aaagttgttg ttaccagcga actgccgtta     480
ggtagcggtc tgggtagcag cgcagcattt tgtgttagcc tgagcgcagc actgctggca     540
ctgagcgata gcgttaaact ggattttagc aatcaaggct ggcagatgtt tgcagaaacc     600
gaactggaac tggtgaataa atgggcattt gaaggcgaaa aaatcatcca tggtaaaccg     660
agcggtattg ataatacagt gagcacctat ggcaacatga tcaaattcaa aagcggtgaa     720
atggtgcgca tcaaaaccaa tatgccgctg aaaatgctga tcaccaatac caaagttggc     780
cgtaatacaa aagccctggt tgcgggtgtt agcgaacgta ccgttcgtca tagcaatgca     840
atgagcagcg tttttaatgc cgttgattgc attagcaatg aactggcagc aattattcag     900
```

```
agtccggtta gtgatgatct ggccattacc gaaaaagaag aaaaactggg cgaactgatg    960

gaaatgaatc agggtctgct gcagtgtatg ggtgtgagcc atgcaagcat tgaaaccgtt   1020

attcgtacca cgctgaaata caaactggca accaaactga ccggtgccgg tggtggtggt   1080

tgtgttctga gcctgctgcc gacactgctg agcggcaccg ttgttgatat tgttattagt   1140

gaactggaag cctgtggttt tcagtgtctg attgcaggta ttggcggtaa tggtgttgaa   1200

attagcttta gcccgagcta agtcgacgtc gac                                1233
```

<210> SEQ ID NO 34
<211> LENGTH: 1456
<212> TYPE: DNA
<213> ORGANISM: Artificial Sequence
<220> FEATURE:
<223> OTHER INFORMATION: 282_pJL1-(CAT5aa)-PMK1_Sce

<400> SEQUENCE: 34

```
tctagaaata attttgttta actttaagaa ggagatatac atatggagaa aaaaatcagt     60

gagttgcgcg cattctcggc accgggaaaa gctttattag cgggcgggta tttagtgttg    120

gatacgaaat atgaagcctt tgtcgtcggg ttatcagccc gcatgcatgc ggtcgcacat    180

ccatacggct ctttacaggg aagcgataag tttgaagtcc gggtcaaatc taaacagttt    240

aaagatggag agtggcttta ccatatcagt ccaaaaagtg ggttcatccc agtgtcaatc    300

ggtgggagca agaatccatt catcgaaaaa gtgatcgcga atgtcttttc atactttaaa    360

ccaaatatgg acgactactg taaccgcaat ttattcgtga tcgatatctt cagcgatgat    420

gcataccata gccaagagga ttcagtgact gaacatcggg ggaatcgccg cttgtctttt    480

cattcacacc gcatcgaaga agtgcctaaa acgggacttg ggtcgtcagc cggcttggtc    540

acggtgttga cgacggcgtt agcatccttt tttgtctcag acctcgaaaa caacgtcgac    600

aaatatcgcg aagtgatcca taacttggcc caggtggcgc attgccaggc gcaaggcaaa    660

atcgggtcag gatttgatgt cgctgctgcc gcctatggga gcatccgcta tcgccgcttc    720

ccgcctgcct tgatcagcaa cttgccggat atcgggtcgg cgacgtacgg gtctaaactt    780

gctcatttag tggatgaaga agactggaac atcacaatca aatcgaatca tttaccatca    840

gggttgacgt tatggatggg ggatatcaag aacggcagtg aaacggtcaa acttgtccaa    900

aaggtcaaaa actggtatga ttcacatatg ccggaatcat taaaaatcta tacggaacta    960

gatcatgcca acagccgctt tatggatggg ttgagcaaat tagatcgatt gcacgagacg   1020

catgacgatt actcagatca aatctttgag agcttggagc ggaacgactg cacttgccag   1080

aagtatccag aaatcacgga agtgcgcgat gccgtggcaa cgatccgccg gtcgtttcgc   1140

aaaatcacga aagaaagcgg cgcagatatc gaaccacctg tccagacgtc attattggat   1200

gattgtcaaa ctttgaaagg ggtgttgacg tgtttgatcc caggcgcggg cggctatgac   1260

gcaatcgccg tcatcacgaa gcaggatgtg gatttgcggg cgcagactgc gaacgacaaa   1320

cgctttagca aggtgcagtg gctcgatgtc acgcaagcgg actggggcgt gcggaaagaa   1380

aaagatcccg aaacgtattt ggataaatga ggatcctgac tcgagcacca ccaccaccac   1440

cactgagatc gtcgac                                                   1456
```

<210> SEQ ID NO 35
<211> LENGTH: 1149
<212> TYPE: DNA
<213> ORGANISM: Artificial Sequence
<220> FEATURE:
<223> OTHER INFORMATION: 329_pJL1-(CAT7aa)-PMK_Sau

<400> SEQUENCE: 35
tctagaaata attttgttta actttaagaa ggagatatac atatgcatat ggagaaaaaa 60
atcatccagg ttaaagcacc gggtaaactg tatattgccg gtgaatatgc agttaccgaa 120
ccgggttata aaagcgttct gattgcactg gatcgttttg ttaccgcaac cattgaagaa 180
gccgatcagt ataaaggcac cattcatagc aaagccctgc atcacaatcc ggttaccttt 240
agccgtgatg aagatagcat tgttattagc gatccgcatg cagcaaaaca gctgaattat 300
gttgtgaccg ccatcgaaat ctttgagcag tatgcaaaaa gctgcgacat tgccatgaaa 360
cattttcatc tgaccatcga tagcaacctg gatgatagca atggtcataa atatggtctg 420
ggtagcagcg cagcagttct ggttagcgtt attaaagtgc tgaacgagtt ctacgatatg 480
aaactgagca acctgtacat ctataaactg gccgttattg ccaacatgaa actgcagagc 540
ctgagcagct gtggtgatat tgcagttagc gtttatagcg gttggctggc atatagcacc 600
tttgatcatg aatgggtgaa acaccagatt gaagatacca ccgttgaaga agtgctgatt 660
aaaaactggc ctggtctgca tattgaaccg ctgcaggcac cggaaaatat ggaagttctg 720
atcggttgga ccggtagtcc ggcaagcagt ccgcattttg ttagcgaagt taaacgtctg 780
aaaagcgatc cgagctttta tggtgatttt ctggaagata gccatcggtg tgttgaaaaa 840
ctgatccatg cctttaaaac caacaacatt aaaggcgtgc agaaaatggt tcgtcagaat 900
cgtaccatta ttcagcgcat ggataaagaa gcaaccgttg atattgaaac cgagaaactg 960
aaatacctgt gcgatattgc cgaaaaatat catggtgcaa gcaaaaccag cggtgccggt 1020
ggtggtgatt gtggtattac cattatcaac aaagatgtgg acaaagagaa aatctacgac 1080
gaatggacca aacatggtat caaaccgctg aaattcaaca tctatcatgg ccagtaagtc 1140
gacgtcgac 1149

<210> SEQ ID NO 36
<211> LENGTH: 1080
<212> TYPE: DNA
<213> ORGANISM: Artificial Sequence
<220> FEATURE:
<223> OTHER INFORMATION: 330_pJL1-(CAT7aa)-PMK_Spn

<400> SEQUENCE: 36
tctagaaata attttgttta actttaagaa ggagatatac atatgcatat ggagaaaaaa 60
atcattgccg ttaaaacctg cggtaaactg tattgggcag gcgaatatgc aattctggaa 120
ccgggtcagc tggcactgat taaagatatt ccgatttata tgcgtgccga aatcgcattt 180
agcgatagct accgtattta tagcgatatg tttgattttg ccgttgacct gcgtccgaat 240
cctgattata gcctgattca agaaaccatt gcactgatgg gtgattttct ggcagttcgt 300
ggtcagaatc tgcgtccgtt tagcctggcc atttatggta aaatggaacg cgaaggcaaa 360
aaattcggtc tgggtagcag cggtagcgtt gttgttctgg ttgttaaagc actgctggcc 420
ctgtataatc tgagcgttga tcagaacctg ctgtttaaac tgaccagcgc agttctgctg 480
aaacgtggtg ataatggtag catgggtgat ctggcatgta ttgcagcaga ggatctggtt 540
ctgtatcaga gctttgatcg tcagaaagtt gcagcatggc tggaagaaga aaatctggca 600
accgttctgg aacgtgattg ggttttagc attagccagg ttaaaccgac actggaatgt 660
gactttctgg ttggttggac caaagaagtt gcagttagca gccacatggt tcagcagatt 720
aaacagaata ttaaccagaa cttcctgacc agcagcaaag aaaccgttgt tagcctggtt 780

-continued gaagcactgg aacagggtaa aagcgaaaaa atcattgaac aggttgaagt ggcaagcaaa 840
ctgctggaag gtctgagcac cgatatctat acaccgctgc tgcgtcagct gaaagaagca 900
agccaggatc tgcaggcagt tgcaaaaagc agtggtgccg gtggtggtga ttgtggtatt 960
gcactgtcat ttgatgcaca gagcaccaaa acactgaaaa atcgttgggc tgatctgggt 1020
attgaactgc tgtatcaaga acgtattggc cacgatgata aaagctaagt cgacgtcgac 1080

<210> SEQ ID NO 37
<211> LENGTH: 1179
<212> TYPE: DNA
<213> ORGANISM: Artificial Sequence
<220> FEATURE:
<223> OTHER INFORMATION: 331_pJL1-(CAT7aa)-PMK_Efa

<400> SEQUENCE: 37
tctagaaata attttgttta actttaagaa ggagatatac atatgcatat ggagaaaaaa 60
atcatcgaag ttaccacacc gggtaaactg tttattgccg gtgaatatgc agttgttgaa 120
ccgggtcatc cggcaattat tgttgcagtt gatcagtttg ttaccgtgac cgttgaagaa 180
accaccgatg aaggtagcat tcagagcgca cagtatagca gcctgccgat tcgttggacc 240
cgtcgtaatg gtgaactggt tctggatatt cgtgaaaacc cgtttcatta tgttctggca 300
gcaattcatc tgaccgaaaa atatgcacaa gagcagaata aagagctgag cttctatcat 360
ctgaaagtta ccagcgaact ggatagcagc aatggtcgta aatatggtct gggtagcagc 420
ggtgcagtta ccgttggcac cgttaaagca ctgaatatct tttatgatct gggccttgaa 480
aacgaggaaa tctttaaact gagcgcactg gcacatctgg cagttcaagg taatggtagc 540
tgtggtgata ttgcagcaag ctgttatggt ggttggattg catttagcac ctttgatcat 600
gattgggtga atcagaaagt tgcaaccgaa acactgaccg atctgctggc aatggattgg 660
cctgaactga tgatttttcc gctgaaagtt ccgaaacagc tgcgtctgct gattggctgg 720
accggtagtc cggcaagcac cagcgatctg gttgatcgtg ttcatcagag caaagaagaa 780
aaacaggcag cctatgaaca gttcctgatg aaaagccgtc tgtgtgttga aaccatgatc 840
aatggcttta acaccggtaa aattagcgtg attcagaagc agattaccaa aaatcgtcag 900
ctgctggcag aactgagcag cctgaccggt gttgttattg aaaccgaagc gctgaaaaat 960
ctgtgtgatc tggcagaaag ctataccggt gcagcaaaaa gcagtggtgc cggtggtggt 1020
gattgtggta ttgtgatttt tcgccagaaa agcggtattc tgccgctgat gaccgcatgg 1080
gaaaaagatg gtattacacc gctgccgctg catgtttata cctatggtca gaaagaatgc 1140
aaagagaaac acgaaagcaa acgttaagtc gacgtcgac 1179

<210> SEQ ID NO 38
<211> LENGTH: 990
<212> TYPE: DNA
<213> ORGANISM: Artificial Sequence
<220> FEATURE:
<223> OTHER INFORMATION: 332_pJL1-(CAT7aa)-PMK_Pze

<400> SEQUENCE: 38
tctagaaata attttgttta actttaagaa ggagatatac atatgcatat ggagaaaaaa 60
atcgatcagg ttattcgtgc aagcgcaccg ggtagcgtta tgattaccgg tgaacatgca 120
gttgtttatg gtcatcgtgc aattgttgca ggtattgaac agcgtgcaca tgttaccatt 180
gttccgcgtg cagatcgtat gtttcgtatt accagccaga ttggtgcacc gcagcagggt 240
agcctggatg atctgcctgc cggtggcacc tatcgttttg ttctggcagc aattgcccgt 300

```
catgcaccgg atctgccgtg tggttttgat atggatatta ccagtggtat tgatccgcgt    360
ttaggtctgg gtagcagcgc agcagttacc gttgcatgtc tgggtgcact gagccgtctg    420
gcaggtcgtg gcaccgaagg tctgcatgat gatgcactgc gtattgttcg tgccattcaa    480
ggtcgtggta gcggtgccga tctggcagcc agcctgcatg gtggttttgt tgcatatcgc    540
gcaccggatg gtggtgcagc acagattgaa gcactgccgg ttccgcctgg tccgtttggt    600
ctgcgttatg caggttataa aaccccgacc gcagaagtgc tgcgtctggt tgccgatcgt    660
atggcaggta atgaagcagc atttgatgcc ctgtatagcc gtatgggtgc cagcgcagat    720
gcagcaattc gtgcagccca aggtctggat tgggcagcat ttcatgatgc gctgaatgaa    780
tatcagcgtc tgatggaaca gctgggtgtt agtgatgata ccctggatgc aattattcgc    840
gaagcacgtg atgccggtgc agcagttgca aaaatttcag gtagcggtct gggtgattgt    900
gttctggccc tgggtgatca gccgaaaggc tttgttccgg caagcattgc agaaaaaggt    960
ctggtttttg atgattaagt cgacgtcgac                                      990
```

<210> SEQ ID NO 39
<211> LENGTH: 1164
<212> TYPE: DNA
<213> ORGANISM: Artificial Sequence
<220> FEATURE:
<223> OTHER INFORMATION: 333_pJL1-(CAT7aa)-PMK_Tha

<400> SEQUENCE: 39

```
tctagaaata attttgttta actttaagaa ggagatatac atatgcatat ggagaaaaaa     60
atcatcgaag ttagcacacc gggtaaactg tatattgccg gtgaatatgc agttgttgaa    120
ccgggtcatc tggcaattat tgcagcagtt gatcagttta tcaacgtgac cattgaaagc    180
gcaaccgaaa atggtagcat tcagagccag cagtatagcg atctgccgat tcgttggacc    240
cgtcgtgaag gtgaactggt tctggatcat cgtgaaaatc cgtttcatta tattctggca    300
gcaattcgtc tgaccgaacg ttatgcaaaa gaacagggca ccctgctgag cttttatcat    360
ctgaaagtta ccagcgaact ggataatagc agcggtcgta aatatggtct gggtagcagt    420
ggtgcagtta ccgttggcac cgttaaagca ctgaacctgt tttatgatct gcaaatggac    480
ccgctgatgc agtttaaaat cgcagcactg gcacatctgg cagttcaagg taatggtagc    540
tgtggtgata ttgcagccag ctgttttggt ggttggctgg catttagcac ctttgatcat    600
cagtgggtta aaaaacgtca agaaacctgg aaaatcagcg acctgctgaa aagcgattgg    660
ccgaaactga gcattcagcc gctgcagagc ccgaaaaata tgcgtctgct gattggctgg    720
accggtagtc cggcaagcac cagcgatctg gttgatcagg ttaatcagag caaagaggat    780
aaagacgaca tccagaaaaa ctatgaacag tttctgaccg atagccatca ttgtgttgag    840
gatctgatgg atggtttcgt taaagatgat gtgaccaaaa tcaagaaaat gatccgcaaa    900
aatcgtaccc tgctgcagaa tctggcaaaa gcaaccaatg ttgttattga aacaccggca    960
ctgaaacagc tgtgtgatct ggcagaaaat tgtggtggtg cagcaaaaag cagcggtgcc   1020
ggtggtggtg attgtggtat tgttattgcc gatcagaaaa ccggtatcct gccgctgatg   1080
agcaaatggg aaaaagcaga tattattccg ctgccgctgc atgtttatca ttatcgtggt   1140
ggtccgaaat aagtcgacgt cgac                                          1164
```

<210> SEQ ID NO 40
<211> LENGTH: 1188
<212> TYPE: DNA

<213> ORGANISM: Artificial Sequence
<220> FEATURE:
<223> OTHER INFORMATION: 334_pJL1-(CAT7aa)-PMK_Eco

<400> SEQUENCE: 40
tctagaaata attttgttta actttaagaa ggagatatac atatgcatat ggagaaaaaa 60
atcctgaaga aaatcaaaca tgatccgacg ctgaatagcc aaggtcaggg ttttgcaccg 120
ggtaaactgt atctggcagg cgaatatgca gttctggcac cgcgtcagcc tgcaattctg 180
ctggcactga atcgttatgt taaagtgacc attaaaccga gcagcaccct gaatcagggc 240
attctgagcc aggcaaaagg tcaggcagat tatcattatc agcgtcagaa tggtagcatt 300
ccgcagaaag aagcatattg gacctattgt ctggcagcca ttcagattgt tgaagttctg 360
tttcgtcaga aaggccaggt tattgccgat tatcatctgg aaaccatgag cgatctggtt 420
gaagaagtta gcggcaaaaa attcggtctg ggtagcagcg gtgcaattac cgttgcaacc 480
attcgtgcac tgctggattt ttatggttat caggccgata gtccgctgga tgtgtataaa 540
ctggccgttc tggccctggt taatctgggt aataatggta gctttggtga tctggcagca 600
gcagcatttg gtggttgggt ttattatcag gcaccggatc gtcagtggct ggcagatcag 660
gttagccaga atcagaccat tgatttcttt ctggaaaata gctggccgaa cctgcagatt 720
gaaagcctgc cggttccgag caaaattgat ttcctggttg catggaccca gagtccggca 780
agcagcgatc attttgttgc aaactttaaa gaagccagcc agcaagaacc gcagcgttat 840
caagaatttc tggccgaaaa taaagatgca gtgctggccc tgaaaaccgc actgatccag 900
gatgatgttg gtcagagcca gagcctgatt aacaaaattg gtcagcagct ggataatctg 960
agccatcatc tgaaactggg tattctgaca ccgcagctgg aaacaatgat tagcctggca 1020
caggtgtatg gttatgcagc aaaaaagcagt ggtgccggtg gtggtgattg tggtattgca 1080
ttaggtggtc tggaagcacg taaaaccgat ctgattcgtg catgggaaaa acaagaaatc 1140
acctatctgg atctgcaaat cagccagacc ttttaagtcg acgtcgac 1188

<210> SEQ ID NO 41
<211> LENGTH: 1291
<212> TYPE: DNA
<213> ORGANISM: Artificial Sequence
<220> FEATURE:
<223> OTHER INFORMATION: 283_pJL1-(CAT5aa)-PMD1_Sce

<400> SEQUENCE: 41
tctagaaata attttgttta actttaagaa ggagatatac atatggagaa aaaaatcact 60
gtgtacacgg cctctgtgac tgcccctgtc aatatcgcca ctttgaagta ttggggaaaa 120
cgggacacaa agttgaacct tcctactaac tcatctatct cggtcacgtt atcacaggat 180
gacctacgca cattaactag cgctgcgacg gccccagagt ttgaacgaga cacgttatgg 240
ttaaacgggg aaccgcactc aatcgacaac gaacgcacgc agaactgcct tcgagacttg 300
cgacagttac gcaaggaaat ggaatcaaag gacgcaagtt tgcctacgtt aagccagtgg 360
aaactacaca tcgtctccga aaacaatttt ccaacggccg cgggcttggc gtcttctgcg 420
gcggggtttg cggccttggt cagcgccatc gcgaagttgt accagttgcc gcaatccacg 480
tccgaaatca gccgcatcgc ccgcaaggga agcggctctg cgtgccgctc attgtttggt 540
gggtacgtcg catgggaaat ggggaaagcg gaagatggcc atgattccat ggccgtccag 600
atcgccgact caagcgactg gccacaaatg aaagcgtgcg tcttagtggt ttcagatatc 660
aaaaaggatg tctcctctac gcaaggcatg cagttgactg tcgccacttc tgaattattt 720

```
aaagaacgca tcgaacatgt cgtcccgaag cgctttgaag tcatgcggaa agcaatcgtg    780

gaaaaagatt tcgcaacttt tgccaaggaa acgatgatgg attctaatag cttccatgca    840

acgtgcttag acagcttccc accgatcttc tacatgaacg acacgagtaa gcggatcatc    900

tcttggtgtc acactatcaa ccaattttac ggggaaacga tcgtggccta cacatttgat    960

gccggcccga acgcggtctt atactactta gcggaaaacg agtcaaaact atttgccttt   1020

atctataaat tatttgggag cgtgccaggg tgggacaaga aatttacgac ggagcaattg   1080

gaggcgttca atcatcagtt tgaatcgagc aattttacgg cccgggaatt ggatttagag   1140

ttacagaagg atgtggcacg cgtcatcttg acgcaggtcg gctccgggcc gcaggaaacg   1200

aatgaaagct taatcgacgc caagacgggc ttgccgaagg aataaggatc ctgactcgag   1260

caccaccacc accaccactg agatcgtcga c                                  1291
```

<210> SEQ ID NO 42
<211> LENGTH: 1056
<212> TYPE: DNA
<213> ORGANISM: Artificial Sequence
<220> FEATURE:
<223> OTHER INFORMATION: 335_pJL1-(CAT7aa)-PMD_Sau

<400> SEQUENCE: 42

```
tctagaaata attttgttta actttaagaa ggagatatac atatgcatat ggagaaaaaa     60

atcatcaaaa gcggtaaagc acgtgcccat accaatattg cactgatcaa atattggggc    120

aaaaaagatg aagccctgat tattccgatg aacaatagca ttagcgttac cctggaaaag    180

ttctacaccg aaaccaaagt gacctttaat gatcagctga cccaggatca gttttggctg    240

aatggtgaaa aagttagcgg caaagaactg gaaaaaatca gcaaatatat ggatatcgtg    300

cgtaatcgtg caggcattga ttggtatgca gaaattgaaa gcgataactt tgttccgacc    360

gcagcaggtc tggcaagcag cgcaagcgcc tatgcagcac tggcagcagc atgtaatcag    420

gcactggata tgcagctgag cgataaagac ctgagccgtc tggcacgtat tggtagcggt    480

agcgcaagcc gtagcattta tggtggtttt gcagaatggg agaaaggtta tagtgatgaa    540

accagctatg cagttccgct ggaaagcaat cattttgaag atgatctggc catgatcttc    600

gttgtgatta accagcatag caaaaaagtt ccgagccgtt atggtatgag tctgacccgt    660

aataccagcc gtttttatca gtactggctg gatcatattg atgaggacct ggcagaagca    720

aaagcagcaa ttcaggataa agatttcaaa cgtctgggcg aagtgattga agaaaatggt    780

ctgcgtatgc atgcaaccaa tctgggtagc accccctccgt ttacctatct ggttcaagaa    840

agctatgacg ttatggcact ggttcatgaa tgtcgtgaag caggttatcc gtgttatttt    900

accatggatg caggtccgaa tgtgaaaatt ctggtggaaa aaaagaacaa acagcagatc    960

atcgataaac tgctgacgca gtttgataac aaccagatta ttgacagcga tatcattgcc   1020

accggcattg aaattatcga ataagtcgac gtcgac                             1056
```

<210> SEQ ID NO 43
<211> LENGTH: 1026
<212> TYPE: DNA
<213> ORGANISM: Artificial Sequence
<220> FEATURE:
<223> OTHER INFORMATION: 336_pJL1-(CAT7aa)-PMD_Spn

<400> SEQUENCE: 43

```
tctagaaata attttgttta actttaagaa ggagatatac atatgcatat ggagaaaaaa     60
```

```
atcgatcgtg aaccggttac cgttcgtagc tatgcaaata ttgccatcat caaatactgg    120
ggcaaaaaga aagaaaaaga gatggttccg gcaaccagca gcattagtct gaccctggaa    180
aatatgtata ccgaaaccac actgagtccg ctgcctgcaa atgttaccgc agatgaattt    240
tacattaatg gccagctgca gaacgaagtt gaacatgcaa aaatgagcaa aatcatcgat    300
cgttatcgtc cggcaggcga aggttttgtt cgtattgata cccagaataa tatgccgacc    360
gcagcaggtc tgagcagcag cagtagcggt ctgagcgcac tgattaaagc atgtaatgcc    420
tatttcaaac tgggcttaga tcgtagtcag ctggcacaag aagcaaaatt tgcaagcggt    480
agcagcagcc gttcatttta tggtccgtta ggtgcatggg ataaagatag cggtgaaatt    540
tatccggttg aaaccgatct gaaactggca atgattatgc tggttctgga agataagaaa    600
aaaccgatta gcagccgtga tggtatgaaa ctgtgtgttg aaaccagcac cacctttgat    660
gattgggttc gtcagagcga aaaagattat caggatatgc tgatctatct gaaagagaac    720
gatttcgcca aaattggtga actgaccgaa aaaaatgccc tggcaatgca tgcaaccacc    780
aaaaccgcaa gtccggcatt tagctatctg accgatgcaa gctatgaagc aatggcattt    840
gttcgtcagc tgcgtgaaaa aggtgaagca tgttatttta ccatggatgc aggtccgaat    900
gtgaaagttt tttgccaaga aaaggatctg gaacacctga gcgaaatttt tggtcagcgt    960
tatcgcctga ttgttagcaa aaccaaagac ctgagccagg atgattgttg ttaagtcgac   1020
gtcgac                                                              1026
```

<210> SEQ ID NO 44
<211> LENGTH: 1338
<212> TYPE: DNA
<213> ORGANISM: Artificial Sequence
<220> FEATURE:
<223> OTHER INFORMATION: 337_pJL1-(CAT7aa)-PMD_Pku

<400> SEQUENCE: 44

```
tctagaaata attttgttta actttaagaa ggagatatac atatgcatat ggagaaaaaa     60
atcgccaatg cagaaaaatg ggttctgacc gttaccgcac agaccccgac caatattgca    120
gttatcaaat attggggtaa aggcgacgag gatctgattc tgccgattaa tgatagcatt    180
agcgttacct tagatccgga ccatctgtgt accaccacca gtgttgcagt tagtccggca    240
tttacccatg atcgtatgtg gctgaatggt aaagaagtta gcctgtcagg cggtcgtttt    300
cagaattgtc tgcgtgaagt tcgtagctgt gcaaatgatg ttgaagatga aaaagaaggc    360
gttctgaaaa gcctgaaagg tctgggtgat ctgcatgttc acatgtgtcc gaccattgat    420
tttccgaccg cagcaggtct ggcaagcagc gcagctggcc tggcatgtct ggtttttagc    480
ctggcaaaac tgatgaacgt gaaagaagat catagccgtc tgagcgcaat tgcacgtcaa    540
ggtagcggta gcgcatgtcg tagcctgtat ggtggttttg ttaatggtag ctttctgaaa    600
gaggaaaacg gtagcgatag cattgcagtt cagctggccg atgaaaaaca ttgggatgat    660
ctggttatta tcattgccgt tgttagcagc cgtcagaaag aaaccagcag caccagcggt    720
atgcgtgaaa ccgttgaaac cagtatgctg ctgcaacatc gtgcaaaaga agttgtgccg    780
gaacgtatta ttcagatgga agaggccatt aaaaaccgcg attttccagc atttgcacgt    840
ctgacctgtg cagatagcaa tcagtttcat gcagtttgtc tggataccct gcctccgatc    900
ttttatatga atgataccag ccatcgtatc atcagctgtg tggaaaaatg gaattgtagc    960
gaaggtacac cgcaggttgc atataccttt gatgcaggtc cgaaatgccg tattaacttt   1020
acccagaccg aaaaactgct gccgaatttt ttcaaaggtt gcagctttca ttttccgcct   1080
```

aatagcgata ccgatctgaa tagctatgtt attggtgatc agaccattct gcaggatgca 1140
ggtattaaag acctgaaaga tattgaagca ctgagcaccc ctccggaaac caaagaaaat 1200
ctgagtgcac agaaatatcg tggtgatgtg agctatttta tctgcaccaa acctggtcgt 1260
ggtccggcag ttgttaatga tgaaagccgt agcctgatta atccggaatt tggtctgccg 1320
aaataagtcg acgtcgac 1338

<210> SEQ ID NO 45
<211> LENGTH: 1071
<212> TYPE: DNA
<213> ORGANISM: Artificial Sequence
<220> FEATURE:
<223> OTHER INFORMATION: 338_pJL1-(CAT7aa)-PMD_Pze

<400> SEQUENCE: 45
tctagaaata attttgttta actttaagaa ggagatatac atatgcatat ggagaaaaaa 60
atcaccgatg cagttcgtga catgattgcc cgtgcaatgg caggcgcaac cgatattcgt 120
gcagccgaag cctatgcacc gagtaatatt gcactgagca aatattgggg taaacgtgat 180
gcagcacgta atctgccgct gaatagcagc gttagcatta gcctggcaaa ttggggtagt 240
catacccgtg ttgaaggtag cggcaccggt catgatgaag tgcatcataa tggcaccctg 300
ttagatccgg gtgatgcatt tgcacgtcgt gcactggcat ttgcagacct gtttcgtggt 360
ggtcgtcatc tgcctctgcg tattaccaca cagaatagca ttccgaccgc agcaggtctg 420
gcaagcagcg caagcggttt tgcagcactg acccgtgcat tagccggtgc atttggtctg 480
gatctggatg ataccgatct gagccgtatt gcacgtattg gtagcggtag cgcagcccgt 540
agcatttggc atggttttgt tcgttggaat cgtggtgaag ccgaagatgg tcatgatagc 600
catggtgttc cgctggatct gcgttggcct ggttttcgta ttgcaattgt tgcagttgat 660
aaaggtccga aaccgtttag cagccgtgat ggcatgaatc ataccgttga aaccagtccg 720
ctgtttccgc cttggcctgc acaggccgaa gcagattgtc gtgttattga agatgcaatt 780
gccgcacgtg atatggcagc actgggtccg cgtgtggaag caaatgccct ggcaatgcat 840
gcaaccatga tggcagcccg tccgcctctg tgttatctga ccggtggtag ctggcaggtt 900
ctggaacgtc tgtggcaggc acgtgcagat ggtctggcag catttgccac catggatgca 960
ggtccgaatg ttaaactgat ttttgaagaa agcagtgccg cagatgttct gtacctgttt 1020
ccggatgcaa gcctgattgc accgtttgaa ggtcgttaag tcgacgtcga c 1071

<210> SEQ ID NO 46
<211> LENGTH: 1047
<212> TYPE: DNA
<213> ORGANISM: Artificial Sequence
<220> FEATURE:
<223> OTHER INFORMATION: 339_pJL1-(CAT7aa)-PMD_Hme

<400> SEQUENCE: 46
tctagaaata attttgttta actttaagaa ggagatatac atatgcatat ggagaaaaaa 60
atcaaagcaa ccgcaaaagc acatccgatt caaggtctgg ttaaatatca tggtatgcgc 120
gatccggaaa ttcgtctgcc gtatcatgat tcaattagcg tttgtaccgc accgagccat 180
accaaaacca ccgttgaatt tctgccggat gcagatgaag atgtttatgt tattggtggt 240
gaagaggttg aaggtcgtgg tgcagaacgt attcgtgatg ttgttgaaca tgtgcgtgat 300
ctggcagatt ttgatcatcg tgttcgtctg gaaagcgaaa atagctttcc gagcaatatt 360

-continued

```
ggttttggca gcagcagctc aggttttgcc gcagccgcaa tggcactggc agaagcagcc    420

gatctggatc tgacccgtcc ggaaatcagc accattgcac gtcgtggtag cagcagcgca    480

gcacgtgcag ttaccggtgc atttagccat ctgtatagcg gtatgaatga taccgattgt    540

cgtagcgaac gtattgaaac ggatctggaa gatgatctgc gtattgttgc agcccatgtt    600

ccggcatata aagaaaccga acaggcacat gcagaagccg cagatagcca catgtttcag    660

gcacgtatgg cacacatgca taagcagatt gatgatatgc gtgatgcact gtatgaagcc    720

gattttgatg cagcatttga actggccgaa catgatagcc tgagcctggc agcaaccacc    780

atgaccggtc cggcaggttg ggtttattgg cagcctcgta ccattgcagt ttttaatgca    840

attcgtgaac tgcgtgccga agaagatatt cctgcatatt ttagcaccga taccggtgcc    900

agcgtttata tcaataccac caccgaatat gttgaccgtg ttgaaaaagt tgttgccgat    960

tgtaatgttg aaaccgatgt ttgggaagtt ggtggtcctg ccgaaattct ggatgaaagt   1020

gatgccctgt tttaagtcga cgtcgac                                       1047
```

<210> SEQ ID NO 47
<211> LENGTH: 1158
<212> TYPE: DNA
<213> ORGANISM: Artificial Sequence
<220> FEATURE:
<223> OTHER INFORMATION: 340_pJL1-(CAT7aa)-PMD_Zga

<400> SEQUENCE: 47

```
tctagaaata attttgttta actttaagaa ggagatatac atatgcatat ggagaaaaaa     60

atcaccgtga aagaatttat cccgagtccg tataccaaac cggttgcaag cggtaatacc    120

cgttataaaa gcccgagtaa tattgccctg gtgaaatatt ggggcaaaaa agaaaatcag    180

attccggcaa atccgagcat tagctttacc ctgaatgaat gtgcaaccgt taccacactg    240

agctatcgta aagcagatcg tccgaatgat gcatttagct ttgaaattag cctggacggc    300

aagaaagaag aaggttttaa accgaaaatc aaaacctttt tcgaacgcgt gtatccgtat    360

ctgccgtttc tgaaagaata tcactttgag attgaaacca gcaacagctt tccgcatagc    420

agcggtattg caagcagcgc cagcggtatg agcgcactgg cactgtgtct gatggaaatt    480

gaacgtaatt tagatccggg tatgagtgcc gatttttttca accgtaaagc aagctttctg    540

gcacgtttag gtagcggtag cgcagcacgt agcattaaag gtagcctggt tcagtggggt    600

gaacatgcag gcaccgaagg tagcagcgat ctgtatggta ttgaatatcc gtataaagtg    660

cacagcgtgt tcaacgatta ttgcgatacc attctgctgg ttgataaagg tcagaaacag    720

gttagcagca ccgttggtca tgatctgatg cataatcatc cgtttagcaa acagcgtttt    780

gatcaggcac atgaaaatct gagcaaactg cgtagcattt ttgaaagcgg caatctggat    840

gaatttattg gtctggttga aagcgaagca ctgaccctgc atgcaatgat gatgaccagc    900

cgtccgtatt ttatcctgat gaaaccgaat acgctggaaa ttatcaatcg catttgggca    960

tatcgtgaag ccaccaaaac acatgtttgt tttaccctgg atgccggtgc aaatgttcat   1020

gttctgtatc cgaaaaatga aaaggcactg gtggaacgtt ttattgcaga tgaactggca   1080

ggttattgtc agaatggtca gtttattcat gatcatgttg gtcgtggtgc ccgtaaaatc   1140

aattaagtcg acgtcgac                                                 1158
```

<210> SEQ ID NO 48
<211> LENGTH: 649
<212> TYPE: DNA
<213> ORGANISM: Artificial Sequence
<220> FEATURE:
<223> OTHER INFORMATION: 284_pJL1-(CAT5aa)-IDI_Eco

<400> SEQUENCE: 48

```
tctagaaata attttgttta actttaagaa ggagatatac atatggagaa aaaaatccaa      60

acggaacacg tcattttatt gaatgcacag ggagttccca cgggtacgct ggaaaagtat     120

gccgcacaca cggcagacac ccgcttacat ctcgcgttct ccagttggct gtttaatgcc     180

aaaggacaat tattagttac ccgccgcgca ctgagcaaaa aagcatggcc tggcgtgtgg     240

actaactcgg tttgtgggca cccacaactg ggagaaagca acgaagacgc agtgatccgc     300

cgttgccgtt atgagcttgg cgtggaaatt acgcctcctg aatctatcta tcctgacttt     360

cgctaccgcg ccaccgatcc gagtggcatt gtggaaaatg aagtgtgtcc ggtatttgcc     420

gcacgcacca ctagtgcgtt acagatcaat gatgatgaag tgatggatta tcaatggtgt     480

gatttagcag atgtattaca cggtattgat gccacgccgt gggcgttcag tccgtggatg     540

gtgatgcagg cgacaaatcg cgaagccaga aaacgattat ctgcatttac ccagcttaaa     600

taaggatcct aactcgagca ccaccaccac caccactgag atcgtcgac                649
```

<210> SEQ ID NO 49
<211> LENGTH: 1150
<212> TYPE: DNA
<213> ORGANISM: Artificial Sequence
<220> FEATURE:
<223> OTHER INFORMATION: 285_pJL1-(CAT5aa)-IDI_Bsu

<400> SEQUENCE: 49

```
tctagaaata attttgttta actttaagaa ggagatatac atatggagaa aaaaatcacc      60

cgtgcagaac gtaaacgtca gcatatcaat catgcactga gcattggtca gaaacgtgaa     120

accggtctgg atgatattac ctttgttcat gttagcctgc cggatctggc actggaacag     180

gttgatatta gcaccaaaat tggtgaactg agcagcagca gcccgatttt tatcaatgca     240

atgaccggtg gtggtggtaa actgacctat gaaattaaca aaagcctggc acgtgcagca     300

agccaggcag gtattccgct ggcagttggt agccagatga gcgcactgaa agatccgtca     360

gagcgtctgt cttatgagat cgtgcggaaa gaaaatccga atggactcat ttttgcgaat     420

ttaggtagcg aggctaccgc cgcgcaggct aaagaggcgg tcgaaatgat tggcgcgaac     480

gcgctgcaga tccatctgaa cgtaattcag gagatcgtga tgccggaagg cgatcgttcg     540

tttagtggtg ccctcaagcg tattgagcag atttgttctc gcgtctcagt gccggttatc     600

gtgaaagagg taggatttgg aatgtcgaaa gcttccgcgg gtaagctgta cgaggcaggg     660

gccgctgcag ttgatattgg cggctatggg ggtacgaact tcagcaaaat tgaaaacctc     720

cgtcgccagc gccaaatctc cttcttcaac agctggggca tctctacggc tgcatcatta     780

gcagagatcc gttctgaatt tccggcaagc accatgattg caagcggtgg tctgcaggat     840

gcactggatg ttgcaaaagc aattgcactg ggtgcaagct gtaccggtat ggcaggtcat     900

tttctgaaag cactgaccga tagcggtgaa gaaggtctgc tggaagaaat tcagctgatt     960

ctggaagaac tgaaactgat tatgaccgtt ctgggtgcac gtaccattgc cgatctgcag    1020

aaagcaccgc tggttattaa aggtgaaacc catcattggc tgacagaacg tggtgttaat    1080

accagcagct atagcgttcg ttaaggatcc tgactcgagc accaccacca ccaccactga    1140

gatcgtcgac                                                           1150
```

<210> SEQ ID NO 50

<211> LENGTH: 939
<212> TYPE: DNA
<213> ORGANISM: Artificial Sequence
<220> FEATURE:
<223> OTHER INFORMATION: 341_pJL1-(CAT7aa)-IDI_Sce

<400> SEQUENCE: 50
tctagaaata attttgttta actttaagaa ggagatatac atatgcatat ggagaaaaaa 60
atcaccgcag ataataacag catgccgcat ggtgcagttt caagctatgc aaaactggtt 120
cagaatcaga caccggaaga tatcctggaa gaatttcctg aaattattcc gctgcagcag 180
cgtccgaata cacgtagcag cgaaaccagc aatgatgaaa gcggtgaaac ctgttttagc 240
ggtcatgatg aagaacaaat caagctgatg aacgaaaact gcattgttct ggattgggat 300
gataatgcaa ttggtgcagg caccaaaaaa gtttgtcatc tgatggaaaa catcgagaaa 360
ggtctgctgc atcgtgcatt tagcgtgttt atctttaatg aacagggtga actgctgctg 420
caacagcgtg caaccgaaaa aatcaccttt ccggatctgt ggaccaatac ctgttgtagc 480
catccgctgt gtattgatga tgaactgggt ctgaaaggta aactggacga taaaatcaaa 540
ggtgcaatta ccgcagccgt tcgcaaactg gatcacgaac tgggtattcc ggaagatgaa 600
accaaaacac gtggcaaatt tcattttctg aaccgcatcc attatatggc accgagcaat 660
gaaccgtggg gtgaacatga aattgattac atcctgttct acaaaatcaa cgccaaagaa 720
aacctgaccg ttaatccgaa tgttaatgaa gtgcgtgatt tcaaatgggt gagcccgaat 780
gatctgaaaa ccatgtttgc cgatccgagc tataaattca ccccgtggtt taaaatcatc 840
tgcgaaaact acctgtttaa ctggtgggaa cagctggatg atctgagcga agttgaaaat 900
gatcgtcaga ttcatcgtat gctgtaagtc gacgtcgac 939

<210> SEQ ID NO 51
<211> LENGTH: 780
<212> TYPE: DNA
<213> ORGANISM: Artificial Sequence
<220> FEATURE:
<223> OTHER INFORMATION: 342_pJL1-(CAT7aa)-IDI_Sly

<400> SEQUENCE: 51
tctagaaata attttgttta actttaagaa ggagatatac atatgcatat ggagaaaaaa 60
atcgttgatg ttattgccga tgcaaatatg gatgcagttc agcgtcgtct gatgtttgat 120
gatgaatgta ttctggtgga cgtgaacgat aaagttgttg gtcatgagag caaatataac 180
tgccacctga tggaaaaaat cgaaagcgaa aatctgctgc atcgtgcctt tagcgttttt 240
ctgtttaaca gcaaatatga gctgctgctg caacagcgta gcgcaaccaa agttaccttt 300
ccgctggttt ggaccaatac ctgttgtagc catccgctgt atcgtgaaag cgaactgatt 360
gaagaaaatg cactgggtgt tcgtaatgca gcacagcgta aactgctgga tgaactgggt 420
attccggcag aagatgttcc ggttgatcag tttacaccgc tgggtcgtat gctgtataaa 480
gcaccgagtg atggtaaatg gggtgaacat gaactggatt atctgctgtt tattgtgcgt 540
gatgttaacg ttcatccgaa tcctgatgaa gttgccgata tcaaatacgt gaatcaagaa 600
cagctgaaag aactgctgcg taaagcagat gccggtgaag aaggtctgaa actgagcccg 660
tggtttcgtc tggttgttga taattttctg ttcaaatggt gggaccatgt tgaaaaaggc 720
accattcaag aggcagcaga tatgaaaacc attcacaaac tgacctaagt cgacgtcgac 780

<210> SEQ ID NO 52
<211> LENGTH: 1164

<212> TYPE: DNA
<213> ORGANISM: Artificial Sequence
<220> FEATURE:
<223> OTHER INFORMATION: 343_pJL1-(CAT7aa)-IDI_Str

<400> SEQUENCE: 52
tctagaaata attttgttta actttaagaa ggagatatac atatgcatat ggagaaaaaa 60
atcaccagcg cacagcgtaa agatgatcat gttcgtctgg caattgaaca gcataatgca 120
catagcggtc gtaaccagtt tgatgatgtt agctttgttc atcatgcact ggcaggtatt 180
gatcgtccgg atgttagcct ggcaaccagc tttgcaggta ttagctggca ggttccgatt 240
tatatcaatg caatgaccgg tggtagcgaa aaaaccggtc tgattaatcg tgatctggca 300
accgcagcac gtgaaaccgg tgttccgatt gcaagcggta gcatgaatgc atatatcaaa 360
gatccgagct gtgcagatac ctttcgtgtt ctgcgtgatg aaaatccgaa tggttttgtg 420
attgccaata ttaacgcaac caccaccgtt gataatgccc agcgtgcaat tgatctgatt 480
gaagcaaatg cactgcagat ccatattaac accgcacaag aaaccccgat gccggaaggt 540
gatcgtagct ttgcaagctg ggttccgcag attgaaaaaa ttgcagcagc agttgatatt 600
ccggtgatcg ttaaagaagt tggtaacggt ctgagccgtc agaccattct gctgctggcc 660
gatctgggtg ttcaggcagc agatgtgagc ggtcgtggtg gcaccgattt tgcacgtatt 720
gaaaatggtc gtcgtgaact gggtgattat gcatttctgc atggttgggg tcagagcacc 780
gcagcatgtc tgctggatgc acaggatatt agcctgccgg ttctggcaag cggtggtgtt 840
cgtcatccgc tggatgttgt tcgtgcactg gccctgggtg cacgtgccgt tggtagcagc 900
gcaggttttc tgcgtaccct gatggatgat ggtgttgatg cactgattac caaactgacc 960
acctggctgg atcagctggc agccctgcag accatgctgg gagcacgtac ccctgccgat 1020
ctgacccgtt gtgatgttct gctgcatggt gaactgcgcg atttttgtgc agatcgtggt 1080
attgataccc gtcgtctggc ccagcgtagc agcagtattg aagcgctgca gacaaccggt 1140
agcacccgtt aagtcgacgt cgac 1164

<210> SEQ ID NO 53
<211> LENGTH: 1122
<212> TYPE: DNA
<213> ORGANISM: Artificial Sequence
<220> FEATURE:
<223> OTHER INFORMATION: 344_pJL1-(CAT7aa)-IDI_Pze

<400> SEQUENCE: 53
tctagaaata attttgttta actttaagaa ggagatatac atatgcatat ggagaaaaaa 60
atcaccgata gcaaagatca tcatgttgca ggtcgtaaac tggatcatct gcgtgcactg 120
gatgatgatg cagatattga tcgtggtgat agcggttttg atcgtattgc actgacccat 180
cgtgcactgc cggaagttga ttttgatgca attgataccg caaccagctt tctgggtcgt 240
gaactgagct ttccgctgct gattagcagc atgaccggtg gtacaggtga agaaattgaa 300
cgtattaatc gtaatctggc agccggtgcc gaagaggcac gtgttgcaat ggcagttggt 360
agccagcgtg ttatgtttac cgatccgagc gcacgtgcat catttgacct gcgtgcccat 420
gcaccgaccg tgccgctgct ggcaaatatt ggtgcagtgc agctgaatat gggtctgggt 480
ctgaaagaat gtctggcagc aattgaagtt ctgcaggcag atggtctgta tctgcacctg 540
aatccgctgc aagaagcagt tcagccggaa ggtgatcgtg attttgccga tctgggtagc 600
aaaattgcag ccattgcacg tgatgttccg gttccggtgc tgctgaaaga agttggctgc 660
ggtctgagcg cagccgatat tgcaattggt ctgcgtgccg gtattcgtca ttttgatgtt 720
gccggtcgcg gtggcaccag ttggagccgt attgaatatc gtcgtcgtca gcgtgcagat 780
gatgatttag gtctggtttt tcaggattgg ggactgcaga ccgttgatgc actgcgtgaa 840
gcacgtccgg cactggcagc acatgatggc accagcgttc tgattgcaag cggtggtatt 900
cgtaatggtg ttgatatggc caaatgtgtt attctgggtg ccgatatgtg tggtgttgca 960
gcaccgctgt taaaagcagc acagaatagc cgtgaagcag ttgttagcgc aattcgcaaa 1020
ctgcatctgg aatttcgtac cgcaatgttt ctgttaggtt gtggcaccct ggccgatctg 1080
aaagataata gcagcctgat tcgtcagtaa gtcgacgtcg ac 1122

<210> SEQ ID NO 54
<211> LENGTH: 1122
<212> TYPE: DNA
<213> ORGANISM: Artificial Sequence
<220> FEATURE:
<223> OTHER INFORMATION: 345_pJL1-(CAT7aa)-IDI_Sau

<400> SEQUENCE: 54
tctagaaata attttgttta actttaagaa ggagatatac atatgcatat ggagaaaaaa 60
atcagcgatt ttcagcgtga acagcgcaaa aatgaacatg ttgaaattgc aatggcacag 120
agtgatgcaa tgcatagcga ttttgataaa atgcgctttg tgcatcattc cattccgagc 180
attaatgtga acgatattga tctgaccagc cagacaccgg atctgacaat gacctatccg 240
gtttatatca atgcaatgac cggtggtagc gaatggacca aaaacattaa tgaaaaactg 300
gcagttgttg cccgtgaaac cggtctggca atggcagttg gtagcaccca tgcagcactg 360
cgtaatccgc gtatggcaga aacctttacc attgcacgta aaatgaatcc ggaaggcatg 420
atttttagca atgttggtgc agatgttccg gttgaaaaag cactggaagc cgttgaactg 480
ctggaagcac aggcactgca gattcatgtt aatagtccgc aagaactggt tatgccggaa 540
ggtaatcgtg aatttgttac ctggctggat aatattgcaa gcattgttag ccgtgtttca 600
gttccggtta tcattaaaga agttggtttc ggcatgagca aagaactgat gcatgatctg 660
cagcagattg gtgttaaata tgttgatgtt agcggtaaag gtggcaccaa ctttgtggat 720
attgaaaatg aacgtcgtgc caacaaagat atggattatc tgagcagctg gggtcagagc 780
accgttgaaa gcctgctgga aaccaccgca tatcagagcg aaattagcgt tttttgcaagc 840 ggtggtctgc gtacaccgct ggatgcaatt aaaagcctgg cactgggtgc aaaagcaacc 900
ggtatgagcc gtccgtttct gaatcaggtt gaaaataatg gtattgccca taccgttgcc 960
tatgtggaaa gctttattga acacatgaaa agcatcatga ccatgctgga tgcgaaaaat 1020
atcgatgatc tgacacagaa gcagatcgtt tttagtccgg aaattctgag ctggattgaa 1080
cagcgtaatc tgaacattca tcgtggctaa gtcgacgtcg ac 1122

<210> SEQ ID NO 55
<211> LENGTH: 702
<212> TYPE: DNA
<213> ORGANISM: Artificial Sequence
<220> FEATURE:
<223> OTHER INFORMATION: 346_pJL1-(CAT7aa)-IDI_Scl

<400> SEQUENCE: 55
tctagaaata attttgttta actttaagaa ggagatatac atatgcatat ggagaaaaaa 60
atcgttatgc cgaccagtcc gacctcaccg accgcagcaa atagcgttag caatggcacc 120
agcaatgatg ttccggatgg tgcagcacgt gaaattctgc tggaactggt tgatgaacat 180
ggcaccacca ttggcaccgc agaaaaactg gcagcacatc agcctccggg tctgctgcat 240
cgtgcattta gcgtttttct gtttgatgat cgtggtcgtc tgctgctgca acagcgtgca 300
ctgggtaaat atcatagccc tggtgtttgg agcaatacct gttgtggtca tccgtatccg 360
ggtgaagcac cgtttgcagc cgcagcacgt cgtacccatg aagaactggg tattagtccg 420
gcactgctgg cagaagcagg caccgttcgt tataatcatc ctgatccgga tagcggtctg 480
gttgaacaag aatataatca cctgtttgtt ggtctggttc aggcaagtcc ggaaccagat 540
ccggaagaag ttggcggtac agtttttgtt acaccgggtg aactggcaga acgtcatgca 600
gcggcaccgt ttagctcatg gtttatgacc gttctggatg cagcccgtcc ggcaattcgt 660
gaactgaccg gtccgagcgg tggttggtaa gtcgacgtcg ac 702

<210> SEQ ID NO 56
<211> LENGTH: 994
<212> TYPE: DNA
<213> ORGANISM: Artificial Sequence
<220> FEATURE:
<223> OTHER INFORMATION: 286_pJL1-(CAT5aa)-GPPS_Agr_F3F

<400> SEQUENCE: 56
tctagaaata attttgttta actttaagaa ggagatatac atatggagaa aaaaatcgaa 60
ttcgacttca acaaatacat ggatagcaaa gccatgaccg ttaatgaagc actgaataaa 120
gcaattccgc tgcgttatcc gcagaaaatc tatgaaagca tgcgttatag cctgctggca 180
ggcggtaaac gtgttcgtcc ggttctgtgt attgcagcat gtgaactggt tggtggcacc 240
gaagaactgg caattccgac cgcatgtgca attgaaatga ttcataccat gagcctgatg 300
catgatgatc tgccgtgtat tgataatgat gacctgcgtc gtggtaaacc gaccaatcat 360
aaaatctttg gtgaagatac cgcagtgacc gcaggtaatg cactgcatag ttatgcattt 420
gaacatattg cagtgagcac cagcaaaacc gttggtgcag atcgtattct gcgtatggtt 480
agcgaactgg gtcgtgcaac cggtagcgaa ggtgttatgg gtggtcagat ggttgatatt 540
gcaagtgaag gtgatccgag cattgatctg cagaccctgg aatggattca tattcataaa 600
accgcaatgc tgctggaatg tagcgttgtt tgtggtgcaa ttattggtgg tgcaagcgaa 660
attgttattg aacgtgcccg tcgttatgca cgttgtgttg gtctgctgtt tcaggttgtt 720
gatgatattc tggatgtgac caaaagcagt gatgaactgg gcaaaaccgc aggcaaagac 780
ctgattagcg ataaagcaac ctatccgaaa ctgatgggtc tggaaaaagc caaagaattt 840
tcagatgaac tgctgaatcg tgccaaaggt gaactgagct gttttgatcc ggttaaagca 900
gcaccgctgc tgggtctggc agattatgtt gcatttcgtc agaactaagg atcctgactc 960
gagcaccacc accaccacca ctgagatcgt cgac 994

<210> SEQ ID NO 57
<211> LENGTH: 969
<212> TYPE: DNA
<213> ORGANISM: Artificial Sequence
<220> FEATURE:
<223> OTHER INFORMATION: 287_pJL1-(CAT5aa)-GPPS2_Pab

<400> SEQUENCE: 57
tctagaaata attttgttta actttaagaa ggagatatac atatggagaa aaaaatcgag 60
ttcgactttg acaagtatat gcacagtaaa gcaatcgccg taaacgaggc tttggataaa 120
gtgatcccgc cccgctaccc ccaaaagatt tatgaatcaa tgcgctatag tttactggca 180

```
ggtggaaaac gtgtgcgccc gatcctgtgt attgcggctt gcgagctgat gggaggcact    240

gaggagttag ctatgccgac cgcatgcgca attgagatga ttcataccat gtctcttatc    300

cacgacgact tgccgtatat cgataatgat gacttacgtc ggggaaaacc gaccaaccat    360

aaagttttcg gcgaagacac cgctattatc gcaggagatg ctctgctgag cttagcattc    420

gagcatgttg cagtgagtac tagccggact ctgggtactg atatcatcct gcgcctgctg    480

agcgaaatcg gtcgtgcaac gggctcggag ggcgtcatgg gcgggcaagt agttgatatt    540

gaatcggagg gagatccctc tatcgacctg gaaaccctgg agtgggtaca tatccataaa    600

acggcagttt tgctcgaatg ctcggtcgtt tgcggtgcaa ttatgggggg tgcctcagag    660

gatgatattg aacgtgcccg tcgttacgcg cgctgcgtcg gcttgctgtt tcaggtcgtc    720

gatgatatcc ttgatgtcag ccagtctagt gaagaactgg gaaaaaccgc tggcaaggat    780

ctgattagcg acaaagccac ttacccaaaa ttaatgggtc tggaaaaagc taaagaattt    840

gccgacgaat tattgaaccg tggtaagcag gaactgtcat gttttgaccc cacgaaagca    900

gcacctctgt ttgcgcttgc agactatatt gccagccggc agaactaagg atcctgactc    960

gaggtcgac                                                            969
```

<210> SEQ ID NO 58
<211> LENGTH: 1134
<212> TYPE: DNA
<213> ORGANISM: Artificial Sequence
<220> FEATURE:
<223> OTHER INFORMATION: 288_pJL1-(CAT5aa)-GPPS_Str

<400> SEQUENCE: 58

```
tctagaaata attttgttta actttaagaa ggagatatac atatggagaa aaaaatcacc     60

accgataccg gtcaggatgc agttggtctg gcacgtcgta ccggtgcaga cctgctgcat    120

cgtgttgaag atcgtctgcg tagcctgctg gcagtcgaac gtgatgcatg ggcggccgtg    180

cacgagcagg cagttgtgcc ggttgacgcc ttatcagagc tgatcgcaag tggcggcaaa    240

cgcatccgcc cggcattctg tatcacgggt tatttagctg ccggtggcga tccagccgaa    300

ccaggtattg tggctgcggg cgcggctctg gaaatgttgc atctttcagc cctggtgcac    360

gacgacgttt tagatgactc cagctcacgc cgtggggtac cgaccgtaca tacccaagct    420

atggccctgc atgaatctag cggttggcag ggcgaaccgc gccgctacgg ggaaggcgtg    480

gctatcctgg taggcgacct ggccttagta tactcagaag agttaatggc ggaagcgcct    540

cgccgcgtcc tgccagaatg gaataaactg cgttcggaag ttatgatcgg tcaatacatg    600

gacgtacatg cagccgctga atttagcgtg gatccgcgta gctcccgcct tattgcgcgc    660

attaaatctg ggcgttatac tatccatcgt ccattagtag taggcgccaa acggggccgc    720

ggtcgcggtg atctggcgcc agcattagaa gagtacggtg aagccgtggg cgaggccttc    780

caactgcgcg atgacttact ggatgcgtct gcaacgccgg ccgaaaccgg gaagccaact    840

ggcctggatt tcacacagca taaaatgacc ttactgctgg gctgggcgat gcagcgcgat    900

gagcatatcc atacgctggt aacggaacca gggcacacgc ccgatgaggt gcgccggcgt    960

ctgttagata cgggcgttcc ggccgatgta gaacggcata tcgcgggctt agtggaacgt   1020

ggctgcaaag ccatcgctga tgcacctgtc gatcaggttt ggcggggcga gctggcagcc   1080

atggccggcc gtgtcgcgta tcgtacggca taaggatcct gactcgaggt cgac         1134
```

<210> SEQ ID NO 59
<211> LENGTH: 966

<212> TYPE: DNA
<213> ORGANISM: Artificial Sequence
<220> FEATURE:
<223> OTHER INFORMATION: 347_pJL1-(CAT7aa)-GPPS_Pgl

<400> SEQUENCE: 59
tctagaaata attttgttta actttaagaa ggagatatac atatgcatat ggagaaaaaa 60
atcgaatttg acttcaaaga atacatgcgc agcaaagcca tgagcgttaa tgaagcactg 120
gatcgtgcag ttccgctgcg ttatccggaa aaaattcatg aagcaatgcg ttatagcctg 180
ctggcaggcg gtaaacgtgt tcgtccgatt ctgtgtattg cagcatgtga actggttggt 240
ggtagcgaag aactggcaat gccgaccgca tgtgcaatgg aaattattca taccatgagc 300
ctgatccatg atgatctgcc tccgatggat aatgatgacc tgcgtcgtgg taaaccgacc 360
aatcataaag tttttggtga aggcaccgca gttttagccg gtgatgcact gctgagcttt 420
gcatttgaac atattgcagt tagcaccagc aaaaccgttg aaagcgatcg tgttctgcgt 480
gttgttagcg aactgggtcg tgcaattggt agtgaaggtg ttgccggtgg tcaggttgca 540
gatattacca gccagggtaa tccgagcgtt ggtctggaaa ccctggaatg gattcatatt 600
cataaaaccg cagttctgct ggaatgtagc gttgcaagcg gtgcaattat tggtggtgca 660
agcgaagatg aaattgaacg tgtgcgtaaa tatgcacgtt gtgttggtct gctgtttcag 720
gttgttgatg atattctgga tgttaccaaa agcagcgagg aactgggtaa aacagcagca 780
aaagacctgc tgagcgataa agcaacctat ccgaaactga tgggtcttga aaaagcaaaa 840
gaatttgcag atgaactgct gggcaaagcc aaagaagaac tgagcttttt taacccgacc 900
aaagcagcac cgctgctggg tttagcagat tatattgcac agcgtcagaa ctaagtcgac 960
gtcgac 966

<210> SEQ ID NO 60
<211> LENGTH: 1188
<212> TYPE: DNA
<213> ORGANISM: Artificial Sequence
<220> FEATURE:
<223> OTHER INFORMATION: 348_pJL1-(CAT7aa)-GPPS_Pku

<400> SEQUENCE: 60
tctagaaata attttgttta actttaagaa ggagatatac atatgcatat ggagaaaaaa 60
atcagcctgg ttaatagcat tacctggtca cagaccagca gcattctgaa cattcagagc 120
aacattagca aaaaactgac cccgtttagc attctgccgc atccgctgac caataatctg 180
ccgattagcc tgtttccgaa tccgaaaagc aatatcagca atagcaatac accgctgagc 240
gcaattctga ccaaagatca gaaaccgcag aatccgccta ccacaccgac ctttgatttc 300
aaaagctata tgctgcagaa agccgatagc gttaataaag cactggatga tagcattccg 360
ctgacagaac cgctgaaaat tcaagaaagc atgcgttata gcctgctggc aggcggtaaa 420
cgtattcgtc cgatgctgtg tattgcagca tgtgaactgg ttggtggtga tgaaagcacc 480
gcaatgcctg cagcctgtgc agttgaaatg gttcatacca tgagcctgat gcatgatgat 540
ctgccgtgta tggataatga tgacctgcgt cgtggtaaac cgaccaatca taaagttttt 600
accgaagatg ttgccgtgtt agccggtgat gcaatgctgg catttagctt tgaacatgtt 660
gcaagcctga caaaaggtgt ttgtagcgaa cgtattgtgc gcgttattta tgaactggca 720
aaatgtgttg gttgcgaagg tctggttgca ggtcaggttg ttgatatttg cagcgaaggt 780
atggatgaag ttggtctgga acatctggaa tttatccatc tgaataaaac cgcagcactg 840
ctggaaggta gcgttgttct gggtgcaatt ttaggtggtg gtagtgatga agaagttgaa 900
aaactgcgta attttgcccg ttgtattggt ctgctgtttc aggttgtgga tgatattctg 960
gatgttacca aaagcagcaa agaactgggt aaaacagcag gtaaagacct ggttgccgat 1020
aaaaccacct atccgaaact gattggtatc gagaaaagca aagaatttgc cgaacgtctg 1080
aatcgtgaag caaaagaaca cctggcaggt tttgatcaga ataaagcagc accgctgatt 1140
gcactggccg attatattgc atatcgtgac aattaagtcg acgtcgac 1188

<210> SEQ ID NO 61
<211> LENGTH: 1131
<212> TYPE: DNA
<213> ORGANISM: Artificial Sequence
<220> FEATURE:
<223> OTHER INFORMATION: 349_pJL1-(CAT7aa)-GPPS*_Sce

<400> SEQUENCE: 61
tctagaaata attttgttta actttaagaa ggagatatac atatgcatat ggagaaaaaa 60
atcgccagcg aaaaagaaat tcgtcgtgaa cgttttctga acgtgtttcc gaaactggtt 120
gaagaactga atgcaagcct gctggcctat ggtatgccga aagaagcatg cgattggtac 180
gcacatagcc tgaattataa cacccctggt ggtaaactga atcgtggtct gagcgttgtt 240
gatacctatg caattctgag caataaaacc gtggaacagc tgggtcaaga ggaatatgaa 300
aaagttgcaa ttcttggctg gtgcattgaa ctgctgcagg catattttct ggttgcagat 360
gatatgatgg acaaaagcat tacccgtcgt ggtcagccgt gttggtataa agttccggaa 420
gttggtgaaa ttgccatcaa tgatgcattt atgctggaag cagcaatcta caaactgctg 480
aaaagccatt ttcgcaacga gaaatattac atcgatatca ccgaactgtt tcacgaagtt 540
acctttcaga ccgaactggg tcagctgatg gatctgatta ccgcaccgga agataaagtt 600
gatctgagca aattcagcct gaaaaagcat agctttatcg tgacctttga aaccgcctat 660
tatagctttt atctgccggt tgcactggca atgtatgttg caggtattac cgatgaaaaa 720
gacctgaaac aggcacgtga tgttctgatt ccgctgggtg aatattttca gatccaggat 780
gattatctgg attgctttgg tacaccggaa caaattggta aaattggcac cgatatccag 840
gataacaaat gtagctgggt tattaacaaa gcactggaac tggcaagcgc agaacagcgt 900
aaaaccctgg atgaaaatta tggcaaaaaa gatagcgttg ccgaggccaa atgcaagaaa 960
atctttaacg acctgaaaat cgagcagctg tatcacgaat atgaagaatc aattgccaag 1020
gacctgaaag ccaaaattag ccaggttgat gaaagccgtg gttttaaagc agatgtgctg 1080
accgcatttc tgaacaaagt gtataaacgc agcaaataag tcgacgtcga c 1131

<210> SEQ ID NO 62
<211> LENGTH: 960
<212> TYPE: DNA
<213> ORGANISM: Artificial Sequence
<220> FEATURE:
<223> OTHER INFORMATION: 318_pJL1-(CAT5aa)-ispA_Ec

<400> SEQUENCE: 62
tctagaaata attttgttta actttaagaa ggagatatac atatggagaa aaaaatcgac 60
tttccgcagc aactcgaagc ctgcgttaag caggccaacc aggcgctgag ccgttttatc 120
gccccactgc cctttcagaa cactcccgtg gtcgaaacca tgcagtatgg cgcattatta 180
ggtggtaagc gcctgcgacc tttcctggtt tatgccaccg gtcatatgtt tggcgttagc 240
acaaacacgc tggacgcacc cgctgctgcc gtagagtgta tccacgctta ctcattaatt 300

```
catgatgatt taccggcgat ggatgatgac gatctgcgcc gcggtttgcc gacctgccat    360
gtgaagtttg gcgaagcaaa cgcgattctc gctggcgacg ctttacaaac gctggcgttc    420
tcgattctaa gcgatgccga tatgccggaa gtgtcggatc gcgacagaat ttcgatgatt    480
tctgaactgg cgagcgccag cggtattgcc ggaatgtgcg gtggtcaggc actagattta    540
gacgcggaag gcaaacacgt acctctggac gcgcttgagc gtattcatcg tcataaaacc    600
ggcgcattga ttcgcgccgc cgttcgcctt ggtgcattaa gcgccggaga taaagggcgt    660
cgtgctctgc cagtactcga caagtacgca gagagcatcg gccttgcctt ccaggttcaa    720
gatgacatcc tggatgtggt aggagatact gcaacgttgg gaaaacgcca gggtgccgac    780
cagcaacttg gtaaaagtac ctaccctgca cttctgggtc ttgagcaagc ccggaagaaa    840
gcccgggatc tgatcgacga tgcccgtcag tcgctgaaac aactggctga acagtcactc    900
gatacctcgg cactggaagc gctagcggac tacatcatcc agcgtaataa ataagtcgac    960
```

<210> SEQ ID NO 63
<211> LENGTH: 1707
<212> TYPE: DNA
<213> ORGANISM: Artificial Sequence
<220> FEATURE:
<223> OTHER INFORMATION: 246_pJL1-(CAT5aa)-LS_Msp

<400> SEQUENCE: 63

```
tctagaaata attttgttta actttaagaa ggagatatac atatggagaa aaaaatccgt     60
cgttcgggga actataaccc gtcacgttgg gatgtgaact tcatccagtc tttactgagc    120
gattataagg aagacaaaca tgtcattcgt gcatccgaac tggttacgtt agtcaaaatg    180
gaattagaga aagaaacaga ccagattcgg caactggaat tgatcgacga tttgcaacgc    240
atgggcttat ctgatcactt ccaaaacgaa tttaaggaga ttctgagctc catctatctg    300
gatcatcatt actataaaaa tccttttccc aaagaagaac gcgacctgta cagtacctct    360
ctggcattcc ggctgctgcg tgaacatggc ttccaggtag cacaagaggt tttcgatagt    420
ttcaaaaatg aagaaggtga atttaaagaa agtctgtccg atgatactcg ggggctcctg    480
caactttatg aagcctcctt tctgctgacc gagggcgaaa ccaccctgga gtccgcccgc    540
gagttcgcaa ccaagtttct ggaagaaaaa gtgaatgaag gggcgtaga tggcgacctg     600
ctcacccgca ttgcgtatag cctggacatc ccgctccact ggcgcattaa acgcccgaac    660
gctccggttt ggattgagtg gtaccgtaag cgccctgata tgaacccggt tgttttagag    720
ctggccatct tagacctgaa catcgtccag gcccagtttc aagaggaact gaaagaaagc    780
tttcgctggt ggcgtaacac cggttttgtg gaaaagttac catttgcacg cgaccgtctt    840
gtcgagtgct acttttggaa tacaggcatt atcgaaccgc gtcagcacgc cagtgcccgt    900
atcatgatgg gaaaagttaa tgcgctgatc accgtgatcg acgacatcta tgatgtgtac    960
ggcaccttag aagagctcga acaattcacc gaccttatcc ggcgctggga tattaattcg   1020
atcgatcagc ttccggatta tatgcagctg tgttttctgg cgcttaataa ttttgttgat   1080
gacacgagtt acgacgttat gaaagaaaaa ggtgtgaacg tgatcccgta cttacgccaa   1140
tcatgggtgg acctggcgga caagtatatg gttgaagccc ggtggtttta tggtggacat   1200
aaaccttcgt tggaagaata tttagaaaat tcttggcagt ctatctccgg cccctgtatg   1260
ttgacccata ttttcttccg tgtcaccgac agctttacga aagaaacggt agactctctc   1320
tataagtacc atgacctggt tcgttggtcc tcctttgtac tgcgccttgc agatgatctg   1380
```

ggcacaagtg tagaagaagt ttctcgtggt gatgtcccta aaagcctcca gtgttatatg 1440
tctgactaca atgcatcgga agcggaggcg cgcaagcatg taaaatggct tatcgctgag 1500
gtgtggaaga aaatgaacgc agagcgcgta agcaaggatt cgccattcgg taaggatttc 1560
attggatgtg cggtggactt agggcggatg gctcagttaa tgtaccacaa cggcgacggt 1620
catggcacgc agcacccaat tattcatcag cagatgacgc ggacgctgtt cgagccgttc 1680
gcgtaaggat cctgactcga ggtcgac 1707

<210> SEQ ID NO 64
<211> LENGTH: 1743
<212> TYPE: DNA
<213> ORGANISM: Artificial Sequence
<220> FEATURE:
<223> OTHER INFORMATION: 247_pJL1-(CAT5aa)-LS_Cli

<400> SEQUENCE: 64
tctagaaata attttgttta actttaagaa ggagatatac atatggagaa aaaaatccgt 60
cggagcgcta actatcaacc gtcaatttgg gaccatgatt ttctgcaatc gctgaactca 120
aactatacag acgaggcgta caaacggcgc gccgaggaac ttcgcggtaa ggtcaaaatt 180
gccattaaag acgtgattga accgctggac cagctcgaac tgattgacaa cctgcaacgt 240
ctcggtctgg cgcatcgctt cgaaacggaa attcgtaata tcttaaataa catctataat 300
aacaacaaag attataactg gcgcaaagaa aatctgtatg caactagcct cgaatttcgg 360
ctgctgcgtc agcatggcta cccggtgtcg caggaggtct tcaatggttt caaagatgat 420
cagggtggtt tcatttgtga tgactttaaa ggaatccttt cgctccacga ggccagctat 480
tattcactgg aaggtgaatc aattatggag gaagcatggc agtttacgtc aaaacacctg 540
aaggaagtga tgatctctaa aaacatggaa gaagatgtgt tcgtcgcgga acaagctaaa 600
cgtgctctgg aactgccgct gcattggaaa gtcccgatgc tggaagcacg ctggtttatc 660
catatttacg aacgccgcga agataaaaat cacctgctgc tggaattagc gaaaatggaa 720
tttaacaccc tgcaggccat ttaccaggaa gaattaaagg aaatctcggg ttggtggaag 780
gatacggggc ttggagagaa actgtccttt gctcgcaacc ggttagtggc gtcgttcttg 840
tggtctatgg ggatcgcgtt cgaaccacaa ttcgcctatt gtcgccgtgt gttaactatc 900
tctattgcac tgattacggt gatcgatgac atttacgacg tatacggtac cctggacgag 960
ttagaaatct ttacggacgc cgtcgaacgg tgggatatca attatgcgct caaacactta 1020
cctggttata tgaaaatgtg ctttctggcg ctgtataatt ttgtaaacga atttgcatat 1080
tatgtgctga agcaacagga ctttgatctg ctgttgtcta tcaaaaacgc ctggctggga 1140
ttgattcaag cttaccttgt tgaagcgaag tggtaccaca gcaaatacac cccgaaactg 1200
gaagagtatc tggagaacgg cctggttagc atcaccgggc ccctgattat taccatctct 1260
tatctgtcag ggaccaaccc aattatcaaa aaagaactgg aatttcttga aagtaacccg 1320
gatattgttc actggtcttc caaaatcttc cgcctgcagg atgatctggg caccagctca 1380
gacgaaattc aacggggcga cgtaccaaaa tcaattcagt gctatatgca tgaaaccggt 1440
gcgagtgagg aggtagcccg tcagcacatc aaggatatga tgcgccaaat gtggaaaaaa 1500
gtcaatgctt ataccgcaga caaggacagt ccgctgaccg gcactacaac ggaatttctg 1560
ctgaacttag tccgtatgag ccattttatg tatttgcatg gcgacggaca cggcgttcag 1620
aaccaggaaa ccattgatgt cggcttcacc ttgctgtttc agccaatccc tttggaagat 1680
aagcacatgg cgtttaccgc aagcccgggc accaaaggct aaggatcctg actcgaggtc 1740
gac 1743

<210> SEQ ID NO 65
<211> LENGTH: 1699
<212> TYPE: DNA
<213> ORGANISM: Artificial Sequence
<220> FEATURE:
<223> OTHER INFORMATION: 248_pJL1-(CAT5aa)-LS_Pfr

<400> SEQUENCE: 65
tctagaaata attttgttta actttaagaa ggagatatac atatggagaa aaaaatccgt 60
cgtagcggta attatagccc gagcttttgg aatgcagatt atattctgag cctgaacaac 120
cattataaag aagaaagccg tcatatgaaa cgtgccggtg aactgattgt tcaggttaaa 180
atggttatgg gcaaagaaac cgatccggtt gtgcagctgg aactgatcga tgatctgcat 240
aaactggcac tgagccatca ttttgagaaa gaaattaaag agatcctgtt caacatcagc 300
atctacgacc ataaaatcat ggttgaacgt gatctgtata gcaccgcact ggcattccgg 360
ttgctccgtc agtatggctt caaggtgccg caggaggttt tcgattgttt taaaaacgac 420
aatggagaat ttaaacggtc tttaagctcc gatacgaaag gtctgctgca gttgtatgaa 480
gcctcctttc tgctgacgga aggtgaaatg acactggaac tggcgcgtga gttcgcgacc 540
atctttcttc aggagaaact gaacgataaa acaatcgacg acgacgatga tgcggataca 600
aacctcattt cttgcgtgcg tcattcactc gatatcccga tccattggcg catccaacgt 660
ccgaacgcca gttggtggat cgatgcctac aaacgccgca gtcacatgaa tcctctgctt 720
gagttagcaa agttagacct gaatattttt caggcacagt ttcaacagga actgaaacag 780
gacctgggtt ggtggaaaaa tacatgtctc gcagagaagc tgccgtttac ccgtgaccgc 840
ctggtggaat gctacttctg gtgcaccggt atcattcagc cgctgcagca tgagaacgct 900
cgcgttactc tggcaaaagt taacgccttg atcaccacgc tggacgacat ttacgatgta 960
tacggcaccc tggaggaact ggaactgttc acggaagcga ttcggcgttg ggacgttagt 1020
agcattgacc acttaccgaa ctatatgcag ctgtgcttcc tcgccctgaa caattttgtc 1080
gatgacaccg cgtacgatgt tatgaaagaa aaggacatta acattatccc gtatctgcgg 1140
aaatcgtggt tggacctcgc cgagacatac ctggtggaag ctaaatggtt ctattcaggc 1200
cataaaccga atatggaaga atatttaaat aatgcgtgga tctcgattag cggtccggtt 1260
atgttgtgcc atgtattctt ccgcgtgact gattccatta cccgcgaaac cgtagaatct 1320
ctgttcaaat atcacgacct tattcgttac tcctctacca tccttcgcct ggcggatgac 1380
ttaggcacaa gcctggaaga ggttagccgt ggtgatgttc cgaaaagcat tcagtgttat 1440
atgaatgata acaacgccag cgaagaagaa gcacgtcgtc acgttcgttg gctgattgca 1500
gaaacctgga aaaaaatcaa cgaagaagtt tggagcgcag atagcccgtt ttgcaaagat 1560
tttattgcat gtgcagcaga tatgggtcgt atggcgcagt ttatgtatca taatggtgat 1620
ggtcatggca ttcagaatcc gcagattcat cagcagatga ccgatattct gtttgaacag 1680
tggctgtaag gatgtcgac 1699

<210> SEQ ID NO 66
<211> LENGTH: 1722
<212> TYPE: DNA
<213> ORGANISM: Artificial Sequence
<220> FEATURE:
<223> OTHER INFORMATION: 350_pJL1-(CAT7aa)-LS_Ste

<400> SEQUENCE: 66
tctagaaata attttgttta actttaagaa ggagatatac atatgcatat ggagaaaaaa 60
atccgtcgta gcggtaacta taaaccgagc cgttgggatg ttgattttat gcagagcctg 120
aatagcgatt atcaagaaga acgtcatcgt accaaagcaa gcgaactgat tacccaggtt 180
aaaaacctgc tggaaaaaga aaccagtgat gatccgattc gtcagctgga actgattgat 240
gatctgcagc gtctgggtct gagcgatcat tttgaacatg aatttaaaga ggtgctgaac 300
agcatctacc tggacaacaa atattacaac atcaacatca tgaaagaaac gaccagcagc 360
cgtgatctgt atagcaccgc actggcattt cgtctgctgc gtgaacatgg ttttcaggtt 420
gcacaagaag ttttcgactg cttcaaaaat gaagagggtg agtttaaagc aagcctgtca 480
gatgatccgc gtggtctgct gcagctgtat gaagcaagct ttctgtttaa agaaggcgaa 540
aacaccctgg aaattgcccg tgaatttgca accaaactgc tgcaagaaaa agtgaacagc 600
tccgatgaaa ttgatgataa tctgctgagc agcattcgtt atagtctgga aattccgacc 660
tattggagcg ttattcgtcc gaatgttagc gtttggattg atgcatatcg taaacgtccg 720
gatatgaatc cggttgttct ggaactggca attctggatg ccaatattat gcaggcacag 780
ctgcaacaag aactgaaaga agcattaggt tggtggcgta atacctggtt tgttgaaaaa 840
ctgccgtttg cacgtgatcg tctggttgaa agctattttt ggagcaccgg tatggttccg 900
cgtcgtcagc ataaaaccgc acgtcagctg atggcaaaag ttattgccct gattaccgtg 960
atggatgata tctatgacgt ttatggtaca ctggaagaac tggaactgtt taccgatgcc 1020
tttcgtcgct gggatgttag cagcattgat catctgccga cctatatgca actgtgtttt 1080
ctgagcatta acaactttgt tgttgacacc gcctacaaca ttcttaaaga aaccggtgtt 1140
aatgtgacca cctatctgga aaaaagctgg gttgatcagg cagaaaatta tctgatggaa 1200
agcaaatggt tctacagcgg tcataaaccg tcactggatg aatacctgga aaatagttgg 1260
attagcgtta gcggtccgtg tgttctgacc catgaatttt ttggtgttac cgatagcctg 1320
gcaaaagata ccctggatag cctgtatgaa tatcacgata ttgttcgttg gagcagctat 1380
ctgctgcgcc tggccgatga tctgggcacc agcgttgaag aggttagccg tggtgatgtt 1440
ccgaaaagca ttcagtgtta tatgaacgat aataacgcca gcgaagaaga agcacgcgaa 1500
cacgttaaag gtctgattcg tgttatgtgg aaaaaaatga atgccgaacg tgttagcgaa 1560
gatagcccgt tttgtaaaga ttttattcgt tgttgtgagg acctgggtcg tatggcacag 1620
tttatgtatc attatggtga tggtcatggc acccagcatg ccaaaattca tcagcagatc 1680
accgattgtc tgtttcagcc gtttgcctaa gtcgacgtcg ac 1722

<210> SEQ ID NO 67
<211> LENGTH: 1710
<212> TYPE: DNA
<213> ORGANISM: Artificial Sequence
<220> FEATURE:
<223> OTHER INFORMATION: 351_pJL1-(CAT7aa)-LS_Lan

<400> SEQUENCE: 67
tctagaaata attttgttta actttaagaa ggagatatac atatgcatat ggagaaaaaa 60
atccgtcgta gcggtaacta taatccgacc gcatgggatt ttaactatat tcagagcctg 120
gacaaccagt acaaaaaaga acgttatagc acccgtcatg cagaactgac cgttcaggtt 180
aaaaaactgc tggaagaaga aatggaagcc gttcagaaac tggaactgat tgaggatctg 240
aaaaatctgg gtatcagcta tccgttcaaa gataacattc agcagatcct gaaccagatt 300
tacaacgaac ataaatgctg ccataacagc gaagtggaag aaaaagacct gtattttacc 360
gcactgcgtt ttcgtctgct gcgtcagcag ggttttgaag ttagccaaga agttttcgac 420
cacttcaaaa atgaaaaagg caccgatttt aaaccgaacc tggcagatga taccaaaggt 480
ctgctgcagc tgtatgaagc aagctttctg ctgcgcgaag ccgaagatac cctggaactg 540
gcacgtcagt ttagcaccaa actgctgcag aaaaaagtgg atgaaaatgg cgacgataaa 600
atcgaagata atctgctgct gtggattcgt cgtagtctgg aactgccgct gcattggcgt 660
gttcagcgtc tggaagcacg tggttttctg gatgcctatg ttcgtcgtcc ggatatgaat 720
ccgattgttt ttgaactggc aaagctggat ttcaatatta cccaggcaac ccagcaagaa 780
gaactgaaag acctgagccg ttggtggaat agcaccggtc tggcagaaaa actgccgttt 840
gcacgtgatc gtgttgttga aagctatttt tgggcaatgg gcacctttga accgcatcag 900
tatggttatc agcgtgaact ggttgcaaaa atcattgcac tggcaaccgt tgttgatgat 960
gtctatgatg tttatggcac cctggaagaa ttagaactgt ttaccgatgc aattcgtcgt 1020
tgggatcgtg aaagcattga tcagctgccg tattatatgc agctgtgttt tctgaccgtg 1080
aacaactttg tgtttgagct ggcacatgat gtgctgaaag ataaaagctt taattgtctg 1140
ccgcatctgc agcgtagctg gctggatctg gccgaagcat atctggttga agcaaaatgg 1200
tatcatagcc gttatacccc gagcctggaa gagtatctga atattgcacg tgttagcgtt 1260
acctgtccga ccattgttag ccagatgtat tttgcactgc cgattccgat tgaaaaaccg 1320
gtgattgaaa tcatgtacaa ataccacgat atcctgtatc tgagcggtat gctgctgcgc 1380
ctgccggatg atctgggcac cgcatcattt gaactgaaac gtggtgatgt tcagaaagcg 1440
gttcagtgct atatgaaaga acgtaatgtt ccggaaaatg aagcccgtga acatgtgaaa 1500
tttctgattc gtgaagccag caagcagatc aataccgcaa tggccaccga ttgtccgttt 1560
accgaagatt ttgcagttgc agcagccaat ctgggtcgtg ttgcaaattt tgtttatgtg 1620
gatggtgatg gttttggtgt tcagcacagc aaaatctatg agcagattgg tacactgatg 1680
tttgaaccgt atccgtaagt cgacgtcgac 1710

<210> SEQ ID NO 68
<211> LENGTH: 1731
<212> TYPE: DNA
<213> ORGANISM: Artificial Sequence
<220> FEATURE:
<223> OTHER INFORMATION: 352_pJL1-(CAT7aa)-LS_Sly

<400> SEQUENCE: 68
tctagaaata attttgttta actttaagaa ggagatatac atatgcatat ggagaaaaaa 60
atccgtcgta gcggtaatta tgaaccgacc atgtggaact atgaatatat ccagagcacc 120
cataatcatc atgtgggcga gaaatatatg aaacgcttta atgaactgaa agccgaaatg 180
aaaaagcatc tgatgatgat gctgcacgaa gaaagccaag aactggaaaa actggaactg 240
attgataatc tgcagcgtct gggtgttagc tatcacttta aagatgaaat cattcagatc 300
ctgcgcagca ttcatgatca gtcaagcagc gaagcaacca gcgcaaatag cctgtattat 360
accgcactga aatttcgtat tctgcgtcag catggctttt atatcagcca ggatattctg 420
aacgacttca aagatgagca gggccatttt aaacagagcc tgtgtaaaga taccaaaggt 480
ctgctgcagc tgtatgaagc aagctttctg agcaccaaaa gcgaaaccag cacactgctg 540
gaaagcgcca ataccttgc aatgagccat ctgaaaaact atctgaatgg tggtgatgaa 600

```
gagaacaact ggatggttaa actggttcgt catgcactgg aagttccgct gcattgtatg    660

atgcttcgtg ttgaaacccg ttggtatatc gacatctatg aaaatattcc gaatgccaat    720

ccgctgctga ttgaactggc caaactggat tttaactttg ttcaggcaat gcaccagcaa    780

gaactgcgta atctgagccg ttggtggaaa aaaagcatgc tggcagaaaa actgccgttt    840

gcacgtgatc gtattgttga agcatttcag tggattaccg gcatgatttt tgagagccaa    900

gaaaatgaat tttgccgcat catgctgacc aaagttaccg caatggcaac cgttattgat    960

gatatctatg atgtttatgg caccctggat gagctggaaa tctttaccca tgcaattcag   1020

cgcatggaaa ttaaagcaat ggatgaactg ccgcactaca tgaaactgtg ttatctggca   1080

ctgtttaata ccagcagcga aattgcatat caggtgctga aagaacaggg cattaacatt   1140

atgccgtatc tgaccaaaag ctgggctgat ctgagcaaaa gttatctgca agaagcacgt   1200

tggtattata gcggttatac cccgagcctg gatgaataca tggaaaatgc atggattagc   1260

gttggtagcc tggttatggt tgttaatgca ttttttctgg tgaccaatcc gatcaccaaa   1320

gaagttctgg aatacctgtt cagcaacaaa tatccggaca ttattcgttg gcctgcaacc   1380

attattcgcc tgaccgatga tctggcgacc agcagcaatg aaatgaaacg tggtgatgtt   1440

ccgaaaagca ttcagtgcta tatgaaagaa aatggtgcca gcgaagaaga agcccgtaaa   1500

catattaacc tgatgatcaa agaaacctgg aaaatgatca ataccgcaca gcatgataac   1560

agcctgtttt gcgaaaaatt catgggttgt gcagttaata ttgcacgtac cggtcagacc   1620

atttatcagc atggtgatgg tcatggtatc cagaattaca aaattcagaa ccgcatcagc   1680

aaactgtttt ttgaaccgat taccatcagc atgccgtaag tcgacgtcga c            1731
```

<210> SEQ ID NO 69
<211> LENGTH: 1785
<212> TYPE: DNA
<213> ORGANISM: Artificial Sequence
<220> FEATURE:
<223> OTHER INFORMATION: 353_pJL1-(CAT7aa)-LS-Pab

<400> SEQUENCE: 69

```
tctagaaata attttgttta actttaagaa ggagatatac atatgcatat ggagaaaaaa     60

atccgtcgtc gtggtaatta tcatagcaat ctgtgggatg atgatttcat tcagagcctg    120

agcaccccgt atggtgaacc gagctatcgt gaacgtgcag aacgtctgaa aggtgagatc    180

aaaaaaatgt ttcgcagcat gagcaaagat gatggcgaac tgattacacc gctgaatgat    240

ctgattcagc gtctgtggat ggttgatagc gtgcagcgtc tgggtattga tcgtcatttc    300

aaaaacgaaa tcaaaagcgc actggactat gtgtatagct attggaatga aaaaggtatt    360

ggttgcggtc gtgatagcgt tgttgccgat ctgaatagca ccgcactggg ttttcgtacc    420

ctgcgtctgc atggttataa tgttagcagc gaagttctga aagtgttcga agatcagaat    480

ggtcagtttg catgtagccc gagcaaaacc gaaggtgaaa ttcgtagcgc actgaatctg    540

tatcgtgcaa gcctgattgc atttccgggt gaaaaagtta tggatgatgc agaaatcttt    600

agcagccgct atctgaaaga agccgttcaa gaaattccgg attgtagcct gagccaagaa    660

attgcctatg cactggaata tggttggcat accaatatgc ctcgtctgga agcacgcaat    720

tatatggatg tttttggtca tccgagcagc ccgtggctga aaaaaaacaa aacacagtat    780

atggacggcg agaaactgct ggaactggca aaactggaat ttaacatttt tcacagcctg    840

cagcaagagg aactgcagta tattagccgt tggtggaaag atagtggtct gccgaaactg    900

gcatttagcc gtcatcgtca tgttgagtat tataccctgg gtagctgtat tgcaaccgat    960
```

ccgaaacatc gtgcatttcg tctgggtttt gttaaaacct gtcatctgaa taccgtgctg 1020
gatgatatct atgatacctt tggcaccatg gatgaaatcg aactgtttac cgaagcagtt 1080
cgtcgttggg acccgagtga aaccgaaagc ctgccggatt atatgaaagg tgtttatatg 1140
gttctgtatg aagccctgac cgaaatggca caagaagcac agaaaacaca gggtcgcgat 1200
accctgaatt atgcacgtaa agcatgggaa atttatctgg acagctatat ccaagaggca 1260
aaatggattg caagcggtta tctgccgacc tttcaagaat attttgagaa cggtaaaatc 1320
agcagcgcat atcgtgcagc agcactgacc ccgattctga ccctggatgt tccgctgccg 1380
gaatacattc tgaaaggcat tgattttccg agccgcttta atgatctggc aagcagcttt 1440
ctgcgcctgc gtggtgatac ccgttgttat aaagcagatc gtgcacgtgg tgaagaagca 1500
agctgtatta gctgttacat gaaagataat ccgggtagca ccgaagaaga tgccctgaat 1560
catattaaca gcatgatcaa cgagatcatc aaagaactga attgggaact gctgcgtccg 1620
gatagcaata ttccgatgcc agcgcgtaaa catgcatttg atattacccg tgcactgcat 1680
cacctgtata aataccgtga tggttttagc gttgcaacca aagaaaccaa aagtctggtt 1740
agccgcatgg ttctggaacc ggtgccgctg taagtcgacg tcgac 1785

<210> SEQ ID NO 70
<211> LENGTH: 2517
<212> TYPE: DNA
<213> ORGANISM: Artificial Sequence
<220> FEATURE:
<223> OTHER INFORMATION: 320_pJL1-(CAT5aa)-BS_Agr

<400> SEQUENCE: 70
tctagaaata attttgttta actttaagaa ggagatatac atatggagaa aaaaatcagc 60
gcgggtgttt ctgcggtttc taaagtttct tctctggttt gcgacctgtc ttctacctct 120
ggtctgatcc gtcgtaccgc gaacccgcac ccgaacgttt ggggttacga cctggttcac 180
tctctgaaat ctccgtacat cgactcttct taccgtgaac gtgcggaagt tctggtttct 240
gaaatcaaag cgatgctgaa cccggcgatc accggtgacg gtgaatctat gatcaccccg 300
tctgcgtacg acaccgcgtg ggttgcgcgt gttccggcga tcgacggttc tgcgcgtccg 360
cagttcccgc agaccgttga ctggattctg aaaaaccagc tgaaagacgg ttcttggggt 420
atccagtctc acttcctgct gtctgaccgt ctgctggcga ccctgtcttg cgttctggtt 480
ctgctgaaat ggaacgttgg tgacctgcag gttgaacagg gtatcgagtt catcaaatct 540
aacctggaac tggttaaaga cgaaaccgac caggactctc tggttaccga cttcgaaatc 600
atcttcccgt ctctgctgcg tgaagcgcag tctctgcgtc tgggtctgcc gtacgacctg 660
ccgtacatcc acctgctgca gaccaaacgt caggaacgtc tggcgaaact gtctcgtgaa 720
gaaatctacg cggttccgtc tccgctgctg tactctctgg aaggtatcca ggacatcgtt 780
gaatgggaac gtatcatgga agttcagtct caggacggtt ctttcctgtc ttctccggcg 840
tctaccgcgt gcgttttcat gcacaccggt gacgcgaaat gcctggagtt cctgaactct 900
gttatgatca aattcggtaa cttcgttccg tgcctgtacc cggttgacct gctggaacgt 960
ctgctgatcg ttgacaacat cgttcgtctg ggtatctacc gtcacttcga aaaagaaatc 1020
aaagaagcgc tggactacgt ttaccgtcac tggaacgaac gtggtatcgg ttggggtcgt 1080
ctgaacccga tcgcggacct ggaaaccacc gcgctgggtt tccgtctgct gcgtctgcac 1140
cgttacaacg tttctccggc gatcttcgac aacttcaaag acgcgaacgg taaattcatc 1200

```
tgctctaccg gtcagttcaa caaagacgtt gcgtctatgc tgaacctgta ccgtgcgtct   1260
cagctggcgt ttccgggtga aaacatcctg gacgaagcga aatctttcgc gaccaaatac   1320
ctgcgtgaag cgctggaaaa atctgaaacc tcttctgcgt ggaacaacaa acagaacctg   1380
tctcaggaaa tcaaatacgc gctgaaaacc tcttggcacg cgtctgttcc gcgtgttgaa   1440
gcgaaacgtt actgccaggt ttaccgtccg gactacgcgc gtatcgcgaa atgcgtttac   1500
aaactgccgt acgtgaacaa cgaaaaattc ctggaactgg gtaaactgga cttcaacatc   1560
atccagtcta tccaccagga agaaatgaaa aacgttacct cttggttccg tgactctggt   1620
ctgccgctgt tcaccttcgc gcgtgaacgt ccgctggagt tctacttcct ggttgcggcg   1680
ggtacctacg aaccgcagta cgcgaaatgc cgtttcctgt tcaccaaagt tgcgtgcctg   1740
cagaccgttc tggacgacat gtacgacacc tacggtaccc tggacgaact gaaactgttc   1800
accgaagcgg ttcgtcgttg ggacctgtct ttcaccgaaa acctgccgga ctacatgaaa   1860
ctgtgctacc agatttacta cgacatcgtt cacgaagttg cgtgggaagc ggaaaaagaa   1920
cagggtcgtg aactggtttc tttcttccgt aaaggttggg aagactacct gctgggttac   1980
tacgaagaag cggaatggct ggcggcggaa tacgttccga ccctggacga atacatcaaa   2040
aacggtatca cctctatcgg tcagcgtatc ctgctgctgt ctggtgttct gatcatggac   2100
ggtcagctgc tgtctcagga agcgctggaa aaagttgact atccgggtcg tcgtgttctg   2160
accgaactga actctctgat ctctcgtctg gcggacgaca ccaaaaccta caaagcggaa   2220
aaagcgcgtg gtgaactggc gtcttctatc gaatgctaca tgaaagacca cccggaatgc   2280
accgaagaag aagcgctgga ccacatctac tctatcctgg aaccggcggt taaagaactg   2340
acccgtgagt tcctgaaacc ggacgacgtt ccgttcgcgt gcaaaaaaat gctgttcgaa   2400
gaaacccgtg ttactatggt tatcttcaaa gacggtgacg gtttcggtgt ttctaaactg   2460
gaagttaaag accacatcaa agaatgcctg atcgaaccgc tgccgctgta agtcgac      2517
```

<210> SEQ ID NO 71
<211> LENGTH: 1848
<212> TYPE: DNA
<213> ORGANISM: Artificial Sequence
<220> FEATURE:
<223> OTHER INFORMATION: 249_11a_pJL1_CATrbs(5aa)_PS_Agr

<400> SEQUENCE: 71

```
tctagaaata attttgttta actttaagaa ggagatatac atatggagaa aaaaatccgt     60
cgtggcaaat ccattacccc gagtatctcg atgagctcta cgacggttgt gacagacgac    120
ggcgtccgcc gtcgtatggg tgattttcat tccaatttat gggacgacga tgtgattcag    180
agcttaccaa cagcgtacga agaaaaatcc tatcttgaac gtgcggaaaa actgattgga    240
gaagtaaaaa acatgtttaa ttccatgagc cttgaggatg gtgaacttat gagtccactg    300
aatgatctga tccagcgcct gtggatcgta gacagcctgg agcggttagg catccaccgt    360
cacttcaaag atgagattaa atcggctttg gattatgtgt attcatactg gggagagaat    420
ggtattgggt gtgggcggga aagtgtggta acagacttga acagcactgc actgggcctg    480
cggaccctgc gcctccacgg ctatccagtc agctctgatg tgtttaaggc ttttaaagga    540
caaaacggac agttttcttg ttccgagaat attcaaaccg atgaagaaat ccgtggcgtg    600
ctgaatttgt tccgtgcaag cctgattgcc tttccgggtg agaaaatcat ggacgaggcc    660
gaaatctttt caaccaaata cctgaaggaa gctctgcaaa agatccctgt atcctcctta    720
tcccgggaaa tcggcgatgt gttggaatac ggctggcata cttatttgcc gcgtttagag    780
```

gcacgcaatt atattcaggt gtttggtcag gacaccgaaa ataccaaaag ctacgttaaa 840
agcaaaaaac ttttggaact ggctaagctg gaatttaaca ttttccagag cttgcagaaa 900
cgtgaactgg aatcgttggt tcgctggtgg aaagaaagcg gctttccgga gatgaccttt 960
tgtcgtcatc gtcatgtgga atattatacc ctggcctcct gcattgcgtt cgaaccgcag 1020
catagtggtt tccgcctcgg atttgcgaaa acttgtcatc tgattaccgt actggatgat 1080
atgtatgata ccttcggcac ggttgatgaa ttagaactgt tcaccgccac tatgaaacgc 1140
tgggacccgt cttcgatcga ttgcttaccg gaatacatga aaggcgtata tatcgccgta 1200
tacgacaccg tgaatgagat ggcgcgcgaa gcggaggagg cccaagggcg cgataccttg 1260
acctatgcac gtgaggcgtg ggaagcctat atcgatagtt acatgcaaga agcccgttgg 1320
atcgccaccg gctatttacc ttcatttgat gagtattatg aaaatggcaa agtcagttgc 1380
ggacatcgta tctcggccct gcagcctatc ttaaccatgg acattccgtt tcccgaccac 1440
atcctgaaag aagttgattt cccgagcaaa ctcaatgatc tcgcgtgtgc cattctccgc 1500
ctgcgcggtg atacgcgctg ctataaggcg gatcgtgcac gtggcgaaga agcgagcagc 1560
atctcctgtt atatgaaaga taaccctggc gtgagcgagg aagatgcttt agatcacatt 1620
aatgccatga tctcagatgt aattaaaggg cttaactggg agttattaaa acctgatatt 1680
aatgtgccca tcagtgcgaa aaaacacgcg ttcgacattg cgcgcgcttt ccactatggt 1740
tataaatatc gcgatggtta tagcgtggcg aatgtagaga cgaaatcgct ggtgacccgg 1800
accctgctgg aatctgtgcc cttatgagga tcctgactcg aggtcgac 1848

<210> SEQ ID NO 72
<211> LENGTH: 1773
<212> TYPE: DNA
<213> ORGANISM: Artificial Sequence
<220> FEATURE:
<223> OTHER INFORMATION: 250_11b_pJL1_CATrbs(5aa)_PS_Pab

<400> SEQUENCE: 72
tctagaaata attttgttta actttaagaa ggagatatac atatggagaa aaaaatccgc 60
cgtatgggtg attttcactc taatctgtgg aacgacgatt ttattcaaag cctgagcacg 120
tcgtacggcg aacctagtta ccgcgaacgc gctgagcgtc tcattggcga agtcaagaaa 180
atgtttaata gcatgtcatc tgaagacggc gagctgatta gcccccataa tgacttaatt 240
caacgcgtgt ggatggtgga cagcgtcgaa cgtctgggca ttgaacgcca cttcaagaat 300
gagattaaaa gcgctctcga ttatgtctat tcctactggt cagaaaaagg catcggctgc 360
gggcgcgaat cggtggtagc cgacctgaac agtacggcct taggcttacg tacactgcgc 420
ctgcatggat atgcagtgtc cgcggacgtt ctcaatttgt ttaaagatca gaatggtcaa 480
tttgcatgct caccatctca gaccgaagaa gaaatccgta gtgtattaaa cctttatcgc 540
gcaagtttaa ttgccttccc gggggaaaaa gtgatggaag aggcggaaat tttctcggcc 600
aagtatctgg aagaggccct gcagaaaatc tccgtcagct cacttagcca agaaatccgt 660
gatgtgctgg aatatggttg gcatacctac ctgccccgga tggaggcgcg caatcatatt 720
gacgtgtttg gccaggacac acagaactct aaaagctgca ttaataccga taaattatta 780
gagcttgcga aattggagtt taatatcttt cactcgttgc agaaacgcga gctggaatat 840
ctggtgcggt ggtggaaaga cagcggctcc ccgcagatga cctttggccg ccatcggcat 900
attgaatact ataccctggc tagctgtatt gcatttgaac cacagcactc tggctttcgt 960

```
ctcggctttg cgaaaacttg ccatatcatc accatcctgg acgacatgta tgataccttt   1020

ggcaccgttg atgagttaga actttttacg gcagccatga agcgctggga cccgagcgca   1080

gcagactgcc ttcctgagta catgaaagta atgtatatga tcgtgtacga caccgtgaac   1140

gaaatgtgtc aggaggcgga aaaagcgcag ggtcgtgaca ccctggatta tgcccgtcag   1200

gcgtgggaag actacctgga ttcttatatg caggaagcta agtggatcgc caccggttac   1260

ttaccgacct tcgaagaata ctatgagaat gggaaagttt catcggggca tcgtgtggct   1320

gcactgcagc cgatcttgac catggacatt ccgtttcctc cgcacatttt gaaagaagtg   1380

gattttccct caaagctgag tgatctggcc tgtgctatcc tgcgcctgcg tggagacact   1440

cgttgttaca aagccgaccg tgcccgtggc gaagaagctt catcgatttc gtgttacatg   1500

aaagataatc ctggcgcgac ggaagaagat gccttggatc atattaatgc catgatcagc   1560

gatgtaattc gtgggttgaa ctgggagctg ttaaagccta attcgagcgt gccgatcagc   1620

agcaaaaagc acgttttcga tatttcacgc gcttttcatt acggctacaa ataccgcgat   1680

ggctactcag tggcaaatat cgaaaccaaa agcttggtca aacgtacagt tattgatccg   1740

gtgactttat aaggatcctg actcgaggtc gac                                 1773
```

<210> SEQ ID NO 73
<211> LENGTH: 1185
<212> TYPE: DNA
<213> ORGANISM: Artificial Sequence
<220> FEATURE:
<223> OTHER INFORMATION: Codon-optimized EcoTHL sequence for E. coli-
      based CFPS

<400> SEQUENCE: 73

```
atgaaaaatt gtgtcatcgt cagtgcggta cgtactgcta tcggtagttt taacggttca     60

ctcgcttcca ccagcgccat cgacctgggg gcgacagtaa ttaaagccgc cattgaacgt    120

gcaaaaatcg attcacaaca cgttgatgaa gtgattatgg gtaacgtgtt acaagccggg    180

ctggggcaaa atccggcgcg tcaggcactg ttaaaaagcg ggctggcaga aacggtgtgc    240

ggattcacgg tcaataaagt atgtggttcg ggtcttaaaa gtgtggcgct tgccgcccag    300

gccattcagg caggtcaggc gcagagcatt gtggcggggg gtatggaaaa tatgagttta    360

gccccctact tactcgatgc aaaagcacgc tctggttatc gtcttggaga cggacaggtt    420

tatgacgtaa tcctgcgcga tggcctgatg tgcgccaccc atggttatca tatggggatt    480

accgccgaaa acgtggctaa agagtacgga attacccgtg aaatgcagga tgaactggcg    540

ctacattcac agcgtaaagc ggcagccgca attgagtccg gtgcttttac agccgaaatc    600

gtcccggtaa atgttgtcac tcgaaagaaa accttcgtct tcagtcaaga cgaattcccg    660

aaagcgaatt caacggctga agcgttaggt gcattgcgcc cggccttcga taaagcagga    720

acagtcaccg ctgggaacgc gtctggtatt aacgacggtg ctgccgctct ggtgattatg    780

gaagaatctg cggcgctggc agcaggcctt acccccctgg ctcgcattaa aagttatgcc    840

agcggtggcg tgccccccgc attgatgggt atggggccag tacctgccac gcaaaaagcg    900

ttacaactgg cggggctgca actggcggat attgatctca ttgaggctaa tgaagcattt    960

gctgcacagt tccttgccgt tgggaaaaac ctgggctttg attctgagaa agtgaatgtc   1020

aacggcgggg ccatcgcgct cgggcatcct atcggtgcca gtggtgctcg tattctggtc   1080

acactattac atgccatgca ggcacgcgat aaaacgctgg ggctggcaac actgtgcatt   1140

ggcggcggtc agggaattgc gatggtgatt gaacggttga attaa                   1185
```

<210> SEQ ID NO 74
<211> LENGTH: 1179
<212> TYPE: DNA
<213> ORGANISM: Artificial Sequence
<220> FEATURE:
<223> OTHER INFORMATION: Codon-optimized CacTHL sequence for E. coli-
based CFPS

<400> SEQUENCE: 74

```
atgaaggaag tggtgatagc tagtgcagtg cggaccgcta ttgggagtta cggcaagtca      60

ttgaaggatg tccctgctgt tgatttggga gccaccgcga ttaaagaggc cgtaaagaaa     120

gctggcataa agcccgagga tgtcaatgaa gttatcctgg ggaacgtttt gcaagctggc     180

ttggggcaaa atccggcccg gcaagcatct tttaaagccg gccttccagt agaaataccc     240

gctatgacga tcaacaaggt atgcggtagc ggacttagaa cagtgtcgct tgcggctcag     300

ataattaagg caggggacgc tgacgttatc attgcgggtg gtatggagaa catgagtcgt     360

gcgccctacc tggcgaacaa tgctagatgg ggttatcgca tggggaacgc gaagttcgtc     420

gatgaaatga taactgacgg cctttgggac gcatttaatg actaccacat gggaatcacc     480

gctgagaaca ttgccgaacg ctggaatata tcgagagaag agcaggacga atttgccctt     540

gcctcacaga aaaaggcgga agaggccatt aaatctggac aattcaaaga tgaaatcgtc     600

ccagtcgtga taaagggcag aaaaggggaa actgttgtgg acacggatga gcacccccgg     660

ttcgggtcaa caatagaggg cttggcaaaa ctgaaacccg cgttcaagaa agatggtaca     720

gtcaccgcgg gtaacgcatc ggggttgaat gattgcgcgg cggtattggt gattatgtct     780

gctgaaaagg ctaaagaatt aggagtaaaa cctttggcca aaattgtcag ctatgggagt     840

gctggagtag accccgcgat catgggatat ggcccgttct acgccacaaa agctgctatt     900

gagaaagctg ggtggaccgt tgatgagctg gacttgattg agtcaaatga agcattcgcc     960

gctcagtcgt tggcggtggc taaggatctt aaatttgata tgaacaaggt caatgtaaac    1020

ggaggcgcga tcgcattagg acatcctata ggtgcaagcg gagcacgcat tctggttact    1080

ttagtccacg ctatgcaaaa gcgggacgct aagaaaggcc tggctacact ttgtatcggc    1140

ggaggccagg gcactgccat tttgttagaa aaatgctaa                           1179
```

<210> SEQ ID NO 75
<211> LENGTH: 1182
<212> TYPE: DNA
<213> ORGANISM: Artificial Sequence
<220> FEATURE:
<223> OTHER INFORMATION: Codon-optimized CklTHL1 sequence for E. coli-
based CFPS

<400> SEQUENCE: 75

```
atgcgtgaag tagtgatagt atctgccgtt cgcacggcta taggatcatt cgggggtact      60

ttgaaggatg tatctgcagt agatttgggt gctattgtaa taaaggaagc tgtaaagcgg     120

gcgggtatta agcccgagca agtggatgag gtaatttttg gtaacgtgat acaggcgggt     180

gtaggacagt cattagcaag acagtcagcc gtgtacgccg gcttgcccgt cgaggtacct     240

gcgtttacag tgaataagct gtgcggtagc ggacttcgca cagtatctct tgctgcctcc     300

ttgatctcga acggtgatgc ggacacaata gtcgttggcg gcagtgaaaa tatgtctgcg     360

agcccttatt taatacccaa ggctcggttc ggttaccgta tgggcgaagc caaaatctat     420

gatgcaatgc tgcacgatgg tttgatagat tcgttcaaca actaccacat gggaattacc     480

gccgagaata tagcggagaa atggggtatt acgagagagg atcaggacaa attcgcttta     540
```

gctagtcagc agaaggccga agcagcgatc aaagctggca aattcaaaga cgaaatcgta 600
cctgtaacgg tcaaaatgaa aaaaaaagag gtcgtgttcg acaccgacga ggatccgcgc 660
tttgggacta caattgaaac tttagcgaaa ttgaagcctg cttttaaacg ggatgggact 720
ggtaccgtca cggcaggaaa cagttctggg atcaacgatt ctagtgccgc acttatcctg 780
atgtcggctg ataaggctaa ggaacttggg gttaaaccga tggcaaaata tgtagatttt 840
gcctcggcag ggcttgatcc tgcaattatg ggttatggtc catattatgc cacaaagaaa 900
gtattggcta aaactaatct tacgattaaa gattttgatt tgatagaggc taacgaggct 960
ttcgctgctc aatcgattgc agtcgcgcgt gacttggagt ttgacatgtc gaaggttaat 1020
gtgaacggtg gggccatagc tctggggcat cctgtgggat gtagtggggc acgtatcctt 1080
gttaccctgc tgcacgaaat gcagaaacgc gacgcaaaga agggcttggc taccttatgt 1140
attgggggag gtcaaggaac agcggtcgta gtggagcgct aa 1182

<210> SEQ ID NO 76
<211> LENGTH: 1182
<212> TYPE: DNA
<213> ORGANISM: Artificial Sequence
<220> FEATURE:
<223> OTHER INFORMATION: Codon-optimized ReuTHLa sequence for E. coli-
based CFPS

<400> SEQUENCE: 76
atgacagacg tcgtaatcgt ttcggcagca agaacagcag ttgggaaatt tggagggagt 60
ttagctaaaa ttcccgctcc cgagctgggg gccgtagtga tcaaagcggc gttagagcgc 120
gctggtgtga aacccgagca ggttagtgaa gtaatcatgg gacaggtact gacggctggt 180
agtggacaaa atccagctag acaagctgca atcaaggcag gacttcctgc gatggtgcct 240
gcgatgacca ttaacaaggt gtgcggttca ggattgaagg cggtcatgtt agcagccaac 300
gcgataatgg ccggagacgc cgagatagta gtggctggag gccaagagaa tatgtctgcg 360
gccccccacg tccttccagg tagtagagat ggttttcgga tgggagacgc caagttagta 420
gacactatga ttgtagacgg tttatgggac gtatacaacc aatatcacat gggaataacg 480
gctgagaacg tcgctaagga atatgggata actcgggaag cccaggacga atttgcggta 540
ggatcgcaaa ataaagccga ggctgctcaa aaggcgggga agtttgatga ggaaattgtt 600
cctgttttaa ttccgcagcg gaaaggagac ccagtagcat tcaaaacgga cgagtttgtc 660
cgccagggcg ctaccttgga ctcaatgtcg ggtcttaaac ctgcgttcga taaagcaggc 720
actgttacag ccgccaacgc cagcggctta aatgatggcg cggctgcagt cgtcgtaatg 780
tcagcagcca aggcgaaaga gcttggcttg acaccattag ctacgattaa atcgtacgcg 840
aatgctggtg tagaccccaa agtcatggga atggggcctg tacccgcgtc gaagagagca 900
ttgtcccggg cggaatggac gccacaagac ctggacctga tggagatcaa tgaagctttc 960
gctgcacagg ctttggcggt tcatcaacag atgggatggg atacttccaa agtcaacgtg 1020
aacggagggg ctatcgcaat aggtcatcct atcggcgcga gcggctgccg gatacttgtc 1080
actttattgc atgaaatgaa gcggagagat gccaagaagg gattggcatc tctgtgtata 1140
ggaggtggca tgggtgtagc tttggctgta gaacgtaagt aa 1182

<210> SEQ ID NO 77
<211> LENGTH: 1185
<212> TYPE: DNA
<213> ORGANISM: Artificial Sequence
<220> FEATURE:
<223> OTHER INFORMATION: Codon-optimized ReuTHLb sequence for E. coli-
based CFPS

<400> SEQUENCE: 77
atgacacgtg aagttgtcgt agtaagtggg gttcgtacgg ccataggtac tttcggaggt 60
tctctgaagg atgttgcccc cgccgagtta ggtgcattag tagtacgtga ggcattagcg 120
cgggcccaag tgtcgggtga tgacgtaggg catgtggttt tcggcaacgt catacagact 180
gagccacgtg atatgtactt gggtcgggta gccgccgtga acggcggggt gacaattaac 240
gctccggcct tgacggtcaa tcggctttgc ggcagcgggc ttcaagctat tgtcagtgca 300
gcccagacca ttcttttggg tgataccgat gtcgcaatcg gcggaggagc agaatcaatg 360
tcgcgcgcgc catatttagc gccagcagcg agatgggggg cccggatggg tgatgcaggg 420
ttagtagata tgatgttagg agcgttgcat gacccatttc atcgtataca catgggagtg 480
acagccgaaa acgtcgctaa agaatacgac atctcgcgcg cgcaacaaga tgaggcagca 540
ttggagagtc acagacgtgc ctcagcagct ataaaagctg ggtatttcaa ggaccagatc 600
gtacctgttg tatccaaggg ccggaaaggt gacgttactt ttgacactga cgaacacgtc 660
cgccacgatg ctaccattga tgatatgacg aaattacgtc ctgtgtttgt aaaggaaaac 720
ggaactgtta ccgctgggaa cgcctcaggg ctgaacgacg cggccgctgc cgttgtaatg 780
atggaacggg ccgaggcgga acgtcgtggt ttgaaaccgc tggcacggtt ggtaagctat 840
ggccacgctg gcgtagatcc aaaggcaatg ggtatcggac ctgttccagc aactaaaatt 900
gctcttgaac gcgctggtct tcaagtcagt gatttagatg taatcgaagc aaatgaggcg 960
ttcgccgcac aagcttgtgc cgtaaccaag gcgctggggt tggatccagc aaaggtgaac 1020
cccaatggga gtggcatatc attggggcac cctataggtg cgacaggcgc gttgattact 1080
gtcaaggcgc tgcatgagtt aaatcgcgta cagggccgtt acgcgcttgt cacaatgtgt 1140
ataggagggg gccaggggat tgccgccatt ttcgaacgca tctaa 1185

<210> SEQ ID NO 78
<211> LENGTH: 1176
<212> TYPE: DNA
<213> ORGANISM: Artificial Sequence
<220> FEATURE:
<223> OTHER INFORMATION: Codon-optimized CklTHL2 sequence for E. coli-
based CFPS

<400> SEQUENCE: 78
atgaaagatg cagttattgt aagtgcagta agaacagcta tagggagttt tggtggaact 60
ttaaaagata tttctgctgt agatttgggg gcaatagtta taaaagaggc tgtaaaaaga 120
gcaggtataa aaccagaaca agtagatgaa gttatatttg gaaatgtaat acaggcaggt 180
cttggacaaa gtccagcgag gcaagctgct gtaaaagcag gcattcctgt agaagtacca 240
gcgtttacac taaataaggt ttgcggttca ggacttagat cagtaagttt ggcagctcag 300
ctcataaaaa ttggagatga tgatattgtt gtagttggtg gaacagaaaa catgtccgct 360
gcaccatatc tacttccaaa ggccagatgg ggacatagaa tgggagaggg aaaattagtt 420
gatgccatga taaaagatgg actttgggaa gcatttaaca attaccacat gggaattaca 480
gctgaaaaca tagcagaaaa atggggaata acaagagata tgcaggatga atttgcatta 540
gcatcccaac agaaggcaga agcagccata aaggcaggaa aatttaaaga tgaaatagtt 600
ccagtaaccg ttaagcagaa aaagaaagaa ataatttttg atactgatga attccctaga 660

```
tttgggacaa ctatagaagc attagcaaaa ttgaaaccat cattcaaaaa agatggaaca    720

gttacagcag gtaatgcttc gggaataaat gatgcagcag cagctttagt tgtaatgagt    780

gcagataagg caaaagaact tggaattaag cctcttgcaa agattgtttc ctatggaagt    840

aaaggattag acccaaccat aatgggatac ggacctttct atgcaacaaa gttggcactt    900

gaaaaagcta acttgtcaat tgcagattta gacttaatag aagcaaatga agcattcgct    960

tcacaaagtt tagcagtagc aaaagattta gaatttgata tgagcaaagt aaatgtaaat   1020

ggaggagcaa tagctcttgg acatccagtt ggctgctctg gtgcaagaat actcgttaca   1080

ttactttatg aaatgcagag aagagatgcg aaaaagggac ttgcaacatt atgtataggg   1140

ggaggaatgg gaactgcact aatagttgaa agataa                             1176
```

```
<210> SEQ ID NO 79
<211> LENGTH: 1179
<212> TYPE: DNA
<213> ORGANISM: Artificial Sequence
<220> FEATURE:
<223> OTHER INFORMATION: Codon-optimized CacTHLm sequence for E. coli-
      based CFPS

<400> SEQUENCE: 79

atgaaagaag ttgtaatagc tagtgcagta agaacagcga ttggatctta tggaaagtct     60

cttaaggatg taccagcagt agatttagga gctacagcta taaaggaagc agttaaaaaa    120

gcaggaataa aaccagagga tgttaatgaa gtcattttag gaaatgttct tcaagcaggt    180

ttaggacaga atccagcaag acaggcatct tttaaagcag gattaccagt tgaaattcca    240

gctatgacta ttaataaggt ttgtggttca ggacttagaa cagttagctt agcagcacaa    300

attataaaag caggagatgc tgacgtaata atagcaggtg gtatggaaaa tatgtctaga    360

gctccttact tagcgaataa cgctagatgg ggatatggaa tgggaaacgc taaatttgtt    420

gatgaaatga tcactgacgg attgtgggat gcatttaatg attacaatat gggaataaca    480

gcagaaaaca tagctgagag atggaacatt tcaagagaag aacaagatga gtttgctctt    540

gcatcacaaa aaaaagctga agaagctata aaatcaggtc aatttaaaga tgaaatagtt    600

cctgtagtaa ttaaaggcag aaagggagaa actgtagttg atacagatga gcaccctaga    660

tttgtatcaa ctatagaagg acttgcaaaa ttaaaacctg ccttcaaaaa agatggaaca    720

gttacagctg gtaatgcatc aggattaaat gactgtgcag cagtacttgt aatcatgagt    780

gcagaaaaag ctaaagagct tggagtaaaa ccacttgcta agatagtttc ttatggttca    840

gcaggagttg acccagcaat aatgggatat ggacctttct atgcaacaaa agcagctatt    900

gaaaaagcag gttggacagt tgatgaatta gatttaatag aatcaaatga agcttttgca    960

gctcaaagtt tagcagtagc aaaagattta aaatttgata tgaataaagt aaatgtaaat   1020

ggaggagcta ttgcccttgg tcatccaatt ggagcatcag gtgcaagaat actcgttact   1080

cttgtacacg caatgcaaaa aagagatgca aaaaaaggct tagcaacttt atgtataggt   1140

ggcggacaag gaacagcaat attgctagaa aagtgctag                          1179
```

```
<210> SEQ ID NO 80
<211> LENGTH: 849
<212> TYPE: DNA
<213> ORGANISM: Artificial Sequence
<220> FEATURE:
<223> OTHER INFORMATION: Codon-optimized CbeHBD sequence for E. coli-
      based CFPS

<400> SEQUENCE: 80
```

```
atgaaaaaga tttttgtgtt gggcgcgggc accatgggtg cgggtatcgt gcaggcgttc     60

gcgcagaaag gttgcgaagt gatcgtgcgc gacattaagg aagaatttgt ggaccgcggc    120

attgcgggca tcaccaaagg cctggaaaag caggtggcga aaggcaaaat gagcgaagaa    180

gataaagaag cgattttaag ccgcatcagc ggcaccaccg atatgaaact ggcggcggac    240

tgcgatctgg tggtggaagc ggcgatcgaa aatatgaaaa tcaagaagga aatcttcgcg    300

gaactggatg gcatctgcaa gccggaagct atcctggcga gcaataccag cagcctgagc    360

atcaccgaag tggcgagcgc gaccaagcgc ccggataaag tgatcggcat gcatttcttt    420

aacccggcgc cggtgatgaa gttggtggaa atcatcaaag gcattgcgac cagccaggaa    480

acctttgatg cggtgaagga actgagcgtg gcgatcggca aagaaccggt ggaagtggcg    540

gaagcgccgg gcttcgtggt gaatcgcatt ctgatcccga tgatcaatga agcgagcttt    600

atcttacagg aaggcattgc gagcgtggaa gatatcgata ccgcgatgaa atatggtgcg    660

aatcatccga tgggcccgct ggcgctgggc gatttgatcg gcctggacgt gtgtctggcg    720

atcatggatg tgctgttcac cgaaaccggt gataataagt accgcgcgtc atcaattctg    780

cgcaaatatg tgcgcgcggg ctggttgggc cgcaaaagcg gcaaaggctt ctatgattac    840

agcaaataa                                                            849
```

<210> SEQ ID NO 81
<211> LENGTH: 849
<212> TYPE: DNA
<213> ORGANISM: Artificial Sequence
<220> FEATURE:
<223> OTHER INFORMATION: Codon-optimized CacHBD sequence for E. coli-based CFPS

<400> SEQUENCE: 81

```
atgaaaaaag tatgtgtcat cggtgccggc acgatgggct cggggattgc tcaagccttc     60

gctgcaaagg gattcgaagt tgtgctgcgt gatatcaagg acgaatttgt ggatcgcggc    120

ctggatttca tcaacaaaaa tctcagcaaa ctggtgaaga aaggcaaaat tgaggaagcc    180

actaaagtgg aaattctgac ccgtatttcc ggcacggttg acctgaatat ggcggccgat    240

tgtgacctgg ttattgaagc ggcggtcgaa cgcatggata tcaagaaaca aatctttgcc    300

gatcttgata acatttgcaa accggagact atcctcgcct caaatacaag cagtttaagt    360

attaccgaag tggcaagcgc tacaaaacgg cccgataaag tgattggaat gcatttttttc    420

aacccagccc cggttatgaa actggttgaa gtgattcgcg gcatcgctac ctcccaagaa    480

acctttgatg cagttaaaga aacctcgatc gccattggta aagatccagt ggaggtagcc    540

gaagcgccgg gcttcgtggt taatcggatc ttaattccga tgattaacga agctgttggc    600

attctggccg aaggcattgc gtccgtggaa gacatcgaca aagcaatgaa attgggtgca    660

aatcacccta tgggtccact cgaacttggc gattttatcg gtcttgatat ttgcctggcg    720

atcatggacg tgctgtattc agagacaggc gatagtaaat accgcccgca cacgctgctg    780

aaaaaatatg ttcgggctgg ctggctgggg cgtaaatctg gtaagggttt ttacgattat    840

tccaaataa                                                            849
```

<210> SEQ ID NO 82
<211> LENGTH: 849
<212> TYPE: DNA
<213> ORGANISM: Artificial Sequence
<220> FEATURE:
<223> OTHER INFORMATION: Codon-optimized CpaHBD sequence for E. coli-based CFPS

<400> SEQUENCE: 82
atgaaaaaga tctttgtgtt gggcgccggc accatgggtg ccggtattgt gcaggccttt 60
gcacagaaag ggtgcgaagt gattgtgcgc gatatcaaag aagaatttgt agatcgcgga 120
atcgctggta ttacgaaagg gttagaaaaa caagtggcta aagggaaaat gagcgaggag 180
gataaagagg ccattctttc gcgcattagc ggcaccaccg atatgaaatt agctgcggat 240
tgtgatctgg tggttgaagc agcaattgaa aacatgaaaa tcaaaaaaga aatttttgcc 300
gagctggatg gcatttgtaa accggaagcc attttagcct caaatacctc tagcctgagt 360
atcaccgaag tagccagcgc gaccaaacgc cccgataaag ttattggaat gcatttcttc 420
aaccctgcac cagtgatgaa actggtggaa attattaagg gaattgcaac cagtcaagaa 480
acgtttgatg cggttaaaga actgtcggtc gctattggca aagagccagt ggaagtcgcc 540
gaagccccgg gctttgtggt caatcggatt ctgatcccga tgattaacga agccagcttt 600
atcttgcagg aaggaattgc gagcgtggaa gatatcgata cggcgatgaa atacggggca 660
aatcacccga tgggcccgct ggctttgggg gacctgattg gcctggacgt ttgcctggcg 720
attatggacg tgttgtttac tgaaaccggc gacaacaagt atcgtgcgag ttcaatcctc 780
cgtaaatatg tgcgggccgg gtggctcggt cgcaaatcgg gcaaaggctt ttatgactac 840
agcaaataa 849

<210> SEQ ID NO 83
<211> LENGTH: 846
<212> TYPE: DNA
<213> ORGANISM: Artificial Sequence
<220> FEATURE:
<223> OTHER INFORMATION: Codon-optimized CsaHBD sequence for E. coli-
based CFPS

<400> SEQUENCE: 83
atgaagattt tcgtgttggg agcggggaca atgggggctg ggatcgtcca gatttttgca 60
gaggccggtt atcaggtgat catgcgtgat atcgaagaga gtttcgtcca gaagggtatc 120
acaaatatta ctaaaaactt agacaaagcc gttaaaaaag aaaaaatcac ggaggaaagc 180
aaaaacgaag tgctgggacg catcatcgcc accacggaca ttaaccttgc aaaagacgca 240
gatttagtta tcgaagcagc cattgaaaac atgaatatta aaaaaaagat ctttgcggag 300
cttgacgacg tttgtaaacc cgaaactatt ctggcgacaa acacgtcatc cttaagtatc 360
accgacgtgg catccgcgac taagcgtcct gacaaggtta ttgggatgca ctttttttaat 420 cctgttccag tcatgaaact ggtagaagta atcaccggta tggcgacgtc ggcggaaacg 480
aaagataccg ttattgaaat taccaagaag gtaggtaagg atccggtaga agtgaaagaa 540
gcaccgggct ttgtagtgaa tcgcatttta atcccgatga tcaatgaagc ggtaggtatc 600
ctggcggata atgtcgctac cgccgaagat attgatatcg caatgaaact gggcgcgaac 660
cacccgatgg gtccgctggc cctggccgat ctgattggga acgatgtgtg tctggccatc 720
atggaaattc tgtacattga atttggggat cctaaatatc ggccgaatcc aatgctgcgg 780
aaaatggtgc gcgcaggtta tctgggccgt aaaacgggca agggctttta tgattattcc 840
aagtaa 846

<210> SEQ ID NO 84
<211> LENGTH: 849
<212> TYPE: DNA

-continued

<213> ORGANISM: Artificial Sequence
<220> FEATURE:
<223> OTHER INFORMATION: Codon-optimized CklHBD1 sequence for E. coli-
based CFPS

<400> SEQUENCE: 84
atgagcatca aatctgtggc cgtactgggc tcggggacga tgagccgtgg tattgttcag 60
gctttcgcag aagcgggtat cgatgtgatc atccgcggtc gcacggaagg cagtatcggg 120
aaagggcttg ctgctgttaa aaaggcgtat gataagaaag tctcaaaagg taaaattagc 180
caagaagacg cagacaaaat cgtgggccgt gtgagtacaa ccactgagct cgaaaaactg 240
gctgattgtg atctcatcat cgaagcggcc tctgaggaca tgaacattaa aaaagactac 300
ttcggcaagc tggaagagat ctgcaaacct gaaacaattt ttgcgacgaa cacatcttcg 360
ttgtccatca cggaagtcgc gacagcgact aaacgcccgg ataaattcat cggtatgcat 420
tttttcaatc cggcaaacgt tatgaaatta gttgagatta tccgcgggat gaatacgtcc 480
caggagacgt ttgacatcat caaagaagcc agcatcaaaa ttggcaaaac ccctgtggaa 540
gtggcggaag cgccgggttt tgtggttaac aaaatcctgg tgccaatgat caacgaagcc 600
gttggcatcc tggccgaagg gattgcatca gcggaagaca ttgacactgc aatgaaactg 660
ggcgccaacc atcctatggg gccgcttgcc ctcggagact taattgggtt agacgtggtc 720
ttagctgtga tggatgtgct gtattcggaa accggcgact ctaaataccg tgcgcatact 780
ctgctgcgca agtatgtccg tgcaggttgg ctgggccgca aaagcggtaa aggtttttc 840 gcctactaa 849

<210> SEQ ID NO 85
<211> LENGTH: 960
<212> TYPE: DNA
<213> ORGANISM: Artificial Sequence
<220> FEATURE:
<223> OTHER INFORMATION: Codon-optimized CklHBD2 sequence for E. coli-
based CFPS

<400> SEQUENCE: 85
atggatatca aaaatgtggc cgtactcggc acgggcacta tgggtaacgg catcgtccag 60
ctgtgcgctg agagcggtct taatgtaaat atgtttggtc ggaccgatgc tagcctcgaa 120
cgcggattta caagtatcaa aacgtccctg aaaaacctgg aggaaaaagg gaaaattaaa 180
acgaatattt ctaaagaaat tctgaagcgt atcaaaggcg taaaaacaat tgaagaagca 240
gtcgaaggcg tggacttcgt gattgaatgt attgcggaag acctggaact gaaacaagaa 300
gtctttagca agctggacga gatctgtgct cccgaagtga tcttagcgag caataccagt 360
ggcctgtcgc cgaccgacat cgctatcaac acgaaacacc cggagcgggt tgtaattgcg 420
cacttttgga acccgccaca gtttattccg ctggtagagg ttgtgccggg aaaacatact 480
gatagtaaaa ccgtggacat caccatggat tggatcgaac atatcggtaa aaaaggcgtg 540
aaaatgcgca aagagtgcct ggggtttatc ggcaaccgtc tgcaactggc ccttctgcgt 600
gaggcacttt atatcgttga acaaggtttc gccacggcgg aggaagttga taaggcaatt 660
gagtatgggc atggccggcg tctccctgtg acgggcccga tctgttccgc ggatctgggc 720
ggtctggata ttttcaataa catcagttcg tatttgttta aagatttatg taacgatact 780
gaaccaagca agcttttgaa atcgaaagtc gacggcggta atctgggctc taaaaccggt 840
aaaggtttct ataactggac acccgagttc ttacaaaaaa agcagaatga acgtattcag 900
ctgctgatgg acttcctgga aaaagacaaa aacgataaaa gcattgaacg caacatttaa 960

<210> SEQ ID NO 86
<211> LENGTH: 786
<212> TYPE: DNA
<213> ORGANISM: Artificial Sequence
<220> FEATURE:
<223> OTHER INFORMATION: Codon-optimized CacCRT sequence for E. coli-
based CFPS

<400> SEQUENCE: 86
atggaactta ataacgtaat cttagaaaag gaaggtaaag tggcggtggt gacaatcaat 60
cgcccgaaag cgctgaacgc tctgaacagc gataccctca aagaaatgga ttatgtgatt 120
ggtgaaatcg aaaacgattc agaagtgtta gcggtgatcc tgaccggcgc gggcgaaaaa 180
agctttgtgg cgggcgcgga tatcagcgag atgaaggaaa tgaacacaat cgaaggtcgc 240
aaattcggaa ttttgggcaa caaagtattt cgccgcctgg aattattaga aaagccggtg 300
attgcggcgg tgaacggttt tgcgctgggc ggaggctgtg aaattgcgat gagctgcgat 360
attcgcattg cgagctcaaa tgcgcgcttt ggtcagccgg aagtgggtct aggcattacc 420
ccgggttttg gtggtaccca gcgcttaagc cgcctggtgg gcatgggaat ggcgaagcaa 480
ttgattttta ccgcgcagaa cattaaggcg gatgaagcgc tgcgcatcgg cttggtgaac 540
aaggtggtgg aaccgagcga actgatgaac accgcgaaag aaatcgcgaa taaaatcgta 600
tcaaacgcgc cggtggcggt gaagctgtca aaacaagcga tcaaccgcgg catgcaatgc 660
gatatcgata ccgcgctggc gtttgaaagc gaagcgtttg gcgaatgttt tagcaccgag 720
gatcagaagg atgcgatgac cgcgttcatt gagaaacgca aaatcgaagg attcaaaaac 780
cgctga 786

<210> SEQ ID NO 87
<211> LENGTH: 795
<212> TYPE: DNA
<213> ORGANISM: Artificial Sequence
<220> FEATURE:
<223> OTHER INFORMATION: Codon-optimized PpuCRT sequence for E. coli-
based CFPS

<400> SEQUENCE: 87
atgacaaccc cgagcagccc tctgttaagc aaagttgagg ctggcgtagc gtggattacc 60
ttgaaccgcc cagaacagcg caacgccctg gatatcccaa ccttaaaaca actgcatgcg 120
ttattagata gccacgcgga tgatccagcg gtacgcgtgg tggtgctgac cggcagcggc 180
cgcagctttt gcgctggcgc ggatctggcg gagtgggctg cggcggaggc tgcgggcacc 240
ctggagagct acggctggac cgagacagcg cacgcgctga tgttgcgcct gcatagcttg 300
gataagccaa ccattgcggc gattaacggc accgcggtgg gcgggggcat ggatctcagc 360
ctgtgctgcg atctgcgcat tgcggcggcg agcgcccgct ttaaagcggg ctataccagc 420
atgggctata gcccagacgc gggcgcgagc tggcatctgc ctcggctgat tggcagcgaa 480
caggcgaaac gcttgttatt tttggacgag ctgtggggcg cggaacacgc gctggccgct 540
gggctggtta gcgaggtttg cgcggatgaa caactgccag cggtggccgc ggaattagcg 600
gggcgcctgg cgaatggccc gacttttgcg tacgcccaga ccaaacagct gattcgcgat 660
ggcgcgcggc gcaccttagc ggaacagctg gaagctgaac gccatgcggg cctgctgtgc 720
ggccgcagcc aggacggcgc ggaagcgctg caagcgagcg tagagcgccg cgcgccacgg 780
ttcaccggcc agtga 795

<210> SEQ ID NO 88
<211> LENGTH: 786
<212> TYPE: DNA
<213> ORGANISM: Artificial Sequence
<220> FEATURE:
<223> OTHER INFORMATION: Codon-optimized CbeCRT sequence for E. coli-
based CFPS

<400> SEQUENCE: 88
atggagttaa agaatgtaat ccttgaaaag gagggccacc ttgctatagt tacgatcaat 60
cgcccgaagg cattaaatgc actgaactca gaaaccctta aagacttgaa tgttgttctg 120
gacgatcttg aagccgacaa caatgtttac gccgtaatcg tcacaggagc aggcgaaaag 180
tcgtttgtag ctggcgcgga catcgcagag atgaaagact taaatgaaga gcaaggaaaa 240
gagttcggga tactgggcaa caatgtcttc agaagacttg aaaaattaga taagcccgta 300
attgcagctg tgagcggttt tgcattaggt gggggctgcg agctggctat gagctgcgac 360
atacgcatag catcggttaa ggccaaattc ggtcaacccg aggttggatt gggcataacg 420
ccgggattcg gcggtactca gcggttagca agaattgttg ggccggggaa agctaaagaa 480
cttatataca cttgtgacat cataaacgcc gaagaagcct accggattgg gttagttaat 540
aaggtagttg agttggagaa gctgatggaa gaggcaaaag cgatggcaaa caagattgca 600
gccaatgctc ccaaagctgt cgcatattgc aaggacgcta ttgatcgggg gatgcaagtt 660
gacattgacg ccgctatatt gatagaagcg gaagactttg ggaaatgttt cgcaacggaa 720
gatcaaacgg aaggaatgac agcattcttg gaaagacgca ccgaaaagaa cttccagaat 780
aagtaa 786

<210> SEQ ID NO 89
<211> LENGTH: 780
<212> TYPE: DNA
<213> ORGANISM: Artificial Sequence
<220> FEATURE:
<223> OTHER INFORMATION: Codon-optimized CklCRT sequence for E. coli-
based CFPS

<400> SEQUENCE: 89
atggagttta agaatataat tctggagaaa gacgggaacg tcgcttccat aacattaaat 60
cgcccgaaag ccctgaatgc cttaaatgct gctacgctga aggaaatcga cgcagcaatc 120
aatgacatcg ctgaagacga caatgtttat gccgtgataa tcacaggttc ggggaaagca 180
ttcgtcgcgg gagccgatat cgcagaaatg aaggacttaa cggccgtaga gggtcgtaaa 240
ttttcggtgt tgggcaataa gatatttcgc aagctggaga ccttggaaaa gccagtgatt 300
gcagctatta acggattcgc actgggtgga ggatgcgagt tgtccctttc atgcgatata 360
cgcatagcgt cgagtaaggc gaaattcggg caacccgagg ttggcttagg gatcacccca 420
ggcttcggag ggactcagcg cctggcccgt gctattggcg tgggaatggc aaaagaactg 480
atttacaccg gtaaggtcat aaacgccgaa gaggcacttc gggtcggact ggtaaataaa 540
gtggtcgagc cagataagtt attagaagaa gcaaagtctc tggtggacgc gatcattgtt 600
aatgctccaa tagccgtacg gatgtgcaaa gctgccataa accaaggatt gcagtgtgat 660
attgataccg cagttgcata cgaagcagag gttttcgggg aatgttttgc tacggaagat 720
cgtgtcgagg gcatgacggc tttcgtggag aagcgtgata aggcttttaa gaataagtaa 780

<210> SEQ ID NO 90
<211> LENGTH: 786

<212> TYPE: DNA
<213> ORGANISM: Artificial Sequence
<220> FEATURE:
<223> OTHER INFORMATION: Codon-optimized CpaCRT sequence for E. coli-based CFPS

<400> SEQUENCE: 90
atggagctga aaaacgtcat actggacaag gaaggaaaga tcgctgtggt taccattaac 60
cgtccgaatg ctcttaatgc acttaattcc gagacactta aagaattgga ttacgtcatc 120
gatgaaatag aaaacgattc gaacgtcttt gccgttattc ttacaggagc tggtgagaaa 180
tcatttgtcg ctggagcgga catcgccgag atgaaggaca tgaacaccat cgagggtcgg 240
aaatttggta ttttaggaaa tcgtgtattt cgtcgtattg aactgctgga aaagccagtg 300
attgcggcgg tcaatgggtt tgccctgggt ggcgggtgtg agctgagcat gtcatgcgat 360
attagaatcg cttcctcgaa cgcccggttt ggacagcctg aggtcggatt gggcattact 420
ccggggtttg gaggtacaca gcgtctggct cgtttggttg gcatgggtat ggcgaagcag 480
attattttca ctgccaagaa tatcaaagcg gatgaagcac tgagaattgg gttggtcaac 540
aaggtggtgg agccgggaga attgatggat actgcaaagg atattgcaaa cacaattgca 600
tccaaggctc caatcgctgt aaaactttcg aaacaggcaa tcaatagagg atttcagtgc 660
gacatcgaca cggctctgtc gtttgagtcc gaagccttcg gcgagtgttt ctcgacggaa 720
gaccagaaag atgcaatgac cgcatttgtg gagaagaaaa aaatcgatgg gttcaagaat 780
agataa 786

<210> SEQ ID NO 91
<211> LENGTH: 786
<212> TYPE: DNA
<213> ORGANISM: Artificial Sequence
<220> FEATURE:
<223> OTHER INFORMATION: Codon-optimized CsaCRT sequence for E. coli-based CFPS

<400> SEQUENCE: 91
atggagttaa agaacgtaat cttggaaaag gagggccatc tggccattgt gacgattaat 60
agaccgaaag ctttaaacgc cttgaactcg gagacactga aagacttgga taccgttatt 120
gaagaccttg aaaaggactc gaacgtatat agcgttatct tgactggcgc aggcgaaaag 180
tcattcgtgg caggagcaga tataagtgag atgaaagact tgaacgaaca gcagggtaag 240
gaatttggga tcttggggaa caatgtcttt cggcgtttgg aaaagcttga taagccagtc 300
atcgctgcca ttagtgggtt tgcgttgggc gggggttgtg aattggcaat gagctgtgac 360
attcgtatcg cctcggagaa agccaaattt ggtcaacctg aggccggtct gggaataacg 420
cctggctttg gtggtactca acgcttagcg cgtattgttg ggttaggcaa ggcaaaagag 480
atgatttata cttgtgatat aataaaagct gaagaggcat atcgcatagg gctggtgaat 540
aagatagtac ccctggagaa cttaatggac gaggctaaag ctatggccaa taaaatcatg 600
gcaaatgcac caaaggccgt aaagtactgc aaggatgcta ttaatcgggg tatgcaagtc 660
gatattgacg ccgcaatttt aattgaagct gaggatttcg gtaaatgctt cgccaccgag 720
gatcaaacgg agggcatgac cgcattcctt gaaagaagaa ccgagaagaa cttccagaac 780
aagtaa 786

<210> SEQ ID NO 92
<211> LENGTH: 2577
<212> TYPE: DNA

<213> ORGANISM: Artificial Sequence
<220> FEATURE:
<223> OTHER INFORMATION: Codon-optimized TdeTER sequence for E. coli-
based CFPS

<400> SEQUENCE: 92
atgaaggtaa ccaaccagaa agagctgaaa caaaaattaa acgaactccg cgaagcgcaa 60
aaaaaattcg cgacgtatac tcaggaacaa gtcgataaga tctttaaaca atgtgccatt 120
gcagcggcca aagaacgcat caacctggcg aagttggccg ttgaagaaac cggaattggt 180
ttagtggaag acaaaattat taagaaccat ttcgctgcgg aatatattta taataaatac 240
aaaaatgaga agacctgcgg aattattgat catgatgata gccttggtat cactaaagta 300
gcagaaccaa tcggtatcgt cgccgccatc gttcctacaa ccaatccgac ctctacggcg 360
atctttaaat cattgattag cctgaaaacg cgtaacgcga tttttttcag ccctcaccca 420
cgcgccaaaa aaagcactat cgctgcggcg aaactgattc tggatgcggc agttaaagcc 480
ggcgcaccta aaaacattat cggctggatc gacgagccta gcatcgagtt gagccaggac 540
ctcatgagtg aagcagatat tatcctcgcc acgggtgggc catctatggt taaagcggcc 600
tactcatctg gtaaaccagc catcggtgtg ggtgcgggca ataccccggc gatcattgac 660
gagagcgccg atattgatat ggccgttagt agcatcattc tgagcaaaac ctacgataac 720
ggcgtaattt gcgcgagtga acagagcatt ttagtgatga actcgatcta tgaaaaagtg 780
aaagaagaat ttgtgaagcg cggttcttac atcctcaacc aaaatgaaat cgcgaaaatc 840
aaagaaacga tgttcaaaaa tggcgcgatc aacgcggata ttgttggcaa atcagcctac 900
attattgcga aaatggcggg tattgaagtc ccccagacca caaagatcct gatcggtgaa 960
gtacagagcg tcgaaaagag cgagctgttc agccacgaga aactgagccc tgttctggcc 1020
atgtacaagg taaaagattt tgacgaagca cttaaaaaag cccaacgcct tatcgaatta 1080
ggagggtctg gccacacgag cagcttgtac atcgacagcc agaataacaa agacaaagtc 1140
aaagaattcg gccttgcaat gaaaacttct cgcaccttta ttaatatgcc gtccagccag 1200
ggcgcctctg gtgatctgta caattttgcc attgccccgt cgtttaccct ggggtgtggg 1260
acctggggcg ggaattcggt atcacagaac gtcgaaccaa aacacctgtt gaatattaaa 1320
tccgtggcag agcgccgcga gaacatgctg tggttcaaag tccctcagaa aatttacttc 1380
aagtacggct gcctgcgttt tgcgctgaaa gaactcaaag acatgaacaa aaaacgtgcg 1440
ttcatcgtta ccgataagga cctgtttaaa ctgggctacg taaacaaaat tactaaagtg 1500
ttggacgaaa tcgatattaa atactccatt tttaccgaca ttaagtcaga cccgaccatc 1560
gacagcgtca aaaaaggggc aaaagaaatg ctgaactttg agccagatac gattatctca 1620
atcggtgggg gctcgcctat ggacgctgcg aaagtgatgc acctgctgta tgagtacccg 1680
gaagcggaga ttgagaacct ggccatcaat tttatggata ttcgtaagcg tatttgcaat 1740
tttccgaaac ttgggacgaa agccatctcc gtcgcgattc cgaccactgc aggtacgggc 1800
agcgaagcca cgccttttgc agttatcacg aacgatgaga ccggtatgaa atatccgctc 1860
acctcgtacg aactgacccc aaatatggcc atcattgata ccgaactgat gctcaatatg 1920
ccccgtaaac tcaccgcagc cactggcatt gacgcactcg tgcacgccat tgaggcttat 1980
gtcagcgtga tggcgaccga ttacaccgat gaattagctc tccgtgcaat caaaatgatt 2040
tttaagtacc tcccgcgtgc gtacaaaaat ggcacgaatg atatcgaggc gcgtgaaaag 2100
atggctcatg ccagcaacat cgccggtatg gcgttcgcta atgccttcct gggtgtatgc 2160

```
cacagtatgg cacacaagct cggcgccatg catcatgtac cacacgggat tgcctgtgcc   2220

gtgttaatcg aggaagtcat taagtacaat gccaccgatt gcccgactaa acagaccgcc   2280

tttccgcagt ataagagccc gaatgcaaaa cgtaaatacg ccgagatcgc tgagtatttg   2340

aatctcaaag gaacgagtga tactgagaaa gtcaccgcct tgatcgaagc catcagcaaa   2400

cttaaaatcg atctgtcgat tccgcagaac attagcgcgg ccggtattaa caagaaagat   2460

ttttacaaca cgctggacaa aatgtctgaa ctggcgtttg acgatcagtg caccacggcg   2520

aacccgcgct atcctctgat ttccgagctc aaggatatct acatcaaaag cttctaa      2577
```

<210> SEQ ID NO 93
<211> LENGTH: 1218
<212> TYPE: DNA
<213> ORGANISM: Artificial Sequence
<220> FEATURE:
<223> OTHER INFORMATION: Codon-optimized FsuTER sequence for E. coli-
      based CFPS

<400> SEQUENCE: 93

```
atgattatta aaccactgat ccgctctaat atgtgtatca acgcgcatcc gaaaggttgt     60

gccgccgacg tgaaacatca aatcgagttc atcaaaaaga aattcacgac ccgctcaatc    120

ccggcggacg cgccaaaaac agtgttagtc ctgggctgct ccactggata cggcttagca    180

tcacgcatcg tcgcggcttt tggttacaag gctgcaacga ttggggtatc gttcgaaaaa    240

gaaggctccg acggaggaat cggtgagagt cgtgagaaaa caggcacccc gggctggtat    300

aacaacatgg cgtttgataa gttcgcgaag gaagccggtc tggatgcggt caccttcaac    360

ggtgacgcct ttagccatga aatgcgtcag aatgttatcg ataccctgaa aaaaatgggt    420

cgcaaagtag atctcttggt ctattctgtc gcaagctcag tccgcgttga tccagataac    480

gggaccatct accgctcagt tctgaagccc atcgacaaag tgttcaccgg ggcgacgatc    540

gattgcctgt ctggtaagat ttcgacaatt tcggccgaac ctgcgacggc agaagaagcg    600

gcgaacacgg tcaaagtgat gggtggcgag gattgggcgt tgtgggtgcg caaactgaaa    660

gaggcaggcg tccttgcgga aggtgttaaa actgtggcct attcctatat cggcccgaaa    720

ctcagccacg ctatctatcg cgacggcact atcgggggtg ccaaaaaaca cttggaagct    780

acggctcttg aacttaacaa agagctccag aatgatctcc atggggaggc gtatgtgtcg    840

gtgaataaag gtttagtgac gcgcagctca gcagtgatcc cgatcattcc gatgtacatt    900

tcggttctgt ttaaagtcat gaaagaaatg ggcaaccacg aaggctgtat tgaacagatg    960

gaacgcctga tgacggaacg cttgtatacc ggctctaaag tgcccaccga cgaaaaccat   1020

ttgatccgta ttgacgatta tgaattggat ccgaaggtcc aggcggaagt tgataagcgc   1080

atggctacag tgactcagga aaatttggcg gaagtgggtg atctggaagg ataccgtcac   1140

gactttttgg caaccaatgg cttcgatatt gacggtgtgg actacgaggc cgatgtgcaa   1200

acgttaacct caatttga                                                 1218
```

<210> SEQ ID NO 94
<211> LENGTH: 1191
<212> TYPE: DNA
<213> ORGANISM: Artificial Sequence
<220> FEATURE:
<223> OTHER INFORMATION: Codon-optimized FjoTER sequence for E. coli-
      based CFPS

<400> SEQUENCE: 94

```
atgatcatcg agccgcgcat gcgcggtttt atctgcctga ctgcgcatcc ggcgggatgt     60
```

```
gaacagaatg ttaaaaatca gatcgagtat attaaatcga aaggggcaat cgccggcgcc    120
aaaaaggttc tggtgatcgg cgcatccacg ggtttcggtt tagcatcccg tatcaccagt    180
gcgttcggct cagatgctgc tacgattggc gtgttcttcg aaaaaccgcc cgtcgaaggt    240
aagacagcgt cgccagggtg gtataattcg gccgcatttg agaaagaggc acataaagcg    300
ggtctttacg ctaaatctat caatggagac gctttcagca acgaaattaa acgtgaaacc    360
ttagatctga tcaaagcgga tttaggtcag gttgatctgg taatttattc gctggcgtcc    420
ccggttcgta cgaacccgaa cacaggtgtg actcaccgca gtgtgttgaa accgatcggt    480
cagactttta caaacaaaac tgtggatttt catacgggga acgtgtccga agtttctatc    540
gcgccggcta atgaagaaga tattgaaaat acggtagcag tgatgggcgg agaagattgg    600
gcgatgtgga ttgatgccct caaaaatgaa aatctgctgg cagagggggc gacgacaatt    660
gcatattcct atattggccc ggaattgacc gaagcggtct accgtaaagg caccattggt    720
cgtgcaaaag accacctgga ggcgaccgct ttcaccatta ctgataccct taaatcgtta    780
ggcggaaaag cgtacgtgtc ggtgaataaa gccttggtta cgcaagcctc gtcggcgatt    840
cctgtgatcc cgctgtatat ctcgctgctt tataaaatta tgaaggagga aggaattcac    900
gagggatgca tcgaacaaat tcagcgcttg ttccaagatc gtttgtataa cggtagcgaa    960
gtgccggttg atgagaaagg ccgcatccgc attgacgatt gggagatgcg cgaggatgtg   1020
caggctaaag ttgcggctct gtggaaggaa gccaccaccg aaaccctgcc atccatcggc   1080
gacctggcag gttaccgtaa tgacttctta aacctgtttg ggtttgaatt tgcgggagtg   1140
gattacaagg cggatacgaa cgaggtcgta aacattgaaa gcatcaaata a            1191
```

<210> SEQ ID NO 95
<211> LENGTH: 2577
<212> TYPE: DNA
<213> ORGANISM: Artificial Sequence
<220> FEATURE:
<223> OTHER INFORMATION: Codon-optimized CacADH sequence for E. coli-
based CFPS

<400> SEQUENCE: 95

```
atgaaggtaa ccaaccagaa agagctgaaa caaaaattaa acgaactccg cgaagcgcaa     60
aaaaaattcg cgacgtatac tcaggaacaa gtcgataaga tctttaaaca atgtgccatt    120
gcagcggcca aagaacgcat caacctggcg aagttggccg ttgaagaaac cggaattggt    180
ttagtggaag acaaaattat taagaaccat ttcgctgcgg aatatattta taataaatac    240
aaaaatgaga agacctgcgg aattattgat catgatgata gccttggtat cactaaagta    300
gcagaaccaa tcggtatcgt cgccgccatc gttcctacaa ccaatccgac ctctacggcg    360
atctttaaat cattgattag cctgaaaacg cgtaacgcga ttttttttcag ccctcaccca    420
cgcgccaaaa aaagcactat cgctgcggcg aaactgattc tggatgcggc agttaaagcc    480
ggcgcaccta aaaacattat cggctggatc gacgagccta gcatcgagtt gagccaggac    540
ctcatgagtg aagcagatat tatcctcgcc acgggtgggc catctatggt taaagcggcc    600
tactcatctg gtaaaccagc catcggtgtg ggtgcgggca ataccccggc gatcattgac    660
gagagcgccg atattgatat ggccgttagt agcatcattc tgagcaaaac ctacgataac    720
ggcgtaattt gcgcgagtga acagagcatt ttagtgatga actcgatcta tgaaaaagtg    780
aaagaagaat ttgtgaagcg cggttcttac atcctcaacc aaaatgaaat cgcgaaaatc    840
aaagaaacga tgttcaaaaa tggcgcgatc aacgcggata ttgttggcaa atcagcctac    900
```

```
attattgcga aaatggcggg tattgaagtc ccccagacca caaagatcct gatcggtgaa    960

gtacagagcg tcgaaaagag cgagctgttc agccacgaga aactgagccc tgttctggcc   1020

atgtacaagg taaaagattt tgacgaagca cttaaaaaag cccaacgcct tatcgaatta   1080

ggagggtctg gccacacgag cagcttgtac atcgacagcc agaataacaa agacaaagtc   1140

aaagaattcg gccttgcaat gaaaacttct cgcaccttta ttaatatgcc gtccagccag   1200

ggcgcctctg gtgatctgta caattttgcc attgccccgt cgtttaccct ggggtgtggg   1260

acctggggcg ggaattcggt atcacagaac gtcgaaccaa aacacctgtt gaatattaaa   1320

tccgtggcag agcgccgcga gaacatgctg tggttcaaag tccctcagaa aatttacttc   1380

aagtacggct gcctgcgttt tgcgctgaaa gaactcaaag acatgaacaa aaaacgtgcg   1440

ttcatcgtta ccgataagga cctgtttaaa ctgggctacg taaacaaaat tactaaagtg   1500

ttggacgaaa tcgatattaa atactccatt tttaccgaca ttaagtcaga cccgaccatc   1560

gacagcgtca aaaaaggggc aaaagaaatg ctgaactttg agccagatac gattatctca   1620

atcggtgggg gctcgcctat ggacgctgcg aaagtgatgc acctgctgta tgagtacccg   1680

gaagcggaga ttgagaacct ggccatcaat tttatggata ttcgtaagcg tatttgcaat   1740

tttccgaaac ttgggacgaa agccatctcc gtcgcgattc cgaccactgc aggtacgggc   1800

agcgaagcca cgccttttgc agttatcacg aacgatgaga ccggtatgaa atatccgctc   1860

acctcgtacg aactgacccc aaatatggcc atcattgata ccgaactgat gctcaatatg   1920

ccccgtaaac tcaccgcagc cactggcatt gacgcactcg tgcacgccat tgaggcttat   1980

gtcagcgtga tggcgaccga ttacaccgat gaattagctc tccgtgcaat caaaatgatt   2040

tttaagtacc tcccgcgtgc gtacaaaaat ggcacgaatg atatcgaggc gcgtgaaaag   2100

atggctcatg ccagcaacat cgccggtatg gcgttcgcta atgccttcct gggtgtatgc   2160

cacagtatgg cacacaagct cggcgccatg catcatgtac cacacgggat tgcctgtgcc   2220

gtgttaatcg aggaagtcat taagtacaat gccaccgatt gcccgactaa acagaccgcc   2280

tttccgcagt ataagagccc gaatgcaaaa cgtaaatacg ccgagatcgc tgagtatttg   2340

aatctcaaag gaacgagtga tactgagaaa gtcaccgcct tgatcgaagc catcagcaaa   2400

cttaaaatcg atctgtcgat tccgcagaac attagcgcgg ccggtattaa caagaaagat   2460

ttttacaaca cgctggacaa aatgtctgaa ctggcgtttg acgatcagtg caccacggcg   2520

aacccgcgct atcctctgat ttccgagctc aaggatatct acatcaaaag cttctaa      2577
```

<210> SEQ ID NO 96
<211> LENGTH: 1194
<212> TYPE: DNA
<213> ORGANISM: Artificial Sequence
<220> FEATURE:
<223> OTHER INFORMATION: Codon-optimized TdeTER sequence for C. autoethanogenum-based CFPS

<400> SEQUENCE: 96

```
atgatagtta aaccaatggt aagaaataat atatgtttaa atgctcaccc acaaggatgt     60

aagaaaggag tagaagatca aatagaatat acgaaaaaaa gaataacagc tgaagtaaag    120

gctggcgcca aagcacctaa aaatgttttg gtactaggat gttcaaatgg ttatggattg    180

gcatcgagaa taaccgctgc ttttggttac ggtgcagcta caataggagt aagttttgaa    240

aaagctggca gtgaaactaa gtacggaact cctggttggt acaataattt agcttttgat    300

gaagcagcta agagagaagg attatattct gtaactatag atggagatgc attttcagat    360
```

```
gaaataaaag cacaggttat agaagaagcc aaaaaaaagg gaataaagtt tgatttaata    420
gtatattcat tagcatctcc tgtaaggaca gatccagata caggaataat gcataaatca    480
gtacttaaac cttttggaaa gacctttacc ggaaaaactg tagacccttt tacaggtgaa    540
ttaaaagaaa taagtgctga accagctaat gatgaagagg ctgctgctac tgttaaagta    600
atgggcggcg aggattggga aagatggata aagcagcttt caaaggaagg attattagaa    660
gaaggctgca ttacacttgc ttattcttat ataggaccag aagcaacgca ggcattatat    720
agaaaaggta caataggaaa agcaaaagaa catctagagg caactgcaca tagactaaat    780
aaggaaaatc caagcattag agcatttgta tctgttaata agggattagt aaccagagcc    840
agcgctgtta tacctgttat acctttgtat ttagcttccc tttttaaagt tatgaaggaa    900
aaaggaaatc atgaaggatg tatagagcaa attactagac tctatgctga acgattgtat    960
agaaaagatg gaactattcc tgttgatgaa gaaaatagaa taagaataga tgattgggag   1020
cttgaagagg atgttcaaaa agcagtttcc gctcttatgg aaaaagttac cggtgaaaat   1080
gcagaaagct taacagacct tgctggatat agacatgatt ttcttgcttc aaatggattt   1140
gatgttgaag gaataaacta tgaagcggaa gttgaaagat ttgatagaat ttaa         1194
```

```
<210> SEQ ID NO 97
<211> LENGTH: 1218
<212> TYPE: DNA
<213> ORGANISM: Artificial Sequence
<220> FEATURE:
<223> OTHER INFORMATION: Codon-optimized FsuTER sequence for C.
      autoethanogenum-based CFPS

<400> SEQUENCE: 97
```

```
atgataataa aaccactaat aagaagcaat atgtgtataa atgcccaccc aaagggatgt     60
gctgctgatg taaaacatca aatagagttt attaaaaaga aattcactac tagatccata    120
cctgcagatg cacctaaaac agtattagtt ttaggatgta gtacaggata tggactagct    180
tctaggatag tggcagcttt tggatataaa gcagctacaa ttggtgtttc ctttgaaaag    240
gaaggttcag atggcggcat aggagaaagt agagaaaaga caggaactcc gggatggtat    300
aacaatatgg cttttgacaa gtttgctaaa gaagcaggtc tggatgcagt tacgtttaat    360
ggagatgctt tttctcatga aatgagacag aatgtaatag atacattaaa aaaaatggga    420
agaaaagtag atttacttgt atattcagta gctagttcag ttagggtaga tccagacaat    480
ggaacaattt atagatcagt tttaaaacca atagacaaag tgtttacagg tgctactata    540
gactgtttgt ctggaaaaat aagtactata tcagctgaac ctgcaactgc tgaggaagct    600
gcaaatacag taaaagttat gggcggcgaa gattgggcct tgtgggttag aaaacttaag    660
gaagcaggag ttttagcaga aggagtaaag acagttgcct acagttatat aggaccaaag    720
ttaagtcatg ctatttacag agatggaact attggcggcg ctaagaaaca tttggaagct    780
acggcacttg aacttaacaa agaacttcaa aatgatttgc atggagaagc ttatgtatct    840
gtaaataagg gattagtaac taggtcatct gctgtaatac ctattatacc tatgtatatt    900
agtgttttgt ttaaagtgat gaaagaaatg ggcaatcatg aaggatgtat agaacaaatg    960
gaaagattaa tgactgagag actttataca ggatcaaaag tacctacaga tgaaaatcat   1020
cttatacgta ttgatgatta tgaacttgat ccaaaagtac aggcagaagt agataaaagg   1080
atggcaactg ttactcaaga aaacttagct gaagttggcg atttagaggg ttatcgtcac   1140
gattttctgg caactaatgg attcgatata gatggagtag attatgaggc tgatgtgcaa   1200
```

acgcttacat ctatttaa 1218

<210> SEQ ID NO 98
<211> LENGTH: 1191
<212> TYPE: DNA
<213> ORGANISM: Artificial Sequence
<220> FEATURE:
<223> OTHER INFORMATION: Codon-optimized FjoTER sequence for C. autoethanogenum-based CFPS

<400> SEQUENCE: 98
atgataattg aaccaagaat gagaggattt atttgcttaa ctgctcatcc tgcaggatgt 60
gaacaaaatg ttaaaaatca aatagaatat ataaaatcaa aaggggcaat tgcaggagca 120
aagaaagtat tagtcatagg agcttcaaca ggatttggtc ttgcttcaag aataacatcg 180
gctttcggtt cagatgcagc tacaatagga gtattttttg aaaaaccacc agtagaaggt 240
aaaacagcaa gtcctggatg gtacaatagt gcagcatttg aaaaagaagc ccataaagca 300
ggattatatg caaaatctat aaatggagat gcttttagta atgaaataaa gagggaaact 360
ttggacctta taaaagcaga ccttggtcag gtagatttag ttatttattc attggcctct 420
cctgtcagaa ccaatcctaa tactggtgta actcatagat cagtacttaa acctataggg 480
caaaccttta caaacaaaac tgttgatttt catactggta atgtatctga agtaagcata 540
gctcctgcca atgaagaaga tattgaaaat acggtagctg tgatgggcgg cgaggattgg 600
gcaatgtgga tagatgcact gaaaaatgaa aatcttctag ctgagggagc aactactatt 660
gcttacagct atataggacc tgagttgact gaagctgtgt acaggaaggg tactatagga 720
agagcaaaag atcatcttga agcaactgct tttactatta ctgatacatt aaaaagttta 780
ggcggcaaag cttatgttag tgtaaataaa gcattagtaa ctcaggcaag cagtgctata 840
cctgttattc ctctatacat aagcttatta tataagatta tgaaagagga aggtattcat 900
gagggatgca ttgaacagat tcagagacta tttcaagata gattatataa cggttccgaa 960
gtaccagtag atgaaaaagg aagaataaga atagatgatt gggaaatgag agaagatgtt 1020
caggcaaaag tagcagcttt atggaaagag gctacaacag agacgcttcc ttcaatagga 1080
gacttagcag gatatagaaa tgattttttg aatttatttg gttttgagtt cgcaggtgtt 1140
gattataaag cggacacaaa tgaagtagta aacatagaat ctataaaata a 1191

<210> SEQ ID NO 99
<211> LENGTH: 2577
<212> TYPE: DNA
<213> ORGANISM: Artificial Sequence
<220> FEATURE:
<223> OTHER INFORMATION: Codon-optimized CacADH sequence for C. autoethanogenum-based CFPS

<400> SEQUENCE: 99
atgaaggtaa ccaaccagaa agagctgaaa caaaaattaa acgaactccg cgaagcgcaa 60
aaaaaattcg cgacgtatac tcaggaacaa gtcgataaga tctttaaaca atgtgccatt 120
gcagcggcca aagaacgcat caacctggcg aagttggccg ttgaagaaac cggaattggt 180
ttagtggaag acaaaattat taagaaccat ttcgctgcgg aatatattta taataaatac 240
aaaaatgaga agacctgcgg aattattgat catgatgata gccttggtat cactaaagta 300
gcagaaccaa tcggtatcgt cgccgccatc gttcctacaa ccaatccgac ctctacggcg 360
atctttaaat cattgattag cctgaaaacg cgtaacgcga ttttttcag ccctcaccca 420

```
cgcgccaaaa aaagcactat cgctgcggcg aaactgattc tggatgcggc agttaaagcc    480
ggcgcaccta aaaacattat cggctggatc gacgagccta gcatcgagtt gagccaggac    540
ctcatgagtg aagcagatat tatcctcgcc acgggtgggc catctatggt taaagcggcc    600
tactcatctg gtaaaccagc catcggtgtg ggtgcgggca ataccccggc gatcattgac    660
gagagcgccg atattgatat ggccgttagt agcatcattc tgagcaaaac ctacgataac    720
ggcgtaattt gcgcgagtga acagagcatt ttagtgatga actcgatcta tgaaaaagtg    780
aaagaagaat ttgtgaagcg cggttcttac atcctcaacc aaaatgaaat cgcgaaaatc    840
aaagaaacga tgttcaaaaa tggcgcgatc aacgcggata ttgttggcaa atcagcctac    900
attattgcga aaatggcggg tattgaagtc ccccagacca caaagatcct gatcggtgaa    960
gtacagagcg tcgaaaagag cgagctgttc agccacgaga aactgagccc tgttctggcc   1020
atgtacaagg taaaagattt tgacgaagca cttaaaaaag cccaacgcct tatcgaatta   1080
ggagggtctg gccacacgag cagcttgtac atcgacagcc agaataacaa agacaaagtc   1140
aaagaattcg gccttgcaat gaaaacttct cgcaccttta ttaatatgcc gtccagccag   1200
ggcgcctctg gtgatctgta caattttgcc attgccccgt cgtttaccct ggggtgtggg   1260
acctggggcg ggaattcggt atcacagaac gtcgaaccaa aacacctgtt gaatattaaa   1320
tccgtggcag agcgccgcga gaacatgctg tggttcaaag tccctcagaa aatttacttc   1380
aagtacggct gcctgcgttt tgcgctgaaa gaactcaaag acatgaacaa aaaacgtgcg   1440
ttcatcgtta ccgataagga cctgtttaaa ctgggctacg taaacaaaat tactaaagtg   1500
ttggacgaaa tcgatattaa atactccatt tttaccgaca ttaagtcaga cccgaccatc   1560
gacagcgtca aaaaaggggc aaaagaaatg ctgaactttg agccagatac gattatctca   1620
atcggtgggg gctcgcctat ggacgctgcg aaagtgatgc acctgctgta tgagtacccg   1680
gaagcggaga ttgagaacct ggccatcaat tttatggata ttcgtaagcg tatttgcaat   1740
tttccgaaac ttgggacgaa agccatctcc gtcgcgattc cgaccactgc aggtacgggc   1800
agcgaagcca cgccttttgc agttatcacg aacgatgaga ccggtatgaa atatccgctc   1860
acctcgtacg aactgacccc aaatatggcc atcattgata ccgaactgat gctcaatatg   1920
ccccgtaaac tcaccgcagc cactggcatt gacgcactcg tgcacgccat tgaggcttat   1980
gtcagcgtga tggcgaccga ttacaccgat gaattagctc tccgtgcaat caaaatgatt   2040
tttaagtacc tcccgcgtgc gtacaaaaat ggcacgaatg atatcgaggc gcgtgaaaag   2100
atggctcatg ccagcaacat cgccggtatg gcgttcgcta atgccttcct gggtgtatgc   2160
cacagtatgg cacacaagct cggcgccatg catcatgtac cacacgggat tgcctgtgcc   2220
gtgttaatcg aggaagtcat taagtacaat gccaccgatt gcccgactaa acagaccgcc   2280
tttccgcagt ataagagccc gaatgcaaaa cgtaaatacg ccgagatcgc tgagtatttg   2340
aatctcaaag gaacgagtga tactgagaaa gtcaccgcct tgatcgaagc catcagcaaa   2400
cttaaaatcg atctgtcgat tccgcagaac attagcgcgg ccggtattaa caagaaagat   2460
ttttacaaca cgctggacaa aatgtctgaa ctggcgtttg acgatcagtg caccacggcg   2520
aacccgcgct atcctctgat ttccgagctc aaggatatct acatcaaaag cttctaa      2577
```

<210> SEQ ID NO 100
<211> LENGTH: 741
<212> TYPE: DNA
<213> ORGANISM: Artificial Sequence
<220> FEATURE:
<223> OTHER INFORMATION: Codon-optimized CnaPhaB sequence for C.

autoethanogenum-based CFPS

<400> SEQUENCE: 100
atgacacaga gaatagctta tgtaactgga ggaatggggg gaattggcac ggcaatatgt 60
cagagattag caaaggatgg ttttagagta gttgcgggtt gtggcccaaa ctcaccgagg 120
agagaaaaat ggttggaaca gcagaaagct ctcggatttg actttatagc tagtgagggt 180
aatgttgctg attgggattc aacaaagaca gcttttgata aggttaagtc agaagtgggt 240
gaagtagatg tgctcataaa taatgctggg atcacaagag atgtagtttt tagaaaaatg 300
acaagagctg actgggatgc tgtaatagat acaaatctta ctagcttatt caatgtaacg 360
aaacaggtta tagatggaat ggcagatagg ggatggggta ggatagtaaa tatttcatca 420
gtaaatggtc aaaaaggaca atttggacaa acaaattatt caactgccaa ggcaggactt 480
catggattta cgatggcact tgcacaggaa gtagctacta aaggagttac tgtaaataca 540
gtttctccag gatacatagc tactgatatg gtaaaagcta ttaggcagga tgtattagat 600
aagattgtag caacaatacc tgtgaagaga cttggcttac ctgaagaaat agcatcaata 660
tgtgcttggt tatccagtga agaatcagga ttttctacag gagctgattt ctccttgaat 720
ggtggacttc acatgggata a 741

<210> SEQ ID NO 101
<211> LENGTH: 795
<212> TYPE: DNA
<213> ORGANISM: Artificial Sequence
<220> FEATURE:
<223> OTHER INFORMATION: Codon-optimized PpuCRT sequence for C. autoethanogenum-based CFPS

<400> SEQUENCE: 101
atgactaccc catcttctcc attattaagc aaagtagaag caggagttgc atggattaca 60
ttaaatagac cagagcagag aaatgcttta gatattccaa ctctaaaaca attacatgca 120
cttctagatt ctcatgcaga tgatcctgct gtaagagttg tagtattgac aggttccggt 180
aggagtttct gtgctggagc agatttagca gagtgggctg ctgcagaagc agcaggaact 240
cttgaaagtt atggctggac tgaaacagca catgctttga tgctgcgttt gcactctttg 300
gataagccta cgattgcagc tataaatggc actgcagtag gcggcggcat ggatttgtct 360
ctttgctgtg atttgagaat agcagcagca tcagcaagat ttaaagctgg atataccagc 420
atgggatatt caccagatgc aggagcatct tggcatcttc caagacttat aggatcagaa 480
caagccaaaa gacttttatt tttagatgaa ttatggggag ctgaacatgc attagcagca 540
ggcttagttt cagaagtatg tgctgatgaa cagcttccag ctgtagcagc tgaacttgca 600
ggaagattgg caaacggccc tacttttgca tatgcacaaa caaaacagct tataagggat 660
ggtgctagaa gaactctagc agagcaactt gaagctgaaa gacatgcagg acttttgtgc 720
ggtcgttctc aggacggagc agaagccttg caggcatcag ttgaaagaag agcacctaga 780
tttactggac aataa 795

<210> SEQ ID NO 102
<211> LENGTH: 41
<212> TYPE: DNA
<213> ORGANISM: Artificial Sequence
<220> FEATURE:
<223> OTHER INFORMATION: Forward primer for cloning PAL2 gene into the pJL1 plasmid

<400> SEQUENCE: 102
tttaagaagg agatatacat atggatcaaa tcgaagcaat g 41

<210> SEQ ID NO 103
<211> LENGTH: 38
<212> TYPE: DNA
<213> ORGANISM: Artificial Sequence
<220> FEATURE:
<223> OTHER INFORMATION: Reverse primer for cloning PAL2 gene into the pJL1 plasmid

<400> SEQUENCE: 103
tttgttagca gccggtcgac ttagcaaatc ggaatcgg 38

<210> SEQ ID NO 104
<211> LENGTH: 48
<212> TYPE: DNA
<213> ORGANISM: Artificial Sequence
<220> FEATURE:
<223> OTHER INFORMATION: NcoI-grsA-F primer

<400> SEQUENCE: 104
attattatcc atggtgttaa acagttctaa aagtatattg attcatgc 48

<210> SEQ ID NO 105
<211> LENGTH: 37
<212> TYPE: DNA
<213> ORGANISM: Artificial Sequence
<220> FEATURE:
<223> OTHER INFORMATION: BamHI-grsA-R primer

<400> SEQUENCE: 105
aataatatgg atccgttaat gaatcggcca acaaatc 37

<210> SEQ ID NO 106
<211> LENGTH: 44
<212> TYPE: DNA
<213> ORGANISM: Artificial Sequence
<220> FEATURE:
<223> OTHER INFORMATION: NcoI-grsB1-F primer

<400> SEQUENCE: 106
attattatcc atggtgagta catttaaaaa agaacatgtt cagg 44

<210> SEQ ID NO 107
<211> LENGTH: 45
<212> TYPE: DNA
<213> ORGANISM: Artificial Sequence
<220> FEATURE:
<223> OTHER INFORMATION: BamHI-grsB1-R primer

<400> SEQUENCE: 107
aataatatgg atccatataa ttagagattt cctgaatggt tggtg 45

<210> SEQ ID NO 108
<211> LENGTH: 5
<212> TYPE: PRT
<213> ORGANISM: Artificial Sequence
<220> FEATURE:
<223> OTHER INFORMATION: Peptide used for capture of acyl-CoA species in Example 7
<220> FEATURE:
<221> NAME/KEY: MISC_FEATURE
<222> LOCATION: (3)..(3)
<223> OTHER INFORMATION: non-natural trimethyl-lysine residue

<400> SEQUENCE: 108

-continued

```
Cys Ala Lys Ser Ala
1               5


<210> SEQ ID NO 109
<211> LENGTH: 5
<212> TYPE: PRT
<213> ORGANISM: Artificial Sequence
<220> FEATURE:
<223> OTHER INFORMATION: Peptide used as an internal standard in Example
      7
<220> FEATURE:
<221> NAME/KEY: MISC_FEATURE
<222> LOCATION: (1)..(1)
<223> OTHER INFORMATION: acetylated serine residue
<220> FEATURE:
<221> NAME/KEY: MISC_FEATURE
<222> LOCATION: (2)..(2)
<223> OTHER INFORMATION: non-natural trimethyl-lysine residue

<400> SEQUENCE: 109

Ser Lys Gly Gly Cys
1               5


<210> SEQ ID NO 110
<211> LENGTH: 60
<212> TYPE: DNA
<213> ORGANISM: Artificial Sequence
<220> FEATURE:
<223> OTHER INFORMATION: Forward primer for cloning enzyme sequences
      into the pJL1 backbone
<220> FEATURE:
<221> NAME/KEY: misc_feature
<222> LOCATION: (41)..(60)
<223> OTHER INFORMATION: region encoding the gene sequence starting at
      the second codon
<220> FEATURE:
<221> NAME/KEY: misc_feature
<222> LOCATION: (41)..(60)
<223> OTHER INFORMATION: n is a, c, g, or t

<400> SEQUENCE: 110

ttaactttaa gaaggagata tacatatgga gaaaaaaatc nnnnnnnnnn nnnnnnnnnn     60


<210> SEQ ID NO 111
<211> LENGTH: 52
<212> TYPE: DNA
<213> ORGANISM: Artificial Sequence
<220> FEATURE:
<223> OTHER INFORMATION: Reverse primer for cloning enzyme sequences
      into the pJL1 backbone
<220> FEATURE:
<221> NAME/KEY: misc_feature
<222> LOCATION: (33)..(52)
<223> OTHER INFORMATION: region encoding the C-terminus of the gene
      sequence including the stop codon
<220> FEATURE:
<221> NAME/KEY: misc_feature
<222> LOCATION: (33)..(52)
<223> OTHER INFORMATION: n is a, c, g, or t

<400> SEQUENCE: 111

ttcctttcgg gctttgttag cagccggtcg acnnnnnnnn nnnnnnnnnn nn             52
```

CELL-FREE PROTEIN SYNTHESIS DRIVEN METABOLIC ENGINEERING

CROSS-REFERENCE TO RELATED PATENT APPLICATIONS

The present application is a continuation-in-part of U.S. application Ser. No. 15/175,497, filed on Jun. 7, 2016, which is pending and claims the benefit of priority under 35 U.S.C. § 119(e) to U.S. Provisional Patent Application No. 62/173,818, filed on Jun. 10, 2015, the content of which are incorporated herein by reference in their entirety.

STATEMENT REGARDING FEDERALLY SPONSORED RESEARCH OR DEVELOPMENT

This invention was made with government support under D14PC00005 awarded by the Defense Advanced Research Projects Agency (DARPA) (subcontract Agreement 10/24/14//D14PC00005/0001 Covitect Inc. STTR Award ST12B-003 to Northwestern University). The government has certain rights in the invention.

REFERENCE TO A SEQUENCE LISTING SUBMITTED VIA EFS-WEB

The content of the ASCII text file of the sequence listing named "702581_01623_ST25.txt" which is 159 kb in size was created on Apr. 6, 2020 and electronically submitted via EFS-Web herewith the application is incorporated herein by reference in its entirety.

FIELD

The invention relates to cell-free systems for metabolic engineering, methods for cell-free metabolic engineering, kits for preparing the systems, and kits for performing the methods. In particular, the invention relates to systems and methods for preparing a chemical product or a natural product in cell-free conditions and to optimizing conditions for preparing a chemical product or natural product in cell-free conditions. The invention also relates to combinatorial cell-free metabolism engineering.

BACKGROUND

For decades scientists and engineers have turned to engineering biological systems for energy, medicine, materials, and more (Guo et al., 2015; Bornscheuer et al., 2012; Curran and Alper, 2012; Rollie et al., 2012). This has been an attractive, sustainable way to produce small molecules, especially when chemical synthesis is insufficient (Brown et al., 2014). The ability to harness organisms that naturally produce molecules of interest has expanded the chemical palate available (Demain, 2013; Harvey et al., 2015). Often when natural producers are not sufficient for production at the optimal quality or quantity, engineers turn to the power to manipulate biology (Kern, 2007). Our ability to introduce heterologous pathways into model microorganisms and metabolically engineer them to maximize small molecule production has led to large scale production of 1,3-propanediol, farnesene, and artemisinin with many more on their way to market (Hodgman and Jewett, 2012; Kwok, 2010). Efforts to make these molecules have resulted in success, but not without a great deal of challenges.

Bringing a biosynthetic molecule to market usually involves tireless efforts and countless hours of design-build-test (DBT) cycles (Kwok, 2010). The production of n-butanol is a prime example of these challenges. A series of Clostridia species are natural producers of this small molecule, and *Clostridia acetobutylicum* and *Clostridia bejinjernickii* are two of which are used in commercial butanol plants (Green, 2011). However, these species are difficult to engineer because of a biphasic metabolism, unknown regulation, and a limited number of species-specific engineering tools (Lüke-Eversloh and Bahl, 2011). Heterologous expression in model microorganisms like *E. coli* and *S. Cerevisiae* of Clostridial metabolism allows butanol production to be more easily engineered (Atsumi et al., 2008; Steen et al., 2008). Starting from a proof-of-concept, scientists have been able to increase titers dramatically by knocking out genes from genomes (Atsumi et al., 2008), increasing redox driving forces by introducing pathway independent enzymes (Shen et al., 2011), and identifying homologous enzymes with better activities (Bond-Watts et al., 2011). Years of iterative metabolic engineering led to these advances and many others in butanol biosynthesis, as is the same for most biosynthetic pathways.

Metabolic engineering is costly and time-consuming (Keasling, 2012). The constraints of cell membranes requiring a complete balancing of fluxes into and out of the cell makes it difficult to express biosynthetic pathways without taking into account the entire metabolic network. While there are many technologies that allow the engineer to better manipulate cells such as MFA, genome engineering, etc., the complexity of cells remains a limitation (Lee et al., 2012; Yadav et al., 2012). Furthermore, the tools we do have to regulate transcription, translation, and the genome require many DBT cycles increasing the time and effort needed to optimize the biosynthesis of interest (Boyle and Silver, 2014). Current DBT cycles are extraordinarily expensive. One estimate of the effort to develop new products has indicated current costs to be ~$10^8$-$10^{10}$ total $*years to develop (Alicia Jackson, DARPA, personal communication). There is a clear need for speeding up and decreasing the cost of metabolic engineering DBT cycles. While techniques continue to be develop to engineer cells, in vitro systems show promise in speeding up DBT cycles because they bypass many in vivo limitations by having direct access to the cellular contents (Sun et al., 2013; You and Zhang, 2013; Siegal-Gaskins et al., 2014).

In vitro systems for biomolecular transformations have been established showing the potential for biomanufacturing and discovery (Dudley et. al, 2015). In particular, cell-free metabolic engineering (CFME) harnessing the power of crude *E. coli* extracts to express heterologous pathways was first spearheaded for the production 2,3-butanediol (Kay and Jewett, 2016). This work led to the development of an extract mixing approach to CFME whereby lysates containing selectively overexpressed heterologous enzymes are mixed together to construct a biosynthetic pathway that can be activated by the addition of simple substrates (Dudley and Jewett, in preparation). This previous work proved the utility of the extract mixing approach to CFME by carrying out a three-step from acetyl-CoA biosynthetic pathway. This approach has many advantages including only expressing one enzyme in each strain, not needing to fine-tune expression, and the lack of the cell membrane.

The approaches outlined above are, however, constrained by the need to express enzymes in cells. As a result, there still remains a need for systems and methods for cell-free metabolic engineering with in vitro expression of enzymes. Further, there still remains a need for systems and method for cell-free metabolic engineering amenable to combinatorial optimization to reduce the costs associated with DBT cycles.

SUMMARY

Disclosed are cell-free systems for metabolic engineering, methods for cell-free metabolic engineering, kits for preparing the systems, and kits for performing the methods. The disclosed systems, methods, and kits may be utilized to prepare a chemical product or a natural product and to optimize conditions for preparing a chemical product or a natural product. The disclosed systems, methods, and kits also may be utilized for combinatorial cell-free metabolism engineering.

BRIEF DESCRIPTION OF THE DRAWINGS

Non-limiting embodiments of the presently disclosed cell-free systems, methods, and kits may be described by way of example with reference to the accompanying figures, which are schematic and may not be intended to be drawn to scale. In the figures, each identical or nearly identical component illustrated may be represented by a single numeral. For purposes of clarity, not every component may be labeled in every figure, nor is every component of each embodiment of the invention shown where illustration is not necessary to allow those of ordinary skill in the art to understand the invention.

FIG. 39. Provides a table showing the gene sequences for biosynthetic enzymes PAL2 (SEQ ID NO: 1) and FDC1 (SEQ ID NO:2).

From the integrated area under the peak (AUP) of the four peaks A, B, C, and D, the AUP for each of the labeling states was calculated as shown. The deconvoluted AUP for each of the labeling states was then used to determine the fraction of $^{13}C$ label, $f^{C13}$, in the observed HMG product; this was done by weighting the AUP for each labeled state by the relative number of labeled carbons in it, then dividing by the sum of all four states. The fraction of unlabeled carbon in the HMG product, $f^{C12}$ can be calculated from these values as well using a similar equation.

Figure 57:
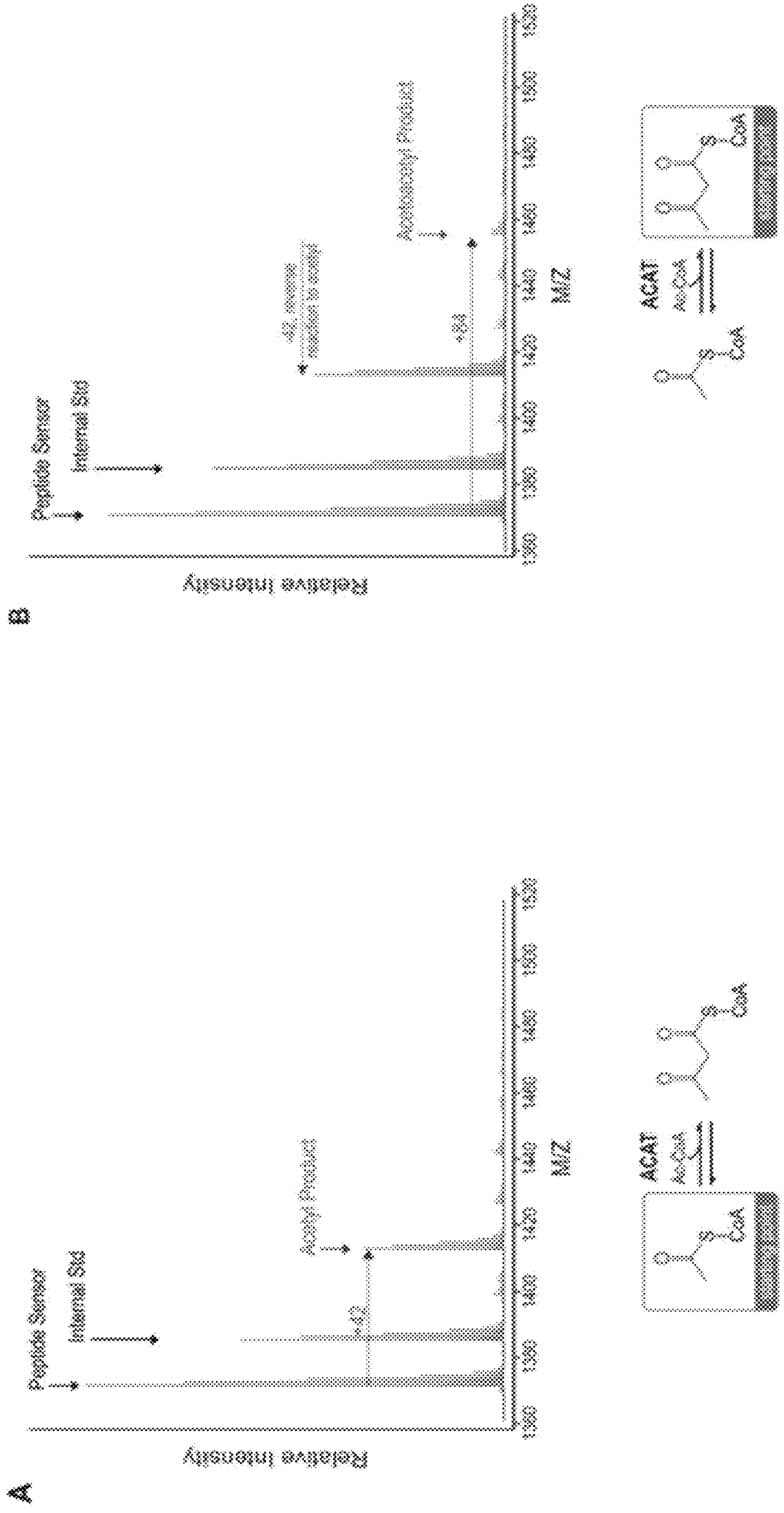

FIG. 57. The pathway intermediate, acetoacetyl-CoA, is not observed. To explore why we do not observe the AA-CoA pathway intermediate, we incubated 1 mM of Ac-CoA or AA-CoA in cell-free lysate overexpressing the ACAT enzyme for 2 hours. The cell free reactions were given 1 mM each of CoA, $NAD^+$, and ATP, but no glucose was provided. A) When this cell-free reaction was incubated with Ac-CoA, this acetyl species is the primary species we capture and detect. B) Conversely, when the cell-free lysate is incubated with AA-CoA, a relatively small amount of acetoacetyl species is detected and the acetyl species is by far the primary product. The ACAT enzyme is reversible and these results suggests that it strongly favors the reverse reaction. In the reactions with the full pathway, the small quantities of AA-CoA produced are likely rapidly converted to HMG-CoA, and so we do not observe any significant accumulation of AA-CoA.

Figure 58:
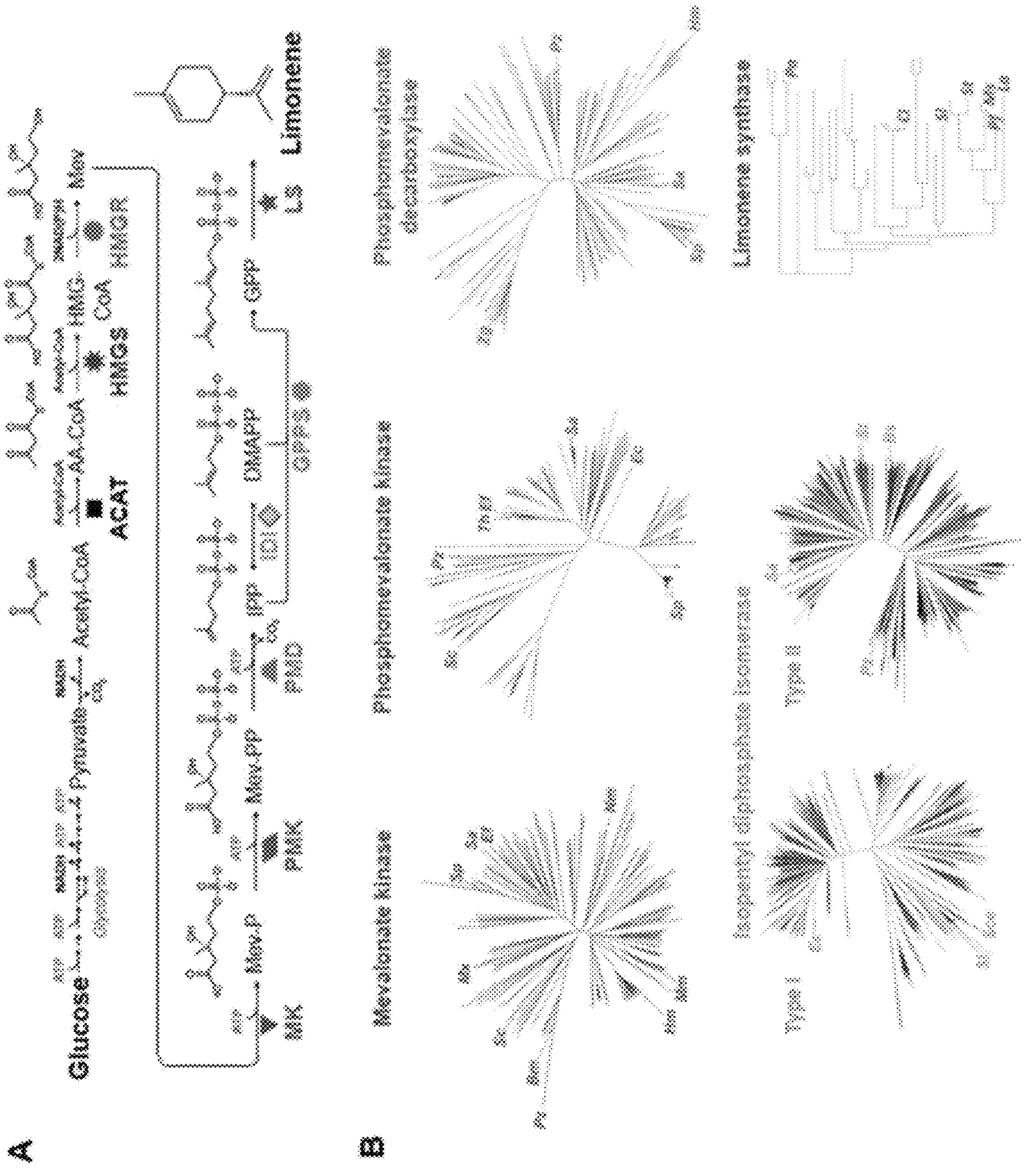

FIG. 58. Cell-free limonene production using enzymes sourced from a variety of organisms. (A) The metabolic pathway from glucose to limonene requires nine enzymes plus glycolysis activity present in the lysate. (B) Phylogenetic comparison of enzyme sequences to select diverse enzyme homologs for testing. AA-CoA, acetoacetyl-CoA; HMG-CoA, 3-hydroxy-3-methylglutaryl-CoA; Mev, mevalonate; Mev-P, mevalonate-5-phosphate; Mev-PP, mevalonate pyrophosphate; IPP, isopentenyl pyrophosphate; DMAPP, dimethylallyl pyrophosphate; GPP, geranyl pyrophosphate; ACAT, acetyl-CoA acetyltransferase; HMGS, hydroxymethylglutaryl-CoA synthase; HMGR, hydroxymethylglutaryl-CoA reductase; MK, mevalonate kinase; PMK, phosphomevalonate kinase; PMD, pyrophosphomevalonate decarboxylase; IDI, isopentenyl pyrophosphate isomerase; GPPS, geranyl diphosphate synthase; LS, limonene synthase.

Figure 59:
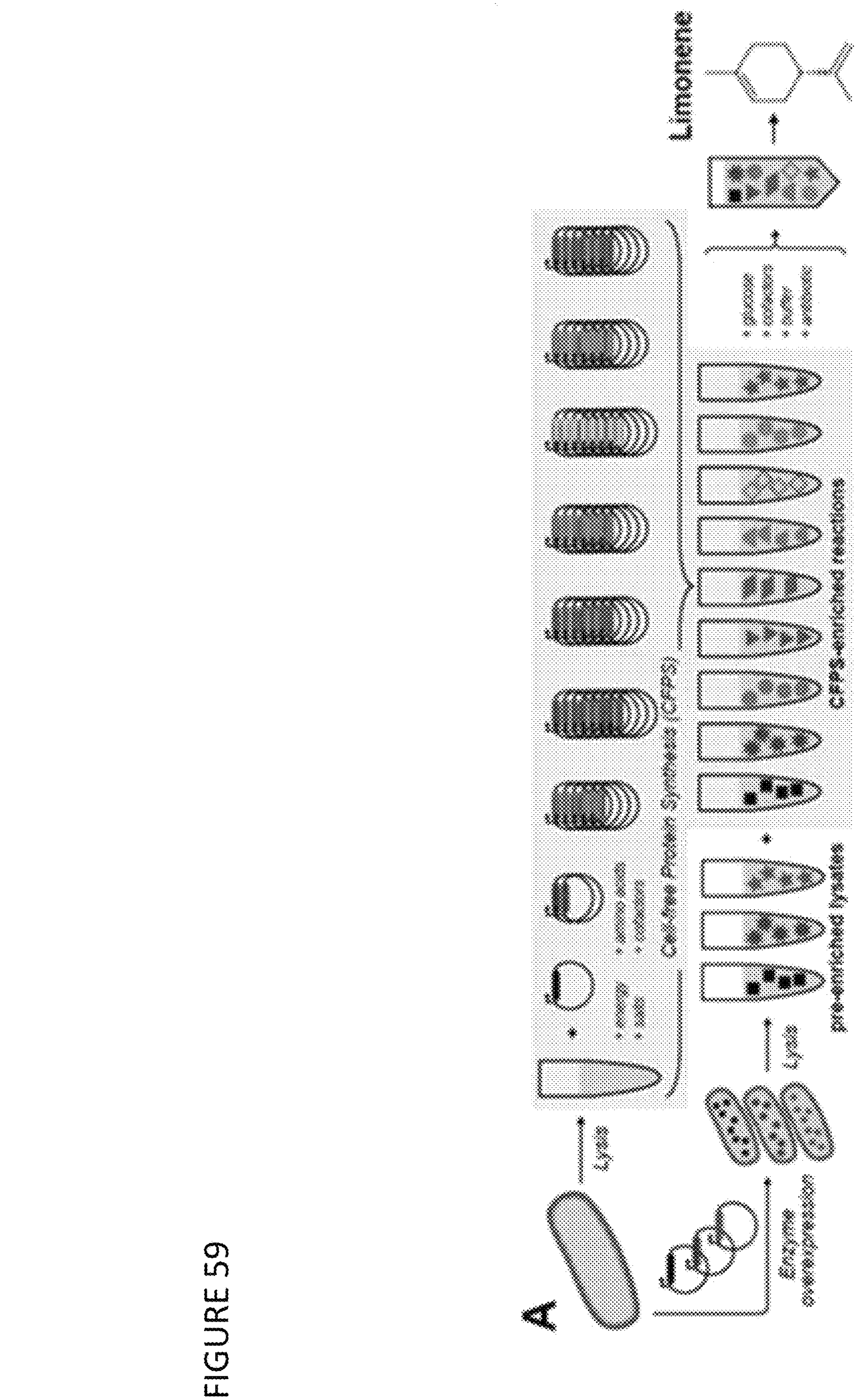

FIG. 59. Initial characterization of enzyme homologs for cell-free production of limonene. (A) Cell-free protein synthesis (CFPS) generates "CFPS-enriched reactions" where each individual reaction expresses a single enzyme homolog. Additionally, enzymes can be overexpressed in vivo and the cell subsequently lysed to generate "pre-enriched lysates". Mixing of glucose substrate and cofactors with enzyme-enriched CFPS reactions and/or pre-enriched lysates produces limonene. (B) Cell-free protein synthesis yields for 54 different enzymes. CFPS reactions with soluble/total protein below 30% were incubated at 16° C. instead of 30° C.; the amount of soluble protein increased for all 14 proteins. (C-D) Cell-free limonene production. Using various enzyme homologs generated by CFPS, the productivity from 3-6 hours (C) and titer at 24 hours (D) of limonene were measured. The standard reaction includes 1.0 μM PmHMGR, 0.4 μM ScMK, 0.4 μM ScPMK, 0.4 μM ScPMD, 2.0 μM EcIDI, and 3.0 μM PaGPPS plus pre-enriched lysates for EcACAT, ScHMGS, and MsLS (enzyme set 1.0). Unless noted by (*, see the Table at FIG. 65 for details), each enzyme homolog is substituted for the standard enzyme at the same concentration. LS homologs are generated via CFPS and compared at 1.0 LVM in a reaction lacking the MsLS pre-enriched lysate. (E) the TREE (Titer, Rate, and Enzyme Expression) score is an empirically generated aggregate value of enzyme solubility, initial productivity, and final titer that enables ranking of enzyme homologs. The (+) symbol represents homologs included in enzyme set 2.0.

Figure 60:
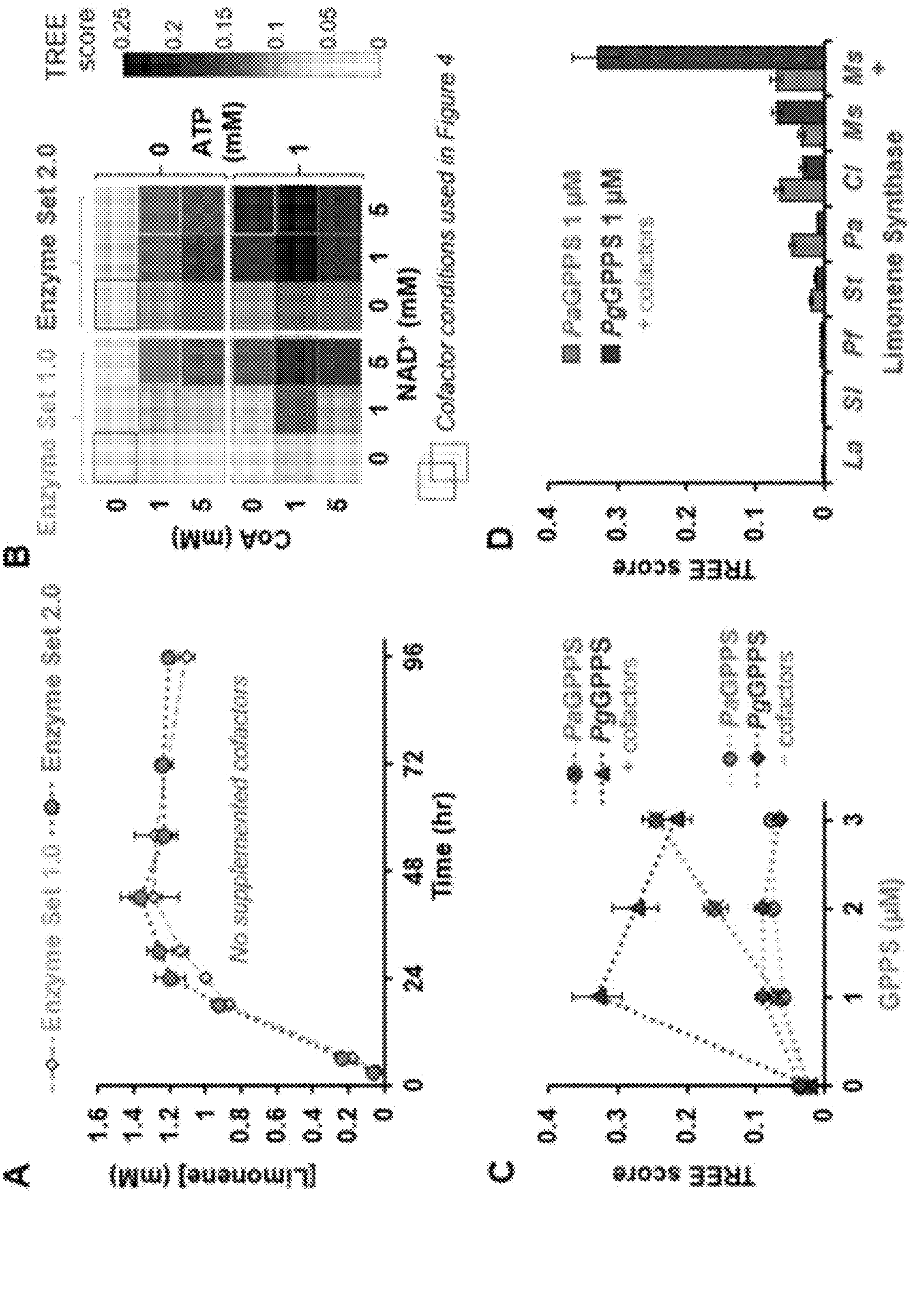

FIG. 60. Comparison of new enzymes homolog set and optimization of cofactors (A) Comparison of initial enzyme homologs (enzyme set 1.0) and an improved set 2.0 containing new homologs for HMGR, MK, PMK, and IDI. (B) Supplementation of cofactors $NAD^+$, CoA, and ATP improves limonene productivity, titer, and TREE score (FIG. 73) compared to no additional cofactors (blue box). Four reaction conditions (in blue, yellow, and green boxes) were selected as cofactor conditions for further experiments. (C) TREE scores of PaGPPS and PgGPPS (the best two GPPS homologs in FIG. 59E) under different enzyme concentrations. These data informed the reduction of GPPS to 1.0 μM for enzyme set 2.2. (D) Re-testing of LS homologs derived from CFPS at a higher concentration (1.8 μM) and using supplemented cofactors.

Figure 61:
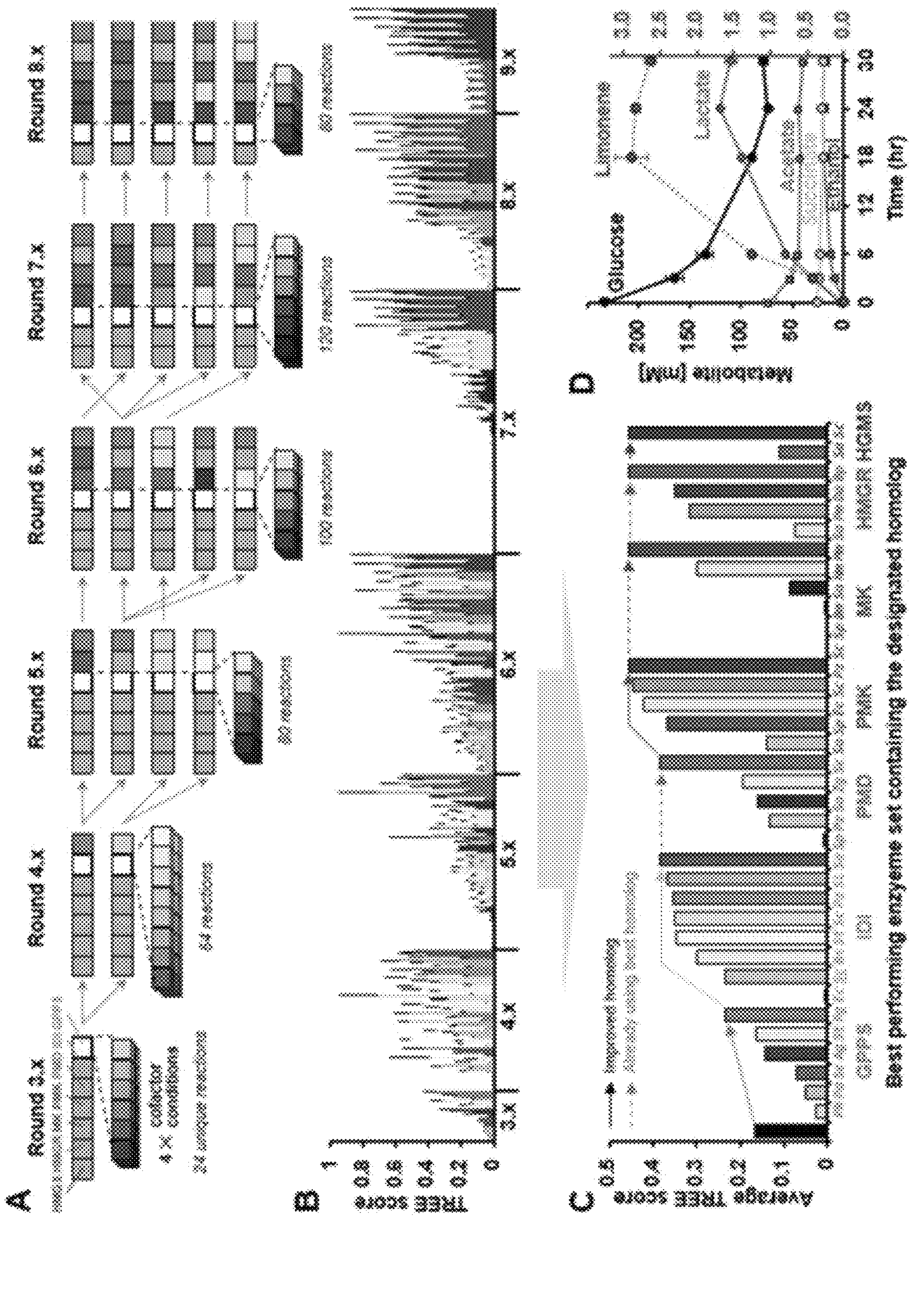

FIG. 61. Iterative testing of enzyme homologs at four different cofactor conditions within multiple different enzyme sets. (A) Conceptual approach: Starting with enzyme set 2.2, active homologs of GPPS were substituted for the default GPPS (PaGPPS). Each GPPS homolog (orange) was tested under four different cofactor conditions and the resulting TREE scores averaged to rank each enzyme set. The top two sets were carried forward into the next iterative experiment in which all active homologs of IDI (yellow) were tested. The top two sets plus the best performing StGPPS sets were again carried forward and all active PMD homologs (green) were tested. Each subsequent iterative experiment used the top five conditions from the previous iteration to test active PMK (blue), PMD (purple), and HMGR (magenta) enzymes in sequence. (B) TREE scores of 408 reactions where each bar is a unique cofactor/enzyme set. (C) The TREE score of each enzyme set was averaged across all four cofactor conditions and the highest score plotted to compare each homolog as a single value. The black bar represents the starting enzyme set 2.1. (D) Production of limonene (mM) and other metabolites over the course of the reaction. The concentration of each enzyme is 0.2 μM HMGR, 0.1 μM MK, 0.2 μM PMK, 0.2 μM PMD, 0.2 μM IDI, and 1.0 μM GPPS plus pre-enriched lysates for EcACAT, ScHMGS, and MsLS; see the Table at FIG. 65 for more detailed description of the reaction components of each enzyme set.

Figure 62:
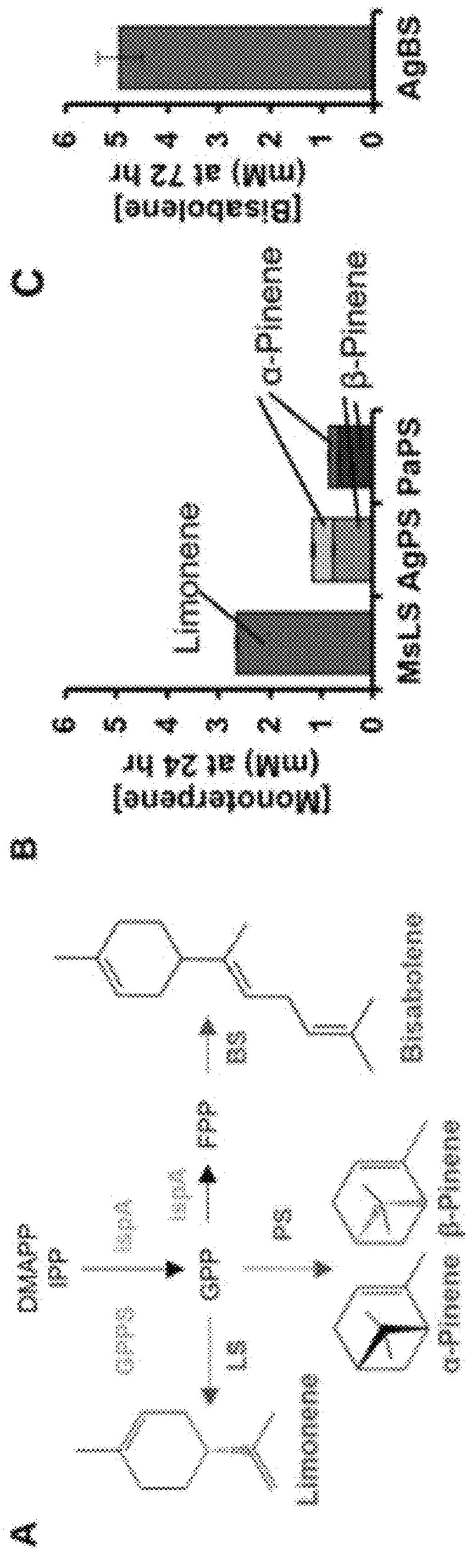
Figure 75:
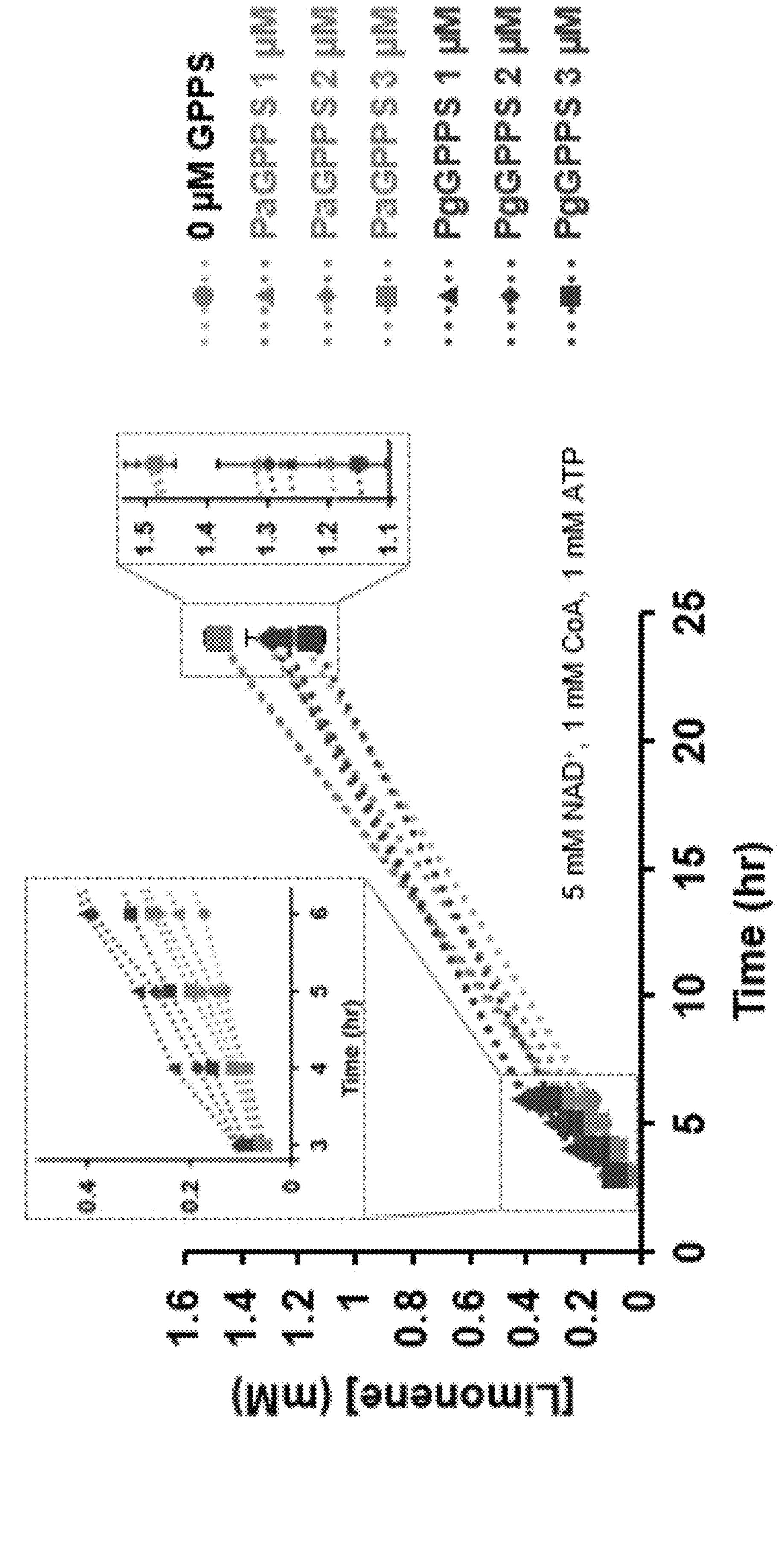

FIG. 62. Synthesis of additional terpenoids. (A) Various terpene synthases can produce different products from the common GPP precursor. (B) Comparison of limonene and pinene production from glucose using CFPS-derived terpene synthases. Pinene synthases (PS) were encoded by sequences from *Abies grandis* (Grand fir) and *Picea abies* (Norway spruce). (C) Production of bisabolene from glucose by CFPS-enriched reactions containing farnesyl diphosphate synthase (EcFPPS encoded by ispA) from *E. coli* and bisabolene synthase (BS) from *Abies grandis*. Limonene, pinene, and bisabolene synthesis reactions use enzyme set 10.0 (see the Table at FIG. 65) and are supplemented with 5 mM $NAD^+$, 1 mM CoA, and 1 mM ATP. FIG. 75 depicts the accumulation of terpenoids over time.

FIG. 63. Provides a table listing the DNA sequences and plasmids used in Example 8.

FIG. 64. Provides a table showing an estimation of overexpresesd protein concentration in pre-enriched lysates. To estimate the concentration of overexpressed proteins in pre-enriched (i.e. CFME) lysates, we used densitometry to estimate the band percentage in a Coomassie stained SDS-PAGE gel using ImageLab software. These percentages are multiplied by the concentration of pre-enriched lysates and converted to a molar concentration using the molecular weight of the protein in question.

FIG. 65. Provides a table detailing the enzyme and cofactor concrntaration used in each experiment of Example 8.

FIG. 66. Provides a table showing metabolic engineering for the production of monoterpenes in Example 8.

FIG. 67. Addition of N-terminal expression tag encoding MEKKI (SEQ ID NO: 13) improves cell-free expression of monoterpene synthases. Each limonene synthase (LS) or pinene synthase (PS) was expressed in CFPS using three different DNA plasmids. The "RBS calculator" version (SEQ ID NO:5) does not contain an N-terminal expression tag but used the Salis RBS Calculator v1.1 to optimize the 27 base pair sequence (colored gray and containing a ribosome binding site; (SEQ ID NO:8) for maximum expression. The "pJL1" version (SEQ ID NO:6) does not contain a variable RBS or N-terminal expression tag but uses the RBS encoded by the pJL1 plasmid (SEQ ID NO:9; Addgene #69496, pJL1 is derived from pY71 (Bundy and Swartz, 2010; Swartz et al., 2004)). The "pJL1-MEKKI" version (SEQ ID NO:7) places the coding sequence of the protein into pJL1 behind an N-terminal tag (SEQ ID NO:10) known to improve in vitro expression. The N-terminal tag is a 15 nucleotide, AT-rich sequence which encodes the first five amino acids (Met-Glu-Lys-Lys-Ile, MEKKI (SEQ ID NO:13)) of chloramphenicol acetyl transferase. Chloramphenicol acetyl transferase has been previously used as a reporter protein during the development of the *E. coli* CFPS system (Jewett and Swartz, 2004; Swartz et al., 2004).

Figure 68:
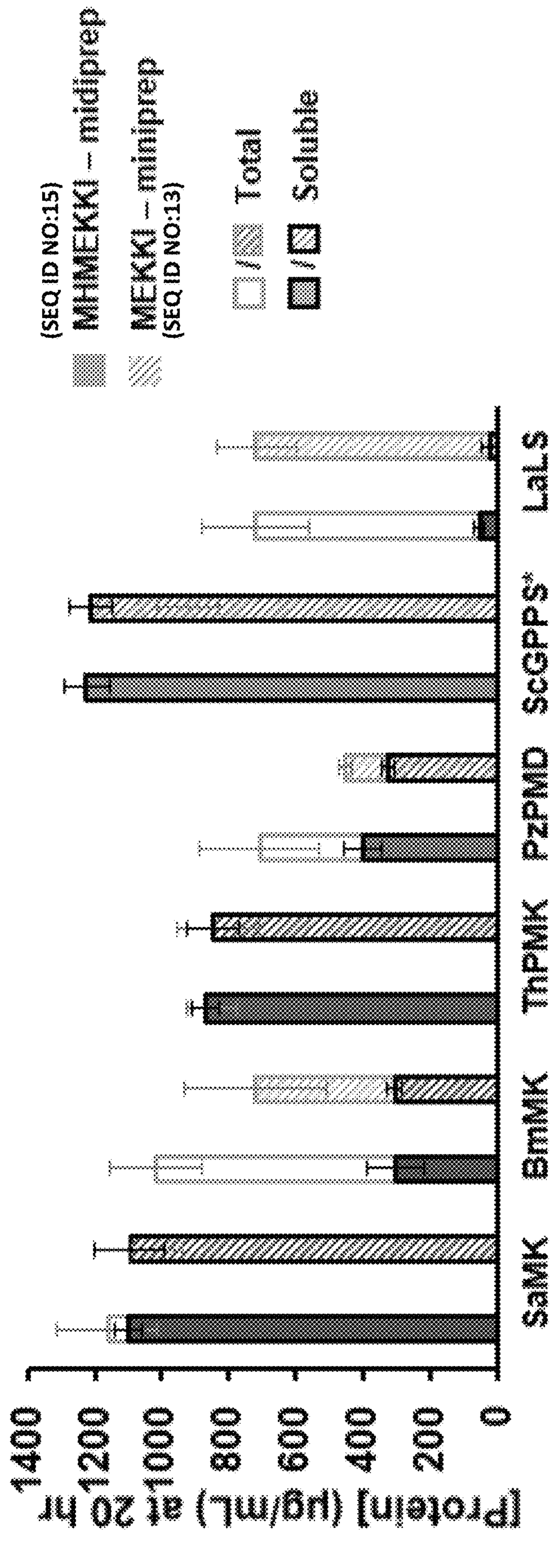

FIG. 68. Two variants of the N-terminal expression tag give similar expression for five different enzymes. Gene sequences were unintentionally synthesized with two different N-terminal expression tags. The first tag sequence is catATGGAGAAAAAAATC (SEQ ID NO: 12) encoding MEKKI (SEQ ID NO: 13) and the second tag sequence is catATGCATATGGAGAAAAAAATC (SEQ ID NO: 14) encoding MHMEKKI (SEQ ID NO: 15). Comparison of the two N-terminal tags (using five different example enzymes) show very similar soluble protein concentrations and both tags ultimately used (see the Table in FIG. 63).

Figure 69:
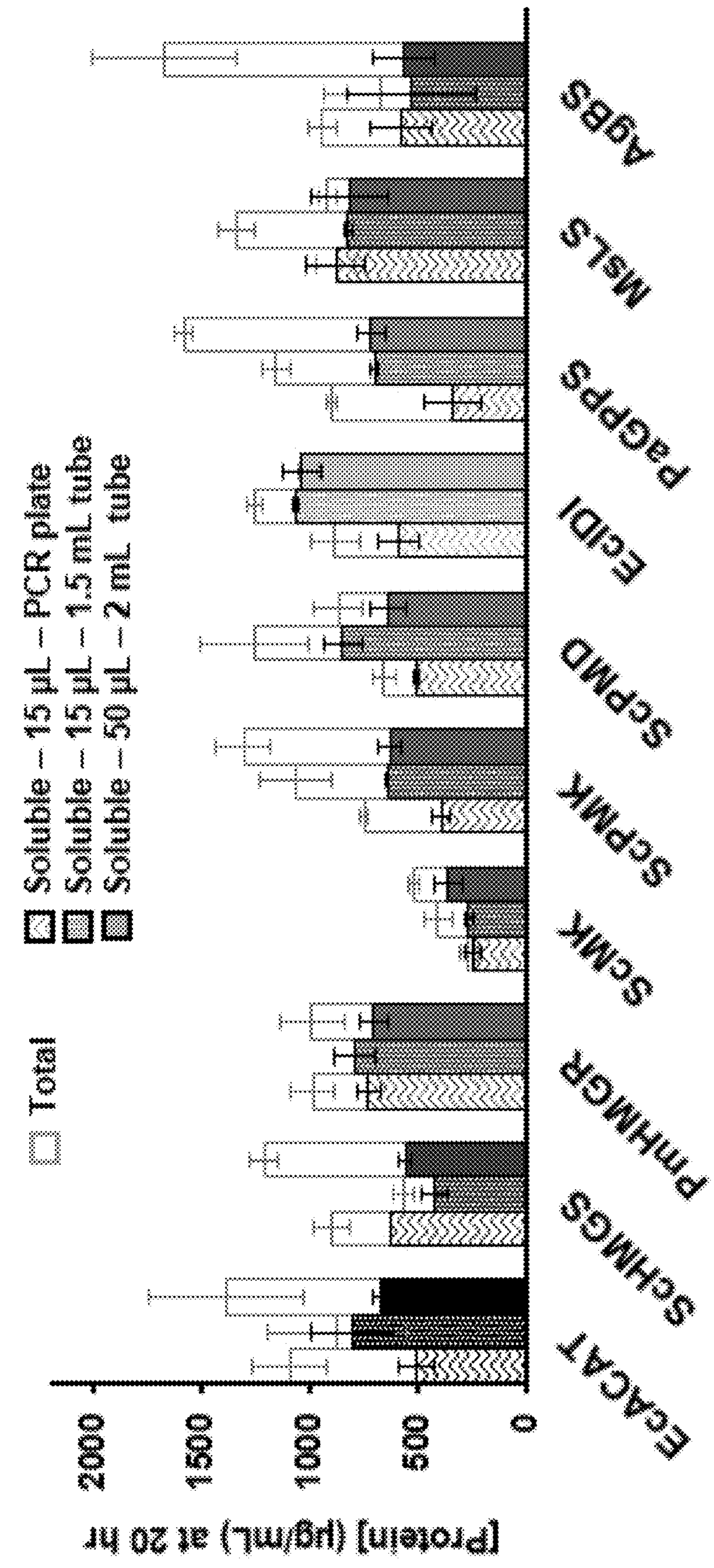

FIG. 69. Protein yields for ten representative proteins remain consistent when scaling up reaction volumes from 15 μL to 50 μL. The standard 15 μL reaction is typically incubated in a 1.5 mL microcentrifuge tube. Due to the large amounts of CFPS reactions required for this manuscript, we wanted to scale up the reaction to minimize pipetting. To keep the reaction environment consistent at a larger reaction volume, 2 mL microcentrifuge tubes are used to incubate 50 μL CFPS reactions. Enzyme expression levels are similar between 15 μL and 50 μL reactions. Alternatively, we tried incubating 15 μL reactions in a PCR plate covered with foil lid (to minimize plastic/reduce pipetting) but found reduced the relative protein expression for some enzymes (PaGPPS) compared to incubation in microcentrifuge tubes. Throughout Example 8, all CFPS reactions were run at the 50 μL scale.

Figure 70:
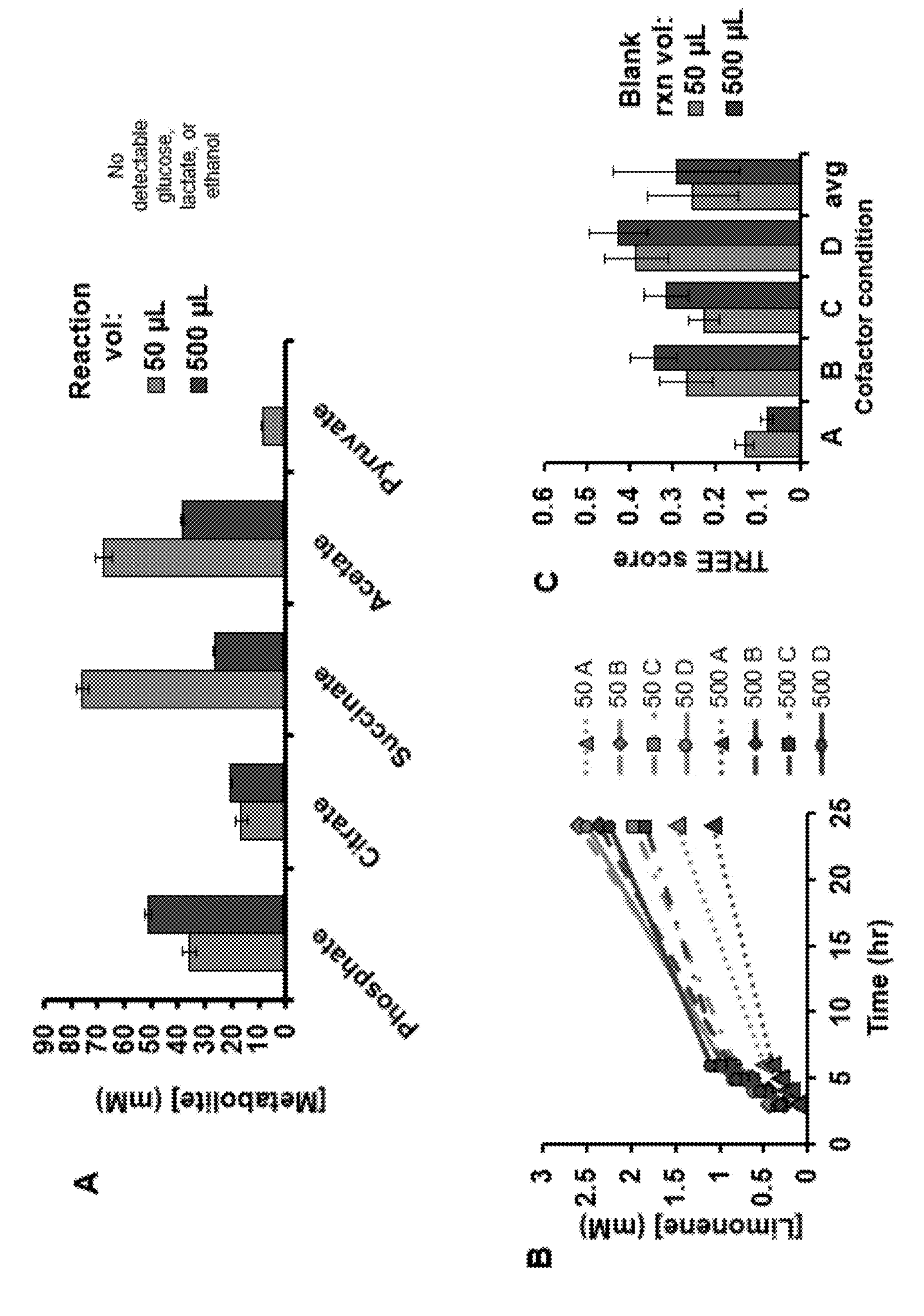

FIG. 70. Scaling volume of CFPS "blank" reactions (i.e. CFPS without a plasmid substrate) from 50 to 500 μL changes the metabolic products. (A) Analysis of metabolites in two CFPS reactions incubated for 20 hours with no DNA template. Phosphate is quantified by kit (Malachite Green Phosphate Assay POMG-25H, BioAssay Systems) while citrate, succinate, acetate, and pyruvate are measured on HPLC using methods previously described (Dudley et al., 2016). (B/C) Testing CFPS blank reaction volume using a glucose-to-limonene CFPS-ME reaction. Limonene titer is plotted (B) and the same data is converted to a TREE score (C). Each L CFPS-ME reaction includes 11.2 μL "blank" CFPS reaction, 3.8 μL CFPS of pathway enzymes, 2.5 μL pre-enriched extracts, and 12.5 μL substrates/cofactors/water. Cofactor conditions A, B, C, D are described in the Table at FIG. 65. Due the metabolic differences between 50 μL and 500 μL "blank" reactions, all "blank" reactions used in Example 8 were made at the 50 μL scale for consistency.

Figure 71:
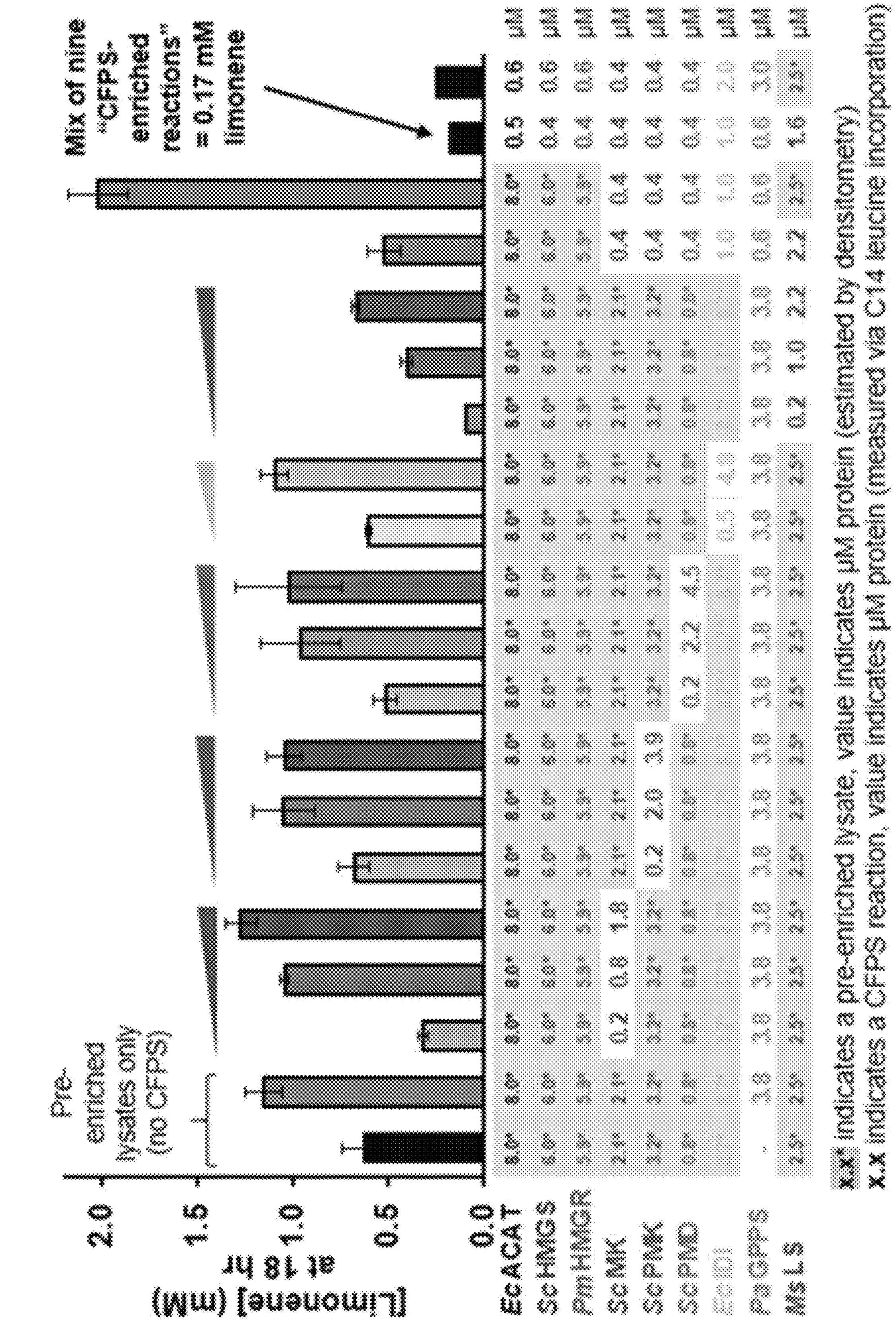

FIG. 71. Mixing of CFPS reactions with pre-enriched lysates indicates minimum enzyme concentrations needed for limonene production. In order to compare the relative activity of pathway enzymes and determine appropriate concentrations for mixing CFPS-enriched reactions, we started with a mixture of 8 pre-enriched lysates capable of producing limonene (leftmost black bar, (Dudley et al., 2019)). We immediately observed that supplementing high concentrations of CFPS reaction expressing PaGPPS increased limonene titer (leftmost gray bar) and used 3.8 μM in subsequent tests. We then removed the pre-enriched lysate encoding MK, PMK, PMD, IDI, and LS and added increasing concentrations of CFPS reaction expressing these reactions. These results informed the initial enzyme concentrations for Enzyme Set 1.0 used in FIG. 59 to be at 1.0 μM PmHMGR, 0.4 μM ScMK, 0.4 μM ScPMK, 0.4 μM ScPMD, 2.0 EcIDI, 3.0 μM PaGPPS. Finally we show that the initial enzyme homologs, mixed as nine CFPS-enriched reactions, can support limonene production.

Figure 72:
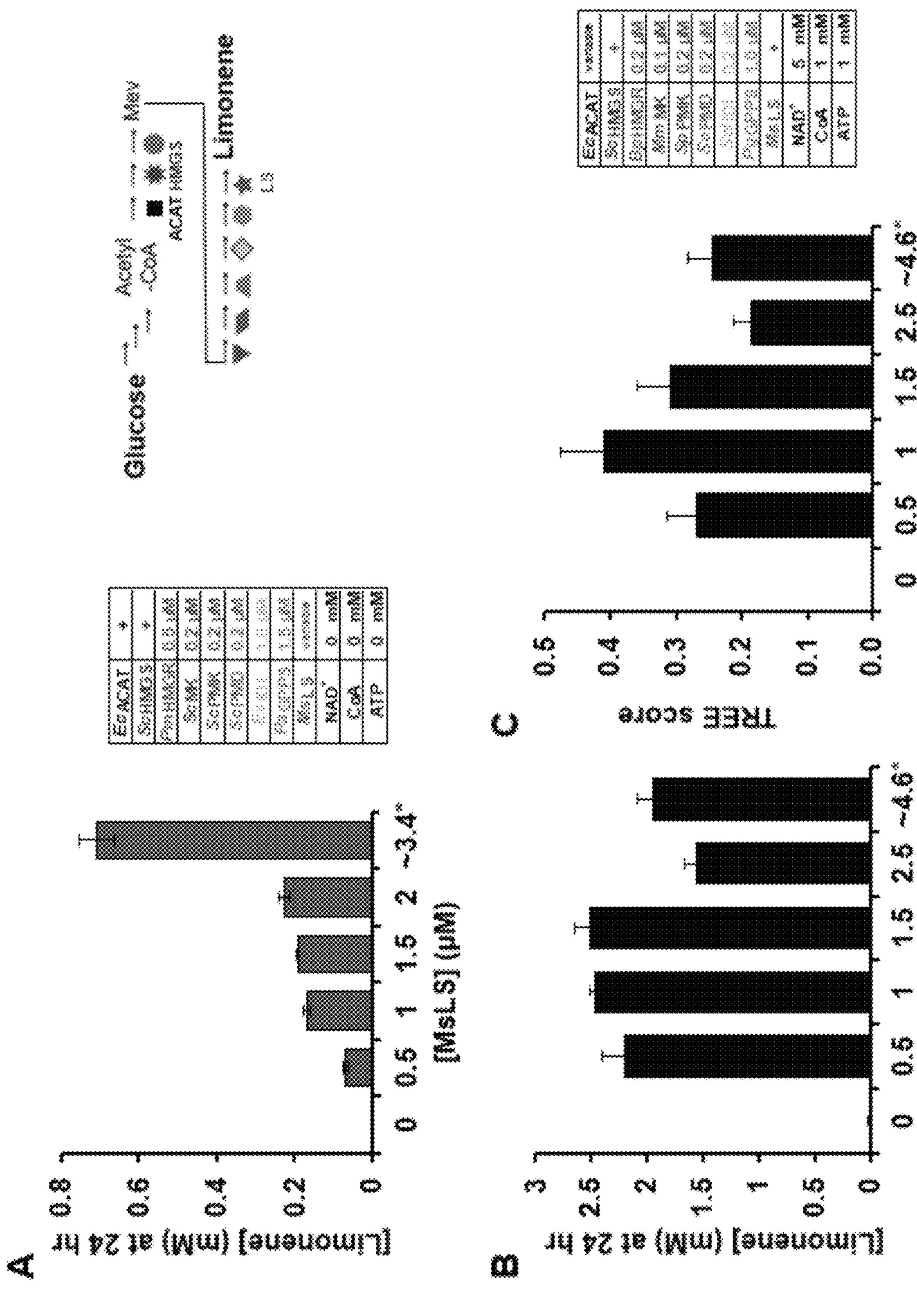

FIG. 72. Use of pre-enriched lysates for LS, ACAT, and HMGS improves limonene production and increases available space in the reaction for other CFPS-generated enzymes. (A) Titration of limonene synthase from *Mentha spicate* (MsLS) generated by CFPS (0.5-2 μM) or pre-enriched lysate (~3.4 μM) suggests LS is a rate-limiting step for limonene production. (B) Titration of acetyl-CoA acetyltransferase from *Escherichia coli* (EcACAT) generated by CFPS (0.5-2.5 μM) or pre-enriched lysate (~4.6 μM) suggests 0.5 LVM ACAT is the minimum enzyme concentration sufficient to produce 2 mM of limonene. (C) Titration of 3-hydroxy-3-methylglutaryl-CoA synthase from *Saccharomyces cerevisiae* (ScHMGS) generated by CFPS (0.2-4 μM) or pre-enriched lysate (~5.5 μM) suggests 3 μM HMGS is the minimum enzyme concentration sufficient to produce 2 mM of limonene. The standard iPROBE reaction used throughout this work dictates that only 15 μL of the 30 μL reaction is available for CFPS reactions; using pre-enriched lysates for ACAT, HMGS, LS not only maximized limonene titer (in the case of LS) but also frees up space for other pathway enzymes generated by CFPS to be included at a higher concentration in the limonene synthesis reaction. Concentrations of ACAT, HMGS, LS in pre-enriched lysates are estimated by densitometry (Table at FIG. 64).

Figure 73:
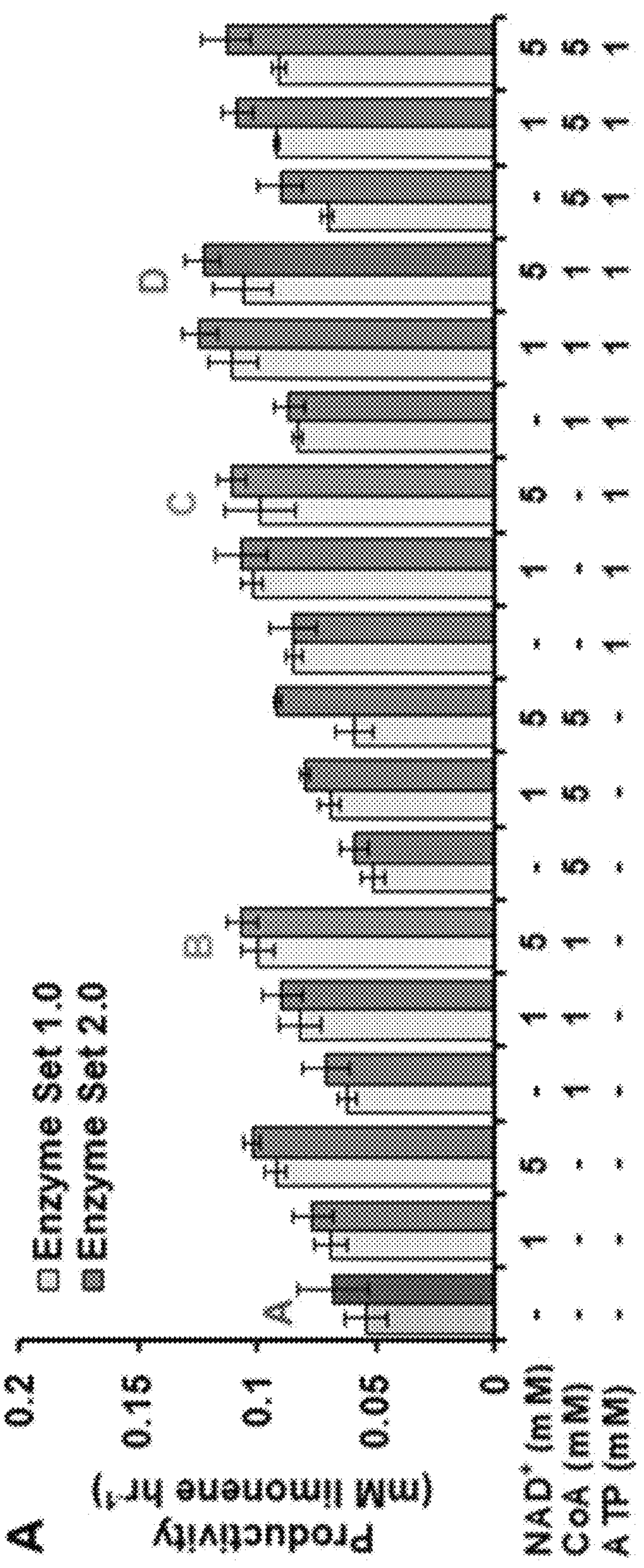

FIG. 73. Supplementation of cofactors $NAD^+$, CoA, and ATP improves limonene productivity (A), titer (B), and TREE score (C). The improved set of enzyme homologs (enzyme set 2.0) has increased productivity and titer compared to the initial set of enzyme homologs (enzyme set 1.0) in nearly all cofactor conditions tested. Four reaction conditions (A, B, C, D) were selected as cofactor conditions for further experiments. Note that plot C is a bar chart representation of the data in FIG. 60B.

Figure 74:
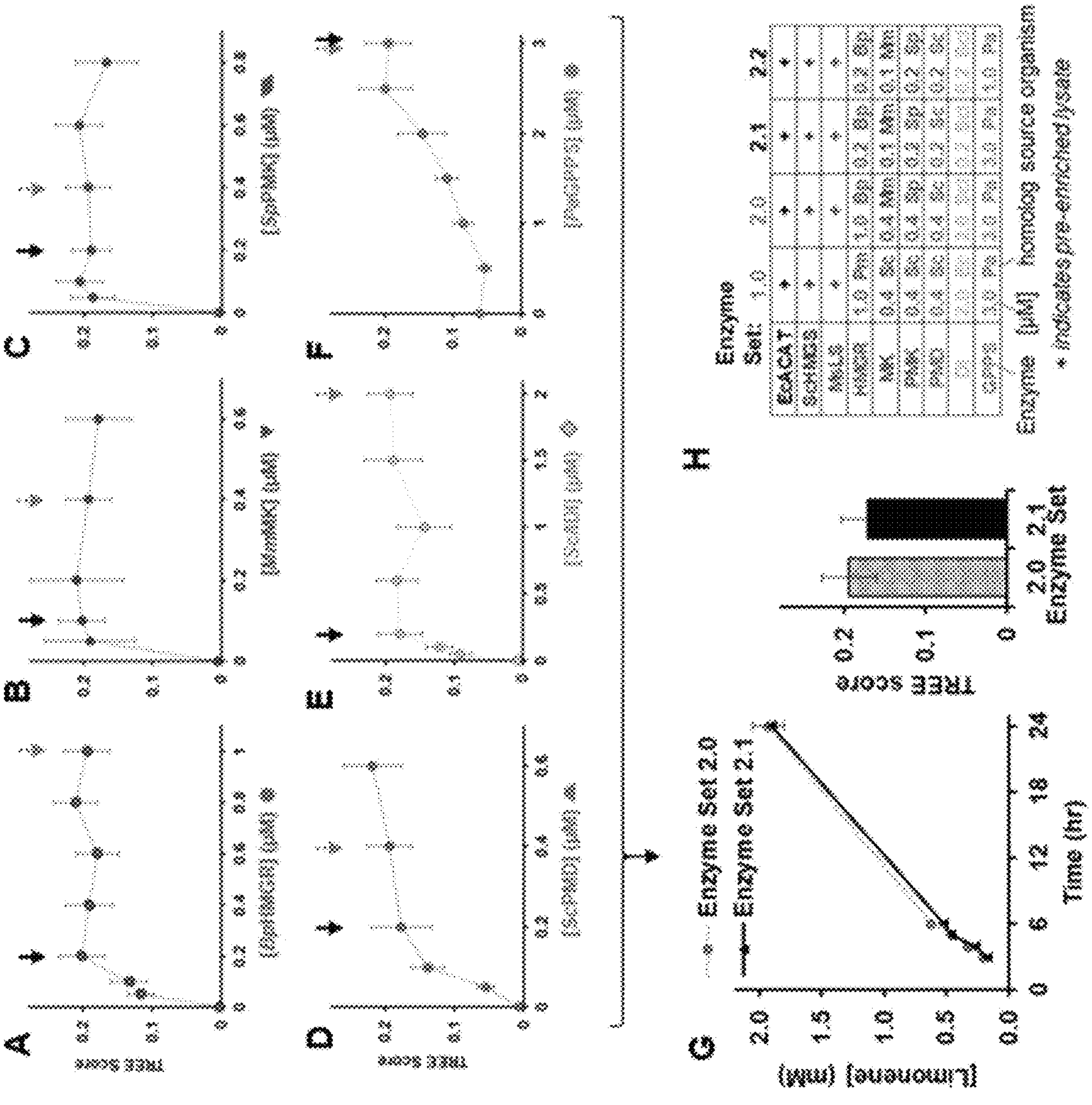

FIG. 74. Reducing enzyme concentrations to enable equivalent limonene production. (A-F) Plots of limonene TREE score as a function of enzyme concentration using cofactor condition D (5 mM $NAD^+$, 1 mM CoA, 1 mM ATP). Pathway enzymes not being adjusted are held at the same concentrations used in enzymes set 2.0. Enzyme set 2.1 uses the same enzyme homologs as set 2.0 but reduces the concentrations of BpHMGR, MmMK, SpPMK, ScPMD, and SclIDI. Black arrows indicate the concentration of each enzyme in set 2.0 while gray arrows indicate concentration of each enzyme in set 2.1. (G) After testing the effect of concentration on each enzyme individually, the concentrations of HMGR, MK, PMK, PMD, and IDI were reduced to create enzyme set 2.1 which has a similar limonene production and TREE score to enzyme set 2.0. (H) Summary of enzyme set components used during cofactor and concentration optimization.

FIG. 75. Limonene production using two different GPPS enzymes at varying concentration. The default homolog for GPPS throughout the study thus far has been PaGPPS; increasing the concentration of PaGPPS maximizes limonene titer (3 μM is one of the largest concentrations possible without exceeding the 15 μL of CFPS reaction included in a 30 μL limonene synthesis reaction). However, comparison with PgGPPS indicates that other GPPS homologs do not require such high enzyme concentrations to support the same limonene titer and that using 1 μM as the benchmark comparison is appropriate for future testing. Thus, enzyme set 2.2 (the starting point in FIG. 61) reduces the concentration of GPPS from 3.0 μM to 1.0 μM in order to more accurately compare the specific activity of GPPS homologs in the next round of homolog screening.

Figure 76:
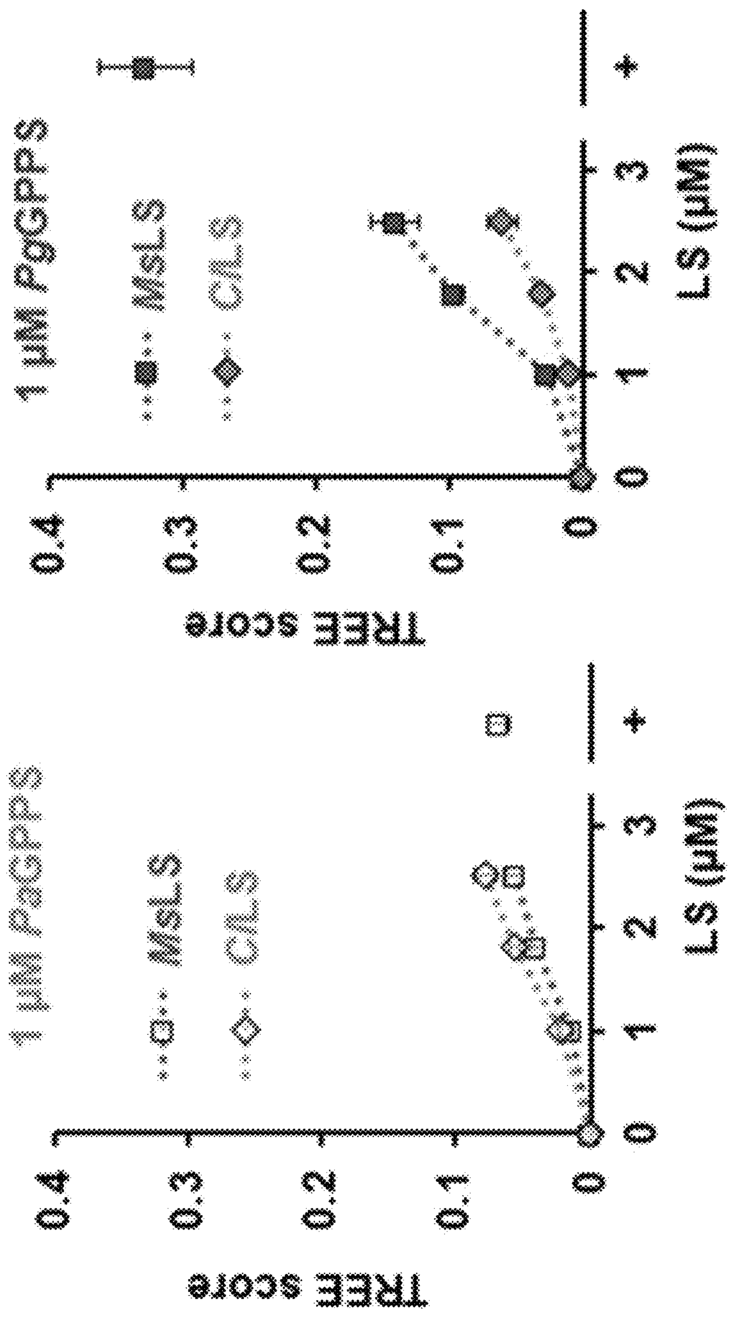

FIG. 76. Testing limonene synthases under improved cofactors and decreased enzyme concentrations. Comparison of MsLS (from *Mentha spicata*) and ClLS (from *Citrus limon*) paired with two differed GPPS enzymes; MsLS is known to produce (4S)-(−)-limonene (Colby et al., 1993) while ClLS typically produces (4R)-(+)-limoenene. (Lücker et al., 2002).

Figure 77:
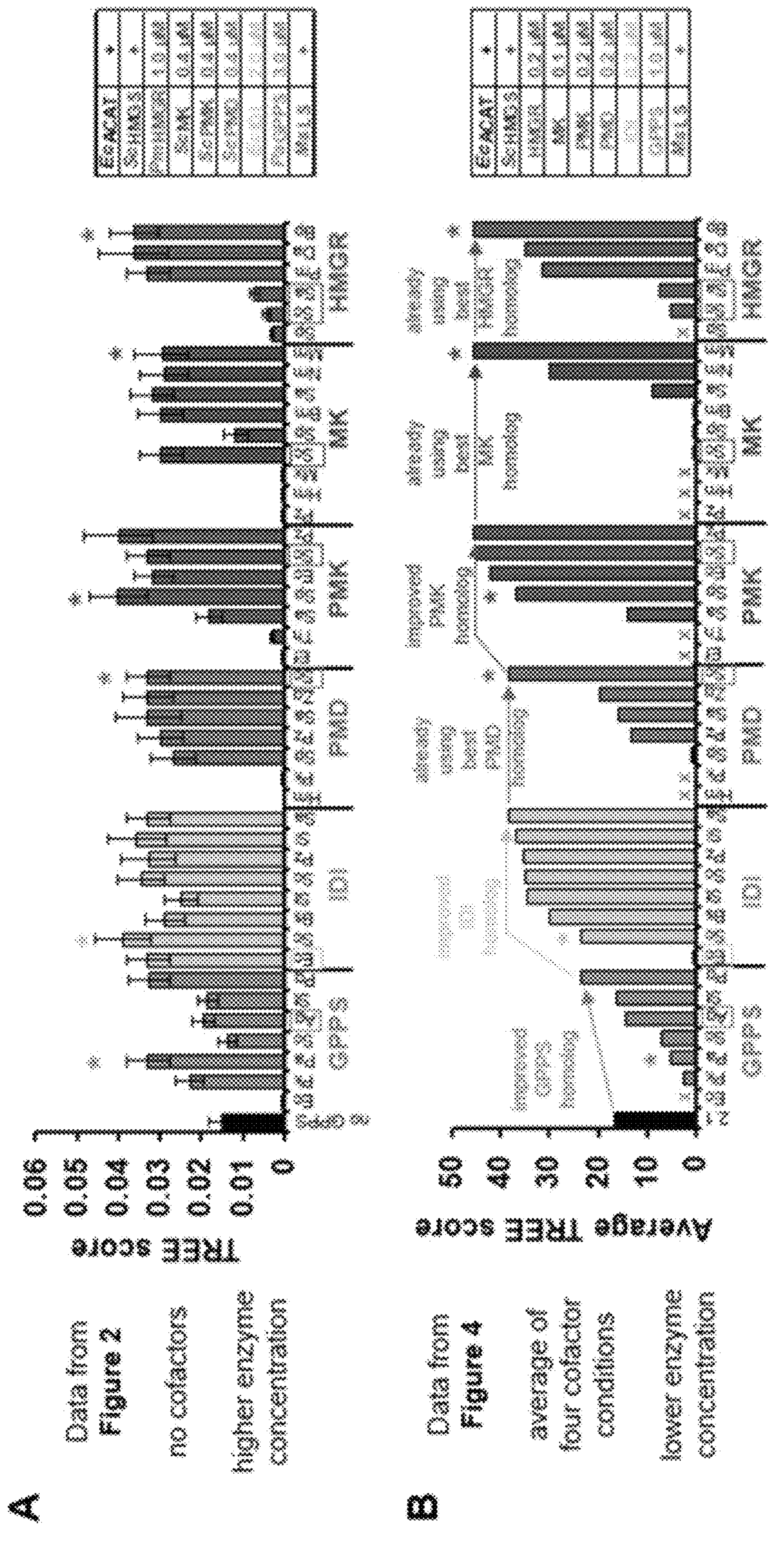

FIG. 77. A more stringent selection condition differentiates similar homologs. (A) The TREE scores from FIG. 59E are replotted; * denoted the enzyme selected as the best candidate when transitioning from enzyme set 1.0 to enzyme set 2.0. (B) The average TREE scores from FIG. 61C are replotted. Homologs marked with "x" were inactive in FIG. 59 and were not retested in FIG. 61. The boxed homologs (AgGPPS, EcIDI, ScPMD, ScPMK, ScMK, and SaHMGR/ScHMGR) indicate some of the commonly used enzyme homologs utilize for metabolic engineering in living cells, for example the production of limonene (Alonso-Gutierrez et al., 2013; Alonso-Gutierrez et al., 2015) and pinene (Sarria et al., 2014).

Figure 78:
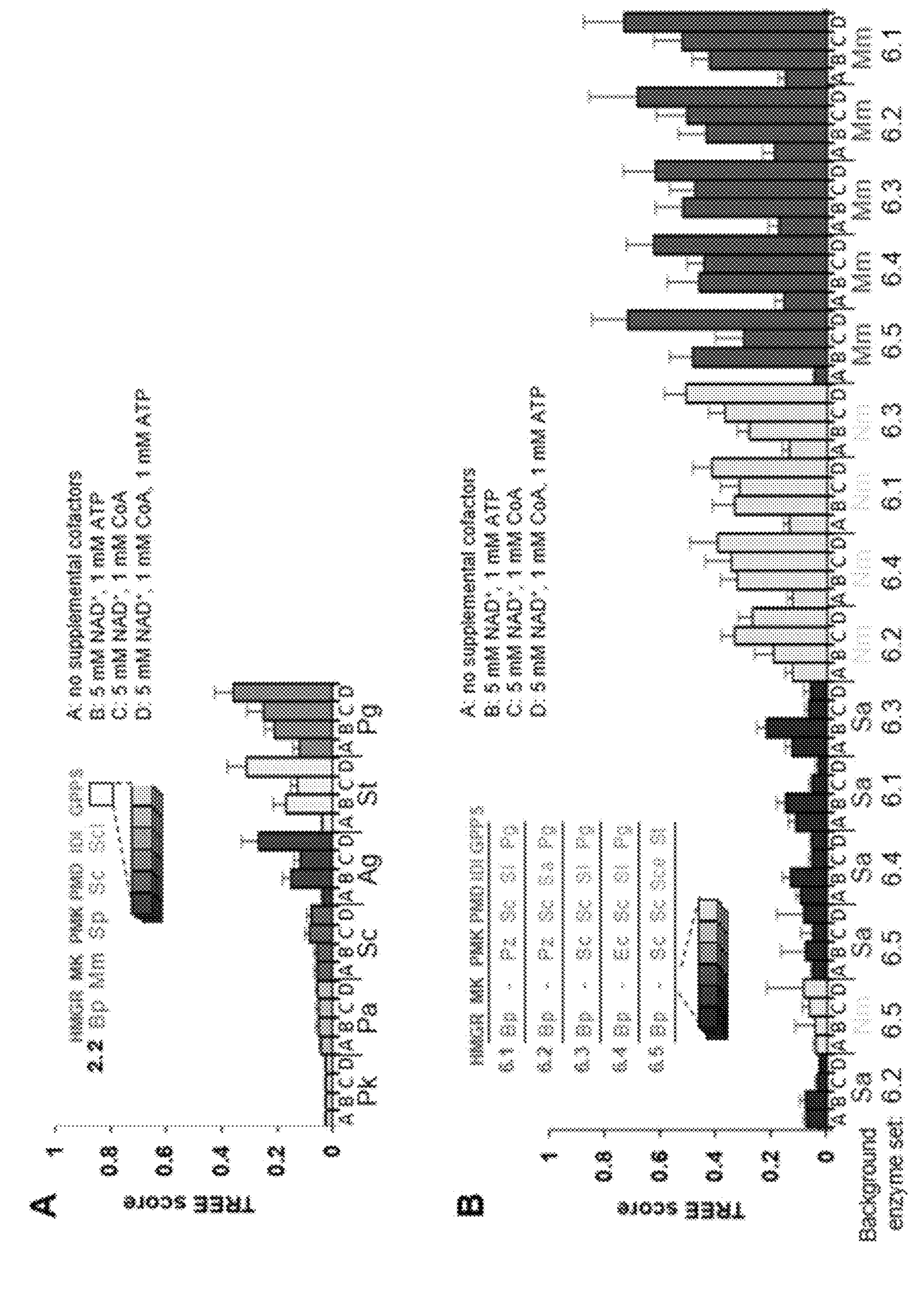

FIG. 78. A-B. TREE scores of selected reactions depicted in FIG. 61D. In particular, SaMK is inhibited by higher CoA concentrations compared to other MK homologs.

Figure 79:
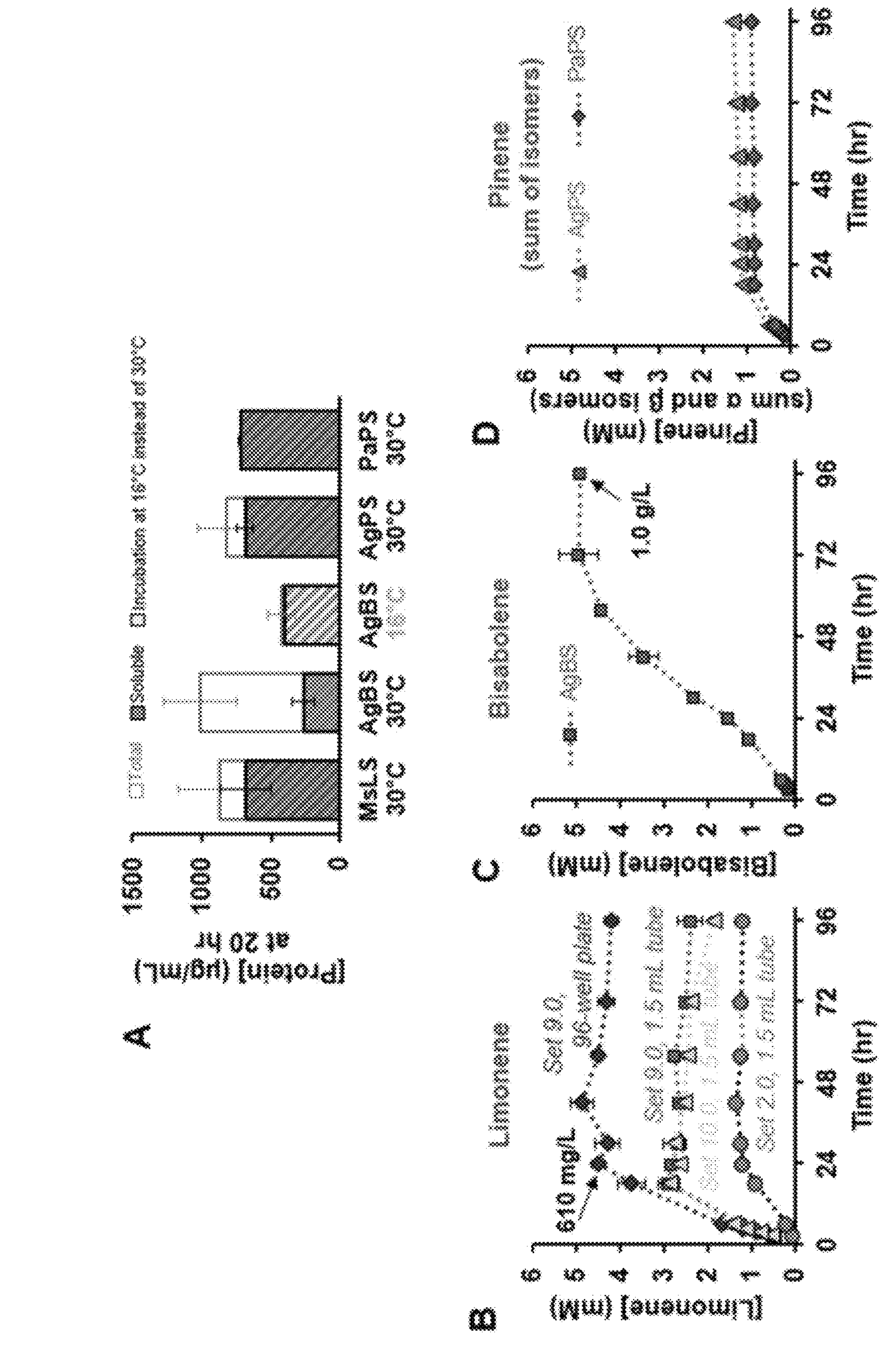

FIG. 79. Production of limonene, pinene, and bisabolene over 96 hours. (A) Cell-free protein synthesis of tepenoid synthases; incubation at 16° C. improves expression of bisabolene synthase from *Abies grandis*. (B) Production of limonene from glucose using Enzymes Sets 2.0, 9.0, and 10.0. Incubation of reactions in a 96-well plate covered in foil rather than a 1.5 mL microcentrifuge tube further increased titer. Set 9.0 uses a pre-enriched MsLS lysate while set 10.0 generates MsLS using CFPS (3.8 μM) (C) Production of bisabolene from glucose by CFPS-enriched reactions containing farnesyl diphosphate synthase (EcFPPS encoded by ispA) from *E. coli* and bisabolene synthase (BS) from *Abies grandis*. (D) Production of pinene from glucose by CFPS-enriched reactions containing pinene synthases (PS) from *Abies grandis* (Grand fir) and *Picea abies* (Norway spruce). (E-F) Pinene exists as two isomers (α or β) that can be distinguished by GC-MS due to different fragmentation patterns and retention times. For biofuel applications, there is no preference for either isomer, however, β-pinene is a more valuable commodity chemical since it is less abundant than α-pinene in turpentine (Sarria et al., 2014). β-pinene is favored in this in vitro system. (G) Farnesol accumulates in all reactions conditions but especially in the bisabolene reaction. (H) The ratio of α or β pinene produced using purified pinene synthases (*A. grandis* (Bohlmann et al., 1997) and *P. abies* (Martin et al., 2004)), this study, and production in cells (Sarria et al., 2014). Unless noted, limonene, pinene, and bisabolene synthesis reactions use enzyme set 10.0 (see Table at FIG. 65) and are supplemented with 5 mM $NAD^+$, 1 mM CoA, and 1 mM ATP.

Figure 80:
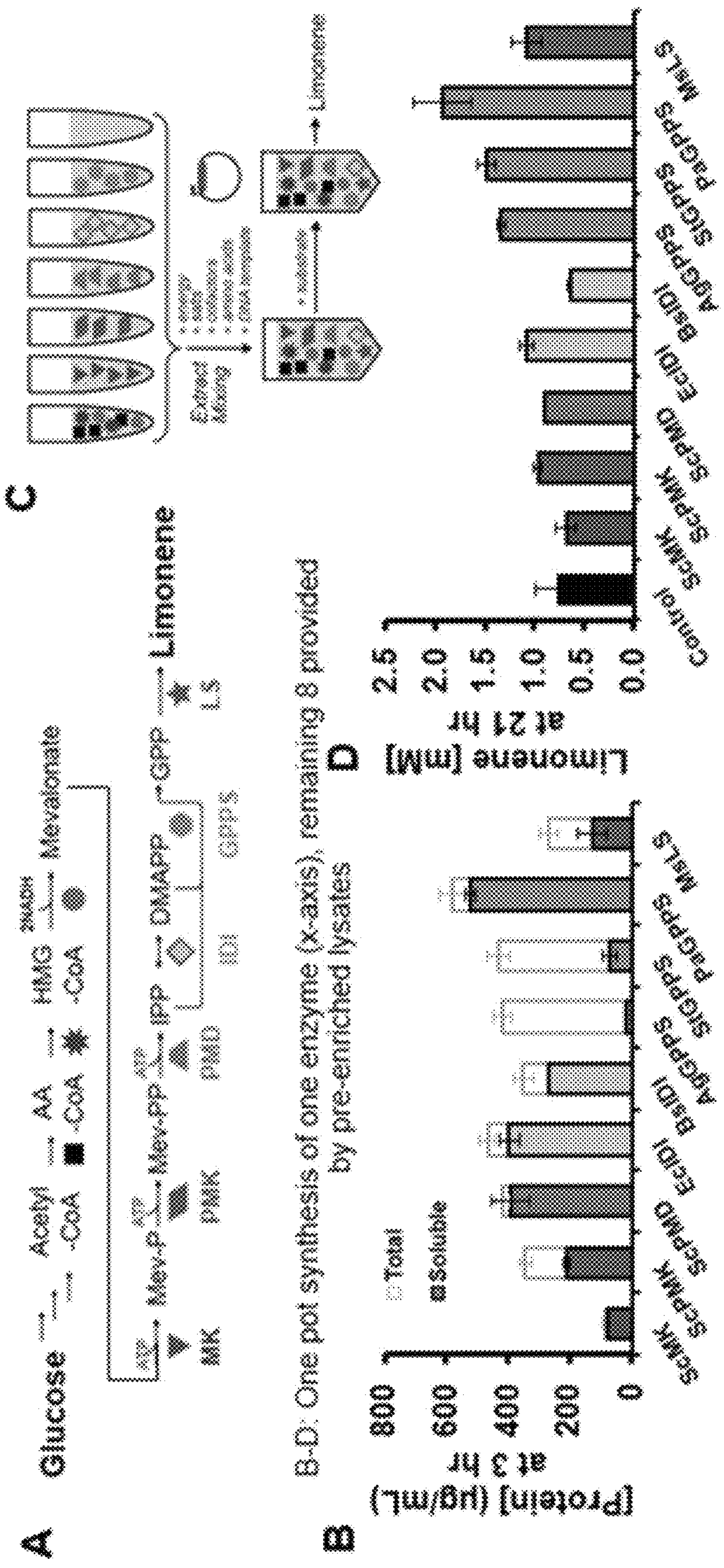

FIG. 80. Simultaneous "one pot" CFPS-ME. The initial conception for Cell-Free Protein Synthesis-driven Metabolic Engineering (CFPS-ME) was developed for a butanol biosynthesis pathway (Karim and Jewett, 2016) and involved expressing multiple pathway enzymes simultaneously from multiple plasmids in a single "one pot" CFPS reaction. We initially tried this approach but found that the equal expression of six enzymes simultaneously was not possible despite adjusting the plasmid concentration of the lowest expressing enzyme. (A) Metabolic pathway from glucose to limonene. (B) Cell-free expression of pathway enzymes measured via $^{14}C$-leucine incorporation after 3 hours. (C) Experimental approach used in panel D depicted for the MsLS enzyme: six pre-enriched lysates containing pathway enzymes 1-8 are mixed with CFPS-reagents and plasmid encoding enzyme 9 (MsLS). After three hours, glucose is added to initiate limonene biosynthesis. (D) The approach is repeated for each pathway enzyme in turn and limonene production measured. Each subsequent reaction synthesizes one pathway enzyme (labeled on the x-axis) via CFPS using a mixture of lysates pre-enriched in the other eight pathway enzymes. The "Control" reaction contains no plasmid but all nine limonene pathway enzymes from pre-enriched lysates (Dudley et al., 2019). (E) The CFPS reaction contains plasmids encoding: MsLS alone (1), MsLS and PaGPPS (2), MsLS, PaGPPS, and EcIDI (3), MsLS, PaGPPS, EcIDI, and ScPMD (4). MsLS, PaGPPS, EcIDI, ScPMD, and ScPMK (5). Reaction (6) contains MsLS, PaGPPS, EcIDI, ScPMD, ScPMK, and ScMK at three different ratios (6A, 6B, 6C). The lysates supporting CFPS are missing the corresponding enzymes being synthesized. As in panel C-D, glucose and buffer are added after 3 hr of protein expression and limonene measured 21 hr later. (F) Autoradiogram of CFPS reactions containing $^{14}C$-leucine after 3 hr. Lanes 1, 2, and 3 uses the same ratios of six plasmids as in panel E where lanes 4-9 are control reactions each expressing only one plasmid template at a time. In conclusion, the two-pot approach detailed in iPROBE (Karim et al., 2020) offers several advantages relative to "one-pot" CFPS-ME (Karim and Jewett, 2016) or CFME (Dudley et al. 2018). For instance, the separation of catalyst synthesis (CFPS) from utilization (metabolite production) enables quantitative control of each pathway enzyme via pipetting and avoids the need to optimize enzyme expression in vivo (Dudley et al. 2018). Method details: To produce a given pathway enzyme, plasmid encoding the enzyme is added to a 20 μL CFPS reaction that is driven by a mixture of pre-enriched lysates at total protein concentration of 10 mg/mL. The standard pre-enriched lysate mix includes 3.5 $mgmL^{-1}$ of a ACAT/HMGS/HMGR combined lysate, 1 mg/mL of MK, PMK, PMD, IDI, GPPS, and 1.5 mg/mL LS. When the pathway enzyme is synthesized by CFPS, the pre-enriched lysate is replaced by "blank" BL21(DE3) lysate containing no enriched enzyme. The reaction is incubated at 30° C. in 1.5 mL microcentrifuge tubes. After three hours, 5 μL of concentrated glucose and Bis-Tris buffer (final concentration of 200 mM and 100 mM, respectively) to make a 25 μL combined reaction. The reaction is incubated for another 21 hours under a 25 μL limonene overlay and the overlay is subsequently measured for limonene production using GC-MS as previously described (Dudley et al., 2019). Selected reactions were separated on an SDS-PAGE gel, exposed by autoradiography, and imaged with a Typhoon 7000 (GE Healthcare Life Sciences, Pittsburgh, PA).

Figure 81:
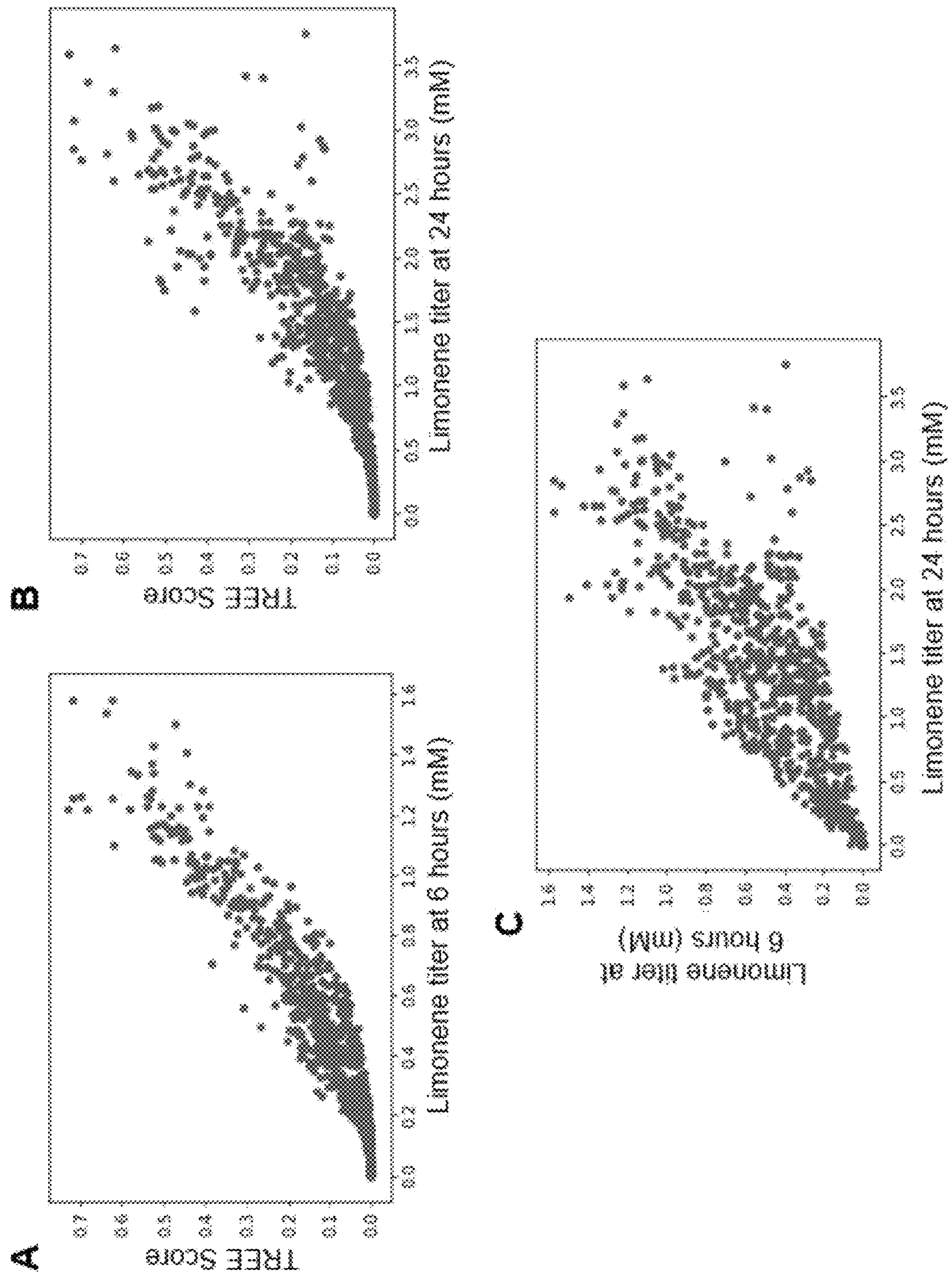

FIG. 81. Plots of the TREE score as a function of its component parameters.

Figure 82:
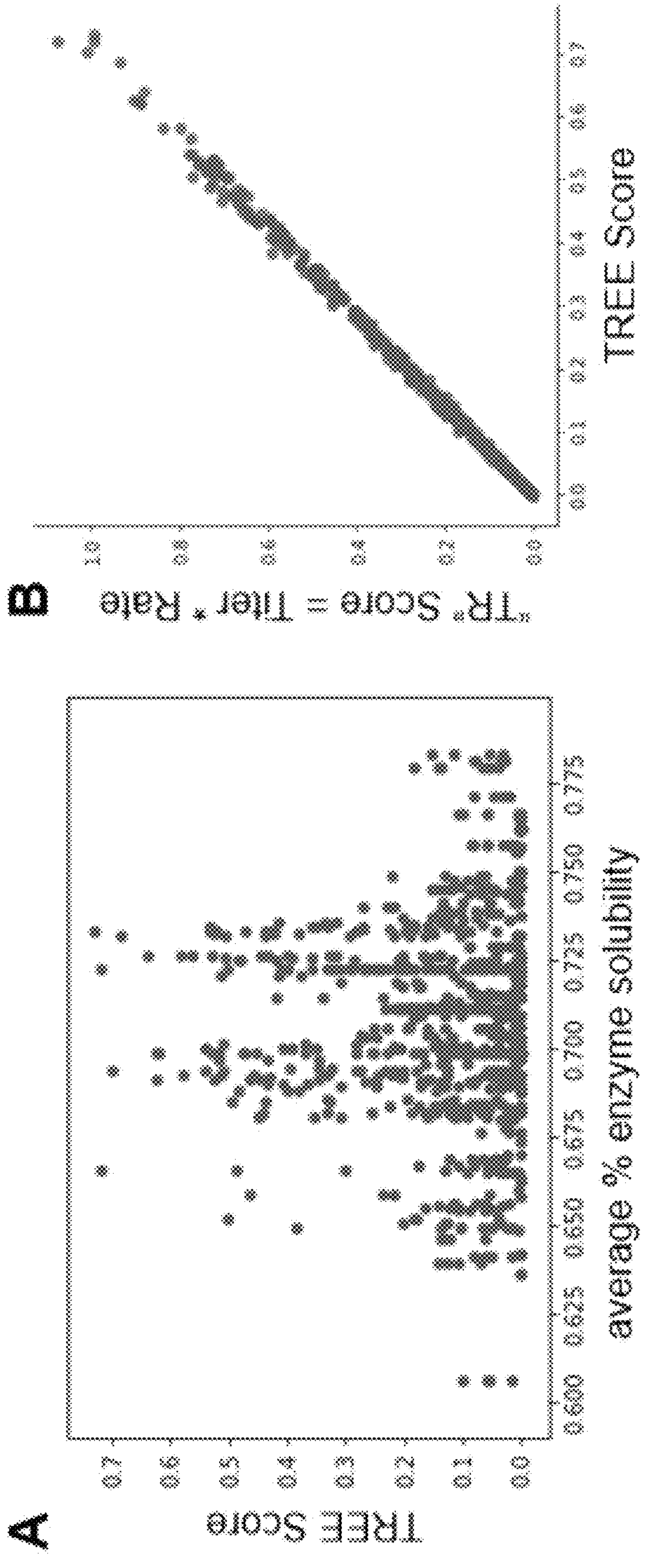

FIG. 82. The sensitivity of the TREE score to average enzyme solubility. The enzyme expression component has a small impact on the final TREE score ("TR" score=titer*rate)

Figure 83:
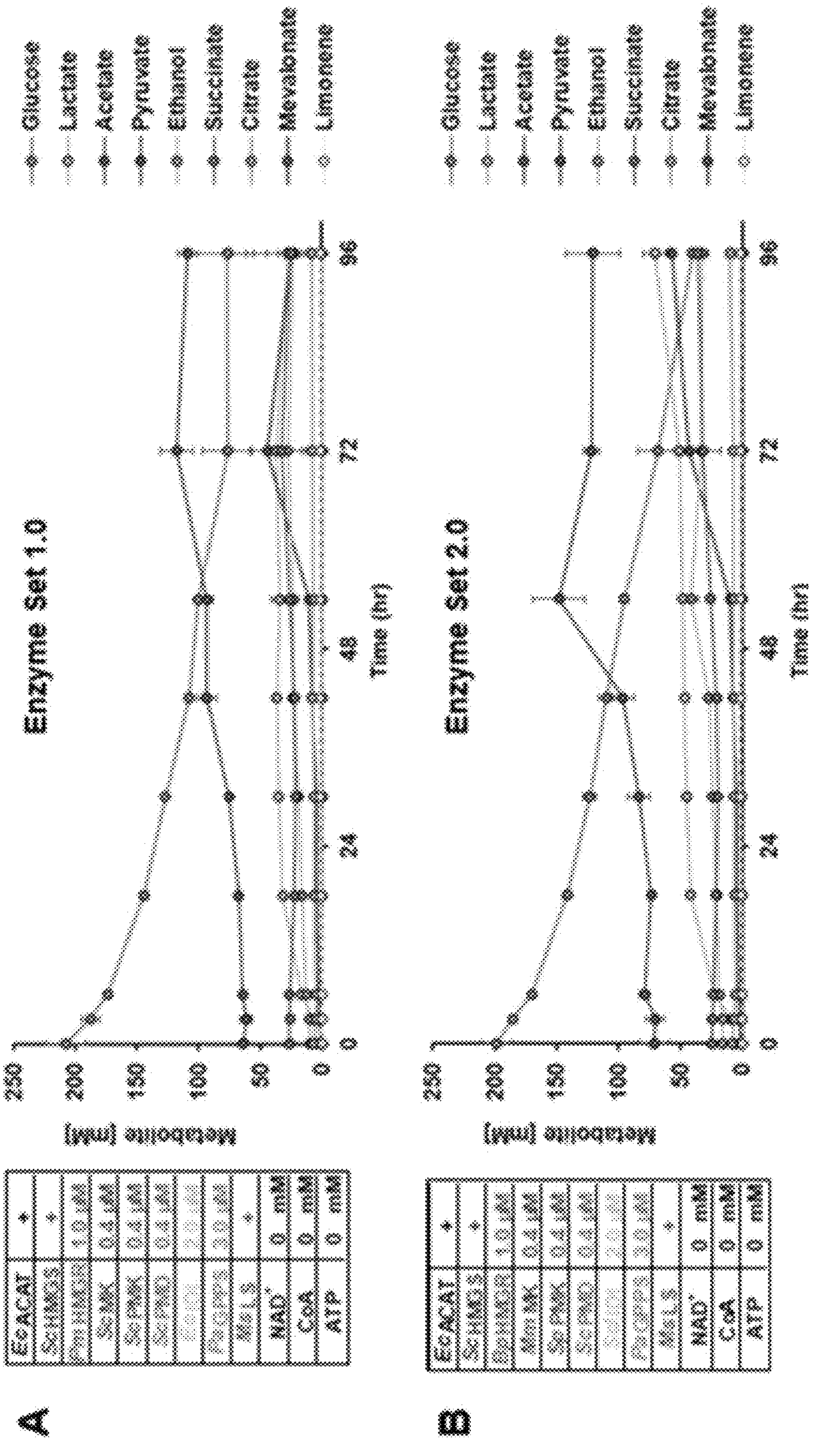

FIG. 83. Metabolite analysis of three enzyme sets. Limonene and mevalonate are detected by GC-MS (Dudley et al., 2016; Dudley et al., 2019) while the remaining metabolites are measured by HPLC (Dudley et al., 2016). Part C is reproduced from FIG. 61D here for comparison. Part D is a replotting of the data in FIG. 60A and FIG. 79B for comparison.

Figure 4:
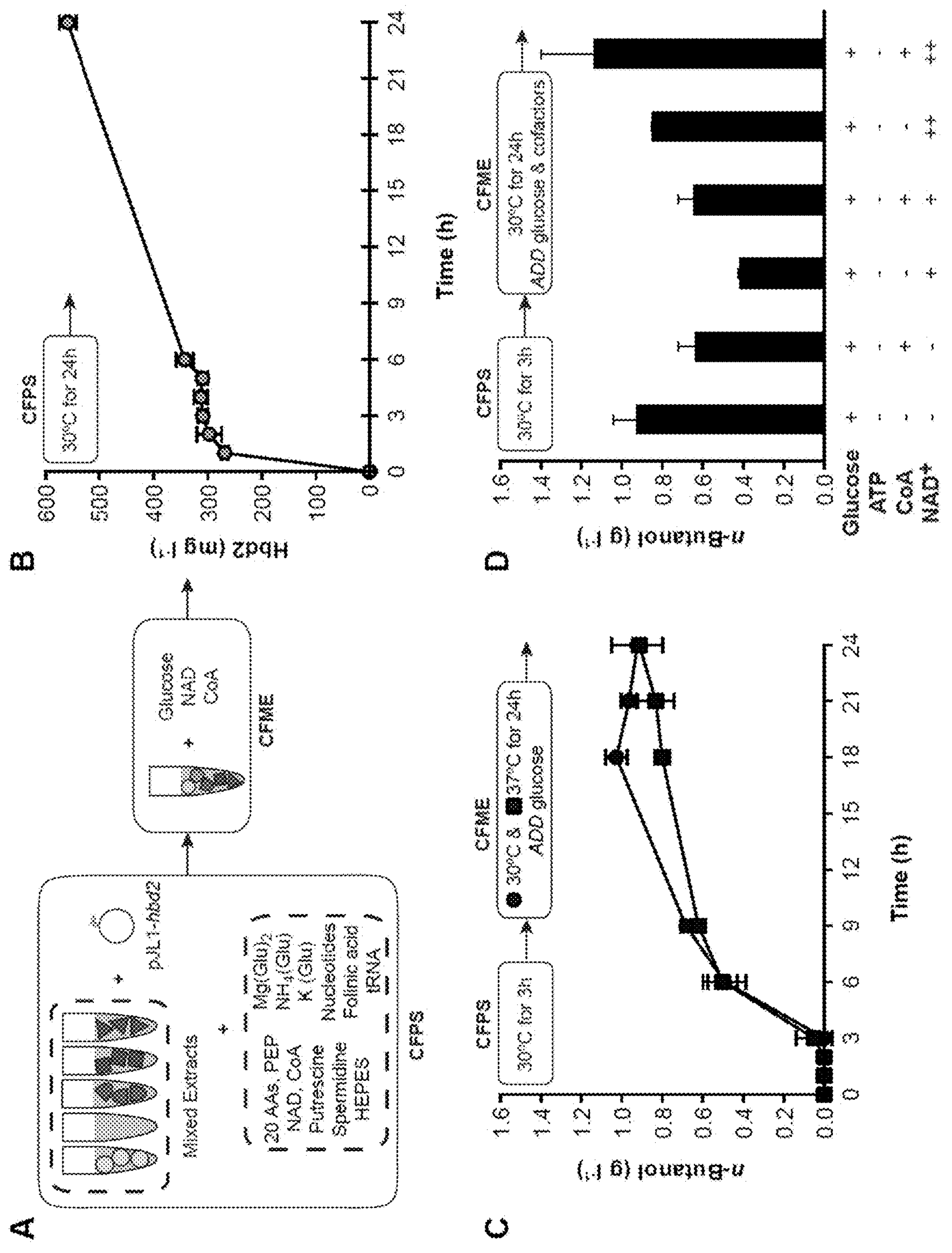
FIG. 4. Cell-free protein synthesis of entry enzyme activates n-butanol production in vitro by CFPS-ME approach. (A) Diagram describing the CFPS-ME experimental design. (B) Cell-free protein synthesis titers of Hbd2 from pJL1-hbd2 in a crude lysate mixture containing AtoB (EC), Crt1 (CA), Ter1 (TD), and AdhE1 (CA) overexpressed as determined by radioactive $^{14}C$-leucine incorporation. CFPS reactions incubated over a 24-hr period at 30° C. (C) n-butanol production in the same mixed lysate system activated by cell-free protein synthesis of Hbd2 run at 30° C. for 3 h. Glucose was added to activate the n-butanol pathway and CFME reactions were incubated over a 24-hr period at both 30° C. and 37° C. (D) Cofactor (ATP, CoA, $NAD^+$) optimization of downstream (ME portion of the CFPS-ME approach) cell-free reactions producing n-butanol were performed. Minus (−) signs represent no cofactor added, plus (+) signs represent mM amounts of cofactor to match conditions in CFME-alone experiments, and plus-plus (++) reactions represent double the amount of that cofactor. Reactions incubated for 24 h at 30° C. All error bars represent standard deviations with n≥3 independent reactions.
Figure 84:
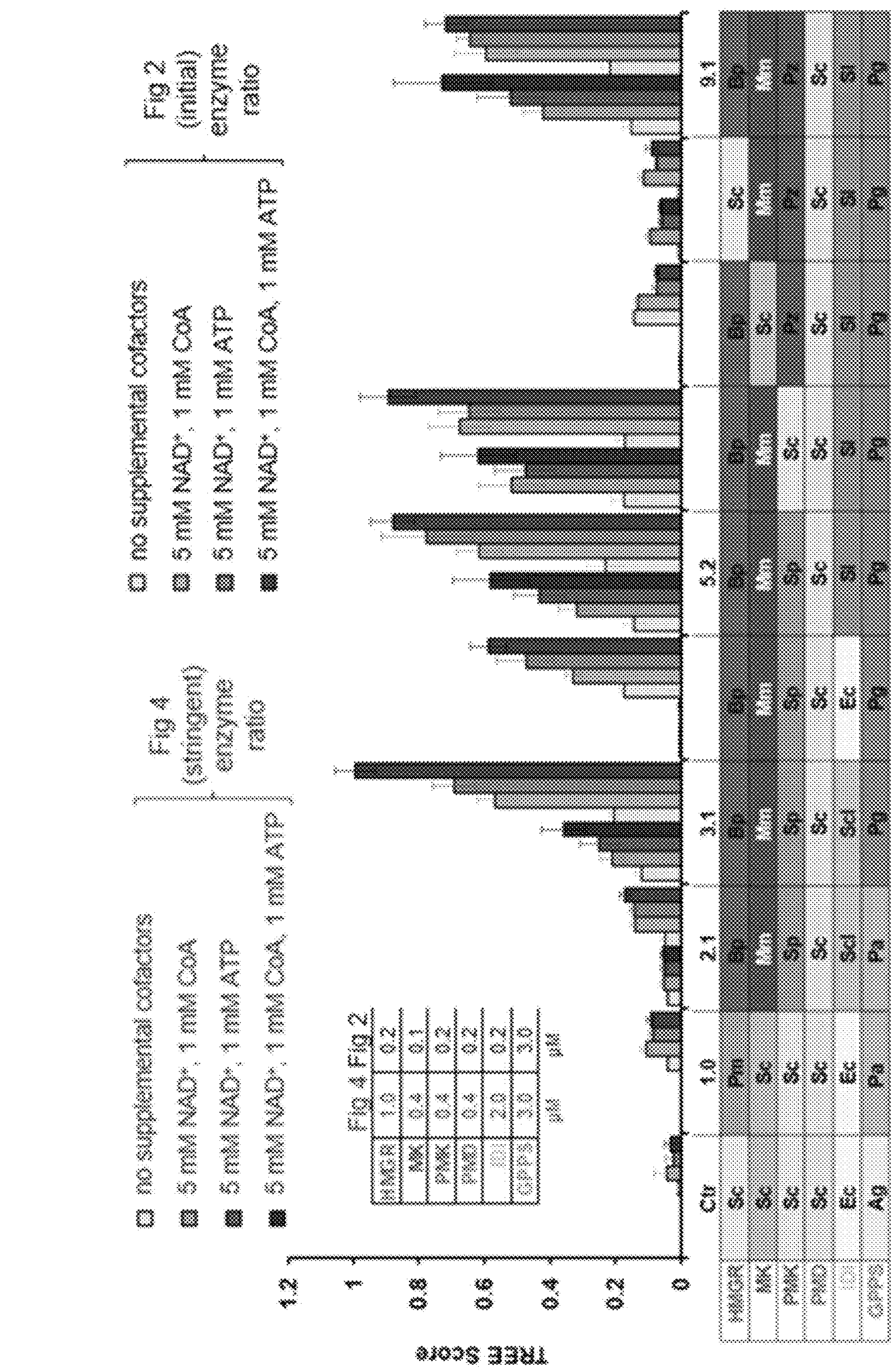

FIG. 84. Comparison of ten enzyme sets at two enzyme ratios and four cofactor concentrations. Nine enzyme sets from FIGS. 59 and 61 are replotted and/or run with the alternate enzyme concentration. For comparison, we also tested a commonly used set of enzyme homologs (Ctr) used to produce limonene (Alonso-Gutierrez et al., 2013; Alonso-Gutierrez et al., 2015) and pinene (Sarria et al., 2014). A higher concentration of enzymes enables limonene production using EcIDI, and ScMK; limonene is not produced when using the lowered (more stringent) enzyme concentrations utilized in FIG. 61. Both enzyme ratios indicate that ScPMK, SpPMK, and PzPMK are relatively similar homologs. The concentrations of enzymes used in "FIG. 59 enzyme ratio" are 1.0 μM HMGR, 0.4 μM MK, 0.4 μM PMK, 0.4 μM PMD, 2.0 μM IDI, and 3.0 μM GPPS plus pre-enriched lysates for EcACAT, ScHMGS, and MsLS. The concentrations of enzymes used in "FIG. 4 enzyme ratio" are 0.2 μM HMGR, 0.1 μM MK, 0.2 μM PMK, 0.2 μM PMD, 0.2 μM IDI, and 3.0 μM GPPS plus pre-enriched lysates for EcACAT, ScHMGS, and MsLS. Homolog source organism: Sc, *Saccharomyces cerevisiae*; Pm, *Pseudomonas mevalonii*; Bp, *Bordetella petrii*; Mm, *Methanosarcina mazei*; Sp, *Streptococcus pneumoniae*; Pz, *Paracoccus zeaxanthinifaciens*; Ec, *Escherichia coli*; Scl, *Streptomyces clavuligerus*; Sl, *Solanum lycopersicym* (tomato); Pa, *Picea abies*; Ag, *Abies grandis*; Pg, *Picea glauca*. Although this figure is not referenced in the context of Example 8, it is provided as a benchmark for the in vivo experiments.

FIG. 85. Gene sequences used in Example 8 (SEQ ID NOs:16-72). XbaI, ribosome binding site (RBS) from pJL1, NdeI (containing ATG start codon), SalI, stop codon, the N-terminal expression tag (MEKKI (SEQ ID NO: 13) or MHMEKKI (SEQ ID NO: 15)) sequence is underlined.

Figure 86:
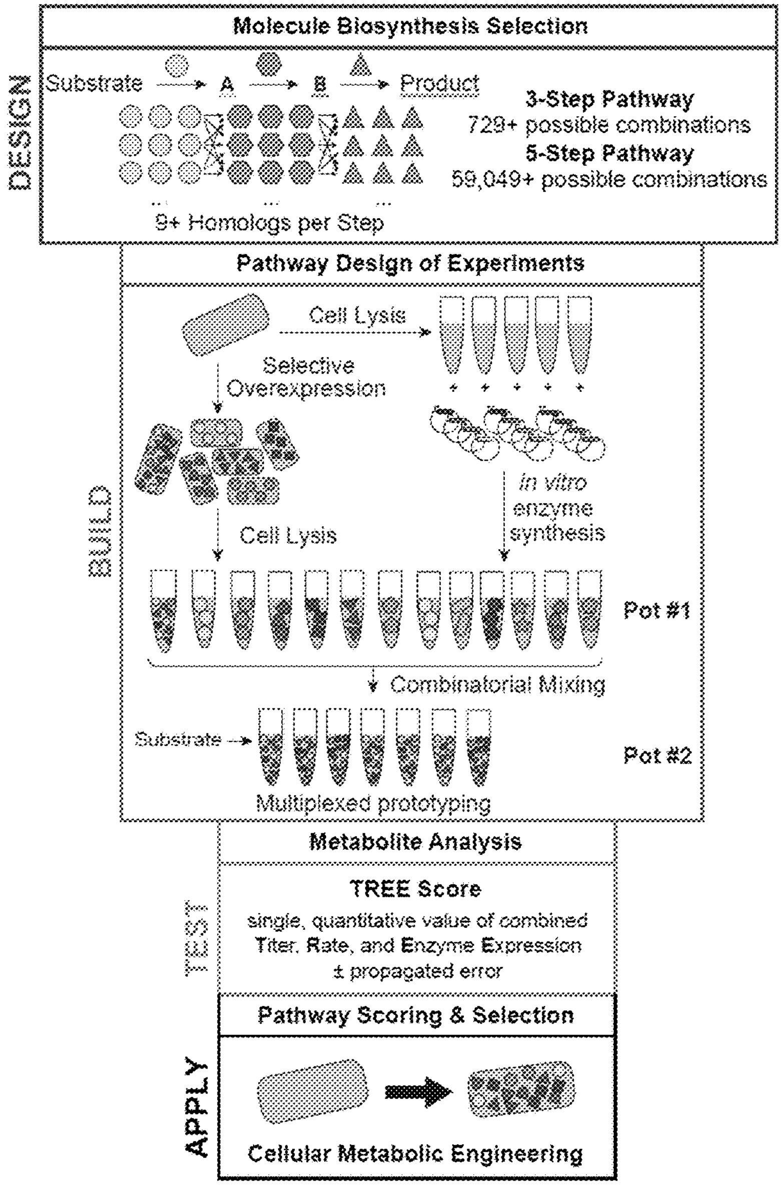

FIG. 86. A two-pot cell-free framework for in vitro prototyping and rapid optimization of biosynthetic enzymes (iPROBE). A schematic overview of the iPROBE approach following a DBT and apply framework is depicted. In the design phase, reaction schemes and enzyme homologs are selected. In the build phase, lysates are enriched with pathway enzymes via overexpression prior to lysis[35] or by cell-free protein synthesis post lysis. Then, lysates are mixed to assemble enzymatic pathway combinations of interest. In the test phase, metabolites are quantified over time and data is reduced into a single quantitative metric for pathway combination ranking and selection. In the apply phase, cell-free pathway combinations are selected and implemented in cellular hosts.

Figure 87:
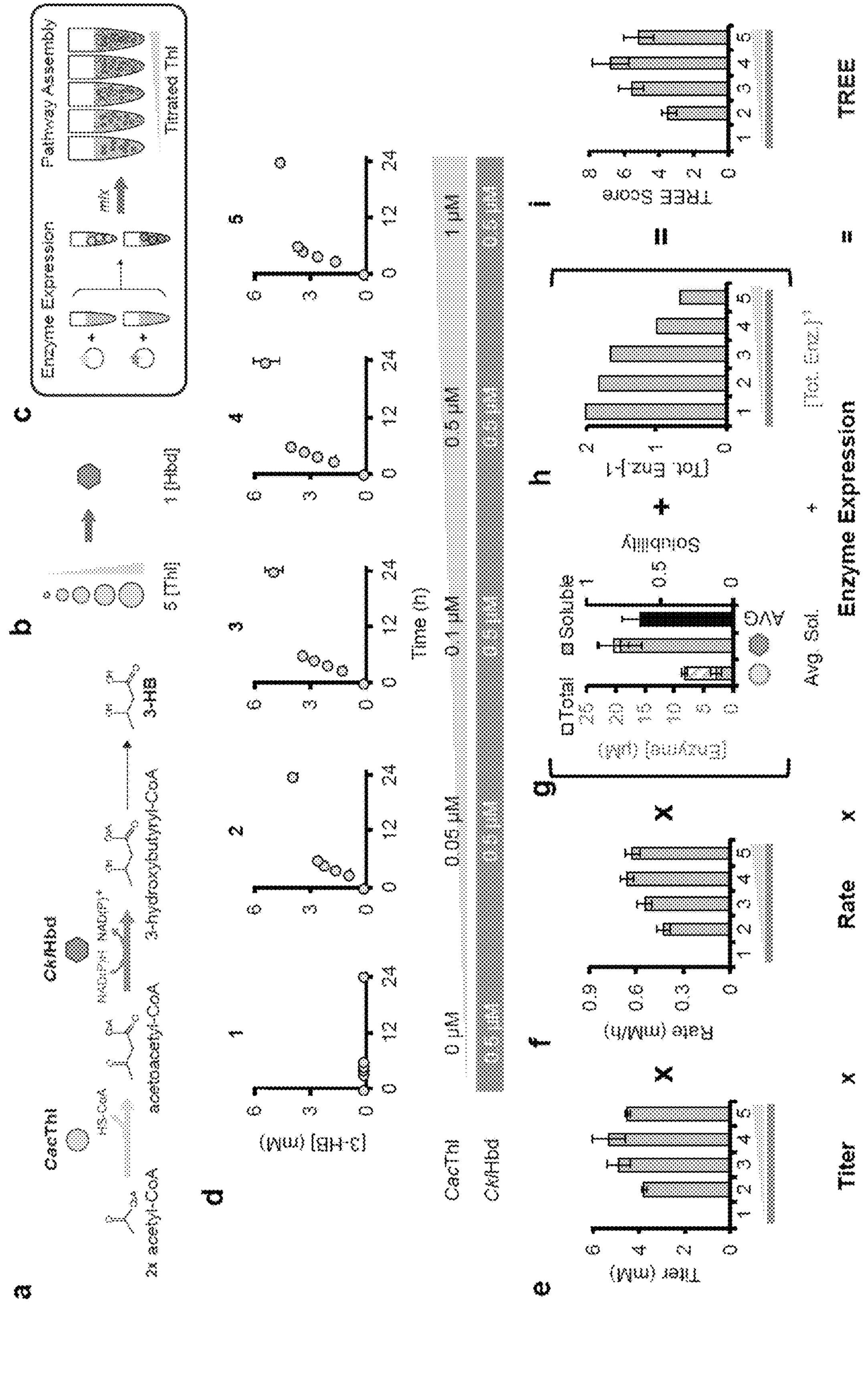

FIG. 87. Individual pathway enzymes can be tuned in pathway context and ranked using TREE scores with iPROBE. (A) The pathway to produce 3-HB from native metabolism (acetyl-CoA) is selected requiring two enzymes not natively present, CacThl and CklHbd. (B) Five pathway combinations are designed to be built and tested varying the concentration of CacThl low to high while maintaining CklHbd at one concentration. (C) The five pathway designs are built by enriching two *E. coli* lysates with CacThl and CklHbd, respectively, by CFPS (Pot #1). Then, the five pathway combinations are assembled by mixing CFPS reactions containing CacThl, CklHbd, and no enzyme (blank) with fresh *E. coli* lysate. Kanamycin, to stop further protein synthesis, glucose and cofactors are added to start biosynthesis of 3-HB. (D) 3-HB is measured at 0, 3, 4, 5, 6, and 24 h after the addition of glucose for each of the five pathway combinations. Error bars are shown at 24 h and represent technical triplicates. From these measurements, 3-HB titer at 24 h (E) and rate of production through 6 h (F) is quantified. Error bars shown for titer represent technical triplicates. Error bars shown for rate represent the standard error of the linear regression. Enzyme expression is quantified by adding the average soluble fraction of each enzyme (G) to the inverse of the total concentration of exogenous enzyme present (H). Error bars shown for enzyme concentrations represent technical triplicates. (I) The TREE is score is then calculated by multiplying the titer by the rate by the enzyme expression for each pathway combination with error bars representing the propagated error.

Figure 88:
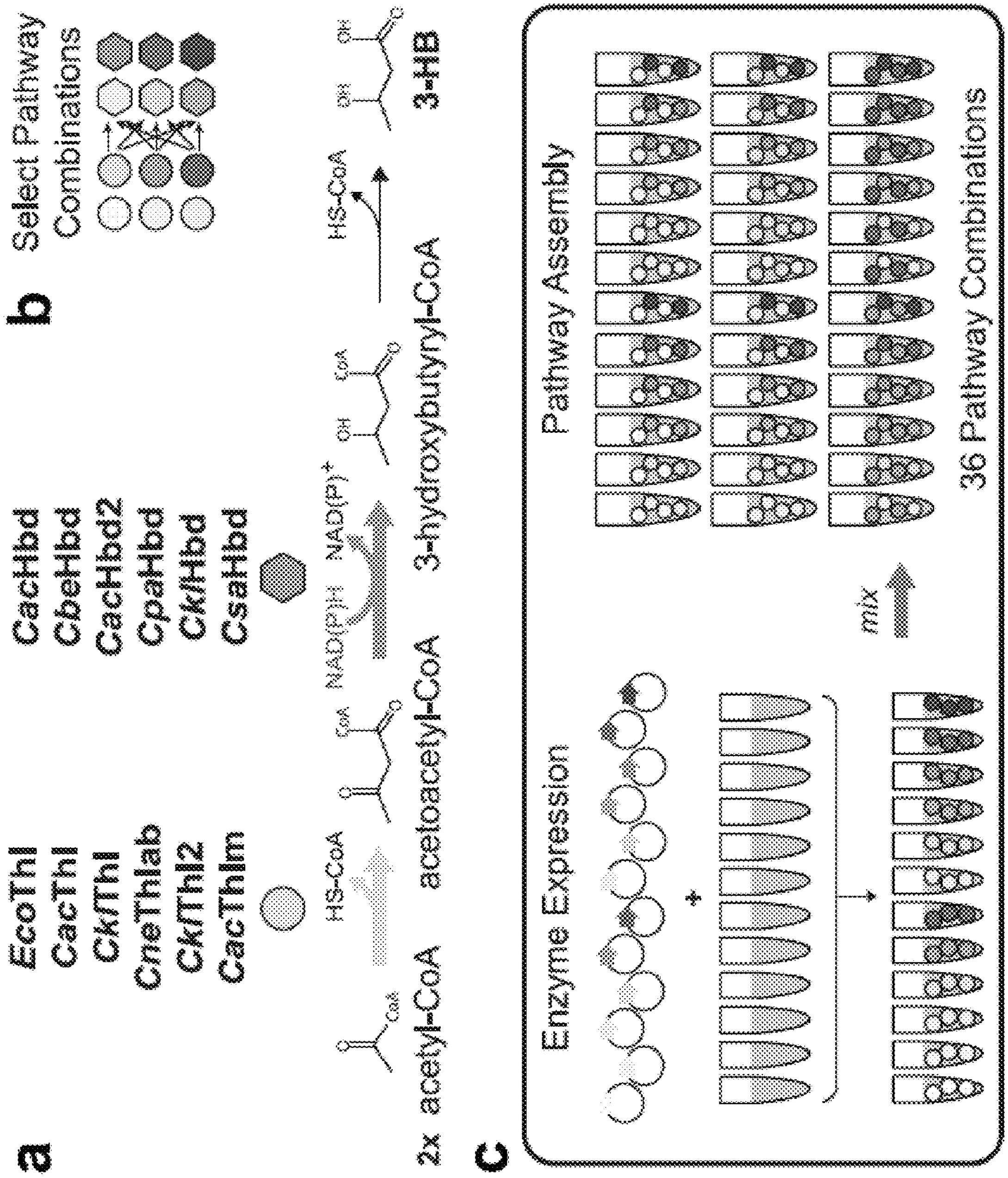

FIG. 88. Enzymatic pathways can be screened with iPROBE to inform *Clostridium* expression for optimizing 3-hydroxybutyrate production. A reaction scheme for the production of 3-HB is presented in panel (a). Six homologs have been selected for each reaction step. The design in (b) includes the testing of six Thl homologs and six Hbd homologs at 0.5 μM each. We built each possible combination in cell-free systems (c) constituting 36 unique pathway combinations. We rapidly built these cell-free pathways by expressing each of the 12 enzyme variants in lysates by CFPS. We then mixed each to try all 36 possible combinations keeping enzyme concentration fixed. (d) 3-HB was measured, and TREE scores were calculated and plotted for each iPROBE pathway combination with propagated error. We then selected four pathway combinations to test in *C. autoethanogenum* (A, B, C, and D). These pathways were built in high copy plasmids with the highest strength promoters in single operons (e). *Clostridium* strains containing these pathway combinations were then fermented on gas and 3-HB was measured over the course of fermentation (f). Labels (A, B, C, and D) are used to signify corresponding cell-free combinations and TREE scores are listed. Error bars represent technical triplicates.

Figure 89:
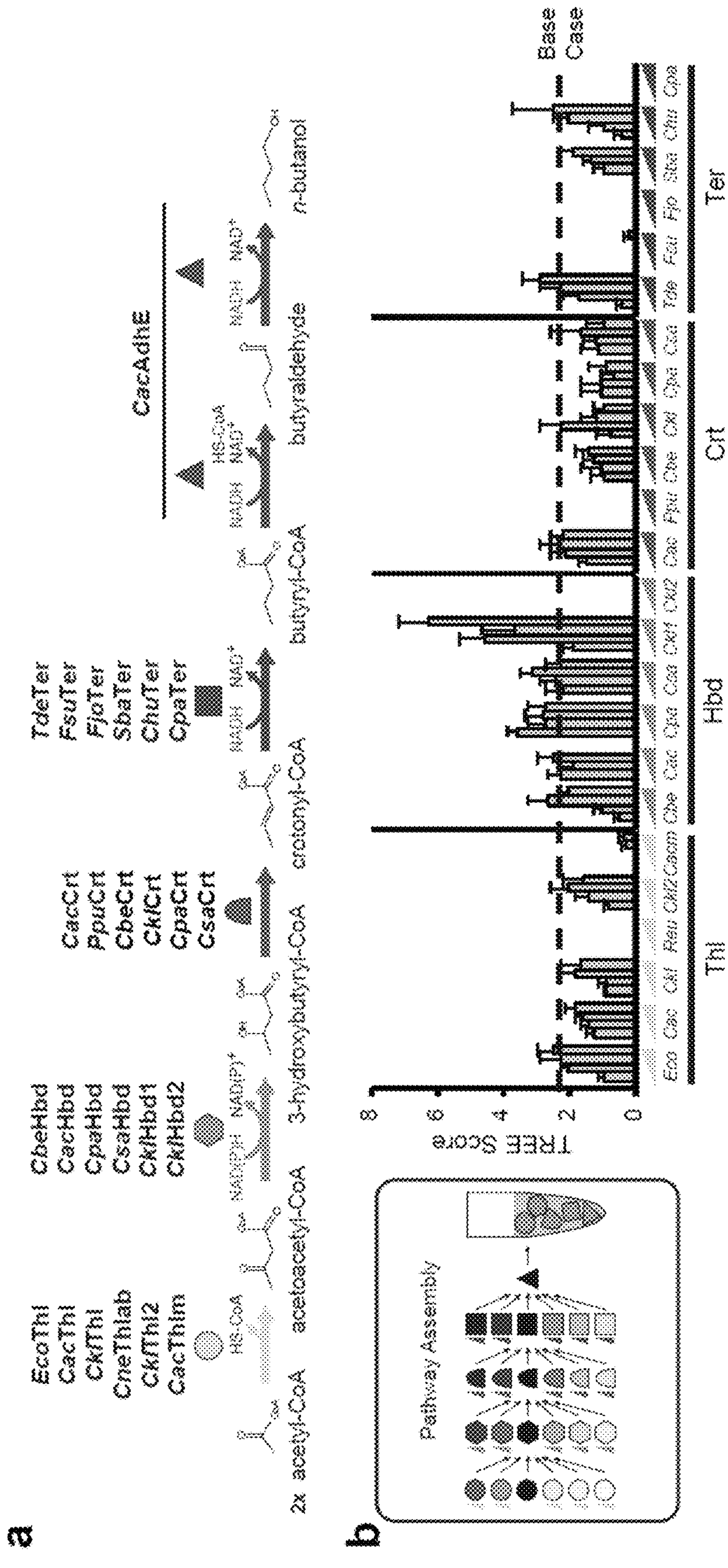

FIG. 89. Cell-free pathway testing combined with data-driven design-of-experiments quickly screens 205 unique pathway combinations and selects pathways for cellular butanol production. A reaction scheme for the production of butanol is presented in panel (a). Six homologs have been selected for each of the first four reaction steps and are shown in panel (a). (b) The strategy for running an initial set of reactions is to test each homolog at 5 concentrations individually with the base case set of enzymes (blue). These 120 pathway combinations are run in cell-free reactions according to the two-pot iPROBE methodology and TREE scores are calculated from 24-h butanol time-courses. The dashed line is placed at the TREE score resulting from the base case set of enzymes. (c) Neural-network-based design of experiments is implemented using the data presented in (b) to predict enzyme sets and concentrations to be constructed. (d) These are then built in cell-free systems. TREE scores are calculated for all newly tested pathway combinations from 24-h butanol time-courses. The black dashed line is placed at the TREE score resulting from the base case set of enzymes, the grey dashed line corresponds to the TREE score of the best case from (b), and the orange dashed line represents the highest TREE score achieved through the data-driven iPROBE approach. (e) Nine pathway combinations (two high-performing pathways, two medium-performing pathways, and five low-performing pathways) were constructed and transformed in vivo in *C. autoethanogenum*. End-point titers of butanol production (relative to the highest in vivo titer) are plotted against in vitro TREE scores for the corresponding pathway combination. Error bars for in vivo titers are relative standard deviations for four to six replicates. Error bars for all TREE scores are propagated error based on TREE score calculations.

Figure 90:
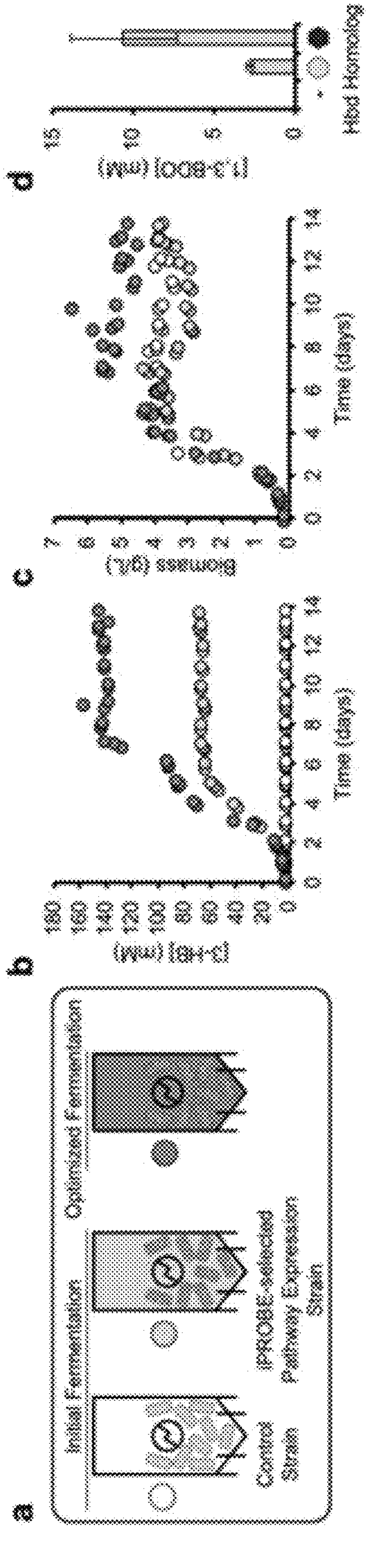

FIG. 90. *Clostridium* fermentations show improved production of 3-HB and identification of a new route to 1,3-butanediol. (A) The iPROBE-selected optimal pathway, CacThl and CklHbd1, for 3-HB production is built in a *C. autoethanogenum* strain and run in a 14-day continuous fermentation on CO/H2/CO2 gas as sole energy and carbon source. Fermentation parameter optimizations were performed for the new strain. Comparing fermentation of the control strain of *C. autoethanogenum* (white circles) to the initial (light grey circles) and optimized (dark grey circles) fermentations of the iPROBE-selected pathway expression strain, (B) 3-HB and (C) biomass were monitored. (D) 1,3-BDO was measured during steady-state fermentation and averages are shown for the control strain (–), the iPROBE-selected pathway expression strain (light green hexagon), and strain containing the PhaB homolog for Hbd (dark green hexagon).

Figure 91:
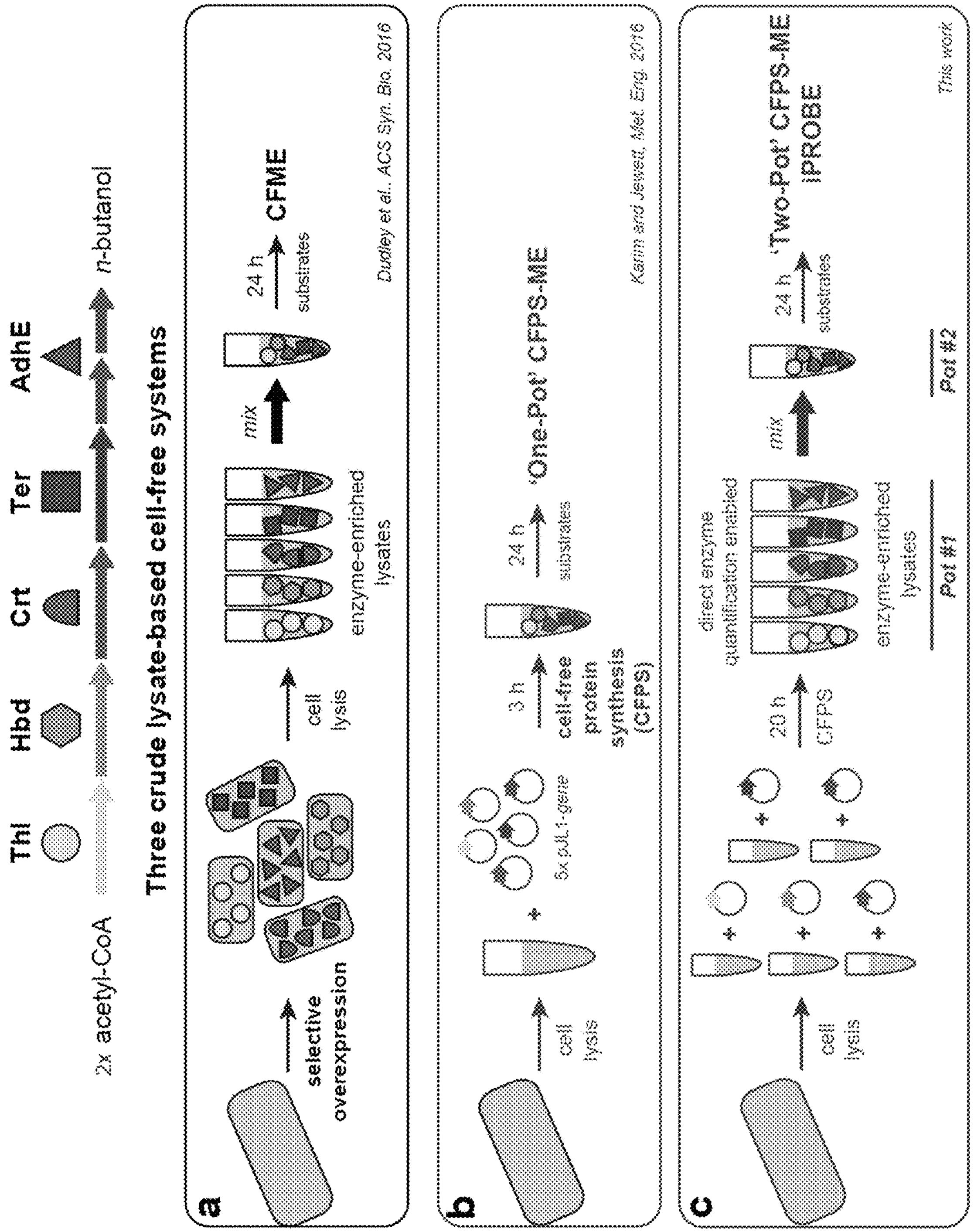

FIG. 91. A two-pot cell-free protein synthesis driven metabolic engineering (CFPS-ME) approach enables modular pathway construction in vitro. A schematic representation of the iPROBE approach (Two-Pot CFPS-ME) relative to previous works in crude lysate-based cell-free prototyping (One-Pot CFPS-ME) is shown. Pathways are assembled in two steps (i.e., 2 pots), where the first step is enzyme synthesis via cell-free protein synthesis (CFPS) and the second step is enzyme utilization via substrate and cofactor addition to activate small molecule synthesis.

Figure 92:
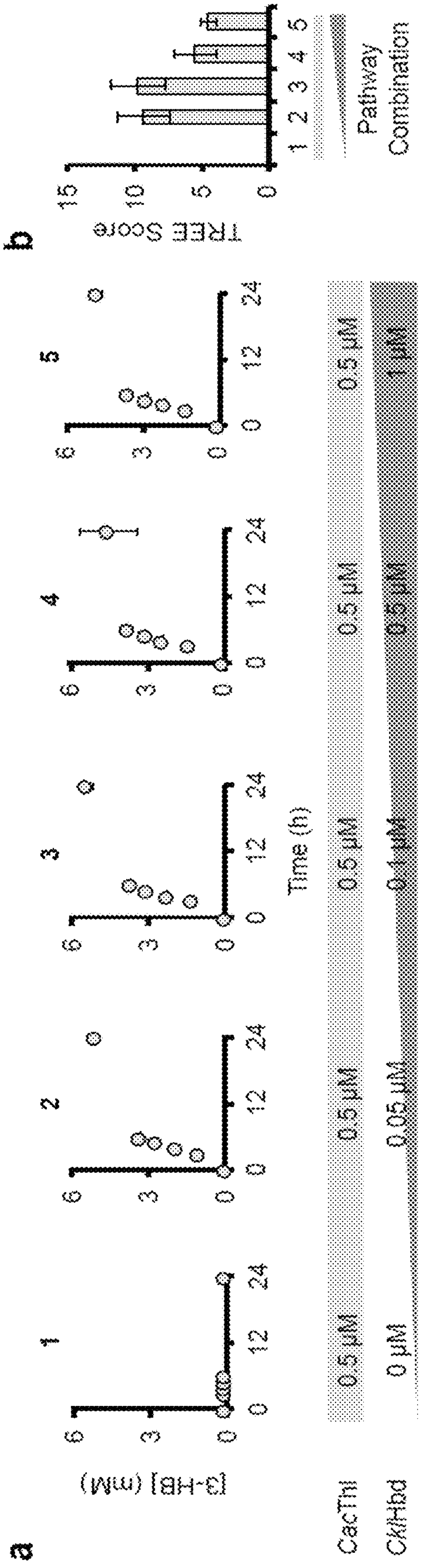

FIG. 92. Hbd can be tuned in pathway context and assessed using TREE scores with iPROBE. Five pathway combinations are designed, built, and tested varying the concentration of CklHbd low to high while maintaining CacThl at one concentration. (A) 3-hydroxybutyrate is measured at 0, 3, 4, 5, 6, and 24 h after the addition of glucose for each of the five pathway combinations. Error bars are shown at 24 h and represent technical triplicates. (B) The TREE is score is then calculated for each pathway combination.

Figure 93:
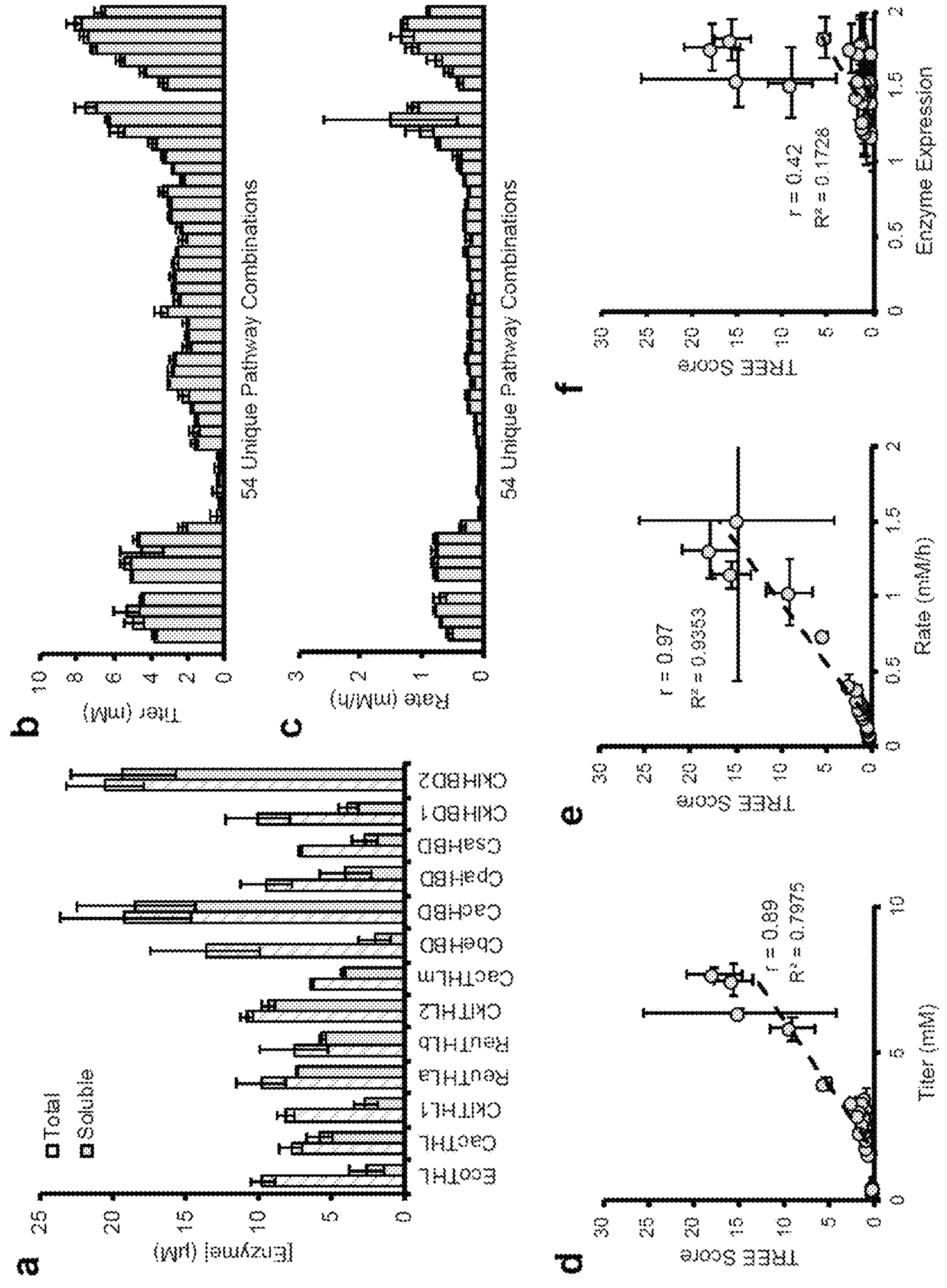

FIG. 93. Cell-free 3-HB titers, rates, and enzyme expression. Six homologs have been selected for each reaction step (Thl and Hbd) for 3-HB production and expressed by cell-free protein synthesis for all of the data represented in this study. Total and soluble yields of protein are displayed in panel (a). Error bars represent technical triplicates. iPROBE was run in 54 combinations listed in Supplemental File A found at Karim, A. S., et al, In vitro prototyping and rapid optimization of biosynthetic enzymes for cellular design. In revision. Nature Chemical Biology. Bio Riv 685768; doi; https://doi.org/10.110/685768 [doi.org], which reference and all supplemental data and files are incorporated herein by reference in their entireties. Titers at 24 h are shown in panel (b) with error bars representing technical triplicates. Rates determined by linear regression between 3 h and 6 h measurements are shown in panel (c) with error bars representing the standard error of the linear regression. The TREE score is plotted against (d) titer, (e) rate, and (f) enzyme expression. Error bars represent error calculation associated with the TREE score and error from titers, rates, and enzyme expression taken from (a), (b), and (c). The $R^2$ value associated with a linear regression and the Pearson correlation coefficient is represented on each plot.

Figure 94:
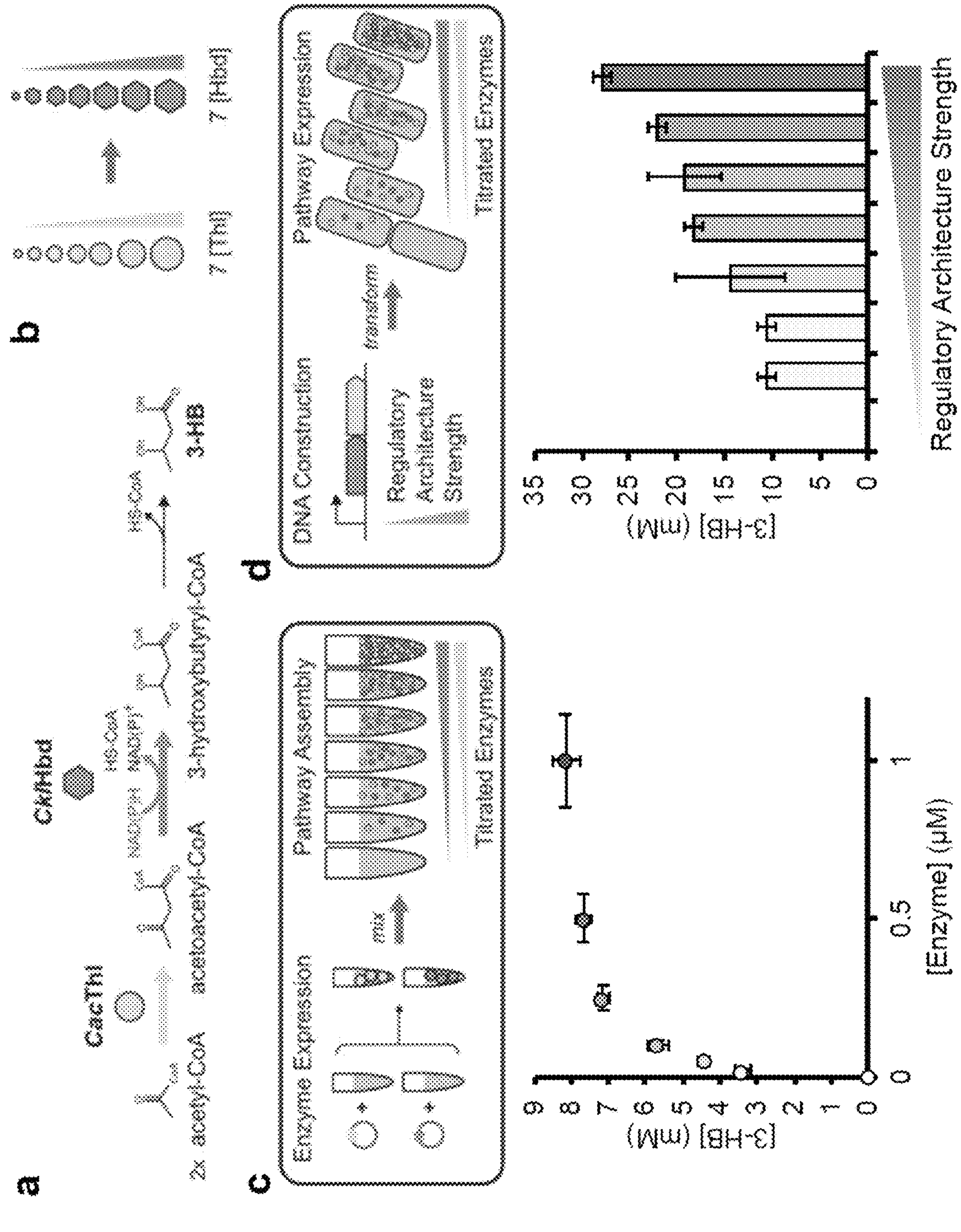

FIG. 94. Enzyme concentrations can be tuned with iPROBE to inform genetic design for *Clostridium* expression of 3-hydroxybutyrate. A reaction scheme for the production of 3-HB is presented in panel (a). The design in (b) includes the co-titration of CacThl and CklHbd at seven concentrations (0, 0.02, 0.05, 0.1, 0.25, 0.5, and 1 μM). We built these seven designs in cell-free systems (c) by CFPS of each enzyme in separate lysates (Pot #1) followed by mixing to assemble full pathways for 3-HB production (Pot #2). We measured 3-HB over the course of 24 h for each. We compared these results to *Clostridium*-based expression by building eight genetic constructs with varying promoters and plasmid copy number (d). We measured final titer of 3-HB for each. Error bars represent technical triplicates. Error bars on enzyme concentrations are technical replicates with n>3.

Figure 95:
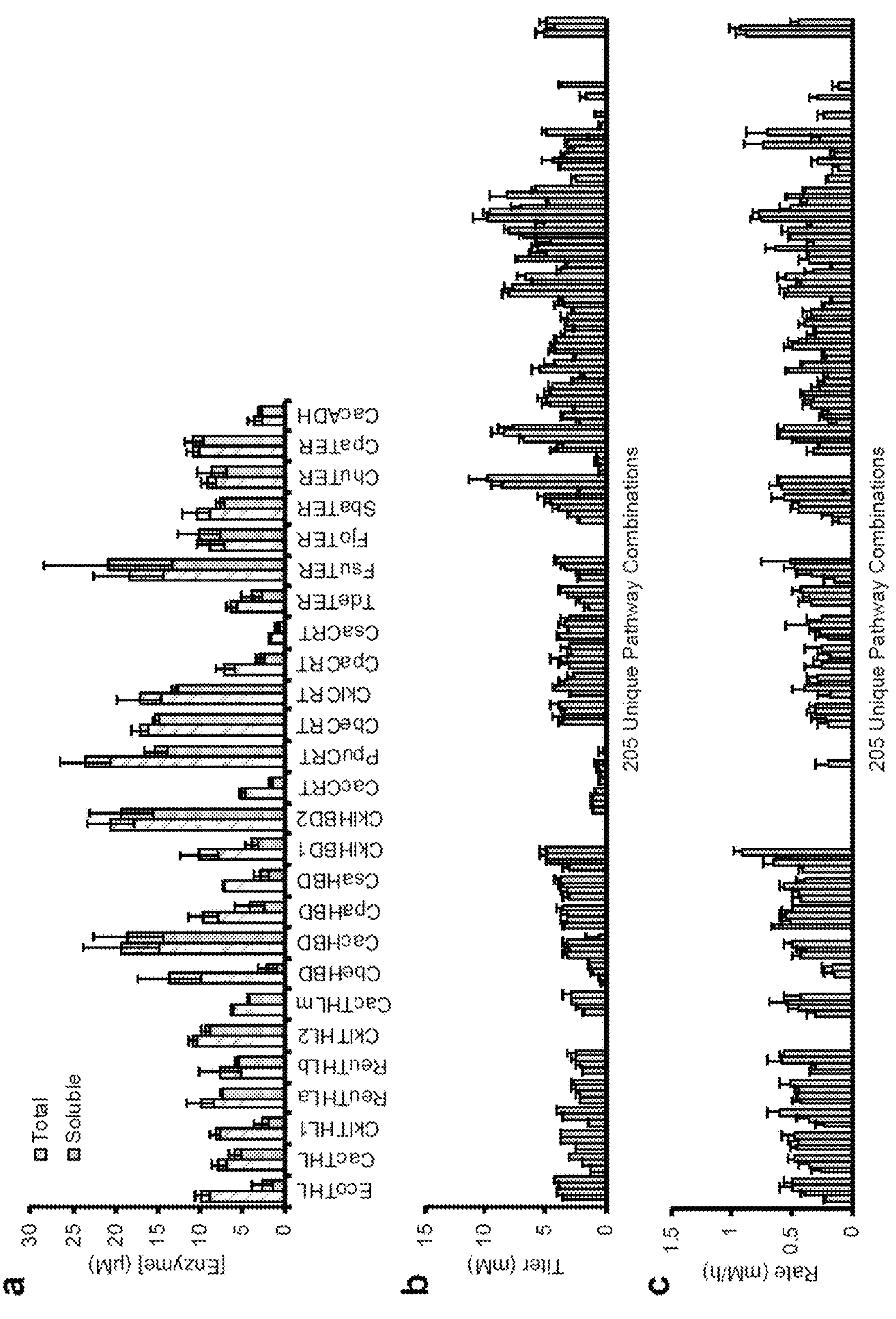

FIG. 95. Cell-free butanol titers, rates, and enzyme expression. Six homologs have been selected for each reaction step (Thl, Hbd, Crt, and Ter) for n-butanol production and expressed by cell-free protein synthesis. Total and soluble yields of protein are displayed in panel (a) with error bars representing technical triplicates. iPROBE was run in 205 combinations listed in Supplemental File A of Karim et al., as referenced in FIG. 93. Titers at 24 h are shown in panel (b) with error bars representing technical triplicates. Rates determined by linear regression between 3 h and 6 h measurements are shown in panel (c) with error bars representing the standard error of the linear regression.

Figure 96:
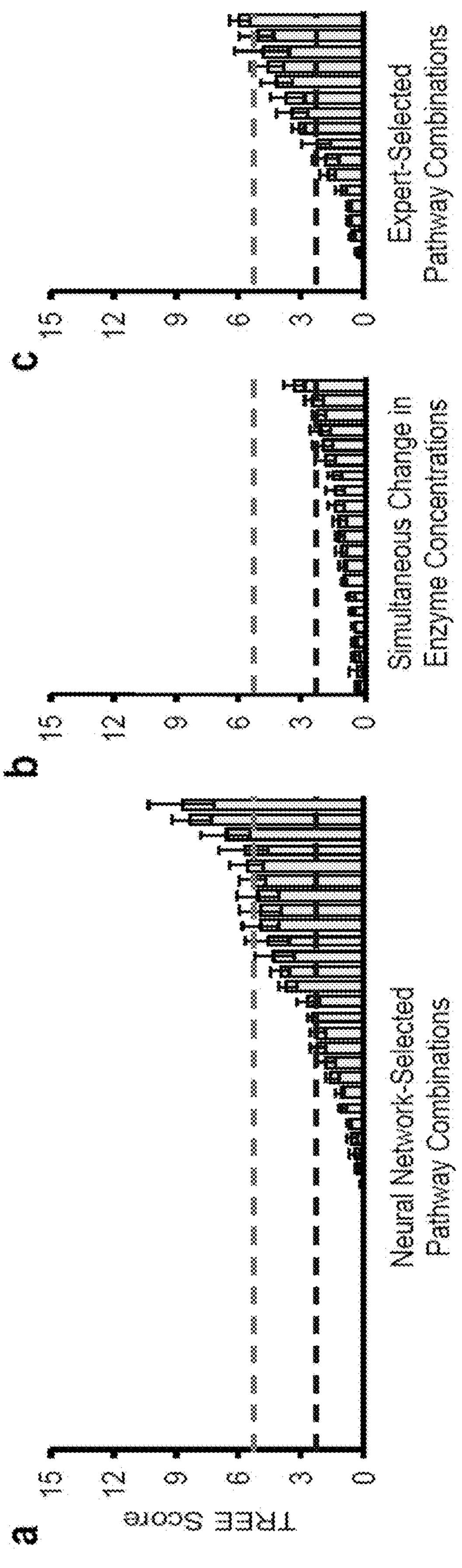

FIG. 96. Cell-free experimental TREE scores for expert-selected and Neural Network-based design of experiments. TREE scores were calculated for pathway combinations experimentally tested with iPROBE for (a) pathway combinations selected from the neural network approach (43 combinations), (b) simultaneous changes in each enzyme's concentration using the base case set of enzymes (21 combinations), and (c) expert-selected pathway combinations based on data in FIG. 90C and understanding of biosynthesis (18 combinations). TREE scores were calculated based on 24 h time-course data of n-butanol production.

Figure 97:
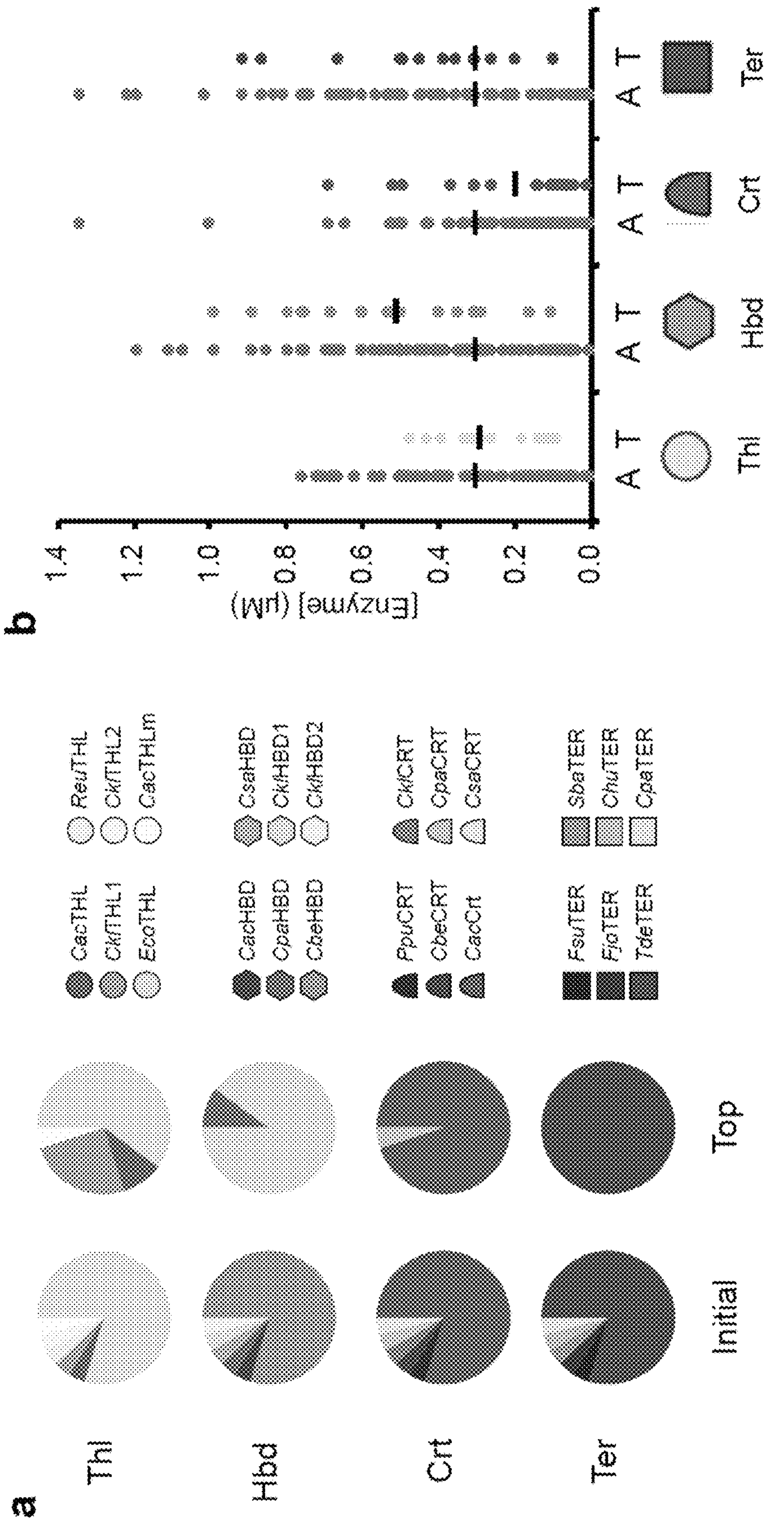

FIG. 97. Analysis of iPROBE reaction compositions show enzyme homolog and concentration trends for butanol production. Each instance of each enzyme homolog of Thl, Hbd, Crt, and Ter tested in the 205 pathway combinations was counted. (A) The percentage of each homolog (six homologs total are represented for each enzymatic step) appearing in the 'initial' 120 combinations and in the 'top' 20 combinations (of all 205) is charted. (B) The concentrations used for each individual pathway enzyme (regardless of which homolog is used) in the assembly of all 205 combinations is plotted (A; grey) next to the concentrations used in assembling the top 20 combinations as ranked by TREE score (T; yellow for Thl, green for Hbd, blue for Crt, and purple for Ter). The median concentration for each enzyme and group is potted as a single black line.

Figure 98:
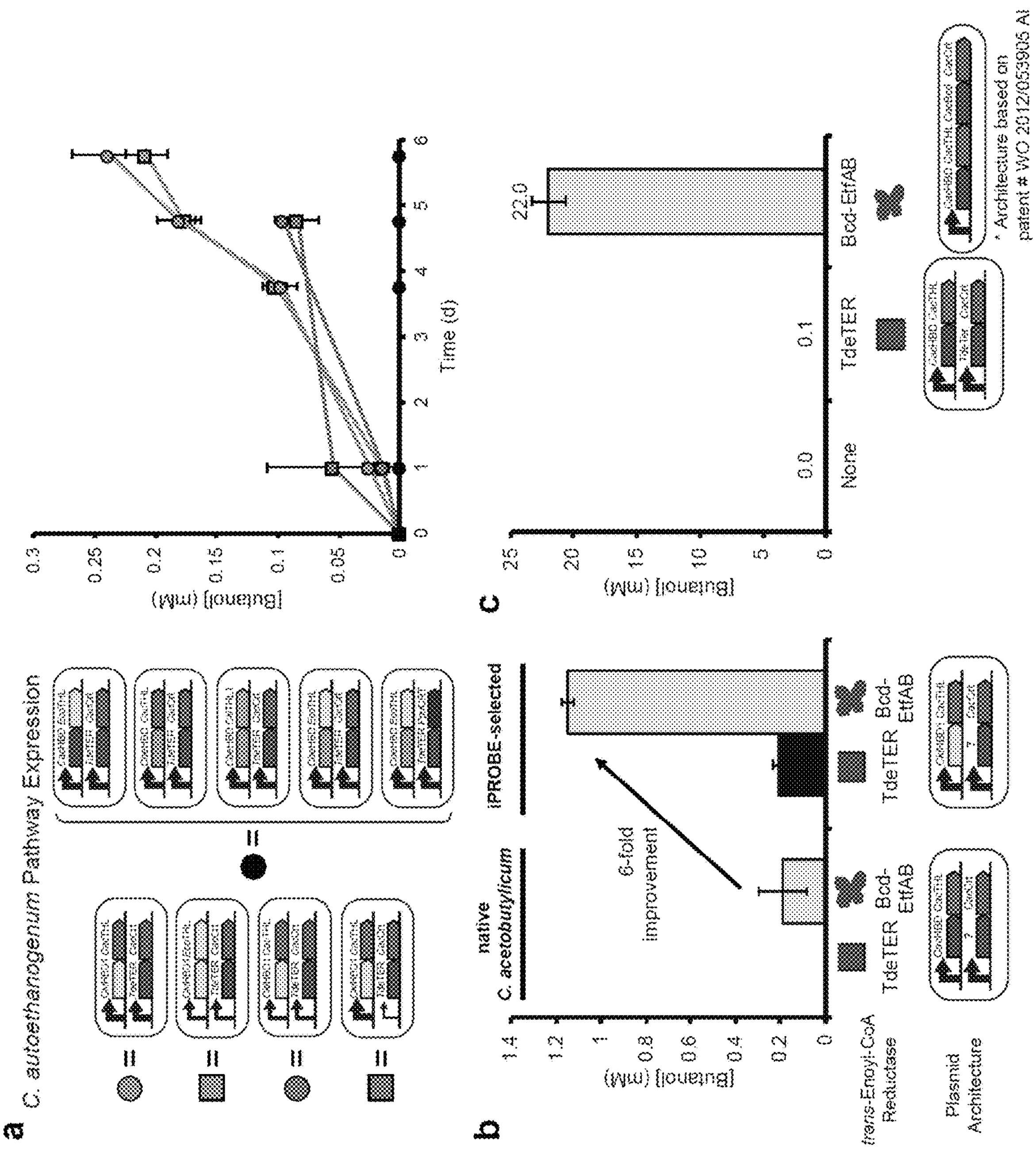

FIG. 98. Cellular butanol expression in *C. autoethanogenum* is significantly enhanced when using Bcd:EtfAB versus TdeTer. (a) Nine pathway combinations (two high-performing pathways, two medium-performing pathways, and five low-performing pathways) were constructed and transformed in vivo in *C. autoethanogenum*. Two plasmids were constructed for each combinations Time-course measurements of butanol production were taken across six days and are plotted. Error bars for in vivo titers are standard deviations for four to six replicates. (b) Four pathway combinations were constructed for n-butanol production containing CacThl, CacHbd (left; traditional Hbd) or CklHbd (right; iPROBE-selected Hbd), CacCrt, and either TdeTer (purple square) or Bcd:EtfAB (purple 'x' shape) were built using the same plasmid architectures as the orange circle in (a). (c) Two pathways for n-butanol production were tested: one pathway contained CacThl, CacHbd, CacCrt, and TdeTer (purple square) built using the same plasmid architecture as the orange circle in (a), and one pathway contained CacThl, CacHbd, CacCrt, and Bcd:EtfAB (purple 'x' shape). *C. autoethanogenum* strains containing these two pathway combinations were then fermented on gas and n-butanol was measured at 4 days. Error bars represent one standard deviation of three biological replicates.

Figure 99:
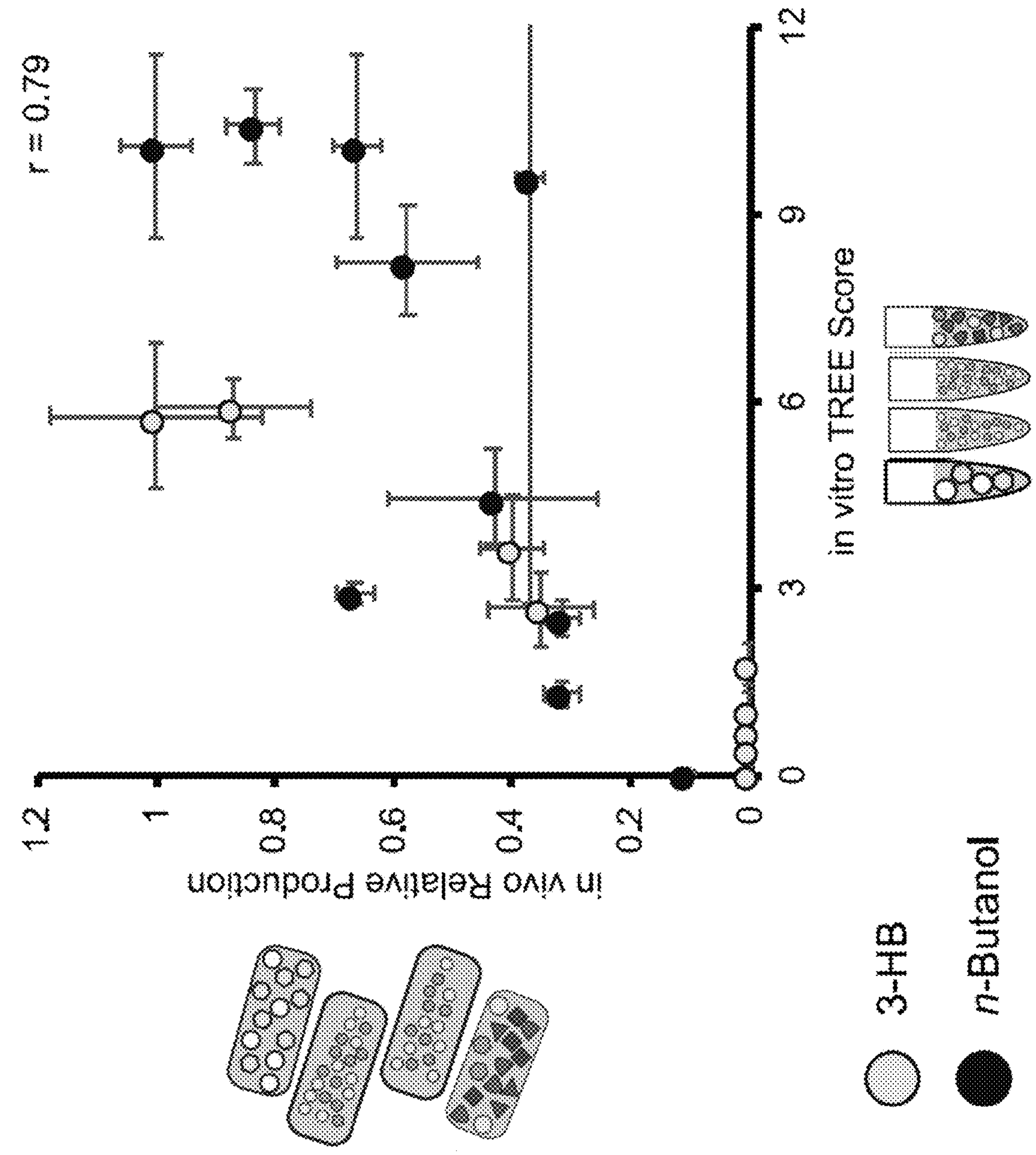

FIG. 99. A positive correlation between cell-free pathway performance and cellular pathway expression. All 19 pathway combinations assembled via iPROBE also expressed in *C. autoethanogenum* are plotted. TREE scores are plotted on the x-axis and in vivo final titers are plotted in the y-axis. Cellular titers were normalized to the highest-producing strains of 3-HB and butanol. Error bars on TREE scores represent the corresponding propagated error. Error bars on in vivo titers are normalized standard deviations from biological triplicates. The Pearson correlation coefficient was calculated for all data points.

Figure 100:
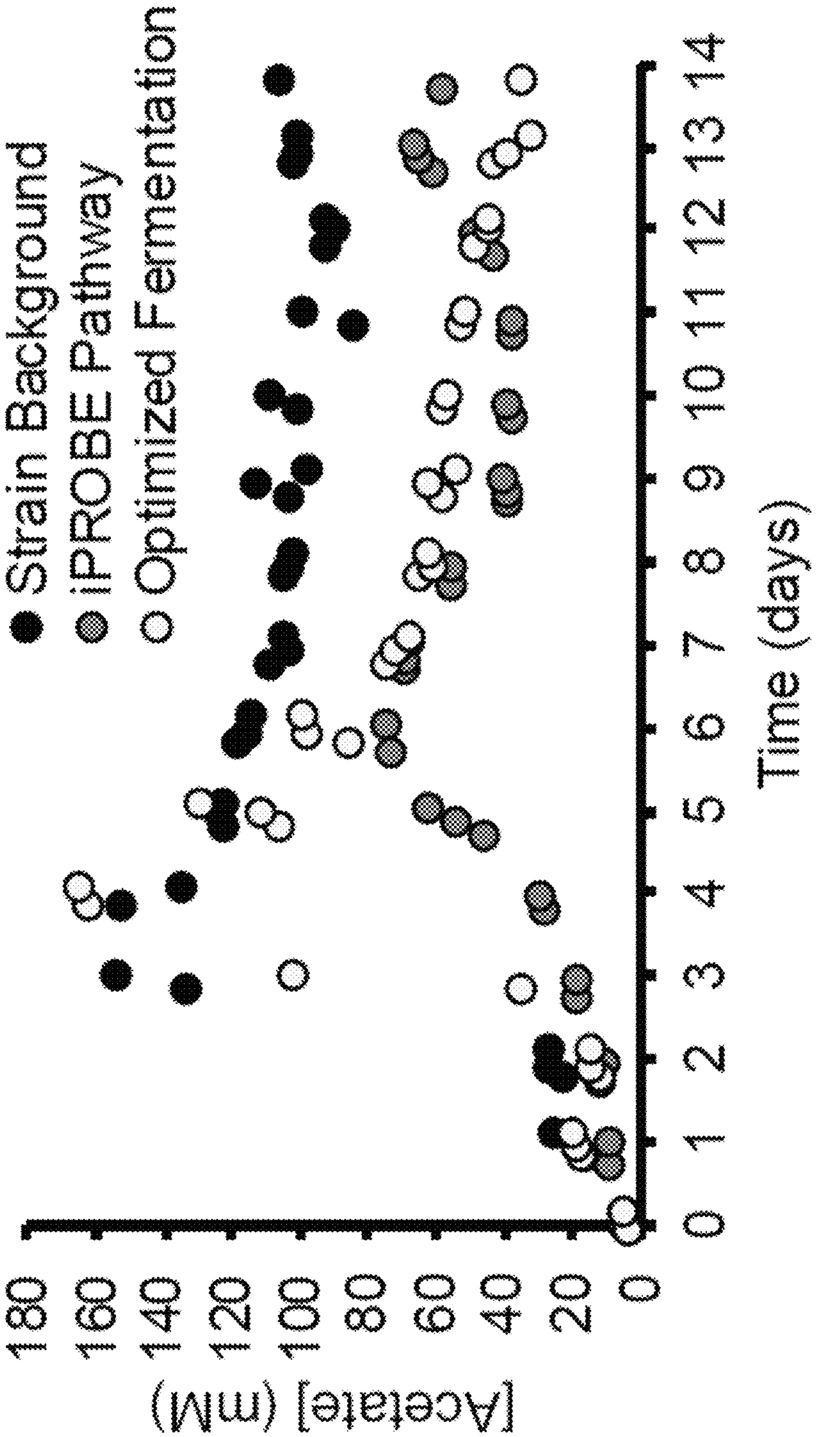

FIG. 100. *Clostridium* fermentations show acetate production. The iPROBE-selected optimal pathway, CacThl and CklHbd1, for 3-HB production is built in a *C. autoethanogenum* strain and run in a 14-day continuous fermentation on $CO/H_2/CO_2$ gas as sole energy and carbon source. Fermentation parameter optimizations were performed for the new strain. Comparing fermentation of the control strain of *C. autoethanogenum* (white circles) to the initial (light grey circles) and optimized (dark grey circles) fermentations of the iPROBE-selected pathway expression strain, acetate was monitored. Each circle represents a single data point.

FIG. 101. Provides a table listing enzymes selected for use in Example 9.

FIG. 102. FIGS. 102A-102W provide the codon-optimized gene sequences for *E. coli*-based CFPS (SEQ ID NOs:73-95). See FIG. 101 for information regarding the enzyme activity, organism, and source.

FIG. 103. FIGS. 103A-103F provide a table showing the codon-optimized gene sequences for *C. autoethanogenum* (SEQ ID NOs:96-101). See FIG. 101 for information regarding the enzyme activity, organism, and source.

DETAILED DESCRIPTION

Disclosed herein are systems and methods for cell-free protein synthesis driven metabolic engineering (CFPS-ME) that include cell-free protein synthesis as an integral step in the metabolic engineering process. The present invention allows for rapid prototyping and debugging of biosynthetic pathways. The present invention may also be implemented as a cell-free combinatorial method for optimization of biosynthetic pathways.

Figure 1:
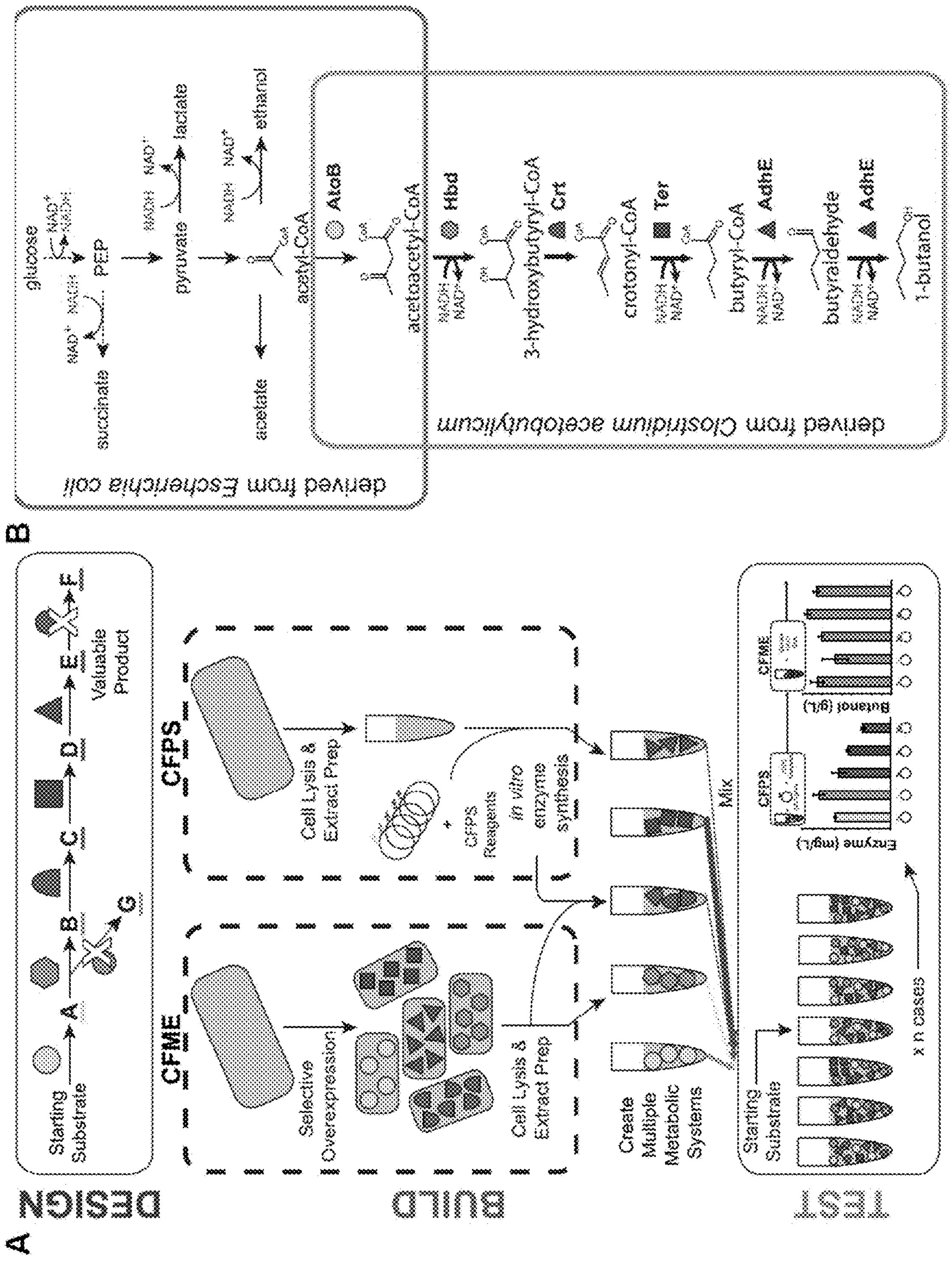
FIG. 1. A cell-free framework for pathway prototyping demonstrated with a 17-step n-butanol model pathway. (A) Methodology for cell-free metabolic engineering (CFME) and cell-free protein synthesis driven metabolic engineering (CFPS-ME). (B) Schematic (non-stoichiometric) representation of the constructed biosynthetic n-butanol pathway. Acetyl-CoA is generated through *E. coli*'s natural glycolysis and funneled into the *C. acetobutylicum*-derived CoA-dependent pathway to produce n-butanol. The butyryl-CoA dehydrogenase (Ter) here is from *Treponema denticola*. Four NADH molecules are needed to produce one molecule of n-butanol.

Cell-free protein synthesis driven metabolic engineering (CFPS-ME). In one aspect of the invention is CFPS-ME. In one embodiment of the invention is a method for the enzymatic preparation of a chemical product or a natural product in vitro. The method comprises providing a CFPS reaction mixture to a protein reaction vessel, expressing a translation template in the protein reaction vessel to prepare an enzyme, and providing the enzyme and a metabolic reaction mixture to a metabolic reaction vessel, wherein the feedstock reacts in the presence of the enzyme to prepare the chemical product or the natural product. In certain embodiments, the protein reaction vessel and the metabolic reaction vessel are the same vessel. The method is illustrated in FIG. 1. Methods for cell-free protein synthesis are provided in WO/2014/144583 to Jewett et al., the disclosure of which is incorporated by reference in its entirety.

The present invention is not limited to any certain enzyme or to any certain feedstock. As described and exemplified below, the enzymes and feedstsocks will be selected based on the chemical product or natural product to be made.

The present invention is not limited to any certain type of chemical product or natural product, but in certain embodiments the chemical product is 1-butanol or an intermediate in the 1-butanol biosynthetic pathway, styrene, 3-hydroxybutyrate, or specific isomers of butanediol. In other exemplary embodments, the natural product is valinomycin, andrimid, enterobactin, gramicidin S, HMG-CoA, or terpenes, such as limonene, pinene and bisabolene.

In certain embodiments, the method may include expressing one or more additional enzymes in a second protein reaction vessel. The second protein reaction vessel may be the same vessel as the protein reaction vessel.

In certain embodiments, the method may further comprise providing a transcription template to prepare the translation template. Where the transcription template is provided, one may additionally provide a polymerase and nucleoside triphosphates (NTPs): ATP, GTP, CTP, and UTP. Preparation of the translation template and preparation for the enzyme from the translation template may occur in the same reaction vessel or different reaction vessels.

An advantage of the present invention is that the cellular extract may provide natural enzyme metabolism from the host strain that may be exploited to perform desired chemical modifications. Natural enzyme metabolism means any process or chemical, including cellular extract enzymes, which may be necessary or beneficial for desired molecular transformations. Natural enzyme metabolism may provide energy, which may facilitate the desired molecular transformations. Natural enzyme metabolism may provide cofactor regeneration, which may facilitate the desired molecular transformation. Natural enzyme metabolism may also provide cellular extract enzymes. In certain embodiments, the cellular extract enzyme may be one or more heterologous enzymes expressed by the host. In certain embodiments, the cellular extract enzyme may be one or more native enzyme expressed by the host. In certain embodiments, the cellular extract enzyme may be a combination of one of more heterologous enzymes and native enzymes expressed by the host. In certain embodiments, the cellular extract enzyme is overexpressed by the host to enrich the extract with the cellular extract enzyme. In certain embodiments, the cellular extract enzyme may transform a chemical product or natural product into a feedstock. In other embodiments, the cellular extract enzyme may further transform the chemical product or the natural product that is formed by the reaction of the feedstock in the presence of the enzyme expressed by cell-free protein synthesis.

Combinatorial approach to CFPS-ME. The present invention, in certain embodiments, may be practiced in a combinatorial manor for rapid prototyping, design, and optimization of biosynthetic pathways. One step in the combinatorial method comprises providing N solutions. The N solutions may comprise one or more solutes. Solutes are typically chosen from those likely to be found in a CFPS reaction mixture and/or a metabolic reaction mixture. The solvent is typically buffer. It is possible that two or more of the N solutions are the same except for differences in the concentration of the solute.

Any of the solutions may be chosen to be combined, and as a result there are $2^N$ possible combinations. Selection criteria may be employed to forbid certain combinations that would limit the number of combinations to something less than $2^N$. One example of a selection criteria is to forbid the combination of two solutions that only differ in concentration of the solute.

Enzyme preparation may be initiated by combining the combinations of the N stock solutions with a CFPS reaction mixture in a cell-free protein synthesis reaction vessel to allow for the translation template to be expressed. It is not necessary for all of the combinations of the N stock salutation with a CFPS reaction mixture to result in the preparation of an enzyme because valuable information from negative results may aid the design and optimization of a biosynthetic pathway.

The method further includes providing the enzyme and a feedstock to a metabolic reaction vessel. The protein synthesis reaction vessel and the metabolic reaction vessel may be the same reaction vessel.

In some embodiments, a method for the enzymatic preparation of a chemical product or natural product in vitro, includes providing a cell-free protein synthesis reaction mixture to a protein reaction vessel, the cell-free protein synthesis reaction mixture comprising a cellular extract from a host strain, a translation template, and cell-free protein synthesis reagents, expressing the translation template in the protein reaction vessel to prepare an enzyme, providing the enzyme, the cellular extract, and a metabolic reaction mixture to a metabolic reaction vessel, the metabolic reaction mixture comprising a feedstock, wherein the feedstock reacts in the presence of the enzyme to prepare the chemical product or the natural product and wherein the cellular extract provides natural enzyme metabolism from the host strain. In some embodiments, the objective of the method is to guide the discovery, design, expression, and optimization of biosynthetic pathway production of valuable molecules and natural products.

In some embodiments, a method for combinatorial cell-free metabolism engineering comprises providing N solutions, combining between one and $2^N$ combinations of the N solutions, providing a cell-free protein synthesis reaction mixture, the cell-free protein synthesis reaction mixture comprising a cellular extract and a translation template, combining the cell-free protein synthesis reaction mixture and at least one of the combinations of the N stock solutions in a cell-free protein synthesis reaction vessel, wherein the translation template is expressed to provide an enzyme; and providing the enzyme and a feedstock to a metabolic reaction vessel, wherein the feedstock is capable of reacting in the presence of the enzyme to form a product. In some embodiments, the objective of the method is to guide the discovery, design, expression, and optimization of biosynthetic pathway production of valuable molecules and natural products.

Kits

In one aspect of the invention, kits for CFPS-ME are disclosed. Kits for CFPS-ME comprising one or more components for the practice of the CFPS-ME method. In one aspect, the kits may comprise one or more components, individually or collectively, for the practice of CFPS. In certain embodiments, the kit may comprise a CFPS reaction mixture or the individual solutes or solutions that may be combined to form a CFPS reaction mixture. In one aspect, the kits may comprise one or more components, individually or collectively, for the practice of ME. In certain embodiments, the kit may comprise a ME reaction mixture or the individual solutes or solutions that may be combined to form a ME reaction mixture. In certain embodiments, the kit further comprises a feedstock.

Definitions

To aid in understanding the invention, several terms are defined below.

Unless defined otherwise, all technical and scientific terms used herein have the same meaning as commonly understood by one of skill in the art. Although any methods and materials similar to or equivalent to those described herein can be used in the practice or testing of the claims, the exemplary methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

The term "about" means within a statistically meaningful range of a value or values such as a stated concentration, length, molecular weight, pH, time frame, temperature, pressure or volume. Such a value or range can be within an order of magnitude, typically within 20%, more typically within 10%, and even more typically within 5% of a given value or range. The allowable variation encompassed by "about" will depend upon the particular system under study.

The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range, and includes the endpoint boundaries defining the range, unless otherwise indicated herein, and each separate value is incorporated into the specification as if it were individually recited herein.

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Letters 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)n sequence, where n is in the range from about 20 to about 200). The region of the primer that is sufficiently complementary to the template to hybridize is referred to herein as the hybridizing region.

The term "promoter" refers to a cis-acting DNA sequence that directs RNA polymerase and other trans-acting transcription factors to initiate RNA transcription from the DNA template that includes the cis-acting DNA sequence.

The terms "target, "target sequence", "target region", and "target nucleic acid," as used herein, are synonymous and refer to a region or sequence of a nucleic acid which is to be amplified, sequenced or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning-A Laboratory Manual, Cold Spring Harbor Laboratory, Cold Spring Harbor, New York; Wetmur, 1991, Critical Review in Biochem. and Mol. Biol. 26(3/4):227-259; and Owczarzy et al., 2008, Biochemistry, 47: 5336-5353, which are incorporated herein by reference).

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

As used herein, a "polymerase" refers to an enzyme that catalyzes the polymerization of nucleotides. "DNA polymerase" catalyzes the polymerization of deoxyribonucleotides. Known DNA polymerases include, for example, Pyrococcusfuriosus (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, "expression template" refers to a nucleic acid that serves as substrate for transcribing at least one RNA that can be translated into a polypeptide or protein. Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

As used herein, "translation template" refers to an RNA product of transcription from an expression template that can be used by ribosomes to synthesize polypeptide or protein.

The term "reaction mixture," as used herein, refers to a solution containing reagents necessary to carry out a given reaction. A reaction mixture is referred to as complete if it contains all reagents necessary to enable the reaction, and incomplete if it contains only a subset of the necessary reagents.

An "amplification reaction mixture", which refers to a solution containing reagents necessary to carry out an amplification reaction, typically contains oligonucleotide primers and a DNA polymerase in a suitable buffer.

A "PCR reaction mixture", which refers to a solution containing the reagents necessary to carry out a PCR reaction, typically contains DNA polymerase, dNTPs, and a divalent metal cation in a suitable buffer.

A "cell-free protein synthesis (CFPS) reaction mixture", which refers to a solution containing the reagents necessary to carry out CFPS, typically contains a crude or partially-purified yeast extract, an RNA translation template, and a suitable reaction buffer for promoting cell-free protein synthesis from the RNA translation template. In some aspects, the CFPS reaction mixture can include exogenous RNA translation template. In other aspects, the CFPS reaction mixture can include a DNA expression template encoding an open reading frame operably linked to a promoter element for a DNA-dependent RNA polymerase. In these other aspects, the CFPS reaction mixture can also include a DNA-dependent RNA polymerase to direct transcription of an RNA translation template encoding the open reading frame. In these other aspects, additional NTP's and divalent cation cofactor can be included in the CFPS reaction mixture A "metabolic reaction mixture", which refers to a solution containing the reagents necessary to carry out an enzyme-mediated metabolic or biosynthetic step, typically includes a feedstock that reacts in the presence of the enzyme to produce a final or intermediate product in the metabolic or biosynthetic pathway. A metabolic reaction mixture may optionally contain a cofactor, e.g. coenzyme-A, NAD, or ATP, or a buffer.

It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention.

Miscellaneous. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

The following examples are illustrative and should not be interpreted to limit the scope of the claimed subject matter.

Example 1: Cell-Free Biosynthesis of n-Butanol

Reference is made to Karim and Jewett, "A cell-free framework for rapid biosynthetic pathway prototyping and enzyme discovery," (Metab. Eng. March 17; 36:116-126, doi: 10.1016/j.ymben.2016.03.002. [Epub ahead of print], hereinafter "Karim 2016")), the content of which is incorporated herein by reference in its entirety.

A. Abstract

Speeding up design-build-test (DBT) cycles is a fundamental challenge facing biochemical engineering. To address this challenge, we report a new cell-free protein synthesis driven metabolic engineering (CFPS-ME) framework for rapid biosynthetic pathway prototyping. In our framework, cell-free cocktails for synthesizing target small molecules are assembled in a mix-and-match fashion from crude cell lysates either containing selectively enriched pathway enzymes from heterologous overexpression or directly producing pathway enzymes in lysates by CFPS. As a model, we apply our approach to n-butanol biosynthesis showing that *Escherichia coli* lysates support a highly active 17-step CoA-dependent n-butanol pathway in vitro. The elevated degree of flexibility in the cell-free environment allows us to manipulate physiochemical conditions, access enzymatic nodes, discover new enzymes, and prototype enzyme sets with linear DNA templates to study pathway performance. We anticipate that CFPS-ME will facilitate efforts to define, manipulate, and understand metabolic pathways for accelerated DBT cycles without the need to reengineer organisms. Highlights of CFPS-ME include the following: Cell-free protein synthesis can reconstitute entire biosynthetic pathways (CFPS-ME); In vitro systems provide greater control and higher resolution in studying metabolism; CFPS-ME enables the in vitro study of pathways in context of native metabolism; Linear DNA with CFPS-ME can bypass in vivo cloning steps in pathway construction; and CFPS-ME allows rapid enzyme prototyping in vitro before putting designs into a host.

B. Introduction

For decades scientists and engineers have turned to engineering biological systems to help meet societal needs in energy, medicine, materials, and more[1-4]. This has been an attractive, sustainable way to produce small molecules, especially when chemical synthesis is untenable[5,6] The ability to harness organisms that naturally produce molecules of interest has expanded the available chemical palate[7,8]. Often when natural producers are insufficient for production at the optimal titer (g $l^{-1}$), yield, or volumetric productivity (g $l^{-1}$ $h^{-1}$), engineers seek to design biosynthetic pathways and regulatory processes in cells to meet certain manufacturing criteria[9,10]. For example, introducing heterologous pathways into model microorganisms and engineering them to maximize a particular biosynthesis has led to large scale production of 1,3-propanediol, farnesene, and artemisinin with many more on their way to market[6,11]. Efforts to make these molecules have resulted in success, but not without a great deal of challenges.

Bringing a biosynthetic molecule to market usually involves countless hours of design-build-test (DBT) cycles[12]. The production of n-butanol is a prime example of these challenges. A series of *Clostridia* species are natural producers of n-butanol during acetone-butanol-ethanol fermentation, and *Clostridia acetobutylicum* and *Clostridia beijerinckii* are two of which are commonly used in commercial n-butanol plants[13]. However, these species are difficult to engineer because of a biphasic metabolism, unknown regulation patterns, and a limited number of species-specific engineering tools[14]. Heterologous expression of *Clostridia* metabolism in model microorganisms like *Escherichia coli* and *Saccharomyces cerevisiae* allows n-butanol production to be more easily engineered but can be accompanied by lower titers[15,16]. Starting with heterologous expression of the n-butanol pathway as a baseline, scientists have been able to increase titers dramatically by knocking out genes from genomes[15], increasing redox driving forces by introducing pathway-independent enzymes[17], and identifying homologous enzymes with better activities[18]. Years of iterative metabolic engineering led to these advances, but titers are still not high enough and scale-up is often too unpredictable to outcompete natural producers for commercial production[19]. As is the same for many biosynthetic pathways, we cannot quickly enough identify optimal biosynthetic systems and discover the best sets of enzymes that work together as a group. Therefore, metabolic engineering remains costly and time-consuming[20,21].

A key challenge in metabolic engineering is balancing the tug-of-war that exists between the cell's physiological and evolutionary objectives on one side and the engineer's process objectives on the other. Put another way, it is very difficult to balance intracellular fluxes to optimally satisfy a very active synthetic pathway while the machinery of the cell is functioning to maintain reproductive viability. Other challenges include: (i) the need for reliable computational selection and design of enzyme homologs for pathway design, (ii) the limited number of feasible homologs and genetic constructs that can be searched in any one project, and (iii) the unknown effects of optimal pathway enzyme expression on the entire metabolic system[22-24].

Many established and emerging technologies seek to address these challenges. For example, metabolic flux analysis and genome engineering offer generalized capabilities to modify living organisms for improving product titers[25,26]. In addition, coupling machine-learning algorithms to multiplexed designs can accelerate efforts to rationally engineer cells[27]. However, DBT cycle time remains a limitation[28]. In vitro systems offer a complementary, yet underutilized approach to speed up DBT cycles with some potential advantages[11,29-31]. For example, the open reaction environment allows for the addition of components such as cofactors and intermediates at any time during a cell-free reaction, which can be maintained at precise concentrations. In addition, cell-free systems have no cell viability constraints. Furthermore, the cell-free format permits DBT iterations without the need to reengineer organisms[30], with the potential to reduce DBT cycle time[31]. Cell-free metabolic engineering (CFME), or using cell-free techniques to aid metabolic engineering efforts, is emerging as a complementary approach to existing strategies for carrying out biomolecular transformations of interest with in vitro ensembles of catalytic proteins, prepared from purified enzymes or crude lysates of cells[32-39].

In this work, we develop a cell-free protein synthesis driven metabolic engineering (CFPS-ME) framework to accelerate DBT cycles for optimizing and debugging biosynthetic pathways (FIG. 1A). The foundational principle is that we can construct discrete metabolic pathways through combinatorial and modular assembly of lysates containing enzyme components produced by overexpression in the lysate chassis strain or by cell-free protein synthesis (CFPS). We focus on using CFPS because these systems can help address the growing demand for simple, inexpensive, and efficient protein production technologies for a wide array of applications[11,29,40-44]. In addition, processes that take days or weeks to design, prepare, and execute in cells can be done more rapidly in a cell-free system, because no time-consuming cloning steps are needed[45]. Three recent advances enable the use of CFPS for CFME. First, Jewett et al. demonstrated the ability to stimulate highly active energy and cofactor regeneration pathways in crude cell lysates[46]. Second, Kay and Jewett showed that crude cell lysate based cell-free systems from *E. coli* could fuel highly active heterologous metabolic transformations[36]. Third, Dudley and Jewett established the ability to build a heterologous biosynthetic pathway by mixing lysates each containing individually overexpressed heterologous enzymes (in preparation). The mix-and-match approach has many advantages including only needing to express one enzyme in each strain, not needing to fine-tune expression, and being able to directly monitor and sample the reaction environment. Here, we extend this approach by demonstrating modular assembly of pathways through the ability to enrich lysates with biosynthetic enzymes using well-defined experimental conditions and CFPS. It is important to note that our goal in this work was not to develop cell-free systems for the highest product titer, an engineered strain for best in vivo synthesis of n-butanol, or industrial applicability. However, we do show that CFPS-ME offers an even faster approach (hours rather than days) for building pathways directly in lysates for the purpose of enzyme selection and pathway design.

To demonstrate CFPS-ME, we selected the model n-butanol biosynthetic pathway derived from *Clostridia* metabolism involving CoA intermediates (FIG. 1B). Endogenous glycolytic enzymes convert glucose to acetyl-CoA, the starting intermediate for n-butanol synthesis, another *E. coli* enzyme takes acetyl-CoA to acetoacetyl-CoA, and heterologous enzymes convert acetoacetyl-CoA to n-butanol. We first show the ability to mix five crude lysates each with selectively overexpressed enzymes to activate the entire 17-step n-butanol production pathway in vitro with high yield and productivities. We then establish the CFPS-ME concept by modularly building the n-butanol pathway with lysates harboring heterologous pathway enzymes expressed by CFPS or having been overexpressed in the chassis source strain. We apply this framework to rapidly screen enzymes for optimal pathway operation and enzyme discovery. We expect that the CFPS-ME framework will increase the resolution at which we can manipulate biosynthetic pathways by examining enzyme kinetics, measuring metabolic flux, determining catalyst stability, studying redox effects, and prototyping metabolism.

C. Material and Methods

1. Bacterial Strains and Plasmids.

*E. coli* NEB Turbo™ (NEB) was used in plasmid cloning transformations and for plasmid preparation. *E. coli* BL21 (DE3) (NEB) was used for protein overexpression and for preparation of all extracts. (See Karim 2016, and Table 1 for strain details). A modified version of pET-22b (Novagen/EMI) Millipore), used in previous studies[36], was used for all constructs for in vivo over-expression of proteins. For in viro expression of proteins, the pJL1 vector was used. Carbenicillin (100 μg $ml^{-1}$) was used with the pET vector system and kanamycin (50 μg $ml^{-1}$) was used with the pJL1 vector system.

Gibson assembly was used for seamless construction of plasmids. (See Karim 2016, and Table 1 for plasmid details). Each gene and vector was amplified via PCR using forward and reverse primers designed with NEB's Gibson Assembly Designer (New England Biolabs, Ipswich MA, USA) and purchased from IDT and Phusion® High-Fidelity DNA polymerase (Finnzymes, Thermo Scientific Molecular Biology). (See Karim 2016, and Table 2 for genes and enzymes and Karim 2016 for primer details). Both PCR products were cleaned and mixed with Gibson assembly reactants and incubated at 50° C. for 60 min. Plasmid DNA from the Gibson assembly reactions were immediately transformed into *E. coli* NEB Turbo cells. Propagated constructs were purified using an EZNA Plasmid Mini Kit (Omega Bio-Tek). Completed constructs were used to transform *E. coli* BL21 (DE3).

Codon optimized versions of each gene were identified using IDT's codon optimization online tool (Integrated DNA Technologies®, Coralville, USA) and NCBI's Basic Local Alignment Search Tool (National Center for Biotechnology Information, U.S. National Library of Medicine, Bethesda MD, USA). These genes were purchased from Gen9, Inc. (Cambridge MA, USA). (See Karim 2016, and SEQ ID NOs:1-18).

2. Cell Extract Preparation.

*E. coli* BL21(DE3) cells (see Karim 2016 and Table 1 for strains) were grown in 2×YTPG media (16 g $l^{-1}$ tryptone, 10 g $l^{-1}$ yeast extract, 5 g $l^{-1}$ NaCl, 7 g $l^{-1}$ potassium phosphate monobasic, 3 g $l^{-1}$ potassium phosphate dibasic, 18 g $l^{-1}$ glucose). These cells were cultured at the 50 ml scale in 250 ml baffled tunair shake flasks (IBI Scientific, Peosta, IA) in a 37° C. incubator with vigorous shaking at 250 rpm. The cultured cells were monitored by spectrophotometry (Genesys 10S UV-Vis, Thermo Fisher Scientific, Waltham, MA). When cells reached $OD_{600}$=0.6-0.8, the cultures were induced with 0.1 mM IPTG. After induction cultures were grown for 4 h at 30° C. Antibiotics were not used during cell growth. The cells were harvested by centrifuging at 8,000 g at 4° C. for 15 min and were washed two times with cold S30 buffer (10 mM Tris-acetate (pH 8.2), 14 mM magnesium acetate, and 60 mM potassium glutamate). After final wash and centrifugation, the pelleted wet cells were weighed, flash frozen in liquid nitrogen, and stored at −80° C. The thawed cells were suspended in 0.8 ml of S30 buffer per 1 g of wet cell mass. In order to lyse cells by sonication, thawed and suspended cells were transferred into 1.5 ml microtube and placed in an ice-water bath to minimize heat damage during sonication. The cells were lysed using a Q125 Sonicator (Qsonica, Newtown, CT) with 3.175 mm diameter probe at frequency of 20 kHz and 50% of amplitude. The input energy (Joules) was monitored and 830 J was used for 1.4 ml of suspended cells. The lysate was then centrifuged twice at 21,100 g at 4° C. for 15 min. All of prepared cell extract was flash frozen in liquid nitrogen and stored at −80° C. until use.

3. Extract Protein Quantification.

The total protein concentration of the extracts was measured by Quick-Start Bradford protein assay kits (Bio-Rad) with a bovine serum albumin standard. The extracts were subsequently run on a Coomassie-blue stained NuPAGE Bis-Tris 12% SDS-PAGF gel with MOPS buffer (Life Technology, Grand Island, NY). The SeeBlue Plus2 pre-stained ladder (Life Technology, Grand Island, NY) was used and ~10 μg of total protein for each sample was loaded on the gel.

4. CFME Reactions.

Reactions were carried out in 1.5 ml Eppendorf tubes at 37° C. in 25 μl volumes. Each reaction consisted of mixing five extracts, containing one enzyme overexpressed each, to complete the biosynthetic n-butanol pathway (2 mg $ml^{-1}$) along with magnesium glutamate (8 mM), ammonium glutamate (10 mM), potassium glutamate (134 mM), glucose (200 mM), dipotassium phosphate (10 mM, pH 7.2), Bis Tris (100 mM), NAD (1 mM), ATP (1 mM), and CoA (0.5 mM), unless otherwise noted. Reactions were terminated by adding 5% w/v trichloroacetic acid in a 1:1 ratio. Precipitated proteins were pelleted by centrifugation at 15,000 g for 10 min. The supernatant was stored at −80° C. until analysis.

5. CFPS-ME Reactions.

CFPS reactions were performed to express enzymes involved in n-butanol production prior to starting the CFME portion of the reactions using a modified PANOx-SP system[47]. A 25 μl CFPS reaction in a 1.5 ml microcentrifuge tube was prepared by mixing the following components: ATP (1.2 mM); GTP, UTP, and CTP (0.85 mM each); folinic acid (34.0 μg $ml^{-1}$); *E. coli* tRNA mixture (170.0 μg $ml^{-1}$); T7 RNA polymerase (100 μg $ml^{-1}$); 20 standard amino acids (2 mM each); nicotinamide adenine dinucleotide (NAD; 0.33 mm); coenzyme-A (0.27 mM); spermidine (1.5 mM); putrescine (1 mM); potassium glutamate (130 mM); ammonium glutamate (10 mM); magnesium glutamate (12 mM); phosphoenolpyruvate (PEP; 33 mM), and cell extract (10 mg $ml^{-1}$). For each reaction plasmid was added at ~13.3 or ~26.6 μg $ml^{-1}$. The n-butanol production portion of the reaction was initiated by spiking in glucose (200 mM) and additional reagents (NAD, CoA) noted throughout the manuscript.

6. Quantification of Protein Produced In Vitro.

Cell-free protein synthesis reactions were performed as noted above (Section 2.5) with radioactive $^{14}$C-Leucine (10 μM) supplemented in addition to all 20 standard amino acids. We used trichloroacetic acid (TCA) to precipitate radioactive protein samples. Radioactivity of TCA-precipitated samples was measured by liquid scintillation counting to then quantify the protein produced as previously reported (MicroBeta2; PerkinElmer)[46,47]. These reactions were also run on a Coomassie-stained SDS-PAGE gel and exposed by autoradiography. Autoradiographs were imaged with a Typhoon 7000 (GE Healthcare Life Sciences, Pittsburgh, PA). Multiple proteins produced in vitro were further quantified by gel image intensity comparisons using ImageJ (NIH).

7. n-Butanol Quantification.

Figure 7:
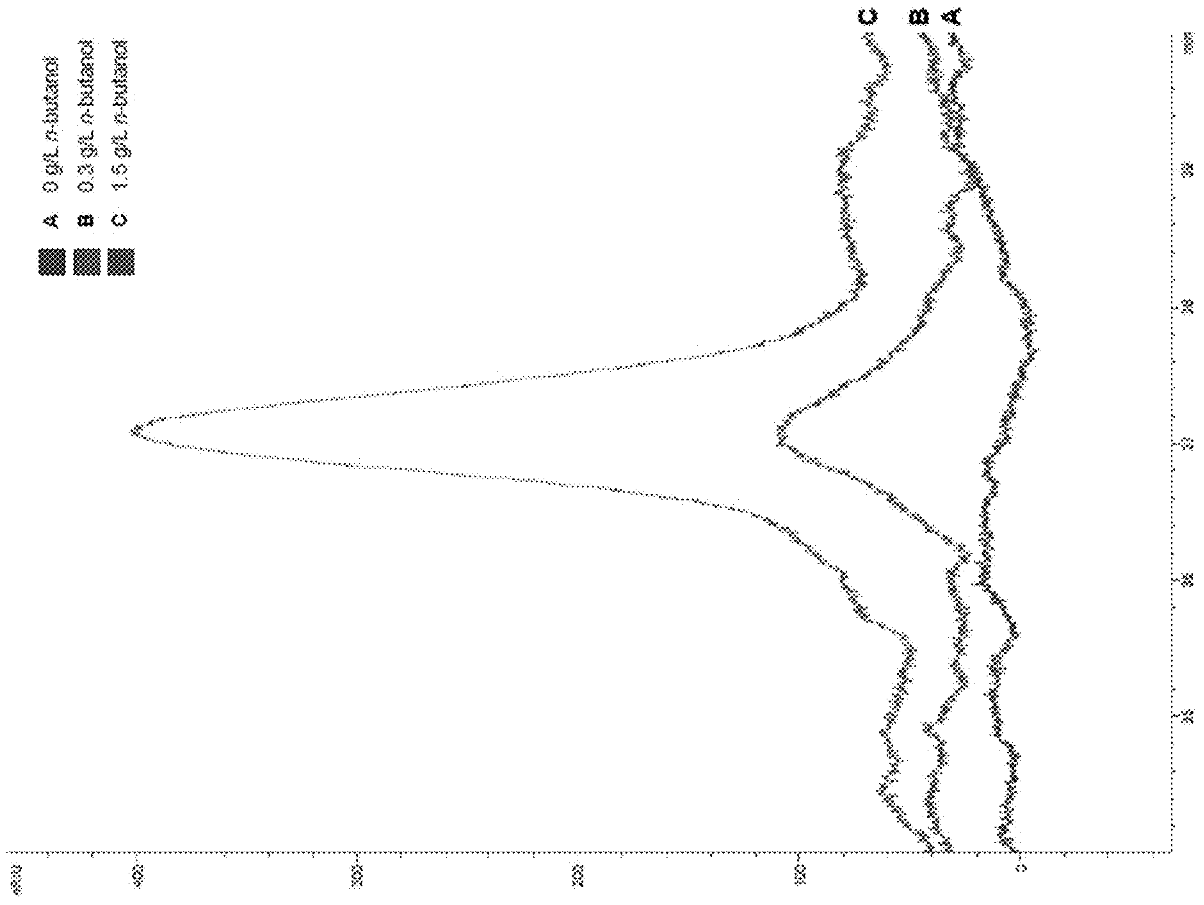
FIG. 7. Example Chromatograms for n-butanol quantification. Three chromatogram n-butanol peaks are overlaid with retention time on the x-axis and relative intensity units of the y-axis. Peak A represents an example cell-free reaction with no n-butanol produced from the reaction. Peak B is a cell-free reaction with ~0.3 g/L of n-butanol produced. Peak C is a cell-free reaction with ~1.5 g/L of n-butanol produced.

High-performance liquid chromatography (HPLC) was used to analyze the components in the reactions. n-Butanol was measured with an Agilent 1260 series HPLC system (Agilent, Santa Clara, CA) via a refractive index (RI) detector. Analytes were separated using the Aminex HPX-87H anion exchange column (Bio-Rad Laboratories) with a 5 mM sulfuric acid mobile phase at 55° C. and a flow rate of 0.6 ml min. Commercial standard of n-butanol was used for quantification of experimental samples by linear interpolation of external standard curves. An example chromatogram for n-butanol is given in FIG. 7.

Results

In developing a framework for biosynthetic pathway prototyping, we constructed a 17-step pathway for the production of n-butanol. n-butanol synthesis was selected as a model because of its importance as a potential biofuel, it is easily quantified by HPLC, and it has multiple heterologous steps. We sought to combine *E. coli*'s endogenous 11-step glycolytic pathway from glucose to acetyl-CoA (AcCoA) with the *Clostridia*-derived six-step n-butanol pathway from AcCoA (FIG. 1B). The idea that natural energy and cofactor regeneration would be harnessed in the lysate to fuel n-butanol production is a distinct break from typical in vitro approaches, which use purified enzymes[32]. Complementary to those systems, our approach allows for studying pathway performance in a setting that better mimics the in vivo operation (e.g., from glucose rather than AcCoA). The crude lysate system also allows us to focus on expressing only the necessary heterologous enzymes to complete the entire pathway. These enzymes include a thiolase to merge two AcCoAs followed by a number of dehydrogenases to perform a series of reductions through CoA intermediates to obtain n-butanol (See Karim 2016, and Table 2 for Genes and Enzymes).

1. Cell-Free Metabolic Engineering for n-butanol Production.

Figure 2:
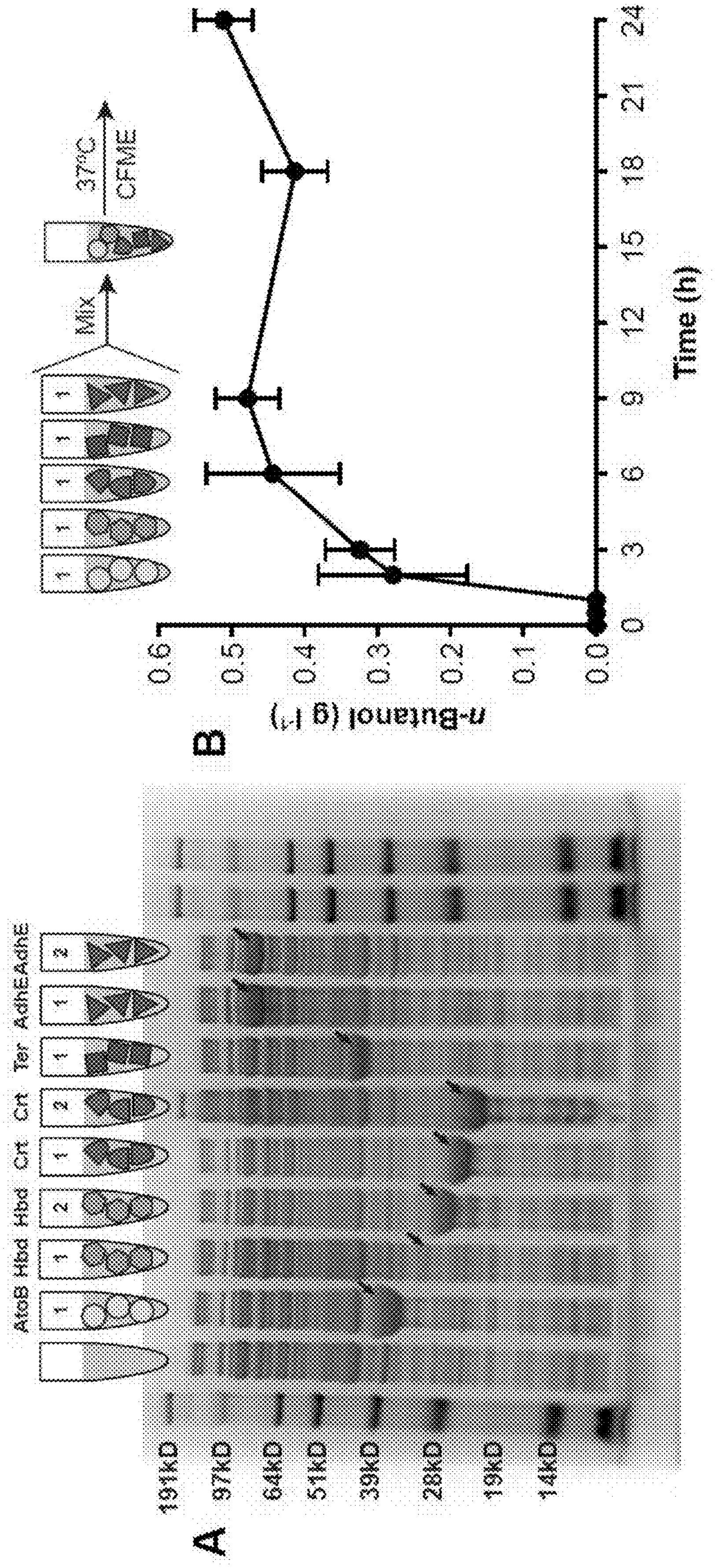
FIG. 2. Biosynthesis of n-butanol achieved via CFME of a coupled *E. coli* and *C. acetobutylicum* metabolic pathway. (A) Via SDS-PAGE, the gel verifies the selective overexpression of pathway enzymes in *E. coli* BL21(DE3) crude cell lysates: AtoB (*Escherichia coli*), Hbd1 (*Clostridia acetobutylicum*, CA), Hbd2 (*Clostridia beijerinckii*, CB), Crt1 (*Clostridium acetobutylicum*, CA), Crt2 (*Pseudomonas putida*, PP), Ter (*Treponema denticola*, TD), AdhE1 (*Clostridium acetobutylicum*, CA), and AdhE2 (*Clostridium pasteurianum*, CP). (B) CFME reactions for n-butanol production from glucose were carried out using five crude lysates mixed together (1:1:1:1:1 based on total protein quantification) with glutamate salts ($Mg^+$, $NH_4^+$, $K^+$), phosphate ($K_2HPO_4$), buffer (Bis Tris), and cofactors (ATP, CoA, $NAD^+$). These lysates individually contained AtoB (EC), Hbd1 (CA), Crt1 (CA), Ter1 (TD), and AdhE1 (CA) selectively overexpressed at 37° C. Error bars represent standard deviations with n≥3 independent reactions.

To enable cell-free biosynthesis of n-butanol, we first introduced genes encoding the five enzymes needed to convert AcCoA to n-butanol individually into our extract source strains, in this case BL21(DE3) (See Karim 2016, Table 1 for Strains and Plasmids, and Karim 2016 for Primers). We selected two homologs each for hydroxybutyryl-CoA dehydrogenase (Hbd), crotonase (Crt), and bifunctional aldehyde/alcohol dehydrogenase functionalities. For the thiolase (AtoB) and butyryl-CoA dehydrogenase (Ter) we chose *E. coli*'s endogenous enzyme and a widely used enzyme from *Treponema denticola*, respectively. Next, we selectively overexpressed each heterologous enzyme in separate strains using a tightly controlled T7 promoter and strong ribosome binding site. As expected, we observed that the heterologous proteins were overexpressed as the dominant bands, with the exception of Hbd1, on an SDS-PAGE gel (FIG. 2A). The low expression of Hbd1 is likely due to RBS used for expression.

After lysis and extract preparation, we then reconstituted the 17-step pathway from glucose to n-butanol by mixing equal total protein concentrations of five separate extracts containing each enzyme. Specifically, we started with the following enzyme set: *E. coli*'s AtoB, *C. acetobutylicum* 's Hbd, Crt, and AdhE2, as well as Ter from *T. denticola*. This set was chosen to include most of *C. acetobutylicum* 's enzyme set, one of the most widely used sets for n-butanol production, along with previously identified best enzymes for thiolase and butyryl-CoA dehydrogenase functions[17,19]. Upon incubation with essential substrates, salts, and cofactors (e.g., magnesium, potassium, and ammonium salts, glucose, phosphate, buffer, NAD, CoA, ATP), we assessed n-butanol synthesis in 25 μl CFME batch reactions carried out for 24 h at 37° C. via high performance liquid chromatography (HPLC). We observed production of 0.51±0.04 g $l^{-1}$ n-butanol (~0.05 mol n-butanol/mol glucose) over the course of a 24 h reaction (FIG. 2B), without any optimization to improve titers. As expected, we also observed lactate, acetate, and ethanol as byproducts seen in previous reports of n-butanol production, which could be addressed through genome modifications (e.g., deletion of ldh gene in the source strain)[19]. Butanol production shows that both the heterologous pathway and endogenous glycolysis is activated with cofactors being regenerated. However, n-butanol production stops after ~9 h. In previous work, substrate depletion was shown to be the most typical cause for reaction termination[36]. One way to avoid this limitation is to run reactions in fed-batch or continuous reactor set-ups or use substrates that are metabolized slower (e.g. polymeric sugars). Except in few instances[39,48], limited cofactor regeneration has historically plagued in vitro synthetic enzymatic pathway conversions[32,34,35]. Here, however, native glycolytic enzymes in the lysate provide a simple route to fuel highly active heterologous metabolic conversions. For example, to produce ~7 mM n-butanol we would need ~56 NADH turnover events, exceeding typical turnover numbers of ~5-20 for purified in vitro systems[32].

Figure 3:
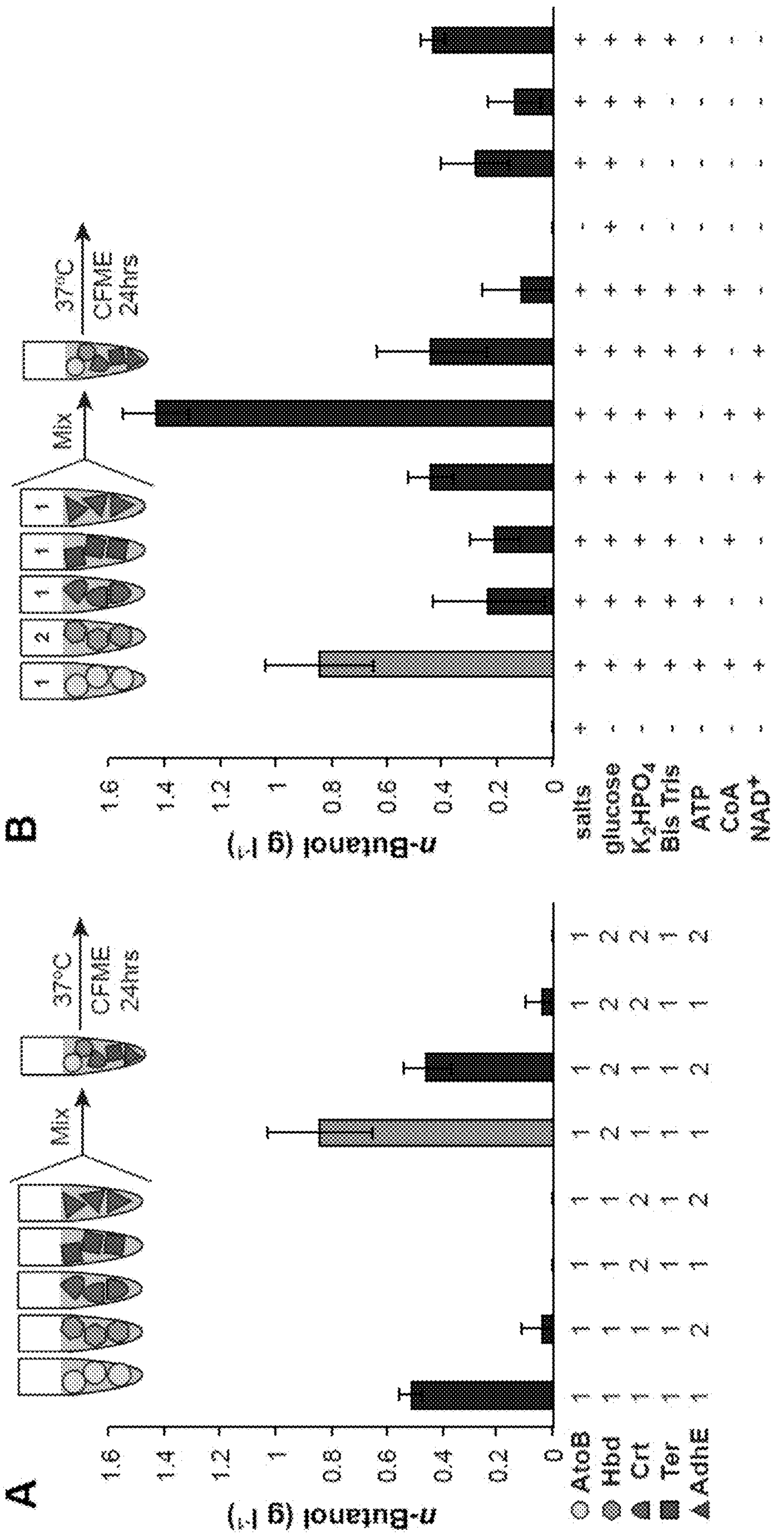
FIG. 3. Enzyme and physiochemical optimizations lead to increased yields of CFME n-butanol production. (A) Reactions for n-butanol production from glucose were performed using different sets of five crude lysates mixed together to obtain unique combinations of selectively overexpressed enzymes with AtoB, Hbd, Crt, Ter, and AdhE activities. Lysate mixes were combined with glutamate salts ($Mg^+$, $NH_4^+$, $K^+$), phosphate ($K_2HPO_4$), buffer (Bis Tris), and cofactors (ATP, CoA, $NAD^+$) and incubated for 24 h at 37° C. (B) To enhance yields and optimize pathway performance, a physiochemical optimization was performed with or without glutamate salts ($Mg^+$, $NH_4^+$, K+), phosphate ($K_2HPO_4$), buffer (Bis Tris), and cofactors (ATP, CoA, $NAD^+$)) of cell-free reactions producing n-butanol. Reactions incubated for 24 h at 37° C. The grey bars represent the same recipe in (A) and in (B). All error bars represent standard deviations with n≥3 independent reactions.
Figure 8:
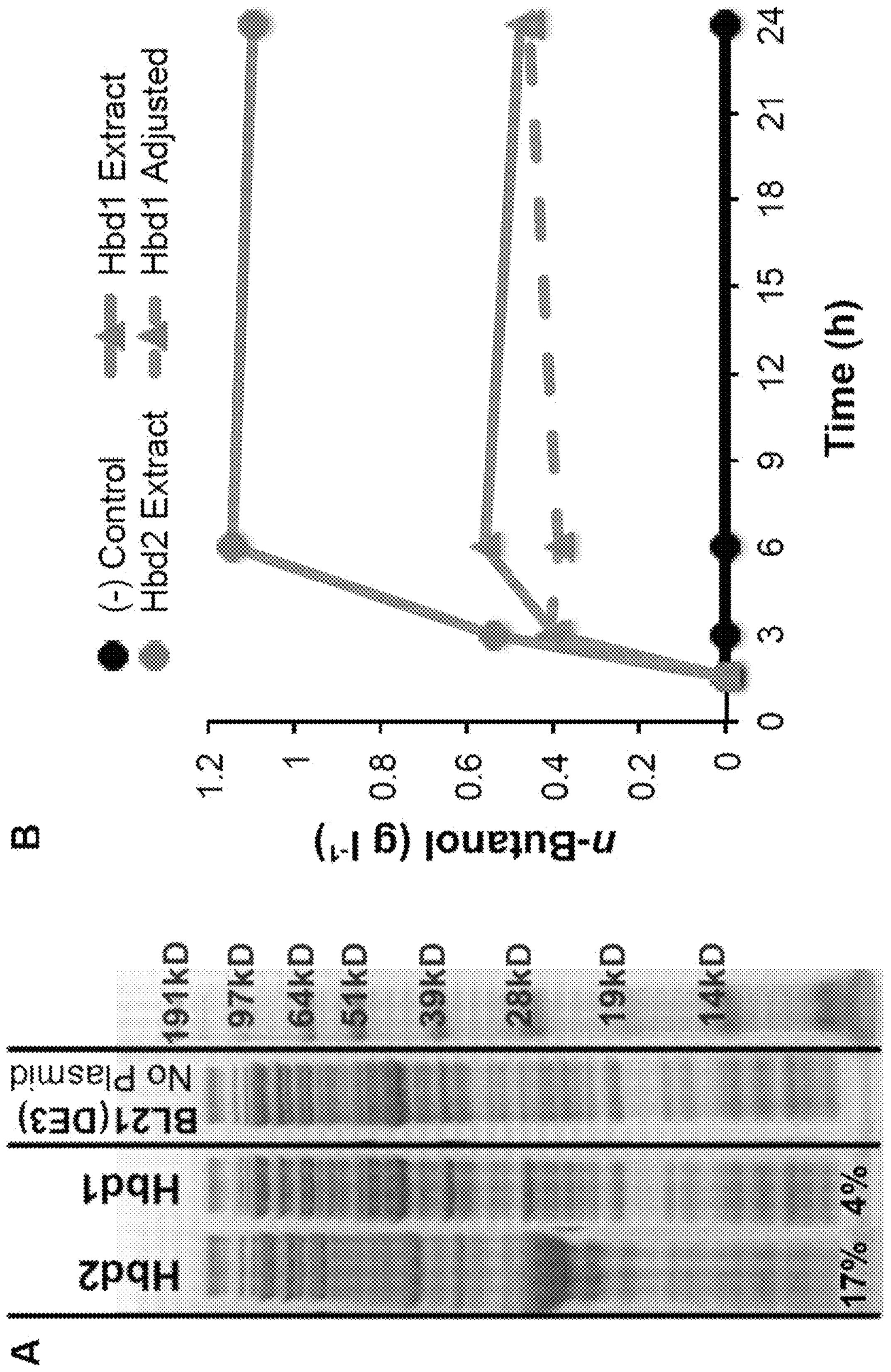
FIG. 8. Adjusting extracts for relative concentrations of selectively overexpressed Hbd1 and Hbd2 does not affect overall n-butanol production by CFME. (A) BL21(DE3) extract containing no overexpressed proteins, overexpressed Hbd1 extract, and overexpressed Hbd2 extract were each separated by SDS-PAGE and stained with Coomassie blue. Using densitometry with ImageJ software, each lane was analyzed for band density to determine approximate, relative amounts of overexpressed protein. Hbd1 extract contained ~4% Hbd1 protein, and Hbd2 extract contained ~17% Hbd2 protein. (B) Each Hbd extract was mixed with extracts containing the other pathway enzymes (AtoB, Crt, Ter, and AdhE) and CFME reactions were run for 24 h (n=1) to make n-butanol. The cases include Hbd2 extract, Hbd1 extract, and Hbd1 extract adjusted to contain approximately the same amount of overexpressed Hbd protein as the Hbd2 extract. Total extract concentration was kept constant at 10 $\mu g\ ml^{-1}$ using a BL21(DE3) extract containing no heterologously expressed proteins to adjust the Hbd extracts. The observed discrepancies in 'Hbd1 Extract' and 'Hbd1 Adjusted' are likely an artifact of sample size.

Following demonstration of activating n-butanol synthesis, we next aimed to modularly build n-butanol synthesis pathways with different enzyme homologs to improve pathway performance. We cycled through multiple distinct ensembles of enzymes by mixing and matching lysates containing different versions of enzymes necessary to complete the biosynthetic n-butanol pathway. Trying out different homologs in this manner allowed us to quickly identify a better set of enzymes producing n-butanol at 0.84±0.19 g $l^{-1}$ (0.09 mol n-butanol/mol glucose) (FIG. 3A). Specifically, we showed that Hbd2 from *C. beijerinckii* enabled a 65% increase in n-butanol synthesis titers over Hbd1 from *C. acetobutylicum*. A follow-up experiment doubling the Hbd1 enzyme did not alter the amount of n-butanol produced, suggesting that this increase was not due to discrepancies in enzyme concentrations in the lysate (FIG. 8). However, further studies of these enzymes would elucidate whether the observed n-butanol production was a result of using BL21(DE3) extract without heterologous genes expressed (used for normalization), which may have more active glycolytic and byproduct pathways that could divert flux away from n-butanol.

Figure 9:
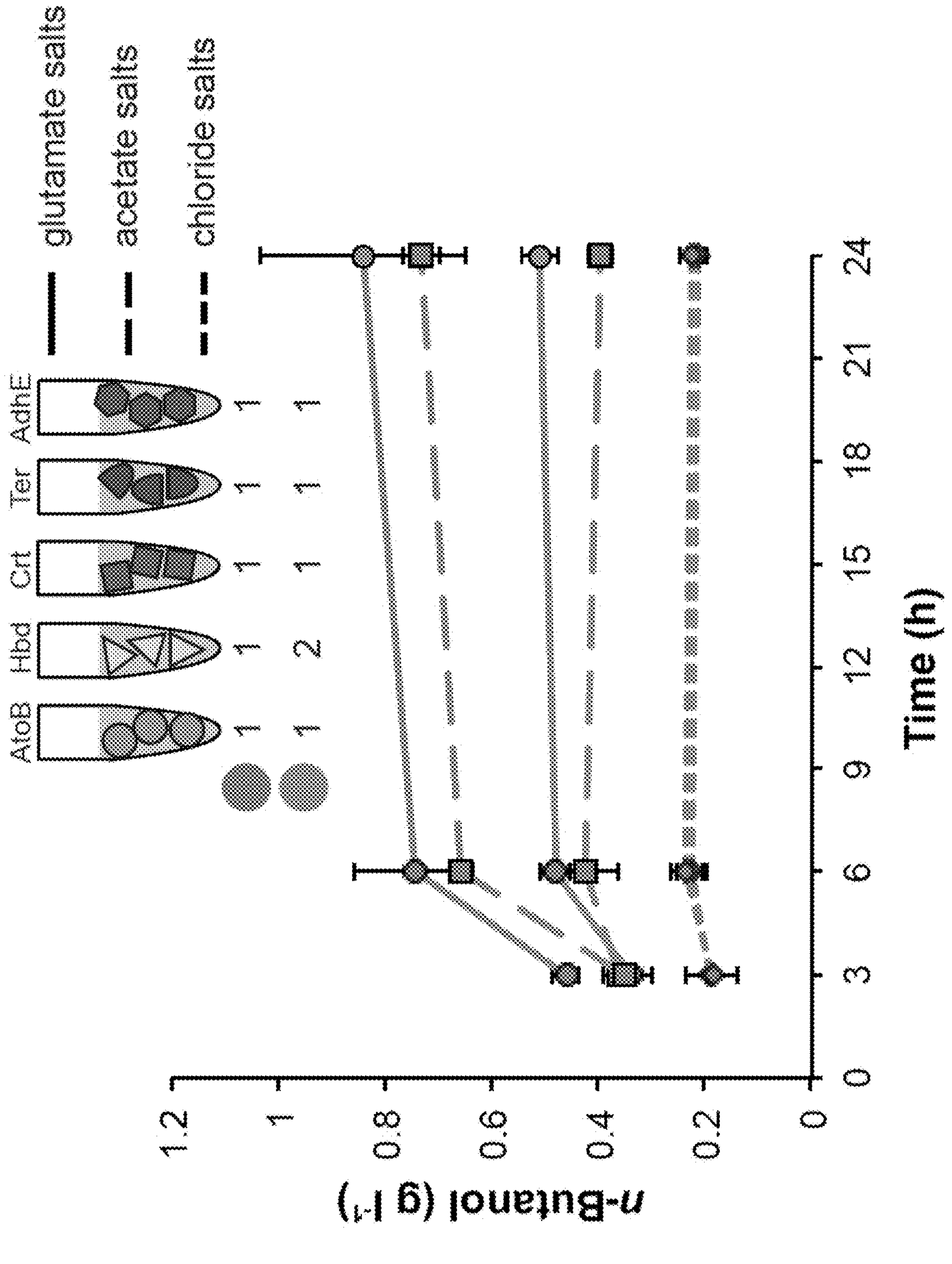
FIG. 9. Inorganic glutamate salt solutions perform the best in CFME reactions. Two different sets of 5 crude lysates mixed together containing selectively overexpressed enzymes with AtoB, Hbd, Crt, Ter, and AdhE activities were used to produce n-butanol from glucose. Bhlue is the original set of extracts (containing Hbd1) and orange is the best enzyme set (containing Hbd2). Lysate mixes were combined with glutamate salts ($Mg^+$, $NH_4^+$, $K^+$) (solid line), acetate salts (long dashed line), or chloride salts (short dashed line). To activate metabolism and start CFME reactions phosphates ($K_2HPO_4$), buffer (Bis Tris), and cofactors (ATP, CoA, $NAD^+$) were added and incubated for 24 h at 37° C. All error bars represent 1 s.d. with n≥3.

While the selection of enzymes is crucial to improving n-butanol production, the value of each physiochemical parameter of the cell-free system also affects n-butanol production and becomes key in further optimization and debugging of the pathway. To demonstrate the facile nature of combinatorial optimizations in our cell-free framework, we explored changes in the ionic composition because the composition of salts added to in vitro systems affects the systems' performance[46,47,49,50]. Specifically, we tested the effect of using glutamate, acetate, and chloride salts on n-butanol production and found that glutamate salts perform more than 15% better than the other salt compositions (FIG. 9). Our results are consistent with previous works, which have shown that glutamate salts better mimic the intracellular cytoplasmic conditions of *E. coli* to co-activate authentic biological processes such as the in vitro co-activation of central metabolism, oxidative phosphorylation, and protein synthesis[46].

Figure 10:
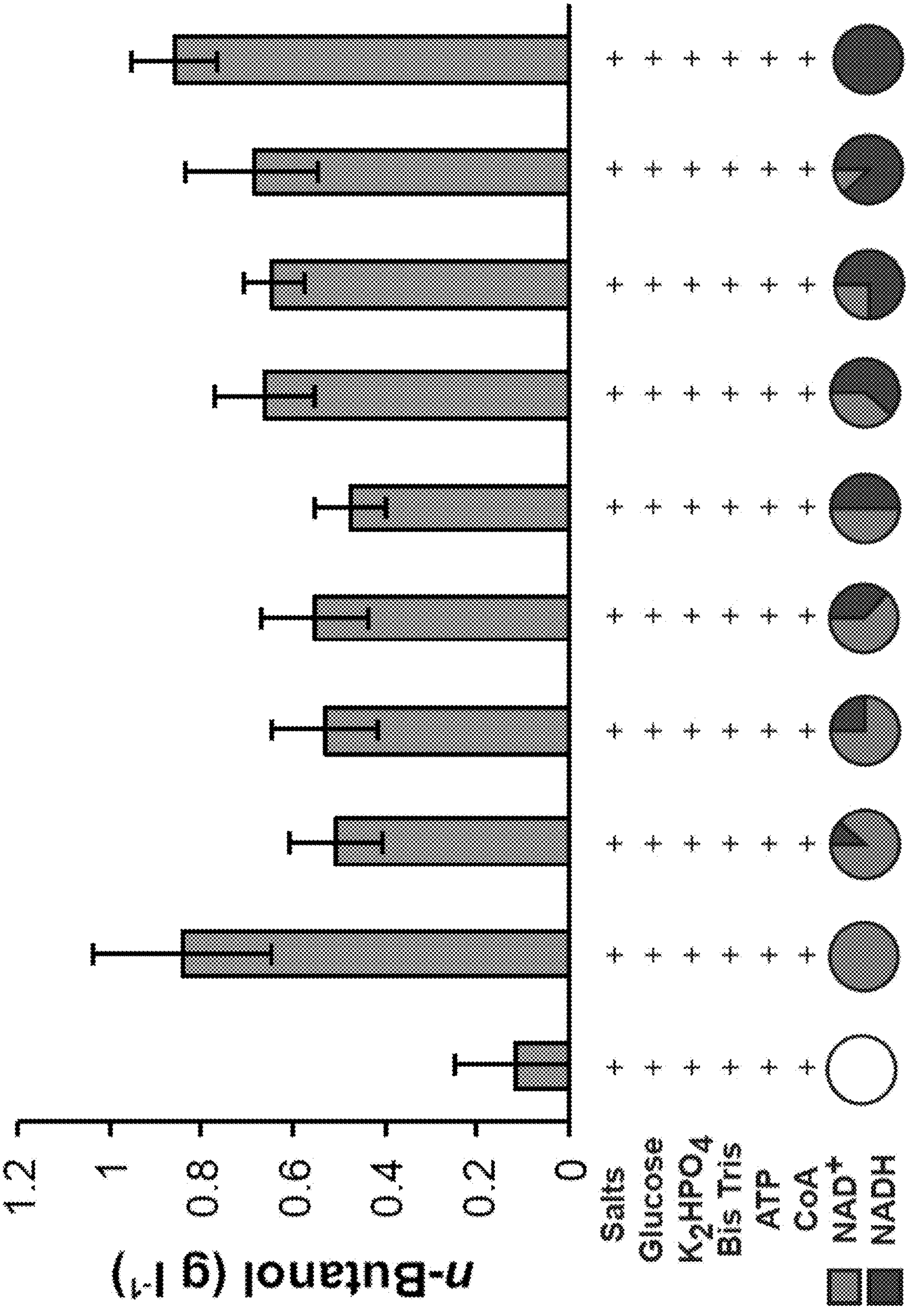
FIG. 10. Comparing initial $NAD^+$ and NADH ratios show relatively little effect on n-butanol production in CFME. Reactions for n-butanol production from glucose using the best set of crude lysates mixed together containing selectively overexpressed enzymes with AtoB, Hbd, Crt, Ter, and AdhE activities (determined as best by previous experiments) were run for 24 h and incubated at 37° C. Extract mixes were combined with glutamate salts ($Mg^+$, $NH_4^+$, $K^+$), phosphates ($K_2HPO_4$), buffer (Bis Tris), and cofactors (ATP, CoA, $NAD^+$, NADH) to initiate CFME reactions. In the key, plus signs (+) indicate the addition of each individual components at levels described in the methods section. The divisions in the circular graphics accompanying each bar with blue being $NAD^+$ and black being NADH indicate ratios of $NAD^+$ to NADH. The total NAD(H) concentration is 0.5 mM. All error bars represent 1 s.d. with n≥3.

Beyond studying pathway performance by altering the ionic composition, the states of critical cofactors (organic molecules necessary for enzyme catalysis) can also be studied. The balance of cofactors, such as oxidized and reduced NAD, is critical to energy regeneration within the lysate by also the heterologous pathway under investigation. In our cell-free framework, the lack of a cell wall enables direct sample acquisition, reaction monitoring, and control. We used this flexibility to study the impact of the ratio of initial cofactors in the reaction to see the ratio's effect on n-butanol production. We found that the ratio of NAD(H) at the start of the reaction (e.g., NAD:NADH: 1:0, 1:0.5, 1:1, 0.5:1, 0:1), keeping the total cofactor concentration at 0.5 mM, plays a minimal role in how much n-butanol can be produced (FIG. 10). This suggests that metabolism in the lysate may control the overall levels of reduced and oxidized cofactor, which is consistent with data from Kay and Jewett[36].

Understanding that some components play more of a role in pathway performance than others, we next performed a number of reactions to identify which added components are necessary for n-butanol production with a particular interest in the three added cofactors (ATP, NAD, and CoA). The supplementation of cofactors to cell-free reactions would be costly and hinder industrial practicality of this technology if it were proposed as a biomanufacturing platform. In our study of cell-free systems as a prototyping framework, we surprisingly found that omitting ATP boosts n-butanol production by greater than 180% from 0.84±0.19 g $l^{-1}$ to 1.43±0.12 g $l^{-1}$ (0.11 mol n-butanol/mol glucose) (FIG. 3B). More unexpectedly, by just adding salts to mimic the cytoplasm and glucose as a starting substrate we are able to produce n-butanol at 0.28±0.12 g $l^{-1}$. In other words, if lysates are prepared without dialysis, as we have done, cofactors remaining in the lysate are sufficient for the cell-free transformation and do not need to be added. Collectively, our results here show that the cell-free framework offers a strategy to explore how enzyme variants, substrates, cofactors, ionic composition, etc. can be varied in unique combinations to influence pathway performance. While CFME (i.e., selective enriching or functionalizing the lysate with pathway enzymes prior to extract generation) provides us with a rather quick way to screen enzyme ensembles and reaction conditions, this approach is limited by the cell's ability to produce the enzymes individually in vivo, a limitation that we address below.

2. Cell-Free Protein Synthesis Driven Metabolic Engineering.

We next aimed to combine CFPS and CFME to modularly build the n-butanol pathway for forward engineering. This is dissimilar from previous works in which synthetic in vitro pathways have been built by purified enzymes or using lysates selectively enriched by heterologously expressed enzymes. Integration of CFPS enables one to speed up DBT cycle time for prospecting biosynthetic pathways. Indeed, using CFPS to express enzymes can reduce the time to build pathways to hours rather than days. As a proof-of-concept of this approach, we tested making Hbd2 (the non-native entry enzyme to the pathway) by CFPS to activate n-butanol production (FIG. 4A). The key idea of the experiment was that the pathway would remain inactive (as downstream enzymes will not have their substrates) until active Hbd2 was synthesized. We chose to validate CFPS-ME in a three-step process. First, we quantified our ability to express Hbd2 in a CFPS reaction comprised of a mixture of lysates harboring selectively enriched pathway enzymes lacking Hbd2. This was important because typical CFPS systems use lysates from cells harvested in mid-late exponential phase, where as our lysates were collected 4 h post-induction of pathway enzymes. Second, we studied the ability to activate the entire pathway by combining CFPS and CFME. Third, we carried out a series of optimizations to try to increase yields.

For CFPS, we used the tunable and well characterized PANOx-SP CFPS system developed by Jewett and Swartz[47] to quantitatively test the synthesis of Hbd2. CFPS reactions at 30° C. were allowed to run for 24 h in batch operation and the yields of cell-free synthesized Hbd2 was quantified by monitoring $^{14}$C-leucine incorporation. We based the system on a mixture of lysates used above, except the lysate with Hbd2 was not included. Endogenous protein synthesis machinery should act to synthesize and fold desired protein products upon incubation with essential substrates (e.g., amino acids, nucleotides, DNA or mRNA, energy substrates, cofactors, and salts). In this case, we showed that when the DNA for the Hbd2 enzyme on a pJL1 vector was added, the mixed extract could produce 559±15 mg $l^{-1}$ of Hbd2 over a 24-hour period (FIG. 4B). Based on this result and the fact that this reaction was over 50% complete by three hours, we chose to run all subsequent CFPS reactions for three hours, which should provide sufficient protein quantities for prototyping.

We next investigated the ability of the cell-free synthesized Hbd2 to activate the full n-butanol pathway. After three hours of CFPS, we initiated n-butanol metabolism by adding 200 mM glucose to the reactions. We showed that CFPS of Hbd2 could activate n-butanol metabolism reaching a titer of 0.92±0.13 g $l^{-1}$ (FIG. 4C). Negative control reactions without synthesis of the Hbd2 did not produce n-butanol. Notably, the CFME portion resulted in the same n-butanol yields when carried out at either 30 or 37° C., so for ease we selected 30° C. for all future experiments to have the CFPS and CFME portions performed at the same temperature. As in the CFME system alone, we found that small molecules, cofactors, etc. can modulate pathway performance. For example, we found that adding both NAD and CoA with glucose to initiate n-butanol metabolism after CFPS gave us 1.22±0.22 g $l^{-1}$ n-butanol (FIG. 4D). Collectively, our results prove for the first time to our knowledge the ability to combine CFPS and CFME to support a highly active biosynthetic pathway.

Figure 5:
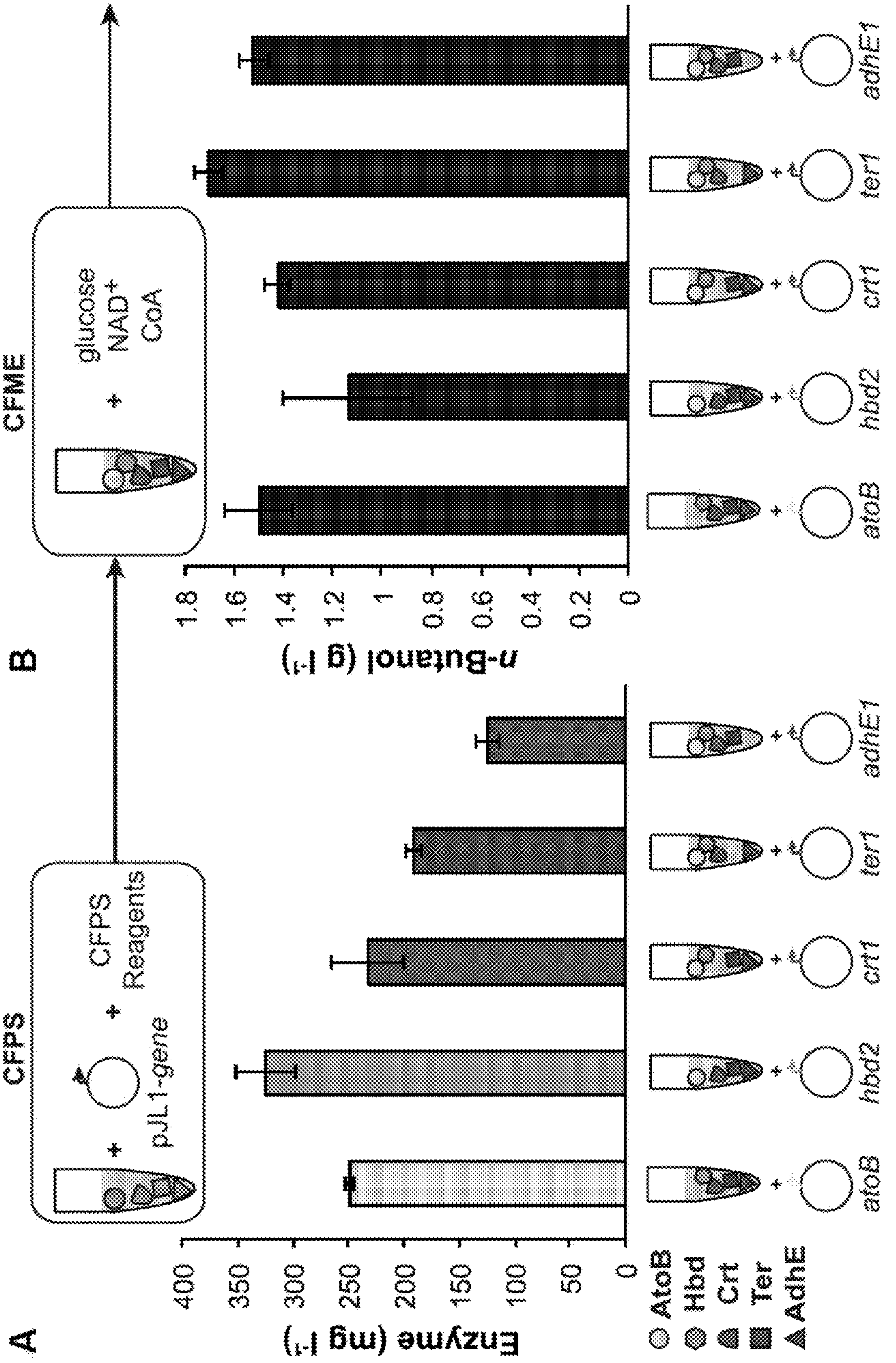
FIG. 5. Using cell-free protein synthesis to activate metabolism from any node in the biosynthetic pathway. (a) Cell-free protein synthesis titers of AtoB (EC), Hbd2 (CB), Crt1 (CA), Ter1 (CA), and AdhE (CA) off pJL1 constructs in separate reaction mixtures as determined by radioactive $^{14}C$-leucine incorporation. Each reaction mixture contained crude lysates with all pathway enzymes except the one made by CFPS. CFPS reactions were incubated for 3 h at 30° C. (b) n-butanol production in the same mixed lysate system activated by CFPS of each enzyme run at 30° C. for 3 h. Glucose, CoA, and NAD were added to activate the n-butanol pathway and CFME reactions were incubated for 24 h at 30° C. (c) n-butanol production activated by CFPS of enzymes in combinations: (1) AtoB (EC); (2) AtoB (EC) and Hbd2 (CB); (3) AtoB (EC), Hbd2 (CB), and Crt1 (CA); (4) AtoB (EC), Hbd2 (CB), Crt1 (CA), and Ter1 (TD); and (5) AtoB (EC), Hbd2 (CB), Crt1 (CA), Ter (TD), and AdhE1 (CA). The CFPS reactions were run at 30° C. for 3 hrs. Glucose, CoA, and $NAD^+$ were added to activate the in-butanol pathway and reactions were incubated for 24 h at 30° C. (d) A plasmid ratio optimization of pJL1-adhE1 vs. all other pJL1 constructs along with a test of three concentrations of T7 polymerase. For each, CFPS was run at 30° C. for 3 h. Glucose, CoA, and $NAD^+$ were added to activate the n-butanol pathway and reactions were incubated for 24 h at 30° C. All error bars represent standard deviations with n≥3 independent reactions.
Figure 5:
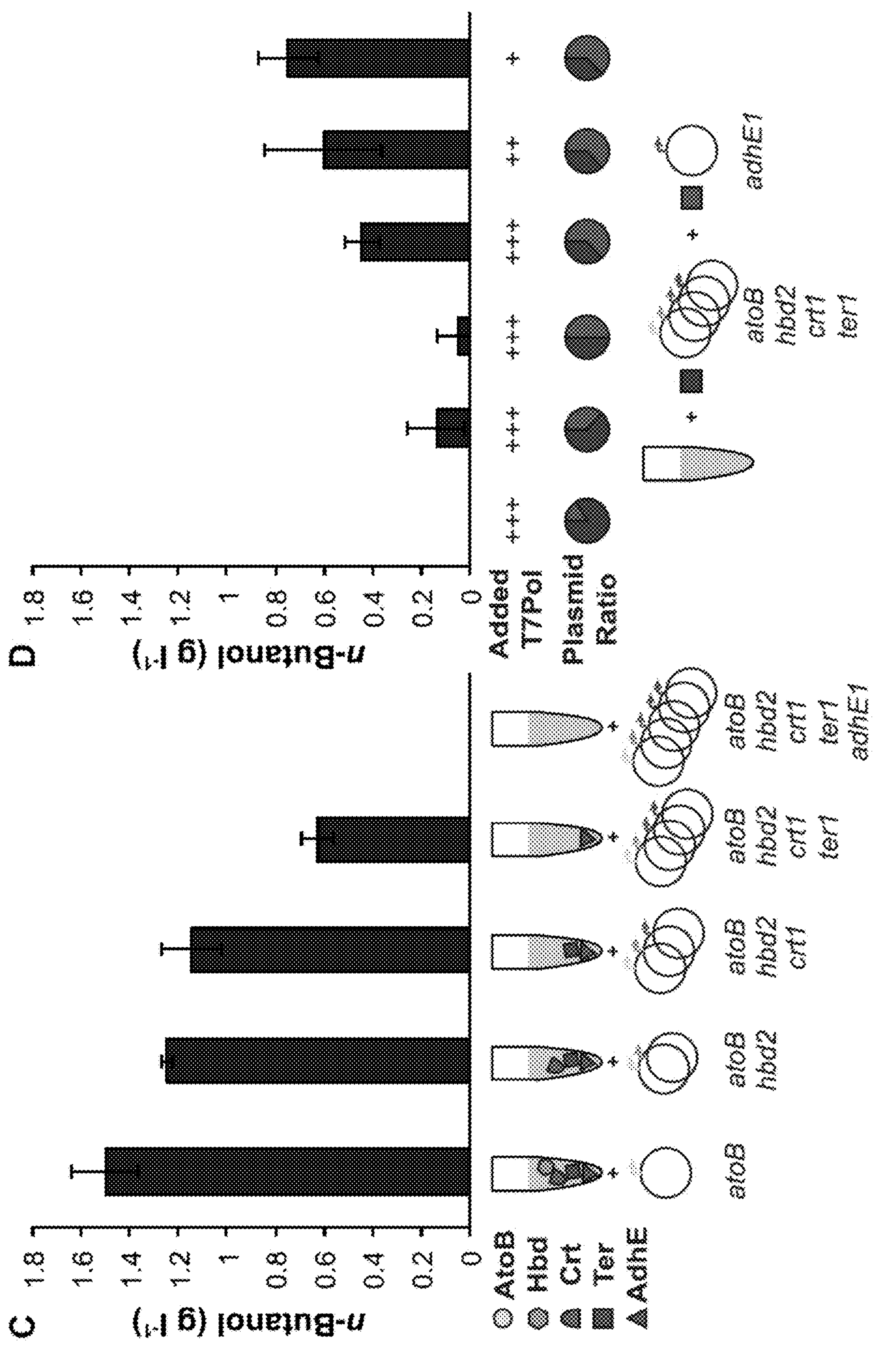
Figure 11:
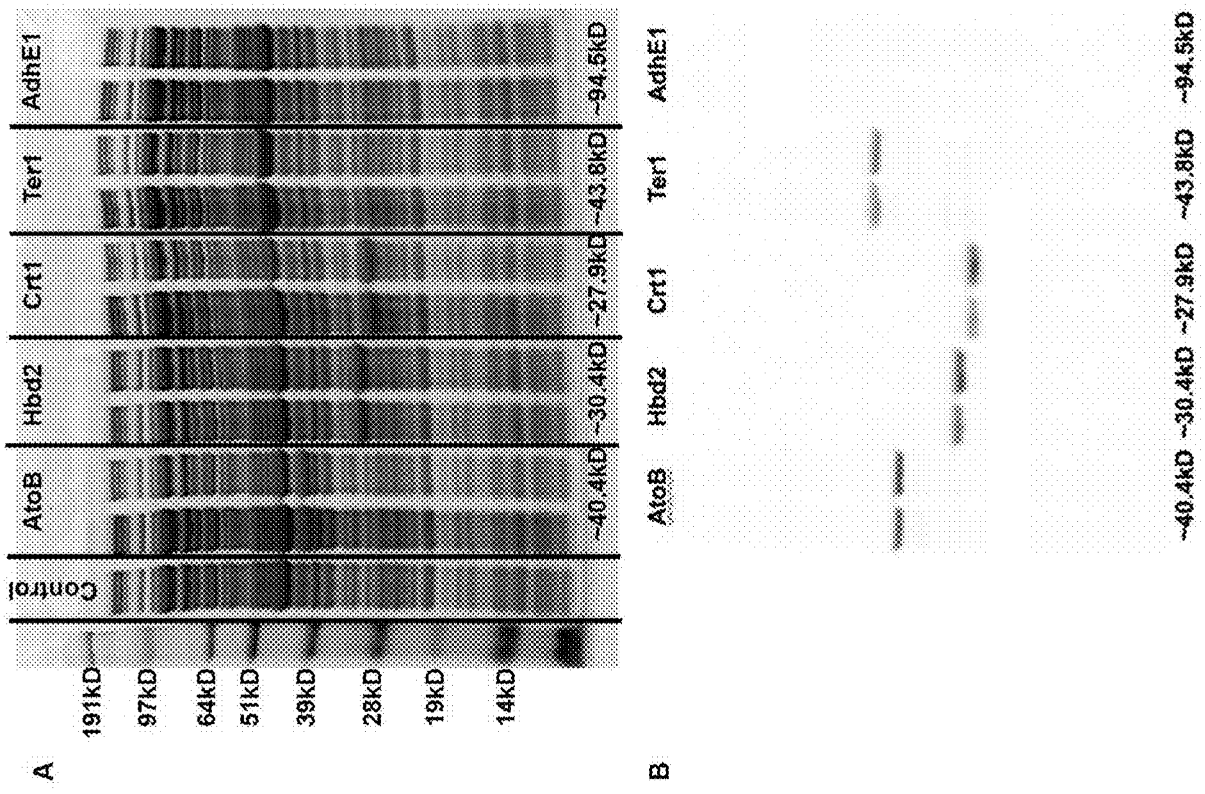
FIG. 11. SDS-PAGE and autoradiogram for CFPS of each individual enzyme show full-length protein formation. (A) SDS-PAGE was run with two replicates of each CFPS reaction performed at standard conditions listed in the methods section and for 3 h at 30° C. producing $^{14}C$-Leu incorporated protein corresponding to each enzyme in the n-butanol pathway. Molecular weights are listed at the bottom of the lanes. (B) An autoradiogram of the same gel showing that each enzyme is expressed in vitro as full-length proteins.

We further extended this proof-of-concept to activate n-butanol production using CFPS at any pathway node by producing each n-butanol pathway enzyme. Using mixed extracts with all but one necessary enzyme, we performed CFPS of the 'missing enzyme' and saw that each enzyme could be produced individually at more than 100 mg $l^{-1}$ without optimization (FIG. 5A). We then proved that full product of each protein is made exclusively in each reaction by an autoradiogram (FIG. 11). After validating expression of each enzyme, we then performed CFPS-ME reactions. We carried out three-hour CFPS reactions and then initiated the n-butanol pathway by adding glucose, NAD, and CoA, because supplementation of CFPS-ME reactions with both NAD and CoA increased n-butanol titers for Hbd2 (FIG.

4D). Strikingly, CFPS-ME could be used for each of the pathway enzymes to produce n-butanol at levels as high as 1.71±0.06 g $l^{-1}$ (FIG. 5B).

Figure 12:
FIG. 12. Protein SDS-PAGE gel and autoradiogram for CFPS of multiple enzymes produced full length product of each protein. SDS-PAGE was run with CFPS reactions containing one, two, three, four, and five DNA plasmids, building up the pathway. Reactions were each run at standard conditions listed in the methods section and for 3 h at 30° C. producing $^{14}C$-Leu incorporated protein corresponding to each enzyme in the n-butanol pathway.
Figure 13:
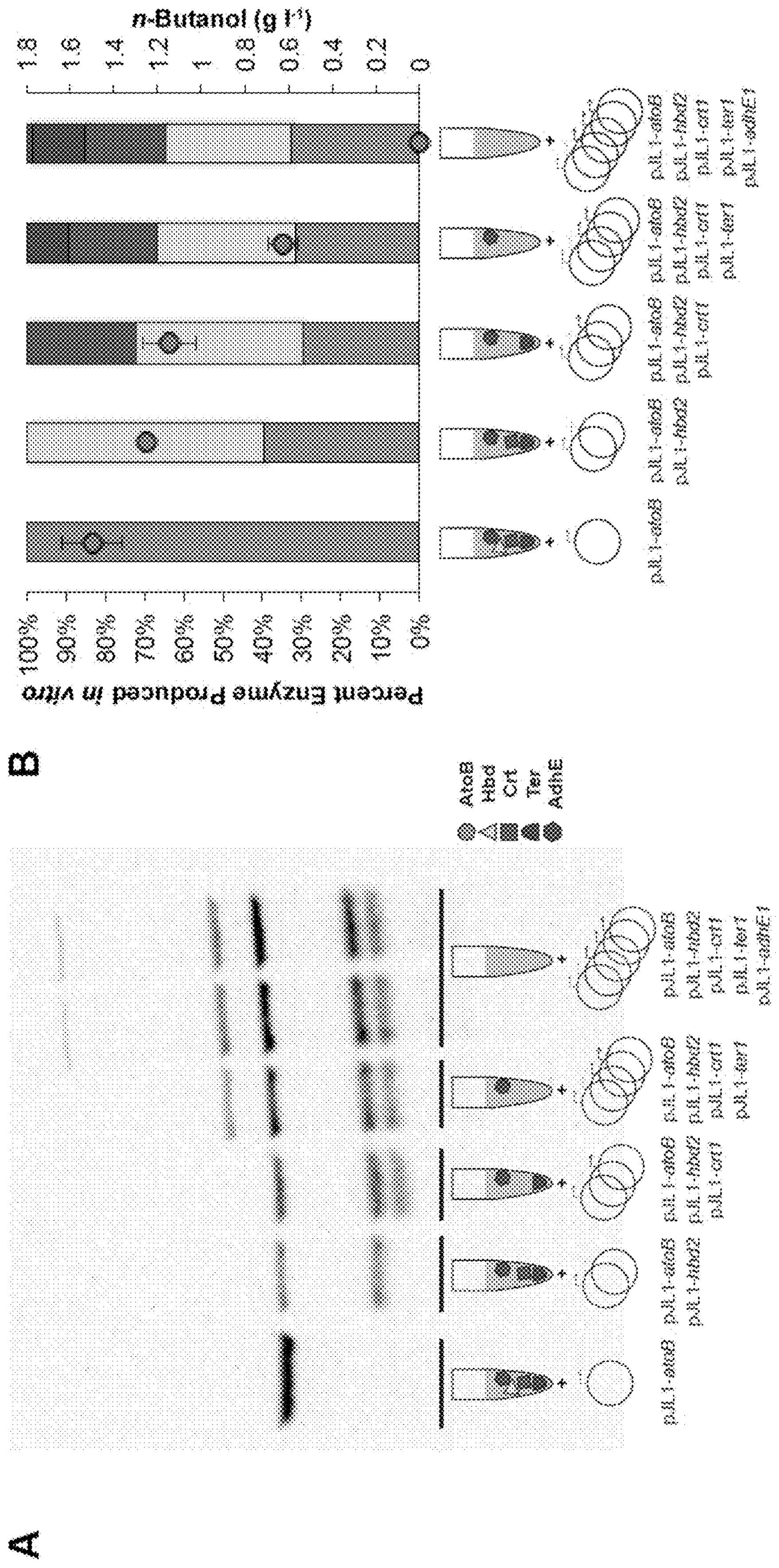
FIG. 13. Quantification of individual enzymes in multiple protein CFPS reactions from autoradiogram indicates a lower yield of downstream pathway enzymes. (A) BL21 (DE3) extract containing overexpressed proteins indicated in the key, different DNA plasmid compositions, and standard CFPS reagents identified in the methods section were incubated at 30° C. for 3 h. Each sample was separated by SDS-PAGE and stained with Coomassie blue. The gel was exposed to autoradiogram showing full-length product of each enzyme resulting from the DNA combinations. (B) Using densitometry with ImageJ software, each lane from the gel in panel A was analyzed for band density to determine approximate, relative amounts of each pathway enzyme produced by CFPS. The bars represent the percent of each enzyme produced in vitro. After CFPS for 3 h at 30° C., each reaction was supplemented with glucose, NAD+, and CoA and incubated at 30° C. for an additional 24 h to measure n-butanol production from each mix. Orange circles indicate n-butanol titers with error bars representing 1 s.d. with n≥3.
Figure 14:
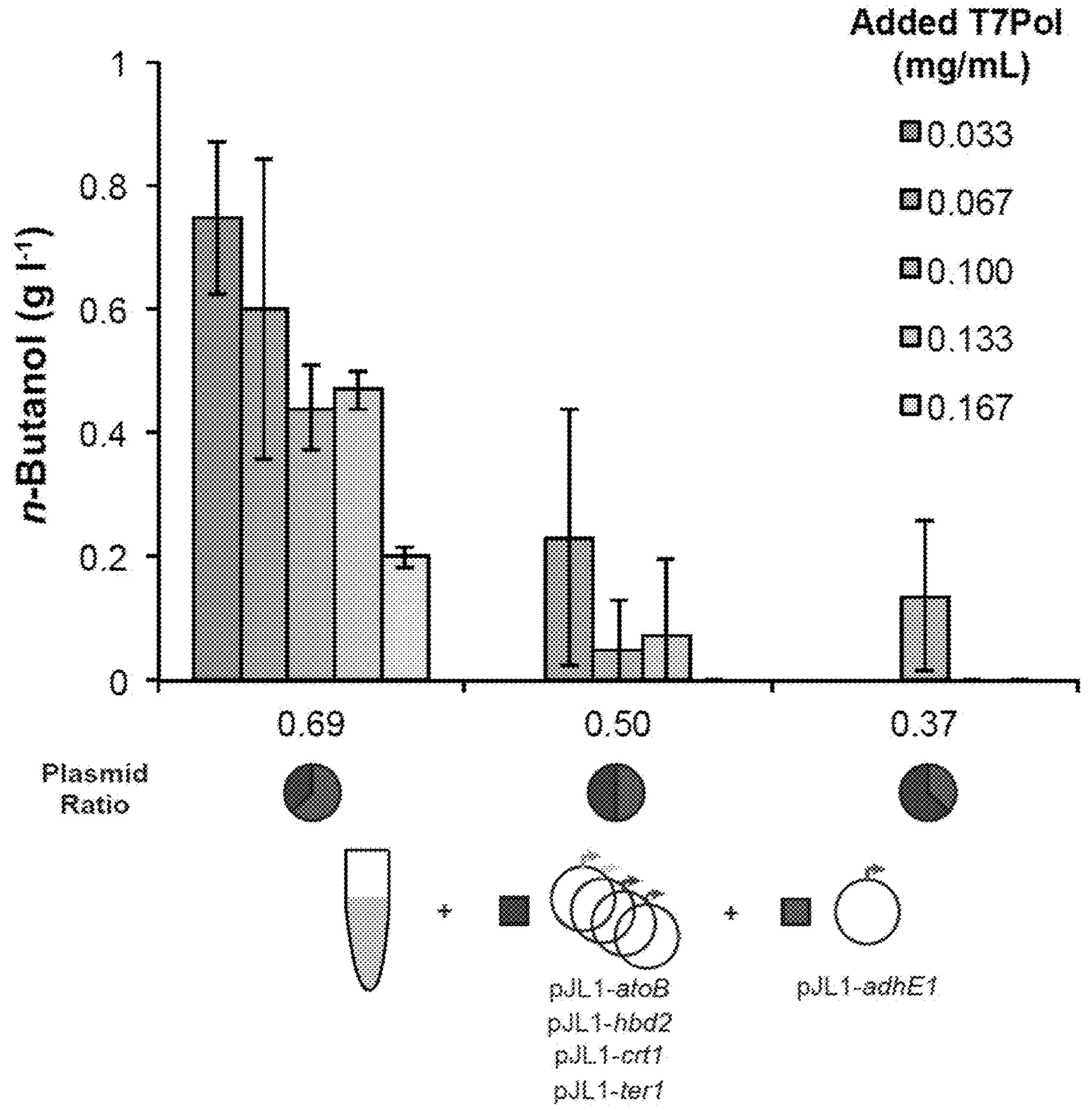
FIG. 14. Plasmid optimization for CFPS-ME of all pathway enzymes in vitro shows the ability to produce n-butanol. CFPS reactions were run in BL21(DE3) extract containing no overexpressed proteins. DNA plasmids encoding each heterologous enzyme were added in equal ratios with pJL1-adhE1 modulated as per the divisions in the circular graphics in the figure key. In the key, black represents equal amounts of plasmids encoding AtoB, Hbd, Crt, and Ter, and red represents the amount of pJL1-adhE1. CFPS reagents were added and incubated at 30° C. for 3 h. Glucose, NAD+, and CoA were added, and samples were further incubated at 30° C. for 24 h. n-Butanol production is measured and differs with varied concentrations of added T7 polymerase. All error bars represent 1 s.d. with n≥3.

We next set out to demonstrate we could build the entire pathway by CFPS of the pathway enzymes in our extracts. To this end, we extended the number of enzymes made in vitro one by one, by adding equal amounts of DNA of each, and saw that when we made one, two, three, and four of the five enzymes necessary in vitro we could produce n-butanol at levels between ~0.6 and ~1.4 g $l^{-1}$ (FIG. 5C). Again, full-length product of each protein is made in each reaction as shown by autoradiogram (FIG. 12). However, as we increase the number of enzymes produced by CFPS, the amount of n-butanol synthesized decreases. In fact, when we tried to produce all five enzymes in vitro we were initially unable to make any n-butanol. We attribute this drop in n-butanol production to there not being enough of the last enzyme in the pathway, AdhE, seen by quantification of the enzymes produced by CFPS (FIG. 13). However, we were able to make all enzymes in vitro at sufficient levels necessary to make n-butanol at 0.75±0.12 g $l^{-1}$ by increasing the plasmid DNA encoding AdhE to more than 50% of the total DNA added, (FIG. 5D; FIG. 14). Reduced T7 polymerase added shows improvements in n-butanol production. Typical CFPS systems supplement T7 polymerase stored in glycerol, and increasing glycerol concentrations can be deleterious to the CFPS system. The extract used in this study contains T7 polymerase expressed in vivo prior to extract preparation, so T7 polymerase in the extract is expected to be sufficient without supplementation. Based on our result that added ATP was deleterious to n-butanol production by CFME (FIG. 3B), the ATP used in CFPS might be expected to inhibit CFPS-ME n-butanol titers if ATP is long-lived. We have previously shown that ATP concentrations are stable around 200 μM over a ~6-8 hour batch CFPS reaction[47]. Though, a negative effect from ATP is expected, it is difficult to use the CFME optimization conditions for CFPS-ME, given the added complexity of protein synthesis. Our results importantly showed that we could build a five-step heterologous pathway to make n-butanol in vitro in three hours.

3. Rapid Prototyping and Enzyme Discovery with CFPS-ME.

The ability to use CFPS-ME to produce enzymes for n-butanol biosynthesis allows us to test pathway enzymes without expressing enzymes in the host cell. As a model case study, we decided to test for improved pathway performance (increased n-butanol production) by swapping out some of our initial Ter and AdhE enzymes for a variety of homologs. In less than a day, we studied 4 Ter and 3 AdhE homologs in a combined CFPS-ME reaction. In all cases, we observed synthesis of n-butanol, though lower than our previous best-performing enzymes (FIG. 6A). Five of these variants come from species never tested before.

Figure 6:
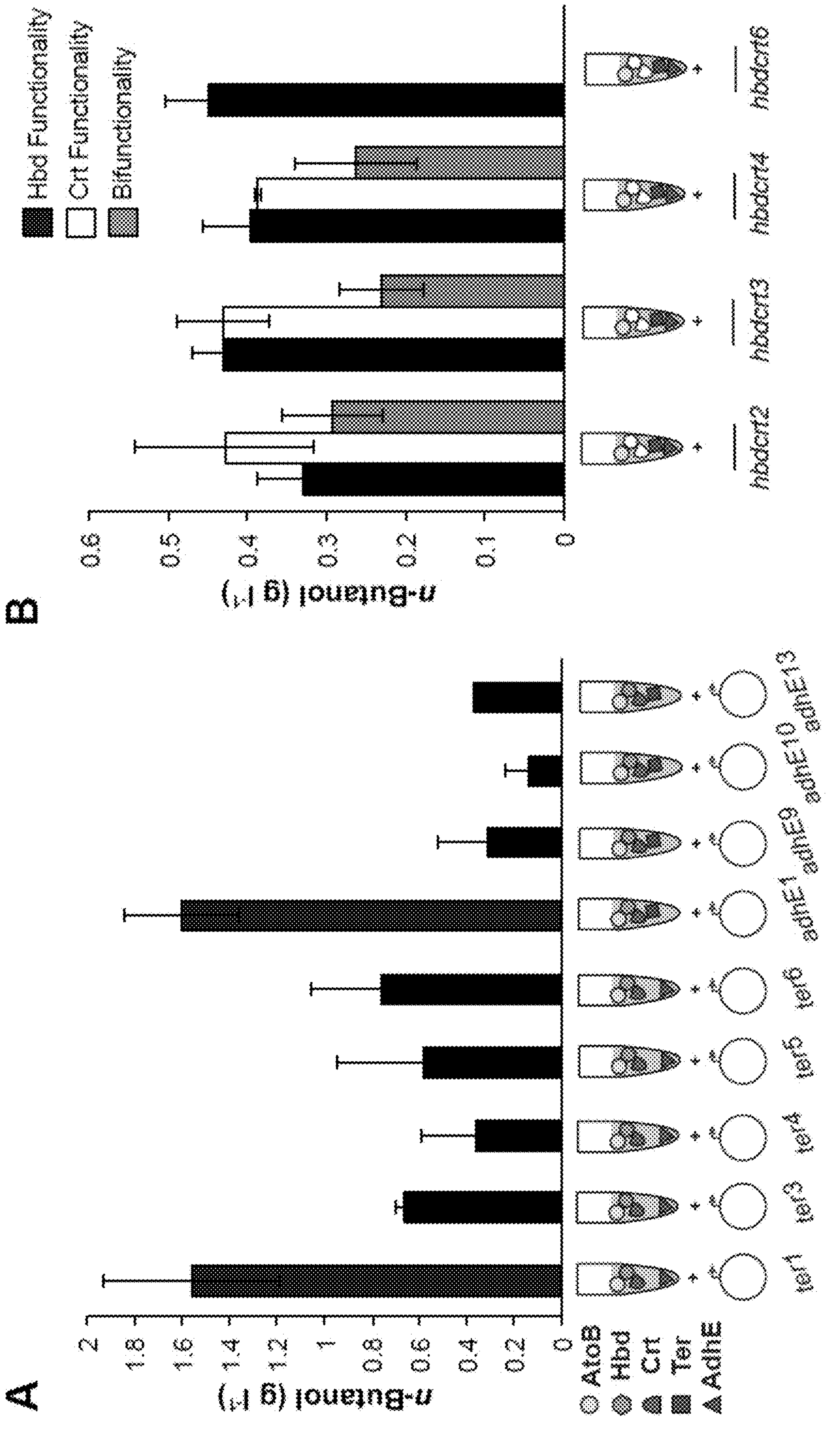
FIG. 6. Using CFPS-ME to rapidly screen pathway enzymes. (A) n-butanol production activated by CFPS of unique Ter homologs and AdhE homologs from pJL1 constructs: Ter3 (*Fibrobacter succinogenes*, FS). Ter4 (*Flavobacterium johnsoniae*, FJ), Ter5 (*Spirochaeta bajacaliforniensis*, SB), Ter6 (*Cytophaga hutchinsonii*, CH), AdhE9 (*Thermosynechococcus* sp. NK55a, TN), AdhE10 (*Providencia burhodogranaricea*, PB), and AdhE13 (*Serratia marcescens*, SM). Ter homologs were expressed in crude lysate mixtures containing AtoB (EC), Hbd2 (CB), Crt1 (CA), and AdhE1 (CA) overexpressed, and AdhE homologs were expressed in lysates containing AtoB (EC), Hbd2 (CB), Crt1 (CA), and Ter1 (TD) overexpressed. (B) n-Butanol production activated by CFPS putative bifunctional enzymes for Hbd and Crt activity: Hbdcrt2 (*Aeropyrum camini*, AC), Hbdcrt3 (*Pyrobaculum aerophilum*, PA), Hbdcrt4 (*Sulfolobus islandicus*, SI), and Hbdcrt6 (*Sulfolobus acidocaldarius*, SA). CFPS reactions were performed from linear DNA in crude lysate mixtures containing: (1) AtoB (EC), Ter1 (TD), and AdhE1 (CA) overexpressed to test bifunctionality, (2), AtoB (EC), Crt1 (CA), Ter1 (TD), and AdhE1 (CA) overexpressed to test Hbd functionality alone, and (3) AtoB (EC), Hbd2 (CB), Ter1 (TD), and AdhE1 (CA) overexpressed to test Crt functionality alone. For each, CFPS was run at 30° C. for 3 h. Glucose, CoA, and $NAD^+$ were added to activate the n-butanol pathway and reactions were incubated for 24 h at 30° C. All error bars represent standard deviations with n≥3 independent reactions.
Figure 15:
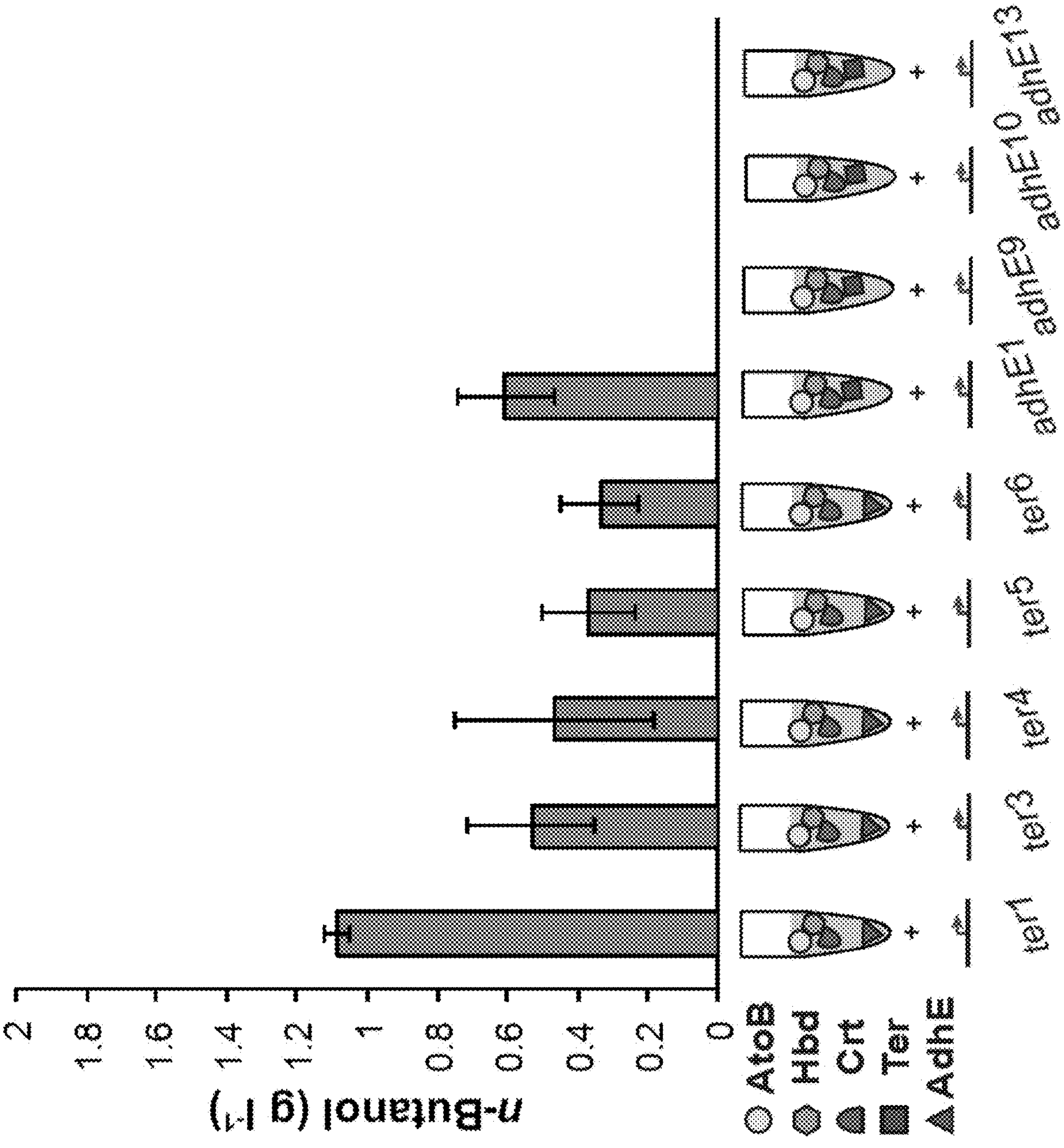
FIG. 15. Using CFPS-ME to rapidly screen pathway enzymes from linear DNA templates. Linear DNA of each enzyme variants were created with the regulatory elements from pJL1 and with a randomized −0.20 bp on each end and used as DNA template in each CFPS reaction. CFPS of each enzyme variant (Ter and AdhE) was used to activate n-butanol production in crude lysate mixtures containing AtoB (EC), Hbd2 (CB), Crt1 (CA), and AdhE1 (CA) overexpressed or AtoB (EC), Hbd2 (CB), Crt1 (CA), and Ter1 (TD) overexpressed, respectively. All error bars represent 1 s.d. with n≥3.

Having demonstrated the ability to explore enzyme homologs using CFPS-ME, we then set out to demonstrate the potential for using linear DNA templates instead of plasmids. Using linear DNA molecules, i.e. PCR products, would expedite the process since the entire process could be done without cells and we could avoid laborious cloning steps. As a model system, we first repeated the experiments presented in FIG. 6 with linear templates and observed that the linear DNA templates can successfully be expressed to complete the n-butanol biosynthesis pathway (FIG. 15). Next, we chose to screen multifunctional enzymes that to our knowledge have never before used for n-butanol production. We selected four enzymes with proposed Hbd and Crt functionalities that were identified by NCBI-BLAST searches. By preparing reactions with three different enzyme mixtures (mixed extracts with overexpressed enzymes prior to lysis) (1) without Hbd, (2) without Crt, and (3) without Hbd and Crt, we could characterize each enzyme variant by their ability to perform each enzymatic function. We discovered that each of these enzymes could activate n-butanol synthesis, and the proposed Hbdcrt6 from *Sulfolobus acidocaldarius* only had Hbd functionality (FIG. 6B). The ability to use linear DNA templates for CFPS-ME makes possible the ability to rapidly screen individual and sets of enzymes completely in vitro. Here, we used this approach to parse out individual functionalities of multi-functional enzymes.

D. Discussion

In this study, we developed a new cell-free framework for prototyping biosynthetic pathways and screening enzymes. In one scenario, we overexpress individual pathway components in cells, lyse these cells, and mix and match lysates in cell-free cocktails to study biochemical pathway performance. In a distinct thrust from typical in vitro systems, our approach allows us to study heterologous pathways in the context of native metabolism. In another scenario, we bypass in vivo expression altogether by using CFPS to enrich lysates with different enzymes for combinatorial assembly of different pathways. The combination of CFPS to express homologs of individual biosynthetic enzymes for studying pathway performance is also a distinction of our workflow. In addition, the use of linear PCR templates, which could be improved by DNA stability techniques (e.g., the addition of purified GamS protein)[30], allows us to avoid in vivo cloning steps altogether. Our CFPS-ME approach should therefore be faster than conventional approaches to select enzymes and pathway designs in cells (hours instead of days/weeks), and enables parallelized pathway construction of combinatorial designs to accelerate DBT cycles.

A key conceptual innovation of our work is that the DBT unit can be cell-free lysates rather than genetic constructs. Engineering large biosynthetic systems composed of many genes in microbes remains challenging[27]. One of the many obstacles is simply how many different genetic designs with beneficial chances are feasible to make. Cell-free systems have already been shown to screen genetic designs to improve enzyme performance at a rapid rate[51]. Our CFPS-ME framework should allow researchers to study more designs than previously possible by rapidly prototyping enzyme performance in vitro before putting designs into a host. As an example, a six-step biosynthetic pathway testing 5 homologs for each enzymatic step would require testing of 15,625 pathway combinations. While this set of combinations exceeds typical pipelines pursued in cells today, our CFPS-ME system could leverage robotic or automated liquid-handling systems to access such design space.

Figure 16:
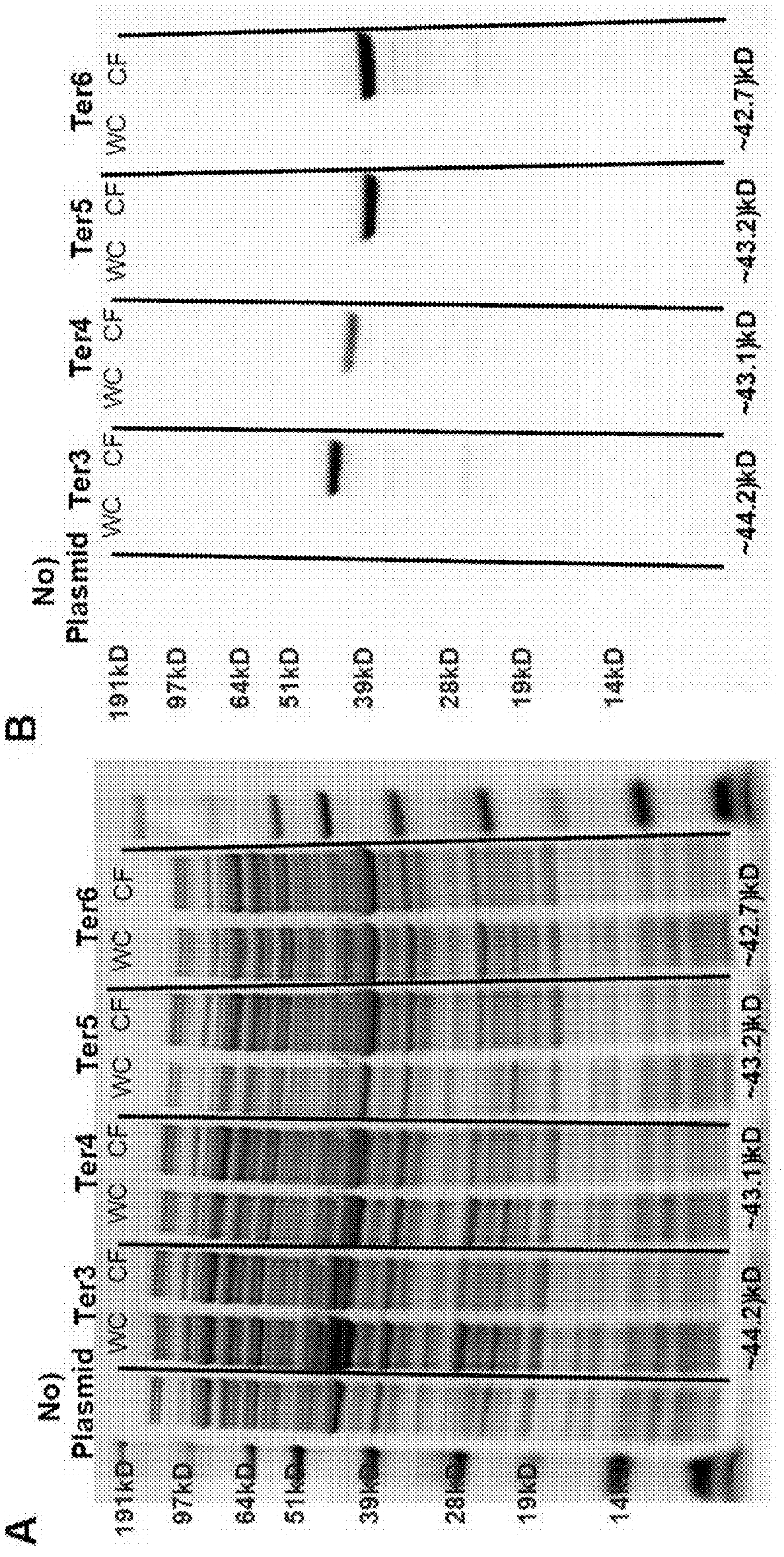
FIG. 16. Expression of Ter homologs in cells versus cell-free. SDS-PAGE was run on samples expressing the Ter homologs screened in FIG. 6. The first lane is the SeeBlue Plus2 Pre-stained standard. The second lane is a no plasmid (negative) control in BL21(DE3). For each homolog, the WC lane is a whole cell sample taken 4 hours after induction, and the CF lane is a cell-free protein synthesis sample taken after 3 hours of expression. (A) Coomassie-stained gel. While expression of Ter5 in the WC lane in an unoptimized (generic RBS) single attempt is unobservable, the other Ter enzymes are expressed, which confirms that our approach holds promise for identifying good enzymes that can be expressed in cells. (B) An autoradiogram of the same gel showing that each enzyme is expressed in vitro. As the in vivo expression did not incorporate radioactive leucine, bands are not expected in the WC lanes in panel B.

The goal of this manuscript was to provide a new approach to building biosynthetic pathways in a modular fashion in vitro. Now achieved, we plan to optimize a large-scale fermentation process with the CFPS-ME approach in the future. Towards this goal, we additionally carried out experiments to show that protein expression in the cell-free system translates to the in vivo system. Specifically, we took all Ter homologs screened in vitro by CFPS-ME (FIG. 6) and expressed them in whole cells in vivo. All but one of the Ter homolog proteins can be expressed in cells on a first pass (as determined by SDS-page expression, FIG. 16). These data show that protein expression in the cell-free system can translate to the in vivo system. Thus our approach holds promise for identifying good enzymes that can be expressed in cells, following a body of work that uses in vitro enzyme assays to identify enzymes with the best-performing biochemical characteristics for desired metabolic transformations prior to putting them into a host. For example, Liao and colleagues showed that in vitro reconstitution could be used to construct the non-oxidative glycolytic pathway prior to in vivo expression[52], and Zhu et al. reconstituted the mevalonate pathway in vitro to study pathway kinetics before using the pathway in vivo for the production of farnesene[53]

Figure 17:
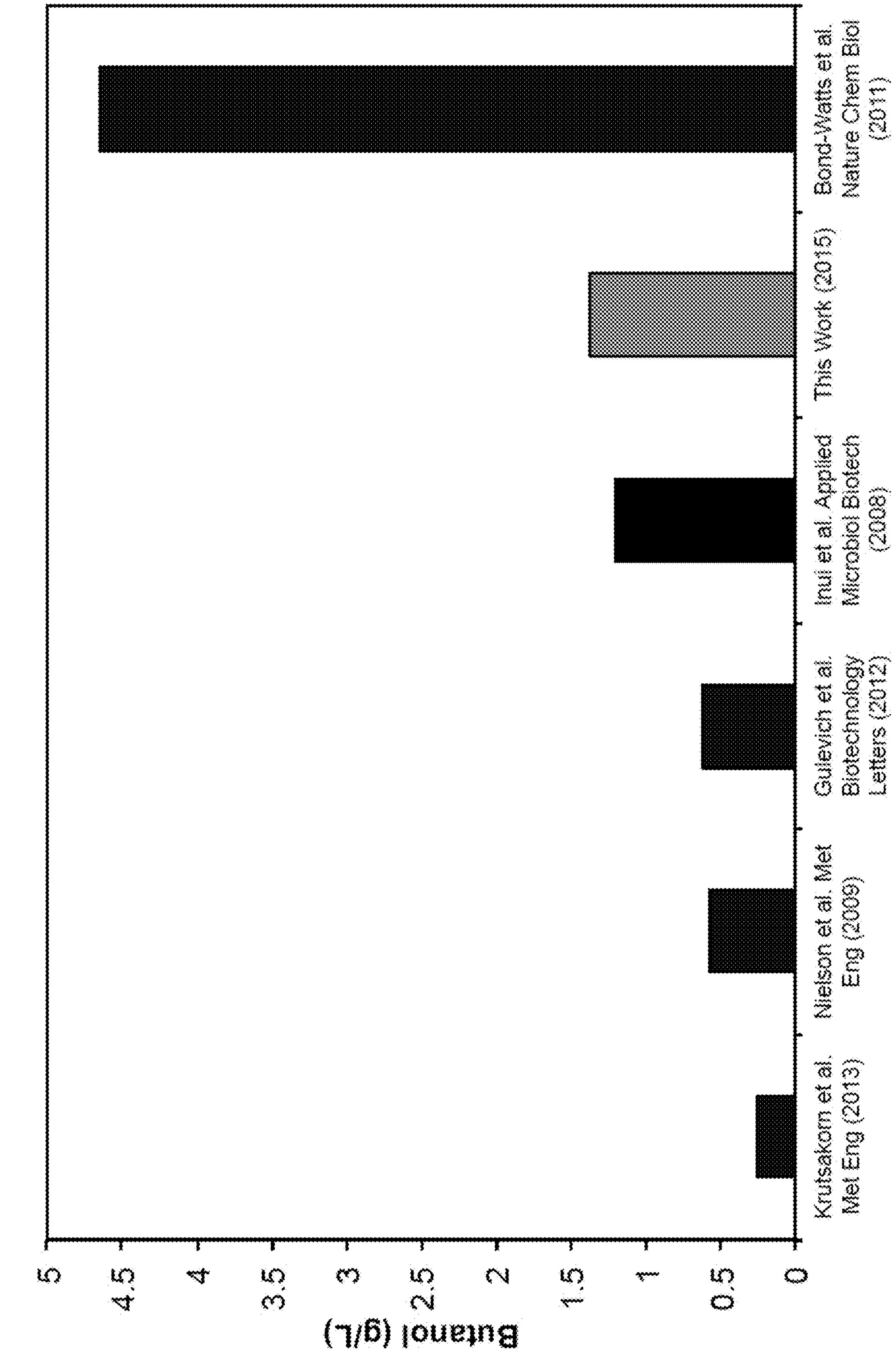
FIG. 17. Comparison of n-butanol production in genomically unmodified hosts. Final titers (g/L) of n-butanol are reported from recent studies using genomically unmodified host strains. The Krustakorn et al. 2013 study is the only other in vitro n-butanol production system (uses purified enzymes). The highest titer from this study is reported in orange.
Figure 18:
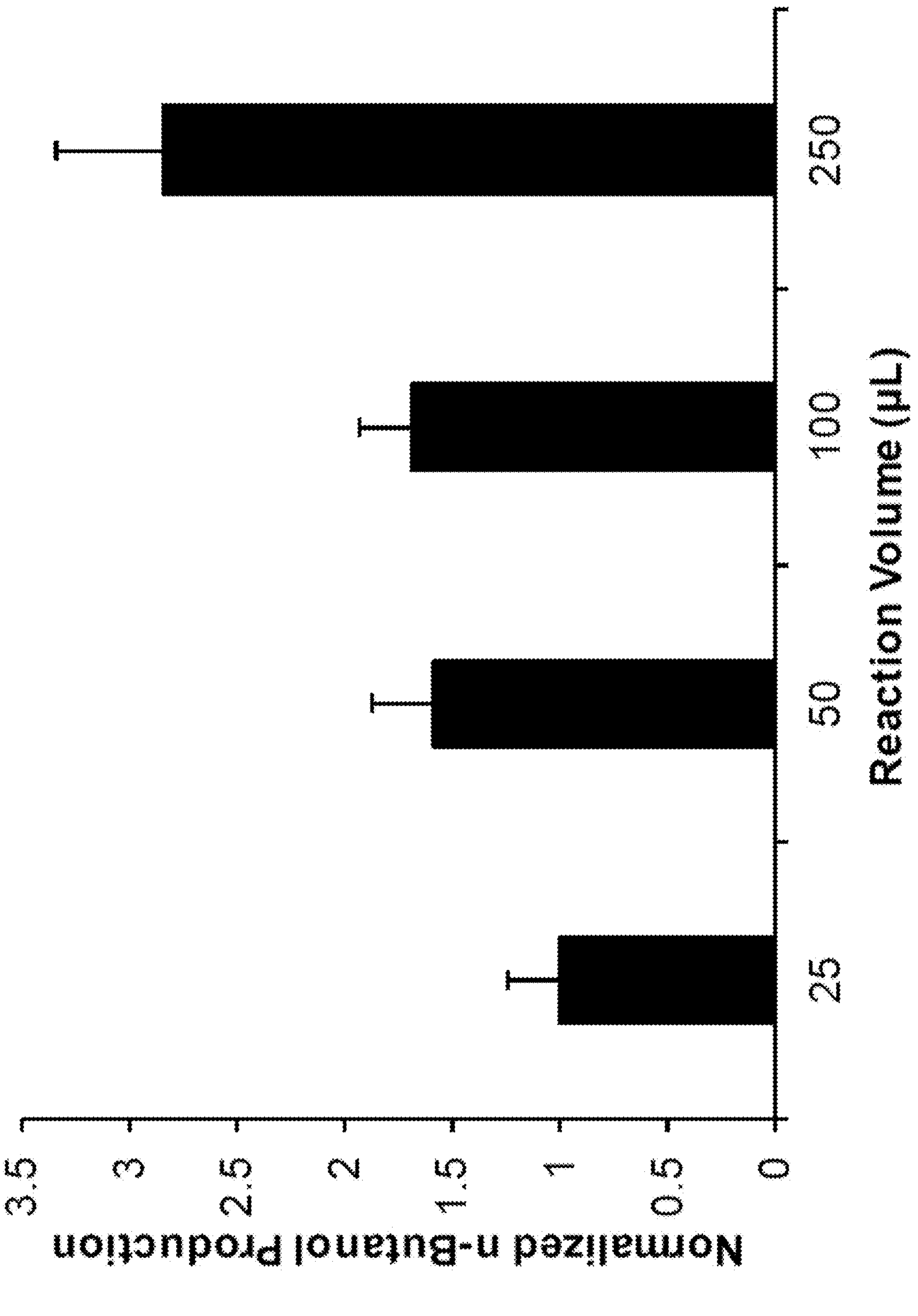
FIG. 18. Scale-up of CFPS-ME reactions. CFPS reactions were run in BL21(DE3) extract containing no overexpressed proteins in 1.5 mL Eppendorf tubes. DNA plasmids encoding each heterologous enzyme were added in equal ratios with pJL1-adhE1 representing 70% of the total DNA. CFPS reagents were added and incubated at 30° C. for 3 h. Glucose, NAD+, and CoA were added, and samples were further incubated at 30° C. for 24 h. The total reaction volumes are listed on the x-axis with the data normalized to 25 μL reactions. Increasing the reaction volume improved overall butanol yields. All error bars represent 1 s.d. with n≥3.

Our cell-free approach mimics the intracellular environment of *E. coli*, where endogenous glycolytic enzymes from the cell extract convert glucose to AcCoA. Thus, our platform enables many different biosynthetic pathways to be studied in the context of central metabolism with enhanced control inherent to in vitro systems. Here, we were able to increase n-butanol production by ~200% of our initial starting conditions (up to ~1.5 g $l^{-1}$) by simply testing the performance of different enzymes sets and adjusting the physicochemical environment. While it is be difficult to compare in a normalized fashion the in vitro process to the in vivo process, our results (given as final measured concentration) are higher than some published reports of n-butanol production in comparable genomically unmodified hosts (FIG. 17)[37,54-56]. However, Bond-Watts et al. notably reported titers of 4.6 g $l^{-1}$ in a genomically unmodified host by selecting a particular set of synergistic enzymes and taking advantage of their chemistries[18]. Given the reasonable yields, we were curious as to how the CFPS-ME reactions would perform at increased scale. We thus performed additional experiments of increasing size reactions to give confidence in our quantitative yields. Specifically, the reaction volume of CFPS-ME reactions was scaled from 25 to 250 μL, an order of magnitude increase (FIG. 18). Our data shows that these reactions are scalable and are consistent with several previous works showing the ability of cell-free systems to scale linearly[36,57-60].

Figure 19:
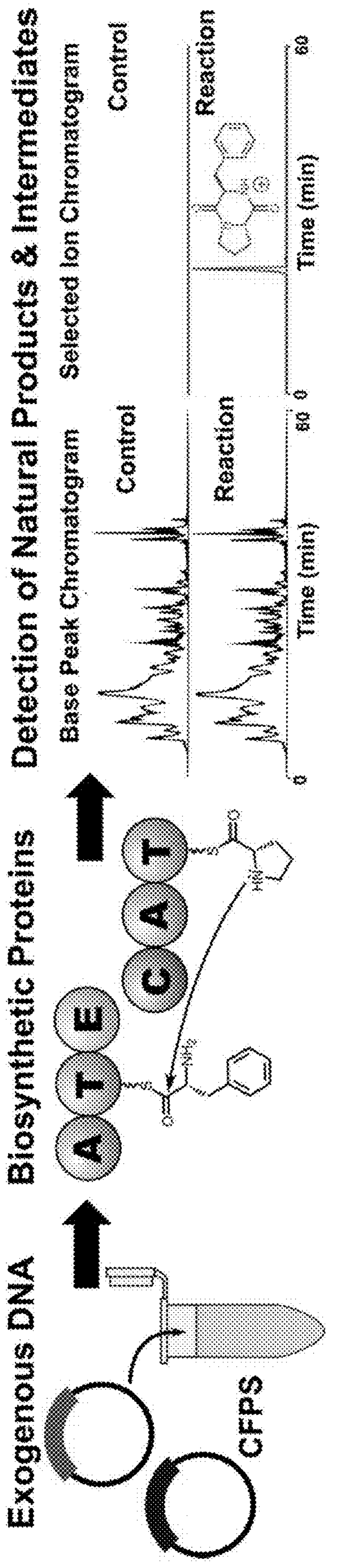
FIG. 19. Overview of a system for cell-free production of natural products via nonribosomal peptide biosynthesis by using cell-free protein synthesis driven metabolic engineering. From left to right, exogenous DNA is used as the input information for the production of biosynthetic enzymes. In the center, nonribosomal peptide synthetase proteins function in concert to select substrates and catalyze the formation of peptide bonds, ultimately resulting in the production of a 2,5-diketopiperazine. Right panel, detection of a D-Phe-L-Pro diketopiperazine (DKP) natural product by LC-MS as the result of in situ production of biosynthesis proteins.
Figure 20:
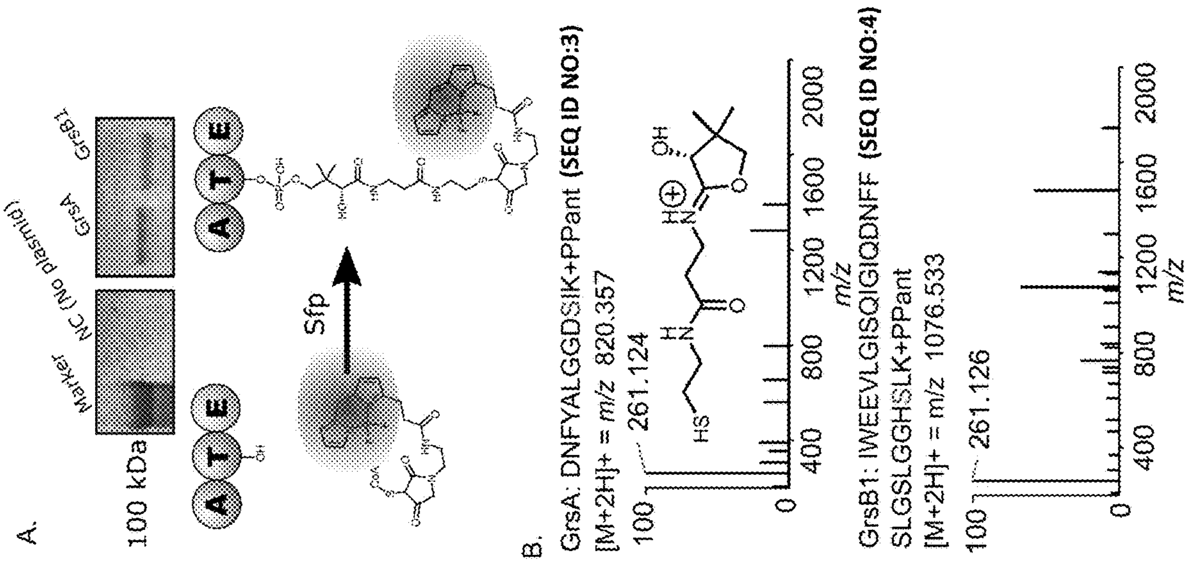
FIG. 20. Experiments showing that GrsA and GrsB1 are present in their active (holo) forms. Panel A shows the fluorescent labeling of GrsA and GrsB1 on the thiolation domain active sites with a conjugated BODIPY-CoA fluorophore. Panel B top shows the $MS^2$ spectrum resulting from the fragmentation of a precursor peptide containing the GrsA phosphopantetheine modification (SEQ ID NO:3). Panel B bottom shows the $MS^2$ spectrum for the corresponding GrsB1 T-domain peptide (SEQ ID NO:4), indicating the mass of the observed pantetheine-derived ion.
Figure 21:
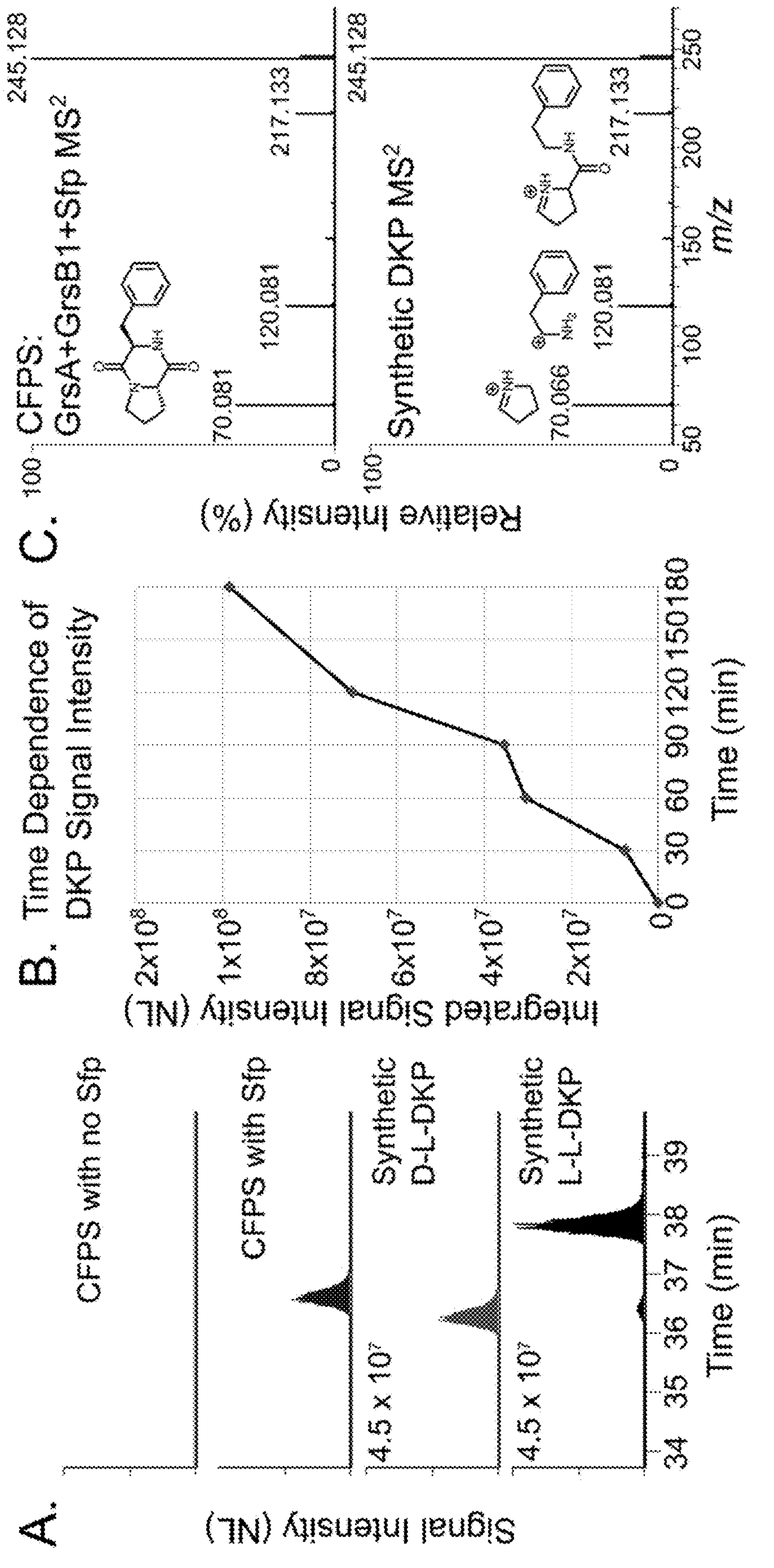
FIG. 21. Detection of D-Phe-L-Pro DKP by LC-MS/MS and comparison to synthetically prepared DKP. A) Retention time comparison of D-L, L-L and CFPS-produced DKP to determine the stereochemistry of the DKP produced by CFPS. This panel also shows that SFr is required for DKP production. B) Time dependent increase in m/z 245.128 signal after Sfp is added to the CFPS reaction. Data points are the average of two technical replicates. C) Comparison of the fragmentation pattern of the CFPS-produced (top) and synthetically prepared DKP (bottom). The spectrum at the bottom of panel C is annotated with predicted fragment ion structures.

Looking forward, specialty chemicals, natural products, and materials offer an extremely diverse set of compounds with a seemingly infinite set of structures and bioactivities. For example, we have applied our approach to reconstruct nonribosomal peptide biosynthesis directly from DNA (FIG. 19). Specifically, we utilized the proteins involved in the first steps of gramicidin S biogenesis as a model to show the potential for making and prospecting natural products with our approach (FIGS. 20 and 21). Our CFPS-ME approach offers a new discovery pipeline to leverage advances in DNA sequencing and DNA synthesis to optimize biosynthetic pathways, discover new enzymes, and test new hypotheses. Because it is an open system, cell-free reactors can be readily interrogated for intermediate product formation, such as by the on-line, high speed LC/MS approaches used by Panke and colleagues for optimization of glycolysis in cell-free extracts[61]. Cell-free systems in tandem with high-end metabolomics could offer a high degree of flexibility to model the kinetics and stability of individual enzymes, measure metabolite fluxes in multistep pathways, and experimentally isolate many other parameters confounded in living organisms. This has potential to speed up metabolic engineering DBT cycles.

E. References for Example 1

1. Bornscheuer, U. T. et al. Engineering the third wave of biocatalysis. Nature 485, 185-194, doi: 10.1038/nature11117 (2012).
2. Fritz, B. R., Timmerman, L. E., Daringer, N. M., Leonard, J. N. & Jewett, M. C. Biology by design: from top to bottom and back. Journal of biomedicine & biotechnology 2010, 232016, doi:10.1155/2010/232016 (2010).
3. Curran, K. A. & Alper, H. S. Expanding the chemical palate of cells by combining systems biology and metabolic engineering. Metabolic engineering 14, 289-297, doi:10.1016/j.ymben.2012.04.006 (2012).
4. Rollié, S., Mangold, M. & Sundmacher, K. Designing biological systems: Systems Engineering meets Synthetic Biology. Chemical Engineering Science 69, 1-29, doi:10.1016/j.ces.2011.10.068 (2012).
5. Erickson, B., Nelson & Winters, P. Perspective on opportunities in industrial biotechnology in renewable chemicals. Biotechnology journal 7, 176-185, doi: 10.1002/biot.201100069 (2012).
6. Nielsen, J. et al. Engineering synergy in biotechnology. Nature chemical biology 10, 319-322, doi:10.1038/nchembio.1519 (2014).
7. Demain, A. L. Importance of microbial natural products and the need to revitalize their discovery. Journal of industrial microbiology & biotechnology 41, 185-201, doi:10.1007/s10295-013-1325-z (2014).
8. Harvey, A. L., Edrada-Ebel, R. & Quinn, R. J. The re-emergence of natural products for drug discovery in the genomics era. Nature reviews. Drug discovery 14, 111-129, doi: 10.1038/nrd4510 (2015).
9. Kern, A., Tilley, E., Hunter, I. S., Legisa, M. & Glieder, A. Engineering primary metabolic pathways of industrial micro-organisms. Journal of biotechnology 129, 6-29, doi:10.1016/j.jbiotec.2006.11.021 (2007).
10. Nielsen, J. Metabolic engineering. Applied Microbiology and Biotechnology 55, 263-283, doi:10.1007/s002530000511 (2001).
11. Hodgman, C. E. & Jewett, M. C. Cell-free synthetic biology: thinking outside the cell. Metabolic engineering 14, 261-269, doi:10.1016/j.ymben.2011.09.002 (2012).
12. Kwok, R. Five hard truths for synthetic biology. Nature 463, 288-290, doi:10.1038/463288a (2010).
13. Green, E. M. Fermentative production of butanol—the industrial perspective. Current opinion in biotechnology 22, 337-343, doi:10.1016/j.copbio.2011.02.004 (2011).
14. Lutke-Eversloh, T. & Bahl, H. Metabolic engineering of *Clostridium acetobutylicum*: recent advances to improve butanol production. Current opinion in biotechnology 22, 634-647, doi:10.1016/j.copbio.2011.01.011 (2011).
15. Atsumi, S. et al. Metabolic engineering of *Escherichia coli* for 1-butanol production. Metabolic engineering 10, 305-311, doi:10.1016/j.ymben.2007.08.003 (2008).
16. Steen, E. J. et al. Metabolic engineering of *Saccharomyces cerevisiae* for the production of n-butanol. Microbial cell factories 7, 36, doi:10.1186/1475-2859-7-36 (2008).
17. Shen, C. R. et al. Driving forces enable high-titer anaerobic 1-butanol synthesis in *Escherichia coli*. Applied and environmental microbiology 77, 2905-2915, doi:10.1128/AEM.03034-10 (2011).
18. Bond-Watts, B. B., Bellerose, R. J. & Chang, M. C. Enzyme mechanism as a kinetic control element for designing synthetic biofuel pathways. Nature chemical biology 7, 222-227, doi:10.1038/nchembio.537 (2011).
19. Dong, H. et al. Engineering *Escherichia coli* Cell Factories for n-Butanol Production. Advances in biochemical engineering/biotechnology, doi:10.1007/10_2015_306 (2015).

20. Keasling, J. D. Manufacturing molecules through metabolic engineering. Science 330, 1355-1358, doi:10.1126/science.1193990 (2010).

21 Keasling, J. D. Synthetic biology and the development of tools for metabolic engineering. Metabolic engineering 14, 189-195, doi:10.1016/j.ymben.2012.01.004 (2012).

22. Jensen, M. K. & Keasling, J. D. Recent applications of synthetic biology tools for yeast metabolic engineering. FEMS Yeast Res, doi: 10.1111/1567-1364.12185 (2014).

23. Dai, Z. & Nielsen, J. Advancing metabolic engineering through systems biology of industrial microorganisms. Current opinion in biotechnology 36, 8-15, doi:10.1016/j.copbio.2015.08.006 (2015).

24. Lee, S. Y. & Kim, H. U. Systems strategies for developing industrial microbial strains. Nat Biotechnol 33, 1061-1072, doi:10.1038/nbt.3365 (2015).

25. Lee, J. W. et al. Systems metabolic engineering of microorganisms for natural and non-natural chemicals. Nature chemical biology 8, 536-546, doi:10.1038/nchembio.970 (2012).

26. Yadav, V. G., De Mey, M., Giaw Lim, C., Kumaran Ajikumar, P. & Stephanopoulos, G. The future of metabolic engineering and synthetic biology: Towards a systematic practice. Metabolic engineering 14, 233-241, doi: 10.1016/j.ymben.2012.02.001 (2012).

27. Smanski, M. J. et al. Functional optimization of gene clusters by combinatorial design and assembly. Nat Biotechnol 32, 1241-1249, doi:10.1038/nbt.3063 (2014).

28. Boyle, P. M. & Silver, P. A. Parts plus pipes: synthetic biology approaches to metabolic engineering. Metabolic engineering 14, 223-232, doi:10.1016/j.ymben.2011.10.003 (2012).

29. Carlson, E. D., Gan, R., Hodgman, C. E. & Jewett, M. C. Cell-free protein synthesis: applications come of age. Biotechnology advances 30, 1185-1194, doi:10.1016/j.biotechadv.2011.09.016 (2012).

30. Sun, Z. Z., Yeung, E., Hayes, C. A., Noireaux, V. & Murray, R. M. Linear DNA for rapid prototyping of synthetic biological circuits in an *Escherichia coli* based TX-TL cell-free system. ACS synthetic biology 3, 387-397, doi:10.1021/sb400131a (2014).

31. Siegal-Gaskins, D., Tuza, Z. A., Kim, J., Noireaux, V. & Murray, R. M. Gene circuit performance characterization and resource usage in a cell-free "breadboard". ACS synthetic biology 3, 416-425, doi:10.1021/sb400203p (2014).

32. Dudley, Q. M., Karim, A. S. & Jewett, M. C. Cell-free metabolic engineering: biomanufacturing beyond the cell. Biotechnology journal 10, 69-82, doi:10.1002/biot.201400330 (2015).

33. Zhang, Y. H. Production of biofuels and biochemicals by in vitro synthetic biosystems: Opportunities and challenges. Biotechnology advances 33, 1467-1483, doi: 10.1016/j.biotechadv.2014.10.009 (2015).

34. You, C. & Zhang, Y. H. Cell-free biosystems for biomanufacturing. Advances in biochemical engineering/biotechnology 131, 89-119, doi: 10.1007/10_2012_159 (2013).

35. Guterl, J. K. et al. Cell-free metabolic engineering: production of chemicals by minimized reaction cascades. ChemSusChem 5, 2165-2172, doi:10.1002/cssc.201200365 (2012).

36. Kay, J. E. & Jewett, M. C. Lysate of engineered *Escherichia coli* supports high-level conversion of glucose to 2,3-butanediol. Metabolic engineering 32, 133-142, doi:10.1016/j.ymben.2015.09.015 (2015).

37. Krutsakorn, B. et al. In vitro production of n-butanol from glucose. Metabolic engineering 20, 84-91, doi:10.1016/j.ymben.2013.09.006 (2013).

38. Ninh, P. H., Honda, K., Sakai, T., Okano, K. & Ohtake, H. Assembly and multiple gene expression of thermophilic enzymes in *Escherichia coli* for in vitro metabolic engineering. Biotechnol Bioeng 112, 189-196, doi:10.1002/bit.25338 (2015).

39. Welch, P. & Scopes, R. K. Studies on cell-free metabolism: Ethanol production by a yeast glycolytic system reconstituted from purified enzymes. Journal of biotechnology 2, 257-273, doi:10.1016/0168-1656(85)90029-x (1985).

40. Swartz, J. R. Transforming biochemical engineering with cell-free biology. AIChE Journal 58, 5-13, doi:10.1002/aic.13701 (2012).

41. Dodevski, I., Markou, G. C. & Sarkar, C. A. Conceptual and methodological advances in cell-free directed evolution. Curr Opin Struct Biol 33, 1-7, doi:10.1016/j.sbi.2015.04.008 (2015).

42. Henrich, E., Hein, C., Dotsch, V. & Bernhard, F. Membrane protein production in *Escherichia coli* cell-free lysates. FEBS Lett 589, 1713-1722, doi: 10.1016/j.febslet.2015.04.045 (2015).

43. Zemella, A., Thoring, L., Hoffmeister, C. & Kubick, S. Cell-Free Protein Synthesis: Pros and Cons of Prokaryotic and Eukaryotic Systems. Chembiochem 16, 2420-2431, doi:10.1002/cbic.201500340 (2015).

44. Noireaux, V., Bar-Ziv, R. & Libchaber, A. Principles of cell-free genetic circuit assembly. Proc Natl Acad Sci USA 100, 12672-12677, doi: 10.1073/pnas.2135496100 (2003).

45. Goshima, N. et al. Human protein factory for converting the transcriptome into an in vitro-expressed proteome. Nature Methods 5, 1011-1017, doi: 10.1038/nmeth. 1273 (2008).

46. Jewett, M. C., Calhoun, K. A., Voloshin, A., Wuu, J. J. & Swartz, J. R. An integrated cell-free metabolic platform for protein production and synthetic biology. Mol Syst Biol 4, 220, doi:10.1038/msb.2008.57 (2008).

47. Jewett, M. C. & Swartz, J. R. Mimicking the *Escherichia coli* cytoplasmic environment activates long-lived and efficient cell-free protein synthesis. Biotechnol Bioeng 86, 19-26, doi:10.1002/bit.20026 (2004).

48. Korman, T. P. et al. A synthetic biochemistry system for the in vitro production of isoprene from glycolysis intermediates. Protein Sci 23, 576-585, doi:10.1002/pro.2436 (2014).

49. Record, M. T., Courtenay, E. S., Cayley, S. & Guttman, H. J. Biophysical compensation mechanisms buffering *E. coli* protein-nucleic acid interactions against changing environments. Trends in Biochemical Sciences 23, 190-194, doi:10.1016/s0968-0004(98)01207-9 (1998).

50. Jewett, M. C., Fritz, B. R., Timmerman, L. E. & Church, G. M. In vitro integration of ribosomal RNA synthesis, ribosome assembly, and translation. Mol Syst Biol 9, 678, doi:10.1038/msb.2013.31 (2013).

51. Daugherty, A. B., Govindarajan, S. & Lutz, S. Improved biocatalysts from a synthetic circular permutation library of the flavin-dependent oxidoreductase old yellow enzyme. J Am Chem Soc 135, 14425-14432, doi:10.1021/ja4074886 (2013).

52. Bogorad, I. W., Lin, T. S. & Liao, J. C. Synthetic non-oxidative glycolysis enables complete carbon conservation. Nature 502, 693-697, doi:10.1038/nature12575 (2013).

53. Zhu, F. et al. In vitro reconstitution of mevalonate pathway and targeted engineering of farnesene overproduction in *Escherichia coli*. Biotechnol Bioeng 111, 1396-1405, doi:10.1002/bit.25198 (2014).

54. Gulevich, A. Y., Skorokhodova, A. Y., Sukhozhenko, A. V., Shakulov, R. S. & Debabov, V. G. Metabolic engineering of *Escherichia coli* for 1-butanol biosynthesis through the inverted aerobic fatty acid beta-oxidation pathway. Biotechnol Lett 34, 463-469, doi:10.1007/s10529-011-0797-z (2012).

55. Nielsen, D. R. et al. Engineering alternative butanol production platforms in heterologous bacteria. Metabolic engineering 11, 262-273, doi:10.1016/j.ymben.2009.05.003 (2009).

56. Inui, M. et al. Expression of *Clostridium acetobutylicum* butanol synthetic genes in *Escherichia coli*. Appl Microbiol Biotechnol 77, 1305-1316, doi:10.1007/s00253-007-1257-5 (2008).

57. Yin, G. et al. Aglycosylated antibodies and antibody fragments produced in a scalable in vitro transcription-translation system. MAbs 4, 217-225, doi:10.4161/mabs.4.2.19202 (2012).

58. Zawada, J. F. et al. Microscale to manufacturing scale-up of cell-free cytokine production—a new approach for shortening protein production development timelines. Biotechnol Bioeng 108, 1570-1578, doi:10.1002/bit.23103 (2011).

59. Voloshin, A. M. & Swartz, J. R. Efficient and scalable method for scaling up cell free protein synthesis in batch mode. Biotechnol Bioeng 91, 516-521, doi:10.1002/bit.20528 (2005).

60. Hong, S. H. et al. Improving cell-free protein synthesis through genome engineering of *Escherichia coli* lacking release factor 1. Chembiochem 16, 844-853, doi: 10.1002/cbic.201402708 (2015).

61. Bujara, M., Schumperli, M., Pellaux, R., Heinemann, M. & Panke, S. Optimization of a blueprint for in vitro glycolysis by metabolic real-time analysis. Nat Chem Biol 7, 271-277, doi:10.1038/nchembio.541 (2011).

F. Tables for Example 1

TABLE 1

Strains and Plasmids.

| Name | Genotype/relevant characteristics | Source |
|---|---|---|
| Strains | | |
| NEB Turbo ™ | F' proA+ B+ lacIq ΔlacZM15/fhuA2 Δ(lac-proAB) glnV galK16 galE15 R(zgb-210::Tn10)TetS endA1 thi-1 Δ(hsdS-mcrB)5 | New England Biolabs |
| BL21 (DE3) | fhuA2 [lon] ompT gal (λ DE3) [dcm] ΔhsdS λ DE3 = λ sBamHIo ΔEcoRI-B int::(lacI::PlacUV5::T7 gene1) i21 Δnin5 | New England Biolabs |
| Strains & Plasmids | | |
| BL21 (DE3) pETBCS-rbsU-atoB | Strain used for protein production and extract preparation of AtoB | This Study |
| BL21 (DE3) pETBCS-rbsU-hbd1 | Strain used for protein production and extract preparation of Hbd1 | This Study |
| BL21 (DE3) pETBCS-rbsU-hbd2 | Strain used for protein production and extract preparation of Hbd2 | This Study |
| BL21 (DE3) pETBCS-rbsU-crt1 | Strain used for protein production and extract preparation of Crt1 | This Study |
| BL21 (DE3) pETBCS-rbsU-crt2 | Strain used for protein production and extract preparation of Crt2 | This Study |
| BL21 (DE3) pETBCS-rbsU-ter1 | Strain used for protein production and extract preparation of Ter1 | This Study |
| BL21 (DE3) pETBCS-rbsU-adhE1 | Strain used for protein production and extract preparation of AdhE1 | This Study |
| BL21 (DE3) pETBCS-rbsU-adhE2 | Strain used for protein production and extract preparation of AdhE2 | This Study |
| pJL1-atoB | Plasmid used for CFPS containing atoB | This Study |
| pJL1-hbd2 | Plasmid used for CFPS containing hbd2 | This Study |
| pJL1-crt1 | Plasmid used for CFPS containing crt1 | This Study |
| pJL1-ter1 | Plasmid used for CFPS containing ter1 | This Study |
| pJL1-adhE1 | Plasmid used for CFPS containing adhE1 | This Study |
| pJL1-hbdcrt2 | Plasmid used for CFPS containing hbdcrt2 | This Study |
| pJL1-hbdcrt3 | Plasmid used for CFPS containing hbdcrt3 | This Study |
| pJL1-hbdcrt4 | Plasmid used for CFPS containing hbdcrt4 | This Study |
| pJL1-hbdcrt6 | Plasmid used for CFPS containing hbdcrt6 | This Study |
| pJL1-ter3 | Plasmid used for CFPS containing ter3 | This Study |
| pJL1-ter4 | Plasmid used for CFPS containing ter4 | This Study |
| pJL1-ter5 | Plasmid used for CFPS containing ter5 | This Study |
| pJL1-ter6 | Plasmid used for CFPS containing ter6 | This Study |
| pJL1-adhE9 | Plasmid used for CFPS containing adhE9 | This Study |
| pJL1-adhE10 | Plasmid used for CFPS containing adhE10 | This Study |
| pJL1-adhE13 | Plasmid used for CFPS containing adhE13 | This Study |

TABLE 2

| Genes and Enzymes. | | | |
|---|---|---|---|
| Gene/ Enzyme | Enyme Activity | Source Organism | Source Database |
| atoB | acetyl-CoA acetyltransferase/thiolase | *Escherichia coli* | GenBank |
| hbd1 | acyl-CoA dehydrogenase | *Clostridium Acetobutylicum* | GenBank |
| hbd2 | acyl-CoA dehydrogenase | *Clostridium beijerinckii* | GenBank |
| crt1 | acyl-CoA dehydrogenase | *Clostridium Acetobutylicum* | GenBank |
| crt2 | acyl-CoA dehydrogenase | *Pseudomonas putida* | GenBank |
| hbdcrt2 | 3-hydroxyacyl-CoA dehydrogenase | *Aeropyrum camini* | NCBI BLAST Search of ADHE2 protein from *C. acetobutyllicum* |
| hbdcrt3 | 3-hydroxyacyl-CoA dehydrogenase | *Pyrobaculum aerophilum* | NCBI BLAST Search of ADHE2 protein from *C. acetobutyllicum* |
| hbdcrt4 | 3-hydroxyacyl-CoA dehydrogenase | *Sulfolobus islandicus* | NCBI BLAST Search of ADHE2 protein from *C. acetobutyllicum* |
| hbdcrt5 | 3-hydroxyacyl-CoA dehydrogenase | *Vulcanisaeta distributa* | NCBI BLAST Search of TER protein from *T. denticola* |
| hbdcrt6 | 3-hydroxybutyryl-CoA dehydrogenase | *Sulfolobus acidocaldarius* | NCBI BLAST Search of TER protein from *T. denticola* |
| ter1 | trans-2-enoyl-CoA reductase | *Treponema denticola* | GenBank |
| ter3 | trans-2-enoyl-CoA reductase | *Fibrobacter succinogenes* | NCBI BLAST Search of TER protein from *T. denticola* |
| ter4 | trans-2-enoyl-CoA reductase | *Flavobacterium johnsoniae* | NCBI BLAST Search of TER protein from *T. denticola* |
| ter5 | trans-2-enoyl-CoA reductase | *Spirochaeta bajacaliforniensis* | NCBI BLAST Search of TER protein from *T. denticola* |
| ter6 | trans-2-enoyl-CoA reductase | *Cytophaga hutchinsonii* | NCBI BLAST Search of HBD-CRT protein from *M. sedula* |
| adhE1 | bifunctional acetaldehyde-CoA/alcohol dehydrogenase | *Clostridium acetobutylicum* | GenBank |
| adhE2 | bifunctional acetaldehyde-CoA/alcohol dehydrogenase | *Clostridium pasteurianum* | NCBI BLAST Search of HBD-CRT protein from *M. sedula* |
| adhE8 | bifunctional acetaldehyde-CoA/alcohol dehydrogenase | *Chitinivibrio alkaliphilus* | NCBI BLAST Search of HBD-CRT protein from *M. sedula* |
| adhE9 | bifunctional acetaldehyde-CoA/alcohol dehydrogenase | *Thermosynechococcus* sp. NK55a | NCBI BLAST Search of HBD-CRT protein from *M. sedula* |
| adhE10 | bifunctional acetaldehyde-CoA/alcohol dehydrogenase | *Providencia burhodogranariea* | NCBI BLAST Search of HBD-CRT protein from *M. sedula* |
| adhE13 | bifunctional acetaldehyde-CoA/alcohol dehydrogenase | *Serratia marcescens* | NCBI BLAST Search of HBD-CRT protein from *M. sedula* |

Example 2: Cell-Free Biosynthesis of the Nonribosomal Macrolactone Peptide Valinomycin

A. Abstract

Natural products are important because of their significant pharmaceutical properties such as antiviral, antimicrobial, and anticancer activity. Recent breakthroughs in DNA sequencing reveal that a great number of cryptic natural product biosynthetic gene clusters are encoded in microbial genomes, for example, those of *Streptomyces* species. However, it is still challenging to access compounds from these clusters because many source organisms are uncultivable or the genes are silent during laboratory cultivations. To address this challenge, here we construct an efficient cell-free platform for the rapid, in vitro total biosynthesis of the nonribosomal peptide valinomycin as a model. We achieve this goal in two ways. First, we used a cell-free protein synthesis (CFPS) system to express the entire valinomycin biosynthetic gene cluster (>19 kb) in a single-pot reaction, giving rise to approximately 37 tg/L of valinomycin after optimization. Second, we coupled CFPS with cell-free metabolic engineering system by mixing two enzyme-enriched cell lysates to perform a two-stage biosynthesis. This strategy improved valinomycin production ~5,000-fold to nearly 30 mg/L. We expect that cell-free biosynthetic systems will provide a new avenue to express, discover, and characterize natural product gene clusters of interest in vitro.

B. Introduction

Natural products originating from living organisms (e.g., microbes, plants, and animals) have complex chemical structures and exhibit diverse biological activities (1). Historically, natural products have served as a rich source for pharmaceuticals like antibiotics to treat human diseases (2). During the so-called 'Golden Era' of antibiotic discovery from the 1940s to 1960s, many notable antibiotics were discovered. However, declining rates of new antibiotic discovery and rising rates of re-discovery through conventional low-throughput fermentation and chemical/biological screening approaches have limited the field (3). As a result, the accelerating problem of antibiotic resistance is projected to soon threaten up to 10 million lives annually (4). This motivates the need for new approaches to discover new antibiotics and natural products for human health.

Several approaches are already emerging. In one approach, the data available to mine for new biosynthesis machinery is rapidly expanding. This expansion results from next-generation DNA sequencing and synthesis (5), improved bioinformatic tools for genome mining and prediction (6), high-throughput mass spectrometry for metabolite analysis (7), and CRISPR-based technology for activation of silent biosynthetic gene clusters (8). Unfortunately, the rate at which new biosynthetic pathways are identified greatly outpaces the capacity to characterize the small molecules for which production is encoded (9). Current approaches are constrained by limitations in cultivating natural product producing organisms in the laboratory. Moreover, establishing heterologous expression systems is difficult. While several heterologous hosts like *Escherichia coli* and *Saccharomyces cerevisiae* have been used for production and discovery of natural products (10-13), engineering these cells remains a time-consuming and laborious process that often requires design-build-test-learn iterations to obtain the optimal cell performance (14). In addition, yields of most compounds are still not satisfactory in heterologous hosts (11). Therefore, a new generation of heterologous expression systems for efficient, high-yielding production of bioactive molecules is highly desirable.

Recently, cell-free systems have emerged as a complementary platform for biomanufacturing (15-18), with potential for natural product biosynthesis. For example, in vitro reconstitution strategies based on purified enzymes (19) have elegantly demonstrated the biosynthesis of polyketides (PKs) (20), nonribosomal peptides (NRPs) (21), and PK/NRP hybrids (22). Yet despite its success, this strategy often suffers from laborious purification process and enzyme instability. To circumvent these shortcomings, we recently demonstrated the use of cell-free protein synthesis (CFPS) systems derived from crude cell lysates to synthesize a NRP molecule (diketopiperazine, DKP) by in vitro coexpression of two large nonribosomal peptide synthetases (NRPS), namely, GrsA (126 kDa) and GrsB1 (121 kDa, the first module of GrsB) (23). While this work represented the first step to apply crude extract-based CFPS to synthesize natural products, DKP is only a shunt product and not the final pathway biosynthesis product gramicidin S. Thus, to date, total biosynthesis of a natural product has not been shown with crude extract-based CFPS systems. Here, we aim to address this gap, using the nonribosomal peptide valinomycin as our model system.

Valinomycin is a 36-membered cyclododecadepsipeptide (see FIG. 22A for the chemical structure), which possesses a broad spectrum of bioactivities such as antifungal (24), antimicrobial (25), insecticidal (26), antiviral (27), and anticancer efficacy (28). Naturally, valinomycin is synthesized by several *Streptomyces* strains via the NRPS enzyme valinomycin synthetase (29-31). Valinomycin synthetase consists of two distinct large NRPSs (Vlm1 370 kDa and Vlm2 284 kDa), and each of them has two modules for the assembly of their dedicated substrates pyruvate, α-ketoisovalerate, and L-valine (FIG. 22A) (32). Our previous studies have achieved the heterologous biosynthesis of valinomycin in vivo by reconstitution of the NRPS genes (vlm1 and vlm2) in *E. coli* (32). The yield of valinomycin reached a milligram per liter level after a systematic bioprocess optimization (33, 34). In the valinomycin biosynthetic gene cluster, a discrete type II thioesterase (TEII) was also identified (29). TEII is a repairing enzyme that usually is associated with NRPS enzymes, playing a key role in regenerating the functionality of NRPS through hydrolysis of either misacylated thiol groups (35) or incorrectly loaded substrates on the thiolation (T) domains (FIG. 22B) (36). Notably, coexpression of the cognate protein TEII with Vlm1 and Vlm2 resulted in the highest production of valinomycin (13 mg/L) in *E. coli* (37), demonstrating the dedicated function of TEII in heterologous valinomycin biosynthesis.

Figure 22:
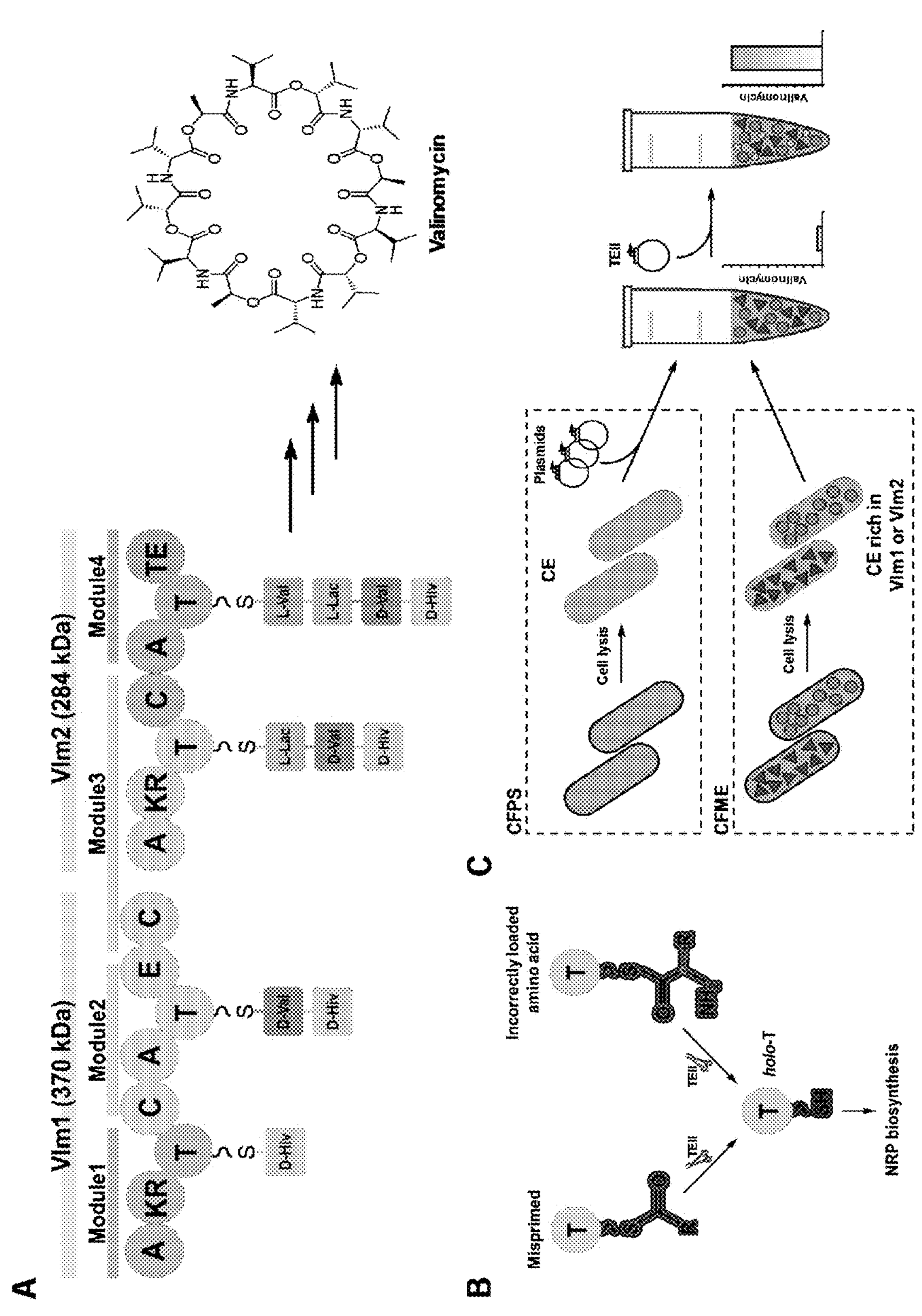
FIG. 22. Reconstitution of valinomycin biosynthetic pathway in vitro. (A) Valinomycin synthetase contains two distinct NRPS enzymes Vlm1 (374 kDa) and Vlm2 (284 kDa) that are composed of adenylation (A), ketoreductase (KR), thiolation (T), condensation (C), epimerase (E), and thioesterase (TE) domains. A domains select and activate three substrates (pyruvate, α-ketoisovalerate (α-Kiv), and L-valine (L-Val)). T domains are responsible for the translocation of the bound aminoacyl or peptidyl intermediate between adjacent catalytic positions. C domains catalyze the formation of peptide bond and elongate the peptide chain. The KR domain in Module 1 reduces α-Kiv to D-hydroxyisovalerate (D-Hiv). The E domain in Module 2 converts L-Val to D-valine (D-Val). The KR domain in Module 3 reduces pyruvate to L-lactate (L-Lac). The four modules of valinomycin synthetase are iteratively reused to assemble three tetradepsipeptide monomers, which are eventually oligomerized and macrolactonized to form the 36-membered cyclododecadepsipeptide valinomycin. (B) Regeneration of the functionality of T domains in NRPS catalyzed by type II thioesterase (TEII). (C) Cell-free biosynthesis of valinomycin with different strategies: cell-free protein synthesis (CFPS), cell-free metabolic engineering (CFME), and a coupled CFPS-MS approach. CE, cell extract.

In this work, we demonstrate that simple cell-free systems enable the total biosynthesis of a complex NRP valinomycin (FIG. 22C). We show this in two ways. First, we use an *E. coli*-based CFPS system to coexpress two enzymes Vlm1 (370 kDa) and Vlm2 (284 kDa) for valinomycin synthesis. Second, cell lysates are enriched with Vlm1 or Vlm2 by cellular expression and then the full metabolic pathway is assembled in vitro to enable valinomycin biosynthesis by mixing two enzyme-enriched cell lysates. In both strategies, TEII substantially improves valinomycin production. Taken together, our current work emphasizes three advancements. First, to our best knowledge, this is the first report to use CFPS for the coexpression of such large NRPS enzymes with catalytic activity. Second, in vitro total biosynthesis of valinomycin showcases the feasibility to produce other complex NRPs with cell-free systems. Third, fine tuning of cell-free reactions allows for enhanced production of target molecules. Looking forward, we envision that cell-free biosynthetic systems will provide a new avenue for the expression of complex natural product gene clusters (e.g., NRPs and PKs), enabling the rapid discovery and synthesis of novel natural products in vitro

C. Results

1. Cell-free synthesis of active Vlm1 and Vlm2 for valinomycin biosynthesis

Figure 23:
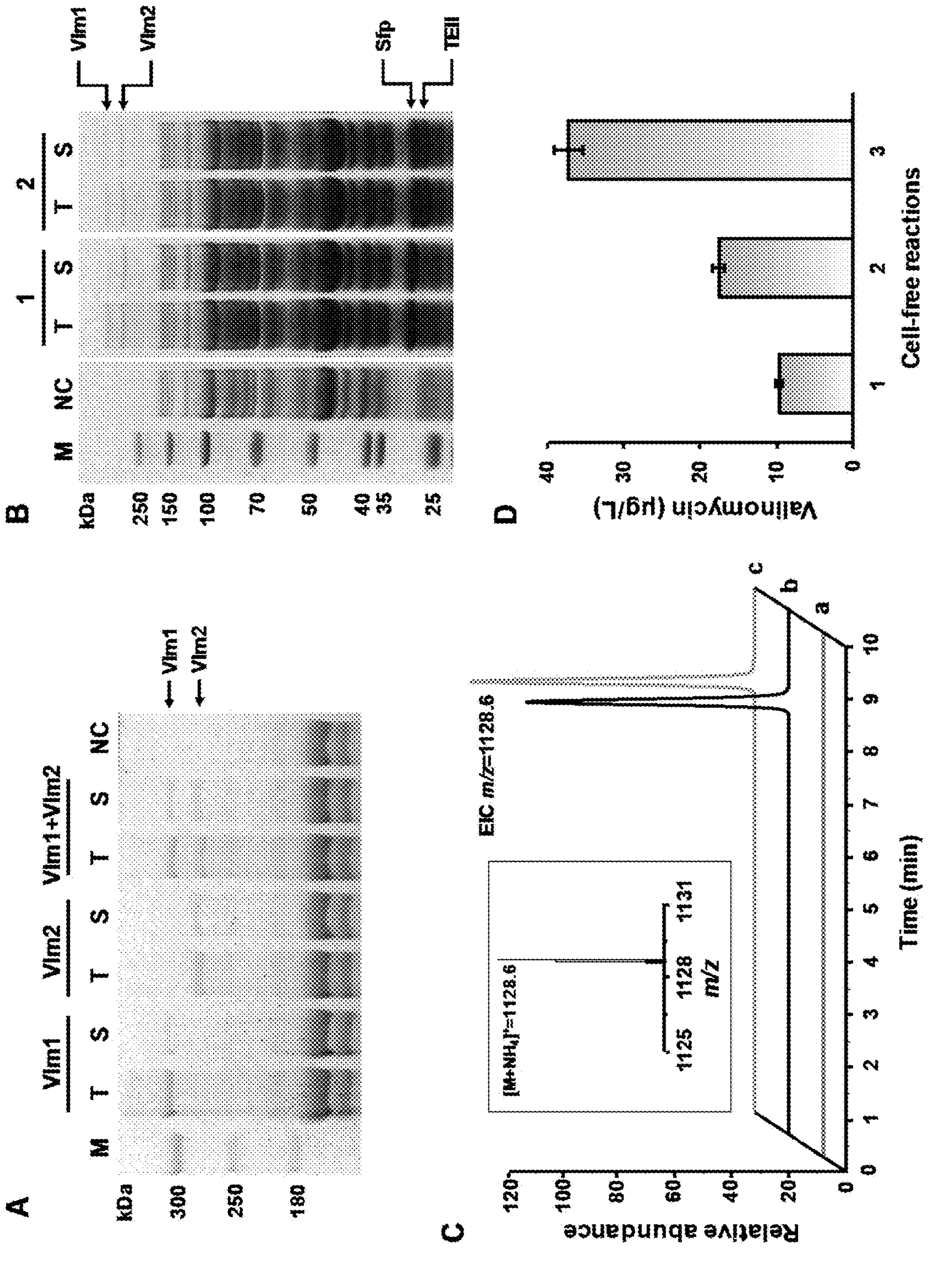
FIG. 23. In vitro biosynthesis of valinomycin using CFPS system. (A) SDS-PAGE (7.5% gel) analysis of Vlm1 and Vlm2 expressed individually or together. T, total protein. S, soluble protein. M, protein molecular weight marker. NC, negative control without plasmid in the reaction. (B) SDS-PAGE (4-12% gel) analysis of coexpressed proteins. 1, coexpression of Vlm1, Vlm2, and Sfp. 2, coexpression of Vlm1, Vlm2, Sfp, and TEII. (C) LC-MS analysis of valinomycin produced by the CFPS reaction. Insert, MS spectrum of valinomycin peak. EIC, extracted ion chromatogram. a, negative control without plasmid in the reaction. b, valinomycin standard. c, CFPS reaction sample. (D) Valinomycin yields from different CFPS reaction conditions. (1) valinomyicn synthesis by coexpression of Vlm1, Vlm2, and Sfp. Valinomyicn synthesis by coexpression of Vlm1, Vlm2, Sfp, and TEII for a total time of (2) 20 h reaction and (3) 24 h reaction, respectively. Values show means with error bars representing standard deviations (S.D.) of at least three independent experiments.

To establish an in vitro platform for valinomycin biosynthesis, we used an *E. coli*-based CFPS system (38) to synthesize the NRPS valinomycin synthetase. The successful expression of the large enzymes Vlm1 (370 kDa) and Vlm2 (284 kDa) was achieved in our cell-free system as shown clearly by SDS-PAGE with correct molecular weight bands (FIG. 23A). Most importantly, both enzymes can be coexpressed solubly in a single-pot cell-free reaction, suggesting the potential of valinomycin formation in vitro.

Once we had successfully expressed the two large Vlm1 and Vlm2 in vitro, we next needed to convert the enzymes to their functional (holo), active form. To be functional the apo-T (thiolation) domains of NRPS enzymes have to be posttranslationally modified by transfer of a phosphopantetheine moiety from coenzyme A (CoA) to a conserved serine residue in the T domain (39). This modification, called priming, of apo-T domains to functional, holo-T domains is carried out by phosphopantetheinyl transferases (PPTases) and consequently leads to active holo-NRPS (40). To enable priming, we chose the promiscuous PPTase Sfp from *Bacillus subtilis* (41), which has been frequently utilized for the phosphopantetheinylation of heterologous NRPS, to activate our Vlm1 and Vlm2 in vitro.

Previously, we added purified Sfp to cell-free reactions to modify NRPS (GrsA and GrsB1) (23). In this work, to avoid the laborious purification process and to demonstrate the robustness of cell-free system, we directly coexpressed the sfp gene with Vlm1 and Vlm2 in a one-pot reaction. As shown in FIG. 23B, all three proteins were coexpressed and easily visible on an SDS-PAGE gel. Notably, cell-free expressed Sfp was able to activate Vlm1 and Vlm2 for the biosynthesis of valinomycin, which was successfully detected by LC-MS from the in vitro reaction mixture (FIG. 23C). While valinomycin was formed, the yield of 9.76±0.23 μg/L was relatively low (FIG. 23D). We next sought to enhance valinomycin biosynthesis yields.

2. Enhancing Valinomycin Biosynthesis by Coexpression of Type II Thioesterase (TEII)

TEII is a discrete protein that often encoded within NRPS gene clusters, playing a repairing (editing) role by removal of nonreactive moieties and aberrant substrates that block the NRP assembly lines (42). In this way, TEII restores the activity of NRPS that allows for further rounds of product biosynthesis. Since coexpression of TEII with its related NRPS in host cells can be used to improve product yields (37), we wondered if a similar benefit would hold true in vitro. Thus, we set out to investigate the effect of TEII on valinomycin production in our cell-free system. To do this, we added the entire gene cluster of valinomycin (vlm1, vlm2, and TEII) as well as the sfp gene, each independently cloned on a single plasmid, to a one-pot CFPS reaction. We carried out the reaction in two steps. In step one, we expressed Vlm1, Vlm2, and Sfp together for an initial 6 h period, allowing for the expression and modification of Vlm1 and Vlm2. In step two we added the TEII plasmid to the cell-free mixture, and allowed the reaction to continue for an addition 14 h. After the reaction, all four proteins were easily visible on an SDS protein gel (FIG. 23B). This, to the best of our knowledge, is the first example of expressing a whole natural product gene cluster (Vlm1, Vlm2, and TEII) and a heterologous modification enzyme (Sfp) together using an *E. coli*-based CFPS system. Furthermore, as we expected the valinomycin yield was significantly improved to 17.59±0.29 μg/L, which is nearly two times higher than that of the reaction without coexpression of TEII (FIG. 23D). The yield was further increased by two-fold up to 37.11±0.84 g/L when the whole reaction time was extended from 20 to 24 h (FIG. 23D). Taken together, our data demonstrate the robustness (i.e., coexpression of four proteins including two large NRPSs, ~300 kDa) and flexibility (i.e., adding plasmids sequentially for timing tunability of gene expression) of the *E. coli* CFPS system for the rapid, total biosynthesis of complex natural products like NRPs in vitro. However, the yield of valinomycin was still about three orders of magnitude lower than previous reports in *E. coli* cells.

3. In Vitro Biosynthesis of Valinomycin Using Cell-Free Metabolic Engineering (CFME)

While total biosynthesis was achieved in the cell-free biosynthesis approach above, we hypothesized that the low valinomycin yields resulted from resource limitations (e.g., energy) caused by the extended reaction duration and expression of four enzymes, especially the two large NRPSs (Vlm1 and Vlm2). In an attempt to bypass such a constraint, we next switched the expression of Vlm1 and Vlm2 from in vitro to in vivo. The key idea was to maximally express proteins in cells, and then mix lysates enriched with these enzymes to increase production of valinomycin in a setting without growth constraints (FIG. 22C). We previously used such an approach, which is called cell-free metabolic engineering (CFME), to efficiently synthesize small molecules (e.g., n-butanol, 2,3-butanediol) (43-46). For example, glycolysis in crude *E. coli* lysates powered the production of butanediol with near theoretical yields, high titers (>80 g/L), and high productivities (>10 g/L/h).

Figure 24:
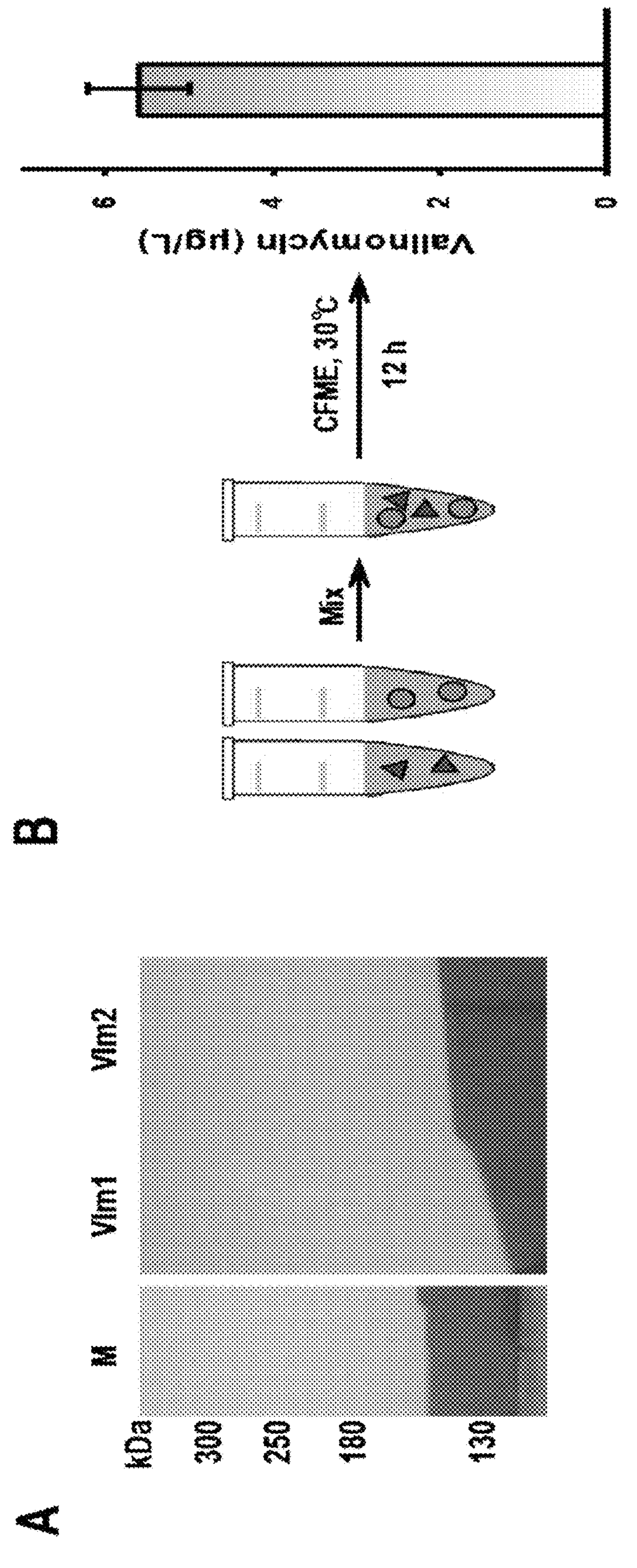
FIG. 24. In vitro biosynthesis of valinomycin using CFME system. (A) SDS-PAGE (7.5% gel) analysis of Vlm1 and Vlm2 overexpressed individually in *E. coli* BAP1. M, protein molecular weight marker. (B) CFME reactions for valinomycin production by mixing two cell lysates. Error bar represents standard deviation (S.D.) of at least three independent experiments.

To demonstrate CFME synthesis of valinomycin, we first introduced genes encoding Vlm1 and Vlm2 individually into the source strain *E. coli* BAP1, which has the sfp gene chromosomally integrated (47). After heterologous expression of each enzyme in vivo, we lysed cell pellets to generate Vlm1 and Vlm2 enriched cell lysates, respectively. As expected, we observed that both enzymes were overexpressed in *E. coli* BAP1 as can be seen on the SDS-PAGE gel (FIG. 24A). In this case, Vlm1 and Vlm2 should be modified by Sfp that is encoded in the genome of BAP1 to be in their active holo form. We next initiated in vitro valinomycin biosynthesis by directly mixing two cell lysates (Vlm1 and Vlm2), acetate salts ($Mg^{2+}$, $NH_4^+$, and $K^+$), cofactors (CoA, NAD, and ATP), and other components. The CFME reaction was carried out for 12 h at 30° C. and valinomycin was analyzed by LC-MS. However, the yield of 5.59±0.60 μg/L was unexpectedly low (FIG. 24B). We, therefore, next set out to optimize the CFME system for enhanced synthesis of valinomycin.

Figure 25:
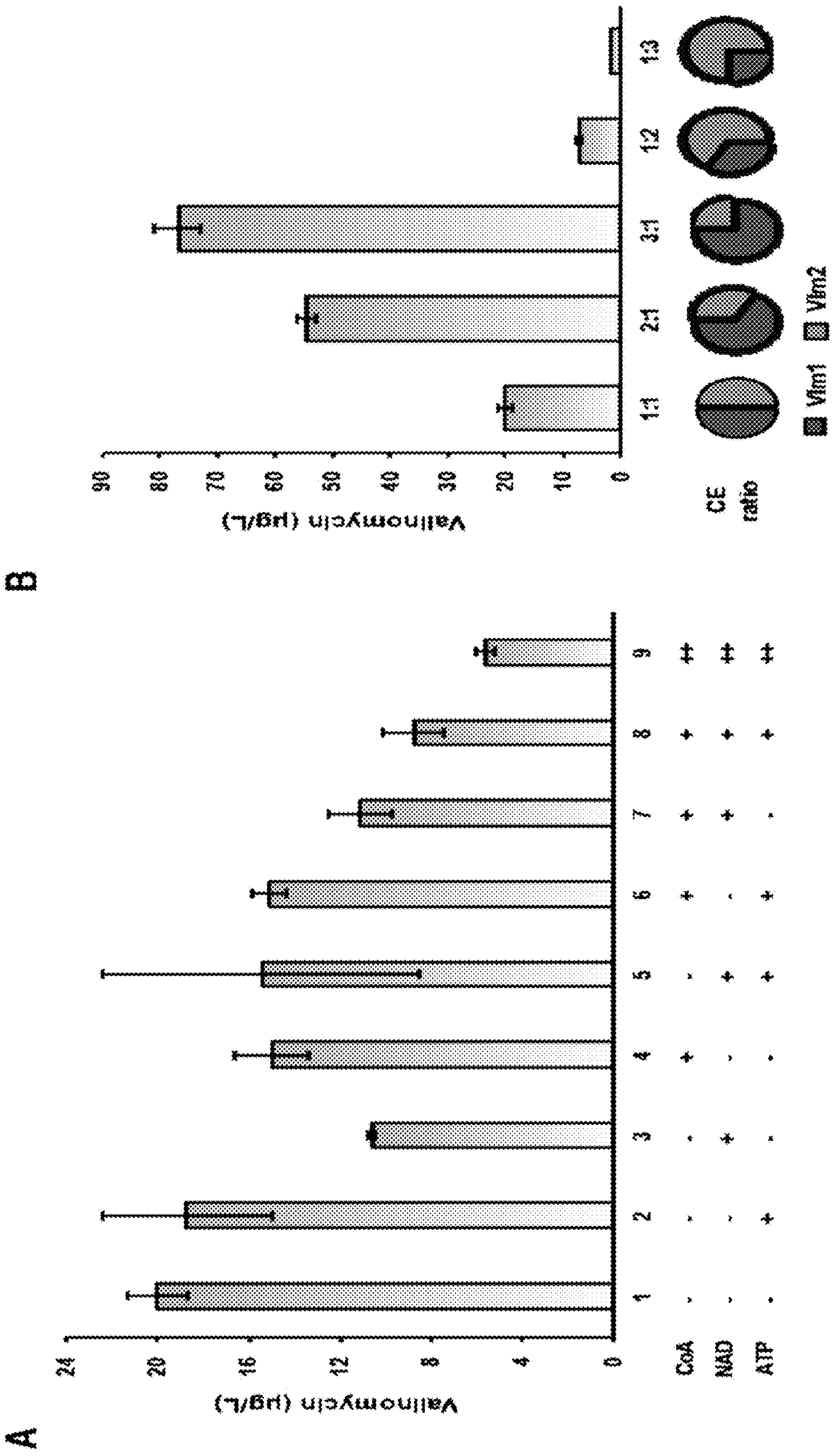
FIG. 25. Optimization of CFME reactions for enhanced valinomycin production. (A) Effect of supplementary cofactors (CoA, NAD, and ATP) on valinomycin formation. −, no cofactor added, +, cofactors were supplemented with 0.1 mM. ++, cofactors were supplemented with 1 mM. (B) Effect of the mass ratio of two cell extracts (CE) on valinomycin production. Values show means with error bars representing standard deviations (S.D.) of at least three independent experiments.

We began our optimization by investigating the effect of supplemental cofactors (CoA, NAD, and ATP) on valinomycin formation. Previous studies suggested that cofactors may play a positive role in the performance of cell-free metabolic pathways (43, 44). When the concentration of CoA, NAD, and ATP were reduced from initial 1 mM to 0.1 mM in our CFME system, the yield of valinomycin was increased by 1.5 times up to 8.77±1.37 μg/L (FIG. 25A). Then, CoA, NAD, and ATP (each at 0.1 mM) were removed one-at-a-time, two-at-a-time, and altogether from CFME reactions. We found the reaction without any supplementary cofactors produced the highest valinomycin of 19.99±1.30 μg/L, which is nearly 4-fold higher than the initial yield (FIG. 25A). Our data are in agreement with previous reports (45, 46) that cofactors from the cell lysate are sufficient to drive product synthesis, in our case, valinomycin. Therefore, we omitted costly cofactors from our CFME system in the following investigations.

A key conceptual shift of our approach is that the design element is a lysate rather than a gene. Once in hand, selectively enriched lysates can be mixed in different ratios to optimize the pathway as this will impact the enzyme concentration. In each 25 μL CFME reaction, we added two cell lysates with a total protein mass of 35 mg/mL. Since Vlm1 and Vlm2 were overexpressed in a similar level (FIG. 24A), we initially added two lysates at a mass ratio of 1:1, generating approximately 20 μg/L valinomycin (FIG. 25B). We next varied the mass ratio of the two lysates to find beneficial enzyme proportions. As shown in FIG. 25B, valinomycin formation in CFME reactions was notably impacted by the mass ratio of cell lysates. It is clear that more Vlm1 enriched cell lysates in the reaction produced more valinomycin with the highest yield of 76.9±3.94 μg/L at a mass ratio of 3:1 (cell lysate-Vlm1:cell lysate-Vlm2). By contrast, valinomycin synthesis was almost abolished when the ratio was 1:3. The results demonstrate that the steps of valinomycin biosynthesis catalyzed by Vlm1 might be rate-limiting.

4. CFPS of TEII Improves Valinomycin Biosynthesis in Coupling with CFME

We next wondered if, as before, addition of TEII would enhance valinomycin yields. We therefore next used a coupled CFPS-CFME (CFPS-ME) system to perform a two-phase biosynthesis (FIG. 26A), whereby the repairing enzyme TEII was expressed by CFPS in the first reaction phase, which could be used to, as shown previously, regenerate the activity of Vlm1 and Vlm2 during the second CFME phase. We initially expressed TEII for 3 h and then added glucose (200 mM) to fuel the CFME process for another 12 h. With this strategy, the yield of valinomycin was dramatically improved to 29.32±1.37 mg/L (FIG. 26A), which is more than 5200 times higher than the initial CFME yield of 5.59±0.60 μg/L. This result demonstrates that (i) a dedicated enzyme can be expressed by the upstream CFPS to efficiently drive the downstream CFME reactions; (ii) in vitro expressed TEII is active to restore the function of in vivo heterologously expressed, but misprimed NRPS enzymes (Vlm1 and Vlm2); and (iii) the CFPS-ME system is robust for the synthesis of complex natural product (valinomycin) from a simple, cheap precursor glucose. Further increase of the TEII expression time (>6 h) reduced the product yields (FIG. 26A), perhaps as a result of consuming more resources for TEII synthesis in the batch reaction that led to the decrease of valinomycin formation.

Figure 26:
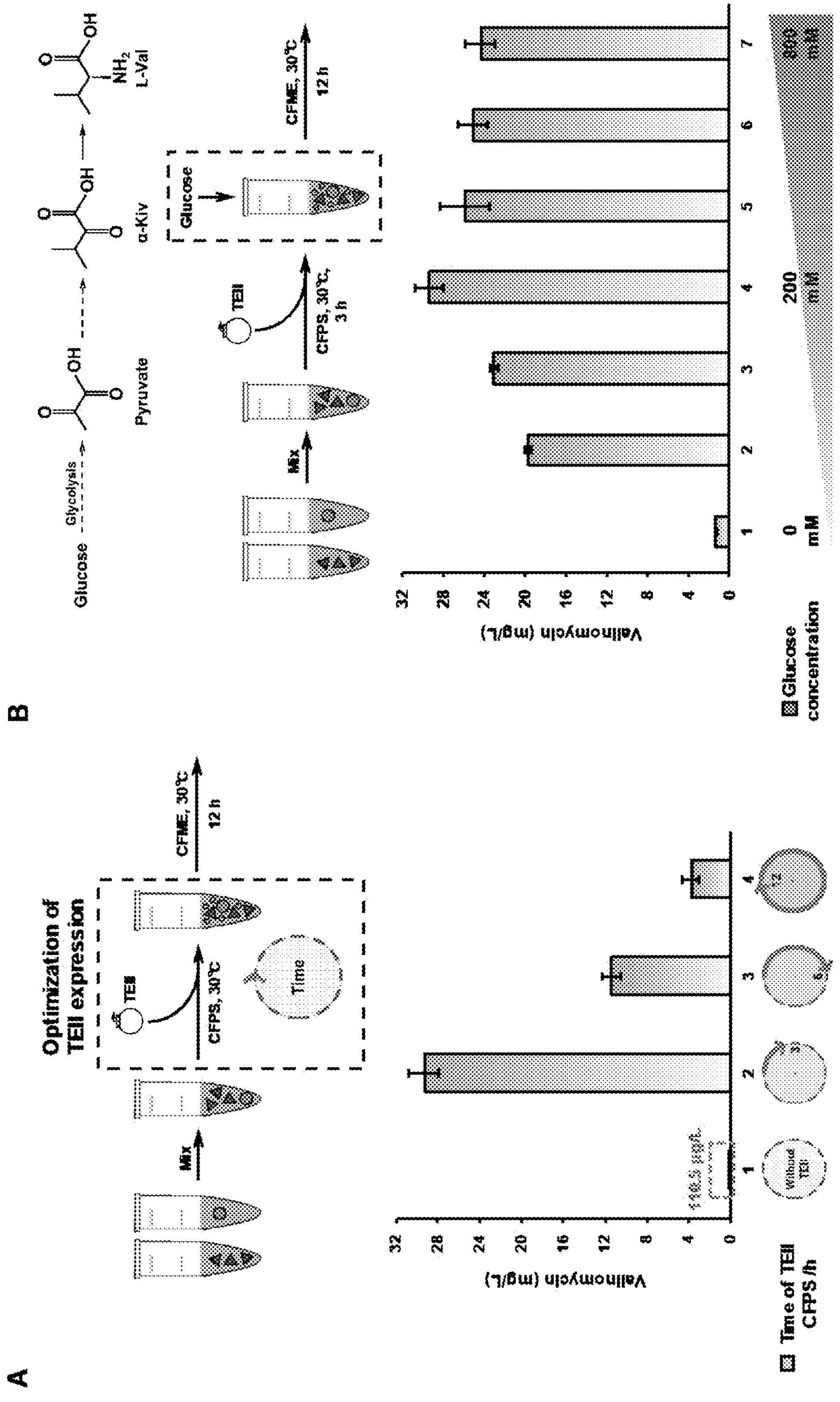
FIG. 26. Boosting valinomycin yields with a coupled CFPS-ME system. (A) Enhancement of valinomycin yields by CFPS of TEII in the upstream of CFME reactions. (B) Investigation of the glucose concentration on valinomycin production. Values show means with error bars representing standard deviations (S.D.) of at least three independent experiments.

To fuel the reaction, glucose is converted to pyruvate in glycolysis by enzymes in the extract, which is further converted in the branched chain amino acid L-valine biosynthetic pathway to α-ketoisovalerate (α-Kiv) and L-valine (32)) (FIG. 26B). To further enhance valinomycin synthesis yields, we next assessed the impact of glucose concentration on valinomycin synthesis, noting that glucose is the key reaction substrate. Specifically, we tested starting glucose concentrations from 0-800 mM. We observed that the product yield was substantially enhanced from 1.3±0.10 mg/L without feeding glucose to 19.6±0.33 mg/L with addition of 50 mM glucose. The yield reached the highest of approximately 30 mg/L at the glucose concentration of 200 mM. When glucose concentrations were increased to 400-800 mM, valinomycin yields were slightly reduced to a stable level of around 25 mg/L. Overall, our data demonstrate the ability to use cheap glucose to fuel a highly active and productive natural product biosynthetic pathway that is constructed by CFPS and CFME in vitro.

D. Discussion

Natural products play, and will continue to play, a significant role in the drug discovery engine (1-3). DNA sequencing and genome mining have revealed that a far greater number of natural product biosynthetic gene clusters exist, but their products remain unknown (9). To access and harness these natural products, rapid and robust approaches need to be developed for their synthesis. In this report, we show that cell-free biology is one such approach. This approach shifts the design-build-test unit from a genetic construct and its associated cell-line to a cell-free lysate. The utility of our cell-free approach is demonstrated by the ability to enable total in vitro synthesis of the nonribosomal macrolactone peptide valinomycin in a single CFPS system and a coupled CFPS-ME system.

Our results have several key features. First, the use of cell-free systems allows for fine tuning of reaction conditions, easy monitoring, and multiple optimization. In recent years, cell-free systems have been utilized not only for the synthesis of various proteins (18), but also for the rapid and high-throughput prototyping of metabolic pathways (43, 48). Despite the wide applications of cell-free systems, total cell-free biosynthesis of both the enzymes and their natural product has not previously been reported. We show, somewhat surprisingly, that cell-free systems are capable large NRPS synthesis. Indeed, we succeeded in cell-free expression of the valinomycin biosynthetic gene cluster (>19 kb), which contains two large NRPSs (Vlm1, 370 kDa and Vlm2, 284 kDa) and one associate repairing enzyme TEII, as well as a heterologous modification enzyme (Sfp). Notably, four enzymes were actively coexpressed in a single-pot CFPS reaction, giving rise to valinomycin formation with a yield of nearly 40 μg/L (FIG. 23D).

Second, cell-free systems enable high-level titers of natural products. We were able to leverage the high degree of flexibility of cell-free system to adjust the way enzymes were enriched in lysates (shifting from cell-free protein synthesis to heterologous overexpression) to facilitate increased natural product titers. Additionally, we could readily tune expression of the TEII enzyme to restore the activity of Vlm1 and Vlm2, as well as increase metabolic flux into pathway precursors (e.g., pyruvate, α-Kiv, and L-Val) by the addition of increased concentrations of glucose (200 mM). Of note, the optimized, coupled CFPS-ME system enabled synthesis of ~30 mg/L valinomycin, which compares favorably to the best previous reports. Several native *Streptomyces* organisms produce 4 to 32 mg/L (31) and a heterologous *E. coli* host was shown to make 13 mg/L (37). However, there may be situations where *E. coli*-based systems are not the best suited for expressing natural product biosynthetic gene clusters. To this point, new CFPS systems have recently been developed from *Streptomyces* species and others that have shown benefits for the soluble expression of high GC-content genes, which are often involved in natural product biosynthetic gene clusters (49, 50).

Third, our cell-free approach is fast. It requires only hours to obtain a target compound, whereas days or weeks may otherwise be needed to cultivate strains for product production. With the price of DNA synthesis declining and assembly of large gene clusters increasing, we anticipate that the ability to directly input DNA to cell-free systems for accessing biosynthetic pathways from clusters assembled using metagenomics for uncultivable organisms could enable new approaches for discovering and studying natural products. In addition, CFPS platforms are shown to work with linear PCR templates (51-53), highlighting the efficiency of cell-free systems for future high-throughput synthesis without laborious cloning work. As such, cell-free biosynthesis system offers a rapid and cost-effective way to synthesize molecules of interest.

In summary, this work, for the first time, demonstrates in vitro total biosynthesis of a complex NRP valinomyicn by cell-free expression of the entire gene cluster. Given the robustness and flexibility of cell-free systems, the reactions can be rationally optimized to increase the biosynthesis performance and thus give rise in high productivity. Looking forward, we believe that cell-free systems hold great potential to create an easy-to-use platform for studying and engineering natural product pathways.

E. Materials and Methods

1. Bacterial Strains and Plasmids

*E. coli* BL21 Star (DE3) was used for preparation of cell extracts to perform CFPS reactions. The strain *E. coli* BAP1, a generous gift from Prof. Yong Wang (Shanghai Institutes for Biological Sciences, Chinese Academy of Sciences, Shanghai, China), was used to overexpress Vlm1 and Vlm2 in vivo. *E. coli* BAP1 is a derivative of *E. coli* BL21 (DE3) with genomic integration of the sfp gene for posttranslational phosphopantetheinylation of NRPSs (47). Plasmids pCTUT7-Vlm1 and pKS01-Vlm2 harboring genes vlm1 (~10 kb) and vlm2 (~8 kb) (32), respectively, were kindly provided by Prof. Peter Neubauer (Technische Universitat Berlin, Germany). Cell-free expression of Sfp and TEII were achieved with plasmids pET28a-Sfp (23) and pJL1-TEII (49), respectively.

2. Preparation of Cell Extracts

All *E. coli* strains were grown in 2×YTPG medium, consisting of (per liter) 10 g yeast extract, 16 g tryptone, 5 g NaCl, 7 g $K_2HPO_4$, 3 g $KH_2PO_4$, and 18 g glucose. Cultivations of *E. coli* BL21 Star (DE3) were performed in 1 L of 2×YTPG in 2.5 L baffled Ultra Yield™ flasks (Thomson Instrument Company, USA). After inoculation (initial $OD_{600}$ of 0.05), cultures were incubated in the shaker at 220 rpm and 34° C. When $OD_{600}$ reached 0.6-0.8, cells were induced with 1 mM isopropyl-β-D-thiogalactopyranoside (IPTG) to express T7 RNA polymerase. Then, cells were grown until an $OD_{600}$ of 3.0 and harvested by centrifugation at 5,000 g and 4° C. for 15 min. Afterwards, cell pellets were washed three times with cold S30 Buffer (10 mM Tris-acetate, 14 mM magnesium acetate, 60 mM potassium acetate, and 2 mM dithiothreitol (DTT)). After the final wash and centrifugation, the pelleted cells were resuspended in S30 Buffer (1 mL per gram of wet cell mass) and lysed by sonication (10 s on/off, 50% of amplitude, input energy ~600 Joules). The lysate was then centrifuged twice at 12,000 g and 4° C. for 10 min. The resulting supernatant was flash frozen in liquid nitrogen and stored at −80° C. until use.

To prepare enzyme-enriched lysates, two strains of *E. coli* BAP1 containing the plasmid pCTUT7-Vlm1 and pKS01-Vlm2, respectively, were grown in 1 L of 2×YTPG and incubated at 30° C. and 250 rpm. At $OD_{600}$ of 0.6-0.8, the cultures were induced with 20 μM IPTG, followed by 5 h cultivation for Vlm1 and Vlm2 expression. Afterwards, cell collection, disruption, and extracts were prepared the same as described above. The total amount of protein in cell extracts was quantified by the Quick-Start Bradford Protein Assay Kit (Bio-Rad). Typically, the total protein concentration of cell extracts was 30-40 mg/mL. Overexpression of Vlm1 and Vlm2 was confirmed by SDS-PAGE protein gels.

3. CFPS Reactions

CFPS reactions were performed at a total volume of 15 μL in 1.5 mL microcentrifuge tubes. Each reaction mixture contained the following components: 12 mM magnesium glutamate, 10 mM ammonium glutamate, 130 mM potassium glutamate, 1.2 mM ATP, 0.85 mM each of GTP, UTP, and CTP, 34 μg/mL folinic acid, 170 μg/mL of *E. coli* tRNA mixture, 2 mM each of 20 standard amino acids, 0.33 mM nicotinamide adenine dinucleotide (NAD), 0.27 mM coenzyme A (CoA), 1.5 mM spermidine, 1 mM putrescine, 4 mM sodium oxalate, 33 mM phosphoenolpyruvate (PEP), appropriate plasmids (see below), and 27% (v/v) of cell extract. In all 15 μL CFPS reactions, each plasmid was added individually or together as follows: 200 ng pCTUT7-Vlm1, 200 ng pKS01-Vlm2, 100 ng pET28a-Sfp, and 200 ng pJL1-TEII. In the case of coexpression of four proteins, pCTUT7-Vlm1, pKS01-Vlm2, and pET28a-Sfp were added together at the beginning for 6 h expression. Then, pJL1-TEII was added to the cell-free mixture for another 14 h reaction unless otherwise noted. Other CFPS reactions were incubated at 30° C. for 20 h. All cell-free expressed proteins were analyzed by SDS-PAGE gels.

4. CFME Reactions

Standard CFME reactions were carried out in 1.5 mL microcentrifuge tubes at 30° C. for 12 h in 25 μL volumes. Reaction components consisted of 8 mM magnesium acetate, 10 mM ammonium acetate, 134 mM potassium acetate, 200 mM glucose, 10 mM dipotassium phosphate (pH 7.2), 1 mM NAD, 1 mM ATP, 1 mM CoA, and 35 mg/mL total protein. The total protein concentration was maintained by adjusting the mass ratio of two lysates (Vlm1 and Vlm2).

5. CFPS-ME Reactions

CFPS synthesis of TEII was scaled up from 15 μL to a 25 μL reaction system. All reagent concentrations were the same as described in the section of "CFPS reactions", except the plasmid (pJL1-TEII, 13.3 μg/mL) and cell extract (35 mg/mL, total protein of two mixed lysates). Unless otherwise noted, cell-free expression of TEII was performed at 30° C. for 3 h, followed by spiking in glucose (200 mM) for valinomycin biosynthesis for another 12 h.

6. Valinomycin Extraction and Quantification

Valinomycin was extracted with three-fold volumes of ethyl acetate from cell-free reactions. After centrifugation at 16,000 g for 5 min, the organic fraction was transferred to a fresh 1.5 mL microcentrifuge tube, air dried, and resuspended in methanol for valinomycin analysis. Valinomycin quantification was performed with an Agilent 6470 Triple Quadrupole LC/MS System equipped with an Eclipse Plus C18 column (2.1×50 mm, 1.8 μm). For valinomycin detection, 2 μL of each sample was injected and separated at a flow rate of 0.4 mL/min with elution buffers A (water+0.1% formic acid) and B (acetonitrile+0.1% formic acid) through a linear gradient elution from 80 to 100% B over 2.5 min, a 100% B wash for 7.5 min, and a post time wash for 10 min with 80% B. Valinomycin concentrations were calculated according to a calibration curve prepared with commercial valinomycin (Sigma) as a standard. All measurements were performed in triplicate.

F. References for Example 2

1. F. E. Koehn, G. T. Carter, The evolving role of natural products in drug discovery. Nat. Rev. Drug Discov. 4, 206-220 (2005).
2. D. J. Newman, G. M. Cragg, Natural products as sources of new drugs from 1981 to 2014. J. Nat. Prod. 79, 629-661 (2016).
3. L. Katz, R. H. Baltz, Natural product discovery: past, present, and future. J. Ind. Microbiol. Biotechnol. 43, 155-176 (2016).
4. J. O'Neill, Tackling drug-resistant infections globally: Final report and recommendations (Wellcome Trust, U K, 2016).
5. M. J. Smanski, H. Zhou, J. Claesen, B. Shen, M. A. Fischbach, C. A. Voigt, Synthetic biology to access and expand nature's chemical diversity. Nat. Rev. Microbiol. 14, 135-149 (2016).
6. K. Blin, S. Shaw, K. Steinke, R. Villebro, N. Ziemert, S. Y. Lee, M. H. Medema, T. Weber, antiSMASH 5.0: updates to the secondary metabolite genome mining pipeline. Nucleic Acids Res. 47, W81-W87 (2019).
7. J. R. Doroghazi, J. C. Albright, A. W. Goering, K. S. Ju, R. R. Haines, K. A. Tchalukov, D. P. Labeda, N. L. Kelleher, W. W. Metcalf, A roadmap for natural product discovery based on large-scale genomics and metabolomics. Nat. Chem. Biol. 10, 963-968 (2014).
8. M. M. Zhang, F. T. Wong, Y. Wang, S. Luo, Y. H. Lim, E. Heng, W. L. Yeo, R. E. Cobb, B. Enghiad, E. L. Ang, H. Zhao, CRISPR-Cas9 strategy for activation of silent *Streptomyces* biosynthetic gene clusters. Nat. Chem. Biol. 13, 607-609 (2017).
9. B. Aigle, S. Lautru, D. Spiteller, J. S. Dickschat, G. L. Challis, P. Leblond, J. L. Pernodet, Genome mining of *Streptomyces ambofaciens*. J. Ind. Microbiol. Biotechnol. 41, 251-263 (2014).
10. H. Zhang, B. A. Boghigian, J. Armando, B. A. Pfeifer, Methods and options for the heterologous production of complex natural products. Nat. Prod. Rep. 28, 125-151 (2011).

11. J. Li, P. Neubauer, *Escherichia coli* as a cell factory for heterologous production of nonribosomal peptides and polyketides. New Biotechnol. 31, 579-585 (2014).
12. Y. Luo, B. Z. Li, D. Liu, L. Zhang, Y. Chen, B. Jia, B. X. Zeng, H. Zhao, Y. J. Yuan, Engineered biosynthesis of natural products in heterologous hosts. Chem. Soc. Rev. 44, 5265-5290 (2015).
13. J. Nielsen, Cell factory engineering for improved production of natural products. Nat. Prod. Rep. DOI: 10.1039/c9np00005d (2019).
14 J. Nielsen, J. D. Keasling, Engineering cellular metabolism. Cell 164, 1185-1197 (2016).
15. Q. M. Dudley, A. S. Karim, M. C. Jewett, Cell-free metabolic engineering: biomanufacturing beyond the cell. Biotechnol. J. 10, 69-82 (2015).
16. J. R. Swartz, Expanding biological applications using cell-free metabolic engineering: an overview. Metab. Eng. 50, 156-172 (2018).
17. B. C. Bundy, J. P. Hunt, M. C. Jewett, J. R. Swartz, D. W. Wood, D. D. Frey, G. Rao, Cell-free biomanufacturing. Curr. Opin. Chem. Eng. 22, 177-183 (2018).
18. W. Q. Liu, L. Zhang, M. Chen, J. Li, Cell-free protein synthesis: recent advances in bacterial extract sources and expanded applications. Biochem. Eng. J. 141, 182-189 (2019).
19. J. Li, L. Zhang, W. Liu, Cell-free synthetic biology for in vitro biosynthesis of pharmaceutical natural products. Synth. Syst. Biotechnol. 3, 83-89 (2018).
20. Q. Cheng, L. Xiang, M. Izumikawa, D. Meluzzi, B. S. Moore, Enzymatic total synthesis of enterocin polyketides. Nat. Chem. Biol. 3, 557-558 (2007).
21. C. J. Balibar, A. R. Howard-Jones, C. T. Walsh, Terrequinone A biosynthesis through L-tryptophan oxidation, dimerization and bisprenylation. Nat. Chem. Biol. 3, 584-592 (2007).
22. C. Greunke, A. Glockle, J. Antosch, T. A. Gulder, Biocatalytic total synthesis of ikarugamycin. Angew. Chem. Int. Ed. 56, 4351-4355 (2017).
23. A. W. Goering, J. Li, R. A. McClure, R. J. Thomson, M. C. Jewett, N. L. Kelleher, In vitro reconstruction of nonribosomal peptide biosynthesis directly from DNA using cell-free protein synthesis. ACS Synth. Biol. 6, 39-44 (2017).
24. C. N. Park, J. M. Lee, D. Lee, B. S. Kim, Antifungal activity of valinomycin, a peptide antibiotic produced by *Streptomyces* sp. strain M10 antagonistic to *Botrytis cinerea*. J. Microbiol. Biotechnol. 18, 880-840 (2008).
25. M. H. Tempelaars, S. Rodrigues, T. Abee, Comparative analysis of antimicrobial activities of valinomycin and cereulide, the *Bacillus cereus* emetic toxin. Appl. Environ. Microbiol. 77, 2755-2762 (2011).
26. R. M. Heisey, J. Huang, S. K. Mishra, J. E. Keller, J. R. Miller, A. R. Putnam, T. D. J. D'Silva, Production of valinomycin, an insecticidal antibiotic, by *Streptomyces griseus* var. flexipertum var. nov. J. Agric. Food Chem. 36, 1283-1286 (1988).
27. C. Y. Wu, J. T. Jan, S. H. Ma, C. J. Kuo, H. F. Juan, Y. S. Cheng, H. H. Hsu, H. C. Huang, D. Wu, A. Brik, F. S. Liang, R. S. Liu, J. M. Fang, S. T. Chen, P. H. Liang, C. H. Wong, Small molecules targeting severe acute respiratory syndrome human coronavirus. Proc. Natl. Acad. Sci. USA 101, 10012-10017 (2004).
28. I. J. Ryoo, H. R. Park, S. J. Choo, J. H. Hwang, Y. M. Park, K. H. Bae, K. Shin-Ya, I. D. Yoo, Selective cytotoxic activity of valinomycin against HT-29 human colon carcinoma cells via down-regulation of GRP78. Biol. Pharm. Bull. 29, 817-820 (2006).
29. Y. Q. Cheng, Deciphering the biosynthetic codes for the potent anti-SARS-CoV cyclodepsipeptide valinomycin in *Streptomyces* tsusimaensis ATCC 15141. ChemBioChem 7, 471-477 (2006).
30. N. A. Magarvey, M. Ehling-Schulz, C. T. Walsh, Characterization of the cereulide NRPS α-hydroxy acid specifying modules: activation of α-keto acids and chiral reduction on the assembly line. J. Am. Chem. Soc. 128, 10698-10699 (2006).
31. A. M. Matter, S. B. Hoot, P. D. Anderson, S. S. Neves, Y. Q. Cheng, Valinomycin biosynthetic gene cluster in *Streptomyces*: conservation, ecology and evolution. PLoS One 4, e7194 (2009).
32. J. Jaitzig, J. Li, R. D. Sussmuth, P. Neubauer, Reconstituted biosynthesis of the nonribosomal macrolactone antibiotic valinomycin in *Escherichia coli*. ACS Synth. Biol. 3, 432-438 (2014).
33. J. Li, J. Jaitzig, F. Hillig, R. Sussmuth, P. Neubauer, Enhanced production of the nonribosomal peptide antibiotic valinomycin in *Escherichia coli* through small-scale high cell density fed-batch cultivation. Appl. Microbiol. Biotechnol. 98, 591-601 (2014).
34. J. Li, J. Jaitzig, P. Lu, R. D. Sussmuth, P. Neubauer, Scale-up bioprocess development for production of the antibiotic valinomycin in *Escherichia coli* based on consistent fed-batch cultivations. Microb. Cell Fact. 14, 83 (2015).
35. D. Schwarzer, H. D. Mootz, U. Linne, M. A. Marahiel, Regeneration of misprimed nonribosomal peptide synthetases by type II thioesterases. Proc. Natl. Acad. Sci. USA 99, 14083-14088 (2002).
36. E. Yeh, R. M. Kohli, S. D. Bruner, C. T. Walsh, Type II thioesterase restores activity of a NRPS module stalled with an aminoacyl-S-enzyme that cannot be elongated. ChemBioChem 5, 1290-1293 (2004).
37. J. Li, J. Jaitzig, L. Theuer, O. E. Legala, R. D. Sussmuth, P. Neubauer, Type II thioesterase improves heterologous biosynthesis of valinomycin in *Escherichia coli*. J. Biotechnol. 193, 16-22 (2015).
38. Y. C. Kwon, M. C. Jewett, High-throughput preparation methods of crude extract for robust cell-free protein synthesis. Sci. Rep. 5, 8663 (2015).
39. M. A. Fischbach, C. T. Walsh, Assembly-line enzymology for polyketide and nonribosomal peptide antibiotics: logic, machinery, and mechanisms. Chem. Rev. 106, 3468-3496 (2006).
40. R. H. Lambalot, A. M. Gehring, R. S. Flugel, P. Zuber, M. LaCelle, M. A. Marahiel, R. Reid, C. Khosla, C. T. Walsh, A new enzyme superfamily—the phosphopantetheinyl transferases. Chem. Biol. 3, 923-936 (1996).
41. L. E. N. Quadri, P. H. Weinreb, M. Lei, M. M. Nakano, P. Zuber, C. T. Walsh, Characterization of Sfp, a *Bacillus subtilis* phosphopantetheinyl transferase for peptidyl carrier protein domains in peptide synthetases. Biochemistry 37, 1585-1595 (1998).
42. M. Kotowska, K. Pawlik, Roles of type II thioesterases and their application for secondary metabolite yield improvement. Appl. Microbiol. Biotechnol. 98, 7735-7746 (2014).
43. A. S. Karim, M. C. Jewett, A cell-free framework for rapid biosynthetic pathway prototyping and enzyme discovery. Metab. Eng. 36, 116-126 (2016).
44. J. E. Kay, M. C. Jewett, Lysate of engineered *Escherichia coli* supports high-level conversion of glucose to 2,3-butanediol. Metab. Eng. 32, 133-142 (2015).
45. Q. M. Dudley, K. C. Anderson, M. C. Jewett, Cell-free mixing of *Escherichia coli* crude extracts to prototype and rationally engineer high-titer mevalonate synthesis. ACS Synth. Biol. 5, 1578-1588 (2016).

46. Q. M. Dudley, C. J. Nash, M. C. Jewett, Cell-free biosynthesis of limonene using enzyme-enriched *Escherichia coli* lysates. Synth. Biol. 4, ysz003 (2019).

47. B. A. Pfeifer, S. J. Admiraal, H. Gramajo, D. E. Cane, C. Khosla, Biosynthesis of complex polyketides in a metabolically engineered strain of *E. coli*. Science 291, 1790-1792 (2001).

48. P. T. O'Kane, Q. M. Dudley, A. K. McMillan, M. C. Jewett, M. Mrksich, High-throughput mapping of CoA metabolites by SAMDI-MS to optimize the cell-free biosynthesis of HMG-CoA. Sci. Adv. 5, eaaw9180 (2019).

49. J. Li, H. Wang, Y. C. Kwon, M. C. Jewett, Establishing a high yielding *Streptomyces*-based cell-free protein synthesis system. Biotechnol. Bioeng. 114, 1343-1353 (2017).

50. J. Li, H. Wang, M. C. Jewett, Expanding the palette of *Streptomyces*-based cell-free protein synthesis systems with enhanced yields. Biochem. Eng. J. 130, 29-33 (2018).

51. Z. Z. Sun, E. Yeung, C. A. Hayes, V. Noireaux, R. M. Murray, Linear DNA for rapid prototyping of synthetic biological circuits in an *Escherichia coli* based TX-TL cell-free system. ACS Synth. Biol. 3, 387-397 (2014).

52. H. Wang, J. Li, M. C. Jewett, Development of a *Pseudomonas putida* cell-free protein synthesis platform for rapid screening of gene regulatory elements. Synth. Biol. 3, ysy003 (2018).

53. S. M. Schinn, A. Broadbent, W. T. Bradley, B. C. Bundy, Protein synthesis directly from PCR: progress and applications of cell-free protein synthesis with linear DNA. N. Biotechnol. 33, 480-487 (2016).

Example 3—Cell-Free Biosynthesis of Andrimid

A. Abstract

Figure 27:
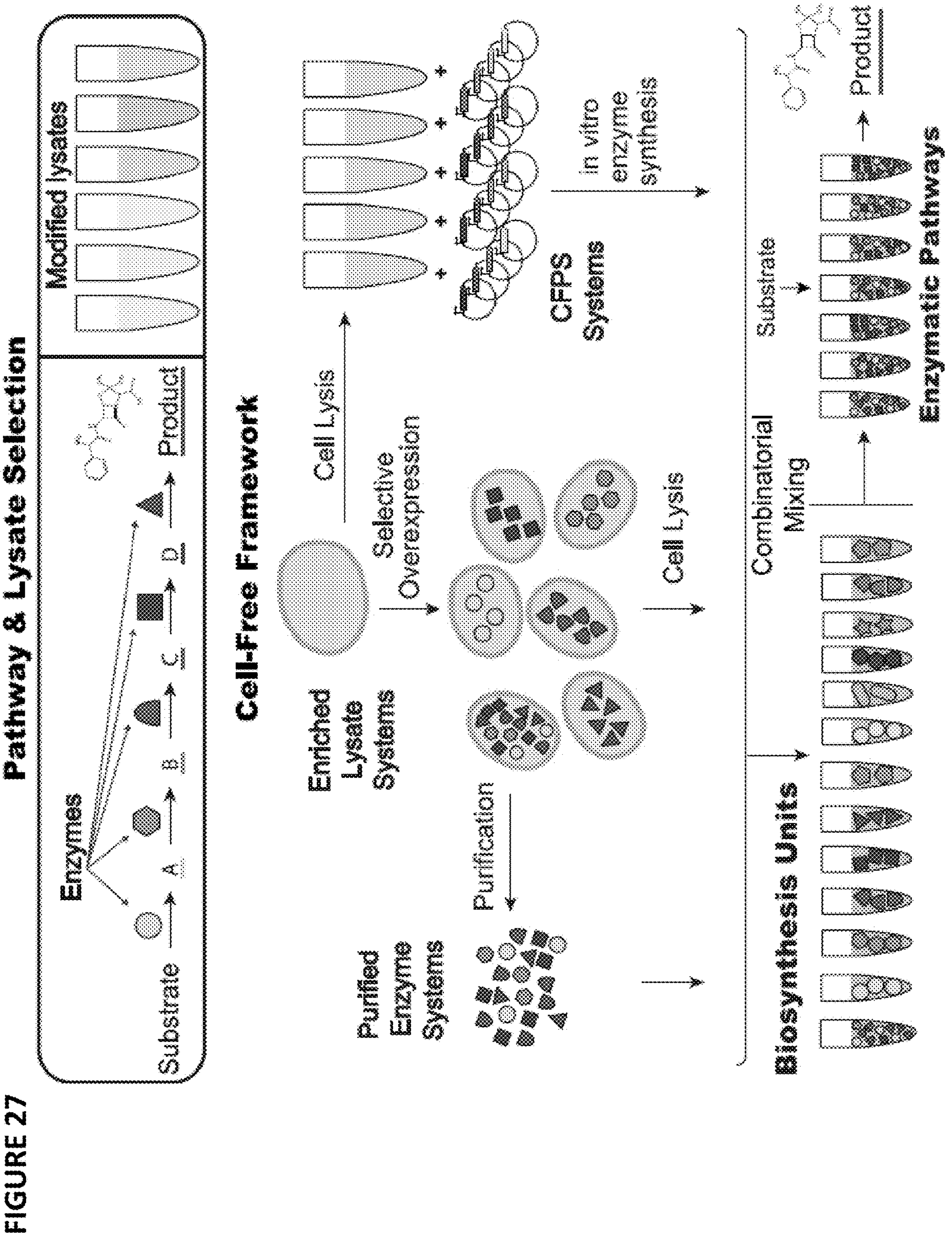
FIG. 27. Cell-free framework for pathway expression. Enzymes in a pathway are overexpressed lysates or made in CFPS to construct cell-free "units" that can then be used to recreate the pathway or combinatorially diversify it.

Our platform's use of newly developed cell-free technologies overcomes many of the challenges of in vivo heterologous expression of natural products including cytotoxicity, silent gene clusters, and low yields. In our approach, the biosynthesis "units" are cell-free lysates or CFPS reactions rather than genetic constructs in live cells, which we can combinatorially assemble into desired pathways by mixing cell specific combinations of lysates enriched with pathway enzymes (1, 2) (FIG. 27). We can mix lysates or CFPS reactions from different strains and different organisms, including for example high natural producers, to optimize the overall capabilities. A key advantage of this approach is we can build a library of these cell-free "units" only once but then can rapidly resample these many times using a DBT approach in different experimental designs to prepare multi-lysate cocktails with varying enzyme combinations and stoichiometry to build a pathway or generate variants, drastically lowering experimental costs for pathway discovery and optimization.

Figure 28:
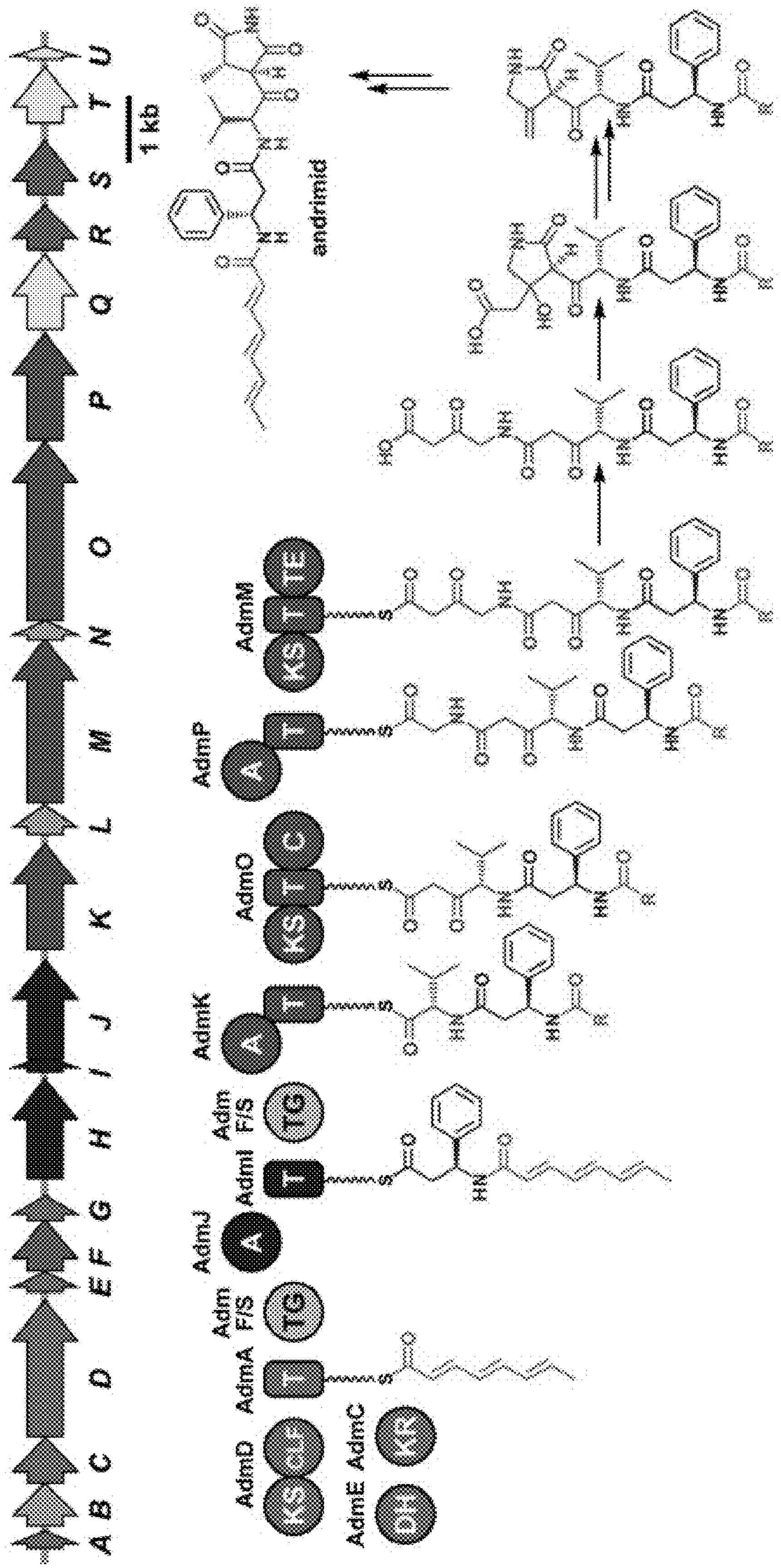
FIG. 28. Andrimid synthesis. a) Andrimid is synthesized via a hybrid 21 gene NRPS/PKS pathway. b) We separately expressed each enzyme in the cluster in CFPS reactions, quantified by radiolabeled leucine incorporation. Upon mixing all 21 enriched lysates together and addition of substrates and cofactors (i.e., malonyl-CoA), we could observe andrimid biosynthesis (c).

B. In Vitro Reconstruction of Andrimid Biosynthesis Directly from DNA Using Cell-Free Systems In unpublished work, we have pursued the synthesis of andrimid (FIG. 28A), a broad-spectrum antibiotic (3). We considered the andrimid pathway because of the large number of genes involved and transcription of the native gene cluster is highly regulated. To enable cell-free biosynthesis of andrimid, we first expressed all of the 21 genes of the pathway each in multiple cell-free reactions in *E. coli*, as detailed in the previous examples, and in the examples to follow (FIG. 28B). Then, we combined 21 enriched lysates with equal molar concentrations of each enzyme, supplemented the mixture with the necessary cofactors and substrates to convert malonyl-CoA to andrimid and observed biosynthesis by LC-MS (FIG. 28C). This work validates our unit operations framework to construct pathways to novel antibiotics.

C. References for Example 3

1. Dudley Q M, Anderson K C, Jewett M C. Cell-Free Mixing of *Escherichia coli* Crude Extracts to Prototype and Rationally Engineer High-Titer Mevalonate Synthesis. ACS synthetic biology. 2016; 5(12):1578-88. doi: 10.1021/acssynbio.6b00154.

2. Karim A S, Jewett M C. A cell-free framework for rapid biosynthetic pathway prototyping and enzyme discovery. Metabolic engineering. 2016; 36:116-26. doi: 10.1016/j.ymben.2016.03.002.

3. Jin M, Fischbach M A, Clardy J. A biosynthetic gene cluster for the acetyl-CoA carboxylase inhibitor andrimid. J Am Chem Soc. 2006; 128(33): 10660-1. doi: 10.1021/ja063194c. PubMed PMID: 16910643; PubMed Central PMCID: PMCPMC2529255.

Example 4—Cell-Free Synthesis of Enterobactin

A. Abstract

Figure 29:
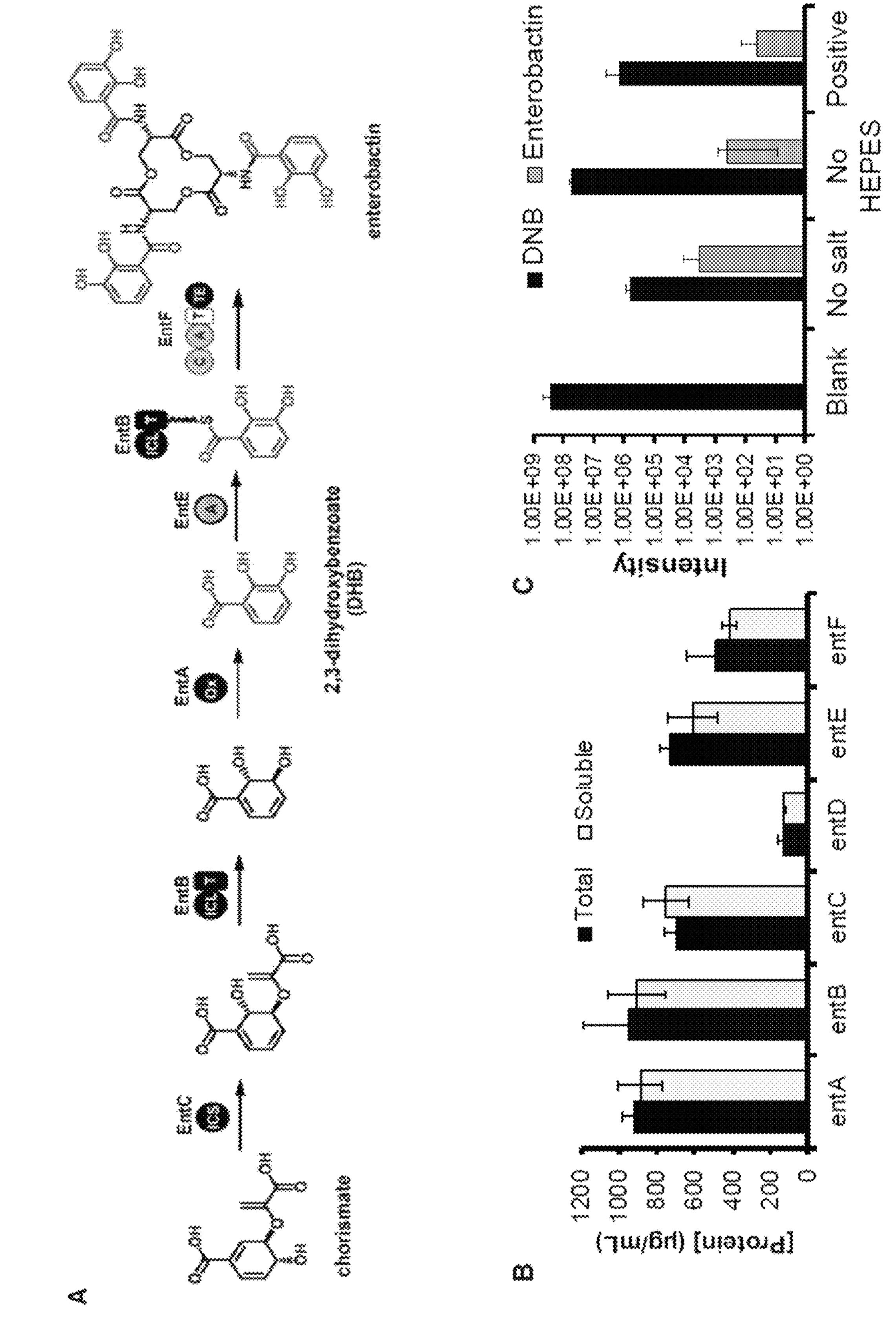
FIG. 29. Characterization of Enterobactin biosynthetic pathway. (A) Schematic representation of enterobactin biosynthetic pathway. (B) CFPS analysis of total and soluble yields of each enzyme in the enterobactin biosynthetic gene cluster. (C) CFPS reactions including EntE, EntB, and EntF were mixed with DHB, HEPES buffer, $Mg^{2+}$, $NH_4^+$, and $K^+$ salts (Positive). Salts and HEPES were also individually left out. A blank was included containing only *E. coli* extract. After 20 h reactions, samples were analyzed for DHB and enterobactin by LC-MS. (D) MS2 spectrum for a CFPS reaction including EntE, EntB, EntF, DHB, HEPES buffer, $Mg^{2+}$, $NH_4^+$, and $K^+$ salts (Positive) and a commercial standard are shown.

We studied cell-free production of enterobactin, a siderophore naturally produced by *E. coli* in iron limited environments but not in cell-free extracts. This pathway involves six proteins EntA-F to create the cyclic enterobactin (FIG. 29A). As described in the previous Examples and in the Examples that follow, we first expressed each of the six enzymes via CFPS and were able to produce near gram per liter quantities for many of these proteins (FIG. 29B). From here we validated the activity of the last steps of the pathway requiring EntB, EntE, and EntF (see FIG. 29A). We produced each of these enzymes separately by CFPS as describe previously, mixed them under different physiochemical conditions, and supplied dihydroxybenzoate (DHB) to initiate the reaction. After 20 h of incubation at 30° C. we observed enterobactin and DHB by LC-MS. Accordingly, enterobactin can be made in cell-free systems from in vitro-expressed EntB, EntE, and EntF (FIG. 29C-D), with yields in the range of ~0.1 μg/L.

Example 5—Cell-Free Biosynthesis of Styrene

A. Abstract

Styrene is an important petroleum-derived molecule that is polymerized to make versatile plastics, including disposable silverware and foamed packaging materials. Finding more sustainable methods, such as biosynthesis, for producing styrene is essential due to the increasing severity of climate change as well as the limited supply of fossil fuels. Recent metabolic engineering efforts have enabled the biological production of styrene in *Escherichia coli*, but styrene toxicity and volatility greatly limit biosynthesis in cells. To address these limitations, we have developed a cell-free styrene biosynthesis platform with the potential for biomanufacturing. Utilizing a cell-free system provides an open reaction environment without cell viability constraints, which allows exquisite control over reaction conditions and greater carbon flux toward product formation rather than cell growth. The two biosynthetic enzymes required for styrene production were generated via cell-free protein synthesis and mixed in defined ratios with supplemented L-phenylalanine and buffer. By altering the time, temperature, pH, and enzyme concentrations in the reaction, this approach increased the cell-free titer of styrene from 5.36 mM to 40.33 mM, an order of magnitude greater than cellular synthesis methods. Cell-free systems offer a complimentary approach to cellular synthesis of small molecules, which can provide particular benefits for producing toxic molecules.

B. Introduction

Metabolic engineering has enabled the production of commodity chemicals and valuable small molecules by genetically modifying microorganisms and overexpressing heterologous enzymes (Keasling, 2010; Nielsen, 2001; Stephanopoulos, 1994; Tyo et al., 2007; Tyo et al., 2010). Target biochemicals, such as butanol (Shen and Liao, 2008) and mevalonate (Martin et al., 2003), are often selected based on their utility for society. An important large-volume commodity chemical is styrene, which is produced globally on the scale of 30 million tons per year; 60% of the product is utilized for molded or foamed polystyrene and the remainder contributes to industrially important copolymers, such as styrene-acrylonitrile and styrene-butadiene (James and Castor, 2011). However, styrene production is an entirely petroleum-derived process that requires large excesses of steam and is responsible for over 100 million tons of greenhouse gas emissions each year (Wu et al., 1981; Zheng and Suh, 2019). Through metabolic engineering of *Escherichia coli*, biosynthesis of styrene from glucose via the shikimate pathway was demonstrated as a potential, sustainable alternative to traditional styrene synthesis, albeit at low titers up to 2.59 mM styrene (McKenna and Nielsen, 2011). Recent efforts utilized genome editing and solvent extraction techniques to increase styrene titers in *E. coli* cultures, but the maximum concentration only reached 3.36 mM (Liu et al., 2018). Clearly, the cellular toxicity of styrene greatly limits biosynthesis titers and the feasibility of commercial styrene synthesis (Araya et al., 2000), so circumventing cellular toxicity could prove useful for the biochemical production of styrene.

Recent advances in cell-free technologies have showcased their utility for studying biological processes and engineering biological systems (Garenne and Noireaux, 2019; Jaroentomeechai et al., 2018; Martin et al., 2018; Silverman et al., 2019). For example, several studies have shown that crude extracts contain native metabolic enzymes and cofactor regeneration responsible for robust cell-free protein synthesis (Caschera and Noireaux, 2014; Jewett et al., 2008; Jewett and Swartz, 2004) and activation of key metabolic reactions in the cell-free environment (Dudley et al., 2015; Jewett and Swartz, 2004; Karim et al., 2018). In fact, cell-free systems have been used for biosynthesis of a wide variety of molecules, including 2,3-butanediol (Kay and Jewett, 2015), mevalonate (Dudley et al., 2016), n-butanol (Karim and Jewett, 2016), terpenes (Dudley et al., 2019; Korman et al., 2017), and polyhydroxyalkanoates (Kelwick et al., 2018). Cell-free systems provide an open reaction environment and rapid design-build-test cycles to reconstitute biosynthetic pathways in vitro to compliment and inform metabolic engineering efforts in cells (Bundy et al., 2018; Dudley et al., 2015; Gregorio et al., 2019; Hodgman and Jewett, 2012; Karim and Jewett, 2016). More importantly, cell-free systems have shown improved tolerance to toxic small molecules compared to living systems (Kay and Jewett, 2019), providing evidence that cell-free biomanufacturing platforms may be advantageous when cellular systems prove impractical.

Figure 30:
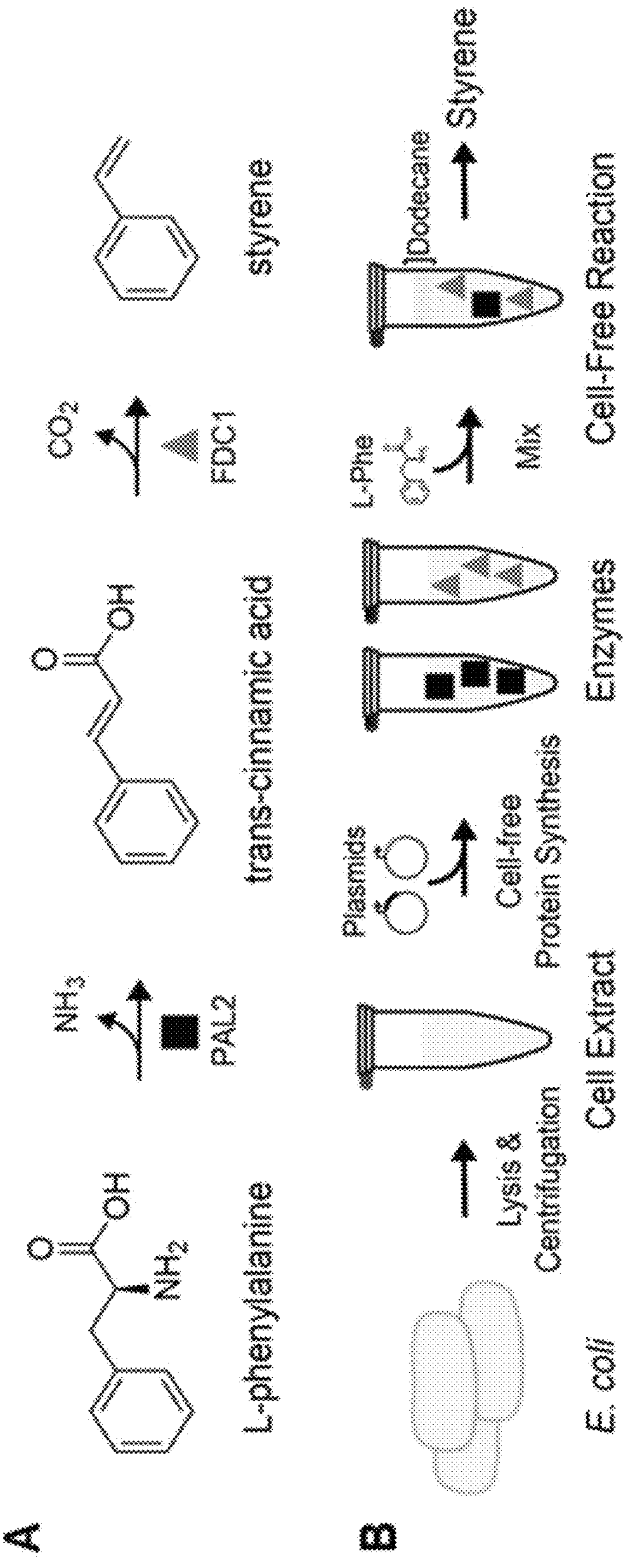
FIG. 30. Enzymatic conversion of L-phenylalanine to styrene. (A) A two-step conversion is catalyzed by phenylalanine ammonia lyase (PAL2) and ferulic acid decarboxylase (FDC1) to produce styrene with ammonia and carbon dioxide as byproducts. (B) The enzymes were synthesized with *E. coli* cell extract and mixed with phenylalanine in quantifiable proportions.

In this work, we established a cell-free platform for styrene biosynthesis to increase the achievable titer in biological systems by circumventing the toxicity limits of styrene in vivo. We constructed this system in two parts. First, we used cell-free protein synthesis in *E. coli* crude extracts to express the two non-native enzymes required to convert L-phenylalanine (L-Phe) to styrene: phenylalanine ammonia lyase 2 (PAL2) from *Arabidopsis thaliana* and ferulic acid decarboxylase 1 (FDC1) from *Saccharomyces cerevisiae* (Liu et al., 2018; McKenna and Nielsen, 2011). Next, we combined these extracts enriched with biosynthetic enzymes with L-Phe and buffer to produce styrene in vitro (FIG. 30). We further optimized the cell-free system by tuning enzyme ratios, reaction temperature, and reaction pH of these reactions to reach styrene titers over 40 mM, an order of magnitude greater than previous cellular efforts. We anticipate this work will expand the application space of cell-free systems and spur new research efforts in the metabolic engineering of toxic chemicals.

C. Materials and Methods

1. Bacterial Strains and Plasmids

Plasmid propagation was performed in *E. coli* DH5α (NEB), and in vitro enzyme expression was performed in cell extract prepared from *E. coli* BL21 Star (DE3) (Life Technologies). Plasmid pSpal2At, containing the PAL2 gene from *Arabadopsis thanliana*, was a gift from David Nielsen (Addgene plasmid 78286). This gene was cloned into the pJL1 plasmid (Addgene plasmid 69496) using Gibson Assembly after PCR amplification with oligonucleotides from IDT (5'-tttaagaaggagatatacatATGGATCAAATCGAAGCAATG-3' (SEQ ID NO: 102) and 5'-tttgttagcagccggtcgacTTAGCAAATCGGAATCGG-3' (SEQ ID NO:103)). The FDC1 gene from *Saccharomyces cerevisiae* was synthesized and cloned into the pJL1 plasmid for expression by Twist Biosciences. Sequences of the PAL2 gene (SEQ ID NO:1) and FDC1 gene (SEQ ID NO:2)_are provided in the Table of FIG. 39. Propagated plasmids were purified using the ZymoPURE Plasmid Miniprep Kit (Zymo Research).

2. Cell Extract Preparation

*E. coli* extracts were prepared as previously described. (Karim and Jewett, 2018; Kwon and Jewett, 2015) In brief, BL21 Star (DE3) cells (Life Technologies) grown in 1 L of 2×YTPG media in full-baffle shake flasks at 37° C. At an $OD_{600}$ of 0.4, 1 mM of IPTG was added to induce T7 RNA polymerase production. Cells were harvested at an $OD_{600}$ of 3.0. Cells were pelleted via centrifugation at 5,000 g for 10 minutes at 4° C., washed three times with cold S30 buffer (10 mM tris acetate, pH 8.2; 14 mM magnesium acetate; 60 mM potassium acetate; and 1 mM dithiothreitol), flash-frozen with liquid nitrogen, and stored at −80° C. For lysis, cells were thawed on ice and resuspended in 1 mL of S30 buffer per gram wet cell mass and then lysed in an EmulsiFlex-B15 homogenizer (Avestin) in a single pass at a pressure of 20,000-25,000 psi. Cellular debris was removed by two rounds of centrifugation at 12,000 g for 30 minutes at 4° C., and the final supernatant was flash-frozen with liquid nitrogen and stored at −80° C. until use.

3. Cell-Free Protein Synthesis (CFPS) Reactions

CFPS reactions for in vitro production of enzymes were assembled with 6 nM template DNA, 10 mg/mL E. coli extract, and the cofactors and crowding agents in 57 mM HEPES buffer. These reactions contained 8 mM magnesium glutamate; 10 mM ammonium glutamate; 130 mM potassium glutamate; 1.2 mM adenosine triphosphate; 0.85 mM each of guanosine, uridine, and cytidine triphosphates; 0.034 mg/mL folinic acid; 0.171 mg/mL transfer RNAs; 33.33 mM phosphoenolpyruvate; 2 mM of all 20 canonical amino acids; 0.40 mM nicotinamide adenine dinucleotide; 0.27 mM cofactor A; 1 mM putrescine; 1.5 mM spermidine. (Jewett and Swartz, 2004) The expression level of each enzyme was quantified using radioactive leucine incorporation assays as previously described. (Jewett et al., 2008) All reagents and chemicals were purchased from Sigma-Aldrich unless otherwise specified.

4. Cell-Free Metabolic Engineering (CFME) Reactions

Styrene biosynthesis reactions contained 8 mM magnesium glutamate, 10 mM ammonium glutamate, 134 mM potassium glutamate, 100 mM BisTris buffer, 0.5 mM kanamycin, varying concentrations of PAL2 and FDC1 enzymes from CFPS ranging from 0.05 to 1 μM, and 25 or 50 mM L-Phe. A layer of dodecane was placed atop the reaction to capture volatile styrene. (Dudley et al., 2019)

5. Metabolite Analysis

Figure 34:
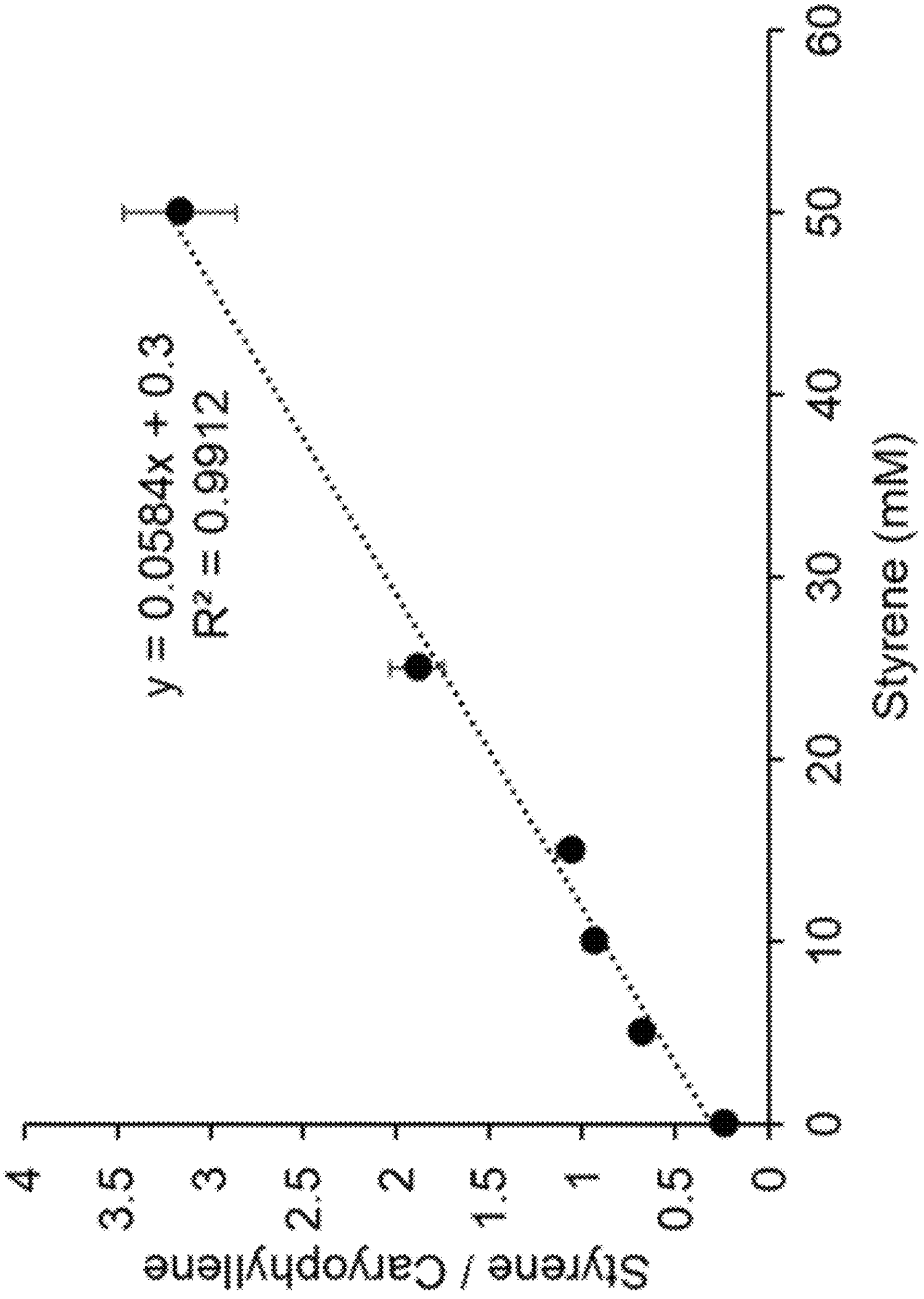
FIG. 34. Styrene standard curve for GC-MS analysis. Dilutions of styrene dissolved in dodecane were mixed with mock cell-free reactions containing GFP in place of biosynthetic enzymes to emulate the composition of experimental samples. In standards and samples, styrene counts were normalized to the trans-caryophyllene internal standard in the ethyl acetate loading solvent. Error bars represent standard deviation of 3 technical replicates.

Styrene was quantified by diluting 20 μL of dodecane overlay into 200 μL of ethyl acetate containing 0.5 mM trans-caryophyllene (Sigma) as an internal standard. 1 L of this mixture was injected into an Agilent 7890A Gas Chromatograph with 5977A MSD (Agilent, Santa Clara, CA) using an Agilent HP-5MS (30 m length×0.25 mm i.d.×0.25 m film) column with helium carrier gas at constant flow of 1 mL-min-1. The inlet temperature was 70° C. and initial column temperature held at 70° C. for 1 minute, increased at 25° C. min-1 to 250° C., and maintained at 250° C. for 3 minutes. The injection volume was 1 L with a split ratio of 20:1. Extracted ion chromatograms (EIC) for 104 m/z (styrene, peak at 2.97 min) and 133 m/z (caryophyllene, peak at 6.34 min) were integrated using Agilent MassHunter Quantitation Analysis software. Concentrations were determined by use of a standard curve (FIG. 34) generated by comparison to styrene (Sigma) standards mixed in dodecane with mock cell-free reactions containing green fluorescent protein in place of the biosynthetic enzymes that were incubated for 24 hours (Dudley et al., 2019).

6. pH Measurements

Samples were analyzed with a Thermo Scientific™ Orion™ ROSS Ultra™ Refillable pH/ATC Triode™. Reactions for which a pH was set prior to reaction start were measured with a mixture of all components except the enzyme-enriched CFPS reactions to avoid premature reaction initiation. Reaction pH was adjusted with glacial acetic acid or 5 N KOH as necessary. Measurements of pH over time were taken after sampling reactions for metabolite analysis.

7. Metabolite Quantification by HPLC

Reactions were quenched by adding 10% w/v tricholoacetic acid (Sigma) in a 1:1 ratio. Precipitated proteins were pelleted by centrifugation at 21,000 g for 10 minutes at 4° C., and 20 L of the supernatant was removed for analysis by high-performance liquid chromatography (HPLC). L-Phe was measured with an Agilent 1260 series HPLC system (Agilent, Santa Clara, CA) via a refractive index (RI) detector after passing through a reverse-phase Hypersil Gold column (4.6 mm×150 mm; Thermo Fisher, USA). 5 L from the prepared samples were injected at a total constant flow rate of 1 mL/min and temperature of 45° C. The column was operated with water (solvent 1) and methanol plus 0.1% trifluoroacetic acid (solvent 2). The eluent began as a mixture of 95% solvent 1 and 5% solvent 2 before a linear gradient was applied over 8 minutes to reach a mixture of 20% solvent 1 and 80% solvent 2. This composition was held constant for 2 minutes before a second linear gradient was applied over the course of 4 minutes to return to its initial composition of 95% solvent 1 and 5% solvent 2.

D. Results & Discussion

To establish a cell-free platform for styrene biosynthesis, we took a two-pronged approach: first establishing enzyme synthesis and pathway assembly, and then optimizing physiochemical conditions for improved production.

1. Enzyme Synthesis and Styrene Pathway Assembly

Figure 31:
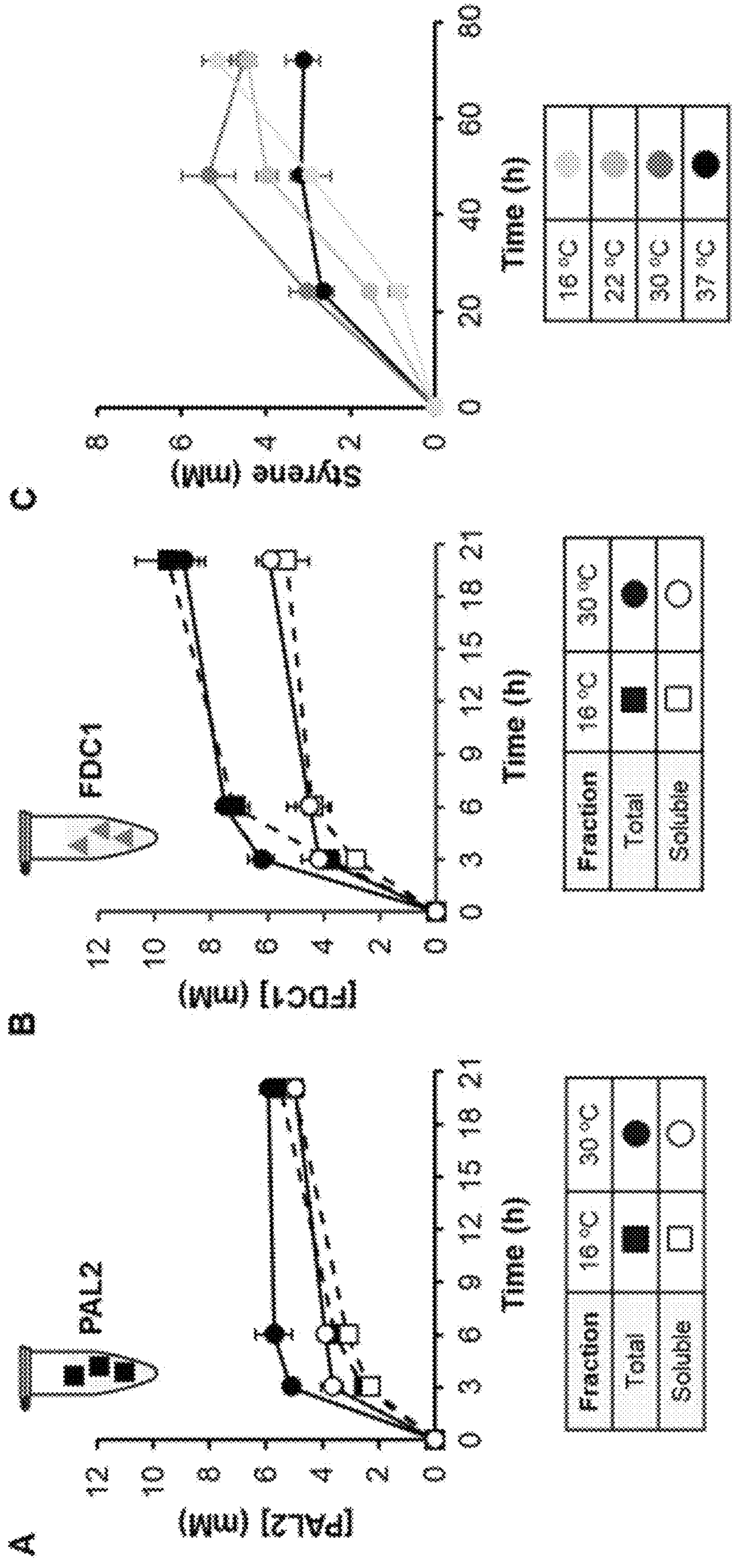
FIG. 31. Expression and activity of the styrene biosynthetic pathway. Expression of PAL2 (A) and FDC1 (B) was assessed by radioactive leucine incorporation, and soluble enzyme fractions were used for subsequent quantification of enzyme concentrations. (C) Combining 0.5 μM PAL2 and FDC1 enabled styrene production, and the maximum titer of 5.36 mM was produced after 48 hours at 30° C. Error bars represent standard deviation (A-B) or standard error (C) of 3 technical replicates.

We first demonstrated the ability to express functional enzymes for this biosynthetic pathway in vitro and to reliably capture the volatile styrene product. Cell-free protein synthesis (CFPS) enables rapid production of the enzymes for styrene biosynthesis, PAL2 and FDC1 (FIG. 31A-B). Using CFPS, we produced 4.99±0.36 μM soluble PAL2 and 5.93±0.47 μM soluble FDC1 over the course of a 20-hour reaction at 30° C. In an attempt to express greater soluble fractions of PAL2 and FDC1, we decreased the temperature of the reactions from the standard 30° C. to 16° C. The decreased temperature increased enzyme solubility at 6 h from ~70% to ~80% for PAL2 and from ~60% to ~67% for FDC1. For both temperatures, a majority (~80%) of the soluble protein made during the reaction is produced by 6 h. Therefore, we chose to run CFPS reactions at 16° C. and stop reactions at 6 h to accelerate the workflow while still obtaining sufficient concentrations of soluble enzymes for all subsequent reactions.

Figure 35:
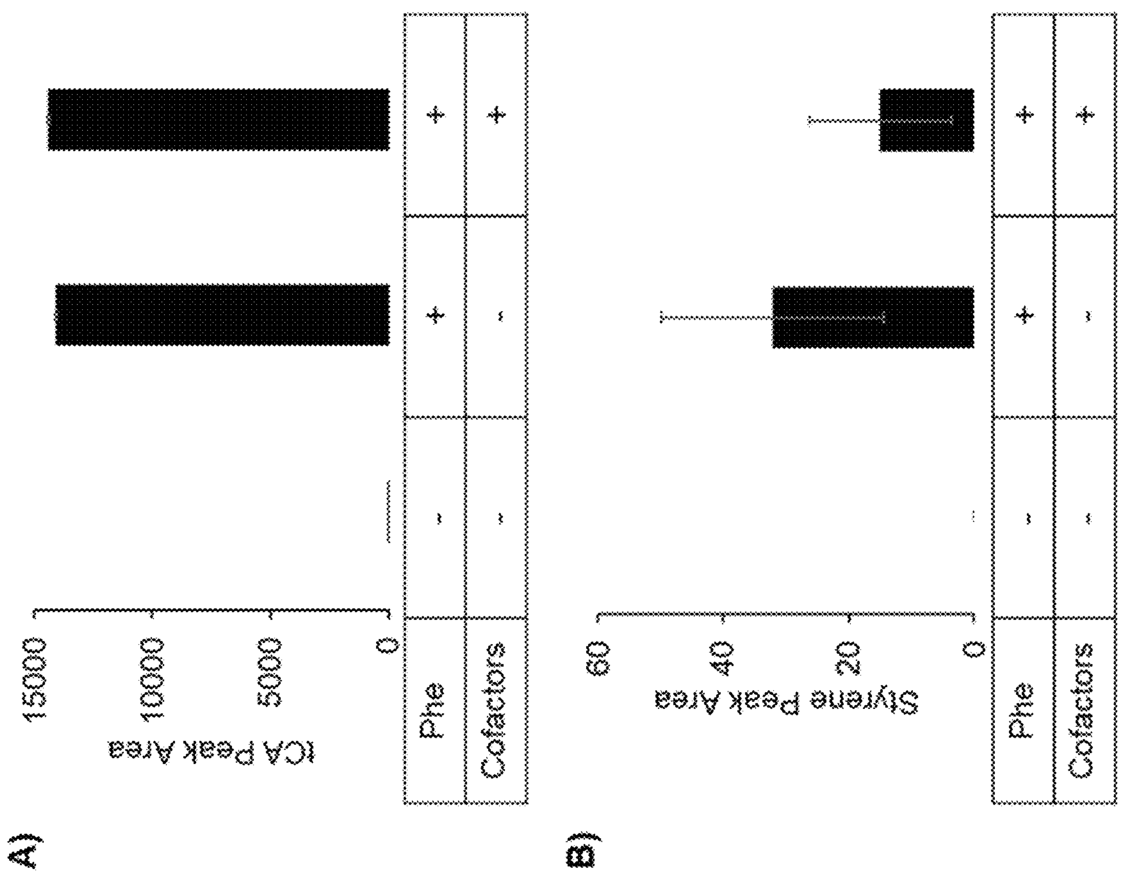
FIG. 35. Verification of enzyme activity. (A) HPLC analysis indicated PAL2 activity in vitro is independent of cofactors, which included 1 mM ATP, NAD, and Coenzyme A. (B) FDC1 is active in the presence of PAL2, but styrene quantification in later experiments was performed using GC-MS for greater accuracy. Error bars represent standard deviation of 2 technical replicates.
Figure 36:
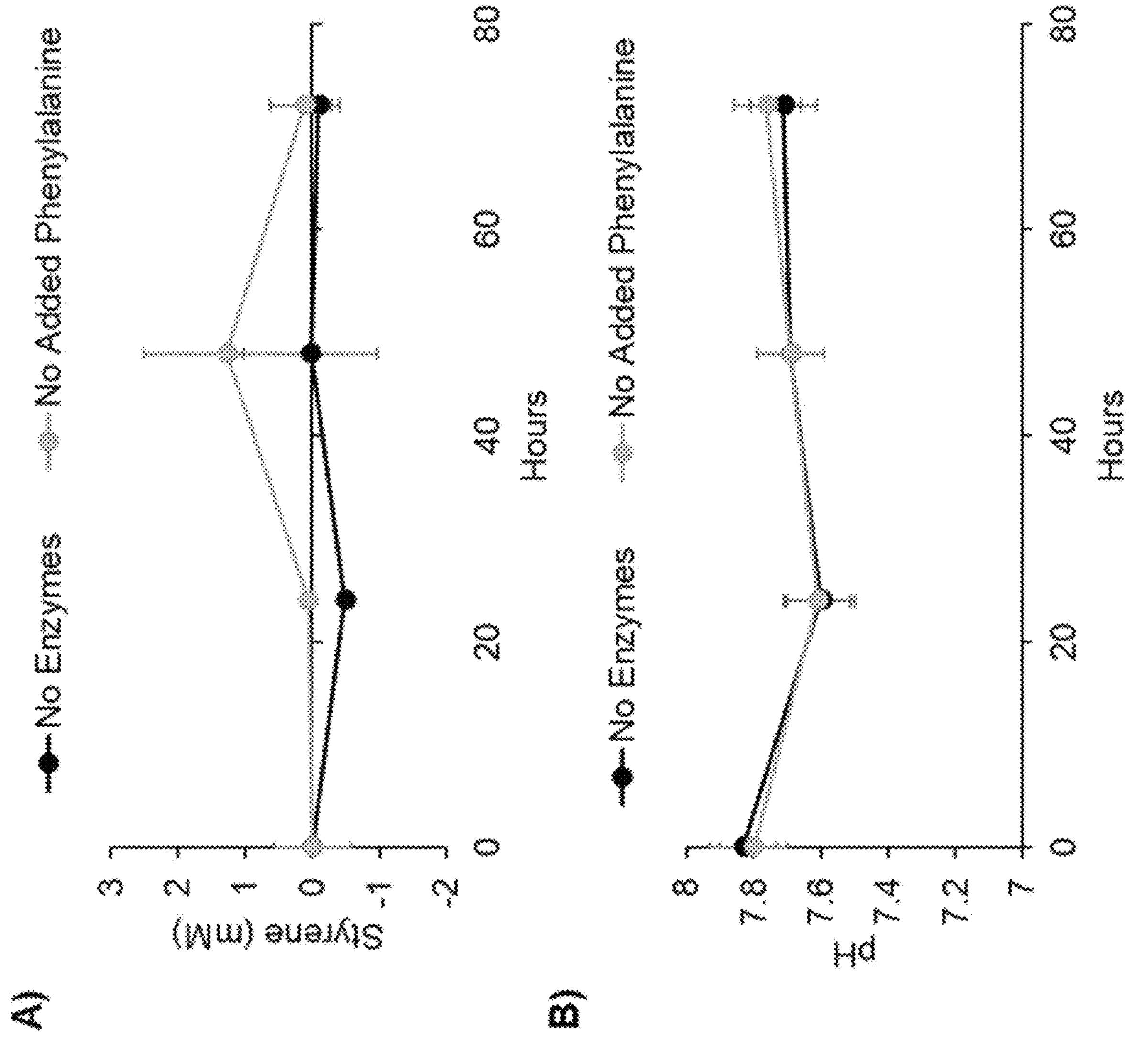
FIG. 36. Styrene biosynthesis requires exogenous enzymes. (A) Reactions without PAL2 and FDC1 or additional phenylalanine do not produce styrene. (B) The pH of these reactions changes little over time, as expected without active glycolysis. Error bars represent standard deviation of 3 technical replicates.
Figure 37:
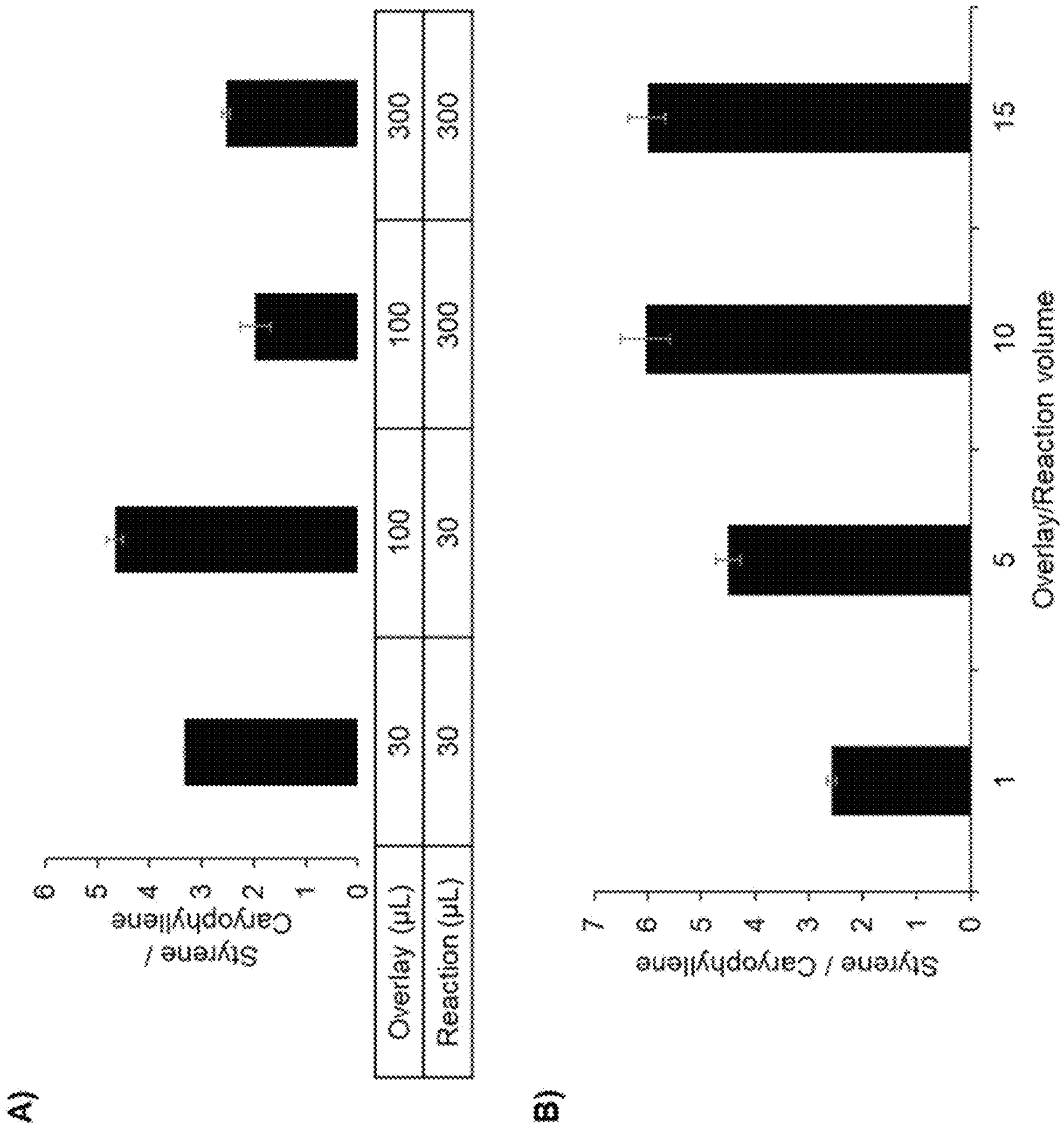
FIG. 37. Capturing styrene with dodecane. (A) Due to the insolubility of styrene in aqueous solutions, a dodecane layer above the reactions was required to trap the product. Altering the reaction and overlay volumes impacted the amount of styrene captured relative to the internal standard, caryophyllene. (B) For 30 L reactions, larger overlays did not inhibit styrene synthesis and captured a greater proportion of styrene per microliter sampled. These reactions contained 0.5 μM PAL2 and FDC1. Error bars represent standard deviation of 3 technical replicates.

To test for activity, we ran several reactions measuring phenylalanine conversion and styrene production. We confirmed that cell-free expressed PAL2 alone converts L-Phe to trans-cinnamic acid (FIG. 35A) and PAL2 combined with FDC1 produces styrene (FIG. 35B) as determined by HPLC. Additionally, no styrene is produced in cell-free reactions lacking the exogenous enzymes and supplemental L-Phe (FIG. 36). Accurate quantification of styrene can be difficult due to its volatility and lack of solubility in aqueous media; therefore, we ran our reactions with a dodecane overlay to capture styrene and detect it by GC-MS. This approach is often used to extract volatile compounds from both in vivo (Liu et al., 2018) and in vitro (Dudley et al., 2019) systems. We found that larger ratios of overlay to reaction volume enabled greater styrene recovery relative to the trans-caryophyllene internal standard without inhibiting biosynthesis (FIG. 37).

After demonstrating enzyme activity and the ability to measure styrene, we investigated the best temperature during the biosynthesis segment of the reaction for producing styrene. After cell-free expression of PAL2 and FDC1, we mixed the enzymes in a second pot reaction at a final concentration of 0.5 μM each. We then incubated reactions containing 25 mM L-Phe at 16, 22, 30, and 37° C. (FIG. 31C). The rate of styrene production was highest at 30° C. and produced a maximum titer of 5.36 mM styrene after 48 hours. This titer demonstrates a ~1.5-fold increase over the observed inhibitory concentration of styrene for E. coli (Liu et al., 2018), confirming the potential for this cell-free platform to produce toxic compounds.

2. Optimization of Enzyme Ratio and Physiochemical Conditions

Figure 38:
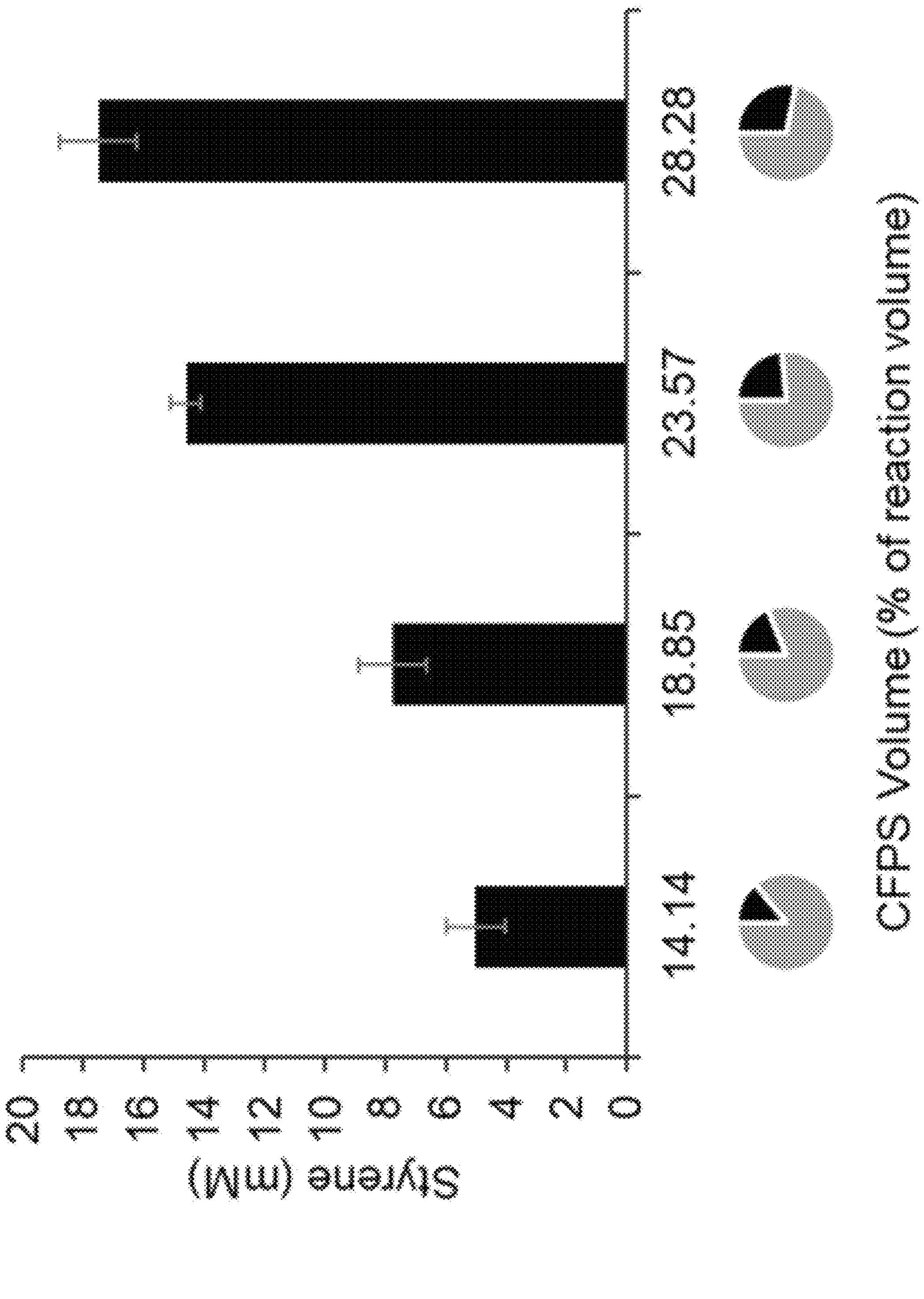
FIG. 38. Assessing the addition of blank CFPS reactions. Reactions in FIG. 33 contained various volumes of CFPS reactions without plasmid so that all reactions contained the same total volume of CFPS regardless of enzyme concentration. For reactions with 0.5 μM enzymes and 25 mM L-phenylalanine, additional CFPS volume increased final styrene titer, which accounts for the difference in titers achieved in FIG. 32 (with 14% CFPS) and FIG. 33 (with 28% CFPS). Error bars represent standard deviation of 3 technical replicates.

We stepped through series of optimizations to improve cell-free styrene synthesis by exploiting the open reaction environment which enables precise control over enzyme concentrations and physiochemical conditions (Karim et al., 2018; Karim and Jewett, 2016). Consistent with our previous work, we first normalized the total volume of CFPS added to a biosynthesis reaction by supplementing with CFPS mixtures without plasmid. By doing this, we minimize detrimental effects that additional CFPS volume, specifically the additional small molecules, tends to cause (e.g., decreased final titers of the desired product) (Karim et al., 2018). However, we also wanted test whether this is universally true or potentially specific to previously studied pathways. We found that biosynthesis reactions with increasing amounts of CFPS fraction result in increased styrene production (FIG. 38). Our reactions are less inhibited by the CFPS mixtures likely because we are observing a two-step biosynthesis from L-Phe rather than longer pathways that take advantage of glycolysis that are known to have competition with several pathways branching from pyruvate and acetyl-CoA. These results suggest that the impact of CFPS reagents should be investigated for each new biosynthetic pathway tested in vitro.

Figure 32:
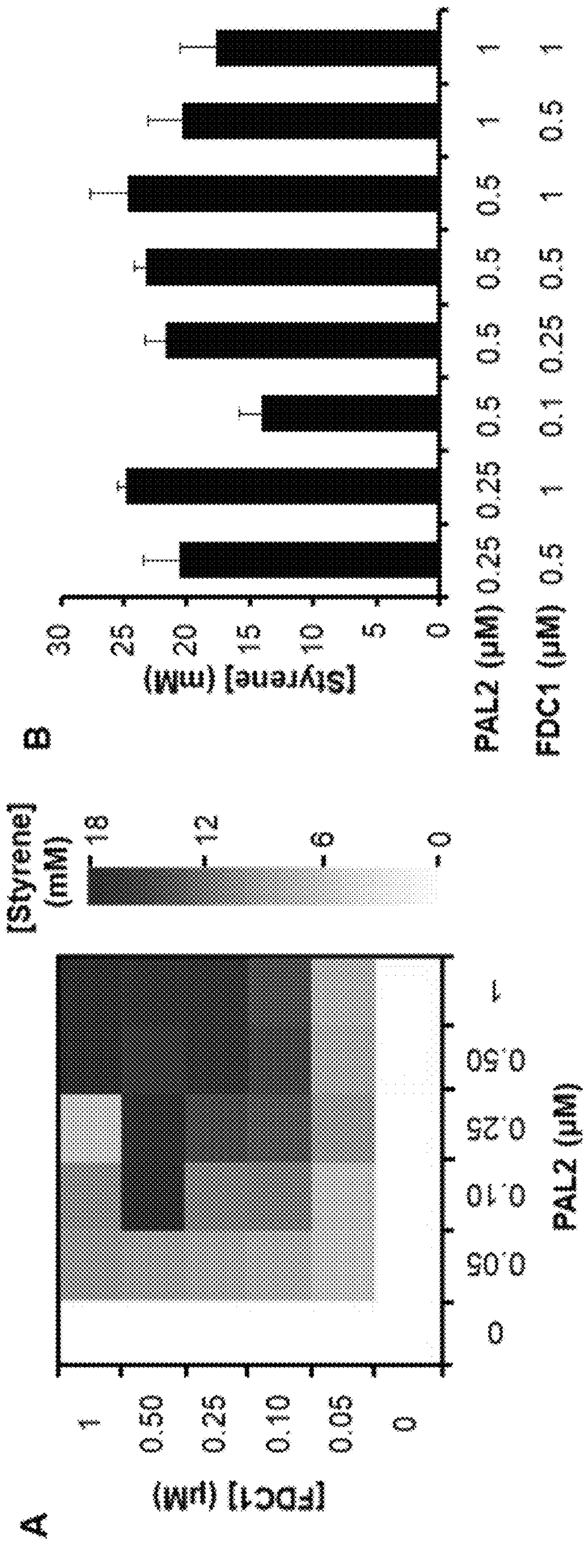
FIG. 32. Modulating enzyme concentrations enhances styrene biosynthesis. (A) Increasing the concentration of each enzyme increased the final titer, as expected. (B) All conditions producing more than 16 mM styrene from 25 mM L-Phe were run with 50 mM L-Phe to identify the optimal enzyme ratio—0.25 μM PAL2 with 1 μM FDC1. Error bars represent standard deviation of 3 technical replicates.

We next decided to tune the biosynthetic enzyme ratio by mixing different volumes of cell-free expressed PAL2 and FDC1 in the reactions. We ran 36 unique reaction conditions varying the final PAL2 and FDC1 concentrations from 0 to 1 μM (FIG. 32A). The best condition produced up to 18.03+/−2.34 mM styrene from 25 mM of added L-Phe. As hypothesized, styrene titer generally increased with increasing enzyme concentrations. However, the best 8 enzyme ratios all produced 16-18 mM styrene, which suggested substrate limitation may prevent higher titers. We doubled the initial concentration of added L-Phe to 50 mM and ran reactions using the top eight enzyme ratio combinations in an attempt to further increase styrene yield. The best reaction condition produced 24.83+/−0.66 mM styrene with 0.25 μM PAL2 and 1 μM FDC1 (FIG. 32B). Increasing the substrate concentration enabled differentiation between the best conditions with 25 mM L-Phe in FIG. 32A, but the modest 6-7 mM increase in product from 25 mM additional substrate indicated diminishing biosynthetic potential; thus, L-Phe concentrations greater than 50 mM were not examined.

3. Optimization of Physiochemical Conditions

Figure 33:
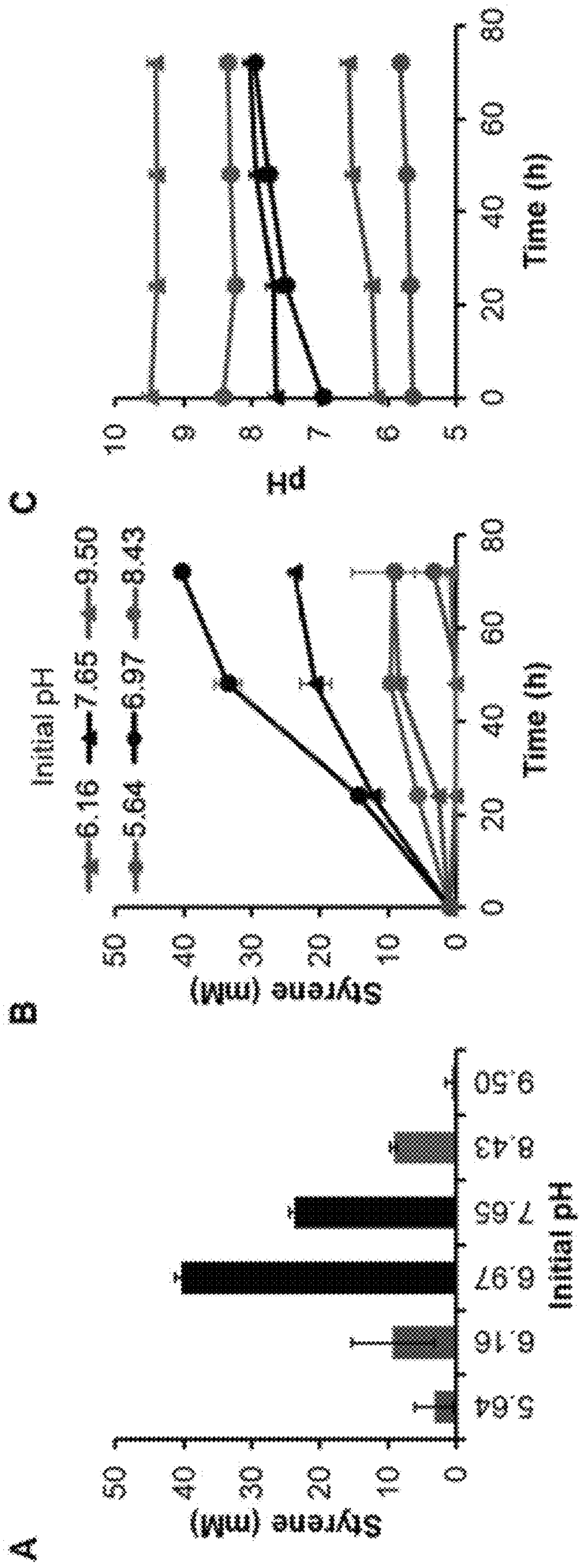
FIG. 33. Styrene biosynthesis is highly pH dependent. Cell-free reactions containing 0.25 μM PAL2 and 1 μM FDC1 were set with several initial pH values and produced a large range of styrene titers. (A) Endpoint titers after 72 hours indicate a clear optimum for reactions starting at neutral pH. (B) The rate of styrene synthesis diminished as the pH deviated from neutral. (C) pH changed little over the course of the reactions. Error bars represent standard deviation of 3 technical replicates.

To further optimize the reaction environment for styrene biosynthesis, we explored a range of acidic and alkaline conditions due to the dramatic changes that pH can cause in cell-free systems (Calhoun and Swartz, 2005; Karim et al., 2019). We tested six different initial pH conditions in reactions for styrene synthesis ranging from pH 5.6 to pH 9.5. Our standard condition began at pH 7.5-7.8 and ended near pH 8 (FIG. 33; dark blue). We observed a strong pH dependence for styrene biosynthesis across the broad pH range, with a maximum titer of 40.33+/−1.03 mM styrene after 72 hours between pH 7 and pH 8 (FIG. 33A). The most alkaline reaction (pH 9.5) produced less than 1 mM styrene, whereas the most acidic reaction (pH 5.6) produced 3.27+/−2.85 mM styrene—nearly equivalent to the highest reported titer from in vivo biosynthesis (Liu et al., 2018). Reaction rates remained steady over 3 full days, which was considerably slower than the reported catalytic rates of purified PAL2 and FDC1 (FIG. 33B) (Cochrane et al., 2004; Payne et al., 2015). Although enzyme behavior can differ in vitro between purified systems and our crude cell extracts, the observed pH optimum for styrene biosynthesis lies within a reasonable range based on reported pH optima of 8.4-8.9 and 6.5 for PAL2 and FDC1, respectively (Cochrane et al., 2004; Lin et al., 2015). Additionally, the reaction pH changed very little over time without active glycolysis producing acetate and lactate, which provided a stable reaction environment without the need for a strong buffer (FIG. 33C).

E. Conclusion

In this study, we demonstrated the substantial increase in styrene titer possible in a cell-free system compared to in vivo biosynthesis through the optimization of reaction temperature, enzyme ratios, and pH. We first determined that PAL2 and FDC1 expressed by *E. coli* CFPS were soluble and active in vitro and that, in combination, these enzymes produced the most styrene at 30° C. Second, we found that cell-free styrene biosynthesis was maximized by combining a low concentration of PAL2 with a high concentration of FDC1, which would maximize conversion of trans-cinnamic acid to styrene. Third, we highlighted the pH sensitivity of in vitro styrene biosynthesis and found that reactions maintained at a neutral pH produced the highest concentration of monomer. These cell-free reactions achieved a maximum styrene titer of 40.33 +/−1.03 mM (4.20+/−0.11 g/L), which surpasses the highest published in vivo titer of 3.36 mM (0.350 g/L) by more than an order of magnitude (Liu et al., 2018). Such high titers of the toxic styrene monomer are possible due to the lack of viability constraints in a cell-free system and the ability to finely tune the reaction environment, which makes this system a powerful example of cell-free biosynthesis as an alternative to traditional methods.

Although the optimal pH for styrene biosynthesis was within a range consistent with the optima for the PAL2 and FDC1 homologs used, the overall reaction rate appeared much slower than expected (Cochrane et al., 2004; Payne et al., 2015). The observed rate of styrene synthesis could be slowed by a number of variables in the complex cell-free reactions, such as an altered chemical environment caused by the dodecane overlay and thermodynamic constraints for PAL2 due to the ammonium salts from CFPS, since ammonia is a byproduct of L-Phe to trans-cinnamic acid conversion. Regardless, the potential impact of this environmentally friendly styrene production method could be further increased by using glucose as the substrate in cell extract from an *E. coli* strain engineered with a highly active shikimate pathway to overproduce L-Phe (Averesch and Kromer, 2018). Enzymes constituting the shikimate pathway could also be produced via CFPS to allow greater control over metabolic flux. With glucose as the initial substrate, it may be necessary to balance styrene recovery in the dodecane with potential oxygen transfer limitations across the overlay, which could slow glycolysis. However, given that L-phenylalanine is an abundant and inexpensive feedstock for synthesizing value-added products, investigating a complete recreation of the styrene biosynthesis pathway is not critical at this time.

For increased potential as a biomanufacturing platform, a strategy for direct styrene polymerization could be investigated. Styrene readily polymerizes in organic solvents upon heating in the presence of a radical initiator, such as benzoyl peroxide, due to the vinyl group (Abere et al., 1945). Replacing the dodecane overlay used for styrene extraction in this study with toluene could enhance the solubility of biosynthesized styrene as the solvent is heated. Despite the substantial increase in titer achieved using a cell-free system, these microliter-scale reactions cannot feasibly produce styrene in the large quantities currently derived from petroleum (James and Castor, 2011). Fortunately, larger scales are possible with cell-free protein synthesis scaling linearly up to 100 L (Zawada et al., 2011), although increasing the scale of biosynthesis reactions with a hydrocarbon overlay presents technical challenges. Furthermore, reaching the capacity of petrochemical plants would not be necessary since smaller scale biomanufacturing facilities would still benefit from an economy of scale for feedstocks while simultaneously reducing capital risk and market saturation (Claypool et al., 2014).

At the laboratory scale, this example of high-titer styrene biosynthesis demonstrates the potential of cell-free systems for the production of toxic compounds that normally originate from petroleum-based processes. Expanding the cell-free approach to producing more value-added chemicals, such as other plastic precursors and biofuels, and increasing the scale of these reactions could spearhead the development of economically viable alternatives to fossil fuel-derived chemicals.

F. REFERENCES FOR EXAMPLE 5

Abere, J., Goldfinger, G., Naidus, H., Mark, H., 1945. Polymerization of Styrene under Various Experimental Conditions. J. Phys. Chem. 49, 211-225.

Araya, P., Chamy, R., Mota, M., Alves, M., 2000. Biodegradability and toxicity of styrene in the anaerobic digestion process. Biotechnology Letters. 22, 1477-1481.

Averesch, N. J. H., Kromer, J. O., 2018. Metabolic Engineering of the Shikimate Pathway for Production of Aromatics and Derived Compounds-Present and Future Strain Construction Strategies. Front Bioeng Biotechnol. 6, 32.

Bundy, B. C., Hunt, J. P., Jewett, M. C., Swartz, J. R., Wood, D. W., Frey, D. D., Rao, G., 2018. Cell-free biomanufacturing. Current Opinion in Chemical Engineering. 22, 177-183.

Calhoun, K. A., Swartz, J. R., 2005. Energizing cell-free protein synthesis with glucose metabolism. Biotechnol Bioeng. 90, 606-13.

Caschera, F., Noireaux, V., 2014. Synthesis of 2.3 mg/ml of protein with an all *Escherichia coli* cell-free transcription-translation system. Biochimie. 99, 162-8.

Claypool, J. T., Raman, D. R., Jarboe, L. R., Nielsen, D. R., 2014. Technoeconomic evaluation of bio-based styrene production by engineered *Escherichia coli*. J Ind Microbiol Biotechnol. 41, 1211-6.

Cochrane, F. C., Davin, L. B., Lewis, N. G., 2004. The *Arabidopsis* phenylalanine ammonia lyase gene family: kinetic characterization of the four PAL isoforms. Phytochemistry. 65, 1557-64.

Dudley, Q. M., Anderson, K. C., Jewett, M. C., 2016. Cell-Free Mixing of *Escherichia coli* Crude Extracts to Prototype and Rationally Engineer High-Titer Mevalonate Synthesis. ACS Synth Biol. 5, 1578-1588.

Dudley, Q. M., Karim, A. S., Jewett, M. C., 2015. Cell-free metabolic engineering: biomanufacturing beyond the cell. Biotechnol J. 10, 69-82.

Dudley, Q. M., Nash, C. J., Jewett, M. C., 2019. Cell-free biosynthesis of limonene using enzyme-enriched *Escherichia coli* lysates. Synth Biol (Oxf). 4, ysz003.

Garenne, D., Noireaux, V., 2019. Cell-free transcription-translation: engineering biology from the nanometer to the millimeter scale. Curr Opin Biotechnol. 58, 19-27.

Gregorio, N. E., Levine, M. Z., Oza, J. P., 2019. A User's Guide to Cell-Free Protein Synthesis. Methods and Protocols. 2.

Hodgman, C. E., Jewett, M. C., 2012. Cell-free synthetic biology: thinking outside the cell. Metab Eng. 14, 261-9.

James, D. H., Castor, W. M., 2011. Styrene. Ullmann's Encyclopedia of Industrial Chemistry.

Jaroentomeechai, T., Stark, J. C., Natarajan, A., Glasscock, C. J., Yates, L. E., Hsu, K. J., Mrksich, M., Jewett, M. C., DeLisa, M. P., 2018. Single-pot glycoprotein biosynthesis using a cell-free transcription-translation system enriched with glycosylation machinery. Nat Commun. 9, 2686.

Jewett, M. C., Calhoun, K. A., Voloshin, A., Wuu, J. J., Swartz, J. R., 2008. An integrated cell-free metabolic platform for protein production and synthetic biology. Mol Syst Biol. 4, 220.

Jewett, M. C., Swartz, J. R., 2004. Mimicking the *Escherichia coli* cytoplasmic environment activates long-lived and efficient cell-free protein synthesis. Biotechnol Bioeng. 86, 19-26.

Karim, A. S., Heggestad, J. T., Crowe, S. A., Jewett, M. C., 2018. Controlling cell-free metabolism through physiochemical perturbations. Metab Eng. 45, 86-94.

Karim, A. S., Jewett, M. C., 2016. A cell-free framework for rapid biosynthetic pathway prototyping and enzyme discovery. Metab Eng. 36, 116-126.

Karim, A. S., Jewett, M. C., 2018. Cell-Free Synthetic Biology for Pathway Prototyping. Methods Enzymol. 608, 31-57.

Karim, A. S., Rasor, B. J., Jewett, M. C., 2019. Enhancing control of cell-free metabolism through pH modulation. Synthetic Biology.

Kay, J. E., Jewett, M. C., 2015. Lysate of engineered *Escherichia coli* supports high-level conversion of glucose to 2,3-butanediol. Metab Eng. 32, 133-142.

Kay, J. E., Jewett, M. C., 2019. A cell-free system for production of 2,3-butanediol is robust to growth-toxic compounds. Metabolic Engineering Communications.

Keasling, J. D., 2010. Manufacturing Molecules Through Metabolic Engineering. Science. 330, 1355-1358.

Kelwick, R., Ricci, L., Chee, S. M., Bell, D., Webb, A. J., Freemont, P. S., 2018. Cell-free prototyping strategies for enhancing the sustainable production of polyhydroxyalkanoates bioplastics. Synthetic Biology. 3.

Korman, T. P., Opgenorth, P. H., Bowie, J. U., 2017. A synthetic biochemistry platform for cell free production of monoterpenes from glucose. Nat Commun. 8, 15526.

Kwon, Y. C., Jewett, M. C., 2015. High-throughput preparation methods of crude extract for robust cell-free protein synthesis. Sci Rep. 5, 8663.

Lin, F., Ferguson, K. L., Boyer, D. R., Lin, X. N., Marsh, E. N., 2015. Isofunctional enzymes PAD1 and UbiX catalyze formation of a novel cofactor required by ferulic acid decarboxylase and 4-hydroxy-3-polyprenylbenzoic acid decarboxylase. ACS Chem Biol. 10, 1137-44.

Liu, C., Men, X., Chen, H., Li, M., Ding, Z., Chen, G., Wang, F., Liu, H., Wang, Q., Zhu, Y., Zhang, H., Xian, M., 2018. A systematic optimization of styrene biosynthesis in *Escherichia coli* BL21(DE3). Biotechnol Biofuels. 11, 14.

Martin, R. W., Des Soye, B. J., Kwon, Y. C., Kay, J., Davis, R. G., Thomas, P. M., Majewska, N. I., Chen, C. X., Marcum, R. D., Weiss, M. G., Stoddart, A. E., Amiram, M., Ranji Charna, A. K., Patel, J. R., Isaacs, F. J., Kelleher, N. L., Hong, S. H., Jewett, M. C., 2018. Cell-free protein synthesis from genomically recoded bacteria enables multisite incorporation of noncanonical amino acids. Nat Commun. 9, 1203.

Martin, V. J., Pitera, D. J., Withers, S. T., Newman, J. D., Keasling, J. D., 2003. Engineering a mevalonate pathway in *Escherichia coli* for production of terpenoids. Nature Biotechnology. 21, 796-802.

McKenna, R., Nielsen, D. R., 2011. Styrene biosynthesis from glucose by engineered *E. coli*. Metab Eng. 13, 544-54.

Nielsen, J., 2001. Metabolic engineering. Applied Microbiology and Biotechnology. 55, 263-283.

Payne, K. A., White, M. D., Fisher, K., Khara, B., Bailey, S. S., Parker, D., Rattray, N. J., Trivedi, D. K., Goodacre, R., Beveridge, R., Barran, P., Rigby, S. E., Scrutton, N. S., Hay, S., Leys, D., 2015. New cofactor supports alpha, beta-unsaturated acid decarboxylation via 1,3-dipolar cycloaddition. Nature. 522, 497-501.

Shen, C. R., Liao, J. C., 2008. Metabolic engineering of *Escherichia coli* for 1-butanol and 1-propanol production via the keto-acid pathways. Metab Eng. 10, 312-20.

Silverman, A. D., Karim, A. S., Jewett, M. C., 2019. Cell-free gene expression: an expanded repertoire of applications. Nat Rev Genet.

Stephanopoulos, G. N., 1994. Metabolic Engineering. Current Opinion in Biotechnology. 5, 196-200.

Tyo, K. E., Alper, H. S., Stephanopoulos, G. N., 2007. Expanding the metabolic engineering toolbox: more options to engineer cells. Trends Biotechnol. 25, 132-7.

Tyo, K. E., Kocharin, K., Nielsen, J., 2010. Toward design-based engineering of industrial microbes. Curr Opin Microbiol. 13, 255-62.

Wu, C., Koylinski, T., Bozik, J., 1981. Preparation of styrene from ethylbenzene U.S. Pat. No. 4,255,599.

Zawada, J. F., Yin, G., Steiner, A. R., Yang, J., Naresh, A., Roy, S. M., Gold, D. S., Heinsohn, H. G., Murray, C. J., 2011. Microscale to manufacturing scale-up of cell-free cytokine production—a new approach for shortening protein production development timelines. Biotechnol Bioeng. 108, 1570-8.

Zheng, J., Suh, S., 2019. Strategies to reduce the global carbon footprint of plastics. Nature Climate Change. 9, 374-378.

Example 6—Cell-Free Synthesis of Gramicidin S

A. Abstract

Genome sequencing has revealed that a far greater number of natural product biosynthetic pathways exist than there are known natural products. To access these molecules directly and deterministically, a new generation of heterologous expression methods is needed. Cell-free protein synthesis has not previously been used to study biosynthesis, and provides a tunable platform with advantages over conventional methods for protein expression. Here, we demonstrate the use of cell-free protein synthesis to biosynthesize a cyclic dipeptide with correct absolute stereochemistry. From a single-pot reaction, we measured the expression of two nonribosomal peptide synthetases larger than 100 kDa, and detected high-level production of a diketopiperazine. Using quantitative LC-MS and synthetically prepared standard, we observed production of this metabolite at levels higher than previously reported from cell-based recombinant expression, approximately 12 mg/mL. Overall, this work illuminates a path forward for the application of cell-free protein synthesis to discovery and characterization of natural product biosynthesis.

B. Introduction

Sequencing of over 10,000 microbial genomes has revealed that the diversity of secondary metabolism covers a largely unexplored region of chemical space[1, 2]. Currently, the rate at which new biosynthetic pathways are identified within biological sequence data greatly outpaces the capacity to characterize the small molecules for which production is encoded. This is at least in part due to the difficulty of cultivating natural product producing organisms in the laboratory, and therefore presents a major opportunity for synthetic biology to establish new methods for robust heterologous expression and characterization of secondary metabolism to unlock access to often bioactive secondary metabolites. Additionally, robust heterologous expression of biosynthetic proteins opens the possibility of rapid design-build-test cycles to re-engineer pathways to produce useful scaffolds beyond those found in nature[3].

Proteins involved in the biosynthesis of complex natural products (NPs) provide a challenge for established heterologous expression platforms because of their sheer size, complex multi-domain structures and occurrence within even larger biosynthetic gene clusters (BGCs). Nonribosomal peptide synthetases (NRPSs) and polyketide synthases (PKSs) are often 100 to >300 kDa proteins that operate like assembly lines, loading and passing covalently attached intermediates between catalytic domains (FIG. 40, center)[4]. Production of NPs by these classes of proteins frequently involves exotic precursors that may not be found in the cytosol of a typical heterologous host such as *Escherichia coli* or *Saccharomyces cerevisiae*[5, 6]

Figure 40:
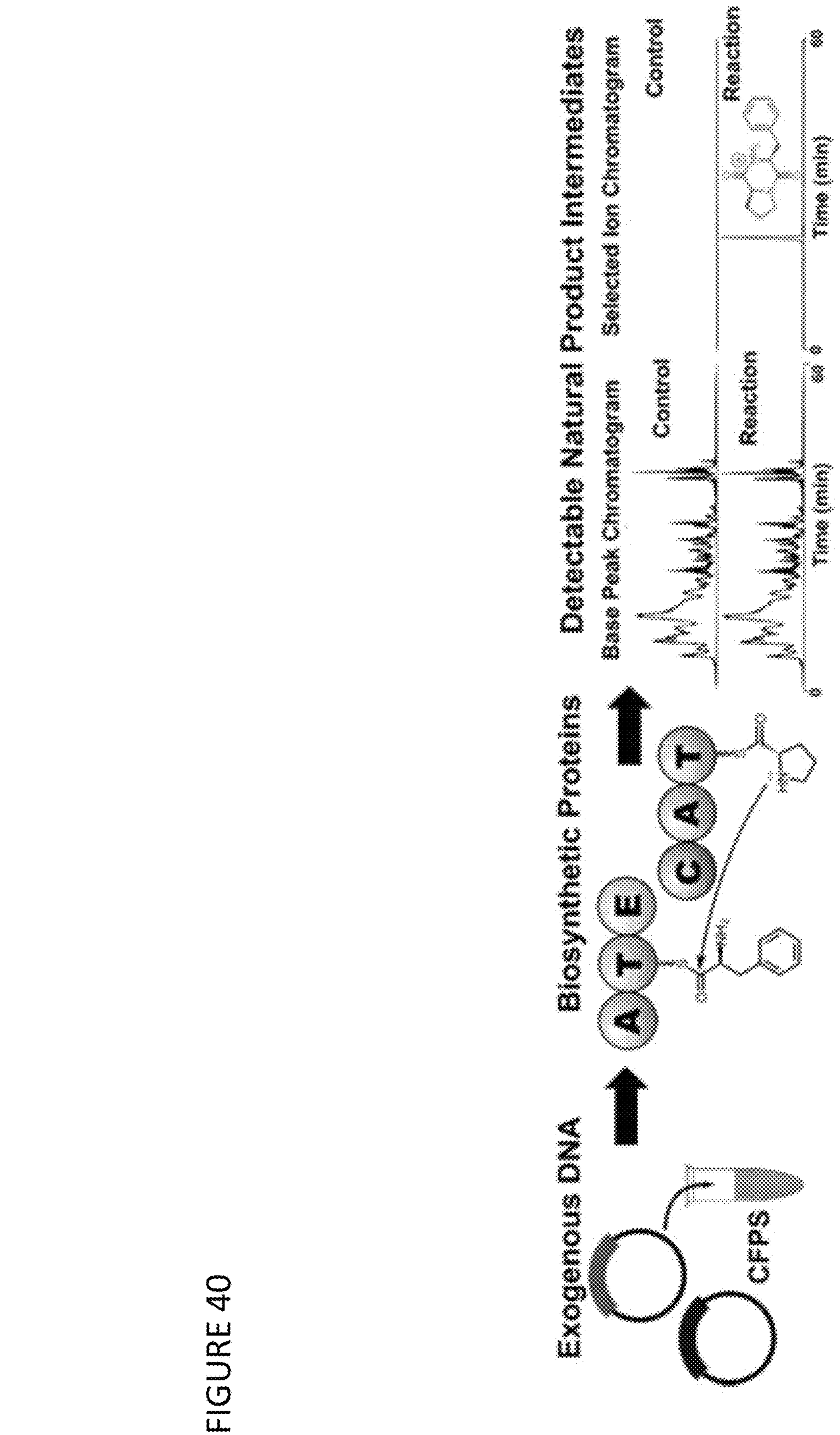
FIG. 40. Overview of a system for cell-free production of natural products via nonribosomal peptide biosynthesis. From left to right, exogenous DNA is used as the input information for the production of biosynthetic enzymes. In the center, nonribosomal peptide synthetase proteins function in concert to select substrates and catalyze the formation of peptide bonds, ultimately resulting in the production of a 2,5-diketopiperazine. Right panel, detection of a D-Phe-L-Pro diketopiperazine natural product by LC-MS as the result of in situ production of biosynthesis proteins.
Figure 41:
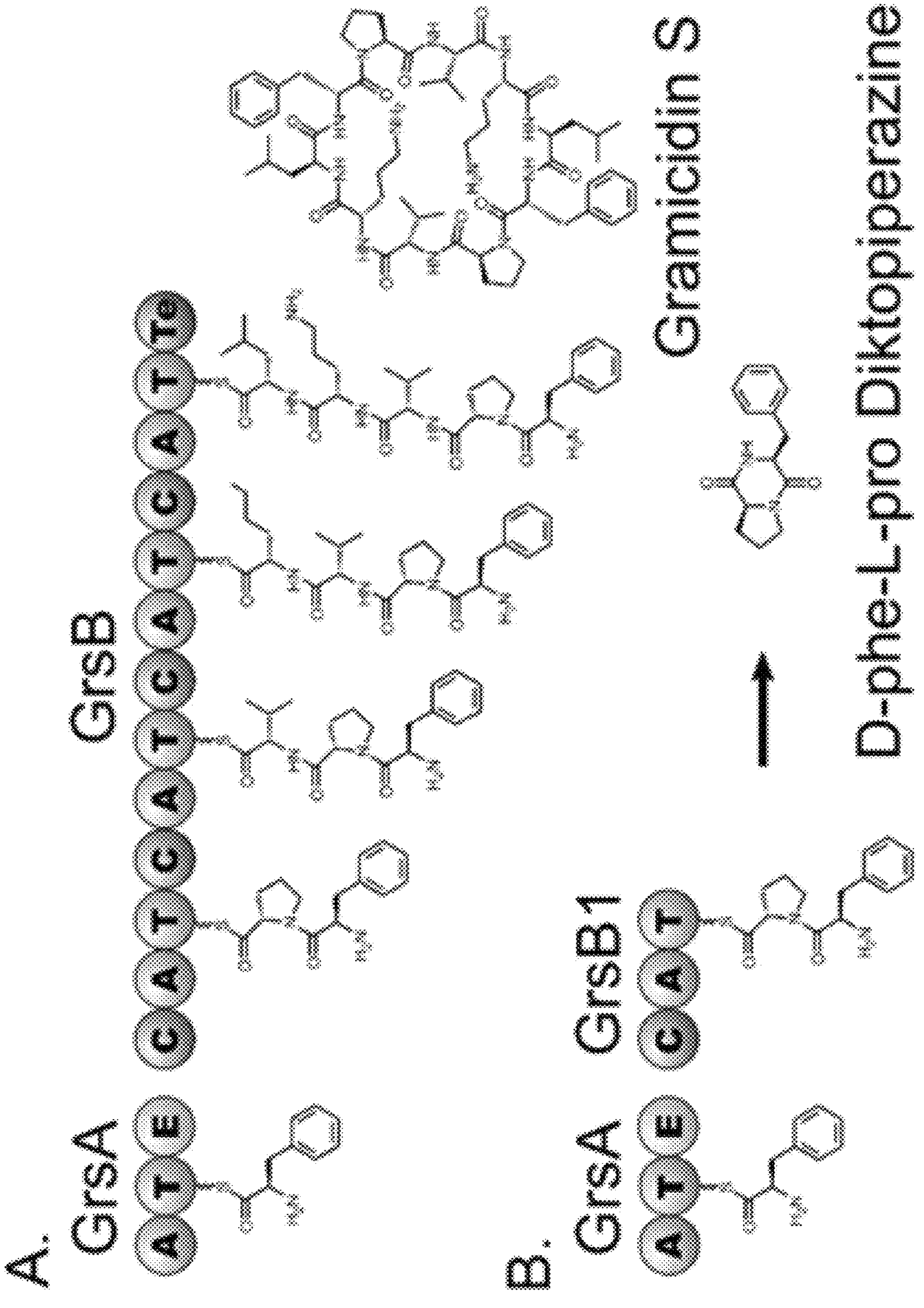
FIG. 41. Panel A (Top) summarizes the biosynthesis of gramicidin S as it occurs in *Brevibacillus brevis*. By turning through the assembly line pathway two times, the complete cyclodecapeptide is produced. Panel B shows how the first two modules interact to form D-Phe-L-Pro DKP.

Cell-free protein synthesis (CFPS) offers an alternative protein expression platform with potential advantages for expressing natural product biosynthetic enzymes (FIG. 40). CFPS is emerging as a robust tool for fundamental and applied research in the areas of synthetic biology and biotechnology[7-9]. Recently, cell-free systems have been shown to enable high yielding synthesis of, for example, active metalloenzymes[10-12], and allow rapid prototyping of biological circuits and pathways[13-16]. For natural products research, CFPS offers flexibility over cell-based expression because the reaction conditions can be more easily controlled: for example, atypical precursors can simply be fed in during the course of a reaction[17] or made in situ using all enzymes from a biosynthetic gene cluster. Biosynthetic pathways could potentially be engineered for higher expression without the need to modify a native host strain[s8]. Reactions can also be performed in the span of a few hours in a "single pot" and have a greater tolerance for producing potentially toxic proteins and metabolites than living cells To investigate the potential of CFPS for studying natural product pathways, we utilized the proteins involved in the first steps of gramicidin S biogenesis as a model. Gramicidin S is biosynthesized by two NRPS proteins, GrsA and GrsB, that catalyze thiotemplated peptide bond formation and release by cyclodimerization to form the cyclic decapeptide (FIG. 41A). A natural shunt product of the gramicidin S pathway is the D-Phe-L-Pro diketopiperazine (DKP) formed by cyclization of the substrates of the first two NRPS modules in the pathway, GrsA and GrsB1[19]. Cyclic dipeptide DKPs have been studied for their diverse biological activity and are produced by many species of bacteria, fungi, and plants[20]. Bacterial DKPs have two known general biosynthetic origins: they are either synthesized by NRPS enzymes, as in the case of the D-Phe-L-Pro-DKP presented here[21], or produced by aminoacyl-tRNA mediated cyclodipeptide synthase pathways as in the case of the antibiotic albonoursin[22]

Here, we report in vitro expression of GrsA and GrsB1, encompassing the first two of five modules of gramicidin S biosynthesis in *Brevibacillus brevis*. Each NRPS module typically consists of the three domains needed to incorporate an amino acid into the nonribosomal peptide: condensation (C), adenylation (A) and thiolation (T). GrsA, as a starter module, does not contain a C-domain; it contains an A and a T-domain, as well as an epimerization (E) domain that converts L-phenylalanine to D-phenylalanine. Previous reports have shown that isolated GrsA and GrsB1 can be harnessed to produce D-Phe-L-Pro DKP (FIG. 41B)[23]. While this diketopiperazine is not the primary product of this pathway in *Brevibacillus brevis*, it has been found to be produced by other microbes[24]. In this report, we demonstrate high-level expression of GrsA and GrsB1, show that they are produced in their functional state when expressed using CFPS, and use these two proteins in a concerted reaction to produce D-Phe-L-Pro DKP with a final yield greater than 10 mg/L.

C. Results and Discussion

To establish an in vitro platform for D-Phe-L-Pro DKP biosynthesis, NRPS proteins GrsA and GrsB1 were expressed using an *E. coli*-based cell-free protein expression system reported previously[25, 26]. GrsA and GrsB1 along with the functionally-equivalent tyrocidine synthetases TycA and TycB1 (often referred to as pheATE and proCAT) have served as the model thiotemplated biosynthetic systems for studying substrate specificity[27] and peptide bond formation[28] in NRPS pathways.

Figure 44:
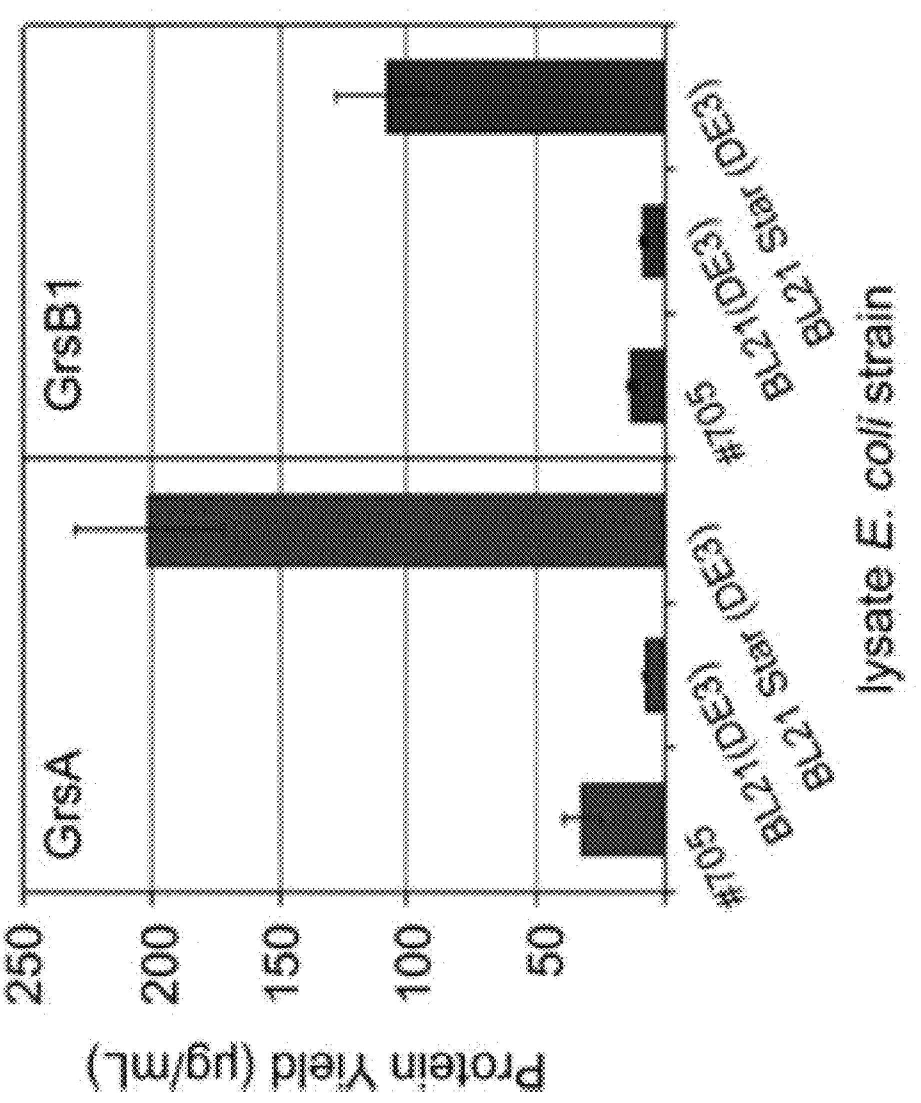
FIG. 44. Production of NRPS proteins GrsA and GrsB1 with lysates prepared from different strains of *E. coli*. Y-axis shows the protein yields determined by incorporation of $^{14}C$-leucine and scintillation counting.
Figure 45:
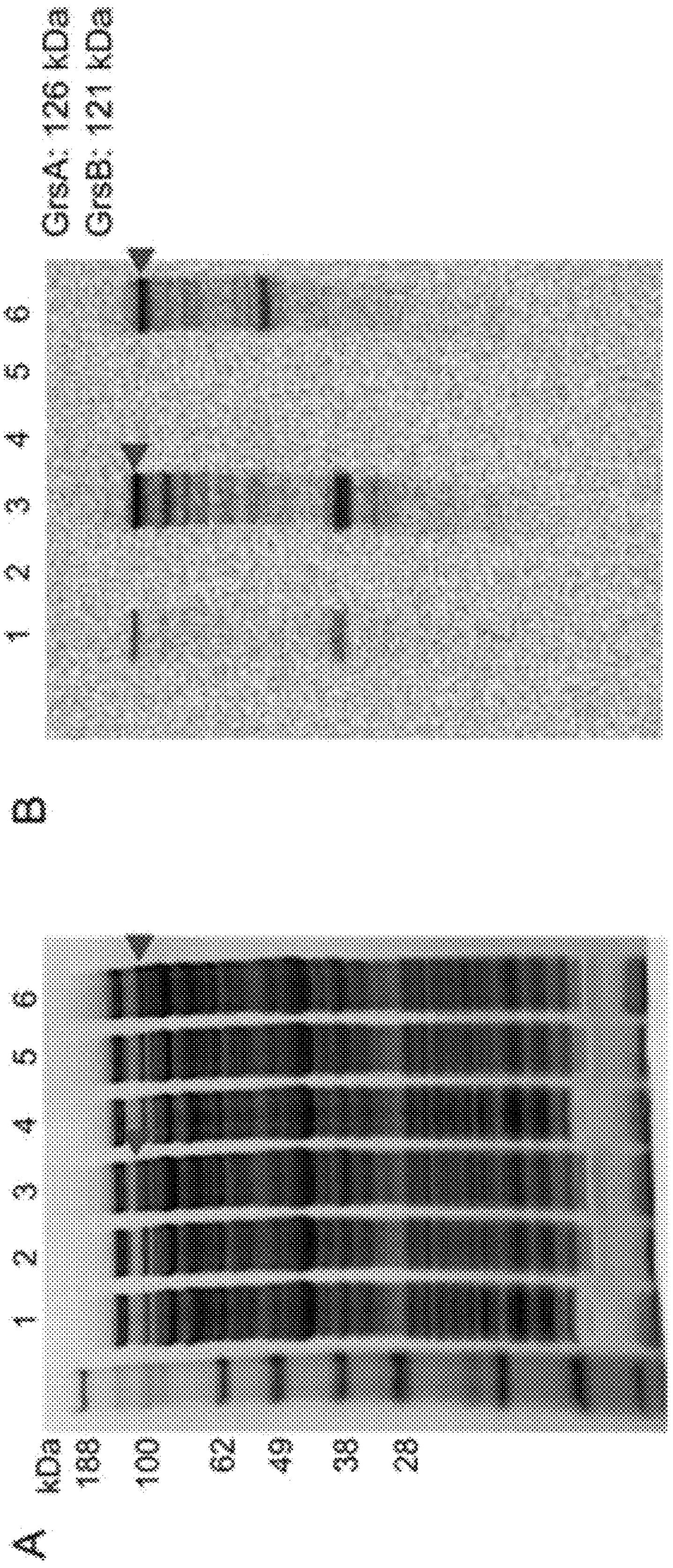
FIG. 45. Autoradiography image showing the production of full-length GrsA and GrsB1 after incorporation of $^{35}S$-methionine. Panel A shows the coommassie stained gel with the expected GrsA and GrsB1 bands marked with a red triangle. Panel B shows the phosphor image of the same gel with GrsA and GrsB1 once again marked with the red triangle. The numbers indicate the following protein/*E. coli* lysate pairs: 1) GrsA, #705; 2) GrsA, BL21(DE3); 3) GrsA, BL21(DE3)star; 4) GrsB1, #705; 5) GrsB1, BL21(DE3); 6) GrsB1, BL21(DE3) star.

Individual plasmids containing the genes grsA and grsB1 were used to express these enzymes in the combined transcription-translation system. Transcription was driven using a T7 RNA polymerase. We tested protein synthesis yields in 17 h batch reactions across three different *E. coli* crude extracts (S30 extracts)[29]. Expression yields of GrsA and GrsB1 were markedly different across the different S30 extracts. For both enzymes, *E. coli* BL21 Star (DE3) extract synthesized the highest amount of NRPS yielding GrsA at 200±29 μg/mL and GrsB1 at 108±19 g/mL (FIG. 44). Fully assembled GrsA (126 kDa) and GrsB1 (121 kDa) with correct molecular weight bands were observed by SDS-PAGE and further confirmed by autoradiogram analysis (FIG. 45). Interestingly, protein titers of greater than 108±19 μg/mL were achieved without optimization of ribosome binding sites, codon usage, etc.

Figure 42:
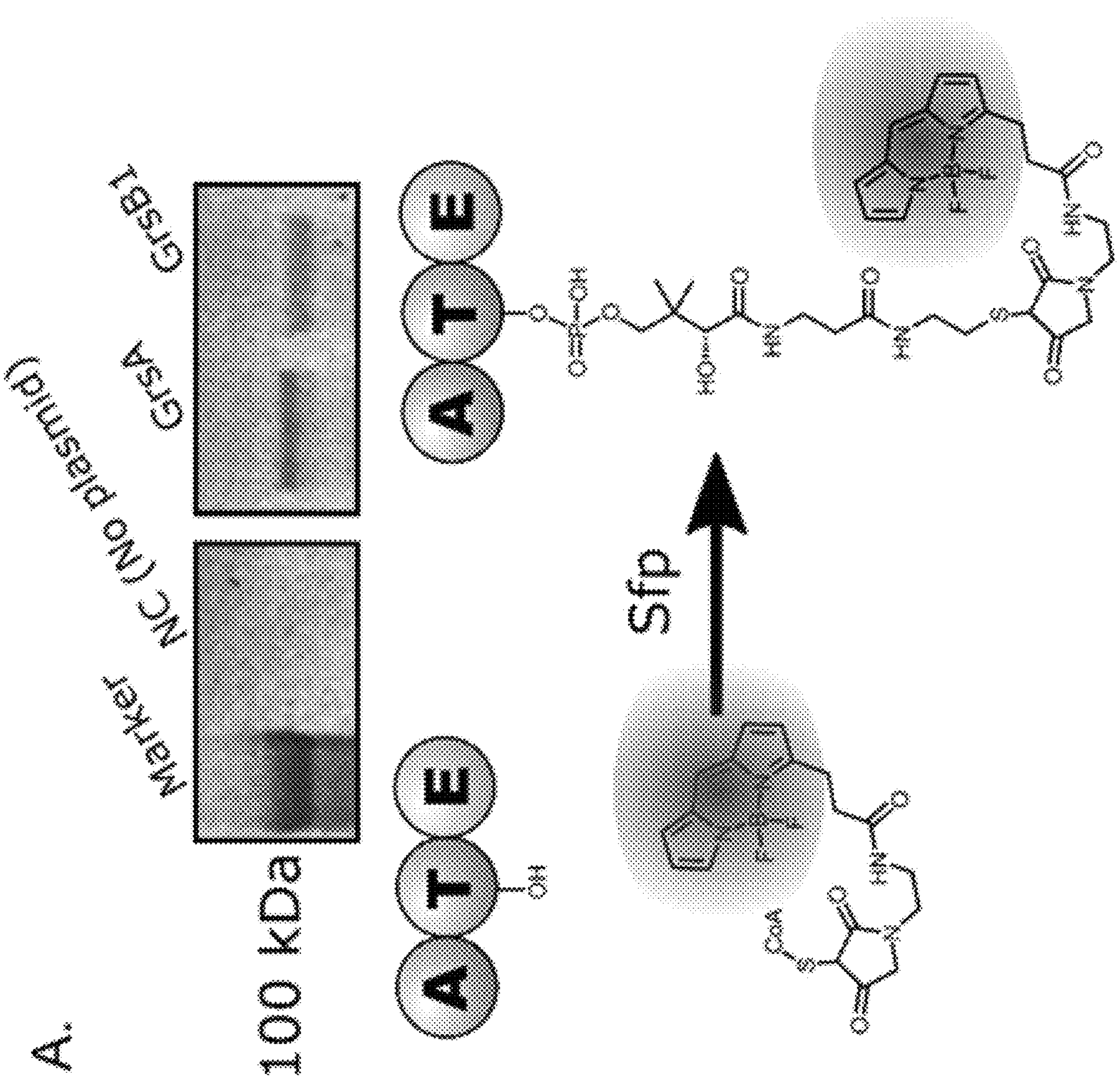
FIG. 42. Experiments showing that GrsA and GrsB1 are present in their active (holo) forms. Panel A shows the fluorescent labeling of GrsA and GrsB1 on the thiolation domain active sites with a conjugated BODIPY-CoA fluorophore (See FIG. 46 for complete gel image). Panel B top shows the $MS^2$ spectrum resulting from the fragmentation of a precursor peptide containing the GrsA phosphopantetheine modification (SEQ ID NO:3). Panel B bottom shows the $MS^2$ spectrum for the corresponding GrsB1 T-domain peptide (SEQ ID NO:4), indicating the mass of the observed pantetheine-derived ion.

Once we had successfully expressed the two large NRPSs, GrsA and GrsB1 in vitro, we showed that the enzymes could be converted to their functional (holo) form using the 4'-phosphopantetheinyl transferase enzyme Sfp from *Bacillus subtilis*. In order to be functional, NRPS proteins require modification by transfer of a phosphopantetheine group from coenzyme A (CoA) to a conserved serine residue in their thiolation (T) domain[30]. To verify that this essential modification is possible in our cell-free system, both GrsA and GrsB1 were labeled with a fluorescent BODIPY-CoA analog by the promiscuous action of Sfp (FIG. 42A). Expression of GrsA and GrsB1 continued for 17 hours in vitro, allowing nascent proteins to fold properly before labeling. After this incubation, BODIPY-CoA and Sfp were added directly to the cell-free expression system, followed by another 3 hour incubation at 30° C. or 37° C.

Phosphopantetheinylation was also detectable by LC-MS/MS using the method described in Miller et al. 2005 (FIG. 42)[31]. GrsA and GrsB1 were prepared in vitro in separate reactions. Following phosphopantetheinylation by Sfp, GrsA with a 6×His tag was captured using cobalt-affinity resin, digested with trypsin, and analyzed by proteomic-style LC-MS/MS. In the GrsA sample, a peptide with the sequence DNFYALGGDSIK (SEQ ID NO:3) and m/z 820.357 was observed, representing the predicted mass of the tryptic peptide with the addition of phosphopantetheine. GrsB1 peptides were detected in a peptide sample prepared by digesting the total lysate with 1:5 trypsin. The T-domain active-site peptide (IWEEVLGISQIGIQDNFF-SLGSLGGHSLK (SEQ ID NO:4), m/z 1076.533) was also observed for GrsB1 with attached phosphopantetheine.

Figure 46:
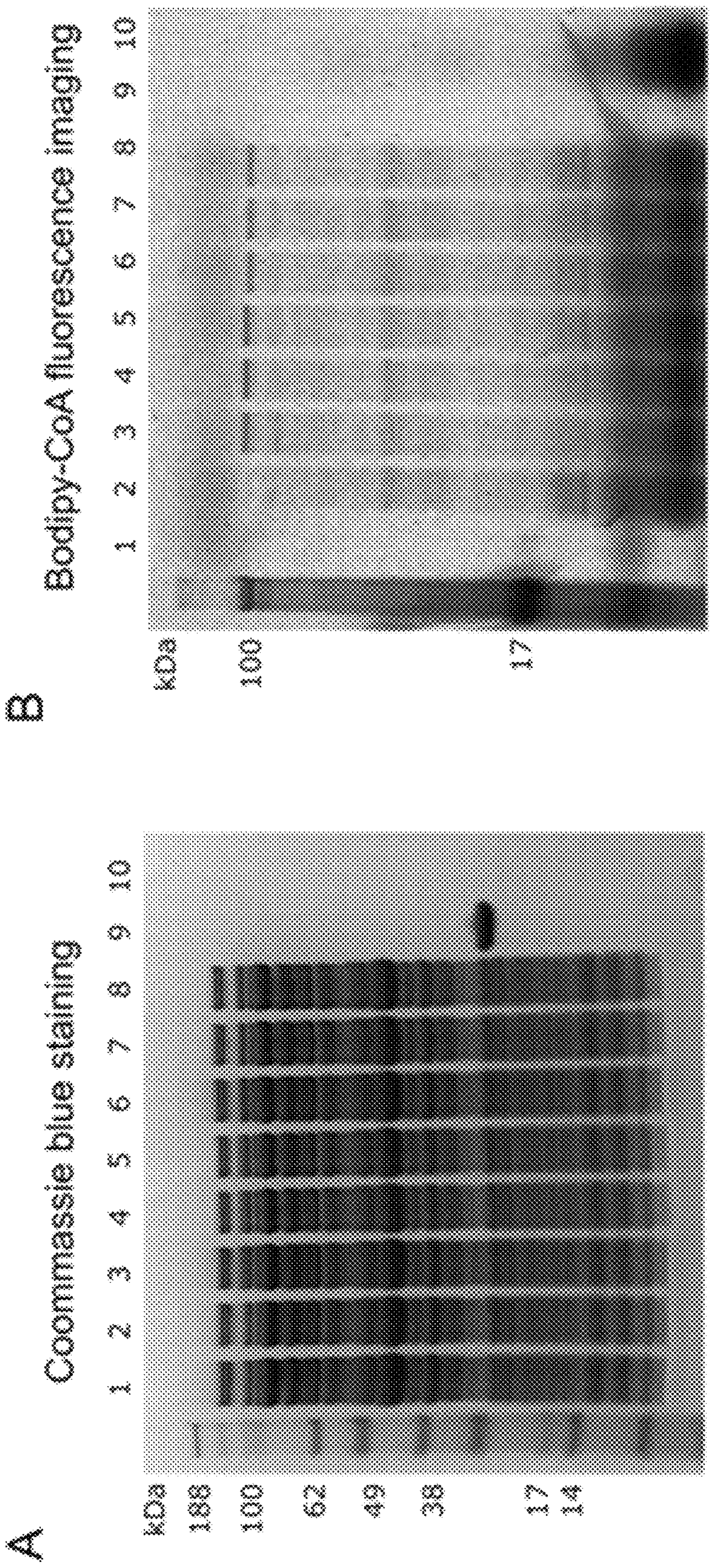
FIG. 46. Labeling of NRPS proteins GrsA and GrsB1 with conjugated BODIPY-CoA. Panel A shows the coommassie stained gel, and panel B shows the fluorescence image acquired at 520 nm. The numbers above the lanes on both images indicate the following conditions: 1) no plasmid, no Bodipy-CoA, no Sfp; 2) no plasmid, 1 μL Bodipy-CoA, 1 μL Sfp; 3) GrsA, after 17 h added 1 μL Bodipy-CoA, 1 μL Sfp, at 30° C. for another 3 h; 4) GrsA, after 17 h, centrifuge at 12000 g, 10 min, 4° C., take out 13 μL supernatant, then add 1 μL Bodipy-CoA, 1 μL Sfp, at 30° C. for another 3 h; 5) GrsA, after 17 h, centrifuge at 12000 g, 10 min, 4° C., remove 13 μL supernatant, then add 1 μL Bodipy-CoA, 1 μL Sfp, at 37° C. for another 3 h; 6-8. GrsB1, the conditions are the same as 3-5; 9—Sfp; 10—Bodipy-CoA.

Successful fluorescence labeling of GrsA and GrsB1 with Bodipy-CoA, and direct LC-MS/MS detection of the Ppant modification (FIG. 46, FIG. 42) demonstrated that, in the current in vitro system, i) both NRPSs were properly folded with accessible conserved serine residues located on T domains; ii) the purified recombinant Sfp is active for the phosphopantetheinylation; and iii) most importantly, the holo-NRPS could be functionally reconstituted for target molecule biosynthesis. In addition, GrsA and GrsB1 were expressed in soluble form and an extended incubation at 37° C. was not necessary for priming the NRPSs by Sfp (FIG. 46). Therefore, we posited that the target compound could be biosynthesized via active holo-NRPSs without further optimization of the reaction conditions or incubation temperature.

Figure 43:
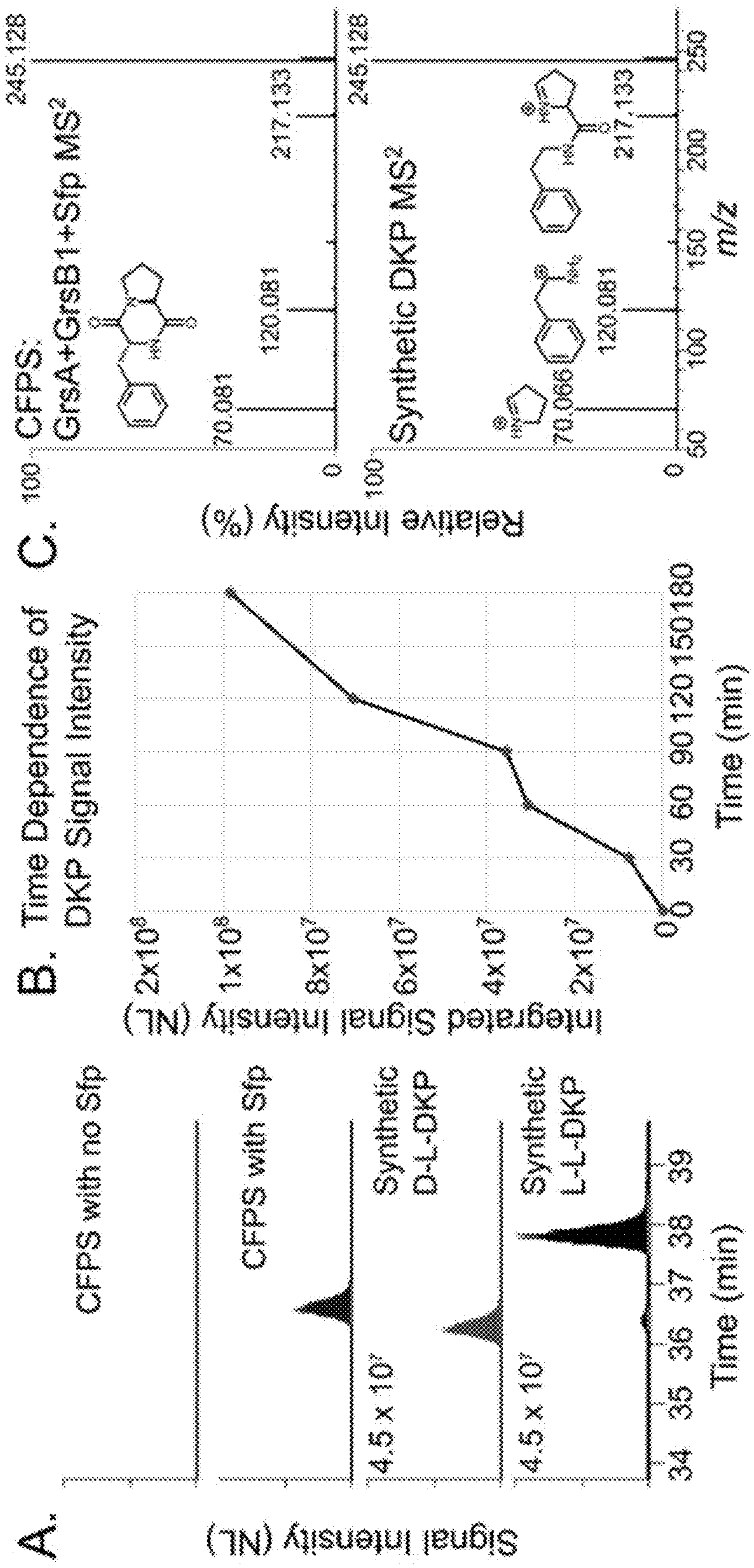
FIG. 43. Detection of D-Phe-L-Pro DKP by LC-MS/MS and comparison to synthetically prepared DKP. A) Retention time comparison of D-L, L-L and CFPS-produced DKP to determine the stereochemistry of the DKP produced by CFPS. This panel also shows that SFP is required for DKP production. B) Time dependent increase in m/z 245.128 signal after Sfp is added to the CFPS reaction. Data points are the average of two technical replicates. C) Comparison of the fragmentation pattern of the CFPS-produced (top) and synthetically prepared DKP (bottom). The spectrum at the bottom of panel C is annotated with predicted fragment ion structures.

We next sought to biosynthesize D-Phe-L-Pro DKP, and instead of expressing of GrsA and GrsB1 separately, the two enzymes were co-expressed in a single-pot mixture allowing reconstitution of the partial NRPS assembly line for product formation in situ. After carrying out the CFPS reaction, we added Sfp to the mixture to initiate biosynthesis, using the same reaction mixture without Sfp as a negative control. The reaction was stopped by extraction with n-butanol and chloroform (4:1, v/v) and the extract was analyzed by metabolomics-style LC-MS/MS. We detected a time-dependent increase in signal intensity of the ion corresponding to predicted DKP ion within 3 ppm mass error tolerance (m/z 245.129) (FIGS. 43A & B).

Figure 47:
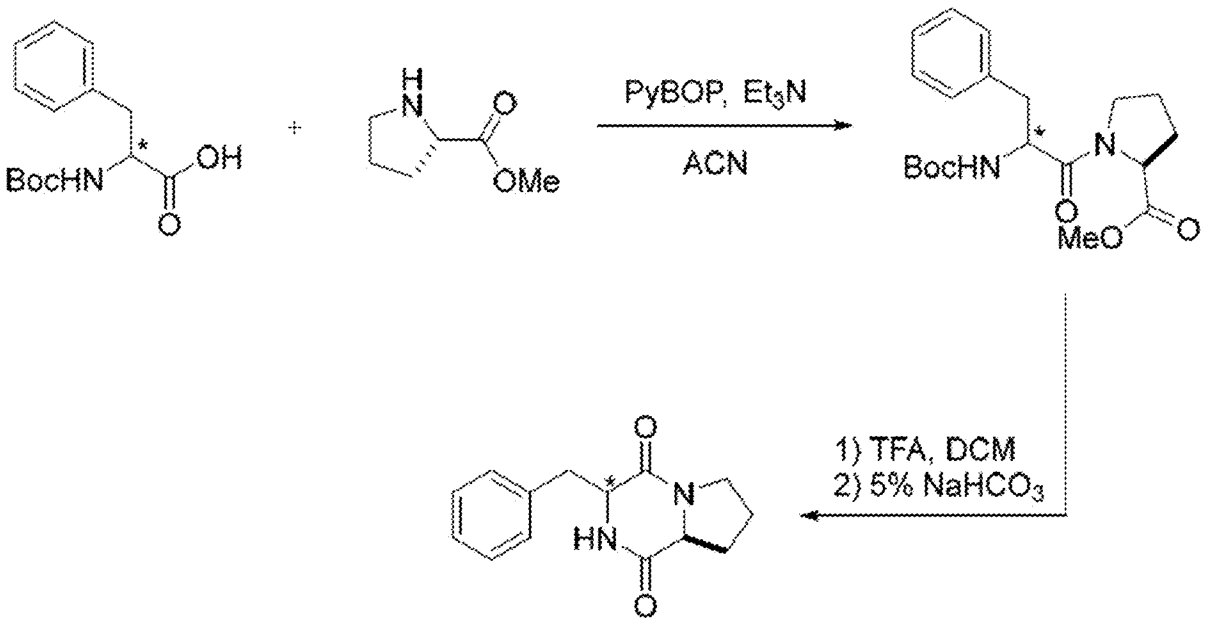
FIG. 47. Is a schematic showing the preparation of synthetic D/L-L DKP.
Figure 48:
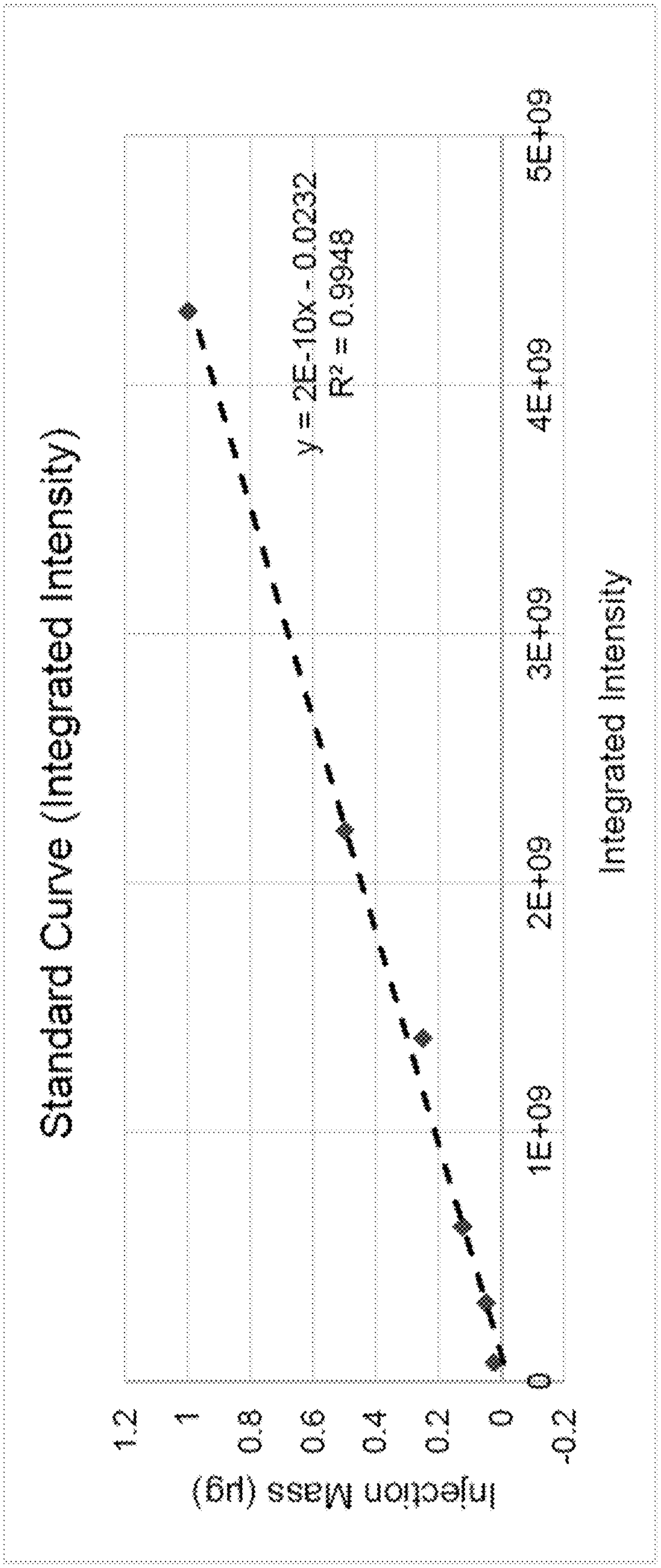
FIG. 48. Shows a graph presenting a standard curve for LC-MS-based quantitation of D-L-DKP.

To verify that the ion observed was the expected D-Phe-L-Pro DKP—and with correct D-L stereochemistry—we prepared both the D-L and L-L DKP as synthetic references (FIG. 47). Based on earlier reporting, we expected the D-L stereoisomer to elute earlier than L-L on a reversed phase HPLC column[32], and its elution profile matched with the metabolite produced with the CFPS reaction. Synthetic DKP was indistinguishable from the CFPS produced metabolite by $MS^2$ analysis (FIG. 43C). We used LC-MS to prepare a standard curve from the integrated intensity of synthetically prepared DKP measured at six different concentrations and used this curve to estimate the quantity of DKP produced by CFPS (FIG. 48). Even without optimization of the system for high titers, we estimated our production of D-Phe-L-Pro DKP at ~12 mg/L, a concentration higher than the 9 mg/L previously reported from recombinant protein expression in *E. coli*[23].

We believe this work to be the first example of natural product biosynthesis from NRPS enzymes produced using an *E. coli*-based in vitro transcription and translation system. CFPS provides a feasible option for exploring natural product biosynthesis, at least for proteins ~130 kDa such as the two presented here. CFPS offers freedom from many of the problematic processes present in cell-based expression systems (e.g., inclusion body formation, protein degradation), and may circumvent the issues of low-expressing or cryptic (non-expressing) BGCs encountered in native-producing organisms. While more investigation will be needed, the production of these two single-module NRPS proteins in vitro and the demonstration of their concerted function provides a groundwork for the study of increasingly complex natural product biosynthesis pathways using CFPS. Indeed, our discovery-centered cell-free approach sets the stage for high-throughput experimentation in a cell-free environment, where design-build-test iterations can be performed without the need to reengineer organisms, DNA for pathway enzymes is directly input with plasmid refactoring, and substrates and cofactors needed for secondary metabolism can be controlled and maintained at defined concentrations[33]

As a resurgence of interest in natural products continues, and the number of sequenced biosynthetic gene clusters continues to grow, we expect that protein expression systems will play an increasingly important role in obtaining and studying new natural products. Especially as the price of DNA synthesis declines, direct expression of entirely synthetic gene clusters (typically 30-120 kilobases in length) will remove barriers to accessing biosynthetic pathways from clusters assembled using metagenomics for uncultivable organisms. By merging bottom-up design principles with innovative cell-free pathway engineering methodologies, our cell-free approach will create a greatly simplified framework for studying and engineering natural product pathways.

D. Methods

1. Preparation of S30 Cell Extracts

E. coli cells were grown in 1 L of 2×YTPG (yeast extract 10 g/L, tryptone 16 g/L, NaCl 5 g/L, $K_2HPO_4$ 7 g/L, $KH_2PO_4$ 3 g/L and glucose 18 g/L, pH 7.2) in a 2.5-L Tunair flask (IBI Scientific, Peosta, IA) at 34° C. and 220 rpm with inoculation of 20 mL overnight cultures (initial $OD_{600}$ of ~0.05). When the $OD_{600}$ reached 3.0, cells were collected by centrifugation at 5,000×g and 4° C. for 15 min. The pellets were washed thrice with cold S30 buffer (10 mM Tris-acetate pH 8.2, 14 mM magnesium acetate, 60 mM potassium acetate, 2 mM dithiothreitol (DTT)). Cells were suspended in 0.8 mL of S30 buffer per gram wet weight and lysed on ice using a Q125 Sonicator (Qsonica, Newtown, CT) for three pulses (50% amplitude, 45 s on and 59 s off). After sonication, 3 µL of DTT (1M) was added per mL of lysate, followed by centrifugation at 12,000×g and 4° C. for 10 min. The supernatant (S30 extract) was flash frozen in liquid nitrogen and stored at −80° C. until use.

2. Cell-Free Protein Synthesis (CFPS) Reactions

The standard CFPS reactions were performed in 1.5 mL microcentrifuge tubes with 15 L mixture composed of the following reagent concentrations: 12 mM magnesium glutamate, 10 mM ammonium glutamate, 130 mM potassium glutamate, 1.2 mM ATP, 0.85 mM each of GTP, UTP, and CTP, 34 µg/mL folinic acid, 170 µg/mL of E. coli tRNA mixture, 2 mM each of 20 standard amino acids, 10 µM of L-[$^{14}$C(U)]-leucine (used only in protein quantitation experiments, 11.1 GBq mmol$^{-1}$, PerkinElmer, Waltham, MA), 0.33 mM nicotinamide adenine dinucleotide (NAD), 0.27 mM coenzyme A (CoA), 1.5 mM spermidine, 1 mM putrescine, 4 mM sodium oxalate, 33 mM phosphoenolpyruvate (PEP), 26.7 µg/mL plasmid, 100 µg/mL T7 RNA polymerase, and 27% (v/v) of S30 cell extract. All CFPS reactions were incubated for 20 h at 30° C. unless otherwise described.

3. Fluorescence Labeling of GrsA and GrsB1

The coenzyme A analog BODIPY-CoA was prepared as previously described[34]. To label thiolation domains of GrsA and GrsB1, standard CFPS reactions with 26.7 µg/mL of each plasmid were incubated at 30° C. for 17 h. Afterwards, labeling reactions were performed following three strategies. Strategy #1): the CFPS system was directly supplemented with 1 µL BODIPY-CoA (1 mg/mL) and 1 µL Sfp (2 mg/mL) and incubated at 30° C. for another 3 h. Strategy #2): the CFPS reaction was first centrifuged at 12,000 g and 4° C. for 10 min. Then, 13 µL of supernatant was transferred to a new 1.5 mL microcentrifuge tube with addition of 1 µL BODIPY-CoA and 1 L Sfp. The mixture was incubated at 30° C. for 3 h. Strategy #3): the treatment of the CFPS reaction was the same as in Strategy #2, but was incubated at 37° C. for 3 h. After the labeling reaction, 3 µL of each sample was loaded on a 4-12% NuPAGE SDS-PAGE gel (Invitrogen). The BODIPY-labeled proteins were visualized by a fluorescence imaging system with 473 nm laser and 520 nm emission filter (Typhoon FLA7000, GE Healthcare Biosciences, Uppsala, Sweden). See supporting information for additional details and fluorescent gel images (FIG. 46).

4. DKP Production In Vitro

D-Phe-L-Pro diketopiperazine (DKP) was biosynthesized by GrsA and GrsB1 expressed in situ. Cell-free co-expression of GrsA and GrsB1 was performed in the 15 µL reaction mixture as described above with addition of both plasmids (each of 26.7 µg/mL). The BL21 Star (DE3) S30 extract was used for the coupled transcription-translation. After incubation of the reaction mixture at 30° C. for 17 h, 1 µL Sfp (2 mg/mL); 1 µL Sfp (2 mg/mL) and 1 µL CoA (5 mM); or 1 µL Sfp (2 mg/mL), 1 µL CoA (5 mM), 1 µL Phe (1 mM) and 1 µL Pro (1 mM) were added directly to the reactions, followed by another 3 h incubation at 30° C. Reactions without plasmids and without addition of Sfp were carried out as negative controls. At the end of the production, all DKP samples were immediately extracted from the reaction mixtures for analysis by LC-MS/MS 5. Quantitation of Synthesized GrsA and GrsB1

The yields of synthesized GrsA and GrsB1 were quantified by the incorporation of $^{14}$C-leucine into trichloroacetic acid (TCA)-measuring precipitated radioactivity using a liquid scintillation counter (MicroBeta2, PerkinElmer, Waltham, MA). After CFPS, 100 µL of 0.1 M NaOH was added to each 15 µL reaction mixture. The NaOH treated samples were incubated at 37° C. for 20 min. Then, 50 µL of the treated sample was loaded onto each of two separate pieces of Whatman 3MM chromatography paper and dried under a heat lamp for 1 h. One piece of filter paper in each pair was placed into a beaker on ice and covered with 5% (v/v) TCA at 4° C. to precipitate the proteins onto the filter paper. After 15 min, the solution was exchanged with fresh TCA. This incubation was performed a total of three times. Following the third precipitation, the filter papers were covered once with 100% ethanol for 10 min at room temperature, and then they were removed from the beaker and allowed to dry under a heat lamp for another 1 h. Radioactivity of both the TCA-precipitated (washed) and non-TCA-precipitated (unwashed) samples was measured using a liquid scintillation counter. The fraction of incorporated $^{14}$C-leucine (washed/unwashed) was used to determine the amount of protein synthesized 6. Expression and Purification of Recombinant Sfp from E. coli pET28-Sfp$^I$ was expressed and purified from BL21(DE3). Sfp was purified from the lysate of 250 mL culture over cobalt resin (Thermo Scientific), and washed in steps of 10, 25, 50 mM imidazole. Pure Sfp protein was eluted with 150 mM imidazole. Following desalting and buffer exchange using Zeba desalting spin columns (Thermo Scientific), the final concentration of Sfp was determined to be 2 mg/mL by the bicinchoninic acid assay. Sfp was stored in 10% glycerol at −80° C. prior to use.

7. Autoradiography Analysis

After the cell-free reaction, 3 μL of each sample was loaded on a 4-12% NuPAGE SDS-PAGE gel (Invitrogen). After running at 120 V for 1.5 h, the gel was stained using SimplyBlue™ SafeStain solution (Invitrogen) and destained in water. Then, the gel was fixed with cellophane films (Bio-Rad), dried overnight in a GelAir Dryer (Bio-Rad) without heating, and exposed for 48 h on a Storage Phosphor Screen (GE Healthcare Biosciences, Pittsburgh, PA). The autoradiogram was scanned using a Storm Imager (GE Healthcare Biosciences, Pittsburgh, PA) and analyzed using Quantity One software (Bio-Rad, Hercules, CA).

8. Synthetic Preparation of Racemic DKP

The scheme shown in FIG. 47 illustrates the preparation of synthetic D/L-L DKP. Methyl (tert-butoxycarbonyl)phenylalanyl-L-prolinate. Boc-Phe-OH (0.1 mmol) and L-proline methyl ester (0.1 mmol) were dissolved in 5 mL of acetonitrile. PyBOP (0.12 mmol) was added to the reaction mixture and allowed to stir at room temperature. Triethylamine (0.2 mmol) was added to the flask. After 12 h, saturated NaCl solution (10 mL) was added to the mixture and extracted with ethyl acetate (3×10 mL). Organic layer was washed with 1 M HCl, 5% $NaHCO_3$, and $H_2O$ sequentially. Organic layer was dried over sodium sulfate and solvent removed under reduced pressure to yield 75 mg of crude material, which was used without further purification. The Boc-protected dipeptide was dissolved in 5 mL of dichloromethane and 5 mL of trifluoroacetic acid and then stirred at room temperature for 1 hour. The solvent was removed under reduced pressure to yield a colorless oil, which was treated with 10 mL of 5% $NaHCO_3$ solution. After stirring for 12 hours, the solvent was removed under reduced pressure-resulting in 48 mg of crude DKP. A portion of this product was used for purification via HPLC.

9. Extraction and Identification of DKP

After DKP production, each 15 L reaction mixture was immediately extracted with 3 volumes of n-butanol/chloroform (4:1, v/v). The organic layer was separated by centrifugation at 16,000×g and 4° C. for 10 min and then transferred to a fresh microcentrifuge tube. After removal of the solvent under vacuum, samples were resuspended in 100 μL of 50% methanol for further analysis by LC-MS.

DKP samples were analyzed on a Q-exactive orbitrap instrument (Thermo) paired with an Agilent 1150 HPLC system. MS parameters were the following: 70 minute run-time, scan range 100-1000 m/z, resolution 35,000. After each full scan, the top five most intense ions selected for HCD fragmentation at 25% collisional energy. LC buffers were $H_2O$+0.1% formic acid and acetonitrile+0.1% formic acid. For each sample 20 μL were injected into the LC system for a 70 minute gradient with a flow rate of 200 μL/min across a 150 mm×2.1 mm reversed-phase (C18) column (Phenomonex). SIC intensities were determined using Xcalibur software (Thermo Scientific) using the mass range of 245.127-245.129 m/z.

10. Bacterial Strains

*Escherichia coli* stains C321.AA.705, BL21(DE3) and BL21 Star (DE3) were used for S30 cell extract preparation. C321.AA.705 was generated from a genetically encoded release factor 1 (RF1) deficient *E. coli* strain[2]. Both BL21 (DE3) and BL21 Star (DE3) were purchased from Life Technologies (Grand Island, NY). *E. coli* DH5α was used for cloning and plasmid maintenance. BL21(DE3) was also used for Sfp expression and purification.

11. Plasmid Construction

Figure 49:
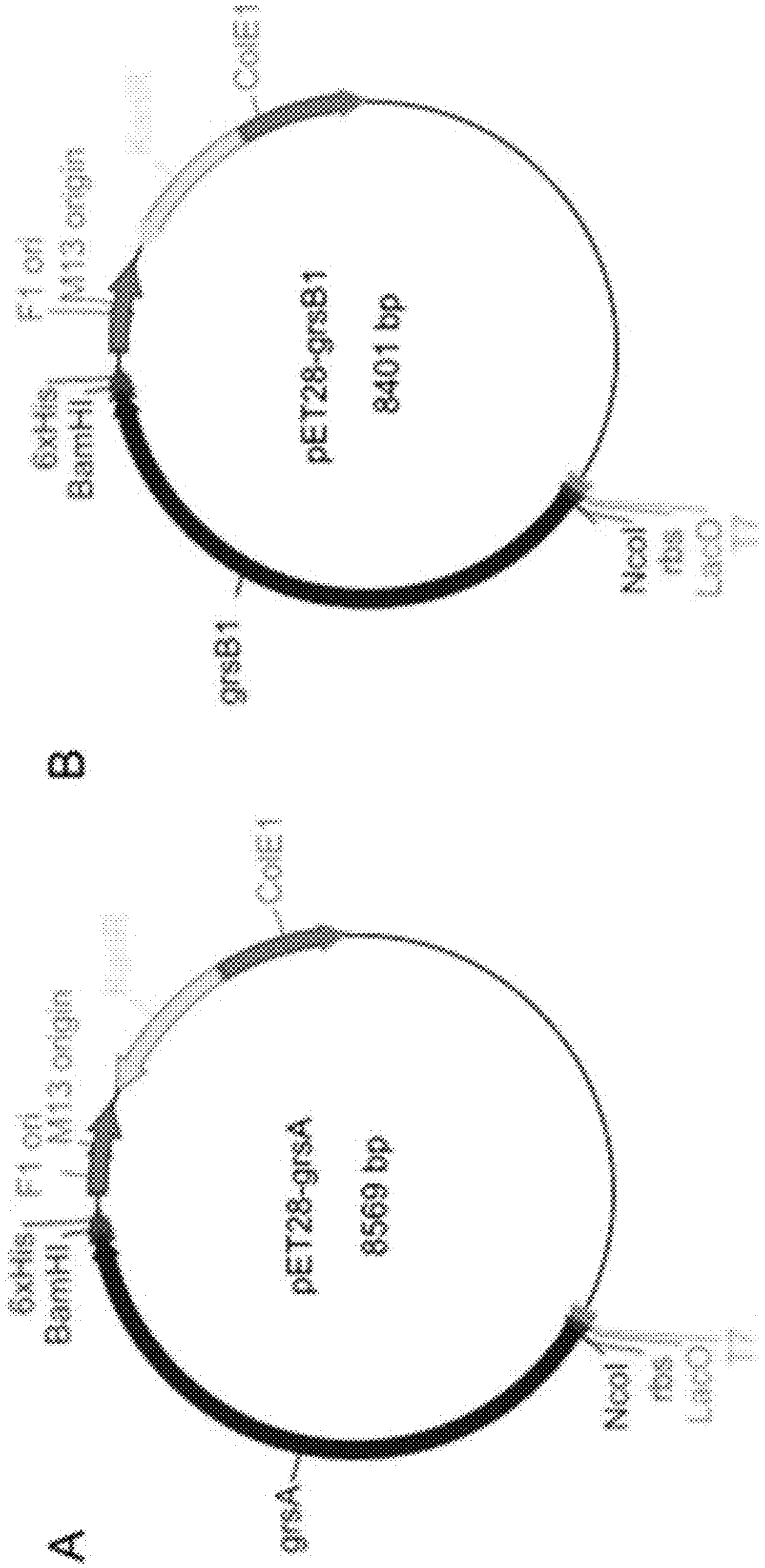
FIG. 49. Shows plasmid maps of grsA (A) and grsB1 (B) expression vectors.

Plasmid construction was performed using a conventional restriction enzyme-ligation scheme. Primers were obtained from Integrated DNA technologies. GrsA and GrsB1 were first cloned from the genomic DNA of *Brevibacillus brevis*. PCR was performed using GoTaq Green Master Mix (Promega, 60 L reaction volume). PCR products and pET28 plasmid were digested with the enzymes NcoI and BamHI (New England Biolabs) and gel extracted using the QIAquick Gel Extraction kit (Qiagen). Digested PCR products and plasmid backbones were ligated to form whole constructs using T4 DNA ligase. See plasmid maps at FIG. 49.

TABLE 6.1

Primers used for amplification of NRPS encoding genes grsA and grsB1.

| Name | Sequence (5' -> 3') |
|---|---|
| NcoI-grsA-F | Attattatccatggtgttaaacagttctaaaa gtatattgattcatgc (SEQ ID NO: 104) |
| BamHI-grsA-R | Aataatatggatccgttaatgaatcggccaac aaatc (SEQ ID NO: 105) |
| NcoI-grsB1-F | Attattatccatggtgagtacatttaaaaaag aacatgttcagg (SEQ ID NO: 106) |
| BamHI-grsB1-R | Aataatatggatccatataattagagatttcc tgaatggttggtg (SEQ ID NO: 107) |

12. Quantitation of DKP Production

A standard curve was prepared using synthetic DKP (preparation described above) by performing injections of 1 μg, 500 ng, 250 ng, 125 ng, 50 ng, and 25 ng on an Agilent 1150 HPLC stack coupled to a Q-Exactive mass spectrometer. Signal intensity was determined from the integrated abundance value of DKP over the course of a 70 minute experiment. A linear equation was fit to the standard curve and used to estimate the abundance of DKP in the sample prepared from CFPS by calculating the total amount of DKP present in a 45 μL butanol/chloroform extraction.

F. REFERENCES FOR EXAMPLE 6

1. Doroghazi, J. R., Albright, J. C., Goering, A. W., Ju, K. S., Haines, R. R., Tchalukov, K. A., Labeda, D. P., Kelleher, N. L., and Metcalf, W. W. (2014) A roadmap for natural product discovery based on large-scale genomics and metabolomics, Nat Chem Biol 10, 963-968.
2. Charlop-Powers, Z., Owen, J. G., Reddy, B. V., Ternei, M. A., and Brady, S. F. (2014) Chemical-biogeographic survey of secondary metabolism in soil, Proc Natl Acad Sci USA 111, 3757-3762.
3. Lowry, B., Walsh, C. T., and Khosla, C. (2015) Reconstitution of Metabolic Pathways: Insights into Nature's Chemical Logic, Synlett 26, 1008-1025.
4. Fischbach, M. A., and Walsh, C. T. (2006) Assembly-line enzymology for polyketide and nonribosomal Peptide antibiotics: logic, machinery, and mechanisms, Chem Rev 106, 3468-3496.
5. Zemella, A., Thoring, L., Hoffmeister, C., and Kubick, S. (2015) Cell-Free Protein Synthesis: Pros and Cons of Prokaryotic and Eukaryotic Systems, Chembiochem 16, 2420-2431.
6. Li, J., and Neubauer, P. (2014) *Escherichia coli* as a cell factory for heterologous production of nonribosomal peptides and polyketides, N Biotechnol 31, 579-585.
7. Sun, Z. Z., Yeung, E., Hayes, C. A., Noireaux, V., and Murray, R. M. (2014) Linear DNA for rapid prototyping of synthetic biological circuits in an *Escherichia coli* based TX-TL cell-free system, ACS Synth Biol 3, 387-397.

8. Carlson, E. D., Gan, R., Hodgman, C. E., and Jewett, M. C. (2012) Cell-free protein synthesis: applications come of age, Biotechnol Adv 30, 1185-1194.
9. Hodgman, C. E., and Jewett, M. C. (2012) Cell-free synthetic biology: thinking outside the cell, Metab Eng 14, 261-269.
10. Kwon, Y. C., Oh, I. S., Lee, N., Lee, K. H., Yoon, Y. J., Lee, E. Y., Kim, B. G., and Kim, D. M. (2013) Integrating cell-free biosyntheses of heme prosthetic group and apoenzyme for the synthesis of functional P450 monooxygenase, Biotechnol Bioeng 110, 1193-1200.
11. Boyer, M. E., Stapleton, J. A., Kuchenreuther, J. M., Wang, C. W., and Swartz, J. R. (2008) Cell-free synthesis and maturation of [FeFe] hydrogenases, Biotechnol Bioeng 99, 59-67.
12. Li, J., Lawton, T. J., Kostecki, J. S., Nisthal, A., Fang, J., Mayo, S. L., Rosenzweig, A. C., and Jewett, M. C. (2016) Cell-free protein synthesis enables high yielding synthesis of an active multicopper oxidase, Biotechnol J 11, 212-218.
13. Takahashi, M. K., Chappell, J., Hayes, C. A., Sun, Z. Z., Kim, J., Singhal, V., Spring, K. J., Al-Khabouri, S., Fall, C. P., Noireaux, V., Murray, R. M., and Lucks, J. B. (2015) Rapidly characterizing the fast dynamics of RNA genetic circuitry with cell-free transcription-translation (TX-TL) systems, ACS Synth Biol 4, 503-515.
14. Garamella, J., Marshall, R., Rustad, M., and Noireaux, V. (2016) The All *E. coli* TX-TL Toolbox 2.0: A Platform for Cell-Free Synthetic Biology, ACS Synth Biol 5, 344-355.
15. Takahashi, M. K., Hayes, C. A., Chappell, J., Sun, Z. Z., Murray, R. M., Noireaux, V., and Lucks, J. B. (2015) Characterizing and prototyping genetic networks with cell-free transcription-translation reactions, Methods 86, 60-72.
16. de Los Santos, E. L., Meyerowitz, J. T., Mayo, S. L., and Murray, R. M. (2016) Engineering Transcriptional Regulator Effector Specificity Using Computational Design and In Vitro Rapid Prototyping: Developing a Vanillin Sensor, ACS Synth Biol 5, 287-295.
17. Stech, M., Brodel, A. K., Quast, R. B., Sachse, R., and Kubick, S. (2013) Cell-free systems: functional modules for synthetic and chemical biology, Adv Biochem Eng Biotechnol 137, 67-102.
18. Chappell, J., Jensen, K., and Freemont, P. S. (2013) Validation of an entirely in vitro approach for rapid prototyping of DNA regulatory elements for synthetic biology, Nucleic Acids Res 41, 3471-3481.
19. Kurotsu, T., Hori, K., Kanda, M., and Saito, Y. (1991) Characterization and location of the L-proline activating fragment from the multifunctional gramicidin S synthetase 2, J Biochem 109, 763-769.
20. Prasad, C. (1995) Bioactive cyclic dipeptides, Peptides 16, 151-164.
21. Loria, R., Bignell, D. R., Moll, S., Huguet-Tapia, J. C., Joshi, M. V., Johnson, E. G., Seipke, R. F., and Gibson, D. M. (2008) Thaxtomin biosynthesis: the path to plant pathogenicity in the genus *Streptomyces*, Antonie Van Leeuwenhoek 94, 3-10.
22. Belin, P., Moutiez, M., Lautru, S., Seguin, J., Pernodet, J. L., and Gondry, M. (2012) The nonribosomal synthesis of diketopiperazines in tRNA-dependent cyclodipeptide synthase pathways, Nat Prod Rep 29, 961-979.
23. Gruenewald, S., Mootz, H. D., Stehmeier, P., and Stachelhaus, T. (2004) In vivo production of artificial nonribosomal peptide products in the heterologous host *Escherichia coli*, Appl Environ Microbiol 70, 3282-3291.
24. Abed, R. M., Dobretsov, S., Al-Fori, M., Gunasekera, S. P., Sudesh, K., and Paul, V. J. (2013) Quorum-sensing inhibitory compounds from extremophilic microorganisms isolated from a hypersaline cyanobacterial mat, J Ind Microbiol Biotechnol 40, 759-772.
25. Jewett, M. C., Calhoun, K. A., Voloshin, A., Wuu, J. J., and Swartz, J. R. (2008) An integrated cell-free metabolic platform for protein production and synthetic biology, Mol Syst Biol 4, 220.
26. Jewett, M. C., and Swartz, J. R. (2004) Mimicking the *Escherichia coli* cytoplasmic environment activates long-lived and efficient cell-free protein synthesis, Biotechnol Bioeng 86, 19-26.
27. Villiers, B. R., and Hollfelder, F. (2009) Mapping the limits of substrate specificity of the adenylation domain of TycA, Chembiochem 10, 671-682.
28. Bergendahl, V., Linne, U., and Marahiel, M. A. (2002) Mutational analysis of the C-domain in nonribosomal peptide synthesis, Eur J Biochem 269, 620-629.
29. Kwon, Y. C., and Jewett, M. C. (2015) High-throughput preparation methods of crude extract for robust cell-free protein synthesis, Sci Rep 5, 8663.
30. Lambalot, R. H., Gehring, A. M., Flugel, R. S., Zuber, P., LaCelle, M., Marahiel, M. A., Reid, R., Khosla, C., and Walsh, C. T. (1996) A new enzyme superfamily—the phosphopantetheinyl transferases, Chem Biol 3, 923-936.
31. Miller, L. M., Mazur, M. T., McLoughlin, S. M., and Kelleher, N. L. (2005) Parallel interrogation of covalent intermediates in the biosynthesis of gramicidin S using high-resolution mass spectrometry, Protein Sci 14, 2702-2712.
32. Stachelhaus, T., and Walsh, C. T. (2000) Mutational analysis of the epimerization domain in the initiation module PheATE of gramicidin S synthetase, Biochemistry 39, 5775-5787.
33. Niederholtmeyer, H., Sun, Z. Z., Hori, Y., Yeung, E., Verpoorte, A., Murray, R. M., and Maerkl, S. J. (2015) Rapid cell-free forward engineering of novel genetic ring oscillators, Elife 4, e09771.
34. La Clair, J. J., Foley, T. L., Schegg, T. R., Regan, C. M., and Burkart, M. D. (2004) Manipulation of carrier proteins in antibiotic biosynthesis, Chem Biol 11, 195-201.

1. Lambalot, R. H., Gehring, A. M., Flugel, R. S., Zuber, P., LaCelle, M., Marahiel, M. A., Reid, R., Khosla, C., and Walsh, C. T. (1996) A new enzyme superfamily—the phosphopantetheinyl transferases, Chem Biol 3, 923-936.
2. Lajoie, M. J., Rovner, A. J., Goodman, D. B., Aerni, H. R., Haimovich, A. D., Kuznetsov, G., Mercer, J. A., Wang, H. H., Carr, P. A., Mosberg, J. A., Rohland, N., Schultz, P. G., Jacobson, J. M., Rinehart, J., Church, G. M., and Isaacs, F. J. (2013) Genomically recoded organisms expand biological functions, Science 342, 357-360

Dudley, Q. M., Karim, A. S. & Jewett, M. C. Cell-free metabolic engineering: biomanufacturing beyond the cell. Biotechnol J 10, 69-82 (2015).

Chappell, J., Jensen, K. & Freemont, P. S. Validation of an entirely in vitro approach for rapid prototyping of DNA regulatory elements for synthetic biology. Nucleic Acids Res 41, 3471-3481 (2013).

Takahashi, M. K. et al. Characterizing and prototyping genetic networks with cell-free transcription-translation reactions. Methods (2015).

Zemella A, Thoring L, Hoffmeister C, Kubick S. 2015. Cell-Free Protein Synthesis: Pros and Cons of Prokaryotic and Eukaryotic Systems. Chembiochem: a European journal of chemical biology.

Stech M, Brodel A K, Quast R B, Sachse R, Kubick S. 2013. Cell-free systems: functional modules for synthetic and chemical biology. Advances in biochemical engineering/biotechnology 137: 67-102.

Zawada, J. F. et al. Microscale to manufacturing scale-up of cell-free cytokine production—a new approach for shortening protein production development timelines. Biotechnol Bioeng 108, 1570-1578 (2011).

Hong, S. H. et al. Improving cell-free protein synthesis through genome engineering of *Escherichia coli* lacking release factor 1. Chembiochem 16, 844-853 (2015).

Kwon, Y. C. & Jewett, M. C. High-throughput preparation methods of crude extract for robust cell-free protein synthesis. Sci Rep 5, 8663 (2015).

de Los Santos E L, Meyerowitz J T, Mayo S L, Murray R M. 2015. Engineering Transcriptional Regulator Effector Specificity Using Computational Design and In Vitro Rapid Prototyping: Developing a Vanillin Sensor. ACS synthetic biology.

Niederholtmeyer H, Sun Z Z, Hori Y, Yeung E, Verpoorte A, Murray R M, Maerkl S J. 2015. Rapid cell-free forward engineering of novel genetic ring oscillators. eLife 4: e09771.

Sun Z Z, Yeung E, Hayes C A, Noireaux V, Murray R M. 2014. Linear DNA for rapid prototyping of synthetic biological circuits in an *Escherichia coli* based TX-TL cell-free system. ACS synthetic biology 3: 387-397.

Jewett, M. C. & Swartz, J. R. Mimicking the *Escherichia coli* cytoplasmic environment activates long-lived and efficient cell-free protein synthesis. *Biotechnol Bioeng* 86, 19-26 (2004).

Example 7—Cell-Free Biosynthesis of HMG-CoA

A. Abstract

Metabolic engineering uses enzymes to produce small molecules with industrial, pharmaceutical, and energy applications. However, efforts to optimize enzymatic pathways for commercial production are limited by the throughput of assays for quantifying metabolic intermediates and end products. We developed a multiplexed method for profiling CoA-dependent pathways that utilizes a cysteine terminated peptide to covalently capture CoA bound metabolites. Captured metabolites are then rapidly separated from the complex mixture by immobilization onto arrays of self-assembled monolayers and directly quantified by SAMDI mass spectrometry. We demonstrate the throughput of the assay by characterizing the cell-free synthesis of HMG-CoA, a key intermediate in the biosynthesis of isoprenoids, collecting over 10,000 individual spectra to map more than 800 unique reaction conditions. We anticipate that our rapid and robust analytical method will accelerate efforts to engineer metabolic pathways.

B. Introduction

Biosynthetic pathways offer new opportunities for producing molecules with medical, energy, and industrial applications at commercial scales (1). Coenzyme A is a central molecule in metabolism and is required in over 100 distinct reactions, serving as an obligate cofactor for 4% of known enzymes (2). Acetyl-CoA serves as the universal precursor for numerous biosynthetic pathways including isoprenoids, fatty acids/alkanes, polyketides, bioplastics, and a number of biofuels (3). In yeast alone, acetyl-CoA is involved in 34 different metabolic reactions (1). A diverse range of bioengineering efforts have used CoA dependent pathways; these include the semi-synthetic production of the antimalarial drug artemisinin (4), the biosynthesis of methyl-butenol as a potential biofuel (5), and the bioengineering of brewer's yeast to produce the hop flavor compounds linalool and geraniol (6). The importance of CoA metabolism has motivated the engineering of organisms such as *S. cerevisiae* as "chassis" strains for overproducing acetyl-CoA (7) or other short chain acyl-CoA biosynthetic precursors (8). While several pathways have been successfully developed at the commercial scale (9), engineering cells is a time-consuming and non-intuitive process that can require hundreds of person years to tune enzymatic pathways (10). Many approaches use an iterative design-build-test (DBT) cycle to test numerous "weak hypotheses" and explore a large parameter space in which the underlying biology is not completely understood, or where the complexity of the system does not yet permit rational design. Recent advances in DNA synthesis and assembly highlight new capabilities to design and build biological systems (11, 12), while emphasizing the need for additional methods to rapidly test biosynthetic reaction systems. For CoA-bound metabolites, the current state-of-the-art detection methods rely on column-based separation, followed by mass spectrometry (13-17). These methods are highly sensitive (pmol of analyte per sample) (18) and can be adapted to measure multiple acyl-CoA compounds in a single analysis (19), but have low throughput, generally requiring greater than 15 minutes per analysis. Colorimetric screens and intracellular metabolite-sensing circuits offer increased throughput, but are typically specific for a single CoA-bound molecule and require laborious redesign to quantitate new target molecules (20).

In this work, we developed an assay based on SAMDI-MS (Self-Assembled Monolayers for MALDI-TOF mass spectrometry) that is capable of rapidly detecting CoA-bound metabolites in high-throughput. In SAMDI, biochemical assays are performed on self-assembled monolayers (SAMs) of alkanethiolates on gold, and the resulting immobilized reaction products are directly quantified using MALDI-TOF mass spectrometry (21). Previously, we have shown that SAMDI can be used as a general assay platform to profile a wide range of enzyme activities in situ and in complex lysates (22-26). Here, we demonstrate how SAMDI can characterize biosynthetic pathways by immobilizing a specific class of metabolites to the surface and obtaining mass spectra to quantitate each metabolite. Specifically, we use selective bioconjugation to capture all acyl intermediates on CoA followed by quantitative analysis by SAMDI-MS. The use of chemically defined monolayers enables the rapid isolation of all acyl-CoA species from complex lysates while simultaneously serving as the platform for detection.

A significant benefit of SAMDI is the compatibility with microtiter formats and laboratory automation to allow evaluation of tens of thousands of reactions per day (22, 24, 27). Here, we use this robust and high-throughput method to characterize a cell-free reaction system engineered to produce hydroxymethylglutaryl-CoA (HMG-CoA), the biosynthetic precursor to mevalonate and isoprenoid metabolites. Cell-free engineering is a powerful approach for accelerating the design and construction of biosynthetic pathways and has the further benefit that it is compatible with assay automation (28). In cell-free reactions, biosynthetic pathways are reconstituted in crude lysates, rather than living cells, bypassing the need for laborious metabolic engineering. These cell-free systems are liberated from the regulatory processes that, in vivo, support cell viability and growth, allowing for the design of synthetic pathways that may be difficult or impossible in living cells (28-30). We demonstrate the combination of cell-free reactions and high-throughput characterization with SAMDI to perform thousands of biosynthetic reactions in a single experiment. This strategy, applied here for the optimization of HMG-CoA biosynthesis, greatly increase the speed at which a large reaction space can be mapped for complex networks of enzymes.

C. Developing a Selective Assay for CoA Metabolites

Figure 50:
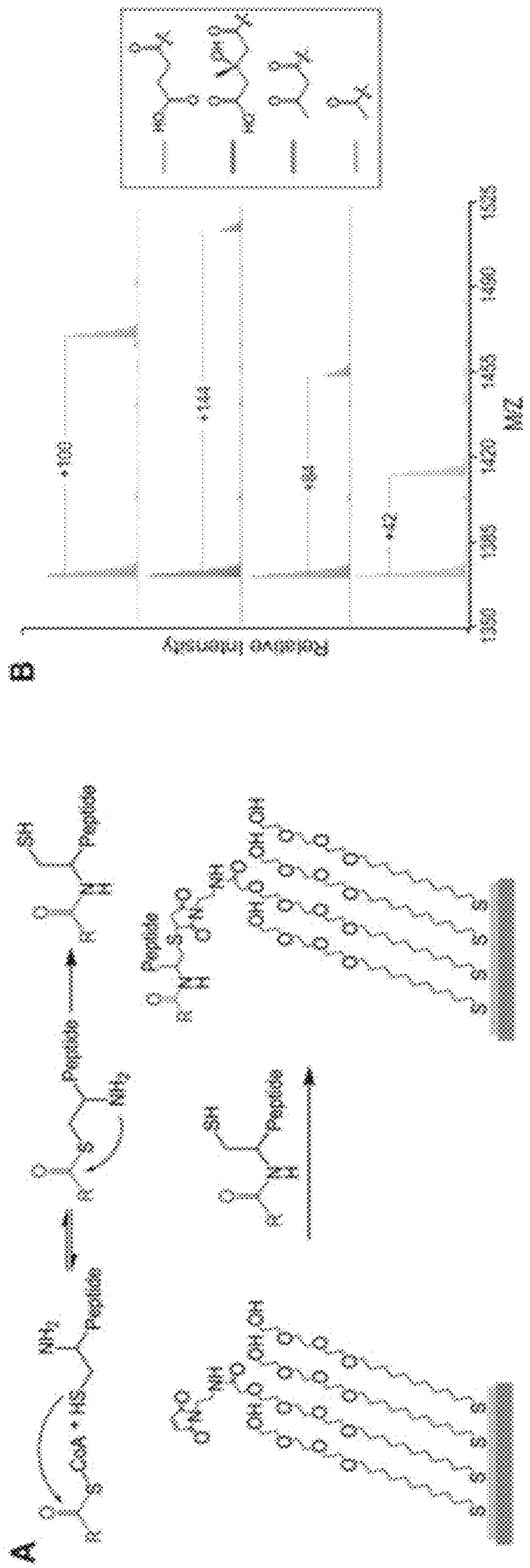
FIG. 50. A generalized approach for capturing CoA-bound metabolites. A) A peptide with an N-terminal cysteine readily reacts with the thioester of RCO-CoA, creating a stable amide bond with the acyl group. After capture, the thiol of the peptide can then be used to immobilize the analyte and peptide onto a maleimide presenting monolayer. B) 500 μM of CoA conjugates of acetyl, acetoacetyl, HMG, and succinyl were reacted with the peptide CAK($Me_3$)SA. The resulting SAMDI spectra show all analytes can be efficiently detected.

We identified the thioester functional group, through which the CoA cofactor binds metabolites, as a unique chemical handle for bio-specific capture. Thioesters have been used extensively to ligate peptides via the native chemical ligation (NCL) chemistry pioneered by Kent and coworkers (31). We recognized that this ligation strategy could also be used to capture acyl moieties from CoA with the specificity required to operate in complex cell lysates. A peptide with an N-terminal cysteine was used for covalent capture, immobilization and detection of CoA metabolites. When the capture peptide is added to reactions containing CoA bound species, it readily scavenges the acyl groups from CoA by a trans-thioesterification reaction followed by a rapid internal rearrangement to irreversibly transfer the captured analyte to the N-terminal amine of the peptide. The reaction mixture is then applied to a monolayer presenting a maleimide group, where the free thiol of the cysteine undergoes immobilization to the monolayer and the lysate can be removed by rinsing (FIG. 50A). The resulting monolayers are covalently tethered to all of the intermediates and products from the CoA biosynthesis and can be directly analyzed by SAMDI mass spectrometry.

NCL has previously seen limited use for in vivo bioconjugation, with this chemical strategy used to label proteins containing N-terminal cysteines with fluorophores that possess thioester handles (32). However, the possibility of cross reactivity of NCL chemistry with biological thioesters, such as acyl-CoA species and intermediates of fatty acid synthesis, has been cited as a limitation of the chemistry for use as a bioconjugation technique (33). In this work, we take advantage of this potential shortcoming, using it to develop an assay targeting acyl-CoA metabolites.

We first validated this chemical strategy for capture and detection using a variety of commercially available, biologically relevant, CoA compounds. These CoA species were each reacted with the capture peptide, of sequence CAK$(Me)_3$SA, in phosphate buffered saline (PBS) at pH 7 and 40° C., at concentrations of 500 μM of CoA species and 1 mM of capture peptide for 2 hrs. The reactions were then applied to self-assembled monolayers presenting maleimide at a density of 20% against a background of tri(ethylene glycol) groups and analyzed by SAMDI mass spectrometry to reveal peaks that correspond to capture of the acyl groups (FIG. 50B). For the purposes of this assay, the capture peptide requires an N-terminal cysteine, and the remaining sequence does not strongly impact the reaction. The peptide used in this work was chosen because of its high ionization efficiency, a characteristic that is important for maximizing the limit of detection in mass spectrometry.

D. Characterization of Pathway Kinetics and Flux

Figure 51:
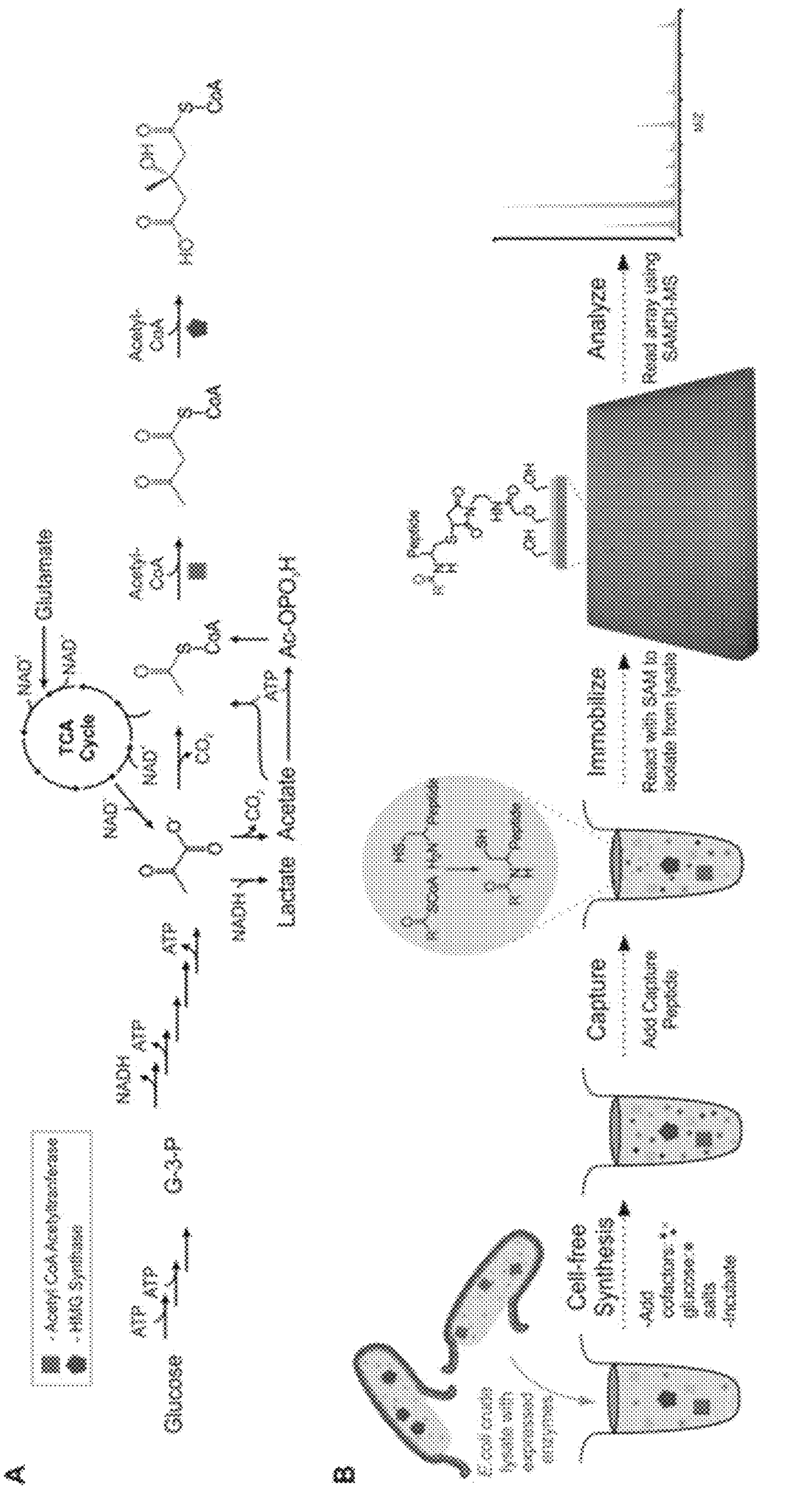
FIG. 51. A cell-free metabolic pathway from glucose to isoprenoid intermediate HMG-CoA. A) Cellular overexpression of ACAT and HMGS and subsequent lysis produces enzyme-enriched lysates which can convert glucose to HMG-CoA, as well as acetate and glutamate. The pathway includes acetyl-CoA and acetoacetyl-CoA intermediates. SAMDI can capture metabolites from crude lysates. B) Cell-free reactions containing lysates, cofactors, salts, and substrate were performed in standard 384 microtiter well plates. Reactions were then quenched, and any CoA-bound products were captured by incubation with sensor peptide. Complex reaction mixtures were printed onto monolayer arrays using liquid handling robotics for isolation and detection. HMG-CoA accumulates in the reaction over time for both C) acetate salts and D) glutamate salts. The dominant carbon source used for HMG production was determined by feeding cell-free reactions $^{13}C$-labeled glucose and $^{13}C$-labeled acetate and monitoring isotopic incorporation into the HMG product. The concentration of cofactors ATP, $NAD^+$, and CoA were set to 1 mM each.

We applied this strategy to analyze the cell-free biosynthesis of HMG-CoA (FIG. 51A)—a biosynthetic precursor to isoprenoids, which represent a diverse and useful class of molecules with applications in pharmaceuticals, flavorings, fragrances, commodity chemicals, and biofuels (4, 34-37). This pathway proceeds from intermediates acetyl-CoA (Ac-CoA) and acetoacetyl-CoA (AA-CoA) to HMG-CoA. We assembled the biosynthetic reactions by mixing crude *E. coli* lysates that separately overexpressed the necessary acetyl-CoA acetyltransferase and HMG synthase enzymes. The cell-free reactions also allowed precise control of the concentrations of glucose substrate, buffer, salts, and cofactors (38). All cell-free reactions were done in standard 384 microtiter well plates and were quenched by addition of formic acid. For capture of CoA metabolites, the pH was adjusted to 6.5 and the capture peptide was introduced. After capture, the reaction mixtures were diluted several fold and applied to arrays of monolayers presenting maleimide functional groups using liquid handling robotics, where captured analytes were selectively isolated from the reaction mixture (FIG. 51B). Analysis was performed using SAMDI arrays of 1536 spots, where each spot is 1 mm in diameter. The reactions from the 384 well plates were each spotted in quadruplicate so that 4 replicate spectra could be averaged for each reaction. For each spot, 0.5 μL of the reaction mixture was used for immobilization.

We first characterized the kinetics of HMG-CoA production in these cell free reaction systems with cofactors ATP, $NAD^+$, and CoA each supplemented at 1 mM (FIG. 51C-D). We measured the rate of HMG-CoA production in two systems containing either acetate or glutamate salts, commonly used in cell-free reactions as necessary counterions for $K^+$, $NH_4^+$, and $Mg^{2+}$ ions (39). Both systems reached similar yields of just over 600 μM of HMG-CoA, though HMG-CoA accumulated more rapidly in the acetate salts, where it was detectible at the earliest reaction times. The same reaction in the glutamate salts required approximately 30 min of reaction time to observe HMG-CoA.

Figure 56:
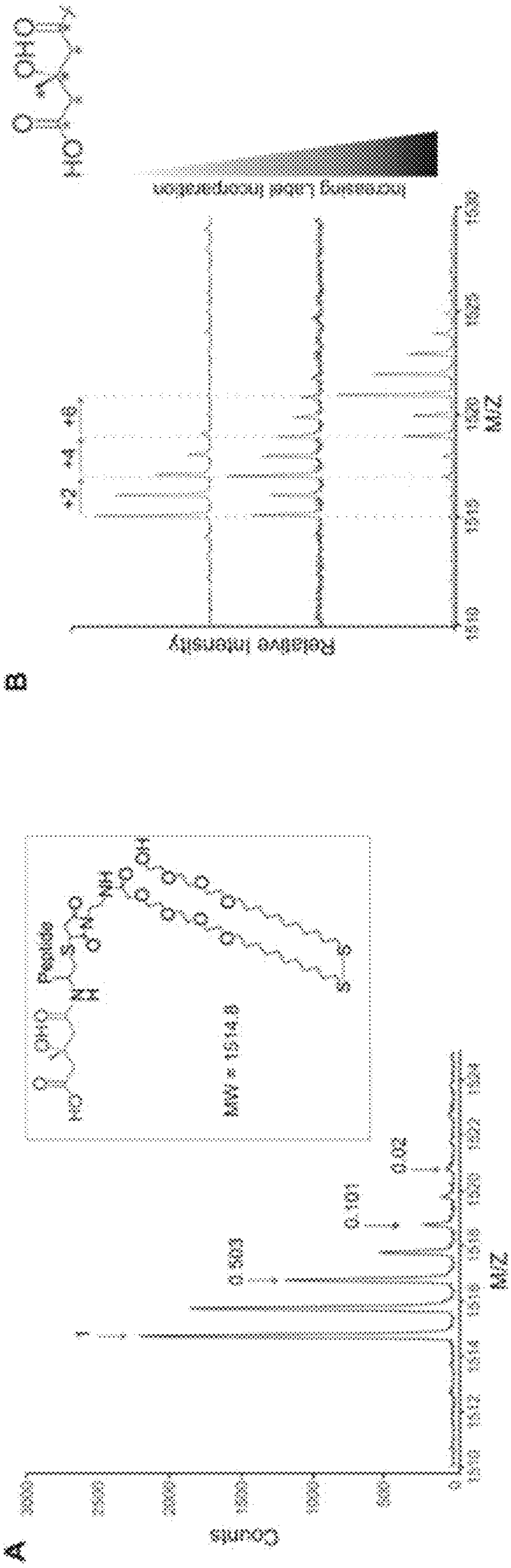
FIG. 56. A) In SAMDI mass spectra, the entire monolayer is desorbed by the laser of the mass spectrometer and detected as a disulfide to a molecule of the tri(ethylene) glycol background. For the HMG adduct, this observed product has a M/Z of just under 1515 mass units. The natural isotopic splitting pattern can be calculated or determined experimentally, giving the relative area of each isotopic peak. B) When the cell-free reaction is provided isotopically labeled $^{13}C_6$ glucose, the incorporation of this label is observed as a peak splitting pattern of +2, +4, and +6 mass units, relative to the unlabeled species. This is because a single 6-carbon molecule of HMG-CoA is synthesized from 3× Ac-CoA units containing 2 carbons that are either labeled or unlabeled, depending on the source of the Ac-CoA. The distribution of these possible HMG labeling states depends on the relative concentrations of unlabeled versus $^{13}C_2$-labeled Ac-CoA in the cell-free reaction. C) The four label states (0, +2, +4, or +6) can each be separately quantified from the convoluted spectra by accounting for the overlap from the natural isotopic splitting of the peaks in front of it.

While glucose is the intended primary carbon source for metabolism, acetate and glutamate act as secondary sources of carbon and can also be metabolized by enzyme pathways native to *E. coli* and converted to HMG-CoA (40) (FIG. 51A). We explored the utilization of these different carbon sources by repeating the experiments with $^{13}C_6$-glucose and quantifying the isotopic incorporation into the final product. Similarly, $^{13}C_2$-acetate was used to monitor metabolic flux from acetate. HMG-CoA is composed of three, 2-carbon acetyl subunits such that four possible label states (0, +2, +4, or +6 mass units) are observed. We quantified the relative abundance of each from the mass spectra and then used these values to determine the fraction of labeled carbon, $f^{C13}$, and the corresponding fraction of unlabeled carbon, $f^{C1\ 2}$, in the HMG-CoA produced (FIG. 56).

We further used the label incorporation to calculate the concentration of HMG-CoA produced. A known amount of commercially available, unlabeled, HMG-CoA was spiked into each capture reaction and the fraction of label incorporation determined before and after. The change in measured label content can be used to calculate the original concentration of HMG-CoA, as described by equation 1 where $f_i^{C12}$ represents the fraction of unlabeled carbon before the spike and $f_{spike}^{C12}$ represents the fraction of unlabeled carbon after the spike. From these values, the initial concentration of HMG-CoA, $[HMG]_i$, can be determined.

$$f_{spike}^{C12} = \frac{f_{initial^*}^{C12}[HMG]_i + [HMG]_{spike}}{[HMG]_i + [HMG]_{spike}} \quad (1)$$

This quantification method is robust to any variations in signal intensity across spectra, as it relies on the peak splitting pattern for the HMG product, and enabled the tracking of both HMG-CoA concentration and carbon usage simultaneously.

The cell-free reactions performed here contained 200 mM of glucose and 150 mM of either acetate or glutamate. We observed that acetate was the primary source of carbon in the acetate system, and for early timepoints it was the source for the bulk of the HMG-CoA produced (FIG. 51C). With longer reaction times, glucose utilization increased and leveled off at 30% of the incorporated carbon. In the glutamate system, glutamate was also a major source of carbon, but the carbon fraction from glucose reached the higher level of 55% after 6 hours (FIG. 51C-D). These results show both acetate and glutamate metabolism is active and both are significant carbon sources and not just passive components of the cell-free system, consistent with previous reports (40).

E. Identification of an Additional Metabolite

It is difficult to independently and quantitatively control the concentrations of cofactors in cell-based metabolic engineering. The cell-free approach used here enables straightforward, independent optimization of buffer composition, cofactor concentrations, and carbon sources to achieve the greatest yield of biosynthetic targets. In particular, supplementation of ATP, $NAD^+$, and CoA can dramatically influence cell-free metabolism (38). As described below, we mapped the dependency of HMG-CoA synthesis over a wide range of these cofactors. However, during initial experiments, we observed an unidentified product bound to the peptide sensor that did not correspond to any of the expected CoA metabolites. This unidentified product gave a mass shift of +72 Da, and this peak increased by 3 mass units when the lysates were supplemented with $^{13}C_6$-glucose. This mass and carbon content was consistent with a lactate-functionalized peptide, but no enzyme in *E. coli* is known to produce lactyl-CoA.

Figure 52:
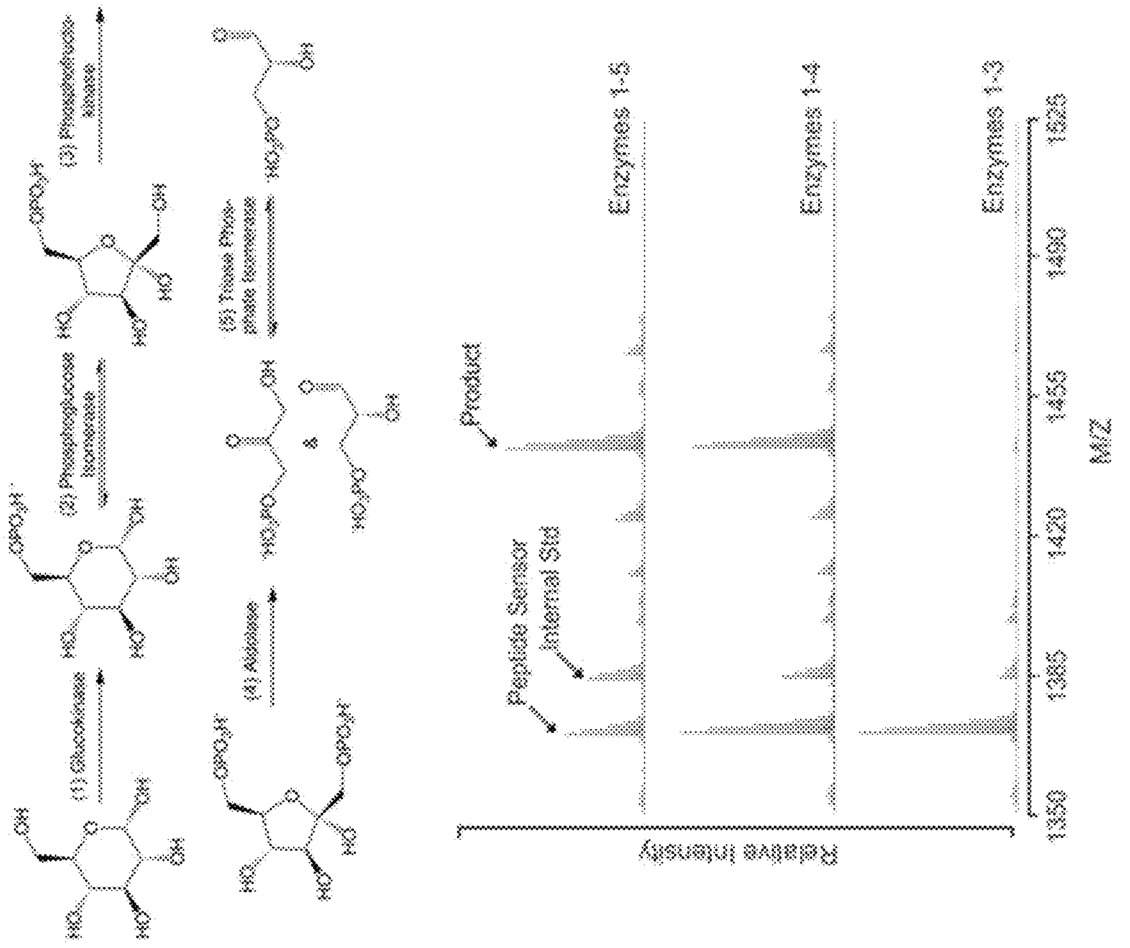
FIG. 52. G3P can be detected. The initial steps of glycolysis were reconstituted in vivo using purified enzymes and fed glucose. When sufficient enzymes are present, G3P is captured and detected.
Figure 53:
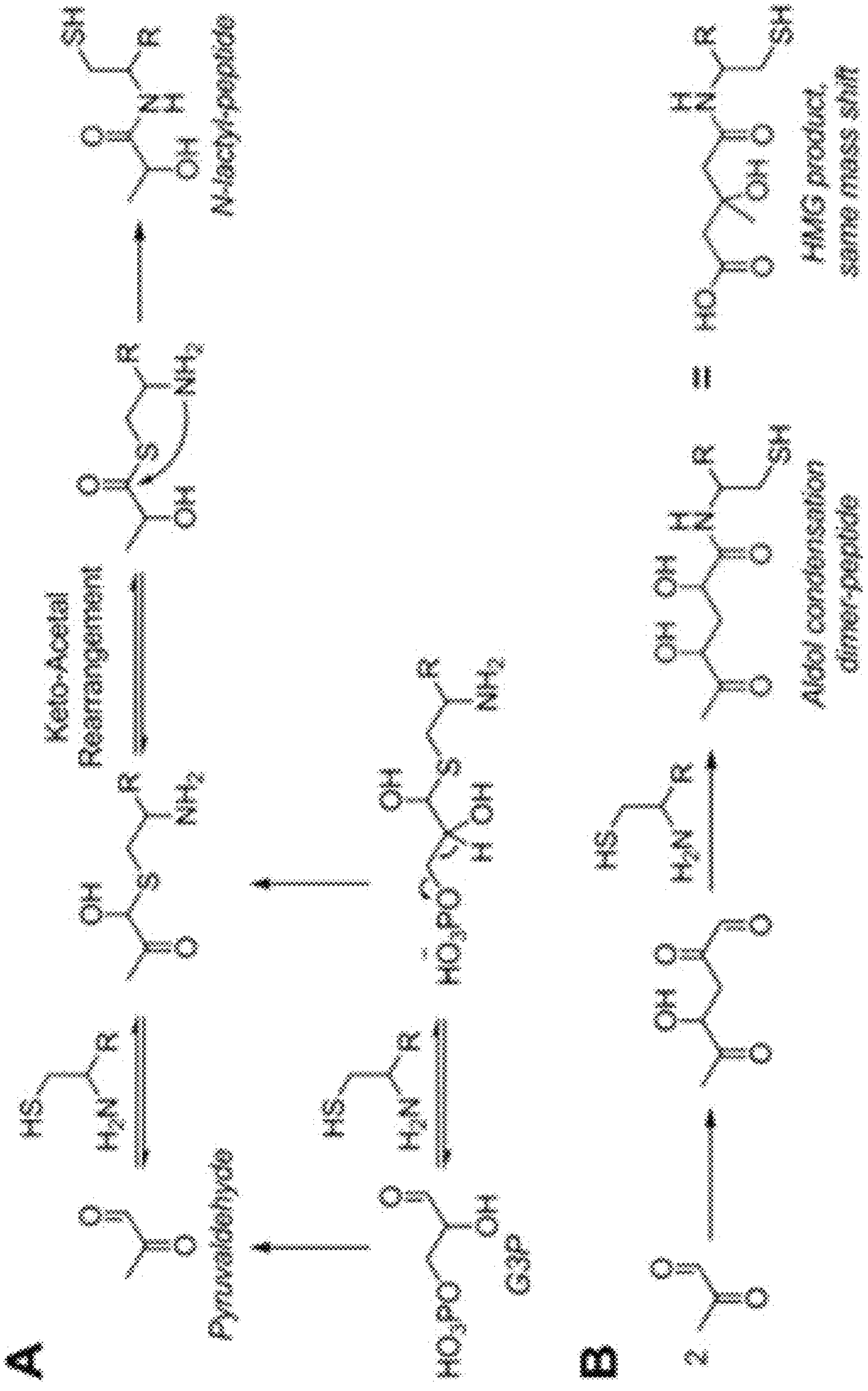
FIG. 53. Derivatives of non-CoA bound, G3P were captured by the sensor peptide. A) A possible mechanism for detection of G3P as N-lactyl-peptide is via pyruvaldehyde, which is known to be generated from G3P and can undergo rearrangement with thiols to form lactyl-thioesters. B) Pyruvaldehyde can also undergo pH-dependent, aldol condensation to yield a 6-carbon species that overlaps in mass with the desired HMG product.

We suspected this unidentified product was derived from glycolysis and identified the source as glyceraldehyde-3-phosphate (G3P) by biochemically reconstituting the initial steps of glycolysis using five purified enzymes (FIG. 52). When the pathway was reconstructed stepwise and fed glucose, this species appeared only when all of the enzymes necessary to produce G3P were present. We hypothesize that the peak derives from a pyruvaldehyde intermediate, which is formed from G3P and dihydroxyacetone phosphate (DHAP) through elimination of the phosphate, and which is a known toxic byproduct of glycolysis (41). The enzyme that interconverts G3P and DHAP, triosephosphate isomerase, has also been shown to catalyze the formation of pyruvaldehyde from these species (42-44). Pyruvaldehyde reacts with thiols, through a thiohemiacetal rearrangement, to produce a lactyl-thioester (45, 46) (FIG. 53A). In this case, the resulting lactyl-thioester can further react to yield a N-lactyl-peptide.

We also observed a peak corresponding to the aldol-condensation product of two molecules of pyruvaldehyde (FIG. 53B). This dimeric adduct results in a product with the same mass shift as HMG-CoA. However, it can be differentiated from HMG because it derives from two 3-carbon subunits and possesses a characteristic +3, +6 labeling pattern when isolated from lysates that are supplemented with $^{13}C_6$ glucose. We found that this aldol condensation product was only observed at a pH above 7. Therefore, to exclude capture of this adduct that can interfere with HMG-CoA detection, we performed all capture reactions at pH 6.5. The thioester rearrangement still proceeds at this pH, but the aldol condensation does not occur.

F. Mapping Metabolite Levels and Pathway Flux

Figure 54:
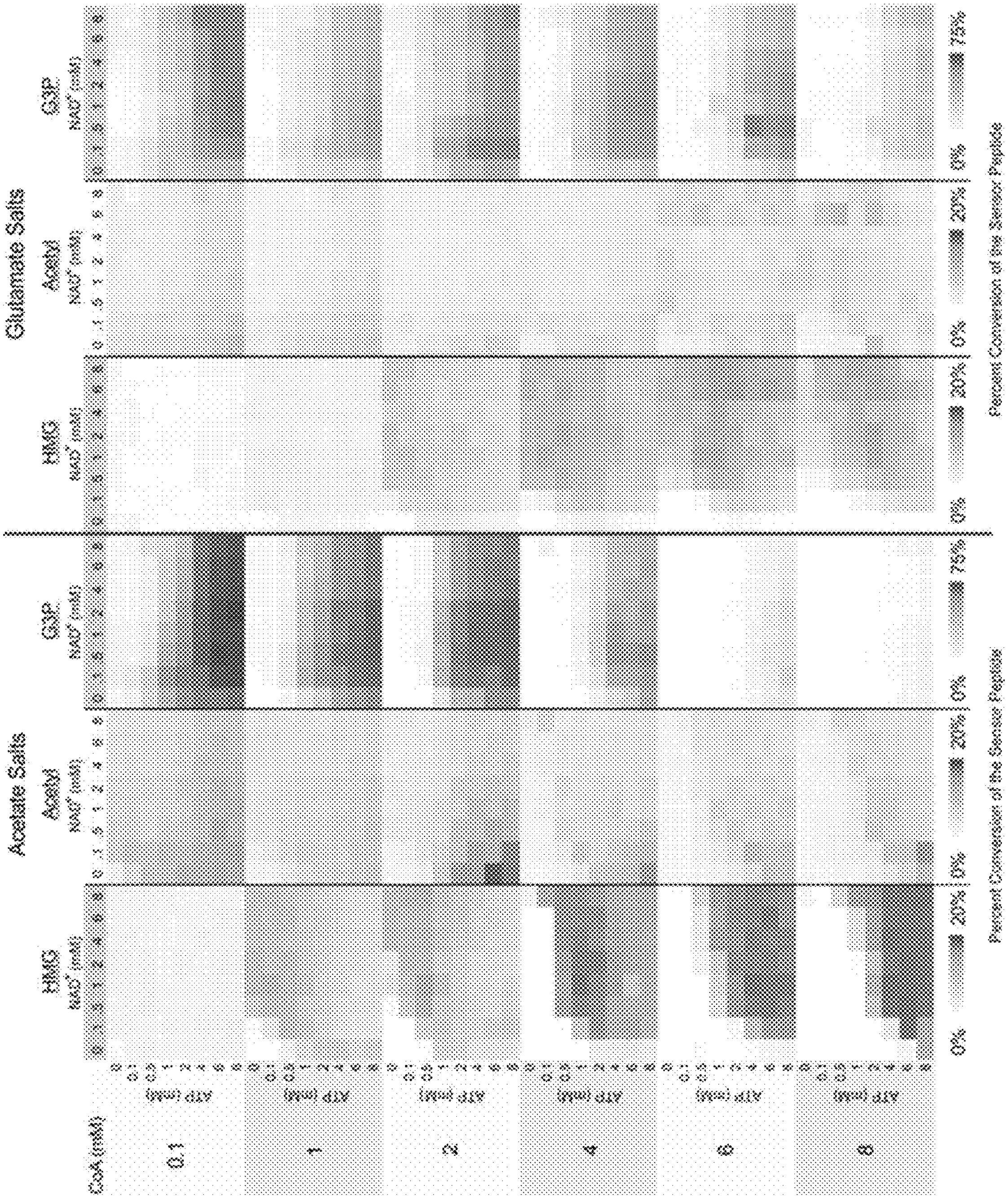
FIG. 54. Parallel measurement of Metabolites. Ac-CoA, HMG-CoA, and G3P production was profiled in 768 unique cofactor conditions. Each product was quantified by calculating percent conversion relative to the unreacted peptide sensor using the area under the curve for each species. All reactions proceeded for 2 hrs at 37° C.

To optimize HMG-CoA production and better understand the effect of cofactor concentrations on the reaction network, we performed a high-throughput experiment that tested 768 unique cofactor conditions—where the concentrations of NAD, CoA and ATP were systematically varied. For each condition three replicate cell-free reactions were performed, and for each reaction four spectra were collected and averaged, totaling over 9,000 individual spectra (FIG. 54). All cell-free reactions were allowed to proceed for 2 hours, quenched, reacted with the capture peptide, and immobilized as described above. Once immobilized, each 1536-spot array can be read by MALDI-TOF MS in just 50 minutes. We did not observe AA-CoA under any conditions tested. In a separate control, we supplemented reactions with commercial AA-CoA and found that it was readily converted back to Ac-CoA, suggesting that the acetyl-CoA acetyltransferase favors the reverse reaction and so no significant amount of AA-CoA accumulates (FIG. 57). For each spectrum, we determined the percent conversion for the three primary observed species (HMG-CoA, Ac-CoA, and G3P) using the integrated areas under the peaks (AUP) for the unreacted capture peptide and the products. Below, equation 2 shows how this calculation was done for HMG and analogous calculation were performed for acetyl and G3P products as well.

$$\text{Percent conversion for } HMG = \frac{AUP_{HMG}}{AUP_{HMG} + AUP_{Ac} + AUP_{G3P} + AUP^{*}_{peptide}} 100\% \qquad (2)$$

These high throughput experiments revealed several notable trends (FIG. 54). First, when low concentrations of CoA and high concentrations of ATP were used, G3P dominated as the major product. This is perhaps not unexpected as low CoA limits the total amount of HMG-CoA the system is capable of synthesizing and the high ATP accelerates the early, pay-in phase of glycolysis. Second, as the concentration of CoA was increased, the amount of G3P decreased; this trade-off was much more significant when reactions were performed in the system using acetate. Thus, G3P was prominent in conditions favoring early glycolysis, but where metabolic flux was unable to proceed to Ac-CoA.

Figure 55:
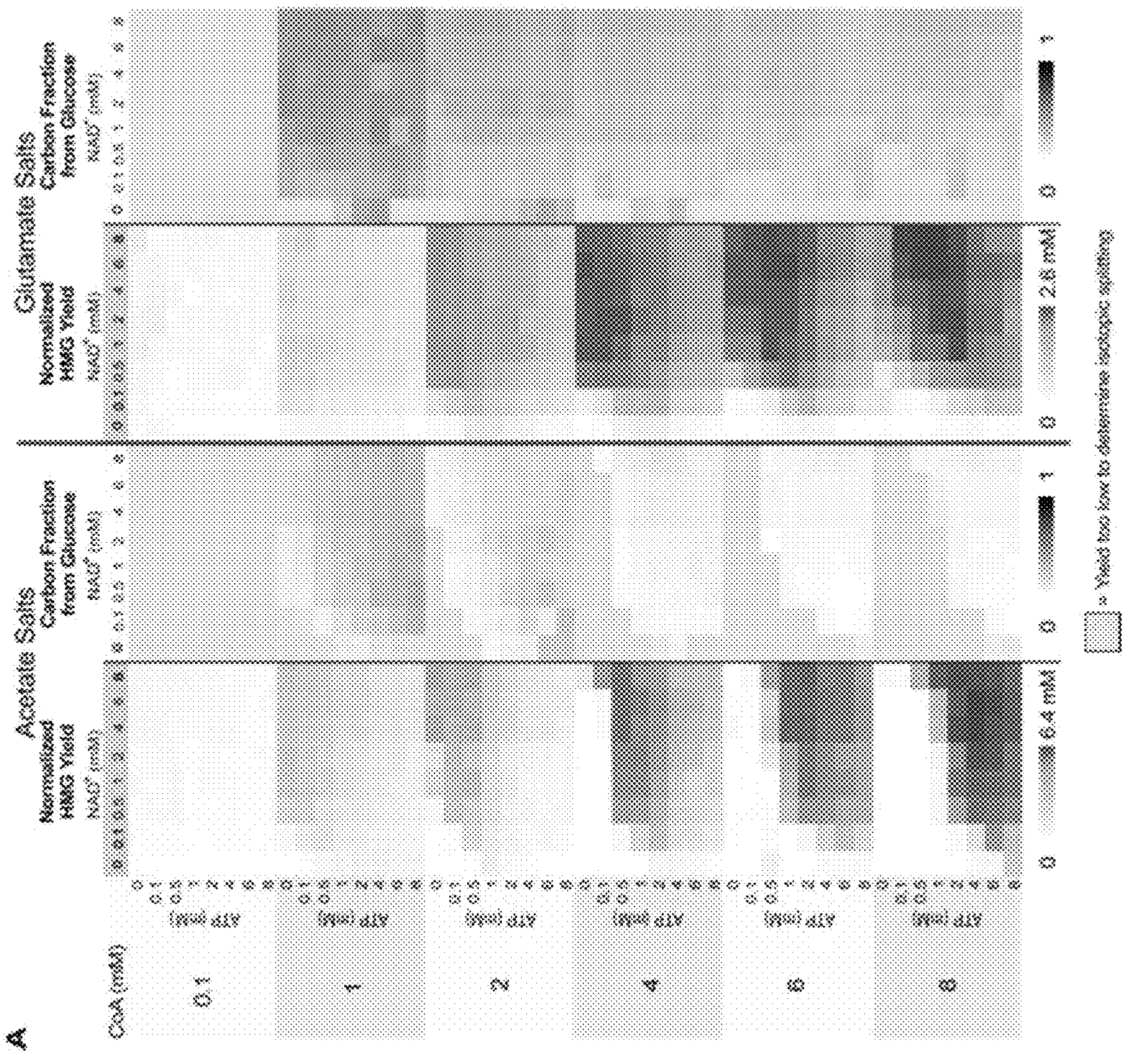
FIG. 55. HMG-CoA concentration and carbon source shifts in response to cofactor conditions A) To analyze HMG-CoA yield across all conditions, the dataset was normalized to an internal standard, a peptide of similar sequence to the sensor without an N-terminal Cys, present at a constant concentration across all reactions. $C^{13}$ labeled glucose was used to concurrently monitor the fraction of HMG-CoA product coming from glucose. HMG production was also visualized as 4D plots for both B) acetate and C) glutamate systems. For the three highest yielding conditions in each system, average [HMG] was determined. In these plots each point represents a specific concentration condition of cofactors with [ATP], [$NAD^+$], [CoA] on the x, y, z axis respectively. Color of each point represents yield with highest yield represented by red. From acetate to glutamate; the red region shifts from high CoA and high ATP, to moderate CoA and low ATP.

We analyzed the same reaction dataset to monitor yield of and metabolic flux to HMG-CoA (FIG. 55A). As described earlier, we used $^{13}C$ labeled glucose to monitor metabolic flux from glucose across the array. For both acetate and glutamate systems, we identified the three reactions that produced the highest concentration of HMG-CoA among the set of 768 reactions. The averages of these highest yielding reactions were 6.4±0.5 mM and 2.6±0.1 mM for the acetate and glutamate systems, respectively. Across the array, the AUP for the HMG-CoA product was normalized to an internal standard present at a constant concentration across all reactions to control for variations in ionization across spectra. For this standard we used the peptide Ac-SK(Me)$_3$GGC which possesses similar ionization efficiency to the capture peptide but lacks an N-terminal cysteine and does not overlap in mass with any species of interest.

Metabolic flux and HMG-CoA production complexly interplayed with cofactor concentrations and we observed significantly different reaction profiles for the systems using acetate and glutamate salts. For the acetate system, higher CoA concentrations improved HMG-CoA titers but also required an associated increase in ATP concentration to achieve this maximal concentration. At low ATP concentrations, increasing available CoA inhibited HMG-CoA production (FIG. 55B). Conversely, over the 2-hour reaction time, the glutamate system reached peak HMG-CoA production at 4 mM CoA. Increasing CoA concentration further to 6 and 8 mM did not increase production of HMG-CoA. However, this shifted the region where highest product concentrations were observed, requiring a shift to higher $NAD^+$ concentration and somewhat higher ATP concentration to maintain the same titers (FIG. 55C).

When product concentration is highest, the fraction of carbon derived from glucose accounted for 5% of product in the acetate salts and 22% in the glutamate salts (FIG. 55A). As in FIG. 52, we see significant incorporation of non-glucose carbon (i.e. acetate and glutamate) in the final product for all cofactor conditions tested. At high CoA concentrations, the glucose incorporation decreased. Counterintuitively, in the acetate system, the best cofactor conditions limit glycolytic flux in favor of optimizing the four-step reaction from acetate to HMG-CoA exclusively. These results suggest that multiple substrates are an important consideration when optimizing cofactors for crude-lysate cell-free metabolic engineering.

Non-intuitive relationships underlie the optimization of complex biological reaction networks. In many cases, understanding the complex interdependency between system variables can only be ascertained by methodical testing of a large number of reaction conditions. In this work, we describe the design of an assay that enables the high-throughput analysis of CoA utilizing metabolic pathways. This assay combines a general strategy for biospecific capture of CoA bound metabolites with simple purification by covalent immobilization onto self-assembled monolayers, that serve as the platform for detection by SAMDI mass spectrometry. We applied this assay to the characterization of a cell-free reaction system for the biosynthesis of HMG-CoA, demonstrating the ability to perform and analyze thousands of individual biosynthetic reactions and to map the reaction space for this complex system with respect to multiple variables.

This assay represents a new, generalizable method for understanding and optimizing biosynthetic pathways. Technologies for rapid characterization can synergize with existing high capacity methods for design and construction of biological systems; such projects can also provide large experimental datasets to inform development of improved design tools. The method described can track multiple metabolites simultaneously and unambiguously using mass spectrometry and is compatible with tracking of metabolic flux using isotopic labeling. When compared to conventional column-based analysis of CoA metabolites, this strategy offers an orders-of-magnitude increase in scale and speed of analysis which should enable high throughput metabolic engineering and decrease the time needed to develop high yielding biosynthetic systems.

G. Materials and Methods

1. Preparation of Enzyme-Enriched Lysates

Two strains of *E. coli* BL21(DE3) containing plasmids pETBCS-ACAT(Eco) and pETBCS-HMGS(Sce) were grown in a 1 liter fermenter at 37° C. (250 rpm) at constant pH (6.95) in rich media (18 $g \cdot L^{-1}$ glucose, 16 $g \cdot L^{-1}$ yeast extract, 10 $g \cdot L^{-1}$ tryptone, 5 $g \cdot L^{-1}$ NaCl, 7 $g \cdot L^{-1}$ potassium phosphate dibasic ($K_2HPO_4$), 3 $g \cdot L^{-1}$ potassium phosphate monobasic ($KH_2PO_4$)) containing 100 $\mu g \cdot mL^{-1}$ carbenicillin (IBI Scientific, Peosta, IA). After induction with 0.1 mM IPTG at $OD_{600}$ 0.6, growth continued for four hours at 30° C. until harvest by centrifugation. See (38) for plasmid sequences and expression characterization. *E. coli* cells were lysed and crude lysates were generated using methods previously described (38).

2. Cell Free Reactions

Cell free reactions were performed at a volume of 15 L in 384-well plates and incubated at 37° C. The standard reaction contained the following components: 200 mM glucose, 100 mM Bis Tris buffer, acetate or glutamate salts (8 mM magnesium, 10 mM ammonium, 134 mM potassium), and 10 mM potassium phosphate ($K_2HPO_4$, pH 7.2). Unless specified, reactions also included 1 mM $NAD^+$, 1 mM ATP, and 1 mM CoA (38). All reagents and chemicals were purchased from Sigma Aldrich (St. Louis, MO). Two lysates, enriched in ACAT(Eco) and HMGS(Sce) respectively, were mixed together at a total protein concentration of 5 $mg \cdot mL^{-1}$ each. Reactions were quenched by precipitating proteins using 2.25 μL of 10% formic acid and immediately stored at −80° C. until peptide incubation. Acetic acid-2-$^{13}$C was neutralized to acetate (pH 7.00) by titration with 45% w/w potassium hydroxide and diluted to 5 M stock concentration.

3. Preparation of Monolayer Arrays

Array plates were prepared by patterning 1536 gold spots, in a standard microtiter format, on steel plates using electron-beam metal evaporation to deposit 5 nM of titanium, followed by 30 nM of gold. These plates were soaked in a solution of disulfide molecules in ethanol for 24-48 hours to form a self-assembled monolayer on the gold surfaces. The solution consisted of a mixture of EG3-alkanethiol disulfide and a mixed disulfide of EG3-alkanethiol and maleimide-terminated EG3-alkanethiol (47). The two disulfide molecules were present in a stoichiometric ratio to yield a 20% maleimide surface density, with an overall concentration of 1 mM. After formation of this primary monolayer on the gold spots, the plates were rinsed with ethanol and dried. The array plates were then soaked in a 10 mM hexadecylphosphonic acid solution in ethanol for 15 minutes. The phosphonic acid terminated hydrocarbon molecules react selectively with the steel background giving it hydrophobic properties that aid with delivery of sub-microliter reaction volumes to the spots.

4. Synthesis of Peptide Reagents

The peptide of the sequence $CAK(Me)_3SA$ (SEQ ID NO:108) was used in this work for capture of acyl-CoA species. The peptide Ac-$SK(Me)_3GGC$ (SEQ ID NO:109) was used as an internal standard for normalization of signal across reactions, as it possesses similar sequence and ionization efficiency to the capture peptide but is mass-resolved and lacks an N-terminal cysteine. Standard FMOC solid phase peptide synthesis on rink-amide resin was used to synthesize both peptides. To introduce the non-natural trimethyl-lysine residue, FMOC-$Lys(Me)_3Cl$ was purchased from Novabiochem and used along with standard amino acid coupling conditions.

5. Capture of CoA Bound Moieties in Lysates

After completion, cell-free reactions were quenched with formic acid to denature the proteins and stop the reactions. The reactions, in 384 well plates, were centrifuged at 3,500×g for 15 minutes to pellet any precipitated protein. For the acyl-CoA capture reactions, 3 μL of this cell-free reaction was transferred to a new 384-well plate and the following species were added, bringing the final reaction volume to 8 μL with the final concentrations as follows: 100 mM phosphate buffer at pH 6.5, 40 mM EDTA, 0.9 mM capture peptide, and 0.1 mM normalization peptide. The well plates were sealed, and the reaction mixtures were incubated at 42° C. for 3 hours. It is important to choose and appropriate concentration of capture peptide. If the concentration is too high, the signal from unreacted sensor peptide may overwhelm the signal from any captured species. In this work the total added peptide concentration was chosen to be 1 mM across all reactions, a reasonable concentration relative to the expected yield from the best cell-free reactions, while also giving good dynamic range for detection of acyl-species in low-yield conditions.

6. Immobilization of Captured Products

The 8 μL capture reactions in 384 well plates were diluted 3-fold to 24 L with 100 mM phosphate buffer at pH 7.2. This serves to dilute the concentration of peptide, which will immobilize efficiently at concentrations as low as 10 micromolar, and adjust the pH to an optimal range for the reaction with maleimide. A TECAN liquid handling robot equipped with a 384-tipped head was used to print the reaction mixtures onto 1536-spot array surfaces, generating 4 replicates per reaction, at a volume of 0.5 L per spot. The surfaces were placed in a humidified chamber and incubated at 37° C. for 60 minutes to allow the cysteine-containing peptides to react with the maleimide functionalized SAM. After reaction, the surfaces were rinsed with 1% SDS detergent, then rinsed with distilled water and dried under a stream of nitrogen gas.

7. Analysis of Reactions

Matrix of THAP in acetonitrile (20 mg/mL) was applied directly to the 1536 spot-surface. The matrix was allowed to dry, and each spot was analyzed by MALDI-TOF mass spectrometry using an AB Sciex 5800 series instrument. Captured metabolites of the cell free reactions were identified by their mass shifts relative to the unreacted capture peptide and quantified by integration of the corresponding peaks.

H. References for Example 7

1. J. Nielsen, J. D. Keasling, Engineering Cellular Metabolism. Cell 164, 1185-1197 (2016).
2. R. Leonardi, Y.-M. Zhang, C. O. Rock, S. Jackowski, Coenzyme A: Back in action. Progress in Lipid Research 44, 125-153 (2005).
3. A. Krivoruchko, Y. Zhang, V. Siewers, Y. Chen, J. Nielsen, Microbial acetyl-CoA metabolism and metabolic engineering. Metabolic engineering 28, 28-42 (2015).
4. C. Paddon et al., High-level semi-synthetic production of the potent antimalarial artemisinin. Nature 496, 528-532 (2013).
5. K. W. George et al., Metabolic engineering for the high-yield production of isoprenoid-based C5 alcohols in *E. coli*. Scientific Reports 5, 11128 (2015).
6. C. M. Denby et al., Industrial brewing yeast engineered for the production of primary flavor determinants in hopped beer. Nature Communications 9, 965 (2018).
7. J. Lian, T. Si, N. U. Nair, H. Zhao, Design and construction of acetyl-CoA overproducing *Saccharomyces cerevisiae* strains. Metabolic Engineering 24, 139-149 (2014).
8. N. Krink-Koutsoubelis et al., Engineered Production of Short-Chain Acyl-Coenzyme A Esters in *Saccharomyces cerevisiae*. ACS Synthetic Biology, (2018).
9. J. Nielsen et al., Engineering synergy in biotechnology. Nature Chemical Biology 10, 319 (2014).
10. J. D. Keasling, Synthetic biology and the development of tools for metabolic engineering. Metabolic Engineering 14, 189-195 (2012).
11. A. A. K. Nielsen et al., Genetic circuit design automation. Science 352, (2016).
12. M. J. Smanski et al., Functional optimization of gene clusters by combinatorial design and assembly. Nature Biotechnology 32, 1241 (2014).
13. C. Magnes et al., Validated comprehensive analytical method for quantification of coenzyme A activated compounds in biological tissues by online solid-phase extraction LC/MS/MS. Analytical chemistry 80, 5736-5742 (2008).
14. W. Lu et al., Metabolomic analysis via reversed-phase ion-pairing liquid chromatography coupled to a stand alone orbitrap mass spectrometer. Analytical chemistry 82, 3212 (2010).
15. S. S. Basu, C. Mesaros, S. L. Gelhaus, I. A. Blair, Stable isotope labeling by essential nutrients in cell culture for preparation of labeled coenzyme A and its thioesters. Analytical chemistry 83, 1363 (2011).
16. M. Zimmermann, V. Thormann, U. Sauer, N. Zamboni, Nontargeted profiling of coenzyme A thioesters in biological samples by tandem mass spectrometry. Analytical chemistry 85, 8284-8290 (2013).
17. Q. Li, S. Zhang, J. M. Berthiaume, B. Simons, G.-F. Zhang, Novel approach in LC-MS/MS using MRM to generate a full profile of acyl-CoAs: discovery of acyl-dephospho-CoAs. Journal of lipid research 55, 592-602 (2014).
18. S. Yang, M. Sadilek, R. E. Synovec, M. E. Lidstrom, Liquid chromatography-tandem quadrupole mass spectrometry and comprehensive two-dimensional gas chromatography-time-of-flight mass spectrometry measurement of targeted metabolites of *Methylobacterium extorquens* AM1 grown on two different carbon sources. Journal of Chromatography A 1216, 3280-3289 (2009).
19. X. Liu et al., High-resolution metabolomics with Acyl-CoA profiling reveals widespread remodeling in response to diet. Molecular & Cellular Proteomics 14, 1489-1500 (2015).
20. F. Zhang, J. M. Carothers, J. D. Keasling, Design of a dynamic sensor-regulator system for production of chemicals and fuels derived from fatty acids. Nature Biotechnology 30, 354-359 (2012).
21. Z. A. Gurard-Levin, M. Mrksich, Combining Self-Assembled Monolayers and Mass Spectrometry for Applications in Biochips. Annual Review of Analytical Chemistry 1, 767-800 (2008).
22. Z. A. Gurard-Levin, M. D. Scholle, A. H. Eisenberg, M. Mrksich, High-throughput screening of small molecule libraries using SAMDI mass spectrometry. ACS combinatorial science 13, 347-350 (2011).
23. H.-Y. Kuo, T. A. DeLuca, W. M. Miller, M. Mrksich, Profiling Deacetylase Activities in Cell Lysates with Peptide Arrays and SAMDI Mass Spectrometry. Analytical chemistry 85, 10635-10642 (2013).
24. L. Ban et al., Discovery of glycosyltransferases using carbohydrate arrays and mass spectrometry. Nature Chemical Biology 8, 769 (2012).
25. L. L. Anderson, E. J. Berns, P. Bugga, A. L. George, M. Mrksich, Measuring Drug Metabolism Kinetics and Drug-Drug Interactions Using Self-Assembled Monolayers for Matrix-Assisted Laser Desorption-Ionization Mass Spectrometry. Analytical chemistry 88, 8604-8609 (2016).

26. W. Kightlinger et al., Design of glycosylation sites by rapid synthesis and analysis of glycosyltransferases. Nature Chemical Biology 14, 627-635 (2018).

27. K. Patel, J. Sherrill, M. Mrksich, M. D. Scholle, Discovery of SIRT3 Inhibitors Using SAMDI Mass Spectrometry. Journal of Biomolecular Screening 20, 842-848 (2015).

28. Q. M. Dudley, A. S. Karim, M. C. Jewett, Cell-free metabolic engineering: Biomanufacturing beyond the cell. Biotechnology Journal 10, 69-82 (2015).

29. C. E. Hodgman, M. C. Jewett, Cell-free synthetic biology: Thinking outside the cell. Metabolic Engineering 14, 261-269 (2012).

30. A. S. Karim, M. C. Jewett, A cell-free framework for rapid biosynthetic pathway prototyping and enzyme discovery. Metabolic Engineering 36, 116-126 (2016).

31. P. Dawson, T. Muir, I. Clark-Lewis, S. Kent, Synthesis of proteins by native chemical ligation. Science 266, 776-779 (1994).

32. D. S. Y. Yeo et al., Cell-permeable small molecule probes for site-specific labeling of proteins. Chemical Communications, 2870-2871 (2003).

33. E. M. Sletten, C. R. Bertozzi, Bioorthogonal Chemistry: Fishing for Selectivity in a Sea of Functionality. Angewandte Chemie International Edition 48, 6974-6998 (2009).

34. J. Bohlmann, C. I. Keeling, Terpenoid biomaterials. The Plant Journal 54, 656-669 (2008).

35. M. D. Leavell, D. J. McPhee, C. J. Paddon, Developing fermentative terpenoid production for commercial usage. Current Opinion in Biotechnology 37, 114-119 (2016).

36. K. W. George, J. Alonso-Gutierrez, J. D. Keasling, T. S. Lee, Isoprenoid Drugs, Biofuels, and Chemicals-Artemisinin, Farnesene, and Beyond. Advances in biochemical engineering/biotechnology 148, 355-389 (2015).

37. Y. Li, B. A. Pfeifer, Heterologous production of plant-derived isoprenoid products in microbes and the application of metabolic engineering and synthetic biology. Current Opinion in Plant Biology 19, 8-13 (2014).

38. Q. M. Dudley, K. C. Anderson, M. C. Jewett, Cell-free mixing of *Escherichia coli* crude extracts to prototype and rationally engineer high-titer mevalonate synthesis. ACS Synthetic Biology 5, 1578-1588 (2016).

39. M. C. Jewett, J. R. Swartz, Mimicking the *Escherichia coli* cytoplasmic environment activates long-lived and efficient cell-free protein synthesis. Biotechnology and Bioengineering 86, 19-26 (2004).

40. M. C. Jewett, K. A. Calhoun, A. Voloshin, J. J. Wuu, J. R. Swartz, An integrated cell-free metabolic platform for protein production and synthetic biology. Molecular Systems Biology 4, (2008).

41. I. Allaman, M. Belanger, P. J. Magistretti, Methylglyoxal, the dark side of glycolysis. Frontiers in Neuroscience 9, (2015).

42. J. P. Richard, Kinetic parameters for the elimination reaction catalyzed by triosephosphate isomerase and an estimation of the reaction's physiological significance. Biochemistry 30, 4581-4585 (1991).

43. R. Iyengar, I. A. Rose, Concentration of activated intermediates of the fructose-1,6-bisphosphate aldolase and triosephosphate isomerase reactions. Biochemistry 20, 1223-1229 (1981).

44. J. P. Richard, Mechanism for the formation of methylglyoxal from triosephosphates. Biochemical Society Transactions 21, 549-553 (1993).

45. A. L. Weber, Formation of the thioester, N-acetyl, S-lactoylcysteine, by reaction of N-acetylcysteine with pyruvaldehyde in aqueous solution. Journal of Molecular Evolution 18, 354-359 (1982).

46. T. Okuyama, S. Komoguchi, T. Fueno, Reaction of thiols with phenylglyoxal to give thiol esters of mandelic acid. II. Intramolecular general-base catalysis and change in rate-determining step. (1982), vol. 104.

47. B. T. Houseman, M. Mrksich, Towards quantitative assays with peptide chips: a surface engineering approach. Trends in Biotechnology. 20, 279-281 (1992).

Example 8: Cell-Free Biosynthesis of Limonene, Pinene and Bisabolene

A. Abstract

Metabolic engineering of microorganisms to produce useful compounds from renewable substrates is a promising means for sustainable, on-demand production of chemicals. However, efforts to design and engineer microbial cell factories are constrained by costly and slow "build" times in which each genetic variation requires re-engineering a new strain. To alleviate this challenge, we have utilized a cell-free approach (termed iPROBE) which uses cell-free protein synthesis (CFPS) to manufacture pathway enzymes in separate reactions that are then mixed to assemble a cell-free, plug-and-play prototyping system for limonene biosynthesis. This approach shortens the time from receiving genes to characterizing active enzymes to ~3 days and allows precise measurement and control of enzyme concentration. We compared 54 enzyme homologs which support nine pathway steps in an initial screen identifying 12 low-activity enzymes. The remaining 42 enzymes were iteratively screened in multiple enzymes sets and in multiple physiochemical conditions to identify enzyme sets which performed robustly. In total, we screened over 590 unique pathway conditions with the best condition producing 4.5 mM (610 mg/L) of limonene in 24 h. Finally, to demonstrate the modularity of this pathway, we also synthesized high titers of the biofuel precursors pinene and bisabolene. We anticipate this prototyping system will provide a controllable and flexible platform for high-throughput screening of enzyme combinations that inform design of microbial cell factories.

B. Introduction

Isoprenoids are a promising class of molecules with over 40,000 known structures and potential uses as pharmaceuticals, flavors, fragrances, pesticides, disinfectants, and chemical feedstocks (Bohlmann and Keeling, 2008; George et al., 2015; Jongedijk et al., 2016). While there have been demonstrations of cellular isoprenoid production at commercial scales (Benjamin et al., 2016; Paddon et al., 2013), efforts to engineer strains for new products have proved challenging. In particular, efforts to explore large sets of heterologous expression conditions are constrained by the need to re-engineer the cell in each iteration. This constraint has limited cellular approaches to 20-40 unique strains in each effort, modifying expression conditions such as ribosome binding site strength (Li et al., 2019; Nowroozi et al., 2014), enzyme expression timing (Alonso-Gutierrez et al., 2015), and plasmid architecture (Yang et al., 2016). New developments in parallelized DNA assembly and robotic liquid handling have enabled the testing of 122 plasmid architectures for the 16-gene refactored nitrogen fixation gene cluster from *Klebsiella oxytoca* (Smanski et al., 2014), the construction of "Marionette" strains for prototyping 243 different expression profiles for lycopene pathway enzymes (Meyer et al., 2019), and the characterization of thousands of ribosome binding site combinations for tuning the production of limonene (Jervis et al., 2019) and naringenin (Zhou et al., 2019). However, these efforts have not been adapted to characterizing enzyme homologs which can significantly enhance performance (Ma et al., 2011; Tsuruta et al., 2009).

Cell-free metabolic engineering offers tremendous flexibility to quickly tune reaction components, substrates, and cofactors (Dudley et al., 2015), giving access to test hundreds of unique pathway expression conditions. Cell-free systems using purified enzymes in particular have shown utility in prototyping metabolic pathways for a range of compounds including fatty acids (Liu et al., 2010), farnesene (Zhu et al., 2014), phenylalanine (Ding et al., 2016), and non-oxidative glycolysis (Bogorad et al., 2013). Crude lysates are becoming increasingly popular for prototyping metabolism because lysates contain competing pathways, alternate substrates, and cofactors (Miguez et al., 2019; Schuh et al., 2019). Additionally, when provided with an energy source, amino acids, NTPs, and excess cofactors, crude lysates contain the translational machinery for cell-free protein synthesis (CFPS) which enables rapid production of proteins (Carlson et al., 2012; Silverman et al., 2019). CFPS decreases the time from DNA to soluble protein and can be used to synthesize functional catalytic enzymes (Karim and Jewett, 2016). The hybrid approach of cell-free protein synthesis metabolic engineering (CFPS-ME) has been successfully adapted to prototype polyhydroxyalkanoate (Kelwick et al., 2018) and 1,4-butanediol (Wu et al., 2015; Wu et al., 2017) production. Yet, even with the rapid ability to synthesize and test enzymes in vitro, these examples have utilized only a small set of enzyme homologs in their optimization strategies.

In this work, we describe a modular, high-throughput isoprenoid production platform for quickly prototyping enzyme homologs, concentrations, and reaction conditions. By expressing pathway enzymes using CFPS in separate reactions and then mixing them together in known concentrations, we assemble pathway combinations for production of the monoterpenoid limonene. This conceptual approach, deemed in vitro Prototyping and Rapid Optimization of Biosynthetic Enzymes (iPROBE), dramatically shortened the time to prototype 3-hydroxybutyrate and n-butanol production for improving in vivo biosynthesis in *Clostridium* (Karim et al., 2020). Here we expand this approach to longer isoprenoid pathways. We use the 9-heterologous enzyme pathway to limonene as a model pathway (FIG. 58A). We screened 590 unique pathway combinations testing 45 different enzyme variants in several reaction (cofactor) conditions. By screening hundreds of enzyme sets and various reaction formats, we were able to improve production 25-fold from our initial setup. We also demonstrated pathway modularity by swapping out the isoprenoid synthetase to produce pinene and bisabolene. Our results suggest that previous cell-free isoprenoid systems, which have reported fewer than 20 enzyme and reaction combinations (Chen et al., 2013; Dirkmann et al., 2018; Korman et al., 2017; Korman et al., 2014; Rodriguez and Leyh, 2014; Zhu et al., 2014), could benefit from screening more enzyme variants. With the ability to test dozens of enzyme homologs in hundreds of combinations without needing to re-engineer a cell or re-assemble DNA, we expect iPROBE to enhance efforts to prototype isoprenoid and other biosynthetic pathways for cellular or cell-free biomanufacturing.

C. Materials and Methods

1. Strain, Plasmid, and Lysate Preparation

All enzyme sequences tested in CFPS were cloned into the pJL1 backbone (Addgene #69496). To assemble plasmids encoding previously tested enzyme homologs (Dudley et al., 2019), the coding sequence of each enzyme was PCR-amplified using forward primer [ttaactttaagaaggagatatacatatggagaaaaaaatcNNNNNNNNNNNNNNNNNNNN (SEQ ID NO:110) where the N-region encodes the gene sequence starting at the second codon (i.e. right after the ATG)] and reverse primer [ttcctttcgggctttgttagcagccggtcgacNNNNNNNNNNN (SEQ ID NO: 111) where the N-region encodes the C-terminus of the gene sequence including the stop codon]. The forward primer adds an N-terminal expression tag to improve cell-free expression which consists of a 15 nucleotide, AT-rich sequence encoding the first five amino acids (Met-Glu-Lys-Lys-Ile, MEKKI (SEQ ID NO: 13)) of chloramphenicol acetyl transferase which was used as a reporter plasmid during development of the *E. coli* CFPS system (Jewett and Swartz, 2004; Swartz et al., 2004). Addition of the MEKKI (SEQ ID NO: 13) sequence demonstrably improved in vitro expression (FIG. 67). The PCR fragment was then mixed with pJL1 backbone digested with the restriction enzymes NdeI and SalI along with reagents for Gibson assembly (Gibson et al., 2009).

To obtain additional sequences for testing, we first generated phylogenetic trees of pathway homologs were generated using Geneious bioinformatics software (Auckland, New Zealand). Sequences for reactions 2.7.1.36 (MK), 2.7.4.2 (PMK), 4.1.1.33 (PMD) 5.3.3.2 (IDI), and 4.3.2.3.16/19/20 (LS) were downloaded from the BRENDA database (Scheer et al., 2010) and aligned in Geneious using a Jukes-Cantor genetic distance model and a Neighbor-Joining tree build method. To choose uncharacterized homologs for testing, we selected 15 sequences from branches of the phylogenetic tree not represented by 30 previously characterized homologs (Table at FIG. 63). These 45 sequences were then codon optimized for expression in *E. coli* synthesized by Gen9 (Cambridge, MA) or Twist Bioscience (San Francisco, CA). Sequences from Twist were delivered cloned into the pJL1 backbone. Gene sequences contained two sequential NdeI recognition sequences at the start of each gene resulting in catATGCATATGGAGAAAAAAATC (SEQ ID NO:14) (encoding MHMEKKI (SEQ ID NO:15)) instead of catATGGAGAAAAAAATC (SEQ ID NO:12) (encoding MEKKI (SEQ ID NO:13)). Upon comparison, the CFPS expression was equivalent for both N-terminal expression tags (FIG. 68) and both tags ultimately used (see Table at FIG. 63).

Lysates pre-enriched with a pathway enzyme were generated as described previously (Dudley et al., 2019). To generate CFPS S30 lysate for cell-free protein synthesis, BL21 Star(DE3) *E. coli* was grown in 1 L of 2×TYPG media in Tunair™ shake flasks at 37° C. (250 rpm). Expression of T7 TRNA polymerase was induced at $OD_{600}$=0.6 by addition of 0.1 mM IPTG and cells were harvested by centrifugation at $OD_{600}$=3.0. Pellets were washed twice in S30 buffer (10 mM tris acetate pH 8.2, 14 mM magnesium acetate, 60 mM potassium acetate, no dithiothreitol (DTT)), flash frozen, and stored at −80° C. Cell pellets were then thawed on ice, resuspended in S30 buffer without DTT (0.8 mL per gram cell pellet), lysed via pressure homogenization with one pass at 20,000 psi (Avestin EmulsiFlex-B15), and centrifuged twice at 30,000×g for 30 minutes. The supernatant (i.e. lysate) was transferred to a new container without disturbing the pellet, aliquoted, and flash frozen for storage at −80° C. Optimal magnesium concentration was determined to be 8 mM based on expression of the plasmid pJL1-sfGFP (Addgene #69496) encoding superfolder Green Fluorescent Protein (sfGFP).

2. Cell-Free Protein Synthesis Reactions

All CFPS reactions used a modified PANOx-SP formula (Jewett and Swartz, 2004). Each reaction contains 13.3 μL of S30 extract for a 50 μL CFPS reaction (FIG. 69) in addition to ATP (1.2 mM), GTP, UTP, CTP (0.85 mM each), folinic acid (34 μg/mL), *E. coli* tRNA mixture (170 μg/mL), 20 standard amino acids (2 mM each), $NAD^+$ (33 mM), coenzyme A (CoA) (0.27 mM), oxalic acid (4 mM), spermidine (1.5 mM), putrescine (1 mM), HEPES (57 mM), potassium glutamate (134 mM), ammonium glutamate (10 mM), magnesium glutamate (8 mM), phosphoenolpyruvate (PEP) (33 mM), and plasmid (13.3 μg/mL) encoding the metabolic pathway enzyme. T7 RNA polymerase was not added to CFPS reactions since extracts were induced with IPTG during cell growth. CFPS reactions of pathway enzymes are incubated for 20 hours at 30° C. or 16° C. (Table at FIG. 63), flash frozen on liquid nitrogen, and stored at −80° C.

3. Quantification of CFPS Protein Production Using Radioactive Amino Acid Incorporation To measure the amount of protein produced in a CFPS reaction, $^{14}$C-leucine (10 μM) was supplemented in addition to the 20 standard amino acids. Reactions were centrifuge at 21,000×g for 10 minutes to pellet insoluble proteins for measurement of soluble protein. Reactions were quenched by addition of equal volume 0.5 M potassium hydroxide and pipetted onto two separate 96-well fiberglass papers (PerkinElmer Printer Filtermat A 1450-421, 90×120 mm) and dried. One paper was subjected to three trichloroacetic acid (TCA) washes (15 min each at 4° C.) to precipitated proteins and dried after rinsing with 100% ethanol. Scintillation wax (PerkinElmer MeltiLex A 1450-441 73×109 mm) was applied and radioactivity was measured using liquid scintillation counting via a MicroBeta2 (PerkinElmer, Waltham, MA). Protein concentration was determined as previously described (Jewett, 2004; Jewett et al., 2008; Jewett and Swartz, 2004) by comparing radioactivity in the total reaction to that of precipitated protein using Equation 1 below.

$$\frac{\mu\text{mol}(14\,C\text{ counts})\text{ leucine in protein}}{\mu\text{mol}(14\,C\text{ counts})\text{ leucine in }rxn}\times\frac{2010\ \mu\text{mol }leucine\text{ in }rsn}{1L\ rxn}\times\frac{\mu\text{mol protein}}{\text{"\#" }\mu\text{mol leucine}}\times\frac{\text{"}mw\text{" }\mu\text{g protein}}{\mu\text{mol protein}}\times\frac{1L}{1000\text{ mL}}=\frac{x\ \mu\text{g protein}}{\text{mL}}.\qquad\text{Equation 1}$$

Note that "#" is number of leucines in the expressed protein and "mw" is the protein molecular weight (g/mol).

4. Mixing of CFPS Reactions and Pre-Enriched Lysates to Produce Limonene

All limonene synthesis reactions are 30 tL in total volume and can be divided into the "CFPS fraction" and the "substrate/lysate/cofactor fraction". The 15 μL CFPS fraction contains six to nine CFPS reactions (thawed on ice) and mixed at concentrations dictated by the experiment. "Blank" CFPS reaction (50 μL volume containing all CFPS reagents, no plasmid, and incubated for 20 h at 30° C., FIG. 70) is added until the total volume of CFPS fraction is 15 μL. The 15 μL "substrate/lysate/cofactor fraction" includes the following components (concentrations are given with respect to the fully assembled 30 plL limonene synthesis reaction): 4 mM magnesium glutamate, 5 mM ammonium glutamate, 65 mM potassium glutamate, 200 mM glucose, 50 μg/mL kanamycin, and 100 mM Bis-Tris (pH 7.4). Since "CFPS fraction" already contains glutamate salts, supplementation of glutamate salts in the "substrate/lysate/cofactor fraction" maintains the overall cation concentrations at 8 mM magnesium, 10 mM ammonium, and 130 mM potassium. Optionally, cofactors ATP, $NAD^+$, and CoA can be supplemented as well (concentrations are given with respect to the fully assembled 30 μL limonene synthesis reaction). The "substrate/lysate/cofactor fraction" also includes fresh S30 lysate(s) at a total protein concentration of 4 mg/mL. Total protein is measured Bradford assay with bovine serum albumin (BSA) as the standard using a microplate protocol (Bio-Rad, Hercules, CA). Typically, three S30 lysates are added each pre-enriched for a single enzyme (EcACAT, ScHMGS, and MsLS) (Dudley et al., 2016; Dudley et al., 2019); each is included at a total protein concentration of 1.33 mg/mL. Based on the level of protein overexpression measured by densitometry (Table at FIG. 64), the final concentration of enriched enzyme in the limonene synthesis reaction is estimated to be ~4.7 μM for EcACAT, ~5.5 μM for ScHMGS, and ~3.4 μM for MsLS, respectively. "Blank lysate" (generated from BL21(DE3) containing no expression plasmid) is added in place of an enzyme-enriched lysate if the given enzyme is included as a CFPS reaction. Limonene synthesis reactions are incubated at 30° C. with a 30 μL dodecane overlay. Limonene in the overlay was quantified at 3, 4, 5, 6, and 24 hours using GC-MS as previously described (Dudley et al., 2019). See Table at FIG. 65 for systematic description of the variable reaction components in each enzyme set tested. The TREE score is calculated using Equations 2 and 3, described below.

$$\text{TREE Score}=\text{Titer}\cdot\text{Rate}\cdot(\text{Average enzyme solubility})\qquad\text{Equation 2}$$

Rationale for the TREE score. One of the perennial challenges of metabolic engineering are appropriate metrics for evaluating enzyme performance. Enzyme pathways in cells generally report titer, rate, and yield (TRY) as well as $K_m$ and $K_{cat}$ values for individual enzyme steps yet there is no consensus value to characterize pathway performance to a single value for ranking pathways or utilizing machine learning algorithms. To address this challenge, we developed the TREE (Titer, Rate, and Enzyme Expression) score which is an aggregate value of enzyme solubility, initial productivity, and final titer. We measured kinetics of limonene production using the baseline enzyme set 1.0 and saw that production is mostly done by 24 hours and the highest productivity is typically between 3-6 hours (FIG. 60). Thus, the TREE score is the product of initial productivity (mM/hr), final titer at 24 hr (mM), and average solubility of 9 overexpressed proteins (%). Error from each component value is propagated to obtain an estimate of TREE score uncertainty. Incorporating the average solubility as a proxy for enzyme expression difficulty allows us to decrease (i.e. penalize) scores of pathways that are likely not to express well in cells.

REE Score error = Equation 3

$$TREE\ \text{score}\cdot\sqrt{\left(\frac{\sigma_{titer}}{\text{Titer}}\right)^2+\left(\frac{\sigma_{rate}}{\text{Rate}}\right)^2+\left(\frac{\text{Average enzyme solubility error}}{\text{Average enzyme solubility}}\right)^2}$$

The titer (mM) is the limonene concentration in the cell-free reaction at 24 hours and Otiter=standard deviation of the three experimental replicates. The rate (mMlhr) is an estimate of initial productivity and is the slope of a linear regression of four single replicate limonene concentrations measured at 3, 4, 5, and 6 hours. Grate is the standard error for the mi slope term of the LINEST regression calculation and is determined using the following formula in Microsoft Excel: =INDEX(LINEST([3 hr titer, 4 hr titer, 5 hr titer, 6 hr titer],[3,4,5,6],1,1),2,1).

D. Results iPROBE enables rapid and controlled assembly of active metabolic pathways in vitro. In our previous work, we demonstrated that nine mixed lysates, each pre-enriched with a pathway enzyme, could produce limonene from glucose with native *E. coli* enzymes supporting the glycolysis part of the pathway (Dudley et al., 2019) (FIG. 58A). This gave a starting point for rebuilding the pathway using lysates enriched, not by heterologous protein expression prior to lysis, but by expressing the protein from a DNA template in the reaction via cell-free protein synthesis (CFPS). In this work our goal was to (1) apply the iPROBE framework to build the nine-enzyme pathway to produce limonene, (2) assess the impact of cofactors on cell-free enzyme performance, (3) iteratively optimize the enzymatic production of limonene, and (4) extend the pathway to additional isoprenoids.

1. Application of the iPROBE Prototyping Paradigm to a Nine-Enzyme Pathway to Produce Limonene We established a cell-free pathway to produce limonene and identified candidate sets of enzyme homologs to improve production. First, we built a pathway to produce limonene using a previously characterized set of nine pathway enzymes with the iPROBE approach, where each enzyme is produced individually via CFPS and the resulting “CFPS-enriched reactions” are mixed with glucose substrate and cofactors to produce the target molecule limonene (FIG. 59A). We find that this initial enzyme set produces 0.17 mM limonene (FIG. 71). We next wanted to sample a diverse range of enzyme sequences because catalytic rate, substrate specificity, and feedback inhibition can vary widely across related enzymes in both primary (Maeda, 2019) and secondary (Schmidt et al., 2018) metabolism. Therefore, we generated phylogenetic trees for several pathway steps using all available sequences in the BRENDA enzyme database (Scheer et al., 2010) (FIG. 58B). We then selected 45 sequences encoding homologs of the nine enzymes of the mevalonate pathway to limonene (SEQ ID NOs:16-72; see sequences at FIG. 85) and assembled them into plasmids for cell-free expression. Half of the selected homologs included uncharacterized enzymes randomly selected from diverse clades while biasing the selection towards homologs suspected to be interesting (e.g., the MK, PMK, PMD, and IDI sequences from *Paracoccus zeaxanthinifaciens* ATCC 21588, a marine bacteria that produces high levels of the isoprenoid zeaxanthin (Berry et al., 2009; Berry et al., 2003)). The other half were kinetically characterized or used in previous metabolic engineering efforts (Table at FIG. 63).

Fifty-one different pathway combinations of the candidate enzymes selected were assembled using iPROBE and screened for limonene production. CFPS generated soluble protein (>30% of total protein) for 40 of the 54 enzymes (FIG. 59B). By decreasing the CFPS incubation temperature from 30° C. to 16° C., we increased soluble protein yields for the remaining 14 enzymes. To test metabolic activity, iPROBE reactions were assembled containing the enzyme homolog of interest plus the remaining set of base-case pathway enzymes (along with pre-enriched lysates of EcACAT, ScHMGS, and MsLS (FIG. 72)). We measured limonene productivity (FIG. 59C) and final titer at 24 hours (FIG. 59D) and then ranked each of these 51 different pathway combinations based on a combined Titer, Rate, and Enzyme Expression (TREE) score (FIG. 59E). This score is a simple, empirical, aggregate value of initial productivity (mM/h), final titer at 24 h (mM), and average solubility of 9 overexpressed proteins (%) (Equations 2 and 3, above; (Karim et al., 2020)). From these data, we observed equivalent or improved productivity relative to the baseline homolog for 2 HMGR, 5 MK, 4 PMK, 4 PMD, 7 IDI, 5 GPPS, and 3 LS homologs. This approach also served as a quick way to rule out several homologs of MK, PMK, PMD, and LS with much lower (or zero) activity; these homologs were excluded from further testing. The relative activity of different HMGRs is very similar to our previous study using pre-enriched lysates (Dudley et al., 2016), as well as in vivo pathway testing (Ma et al., 2011) which suggests that expression of enzymes via CFPS produces proteins with similar properties to those generated with these other methods.

2. Cofactors are a Key Parameter in Testing Multi-Enzyme Pathways

We next wanted to compare the best enzymes from the initial screen to our enzyme set 1.0. To do this, we selected six homologs as best candidates using the TREE score metric (FIG. 59E) for enzyme set 2.0: HMGR from *Bordtella petrii*, MK from *Methanosarcina mazei*, PMK from *Enterococcus faecalis*, PMD from *S. cerevisiae*, IDI from *Streptomyces clavuligerus*, and GPPS from *Picea abies* (Norway spruce). Each selected homolog was highest performing in the TREE score with the exception of MmMK which was chosen over similarly performing homologs due to its known lack of inhibition from downstream isoprenoid metabolites (Primak et al., 2011). We then compared the initial enzyme set 1.0 to the improved set 2.0 containing new homologs for HMGR, MK, PMK, and IDI over 96 hours and found that enzyme set 2.0 did not improve limonene production (FIG. 60A). While the first round of enzyme screening was successfully able to identify active and inactive enzyme homologs, there were only small differences between active homologs (FIG. 59E; FIG. 60A).

We next endeavored to increase the sensitivity of the cell-free system by optimizing cofactors and tuning enzyme concentrations. We know that cofactors are important parameter in optimizing the performance of in vitro enzyme pathways (Dudley et al., 2016; Karim et al., 2018; O'Kane et al., 2019), having previously shown 100-fold differences in metabolite concentrations across 768 unique cofactor conditions of ATP, $NAD^+$, and CoA (O'Kane et al., 2019). Therefore, we tested enzyme sets 1.0 and 2.0 in 18 different cofactor conditions (FIG. 60B) and increased both limonene productivity and titer by two-fold (FIG. 73). We found that enzyme set 2.0 is better than or equivalent to enzyme set 1.0 in all cofactor conditions but the differences are more pronounced at optimized cofactor conditions. Next, we wanted to reduce the concentration of enzymes that are not rate-limiting to leave additional space in the reaction for other CFPS-derived enzymes and potentially differentiate less-active homologs from more-active ones. We titrated the concentration of each CFPS-derived pathway enzyme individually using enzyme set 2.0 (FIG. 74) and found that we could reduce the concentrations of HMGR, MK, PMK, PMD, and IDI (enzyme set 2.1) to produce equivalent levels of limonene (FIG. 74G).

We next examined GPPS, a key enzyme that directs metabolic flux towards ten-carbon GPP and competes with native metabolism which typically generates fifteen-carbon farnesyl pyrophosphate. At high protein concentrations (3 μM), PaGPPS from *Picea abies* produces the highest limonene final titer, however PgGPPS from *Picea glauca* has a higher productivity from 3-6 hours and produces the best TREE score at a lower concentration (1 μM) (FIG. 60C; FIG. 75). Thus, PgGPPS appears to have a higher catalytic rate than PaGPPS but could be less stable and may be inactivated as the reaction proceeds. We therefore reduced the concentration of GPPS from 3.0 μM (Set 2.1) to 1.0 μM (Set 2.2) for further experiments. At this point, the reduced concentrations of upstream pathway enzymes enabled more space for higher concentrations of the final enzyme (limonene synthase). We retested all LS homologs at a higher concentration (particularly those that did not express well in the cell-free system). The pre-enriched lysate of MsLS from *Mentha spicata* again produces the highest TREE score but the difference was far more pronounced when using PgGPPS rather than PaGPPS (FIG. 60D; FIG. 76). This result highlights the importance of testing enzyme homologs in a variety of pathway contexts.

3. Iterative Screening of Active Enzyme Homologs Under Multiple Cofactor Conditions To demonstrate the full potential of our cell-free approach, we tested all active enzyme homologs in an iterative experimental approach that characterized 102 enzyme sets tested in four different cofactor concentrations for a total of 408 unique combinations (FIG. 61). At this point, the primary experimental limitation was not enzyme expression or pathway assembly but product quantitation via GC-MS; this prohibited testing the full combinatorial space of 6*8*5*5*6*4*2=57,600 enzyme sets. The iterative testing approach started by substituting each the six active GPPS homologs and measuring the TREE score under four different cofactor conditions (24 unique conditions; Round 3.x) (FIG. 61A). The two enzyme sets with the highest average TREE score over four cofactor concentrations (FIG. 61B) were selected to move forward in our screens using the logic that the "most robust" enzymes will be active under multiple cofactor conditions. These sets, differing in GPPS homolog, were then used to test the eight active IDI homologs combinatorially. We assembled 64 unique pathway conditions (enzyme sets and cofactor conditions; Round 4.x) and measured TREE scores for each (FIG. 61B). Four enzyme sets were selected and carried forward to be the context for combinatorial testing of all PMD homologs (80 unique conditions; Round 5.x). Thereafter, each experiment used the best scoring five conditions from the previous iteration to test active PMK (Round 6.x), PMD (Round 7.x), and HMGR (Round 8.x) homologs sequentially.

The higher limonene production and reduced enzyme concentrations proved to be a more stringent screen for comparing enzyme homologs relative to FIG. 59. The iterative experiment found clear differences between MK and PMD homologs that produced the same amount of limonene in earlier experiments (FIG. 61C, FIG. 77). Additionally, we found that EcIDI from *Escherichia coli* (one of the most common enzymes used for in vivo terpenoid production) is far less active at reduced concentration compared to other IDI homologs. Finally, we wish to highlight that some enzyme sets showed a variable ranking depending on which cofactor concentration was used. For example, SaHMGR, SaMK, and PzPMK prefer no supplemental CoA while StGPPS is highly active under optimal cofactors but quite low without cofactor supplementation (FIG. 78). The final enzyme set 9.0 included EcACAT, ScHMGS, BpHMGR, MmMK, PzPMK, ScPMD, SlIDI, PgGPPS, and MsLS (FIG. 61D).

4. Bioproduction of Additional Terpenoids

To demonstrate the modularity and flexibility of the cell-free system, we substituted the final enzyme to generate the biofuel precursors pinene and bisabolene (FIG. 62A). Pinene is a useful precursor molecule for various perfumes and bisabolene can be chemically hydrogenated to bisabolane which has nearly identical properties to D2 diesel fuel (Peralta-Yahya et al., 2011). We compared two pinene synthase homologs which produce similar levels of pinene while producing more 3-pinene compared to previous in vitro and in vivo studies (FIG. 79). When using 3.8 μM of CFPS-derived monoterpene synthase, the limonene synthase produces higher amounts of product compared to the pinene synthases (FIG. 62B). A cell-free system composed of two pre-enriched lysates and seven CFPS-enriched reactions (including 1.0 μM EcGPPS/FPPS (ispA) and 1.6 μM AgBS) produces 4.94±0.73 mM (1010 mg/L) bisabolene after 72 hours (FIG. 62C, FIG. 79). This is similar to the best bisabolene titer achieved in cells (912 mg/L) (Peralta-Yahya et al., 2011).

E. Discussion

Cell-free prototyping has tremendous potential to accelerate the Design-Build-Test cycles for metabolic engineering. In this work, we tested over 590 conditions of different enzyme homologs, enzyme concentrations, and cofactor conditions. Cell-free protein synthesis enables the production of active enzyme in just days without requiring protein purification or extensive expression optimization. In the initial conceptions of CFPS-ME, our group utilized a one-pot strategy in which multiple plasmids were added to a single CFPS reaction (Karim and Jewett, 2016), this approach proved challenging to implement to produce limonene (FIG. 80). The two-pot method utilized by iPROBE in which the concentrations of each enzyme are explicitly controlled ultimately proved effective in the nine-step limonene pathway. The final enzyme set 9.0 in a 96-well plate reaction configuration (rather than 1.5 mL microcentrifuge tube) produces 4.49±0.14 mM (610 mg/L) limonene in 24 h (FIG. 79). These rates and titers are similar to recent in vivo efforts (Table at FIG. 66) though lower than a cell-free system utilizing purified enzymes (Korman et al., 2017).

Cell-free prototyping has proved useful for several enzymatic pathways including fatty acids (Liu et al., 2010), farnesene (Zhu et al., 2014), phenylalanine (Ding et al., 2016), non-oxidative glycolysis (Bogorad et al., 2013), polyhydroxyalkanoates (Kelwick et al., 2018), 1,4-butanediol (Wu et al., 2015; Wu et al., 2017), and 3-hydroxybutyrate/n-butanol (Karim et al., 2020). In this work, we found that several enzyme steps including GPPS, IDI, and MK showed strong differences between homologs and PgGPPS, SlIDI, and MmMK (FIG. 79) are promising candidates for further efforts to improve in vivo isoprenoid titers. Two recent efforts utilized MmMK in place of ScMK to produce 1.29 g/L limonene (Wu et al., 2019) and to improve isoprene titers 1.4-fold (Li et al., 2019); however, promoter swapping or ribosome binding site tuning was needed to realize these improvements. In general, this highlights the substantial efforts required to achieve high production in cells and the difficulty of deconvoluting the interacting effects of enzyme activity, expression level, and dynamic responses from the chassis organism. Recently, an exciting approach combining machine learning with ribosome site optimization produced limonene in *E. coli* at high titers using a standard set of enzyme homologs (EcACAT, SaHMG, SaHMGR, ScMK, ScPMK, ScPMD, EcIDI, AgGGPS, MsLS) (Jervis et al., 2019).

We developed the TREE score as a method for consolidating three performance parameters (final titer, initial rate, and enzyme solubility) into a single metric. Plotting the TREE score as a function of its component parts suggests that initial productivity has the strongest influence on the score (FIG. 81) and that the effect of enzyme solubility is relatively small (FIG. 82). Furthermore, our group has shown it useful in predicting pathway performance in *Clostridium* (Karim et al., 2020). Ultimately, the TREE score will require additional in vivo data to validate its effectiveness and potential improvements. The TREE score represents an important first step in developing a ranking system for high-throughput pathway prototyping.

Our study also highlights the importance of enzyme and cofactor concentrations on cell-free pathway activity. In the first round of homolog screening (higher enzyme concentration and non-optimal cofactors (FIG. 59)), the "active" homologs generally produced similar amounts limonene compared to the default homolog. After reducing each enzyme closer to its rate-liming concentration (FIG. 74) and increasing limonene titer via cofactor tuning, re-testing the same homologs (FIG. 61) illuminated differences in activity not seen in the first round. In general, trends of relative homolog activity are similar across different cofactor conditions (FIG. 61) though there are a small number of exceptions such as PzPMK, SaMK, SaHMGR, and StGPPS (FIG. 78). To better understand the correlation between cofactor condition and enzyme performance, we measured a panel of metabolites over time for enzyme sets 1.0, 2.0, and 9.0. The supplementation of $NAD^+$ in enzyme set 9.0 increases lactate production and glycolytic turnover as lactate recycles excess NADH back to $NAD^+$ (FIG. 61D, FIG. 83) (Dudley et al., 2016; Dudley et al., 2019). This, in turn, increases glucose consumption and provides more substrates for downstream components of the pathway. While we had previously known that cofactors could improve pathway performance 100-fold (O'Kane et al., 2019), the performance difference between sets of enzymes at different cofactor conditions had never been described until this study.

Looking forward, there are a number of promising strategies for improving the production of industrially relevant monoterpenoids in vitro and in cells. New pathway routes to utilize neryl pyrophosphate as a substrate for monoterpene synthases rather than GPP have helped decouple pathway production from competition by enzymes essential for growth such as EcGPPS/FPPS (ispA) in *E. coli* (Cheng et al., 2019; Ignea et al., 2019; Wu et al., 2019). Additionally, alternate enzymatic pathways for producing IPP and DMAPP precursors using prenol or isoprenol as an intermediate have been successful (Chatzivasileiou et al., 2019; Clomburg et al., 2019; Lund et al., 2019) and have already been adapted for cell-free isoprenoid production (Ward et al., 2019).

In summary, we anticipate that cell-free prototyping will facilitate the rapid design-build-test cycles of biosynthetic pathways and decrease the amount of time needed for cellular pathway tuning. As the iPROBE framework facilitates large numbers (500+) of enzyme combinations and cofactor conditions without needing requiring large-scale DNA assembly or metabolic engineering of living cells, this approach could be adapted to other pathways for screening enzyme activity, testing for interacting effects between component parts, and analysis of byproduct pathways. These abilities will be synergistically enhanced as new methods are developed for measuring target metabolites at high throughput (O'Kane et al., 2019). This work demonstrates (1) the longest pathway utilized by iPROBE (nine steps) to date, (2) the most unique reaction conditions tested (590+), and (3) the importance of cofactors and enzyme concentration when comparing the activity of enzyme homologs. In future efforts, we look forward to more comparisons of enzyme performance in cell-free versus living cells which will provide additional insights for incorporating iPROBE into the standard design-build-test cycle of cellular metabolic engineering.

F. References for Example 8

Alonso-Gutierrez, J., Kim, E.-M., Batth, T. S., Cho, N., Hu, Q., Chan, L. J. G., Petzold, C. J., Hillson, N. J., Adams, P. D., Keasling, J. D., 2015. Principal component analysis of proteomics (PCAP) as a tool to direct metabolic engineering. Metabolic engineering. 28, 123-133.

Benjamin, K. R., Silva, I. R., Cherubim, J. P., McPhee, D., Paddon, C. J., 2016. Developing commercial production of semi-synthetic artemisinin, and of 3-Farnesene, an Isoprenoid Produced by Fermentation of Brazilian Sugar. Journal of the Brazilian Chemical Society. 27, 1339-1345.

Berry, A., Huembelin, M., Lopez-Ulibarri, R., Production of Coenzyme Q-10. Vol. US20090226986 A1, 2009.

Berry, A., Janssens, D., Humbelin, M., Jore, J. P., Hoste, B., Cleenwerck, I., Vancanneyt, M., Bretzel, W., Mayer, A. F., Lopez-Ulibarri, R., 2003. *Paracoccus* zeaxanthinifaciens sp. nov., a zeaxanthin-producing bacterium. Int. J. Syst. Evol. Microbiol. 53, 231-238.

Bogorad, I. W., Lin, T.-S., Liao, J. C., 2013. Synthetic non-oxidative glycolysis enables complete carbon conservation. Nature. 502, 693-697.

Bohlmann, J., Keeling, C. I., 2008. Terpenoid biomaterials. Plant J. 54, 656-669.

Carlson, E. D., Gan, R., Hodgman, C. E., Jewett, M. C., 2012. Cell-free protein synthesis: applications come of age. Biotechnol. Adv. 30, 1185-1194.

Chatzivasileiou, A. O., Ward, V., Edgar, S. M., Stephanopoulos, G., 2019. Two-step pathway for isoprenoid synthesis. Proc. Natl. Acad. Sci. USA. 116, 506-511.

Chen, X., Zhang, C., Zou, R., Zhou, K., Stephanopoulos, G., Too, H. P., 2013. Statistical Experimental Design Guided Optimization of a One-Pot Biphasic Multienzyme Total Synthesis of Amorpha-4, 11-diene. PloS One. 8, e79650.

Cheng, S., Liu, X., Jiang, G., Wu, J., Zhang, J.-l., Lei, D., Yuan, Y.-J., Qiao, J., Zhao, G.-R., 2019. Orthogonal Engineering of Biosynthetic Pathway for Efficient Production of Limonene in *Saccharomyces cerevisiae*. ACS Syn. Biol.

Clomburg, J. M., Qian, S., Tan, Z., Cheong, S., Gonzalez, R., 2019. The isoprenoid alcohol pathway, a synthetic route for isoprenoid biosynthesis. Proc. Natl. Acad. Sci. USA. 116, 12810-12815.

Ding, D., Liu, Y., Xu, Y., Zheng, P., Li, H., Zhang, D., Sun, J., 2016. Improving the Production of L-Phenylalanine by Identifying Key Enzymes Through Multi-Enzyme Reaction System in vitro. Sci. Rep. 6.

Dirkmann, M., Nowack, J., Schulz, F., 2018. An in Vitro Biosynthesis of Sesquiterpenes Starting from Acetic Acid. ChemBioChem. 19, 2146-2151.

Dudley, Q. M., Anderson, K. C., Jewett, M. C., 2016. Cell-free mixing of *Escherichia coli* crude extracts to prototype and rationally engineer high-titer mevalonate synthesis. ACS Syn. Biol. 5, 1578-1588.

Dudley, Q. M., Karim, A. S., Jewett, M. C., 2015. Cell-free metabolic engineering: Biomanufacturing beyond the cell. Biotechnology Journal. 10, 69-82.

Dudley, Q. M., Nash, C. J., Jewett, M. C., 2019. Cell-free biosynthesis of limonene using *Escherichia coli* crude extracts Synthetic Biology. 4, ysz003.

George, K. W., Alonso-Gutierrez, J., Keasling, J. D., Lee, T. S., 2015. Isoprenoid Drugs, Biofuels, and Chemicals—Artemisinin, Farnesene, and Beyond. Advances in biochemical engineering/biotechnology. 148, 355-389.

Gibson, D. G., Young, L., Chuang, R.-Y., Venter, J. C., Hutchison, C. A., Smith, H. O., 2009. Enzymatic assembly of DNA molecules up to several hundred kilobases. Nat. Methods. 6, 343-345.

Ignea, C., Raadam, M. H., Motawia, M. S., Makris, A. M., Vickers, C. E., Kampranis, S. C., 2019. Orthogonal monoterpenoid biosynthesis in yeast constructed on an isomeric substrate. Nat. Commun. 10, 1-15.

Jervis, A. J., Carbonell, P., Vinaixa, M., Dunstan, M. S., Hollywood, K. A., Robinson, C. J., Rattray, N. J., Yan, C., Swainston, N., Currin, A., Sung, R., Toogood, H., Taylor, S., Faulon, J.-L., Breitling, R., Takano, E., Scrutton, N. S., 2019. Machine learning of designed translational control allows predictive pathway optimization in *Escherichia coli*. ACS Syn. Biol. 8, 127-136.

Jewett, M. C., The impact of cytoplasmic mimicry on cell-free biology. Vol. Doctor of Philosophy. Stanford Univeristy, 2004.

Jewett, M. C., Calhoun, K. A., Voloshin, A., Wuu, J. J., Swartz, J. R., 2008. An integrated cell-free metabolic platform for protein production and synthetic biology. Mol. Syst. Biol. 4, 220.

Jewett, M. C., Swartz, J. R., 2004. Mimicking the *Escherichia coli* cytoplasmic environment activates long-lived and efficient cell-free protein synthesis. Biotechnol. Bioeng. 86, 19-26.

Jongedijk, E., Cankar, K., Buchhaupt, M., Schrader, J., Bouwmeester, H., Beekwilder, J., 2016. Biotechnological production of limonene in microorganisms. Applied Microbiology and Biotechnology. 100, 2927-2938.

Karim, A., Dudley, Q. M., Juminaga, A., Abdella, T., Crowe, S., Heggestad, J., Grubbe, W., Rasor, B., Coar, D., Torculas, M., Jensen, R., Stuart, J., Simpson, S. D., Kopke, M., Jewett, M. C., 2020. In vitro prototyping and rapid optimization of biosynthetic enzymes for cellular design. Nat. Chem. Biol.

Karim, A. S., Heggestad, J. T., Crowe, S. A., Jewett, M. C., 2018. Controlling cell-free metabolism through physiochemical perturbations. Metabolic engineering. 45, 86-94.

Karim, A. S., Jewett, M. C., 2016. A cell-free framework for rapid biosynthetic pathway prototyping and enzyme discovery. Metabolic Engineering. 36, 116-126.

Kelwick, R., Ricci, L., Chee, S. M., Bell, D., Webb, A. J., Freemont, P. S., 2018. Cell-free prototyping strategies for enhancing the sustainable production of polyhydroxyalkanoates bioplastics. Synthetic Biology. 3, ysy016.

Korman, T. P., Opgenorth, P. H., Bowie, J. U., 2017. A synthetic biochemistry platform for cell free production of monoterpenes from glucose. Nat. Commun. 8, 15526.

Korman, T. P., Sahachartsiri, B., Li, D., Vinokur, J. M., Eisenberg, D., Bowie, J. U., 2014. A synthetic biochemistry system for the in vitro production of isoprene from glycolysis intermediates. Protein Science. 23, 576-585.

Li, M., Chen, H., Liu, C., Guo, J., Xu, X., Zhang, H., Nian, R., Xian, M., 2019. Improvement of isoprene production in *Escherichia coli* by rational optimization of RBSs and key enzymes screening. Microbial cell factories. 18, 4.

Liu, T., Vora, H., Khosla, C., 2010. Quantitative analysis and engineering of fatty acid biosynthesis in *E. coli*. Metabolic Engineering. 12, 378-386.

Lund, S., Hall, R., Williams, G. J., 2019. An Artificial Pathway for Isoprenoid Biosynthesis Decoupled from Native Hemiterpene Metabolism. ACS Syn. Biol. 8, 232-238.

Ma, S. M., Garcia, D. E., Redding-Johanson, A. M., Friedland, G. D., Chan, R., Batth, T. S., Haliburton, J. R., Chivian, D., Keasling, J. D., Petzold, C. J., Lee, T. S., Chhabra, S. R., 2011. Optimization of a heterologous mevalonate pathway through the use of variant HMG-CoA reductases. Metabolic Engineering. 13, 588-597.

Maeda, H. A., 2019. Harnessing evolutionary diversification of primary metabolism for plant synthetic biology. Journal of Biological Chemistry. 294, 16549-16566.

Meyer, A. J., Segall-Shapiro, T. H., Glassey, E., Zhang, J., Voigt, C. A., 2019. *Escherichia coli* "Marionette" strains with 12 highly optimized small-molecule sensors. Nat. Chem. Biol. 15, 196.

Miguez, A. M., McNerney, M. P., Styczynski, M. P., 2019. Metabolic Profiling of *Escherichia coli*-Based Cell-Free Expression Systems for Process Optimization. Industrial & Engineering Chemistry Research. 58, 22472-22482.

Nowroozi, F. F., Baidoo, E. E., Ermakov, S., Redding-Johanson, A. M., Batth, T. S., Petzold, C. J., Keasling, J. D., 2014. Metabolic pathway optimization using ribosome binding site variants and combinatorial gene assembly. Applied microbiology and biotechnology. 98, 1567-1581.

O'Kane, P. T., Dudley, Q. M., McMillan, A. K., Jewett, M. C., Mrksich, M., 2019. High-throughput mapping of CoA metabolites by SAMDI-MS to optimize the cell-free biosynthesis of HMG-CoA. Science advances. 5, eaaw9180.

Paddon, C., Westfall, P., Pitera, D., Benjamin, K., Fisher, K., McPhee, D., Leavell, M., Tai, A., Main, A., Eng, D., 2013. High-level semi-synthetic production of the potent antimalarial artemisinin. Nature. 496, 528-532.

Peralta-Yahya, P. P., Ouellet, M., Chan, R., Mukhopadhyay, A., Keasling, J. D., Lee, T. S., 2011. Identification and microbial production of a terpene-based advanced biofuel. Nat. Commun. 2, 483.

Primak, Y. A., Du, M., Miller, M. C., Wells, D. H., Nielsen, A. T., Weyler, W., Beck, Z. Q., 2011. Characterization of a feedback-resistant mevalonate kinase from the archaeon *Methanosarcina mazei*. Applied and Environmental Microbiology. 77, 7772-7778.

Rodriguez, S. B., Leyh, T. S., 2014. An enzymatic platform for the synthesis of isoprenoid precursors. PLoS One. 9, e105594.

Scheer, M., Grote, A., Chang, A., Schomburg, I., Munaretto, C., Rother, M., Sohngen, C., Stelzer, M., Thiele, J., Schomburg, D., 2010. BRENDA, the enzyme information system in 2011. Nucleic Acids Res. 39, D670-D676.

Schmidt, K., Petersen, J., Munkert, J., Egerer-Sieber, C., Hornig, M., Muller, Y. A., Kreis, W., 2018. PRISEs (progesterone 5β-reductase and/or iridoid synthase-like 1, 4-enone reductases): Catalytic and substrate promiscuity allows for realization of multiple pathways in plant metabolism. Phytochemistry. 156, 9-19.

Schuh, L. K., Weyler, C., Heinzle, E., 2019. In-depth characterization of genome-scale network reconstructions for the in vitro synthesis in cell-free systems. Biotechnol. Bioeng.

Silverman, A. D., Karim, A. S., Jewett, M. C., 2019. Cell-free gene expression: an expanded repertoire of applications. Nature Reviews Genetics. 1-20.

Smanski, M. J., Bhatia, S., Zhao, D., Park, Y., L, B. A. W., Giannoukos, G., Ciulla, D., Busby, M., Gordon, D. B., Densmore, D., Voigt, C. A., 2014. Functional optimization of gene clusters by combinatorial design and assembly. Nat. Biotechnol. 32, 1241-9.

Swartz, J. R., Jewett, M. C., Woodrow, K. A., 2004. Cell-free protein synthesis with prokaryotic combined transcription-translation. In: Balbas, P., Lorence, A., Eds.), Recombinant gene expression: reviews and protocols. Springer, pp. 169-182.

Tsuruta, H., Paddon, C. J., Eng, D., Lenihan, J. R., Horning, T., Anthony, L. C., Regentin, R., Keasling, J. D., Renninger, N. S., Newman, J. D., 2009. High-level production of amorpha-4, 11-diene, a precursor of the antimalarial agent artemisinin, in *Escherichia coli*. PloS One. 4, e4489.

Ward, V. C., Chatzivasileiou, A. O., Stephanopoulos, G., 2019. Cell free biosynthesis of isoprenoids from isopentenol. Biotechnol. Bioeng.

Wu, J., Cheng, S., Cao, J., Qiao, J., Zhao, G.-R., 2019. Systematic Optimization of Limonene Production in Engineered *Escherichia coli*. J. Agric. Food Chem. 67, 7087-7097.

Wu, Y. Y., Culler, S., Khandurina, J., Van Dien, S., Murray, R. M., 2015. Prototyping 1, 4-butanediol (BDO) biosynthesis pathway in a cell-free transcription-translation (TX-TL) system. bioRxiv. 017814.

Wu, Y. Y., Sato, H., Huang, H., Culler, S. J., Khandurina, J., Nagarajan, H., Yang, T. H., Van Dien, S., Murray, R. M., 2017. System-level studies of a cell-free transcription-translation platform for metabolic engineering. bioRxiv. 172007.

Yang, L., Wang, C., Zhou, J., Kim, S.-W., 2016. Combinatorial engineering of hybrid mevalonate pathways in *Escherichia coli* for protoilludene production. Microbial Cell Factories. 15, 14.

Zhou, S., Lyu, Y., Li, H., Koffas, M. A., Zhou, J., 2019. Fine-tuning the (2S)-naringenin synthetic pathway using an iterative high-throughput balancing strategy. Biotechnol. Bioeng. 116, 1392-1404.

Zhu, F., Zhong, X., Hu, M., Lu, L., Deng, Z., Liu, T., 2014. In vitro reconstitution of mevalonate pathway and targeted engineering of farnesene overproduction in *Escherichia coli*. Biotechnol. Bioeng. 111, 1396-1405.

Aharoni, A., Giri, A. P., Deuerlein, S., Griepink, F., de Kogel, W.-J., Verstappen, F. W., Verhoeven, H. A., Jongsma, M. A., Schwab, W., Bouwmeester, H. J., 2003. Terpenoid metabolism in wild-type and transgenic *Arabidopsis* plants. Plant Cell. 15, 2866-2884.

Alonso-Gutierrez, J., Chan, R., Batth, T. S., Adams, P. D., Keasling, J. D., Petzold, C. J., Lee, T. S., 2013. Metabolic engineering of *Escherichia coli* for limonene and perillyl alcohol production. Metabolic Engineering. 19, 33-41.

Alonso-Gutierrez, J., Kim, E.-M., Batth, T. S., Cho, N., Hu, Q., Chan, L. J. G., Petzold, C. J., Hillson, N. J., Adams, P. D., Keasling, J. D., 2015. Principal component analysis of proteomics (PCAP) as a tool to direct metabolic engineering. Metabolic engineering. 28, 123-133.

Amiri, P., Shahpiri, A., Asadollahi, M. A., Momenbeik, F., Partow, S., 2016. Metabolic engineering of *Saccharomyces cerevisiae* for linalool production. Biotechnology letters. 38, 503-508.

Anderson, M. S., Muehlbacher, M., Street, I., Proffitt, J., Poulter, C., 1989. Isopentenyl diphosphate: dimethylallyl diphosphate isomerase. An improved purification of the enzyme and isolation of the gene from *Saccharomyces cerevisiae*. Journal of Biological Chemistry. 264, 19169-19175.

Behrendorff, J. B., Vickers, C. E., Chrysanthopoulos, P., Nielsen, L. K., 2013. 2,2-Diphenyl-1-picrylhydrazyl as a screening tool for recombinant monoterpene biosynthesis. Microbial Cell Factories. 12, 76.

Berry, A., Huembelin, M., Lopez-Ulibarri, R., Production of Coenzyme Q-10. Vol. US20090226986 A1, 2009.

Berthelot, K., Estevez, Y., Quiliano, M., Baldera-Aguayo, P. A., Zimic, M., Pribat, A., Bakleh, M.-E., Teyssier, E., Gallusci, P., Gardrat, C., 2016. HbIDI, SlIDI and EcIDI: a comparative study of isopentenyl diphosphate isomerase activity and structure. Biochimie. 127, 133-143.

Bohlmann, J., Steele, C. L., Croteau, R., 1997. Monoterpene synthases from Grand Fir (*Abies grandis*) cDNA isolation, characterization, and functional expression of myrcene synthase, (−)-(4S)-limonene synthase, and (−)-(1S, 5S)-pinene synthase. Journal of Biological Chemistry. 272, 21784-21792.

Bundy, B. C., Swartz, J. R., 2010. Site-specific incorporation of p-propargyloxyphenylalanine in a cell-free environment for direct protein-protein click conjugation. Bioconj. Chem. 21, 255-263.

Burke, C., Croteau, R., 2002. Geranyl diphosphate synthase from *Abies grandis*: cDNA isolation, functional expression, and characterization. Archives of biochemistry and biophysics. 405, 130-136.

Carter, O. A., Peters, R. J., Croteau, R., 2003. Monoterpene biosynthesis pathway construction in *Escherichia coli*. Phytochemistry. 64, 425-433.

Chen, F., Li, W., Jiang, L., Pu, X., Yang, Y., Zhang, G., Luo, Y., 2016. Functional characterization of a geraniol synthase-encoding gene from Camptotheca *acuminata* and its application in production of geraniol in *Escherichia coli*. Journal of Industrial Microbiology & Biotechnology. 43, 1281-1292.

Cheng, S., Liu, X., Jiang, G., Wu, J., Zhang, J.-l., Lei, D., Yuan, Y.-J., Qiao, J., Zhao, G.-R., 2019. Orthogonal Engineering of Biosynthetic Pathway for Efficient Production of Limonene in *Saccharomyces cerevisiae*. ACS Syn. Biol.

Colby, S., Alonso, W., Katahira, E., McGarvey, D., Croteau, R., 1993. 4S-limonene synthase from the oil glands of spearmint (*Mentha spicata*). cDNA isolation, characterization, and bacterial expression of the catalytically active monoterpene cyclase. Journal of Biological Chemistry. 268, 23016-23024.

Davies, F. K., Work, V. H., Beliaev, A. S., Posewitz, M. C., 2014. Engineering limonene and bisabolene production in wild type and a glycogen-deficient mutant of Synechococcus sp. PCC 7002. Frontiers in Bioengineering and Biotechnology. 2, 21.
Dong, L., Jongedijk, E., Bouwmeester, H., Van Der Krol, A., 2016. Monoterpene biosynthesis potential of plant subcellular compartments. New Phytol. 209, 679-690.
Doun, S. S., Burgner, J. W., Briggs, S. D., Rodwell, V. W., 2005. *Enterococcus faecalis* phosphomevalonate kinase. Protein Science. 14, 1134-1139.
Du, F.-L., Yu, H.-L., Xu, J.-H., Li, C.-X., 2014. Enhanced limonene production by optimizing the expression of limonene biosynthesis and MEP pathway genes in *E. coli*. Bioresources and Bioprocessing. 1, 1.
Dudley, Q. M., Anderson, K. C., Jewett, M. C., 2016. Cell-free mixing of *Escherichia coli* crude extracts to prototype and rationally engineer high-titer mevalonate synthesis. ACS Syn. Biol. 5, 1578-1588.
Dudley, Q. M., Nash, C. J., Jewett, M. C., 2019. Cell-free biosynthesis of limonene using *Escherichia coli* crude extracts Synthetic Biology. 4, ysz003.
Dueber, J. E., Wu, G. C., Malmirchegini, G. R., Moon, T. S., Petzold, C. J., Ullal, A. V., Prather, K. L., Keasling, J. D., 2009. Synthetic protein scaffolds provide modular control over metabolic flux. Nat. Biotechnol. 27, 753-759.
Dunlop, M. J., Dossani, Z. Y., Szmidt, H. L., Chu, H. C., Lee, T. S., Keasling, J. D., Hadi, M. Z., Mukhopadhyay, A., 2011. Engineering microbial biofuel tolerance and export using efflux pumps. Mol. Syst. Biol. 7, 487.
Falara, V., Akhtar, T. A., Nguyen, T. T., Spyropoulou, E. A., Bleeker, P. M., Schauvinhold, I., Matsuba, Y., Bonini, M. E., Schilmiller, A. L., Last, R. L., 2011. The tomato terpene synthase gene family. Plant Physiol. 157, 770-789.
Fischer, M. J., Meyer, S., Claudel, P., Bergdoll, M., Karst, F., 2011. Metabolic engineering of monoterpene synthesis in yeast. Biotechnol. Bioeng. 108, 1883-1892.
Fischer, M. J., Meyer, S., Claudel, P., Perrin, M., Ginglinger, J. F., Gertz, C., Masson, J. E., Werck-Reinhardt, D., Hugueney, P., Karst, F., 2013. Specificity of *Ocimum basilicum* geraniol synthase modified by its expression in different heterologous systems. Journal of biotechnology. 163, 24-29.
Ignea, C., Cvetkovic, I., Loupassaki, S., Kefalas, P., Johnson, C. B., Kampranis, S. C., Makris, A. M., 2011. Improving yeast strains using recyclable integration cassettes, for the production of plant terpenoids. Microbial cell factories. 10, 4.
Ignea, C., Pontini, M., Maffei, M. E., Makris, A. M., Kampranis, S. C., 2014. Engineering monoterpene production in yeast using a synthetic dominant negative geranyl diphosphate synthase. ACS Syn. Biol. 3, 298-306.
Jervis, A. J., Carbonell, P., Vinaixa, M., Dunstan, M. S., Hollywood, K. A., Robinson, C. J., Rattray, N. J., Yan, C., Swainston, N., Currin, A., Sung, R., Toogood, H., Taylor, S., Faulon, J.-L., Breitling, R., Takano, E., Scrutton, N. S., 2019. Machine learning of designed translational control allows predictive pathway optimization in *Escherichia coli*. ACS Syn. Biol. 8, 127-136. Jewett, M. C., Swartz, J. R., 2004. Mimicking the *Escherichia coli* cytoplasmic environment activates long-lived and efficient cell-free protein synthesis. Biotechnol. Bioeng. 86, 19-26.
Jongedijk, E., Cankar, K., Buchhaupt, M., Schrader, J., Bouwmeester, H., Beekwilder, J., 2016. Biotechnological production of limonene in microorganisms. Applied Microbiology and Biotechnology. 100, 2927-2938.
Jongedijk, E., Cankar, K., Ranzijn, J., Krol, S., Bouwmeester, H., Beekwilder, J., 2015. Capturing of the monoterpene olefin limonene produced in *Saccharomyces cerevisiae*. Yeast. 32, 159-171.
Kaneda, K., Kuzuyama, T., Takagi, M., Hayakawa, Y., Seto, H., 2001. An unusual isopentenyl diphosphate isomerase found in the mevalonate pathway gene cluster from *Streptomyces* sp. strain CL190. Proc. Natl. Acad. Sci. USA. 98, 932-937.
Kang, M.-K., Eom, J.-H., Kim, Y., Um, Y., Woo, H. M., 2014. Biosynthesis of pinene from glucose using metabolically-engineered *Corynebacterium glutamicum*. Biotechnology letters. 36, 2069-2077.
Kao, C.-1., Kittleman, W., Zhang, H., Seto, H., Liu, H.-w., 2005. Stereochemical Analysis of Isopentenyl Diphosphate Isomerase Type II from *Staphylococcus aureus* Using Chemically Synthesized (S)- and (R)-[2-2H] Isopentenyl Diphosphates. Organic Letters. 7, 5677-5680.
Karim, A., Dudley, Q. M., Juminaga, A., Abdella, T., Crowe, S., Heggestad, J., Grubbe, W., Rasor, B., Coar, D., Torculas, M., Jensen, R., Stuart, J., Simpson, S. D., Kopke, M., Jewett, M. C., 2020. A bridge between cell-free experimentation and cellular metabolic engineering. TBD.
Karim, A. S., Jewett, M. C., 2016. A cell-free framework for rapid biosynthetic pathway prototyping and enzyme discovery. Metabolic Engineering. 36, 116-126.
Kim, E.-M., Eom, J.-H., Um, Y., Kim, Y., Woo, H. M., 2015. Microbial synthesis of myrcene by metabolically engineered *Escherichia coli*. J. Agric. Food Chem. 63, 4606-4612.
Kiyota, H., Okuda, Y., Ito, M., Hirai, M. Y., Ikeuchi, M., 2014. Engineering of cyanobacteria for the photosynthetic production of limonene from CO2. Journal of biotechnology. 185, 1-7.
Korman, T. P., Opgenorth, P. H., Bowie, J. U., 2017. A synthetic biochemistry platform for cell free production of monoterpenes from glucose. Nat. Commun. 8, 15526.
Kumari, U., Vishwakarma, R. K., Sonawane, P., Abbassi, S., Khan, B. M., 2015.
Biochemical characterization of recombinant mevalonate kinase from Bacopa monniera. Int. J. Biol. Macromol. 72, 776-783.
Landmann, C., Fink, B., Festner, M., Dregus, M., Engel, K.-H., Schwab, W., 2007. Cloning and functional characterization of three terpene synthases from lavender (*Lavandula angustifolia*). Archives of Biochemistry and Biophysics. 465, 417-429.
Lefurgy, S. T., Rodriguez, S. B., Park, C. S., Cahill, S., Silverman, R. B., Leyh, T. S., 2010. Probing ligand-binding pockets of the mevalonate pathway enzymes from *Streptococcus pneumoniae*. Journal of Biological Chemistry. 285, 20654-20663.
Liu, W., Xu, X., Zhang, R., Cheng, T., Cao, Y., Li, X., Guo, J., Liu, H., Xian, M., 2016. Engineering *Escherichia coli* for high-yield geraniol production with biotransformation of geranyl acetate to geraniol under fed-batch culture. Biotechnology for biofuels. 9, 1.
Lticker, J., El Tamer, M. K., Schwab, W., Verstappen, F. W., van der Plas, L. H., Bouwmeester, H. J., Verhoeven, H. A., 2002. Monoterpene biosynthesis in lemon (*Citrus limon*). Eur. J. Biochem. 269, 3160-3171.
Martin, D. M., Faldt, J., Bohlmann, J., 2004. Functional characterization of nine Norway spruce TPS genes and evolution of gymnosperm terpene synthases of the TPS-d subfamily. Plant Physiol. 135, 1908-1927.

Reiling, K. K., Yoshikuni, Y., Martin, V. J., Newman, J., Bohlmann, J., Keasling, J. D., 2004. Mono and diterpene production in *Escherichia coli*. Biotechnol. Bioeng. 87, 200-212.

Rodriguez, S. B., Leyh, T. S., 2014. An enzymatic platform for the synthesis of isoprenoid precursors. PLoS One. 9, e105594.

Sarria, S., Wong, B., Martin, H. G., Keasling, J. D., Peralta-Yahya, P., 2014. Microbial synthesis of pinene. ACS Syn. Biol. 3, 466-475.

Schmidt, A., Gershenzon, J., 2008. Cloning and characterization of two different types of geranyl diphosphate synthases from Norway spruce (*Picea abies*). Phytochemistry. 69, 49-57.

Singh, H., Gahlan, P., Kumar, S., 2013. Cloning and expression analysis of ten genes associated with picrosides biosynthesis in Picrorhiza kurrooa. Gene. 515, 320-328.

Swartz, J. R., Jewett, M. C., Woodrow, K. A., 2004. Cell-free protein synthesis with prokaryotic combined transcription-translation. In: Balbas, P., Lorence, A., Eds.), Recombinant gene expression: reviews and protocols. Springer, pp. 169-182.

Tsuruta, H., Paddon, C. J., Eng, D., Lenihan, J. R., Horning, T., Anthony, L. C., Regentin, R., Keasling, J. D., Renninger, N. S., Newman, J. D., 2009. High-level production of amorpha-4, 11-diene, a precursor of the antimalarial agent artemisinin, in *Escherichia coli*. PloS One. 4, e4489.

Voynova, N. E., Rios, S. E., Miziorko, H. M., 2004. *Staphylococcus aureus* mevalonate kinase: isolation and characterization of an enzyme of the isoprenoid biosynthetic pathway. Journal of bacteriology. 186, 61-67.

Wang, J., Xiong, Z., Li, S., Wang, Y., 2015. Exploiting exogenous MEP pathway genes to improve the downstream isoprenoid pathway effects and enhance isoprenoid production in *Escherichia coli*. Process Biochemistry. 50, 24-32.

Weaver, L. J., Sousa, M. M., Wang, G., Baidoo, E., Petzold, C. J., Keasling, J. D., 2014. A kinetic-based approach to understanding heterologous mevalonate pathway function in *E. coli*. Biotechnol. Bioeng. 112, 111-119.

Willrodt, C., David, C., Cornelissen, S., Btihler, B., Julsing, M. K., Schmid, A., 2014. Engineering the productivity of recombinant *Escherichia coli* for limonene formation from glycerol in minimal media. Biotechnology Journal. 9, 1000-1012.

Wu, J., Cheng, S., Cao, J., Qiao, J., Zhao, G.-R., 2019. Systematic Optimization of Limonene Production in Engineered *Escherichia coli*. J. Agric. Food Chem. 67, 7087-7097.

Yang, L., Wang, C., Zhou, J., Kim, S.-W., 2016. Combinatorial engineering of hybrid mevalonate pathways in *Escherichia coli* for protoilludene production. Microbial Cell Factories. 15, 14.

Yoon, S.-H., Lee, S.-H., Das, A., Ryu, H.-K., Jang, H.-J., Kim, J.-Y., Oh, D.-K., Keasling, J. D., Kim, S.-W., 2009. Combinatorial expression of bacterial whole mevalonate pathway for the production of β-carotene in *E. coli*. Journal of Biotechnology. 140, 218-226.

Yuba, A., Yazaki, K., Tabata, M., Honda, G., Croteau, R., 1996. cDNA Cloning, Characterization, and Functional Expression of 4S-(−)-Limonene Synthase fromPerilla *frutescens*. Archives of biochemistry and biophysics. 332, 280-287.

Zhang, H., Liu, Q., Cao, Y., Feng, X., Zheng, Y., Zou, H., Liu, H., Yang, J., Xian, M., 2014. Microbial production of sabinene—a new terpene-based precursor of advanced biofuel. Microbial cell factories. 13, 20.

Zhao, J., Bao, X., Li, C., Shen, Y., Hou, J., 2016. Improving monoterpene geraniol production through geranyl diphosphate synthesis regulation in *Saccharomyces cerevisiae*. Applied Microbiology and Biotechnology. 100, 4561-4571.

Zhou, J., Wang, C., Yoon, S.-H., Jang, H.-J., Choi, E.-S., Kim, S.-W., 2014. Engineering *Escherichia coli* for selective geraniol production with minimized endogenous dehydrogenation. Journal of biotechnology. 169, 42-50.

Zurbriggen, A., Kirst, H., *Melis*, A., 2012. Isoprene production via the mevalonic acid pathway in *Escherichia coli* (Bacteria). BioEnergy Research. 5, 814-828.

Example 9: Cell-Free Biosynthesis of 3-hydroxybutyrate, n-butanol and (s)-(+)-1,3-butanediol

A. Abstract

The design and optimization of biosynthetic pathways for industrially relevant, non-model organisms is a challenge. Here we describe a platform for in vitro Prototyping and Rapid Optimization of Biosynthetic Enzymes (iPROBE) to accelerate this process. In iPROBE, cell lysates are enriched with biosynthetic enzymes by cell-free protein synthesis and then metabolic pathways are assembled in a mix-and-match fashion to assess pathway performance. We demonstrate iPROBE by assessing 54 different cell-free pathways for 3-hydroxybutyrate production and optimizing a 6-step n-butanol pathway across 205 permutations using data-driven design. After screening a selection of these pathways in cells, we observed a strong correlation (r=0.79) between cell-free and cellular performance. We then scaled up our highest performing pathway, improving in vivo 3-HB production in *Clostridium* by 20-fold to 14.63±0.48 g/L. We also identified a new biosynthetic route to (S)-(+)-1,3-butanediol. We expect iPROBE to accelerate design-build-test cycles for industrial biotechnology.

B. Introduction

For decades, scientists and engineers have turned to biological systems for making energy, medicines, and materials-especially when chemical synthesis is untenable. Unfortunately, biological production of small molecules does not often provide the desired titer, rate, or yield because natural sources (e.g., plants) are difficult to optimize and may not scale easily. Thus, engineers seek to design enzymatic reaction schemes in model microorganisms to meet manufacturing criteria.[1] Success in these endeavors depends upon identifying sets of enzymes that can convert readily available molecules (e.g., glucose) to target products, with each enzyme performing one of a series of chemical modifications. Unfortunately, this is difficult because design-build-test (DBT) cycles-iterations of re-engineering organisms to test new sets of enzymes—are detrimentally slow.[2,3] As a result, a typical project today might only initially explore dozens of variants of an enzymatic reaction pathway. This is often insufficient to identify a commercially relevant solution because selecting productive enzymes using existing single-enzyme kinetic data has limited applicability in multi-enzyme pathways and consequently requires more DBT iterations.[4] This challenge is exacerbated in industrially-relevant, non-model organisms (such as clostridia) for which genetic tools are not as sophisticated, high-throughput workflows are often lacking, there exist transformation idiosyncrasies, and there is reduced availability of validated genetic parts.

Yet, many industrial bioprocesses (e.g., synthesis of amino acids,[5] organic acids,[6-8] solvents[9,10]) rely on non-model organisms as they offer exceptional substrate and metabolite diversity, as well as tolerance to metabolic end-products and contaminants, making them excellent chassis for biochemical production of exotic molecules from an array of possible feedstocks. *Clostridia* specifically were used industrially in acetone-butanol-ethanol (ABE) fermentations in the early-to-mid 20$^{th}$ century because of their unique solventogenic metabolism to produce large amounts of solvents (e.g., acetone and butanol) but were eventually phased out of use due to the success of petroleum until recently.[11] In addition, cellulolytic clostridia can degrade lignocellulosic biomass and acetogenic clostridia can robustly ferment on a variety of abundant, low-cost C1 gases including waste gases from industrial sources (e.g., steel mills, processing plants or refineries) or syngas generated from any biomass resource (e.g., municipal solid waste or agricultural waste).[12] Acetogenic clostridia have recently proven industrially relevant for full commercial scale ethanol production using emissions from the steel making process.[13] However, these strains tend to lack the natural machinery to produce such solvents or other more complex products, and the tools to engineer them are underdeveloped with the solutions established for *E. coli* and yeast not being directly transferrable.[14] In fact, until a few years ago, *Clostridium* organisms were considered genetically inaccessible with only a handful of genomic modifications being reported.[15,16] While developing tools for engineering clostridia is ongoing and promising progress has been made,[17,18] discovering methods to speed up metabolic engineering DBT cycles for these and other non-model organisms would accelerate the re-industrialization of such organisms.[14,19]

Cell-free systems provide many advantages for accelerating DBT cycles.[20-22] For example, the open reaction environment allows direct monitoring and manipulation of the system to study pathway performance. As a result, many groups have used purified enzyme systems to study enzyme kinetics and inform cellular expression: testing enzymatic pathway performance in vitro, down-selecting promising pathway combinations, and implementing those in cells.[20,23-26] Crude lysates are becoming an increasingly popular alternative to purified systems to build biosynthetic pathways because they inherently provide the context of native-like metabolic networks as well as negate the need for purification.[27-29] For instance, pioneering work demonstrated that DHAP can be made in crude lysates and real-time monitoring can optimize production.[29] In addition, our group has shown that 2,3-butanediol,[30] mevalonate,[28] n-butanol,[27,31] limonene,[32,33] and more complex products[34] can be constructed in crude lysates with high productivities (>g/L/h). However, to our knowledge, no attempts have been made using cell-free prototyping to improve engineering of industrially relevant, non-model organisms.

To address this opportunity, we report a new in vitro Prototyping and Rapid Optimization of Biosynthetic Enzymes approach (termed iPROBE) to inform cellular metabolic engineering. The foundational principle is that we can construct discrete enzymatic pathways through modular assembly of cell lysates containing pathway enzymes produced by cell-free protein synthesis rather than by living organisms (FIG. 86). This reduces the overall time to build pathways from weeks (or usually months) to a few days, providing an increased capability to test numerous pathways by avoiding inherent limitations of cell growth and thus diminishing the reliance on single-enzyme kinetic data. A key conceptual innovation is that the DBT unit can be cellular lysates rather than genetic constructs, allowing us to perform DBT iterations without the need to re-engineer organisms. The rapid ability to build pathways in vitro using iPROBE allows us to generate large amounts of data describing pathway operation under several operating conditions. We demonstrate iPROBE in two ways. First, we use a new quantitative ranking system to bridge cell-free data and cellular metabolic engineering for the production of 3-hydroxybutyrate (3-HB) in *Clostridium autoethanogenum* from C1 gas. Specifically, we tested 54 different enzyme combinations for 3-HB in vitro, identify pathway combinations that produce at high-titers in vivo, and we show that cell-free and in vivo pathway performance is correlated (r>0.7). Second, we show the utility of iPROBE by increasing cell-free n-butanol production ~4-fold in less than two weeks by assessing performance of 205 pathways using data-driven design-of-experiments. We then selected 9 pathway combinations from the iPROBE screen to assess butanol production in *C. autoethanogenum* strains, observing a strong correlation (r>0.9) between in cell and cell-free pathway performance. Finally, we show that we can scale up the best 3-HB-producing *C. autoethanogenum* strain containing an iPROBE-selected pathway to achieve the highest reported titers of 3-HB in clostridia at rates of >1.5 g/L/h in a continuous system. This work also led to identification of a new route to (S)-(+)-1,3-butanediol (1,3-BDO) in vivo, both non-native products for acetogenic clostridia and to our knowledge the first demonstration for biological production of the (S)-(+)-isomer of 1,3-butanediol.

C. Results

1. Establishing a Two-Pot, Cell-Free Framework for Pathway Prototyping

We selected 3-hydroxybutyrate (3-HB) biosynthesis as our first example for pathway prototyping with iPROBE given it is non-native to clostridia and its importance as a high-value specialty chemical.[36,37] Our vision was to demonstrate modular assembly of the pathway by mixing multiple *E. coli* crude cell lysates each individually enriched with a pathway enzyme, identify best sets of enzymes and their ratios for pathway operation, and inform cellular design in an industrially proven,[12] non-model host organism, in this case acetogenic *Clostridium autoethanogenum* (FIG. 86). A unique feature of the iPROBE approach, relative to previous work in crude lysate-based cell-free prototyping,[27,31-33,35] is that pathways are assembled in two steps (i.e., 2 pots), where the first step is enzyme synthesis via cell-free protein synthesis (CFPS) and the second step is enzyme utilization via substrate and cofactor addition to activate small molecule synthesis (FIG. 91). While all approaches are crude lysate-based, previous methods relied on enzyme overexpression in living *E. coli* prior to cell-lysis (CFME) or one-pot CFPS and metabolic initiation ('One Pot' CFPS-ME). We believe this new two-pot workflow (iPROBE) used throughout this study is important for three reasons. First, it allows us to precisely quantify protein expression yields. With known protein expression yields at hand, we are able to control concentrations of enzymes in iPROBE pathways to assess pathway performance with different protein ratios, which we showed was important in optimizing the butanol pathway. Second, having exact enzyme concentrations enabled by the two-step approach allows us to ensure that biosynthetic pathways are not imbalanced (i.e., one enzyme 10× more or less than all of the others, which could skew interpretations of pathway performance). Third, negative physiochemical effects of the CFPS reaction[31] on small molecule biosynthesis can be reduced.

We first set out to use iPROBE to study the impact of enzyme ratios on pathway performance for the non-native pathway to 3-HB (FIG. 87A). From acetyl-CoA, a key intermediate in both *E. coli* and *Clostridium*, three enzymes are required to make 3-HB: a thiolase (Thl), a hydroxybutyryl-CoA dehydrogenase (Hbd), and a thioesterase. *E. coli* and *C. autoethanogenum* have native thioesterases that convert 3-hydroxybutyryl-CoA to 3-hydroxybutyrate.[38] For optimal production, these native thioesterases or ones with a high-degree of specificity for 3-hydroxybutyryl-CoA will need to be overexpressed. However, for screening purposes these native enzymes were sufficient; only two, non-native enzymes (Thl and Hbd) were required to be overexpressed. We initially selected a Thl gene from *Clostridium acetobutylicum* (Cac) and a Hbd gene from *Clostridium kluyveri* (Ckl) (Table at FIG. 101). We used the well-characterized *E. coli*-based PANOx-SP CFPS system[39] to produce CacThl and CklHbd, with soluble concentrations of 5.85±0.82 μM and 19.31±3.65 M, respectively. Thioesterases were not produced via CFPS because they are natively present and active in *E. coli* lysates. Then, we designed five unique pathway combinations titrating different concentrations of thiolases (Thl) while maintaining a constant concentration of Hbd by mixing different ratios of CFPS reactions (keeping total CFPS reaction added constant using blank reactions containing no protein produced in vitro) (FIG. 87B-C). Upon incubation with essential substrates, salts, and cofactors (e.g., glucose, NAD, CoA, ATP), we assessed 3-HB synthesis at 0, 3, 4, 5, 6, and 24 h for each of the five pathway combinations via high performance liquid chromatography (HPLC) (FIG. 87D). The cell lysate contains endogenous enzymes for glycolysis that regenerate NADH[40] and convert glucose to acetyl-CoA, providing the starting intermediate for 3-HB biosynthesis. As expected, no 3-HB was produced in the absence of Thl. The highest 3-HB titers were observed for 0.5 μM CacThl and 0.5 μM CklHbd. We performed a similar titration of CklHbd while maintaining a constant concentration of CacThl (FIG. 92). Taken together, our data show that crude lysates enriched by CFPS can be used to assemble metabolic reactions and sets the stage to optimize pathways using a two-pot cell-free approach 2. Developing a Metric to Quantify Biosynthetic Pathway Performance To optimize pathways with iPROBE, we next defined a pathway ranking system that would enable assessment of activity in the cell-free environment and hold potential to inform cellular design. The basis of this ranking system is a single, quantitative metric for our cell-free experiments. We call this metric the TREE score (for titer, rate, and enzyme expression; important metrics for defining the success of cell-based metabolic engineering). The TREE score combines, through multiplication, titer at reaction completion, rate during the most productive phase of pathway operation, and enzyme expression as measured by soluble protein fraction and total enzyme amount. Using our initial set of data (FIG. 87) as a guide, the TREE score is obtained by multiplying 3-HB titer at 24 h, the linear 3-HB production rate between 3 and 6 h, and the sum of the average soluble fraction of the pathway enzymes, Thl and Hbd, and the inverse of the total enzyme concentration for each of the five pathway combinations (FIG. 87E-I). While the TREE score rankings are not largely different from the titers (r=0.89 for all 3-HB data in this study) or rates (r=0.91 for all 3-HB data in this study) alone (all 3-HB pathway TREE scores shown in FIG. 93), they exaggerate differences that might arise from each component of the score. For example, combining titer and rate enables use of both in ranking cell-free pathway performance which is helpful as it is unknown whether cell-free titer or rate is more or less important for informing cellular metabolic engineering. Additionally, we included the enzyme expression component to penalize a given pathway if in vitro expression is poor, decreasing its overall pathway rank. Typically, enzymes that are unable to be expressed (either lowly expressed or insoluble) in vitro are challenging to express in vivo. Thus, the average solubility of all the pathway enzymes overexpressed in the lysate was used to acquire a sense of how difficult the pathway might be to express. The inverse enzyme amount was used to penalize in vitro combinations that had high concentrations of enzyme which might improve a pathway's performance but would not be feasible in cells. While there are multiple ways one could imagine ranking pathways or weighting the TREE score factors, reducing the complexity of available cell-free data was important as it enabled a rapid approach to rank pathways for iPROBE.

3. iPROBE Informs Selection of Genetic Regulatory Architectures in *Clostridium*

With a pathway ranking system at hand, we next aimed to validate that cell-free experiments could generate design parameters for DNA construction of biosynthetic pathways in cells, a difficult challenge since gene expression tools are often not available in non-model organisms. Gene expression involves designing a coding sequence, 5' and 3' regulatory elements, and vector maintenance components, among other parts. Selection of the promoter regulatory strengths (e.g., high, medium, low) for the expression of a coding sequence, in particular, is an essential factor for pathway tuning. Thus, we set out to develop a correlation between specific enzyme concentrations in iPROBE and specific strength regulatory architectures, relative promoter strengths and plasmid copy number for a single operon comprising the 3-HB pathway, for expression in *C. autoethanogenum*. To achieve this goal, we built cell-free pathway combinations for 3-HB by co-titrating seven different enzyme concentrations of Thl and Hbd in our reactions (FIG. 94). Specifically, we built seven cell-free reactions in increasing total concentration added, combining CacThl and CklHbd at equimolar amounts. We ran each cell-free reaction for 24 h and measured the titer of 3-HB produced (FIG. 94C). We observed that as the amount of enzyme added increases, the amount of 3-HB increased up to a threshold amount of 1 μM of each enzyme added. In parallel, we constructed plasmids expressing CacThl and CklHbd under eight regulatory architectures (change in promoter strength and plasmid copy number) of increasing strength and transformed them into separate strains of *C. autoethanogenum*. We ran small-scale bottle fermentations of each strain under anaerobic conditions on carbon monoxide (CO), hydrogen ($H_2$), and carbon dioxide ($CO_2$) gas and measured stationary phase titers of 3-HB (FIG. 94D). In vivo, we found that increases in expression strength led to higher 3-HB titers, but did not saturate in 3-HB expression, whereas, the in vitro data show saturation with increasing enzyme amount (FIG. 94). These data suggest a limitation of the dynamic range of expression possible with current, well-characterized genetic parts available for use in *C. autoethanogenum*. However, given the trends observed, we used this data to build an initial cell-free to cell correlation that connects cell-free 3-HB production and corresponding enzyme concentrations to cellular 3-HB production and corresponding plasmid regulatory strength. We found that generally using <0.1 μM enzyme in vitro corresponds to low regulatory strengths in vivo, using 0.1-0.3 μM enzyme in vitro corresponds to medium strengths in vivo, and using >0.3 μM enzyme in vitro corresponds to high strengths in vivo. In principle, this allows us to screen many different pathway combinations in cell-free systems and provide a rational recommendation for plasmid construction of those pathway combinations in *Clostridium*, which is what we did next.

4. iPROBE can Inform the Selection of Pathway Enzymes in *Clostridium*

To showcase the iPROBE approach, we next screened several possible 3-HB pathway combinations using cell-free experiments, ranked a subset of candidate cellular pathway combinations using the TREE score, and showed cellular *C. autoethanogenum* 3-HB biosynthesis from $CO/H_2/CO_2$ gas correlates with cell-free experimental results. To do this, we tested six enzyme homologs of each Thl and Hbd originating from different *Clostridium* species as these would be best initial candidates for *Clostridium* expression (FIG. 88A; Table at FIG. 101). We selected all pathway combinations of the 12 enzymes keeping a fixed total concentration of soluble enzyme added (high expression levels) to build in cell-free reactions (FIG. 88B-C). By measuring 3-HB production over the course of 24 h along with soluble enzyme expression for each of the enzymes (FIG. 93), we are able to calculate TREE scores for each of the 36 pathway combinations (FIG. 88D). We found that a majority of pathway combinations perform poorly with only a handful achieving TREE scores above a value of 2. The top six pathways contained CklHbd1 for the second step. This indicated to us that iPROBE helped select a top-performing enzyme for cellular efforts in a single screen that took less than a week to build. Testing 36 pathway combinations in clostridia could have taken more than 6 months using our current workflows. Thus, we wanted to use this information to down-select the number of combinations to test in acetogenic clostridia due to the current limitations in high-throughput strain testing. We selected a subset of four pathway combinations from the iPROBE screening to test in *C. autoethanogenum* labeled A (CklThl1/CacHbd), B (CklThl2/CklHbd1), C (CklThl1/CklHbd1), and D (CacThl/CklHbd1). These pathways represent our highest-performing pathway, two that fell in the middle (C having a large degree of variability in performance), and one of our low-performers. We constructed and transformed DNA with strong regulatory architectures and each of the four-pathway enzyme sets into separate strains of *C. autoethanogenum* (FIG. 88E). We ran small-scale bottle fermentations of each strain under anaerobic conditions on $CO/H_2/CO_2$ gas mixture and measured 3-HB titers at four time-points during the fermentation (FIG. 88F). We observed that the best cell-free pathway combination as determined by TREE score (D) also performs the best of the four in *Clostridium* cells, achieving 33.3±1.4 mM. The worst pathway combination in cell-free experiments (A) is also the worst performer in *C. autoethanogenum*. The other two pathway combinations (B, C), which were not statistically different in the cell-free environment, fall in the middle in cellular experiments. Notably, we did not see detectable levels of non-specific products such as acetoacetate or acetone. The exact ranking of pathways B, C, and D differ between in vitro and in vivo construction, but all three of these designs are much better than a majority of the 36 combinations tested in the cell-free environment. At a high-level, these data suggest that the cell-free system is useful for guiding pathway selection in cells; while the *E. coli*-based lysate conditions do not necessarily approximate the in vivo clostridia conditions (e.g., pH, small molecule concentrations, axillary proteins, aerobic vs. anaerobic), the cell-free environment remains a powerful prototyping environment for assessing biochemical information and informing design. This is especially true for down-selecting pathway combinations that should not be tested in cells (i.e., produce little to no product). In fact, the best pathway designs tested in two recent studies that explored autotrophic 3-HB production in acetogenic clostridia produced ~4 mM and ~1 mM 3-HB.[41,42] Their pathways correspond to TREE scores of 1.06±0.07 and 0.02±0.00, respectively. Based on our iPROBE screening we would have suggested not testing these combinations in vivo. For context, our best pathway had a TREE score of 17.76±3.08. In sum, iPROBE offers a framework to rapidly design, build, and test pathway combinations in cell-free experiments in a matter of days, bypassing DNA construction and transformation limitations, and to facilitate implementation of promising pathway combinations for engineering success in cells.

5. Cell-Free Pathway Prototyping for n-Butanol Biosynthesis

Having demonstrated the use of iPROBE to optimize the 3-HB pathway for informing cellular design in *C. autoethanogenum*, we next aimed to show that iPROBE could be used to optimize longer pathways. We selected the 6-step pathway from acetyl-CoA to n-butanol as a model pathway for this because butanol is an important solvent and drop-in fuel with US$5 billion/year market (FIG. 89A). The key idea was to use iPROBE to optimize cell-free butanol production by constructing pathway variants with different enzyme homologs and enzyme ratios. The challenge with this optimization goal is the number of possible permutations. Indeed, testing just six homologs for each of the first four steps of the pathway at three different enzyme concentrations would alone require 314,928 pathway combinations, which exceeds typical HPLC analytical pipelines. To optimize enzyme homologs and concentrations simultaneously while also managing the landscape of testable hypotheses, we implemented a design-of-experiments using a neural-network-based algorithm to predict beneficial pathway combinations. While kinetic models are useful in making rational predictions, neural-network-based approaches can be used to make predictions independent of the molecular understanding of a biosynthetic pathway as well as with a small initial data set to train the models.

In creating the initial data set to guide improvements in titer, we chose six homologs of each Thl, Hbd, Crt, and Ter (Table at FIG. 101; FIG. 89A). We tested five concentrations for each enzyme homolog in a pathway context consisting of our base set of enzymes (FIG. 89A, highlighted in blue), totaling 120 pathway combinations. We built these combinations in cell-free reactions from enzymes produced by CFPS, measured butanol production over time, and calculated TREE scores for each (FIG. 89B; FIG. 95). In total, we collected these additional data in five experimental sets of 20 pathway combinations with each set taking five days (three days of HPLC time). A majority of the enzyme homologs did not out-perform the original enzyme set (EcoThl/CbeHbd/CacCrt/TdeTer). This result is not surprising as this original enzyme set (our base case) has been extensively characterized and tested throughout the literature.[43-45] However, we find that CklHbd1 can double the TREE score at high concentrations and even out-performs the base case CbeHbd at lower concentrations. This agrees with a recent independent study that found a 1.6-fold improvement in ABE fermentation with *C. acetobutylicum* by replacing the native Hbd with the CklHbd1.[46]

With this initial dataset (120 pathway combinations) collected (FIG. 89B), we identified ten neural network architectures based on a combination of heuristic search for model design and 10-fold cross validation (training and testing) for model scoring. We then optimized each of these models using a gradient-free optimization strategy to maximum butanol production. We used the ten best architectures (most accurate predictions and highest model entropy) to make pathway combination predictions (homolog set and enzyme ratios) and maximize the TREE score, which we could then build with the cell-free framework (FIG. 89C). Design predictions suggesting enzyme concentrations of <0.01 μM (a majority <2 nM) were ruled out due to experimental constraints, and we built the remaining 43 predictions in cell-free reactions (FIG. 96A). To evaluate our design-of-experiments approach, we compared the results with two additional sets of experiments: (i) a set varying enzyme ratios more thoroughly using only the base set enzymes (21 pathway combinations; FIG. 96B) and (ii) a hand-selected set of 18 pathway combinations based on our understanding of the biosynthesis (FIG. 96C). In total we tested 205 unique pathway combinations (base set combinations, initial round combinations, and data-driven designs) (FIG. 89D; FIG. 95). Nearly 20% of the total pathway combinations screened have higher TREE scores than our base case. Without testing every possible combination, we were able to rapidly test a manageable subset achieving ~4 times higher TREE scores (~2.5 times higher titer and 58% increase in rate) over the base case pathway combination. The consensus enzyme set for top-performing pathways included EcoThl, CklHbd1, CacCrt, and TdeTer with variations in enzyme concentrations. Five of the top six TREE scores each arose from pathways predicted from the neural-network-based approach and were much better than our hand-selected set, highlighting that this approach can be used with a lack of apriori knowledge of the pathway. These results showcase the benefit from merging computational and experimental design.

Analysis of the iPROBE pathway combinations shows several key design parameters. First, we observed that there are specific enzyme homologs and concentrations that improve the TREE score. For example, the chosen thiolase does not seem to matter in the 20 top-performing combinations whereas the selection of Hbd does (FIG. 97A). Indeed, the iPROBE approach was used to discover that the *C. kluyveri* Hbd1 enzyme was superior to the rest. Second, iPROBE enables identification of enzymes to not test in clostridia. Specifically, ReuThl, CklHbd2, PpuCrt, FsuTer, FjoTer, and CpaTer all underperformed in the cell-free context. Being limited by throughput in non-model organisms, it is important to identify both promising and not promising enzyme candidates. Third, we noticed that in the 20 top-performing combinations Hbd is present at significantly ($p<0.001$) higher concentrations and the median Crt concentration is lower, though not significantly, than the initial 0.3 μM (FIG. 97B). This suggests that higher concentrations of Hbd and Ter than Crt are optimal for effective pathway operation, which can be achieved in vivo by constructing plasmids with proper genetic architectures. However, this hypothesis should be further investigated by measuring enzyme abundance, metabolic fluxes, and metabolite concentrations with high-end metabolomics with high-end metabolomics.

We next assessed iPROBE's ability to inform cellular design by constructing representative pathway combinations from the iPROBE screening in *C. autoethanogenum* strains to produce butanol. While we tried to cover a wide range of TREE scores, challenges with transformation limited us to two pathway combinations scoring among the top five combinations (CacThl/CklHbd1/CacCrt/TdeTer and EcoThl/CklHbd1/CacCrt/TdeTer), two pathway combinations in the middle range of the data set, and five pathway combinations near the tail-end of all combinations tested. These combinations are listed in FIG. 98A. To avoid diverting flux toward 3-HB, we identified and knocked-out a native thioesterase able to hydrolyze 3-HB-CoA from our screening strain. After monitoring butanol production over the course of six days (FIG. 98A), we see a promising correlation between in vivo expression in *C. autoethanogenum* and TREE scores from iPROBE (FIG. 89E). This further emphasizes that selecting top-performing pathways from iPROBE can improve production in *Clostridium* organisms and decreases the number of strains that need to be tested. Importantly, the iPROBE-derived hypothesis that keeping crotonyl-CoA at minimal concentrations by balancing Hbd and Ter expression, higher than Crt, improves pathway performance is corroborated by the combinations tested in vivo. We see lower butanol production (gray squares) when Hbd is expressed highly and Ter is expressed lowly but higher production (orange circles) when both are expressed highly. A mechanistic understanding of this perceived toxicity still needs to be elucidated, but iPROBE can generate probable hypotheses.

While overall butanol production was low in *C. autoethanogenum*, we were able to increase production using the iPROBE-selected CklHbd from 0 mM to 0.2±0.0 mM. In addition, when comparing two butanol synthesis pathways in vivo-one with the standard CacHbd and one with the iPROBE-selected CklHbd-we increased butanol production 6-fold from 0.2±0.0 mM to 1.1±0.0 mM (FIG. 98B) by replacing the trans-2-enoyl-CoA reductase (Ter) enzyme with the ferredoxin-dependent electron bifurcating enzyme complex (Bcd-EtfA:EtfB) naturally used for these activities in clostridia.[47] This is not surprising in light of a recent study that showed Ter is detrimental to ABE fermentation when introduced in *C. acetobutylicum.*[48] Using the Bcd-EtfA:EtfB complex, we were also able to increase production to 22.0±0.1 mM by manipulating the plasmid architecture (FIG. 98C). For comparison, the previously best reported butanol production in engineered acetogenic clostridia was ~2 mM.[15] Moreover, the Bcd-EtfA:EtfB complex is a delicate complex that is extremely oxygen sensitive[49] and has so far been inactive in *E. coli* lysates (in alignment with previous reports that highlighted difficulties expressing Bcd in *E. coli*),[44] highlighting an area for potential improvement of iPROBE (i.e., compatibility of *E. coli* lysates with non-model organisms). Taken together, we observed that iPROBE strongly correlated with cellular performance (FIG. 99, r=0.79) for 20 pathways tested for both 3-HB production and n-butanol synthesis. Overall, this work demonstrates the power of coupling data-driven design-of-experiments with a cell-free prototyping framework to select feasible subsets of pathways worth testing in vivo for non-model organisms.

6. Scaled-Up Fermentations of iPROBE-Selected Pathway

As a final validation of our integrated iPROBE approach, we next set out to use in-house facilities to scale cell growth of an iPROBE-selected pathway from bench to continuous fermentation scales (FIG. 90A). Specifically, the best performing strain for 3-HB production selected by iPROBE was chosen for process scale-up from 0.1-L bottle fermentations to 1.5-L continuous fermentations using $CO/H_2/CO_2$ gas as the sole carbon and energy source. Over a 2-week fermentation, we monitored 3-HB and biomass in a control strain and our iPROBE-selected strain with and without optimized fermentation conditions (FIG. 90B-C). In optimized fermentations we observed high-titers of 3-HB, −15 g/L (140 mM) at rates of >1.5 g/L/h in a continuous system. This is not only higher than the previously reported concentration in acetogenic *Clostridium,*[41,42] but to our knowledge also exceeds the previously highest-reported concentration for traditional model organisms like *E. coli* (titer of ~12 g/L and rate of ~0.25 g/L/h in fed-batch)[38,50] and yeast (titer of ~12 g/L and rate of ~0.05 g/L/h in fed-batch)[51] without any additional genomic modifications to optimize flux into the pathway. This shows the utility of iPROBE in identifying pathways for industrial strain development. As expected with an acetogenic host, we observe the production of acetate as a byproduct during fermentation (FIG. 100). Implementing the heterologous production of 3-HB in this strain, however, results in less acetate produced over time. We anticipate that genome modifications to increase flux could further improve fermentation titers. For example, a recent study reported a 2.6-fold improvement in 3-HB production in a related engineered acetogenic *Clostridium* by downregulation of two native genes related to acetate production.[41]

Surprisingly, we also observed production of a novel metabolite, 1,3-butanediol (1,3-BDO), at 3-5% of the 3-HB levels and up to 0.5 g/L (FIG. 90D). This is attributed to nonspecific activity of a native aldehyde:ferredoxin oxidoreductase (AOR) and alcohol dehydrogenase able to reduce 3-HB to 3-hydroxybutyraldehyde and further to 1,3-BDO. Indeed, no 1,3-BDO was observed when transforming the pathway into a previously generated AOR-knockout strain.[52] These enzymes have previously been shown to reduce a range of carboxylic acids to their corresponding aldehydes and alcohols through reduced ferredoxin.[15,53] While the (R)-(−)-form of 1,3-BDO has been produced via other routes,[54-56] when using the *C. kluyveri*-derived Hbd we also detected the (S)-(+)-form of 1,3-BDO as determined by chiral analysis, which to our knowledge has never been produced in a biological system before. This chiral specificity is determined by the chosen 3-hydroxybutyryl-CoA dehydrogenase. Further investigation could elucidate the mechanism of the biosynthetic route. Given that 1,3-BDO is used in cosmetics and can also be converted to 1,3-butadiene used in nylon and rubber production with a US$20 billion/year market,[36,57] the discovery of this pathway is important. In sum, iPROBE provides a quick and powerful DBT framework to optimize and discover biosynthetic pathways for cellular metabolic engineering efforts, including those in non-model hosts.

D. Conclusion

We demonstrate a new, two-pot framework, iPROBE, that incorporates a modular cell-free platform for constructing biosynthetic pathways with a quantitative metric for pathway performance selection (the TREE score). We establish that iPROBE can be used to engineer and improve small molecule biosynthesis in non-model organisms that can be arduous to manipulate. In one example, we show that by screening 54 biosynthetic pathway combinations for the production of 3-HB in cell-free reactions, we can rationally select a handful of pathways to inform cellular metabolic engineering in clostridia. Specifically, iPROBE enabled the construction of a strain of *C. autoethanogenum* that produces high-titers and yields of 3-HB (~20× higher than the previous highest reported concentration in the literature) in continuous fermentations with carbon monoxide/hydrogen/carbon dioxide gas as sole source of carbon and energy. The scale-up work also led to the identification of a new route to 1,3-BDO and the first production to our knowledge of the (S)-isomer of this molecule in a biological system. In another example, we show the ability to use iPROBE in conjunction with data-driven design-of-experiments to reduce an exceedingly large landscape of testable pathway designs, test a subset of 205 pathway combinations in vitro for the production of butanol, and show that by testing a further subset of designs in vivo we can improve butanol production in acetogenic clostridia. Importantly, we show, for the first time to our knowledge, the ability of *E. coli* crude lysate systems to prototype hundreds of biosynthetic pathway designs to inform cellular design and demonstrate a strong correlation with in vivo pathway performance (FIG. 99).

Despite the inherent contextual differences in *E. coli* lysates and clostridia cells, including that the lysate context will likely not capture several important characteristics of the non-model organism (e.g., oxygen sensitivity), we have successfully demonstrated that iPROBE facilitates cellular design in three ways: (i) identifying sets of enzymes that work well together to produce a desired biochemical, (ii) down-selecting poor performing pathway/enzyme candidates, and (iii) evaluating optimal ratios of enzymes and potential synergy between enzymes prior to embarking on laborious experiments in these organisms. Highlighting the utility of iPROBE for accelerating DBT cycles, the 205 pathway combinations for butanol were built cumulatively in 12 days (excluding HPLC time) in cell-free reactions, which we estimate would have taken at least 6 months in clostridia. While not all issues with engineering non-model organism expression are mitigated by iPROBE, it complements and enhances in vivo strategies.

Future developments of iPROBE could seek to improve the ability to design and optimize biosynthetic pathways in non-model organisms using cell-free methods. For example, efforts to mimic physiochemical conditions of the organism of interest (e.g., cofactors) and various conditions that mimic the phase of fermentation used during product production (e.g., batch vs. semi-continuous, aerobic vs. anaerobic) could be explored. Additionally, creating productive cell-free gene systems directly from clostridia (or a non-model organisms of choice) could facilitate prototyping DNA elements (i.e., promoters, codon usage) as well as native metabolic and regulatory networks to better inform pathway design. In addition to enhancing the prototyping environment, refining the TREE score (e.g., by weighting each factor) with more in vitro to in vivo correlation data will help identify the minimal amount of cell-free data (e.g., rate, endpoint titer, enzyme expression) needed to accurately inform in vivo pathway performance. Indeed, we believe the TREE score metric only serves as a starting point and anticipate it evolving and improving in subsequent works. Finally, we note that while we focused on informing design in industrially relevant, non-model organisms many of our findings and tools could be applied to conventional hosts.

Looking forward, we anticipate that iPROBE will facilitate design-build-test cycles for biosynthetic pathways by enabling the rapid study of pathway enzyme ratios, tuning individual enzymes in the context of a multi-step pathway, screening enzyme variants for high-performance enzymes, and discovering enzyme functionalities. This in turn will decrease the number of strains that need to be engineered in vivo and time required to achieve desired process objectives. This will increase the flexibility of biological processes to adapt to new markets, expand the range of fossil-derived products that can be displaced with bio-derived alternatives, and enhance the economic benefits for co-produced fuels.

E. Methods

1. Bacterial Strains and Plasmids

*Escherichia coli* BL21(DE3) (NEB) was used for preparation of cell extracts which were used to express all exogenous proteins in vitro.[35] A derivate of *Clostridium autoethanogenum* DSM10061 obtained from the German Collection of Microorganisms and Cell Cultures GmbH (DSMZ; Braunschweig, Germany) was used for in vivo characterization and fermentations.[58] For butanol production, this strain was used with a native thioesterase (CAETHG_1524) knockout made using Triple Cross recombination as described previously.[59]

Twenty-three enzymes were examined in this study (Table at FIG. 101). DNA for all enzyme homologs tested were codon adapted for *E. coli* using IDT codon optimizer. Non-clostridial sequences were codon adapted for *C. autoethanogenum* using a LanzaTech in-house codon optimizer, and all native clostridial genes were used as is. *E. coli* (SEQ ID NOs:73-95) and *C. autoethanogenum* (SEQ ID NOs:96-101) adapted sequences are listed in FIG. 102, A-W and FIG. 103, A-F, respectively. For the cell-free work, the pJL1 plasmid (Addgene #69496) was used. The modular pMTL80000 plasmid system[60] along with acsA[52], fdx[52], pta[61] and pfor[62] promoters were used for the *C. autoethanogenum* plasmid expression.

2. Cell Extract Preparation

*E. coli* BL21(DE3) cells were grown, harvested, lysed, and prepared using previously described methods.[27,63]

3. iPROBE Reactions

Cell-free protein synthesis (CFPS) reactions were performed to express each enzyme individually using a modified PANOx-SP system described in previous pubications.[39,64] Fifty-μL CFPS reactions were carried out for each individual enzyme in 2-mL microcentrifuge tubes. Enzyme concentrations in CFPS reactions were quantified by $^{14}$C-leucine incorporation during in vitro translation. Then reactions performed for identical enzymes were pooled together when multiple reaction tube-volumes were needed to keep a consistent 50-μL reaction volume and geometry for every CFPS reaction. Based on molar quantities of exogenous enzymes in each CFPS reaction determined by radioactive measurement, CFPS reactions were mixed to assemble complete biosynthetic pathways in 1.5-mL microcentrifuge tubes. CFPS reactions constitute 15 L of a 30-L-total second reaction. When the total CFPS reaction mixture constituted less than 15 μL, 'blank' CFPS reaction was added to make the total amount of CFPS reaction up to 15 μL. The 'blank' reactions consist of a typical CFPS reaction with no DNA added. This 15 μL CFPS mixture was then added to fresh extract (8 mg/mL), kanamycin (50 μg/ml), glucose (120 mM), magnesium glutamate (8 mM), ammonium glutamate (10 mM), potassium glutamate (134 mM), glucose (200 mM), Bis Tris pH 7.8 (100 mM), NAD (3 mM), and CoA (3 mM); final reaction concentrations are listed. Reactions proceeded over 24 h at 30° C. Measurements from samples were taken at 0, 3, 4, 5, 6, and 24 h.

4. Quantification of Protein Produced In Vitro

CFPS reactions were performed with radioactive $^{14}$C-Leucine (10 μM) supplemented in addition to all 20 standard amino acids. We used trichloroacetic acid (TCA) to precipitate radioactive protein samples. Radioactive counts from TCA-precipitated samples was measured by liquid scintillation to then quantify soluble and total yields of each protein produced as previously reported (MicroBeta2; PerkinElmer).[39,40]

5. Metabolite Quantification

High-performance liquid chromatography (HPLC) was used to analyze 3-HB and n-butanol. We used an Agilent 1260 series HPLC system (Agilent, Santa Clara, CA) via a refractive index (RI) detector. 3-HB and n-butanol were separated with 5 mM sulfuric acid as the mobile phase and one of two column conditions: (1) an Aminex HPX-87H or Fast Acids anion exchange columns (Bio-Rad Laboratories) at 35 or 55° C. and a flow rate of 0.6 ml min$^{-1}$ or (2) a Alltech IOA-2000 column (Hichrom Ltd, Reading, UK) at 35 or 65° C. and flow rate of 0.7 ml min$^{-1}$ as described earlier.[65] 1,3-butanediol was measured using gas chromatography (GC) analysis, employing an Agilent 6890N GC equipped a Agilent CP-SIL 5CB-MS (50 m×0.25 m×0.25 μm) column, autosampler and a flame ionization detector (FID) as described elsewhere.[65] For chiral analysis of (S)-(+)-1,3-Butanediol and (R)-(−)-1,3-Butanediol an Agilent 6890N GC equipped with a Restek Rt®-bDEXse 30 m×0.25 mm ID×0.25 m df column and a flame ionization detector (FID) was used. Samples were prepared by heating for 5 minutes at 80° C., followed by a 3-minute centrifugation at 14,000 rpm. Exactly 400 μL of supernatant was then transferred to a 2-mL glass autosampler vial and 100 μL of and Internal Standard solution (5-methyl-1-hexanol and tetrahydrofuran in ethanol) was added. The capped vial was then briefly vortexed. Sample vials then were transferred to an autosampler for analysis using a 1.0 μL injection, a split ratio of 60 to 1, and an inlet temperature of 230° C. Chromatography was performed with an oven program of 50° C. with a 0.5 min hold to a ramp of 3° C./min to 70° C. to a ramp of 2° C./min to 100° C. with a final ramp at 15° C./min to 220° C. with a final 2-min hold. The column flow rate was 30 cm/sec using helium as the carrier gas. The FID was kept at 230° C. Quantitation was performed using a linear internal standard calibration.

6. TREE Score Calculations

The TREE Score is calculated by multiplying the titer by the rate by enzyme expression metric.

$$\text{TREE Score}=\text{Titer}\cdot\text{Rate}\cdot(\text{Average Solubility}+[\text{Total Enzyme}]^{-1})$$

The titer is the metabolite concentration (mM) in the cell-free reaction at 24 h, when the reaction is complete. The error associated with titer is the standard deviation of reaction triplicates. The rate is the slope of the linear regression of metabolite concentrations (mM/h) taken at 3, 4, 5, and 6 h time points. The rate-associated error is the standard error of the slope calculated by the linear regression. The average soluble fraction term is calculated by first determining the soluble fraction (soluble protein/total protein, n=3) for each individual enzyme via $^{14}$C-leucine incorporation. The average soluble fraction is then the average value of soluble enzyme fractions (mM soluble/mM total protein) (in this case, five enzymes) and the error associated with the soluble fraction term is propagated error. The concentration of total enzyme is calculated by the addition of the final concentrations of each enzyme (mM soluble protein) in the reaction with propagated error. The final error on the TREE score is the propagated error of each individual component.

7. In Vivo Gas Fermentations

In vivo cultivation and small-scale bottle fermentation studies were carried out as described earlier using a synthetic gas blend consisting of 50% CO, 10% $H_2$, 40% $CO_2$ (Airgas, Radnor, PA).[62] Continuous fermentations were carried out in 1.5 L continuous stirred tank reactors (CSTRs) with constant gas flow as described elsewhere.[65,66]

8. Design-of-Experiments Using Neural Networks

A neural network-based approach was used to explore the vast landscape of possible experimental designs. We first processed the cell-free butanol dataset and then developed and optimized the neural network to provide cell-free pathway recommendations. Modeling enzymatic pathways requires a mix of continuous and categorical variables. Because many machine learning algorithms require numeric input and output variables, we used one-hot encoding, which is a process that converts categorical variables into a numerical form that machine learning algorithms can use. This method treats categorical variables as a multidimensional binary input that must sum to one. The concentration values were used as is, resulting in a 30 variable input matrix: 25 variables representing the categorical variation (i.e., different homologs) and 5 representing the concentration. We used these features to then build our deep neural network regressions.

We generated and evaluated neural network architectures based on a combination of heuristic search for model design and 10-fold cross validation for model scoring. We limited our model architecture search to fully connected layers but varied the number of hidden layers (between 5 and 15 layers) and the number of nodes in each layer (between 5 and 15 nodes). We first randomly generated hundreds of model architectures based on these criteria. Using a Genetic Algorithm (GA) we performed crossovers and mutations on the current model architectures, which were then trained using the back-projection method and scored using 10-fold cross validation. Although no direct regularization methods were used the cross-validation step reduces the chance of over fitting. We proceeded using the GA hundreds of times with thousands of iterations. Of the final 100 model architectures created, the top 10 models were chosen such that these models had the highest scores and highest design entropy. This ensures model diversity which highlights data ambiguity (i.e., model conclusions drawn from the same data set).

We then optimized each of these 10 models using the Nelder Mead Simplex which provides a gradient-free optimization strategy to find local minimum; in our case maximum butanol production. This method generated 10 recommendations per model yielding a total of 100 recommendations. From this we selected the top 10 recommendations that maximized both the average predicted butanol production (TREE score) and maximized the input entropy. This method ensured that we were not over sampling in an area and sets the basis for our hybrid exploration and exploitation-based sampling strategy. Each of these represents an exploitation-based recommendation, but through enforcing diversity in models and the recommendation vector we also were able to explore the sample space. From these optimized models, ten predictions were selected from each of the top 10 architectures to be constructed in the cell-free environment. We removed predictions that were impossible experimentally (i.e., concentrations too low to pipet accurate volumes).

9. Statistics

All error bars on metabolite and protein quantification represent one standard deviation derived from technical triplicates. All error bars on TREE score values are propagated error as described in the TREE score calculation. In comparing the significance of enzyme concentration on TREE scores for butanol production in FIG. 98B we used the Mann-Whitney test to determine whether enzyme concentrations of the enzyme combinations that produced the top 20 TREE scores are greater than the enzyme concentrations of the entire data set.

F. References for Example 9

1. Nielsen, J. et al. Engineering synergy in biotechnology. Nature chemical biology 10, 319-322, doi:10.1038/nchembio.1519 (2014).
2. Keasling, J. D. Synthetic biology and the development of tools for metabolic engineering. Metabolic engineering 14, 189-195, doi:10.1016/j.ymben.2012.01.004 (2012).
3. Nielsen, J. & Keasling, J. D. Engineering cellular metabolism. Cell 164, 1185-1197, doi:10.1016/j.cell.2016.02.004 (2016).
4. Davidi, D. et al. Global characterization of in vivo enzyme catalytic rates and their correspondence to in vitro kcat measurements. Proceedings of the National Academy of Sciences of the United States of America 113, 3401-3406, doi:10.1073/pnas. 1514240113 (2016).
5. Leuchtenberger, W., Huthmacher, K. & Drauz, K. Biotechnological production of amino acids and derivatives: current status and prospects. Appl Microbiol Biotechnol 69, 1-8, doi:10.1007/s00253-005-0155-y (2005).
6. Nghiem, N., Kleff, S. & Schwegmann, S. Succinic Acid: Technology Development and Commercialization. Fermentation 3, doi:10.3390/fermentation3020026 (2017).
7. Cubas-Cano, E., Gonzalez-Fernandez, C., Ballesteros, M. & Tomas-Pej6, E.

Biotechnological advances in lactic acid production by lactic acid bacteria: lignocellulose as novel substrate. Biofuels, Bioproducts and Biorefining 12, 290-303, doi:10.1002/bbb.1852 (2018).

8. Rodriguez, B. A., Stowers, C. C., Pham, V. & Cox, B. M. The production of propionic acid, propanol and propylene via sugar fermentation: an industrial perspective on the progress, technical challenges and future outlook. Green Chem. 16, 1066-1076, doi: 10.1039/c3gc42000k (2014).
9. Green, E. M. Fermentative production of butanol—the industrial perspective. Current opinion in biotechnology 22, 337-343, doi:10.1016/j.copbio.2011.02.004 (2011).
10. Jiang, Y., Liu, J., Jiang, W., Yang, Y. & Yang, S. Current status and prospects of industrial bio-production of n-butanol in China. Biotechnology advances 33, 1493-1501, doi:10.1016/j.biotechadv.2014.10.007 (2015).
11. Jones, D. T. & Woods, D. R. Acetone-butanol fermentation revisited. Microbiol. Rev. 50, 484-524 (1986).
12. Tracy, B. P., Jones, S. W., Fast, A. G., Indurthi, D. C. & Papoutsakis, E. T. *Clostridia*: the importance of their exceptional substrate and metabolite diversity for biofuel and biorefinery applications. Current opinion in biotechnology 23, 364-381, doi:10.1016/j.copbio.2011.10.008 (2012).
13. Takors, R. et al. Using gas mixtures of CO, CO2 and H2 as microbial substrates: the do's and don'ts of successful technology transfer from laboratory to production scale. Microb Biotechnol 11, 606-625, doi:10.1111/1751-7915.13270 (2018).
14. Burk, M. J. & Van Dien, S. Biotechnology for Chemical Production: Challenges and Opportunities. Trends in biotechnology 34, 187-190, doi:10.1016/j.tibtech.2015.10.007 (2016).

15. Kopke, M. et al. *Clostridium ljungdahlii* represents a microbial production platform based on syngas. Proceedings of the National Academy of Sciences of the United States of America 107, 13087-13092, doi:10.1073/pnas.1004716107 (2010).
16. Papoutsakis, E. T. Engineering solventogenic clostridia. Current opinion in biotechnology 19, 420-429, doi:10.1016/j.copbio.2008.08.003 (2008).
17. Charubin, K., Bennett, R. K., Fast, A. G. & Papoutsakis, E. T. Engineering *Clostridium* Organisms as Microbial Cell-Factories: Challenges & Opportunities. Metabolic engineering, doi:10.1016/j.ymben.2018.07.012 (2018).
18. Joseph, R. C., Kim, N. M. & Sandoval, N. R. Recent Developments of the Synthetic Biology Toolkit for *Clostridium*. Front Microbiol 9, 154, doi:10.3389/fmicb.2018.00154 (2018).
19. Academies, N. R. C. o. t. N. Industrialization of Biology: A Roadmap to Accelerate the Advanced Manufacturing of Chemicals. (2015).
20. Dudley, Q. M., Karim, A. S. & Jewett, M. C. Cell-free metabolic engineering: biomanufacturing beyond the cell. Biotechnology journal 10, 69-82, doi:10.1002/biot.201400330 (2015).
21. Morgado, G., Gerngross, D., Roberts, T. M. & Panke, S. Synthetic Biology for Cell-Free Biosynthesis: Fundamentals of Designing Novel In Vitro Multi-Enzyme Reaction Networks. Advances in biochemical engineering/biotechnology, doi:10.1007/10_2016_13 (2016).
22. Dong, H. et al. Engineering *Escherichia coli* Cell Factories for n-Butanol Production. Advances in biochemical engineering/biotechnology, doi:10.1007/10_2015_306 (2015).
23. Bogorad, I. W., Lin, T. S. & Liao, J. C. Synthetic non-oxidative glycolysis enables complete carbon conservation. Nature 502, 693-697, doi:10.1038/nature12575 (2013).
24. Zhu, F. et al. In vitro reconstitution of mevalonate pathway and targeted engineering of farnesene overproduction in *Escherichia coli*. Biotechnology and bioengineering 111, 1396-1405, doi:10.1002/bit.25198 (2014).
25. Wu, Y. Y. et al. System-level studies of a cell-free transcription-translation platform for metabolic engineering. BioRxiv Preprint, doi: 10.1101/172007 (2017).
26. Kelwick, R. et al. Cell-free prototyping strategies for enhancing the sustainable production of polyhydroxyalkanoates bioplastics. BioRxiv Preprint, doi:10.1101/225144 (2017).
27. Karim, A. S. & Jewett, M. C. A cell-free framework for rapid biosynthetic pathway prototyping and enzyme discovery. Metabolic engineering 36, 116-126, doi:10.1016/j.ymben.2016.03.002 (2016).
28. Dudley, Q. M., Anderson, K. C. & Jewett, M. C. Cell-free mixing of *Escherichia coli* crude extracts to prototype and rationally engineer high-titer mevalonate synthesis. ACS synthetic biology, doi:10.1021/acssynbio.6b00154 (2016).
29. Hold, C., Billerbeck, S. & Panke, S. Forward design of a complex enzyme cascade reaction. Nature communications 7, 12971, doi:10.1038/ncomms12971 (2016).
30. Kay, J. E. & Jewett, M. C. Lysate of engineered *Escherichia coli* supports high-level conversion of glucose to 2,3-butanediol. Metabolic engineering 32, 133-142, doi:10.1016/j.ymben.2015.09.015 (2015).
31. Karim, A. S., Heggestad, J. T., Crowe, S. A. & Jewett, M. C. Controlling cell-free metabolism through physiochemical perturbations. Metabolic engineering 45, 86-94, doi:10.1016/j.ymben.2017.11.005 (2018).
32. Dudley, Q. M., Nash, C. J. & Jewett, M. C. Cell-free biosynthesis of limonene using enzyme-enriched *Escherichia coli* lysates. Synthetic Biology 4, doi:10.1093/synbio/ysz003 (2019).
33. Casini, A. et al. A Pressure Test to Make 10 Molecules in 90 Days: External Evaluation of Methods to Engineer Biology. Journal of the American Chemical Society 140, 4302-4316, doi:10.1021/jacs.7b13292 (2018).
34. Goering, A. W. et al. In vitro reconstruction of nonribosomal peptide biosynthesis directly from DNA using cell-free protein synthesis. ACS synthetic biology, doi:10.1021/acssynbio.6b00160 (2016).
35. Karim, A. S. & Jewett, M. C. Cell-Free Synthetic Biology for Pathway Prototyping. Methods Enzymol 608, 31-57, doi:10.1016/bs.mie.2018.04.029 (2018).
36. Clomburg, J. M., Crumbley, A. M. & Gonzalez, R. Industrial biomanufacturing: The future of chemical production. Science 355, doi:10.1126/science.aag0804 (2017).
37. Adkins, J., Pugh, S., McKenna, R. & Nielsen, D. R. Engineering microbial chemical factories to produce renewable "biomonomers". Front Microbiol 3, 313, doi:10.3389/fmicb.2012.00313 (2012).
38. Tseng, H. C., Martin, C. H., Nielsen, D. R. & Prather, K. L. Metabolic engineering of *Escherichia coli* for enhanced production of (R)- and (S)-3-hydroxybutyrate. Applied and environmental microbiology 75, 3137-3145, doi:10.1128/AEM.02667-08 (2009).
39. Jewett, M. C. & Swartz, J. R. Mimicking the *Escherichia coli* cytoplasmic environment activates long-lived and efficient cell-free protein synthesis. Biotechnology and bioengineering 86, 19-26, doi:10.1002/bit.20026 (2004).
40. Jewett, M. C., Calhoun, K. A., Voloshin, A., Wuu, J. J. & Swartz, J. R. An integrated cell-free metabolic platform for protein production and synthetic biology. Mol Syst Biol 4, 220, doi:10.1038/msb.2008.57 (2008).
41. Woolston, B. M., Emerson, D. F., Currie, D. H. & Stephanopoulos, G. Rediverting carbon flux in *Clostridium ljungdahlii* using CRISPR interference (CRISPRi). Metabolic engineering 48, 243-253, doi:10.1016/j.ymben.2018.06.006 (2018).
42. Fluchter, S. et al. Anaerobic production of poly(3-hydroxybutyrate) (PHB) and its precursor 3-hydroxybutyrate (3-HB) from synthesis gas by autotrophic clostridia. Biomacromolecules, doi:10.1021/acs.biomac.9b00342 (2019).
43. Shen, C. R. et al. Driving forces enable high-titer anaerobic 1-butanol synthesis in *Escherichia coli*. Applied and environmental microbiology 77, 2905-2915, doi:10.1128/AEM.03034-10 (2011).
44. Atsumi, S. et al. Metabolic engineering of *Escherichia coli* for 1-butanol production. Metabolic engineering 10, 305-311, doi:10.1016/j.ymben.2007.08.003 (2008).
45. Inui, M. et al. Expression of *Clostridium acetobutylicum* butanol synthetic genes in *Escherichia coli*. Appl Microbiol Biotechnol 77, 1305-1316, doi:10.1007/s00253-007-1257-5 (2008).
46. Nguyen, N. P., Raynaud, C., Meynial-Salles, I. & Soucaille, P. Reviving the Weizmann process for commercial n-butanol production. Nature communications 9, 3682, doi:10.1038/s41467-018-05661-z (2018).
47. Li, F. et al. Coupled ferredoxin and crotonyl coenzyme A (CoA) reduction with NADH catalyzed by the butyryl-CoA dehydrogenase/Etf complex from *Clostridium kluyveri*. J Bacteriol 190, 843-850, doi: 10.1128/JB.01417-07 (2008).

48. Qi, F. et al. Improvement of butanol production in *Clostridium acetobutylicum* through enhancement of NAD(P)H availability. Journal of industrial microbiology & biotechnology 45, 993-1002, doi:10.1007/s10295-018-2068-7 (2018).
49. Chowdhury, N. P., Kahnt, J. & Buckel, W. Reduction of ferredoxin or oxygen by flavin-based electron bifurcation in Megasphaera elsdenii. FEBS J 282, 3149-3160, doi:10.1111/febs.13308 (2015).
50. Gao, H. J., Wu, Q. & Chen, G. Q. Enhanced production of D-(−)-3-hydroxybutyric acid by recombinant *Escherichia coli*. FEMS Microbiol Lett 213, 59-65, doi:10.1111/j.1574-6968.2002.tb 11286.x (2002).
51. Yun, E. J. et al. Production of (S)-3-hydroxybutyrate by metabolically engineered *Saccharomyces cerevisiae*. J Biotechnol 209, 23-30, doi:10.1016/j.jbiotec.2015.05.017 (2015).
52. Liew, F. et al. Metabolic engineering of *Clostridium autoethanogenum* for selective alcohol production. Metabolic engineering 40, 104-114, doi:10.1016/j.ymben.2017.01.007 (2017).
53. Perez, J. M., Richter, H., Loftus, S. E. & Angenent, L. T. Biocatalytic reduction of short-chain carboxylic acids into their corresponding alcohols with syngas fermentation. Biotechnology and bioengineering 110, 1066-1077, doi:10.1002/bit.24786 (2013).
54. Nemr, K. et al. Engineering a short, aldolase-based pathway for (R)-1,3-butanediol production in *Escherichia coli*. Metabolic engineering 48, 13-24, doi:10.1016/j.ymben.2018.04.013 (2018).
55. Kataoka, N., Vangnai, A. S., Pongtharangkul, T., Yakushi, T. & Matsushita, K. Production of 1,3-diols in *Escherichia coli*. Bioresour Technol 245, 1538-1541, doi:10.1016/j.biortech.2017.05.082 (2017).
56. Kataoka, N. et al. Enhancement of (R)-1,3-butanediol production by engineered *Escherichia coli* using a bioreactor system with strict regulation of overall oxygen transfer coefficient and pH. Biosci Biotechnol Biochem 78, 695-700, doi:10.1080/09168451.2014.891933 (2014).
57. Jing, F. et al. Direct dehydration of 1,3-butanediol into butadiene over aluminosilicate catalysts. Catalysis Science & Technology 6, 5830-5840, doi: 10.1039/c5cy02211h (2016).
58. Heijstra, B. D., Kern, E., Koepke, M., Segovia, S. & Liew, F. M. Novel bacteria and methods of use thereof. US 20130217096A1 (2013).
59. Liew, F. et al. Gas Fermentation-A Flexible Platform for Commercial Scale Production of Low-Carbon-Fuels and Chemicals from Waste and Renewable Feedstocks. Front Microbiol 7, 694, doi:10.3389/fmicb.2016.00694 (2016).
60. Heap, J. T., Pennington, O. J., Cartman, S. T. & Minton, N. P. A modular system for *Clostridium* shuttle plasmids. J Microbiol Methods 78, 79-85, doi:10.1016/j.mimet.2009.05.004 (2009).
61. Nagaraju, S., Davies, N. K., Walker, D. J., Kopke, M. & Simpson, S. D. Genome editing of *Clostridium autoethanogenum* using CRISPR/Cas9. Biotechnol Biofuels 9, 219, doi:10.1186/s13068-016-0638-3 (2016).
62. Köpke, M. et al. 2,3-butanediol production by acetogenic bacteria, an alternative route to chemical synthesis, using industrial waste gas. Applied and environmental microbiology 77, 5467-5475, doi:10.1128/AEM.00355-11 (2011).
63. Kwon, Y. C. & Jewett, M. C. High-throughput preparation methods of crude extract for robust cell-free protein synthesis. Sci Rep 5, 8663, doi:10.1038/srep08663 (2015).
64. Jewett, M. C. & Swartz, J. R. Substrate replenishment extends protein synthesis with an in vitro translation system designed to mimic the cytoplasm. Biotechnology and bioengineering 87, 465-471, doi:10.1002/bit.20139 (2004).
65. Koepke, M., Jensen, R. O., Behrendorff, J. B. Y. H. & Hill, R. E. Genetically engineered bacterium comprising energy-generating fermentation pathway. U.S. Pat. No. 9,738,875 (2017).
66. Valgepea, K. et al. Maintenance of ATP Homeostasis Triggers Metabolic Shifts in Gas-Fermenting Acetogens. Cell Syst 4, 505-515 e505, doi:10.1016/j.cels.2017.04.008 (2017).

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

What is claimed:

1. A cell-free method for synthesizing a non-ribosomal peptide target protein without the use of a transcription or translation template encoding the target protein, the method comprising:

a) contacting a translation template encoding a non-ribosomal peptide synthase ("NRPS") that is specific for the synthesis of the target protein with a cellular extract from a host strain, the extract comprising natural enzyme metabolism from the host strain;
   wherein the translation template is translated once it is contacted with the cellular extract, thereby providing a NRPS-containing extract;

b) contacting the NRPS-containing extract to a feedstock, the feedstock comprising components for the formation of the target protein.

2. The method of claim 1, wherein step (a) occurs in a first reaction vessel, and step (b) occurs in a second reaction vessel different than the first reaction vessel.

3. The method of claim 1, wherein the enzyme prepared in step (a) is heterologous relative to the cellular extract.

4. The method of claim 3, wherein the cellular extract is a prokaryotic cellular extract.

5. The method of claim 4, wherein the prokaryotic cellular extract is an *E. coli* cellular extract.

6. The method of claim 1, wherein step (a) comprises adding at least two different translation templates to the cellular extract, wherein each translation template encodes a different NRPS.

7. The method of claim 6, wherein each different translation template is contacted with the cellular extract in a separate reaction vessel.

8. The method of claim 1, wherein:

a) when the target peptide is valinomycin or intermediates or derivatives thereof, the NRPS is one or more of Vlm1 and Vlm2;

b) when the target peptide is andrimid or intermediates or derivatives thereof, the NRPS is one or more of AdmA, AdmB, AdmC, AdmD, AdmE, AdmF, AdmG, AdmH, AdmI, AdmJ, AdmK, AdmL, AdmM, AdmN, AdmO, AdmP, AdmQ, AdmR, AdmS, AdmT, AdmU;

c) when the target peptide is enterobactin or intermediates or derivatives thereof, the NRPS is one or more of EntA, EntB, EntC, EntD, EntE, EntF;

d) when the target peptide is styrene or intermediates or derivatives thereof, the NRPS is one or more of Pal22 and FDC1;

e) when the target peptide is Gramicidin S or intermediates or derivatives thereof, the NRPS is one or more of GrsA and GrsB;

f) when the target peptide is limonene or intermediates or derivatives thereof, the NRPS is one or more of ACAT, HMGS, HMGR, MK, PMK, PMDIDI, GPPS, and LS;

g) when the target peptide is pinene or intermediates or derivatives thereof, the NRPS is ACAT, HMGS, HMGR, MK, PMK, PMDIDI, GPPS, and PS;

h) when the target peptide is bisabolene or intermediates or derivatives thereof, the NRPS is ACAT, HMGS, HMGR, MK, PMK, PMDIDI, GPPS, FPP; or i) when the target peptide is 3-hydroxybutyrate or intermediates or derivatives thereof, the NRPS is Th1, Hbd, Crt and Ter.

9. The method of claim 1, wherein the cellular extract further comprises a reaction buffer, additional amino acids, and a tRNA mixture.

10. The method of claim 1, wherein the feedstock comprises one or more energy sources, salts, amino acids, cofactors, antibiotics or buffers.

11. The method of claim 10, wherein the feedstock comprises one or more of glucose, CoA, malonyl-CoA, acetyl-CoA, 4'-phosphopantetheinyl transferase enzyme Sfp, ATP, NAD, NADH, NADP, NADPH, FMN, SAM, potassium, magnesium, ammonium, glutamate, acetate, and any of the 20 amino acids.

12. The method of claim 2, wherein step (b) comprises adjusting the amount of NRPS-containing extract added to the feedstock, thereby tuning an amount of the target protein produced.

13. The method of claim 7, wherein step (b) comprises adjusting the ratio of different NRPS-containing extracts added to the feedstock, thereby tuning an amount of an intermediate of the target protein produced, an amount of a variant of the target protein produced, or an amount of the target protein produced.

14. The method of claim 1, wherein the translation template encoding the non-ribosomal peptide synthase is linear.

15. The method of claim 1, wherein the translation template encoding the non-ribosomal peptide synthase is a plasmid.

* * * * *